(12) United States Patent
Juneja

(10) Patent No.: US 11,793,867 B2
(45) Date of Patent: Oct. 24, 2023

(54) NEOANTIGENS AND USES THEREOF

(71) Applicant: BIONTECH US INC., Cambridge, MA (US)

(72) Inventor: Vikram Juneja, Waltham, MA (US)

(73) Assignee: BIONTECH US INC., Cambridge, MA (US)

(*) Notice: Subject to any disclaimer, the term of this patent is extended or adjusted under 35 U.S.C. 154(b) by 461 days.

(21) Appl. No.: 16/955,436

(22) PCT Filed: Dec. 18, 2018

(86) PCT No.: PCT/US2018/066255
§ 371 (c)(1),
(2) Date: Jun. 18, 2020

(87) PCT Pub. No.: WO2019/126186
PCT Pub. Date: Jun. 27, 2019

(65) Prior Publication Data
US 2021/0177954 A1 Jun. 17, 2021

Related U.S. Application Data

(60) Provisional application No. 62/607,148, filed on Dec. 18, 2017.

(51) Int. Cl.
| | | |
|---|---|---|
| A61K 39/00 | (2006.01) | |
| A61P 35/00 | (2006.01) | |
| A61K 35/17 | (2015.01) | |
| C07K 14/47 | (2006.01) | |
| C07K 14/725 | (2006.01) | |
| C07K 4/12 | (2006.01) | |

(52) U.S. Cl.
CPC ...... *A61K 39/001152* (2018.08); *A61K 35/17* (2013.01); *A61K 39/001114* (2018.08); *A61K 39/001164* (2018.08); *A61P 35/00* (2018.01); *C07K 14/4748* (2013.01); *C07K 14/7051* (2013.01); *A61K 2039/5154* (2013.01); *A61K 2039/572* (2013.01); *C07K 4/12* (2013.01)

(58) Field of Classification Search
CPC . A61K 39/001152; A61K 35/17; A61P 35/00; C07K 14/4748; C07K 14/7051
See application file for complete search history.

(56) References Cited

U.S. PATENT DOCUMENTS

| | | | |
|---|---|---|---|
| 4,588,585 A | 5/1986 | Mark et al. | |
| 4,683,195 A | 7/1987 | Mullis et al. | |
| 4,722,848 A | 2/1988 | Paoletti et al. | |
| 5,185,146 A | 2/1993 | Altenburger | |
| 5,580,859 A | 12/1996 | Felgner et al. | |
| 5,589,466 A | 12/1996 | Felgner et al. | |
| 5,658,785 A | 8/1997 | Johnson | |
| 5,833,975 A | 11/1998 | Paoletti et al. | |
| 5,942,235 A | 8/1999 | Paoletti | |
| 5,973,007 A | 10/1999 | Demarchez et al. | |
| 6,090,393 A | 7/2000 | Fischer | |
| 6,156,567 A | 12/2000 | Fischer | |
| 6,258,595 B1 | 7/2001 | Gao et al. | |
| 6,265,189 B1 | 7/2001 | Paoletti et al. | |
| 6,277,558 B1 | 8/2001 | Hudson | |
| 6,309,647 B1 | 10/2001 | Paoletti et al. | |
| 6,440,663 B1 | 8/2002 | Scanlan et al. | |
| 6,475,769 B1 | 11/2002 | Wilson et al. | |
| 6,537,540 B1 | 3/2003 | Burstein et al. | |
| 6,537,594 B1 | 3/2003 | Paoletti et al. | |
| 6,780,407 B1 | 8/2004 | Paoletti et al. | |
| 6,793,926 B1 | 9/2004 | Rasty et al. | |
| 6,869,794 B2 | 3/2005 | Vogels et al. | |
| 6,893,865 B1 | 5/2005 | Lockert et al. | |
| 6,913,922 B1 | 7/2005 | Bout et al. | |
| 6,924,128 B2 | 8/2005 | Allen | |
| 6,936,466 B2 | 8/2005 | Feldhaus | |
| 6,953,690 B1 | 10/2005 | Gao et al. | |
| 7,029,848 B2 | 4/2006 | Vogels et al. | |
| 7,115,391 B1 | 10/2006 | Chen et al. | |
| 7,172,893 B2 | 2/2007 | Rabinowitz et al. | |
| 7,255,862 B1 | 8/2007 | Tartaglia et al. | |
| 8,092,780 B2 | 1/2012 | Livingston et al. | |
| 8,309,098 B2 | 11/2012 | Howley et al. | |

(Continued)

FOREIGN PATENT DOCUMENTS

| | | | |
|---|---|---|---|
| CA | 2343602 A1 | 10/2001 | |
| EP | 1338606 A1 | 8/2003 | |

(Continued)

OTHER PUBLICATIONS

Kreiter et. al. (2015, Nature, 520(7549):692-6. Mutant MHC class II epitopes drive therapeutic immune responses to cancer) (Year: 2015).*
Alonso et al. Biodegradable microspheres as controlled-release tetanus toxoid delivery systems. Vaccine 12(4):299-306 (1994).
Altman et al., Phenotypic analysis of antigen-specific T lymphocytes, Science, 274(5284):94-6 (1996).
Bock et al., "Reference Maps of human ES and iPS cell variation enable high-throughput characterization of pluripotent cell lines," Cell, 144:439-452 (2011).
Boyle et al., "Gel-free multiplexed reduced representation bisulfite sequencing for large-scale DNA methylation profiling," Genome Biol, 13:R92 (2012).
Brash et al., Strontium phosphate transfection of human cells in primary culture: stable expression of the simian virus 40 large-T-antigen gene in primary human bronchial epithelial cells, Mol. Cell Biol., 7: 2031-2034 (1987).

(Continued)

*Primary Examiner* — Julie Wu
*Assistant Examiner* — Francesca Edgingtongiordan
(74) *Attorney, Agent, or Firm* — Wilson Sonsini Goodrich & Rosati

(57) ABSTRACT

Disclosed herein relates to immunotherapeutic compositions comprising immunotherapeutic peptides comprising neoepitopes, polynucleotides encoding the immunotherapeutic peptides, antigen presenting cells comprising the immunotherapeutic peptides or polynucleotides, or T cell receptors specific for the neoepitopes. Also disclosed herein is use of the immunotherapeutic compositions.

17 Claims, 50 Drawing Sheets
Specification includes a Sequence Listing.

(56) References Cited

U.S. PATENT DOCUMENTS

| | | |
|---|---|---|
| 8,501,167 B2 | 8/2013 | Apelian et al. |
| 8,906,006 B2 | 12/2014 | Chornenky et al. |
| 8,999,937 B2 | 4/2015 | Srinivasan |
| 9,862,927 B2 | 1/2018 | Banchereau et al. |
| 2003/0124128 A1 | 7/2003 | Lillie et al. |
| 2004/0029114 A1 | 2/2004 | Mack et al. |
| 2004/0076955 A1 | 4/2004 | Mack et al. |
| 2004/0087478 A1 | 5/2004 | Gillen et al. |
| 2005/0222062 A1 | 10/2005 | Arai et al. |
| 2005/0287127 A1 | 12/2005 | Li et al. |
| 2006/0258607 A1 | 11/2006 | Jarosch et al. |
| 2007/0055049 A1 | 3/2007 | Grey et al. |
| 2007/0134197 A1 | 6/2007 | Eichner et al. |
| 2009/0136494 A1 | 5/2009 | Ponath et al. |
| 2009/0270482 A1 | 10/2009 | Schuebeler et al. |
| 2010/0105051 A1 | 4/2010 | Lillie et al. |
| 2011/0092388 A1 | 4/2011 | Lillie et al. |
| 2011/0097743 A1 | 4/2011 | Bihain et al. |
| 2011/0182937 A1 | 7/2011 | Banchereau et al. |
| 2011/0257890 A1 | 10/2011 | Weinschenk et al. |
| 2012/0082691 A1 | 4/2012 | Rammensee |
| 2012/0288509 A1 | 11/2012 | Schuebeler et al. |
| 2012/0288539 A1 | 11/2012 | Eber |
| 2013/0210014 A1 | 8/2013 | Sharman |
| 2013/0323279 A1 | 12/2013 | Nixon et al. |
| 2013/0338077 A1 | 12/2013 | Srinivasan |
| 2014/0056986 A1 | 2/2014 | Desai et al. |
| 2016/0252511 A1 | 9/2016 | Czerniecki et al. |
| 2016/0317654 A1 | 11/2016 | Noelle et al. |
| 2016/0331822 A1 | 11/2016 | Hacohen et al. |
| 2016/0331834 A1 | 11/2016 | Mondoulet et al. |
| 2016/0377631 A1 | 12/2016 | Kuchroo et al. |
| 2017/0114413 A1 | 4/2017 | Hahn et al. |
| 2017/0160269 A1 | 6/2017 | Linnemann et al. |
| 2017/0204140 A1 | 7/2017 | Suphioglu |
| 2017/0253633 A1 | 9/2017 | Mahr et al. |
| 2017/0261508 A1 | 9/2017 | Czerniecki et al. |
| 2018/0088121 A1 | 3/2018 | Gerhard et al. |
| 2019/0099475 A1 | 4/2019 | Benz et al. |

FOREIGN PATENT DOCUMENTS

| | | |
|---|---|---|
| EP | 1498145 A1 | 1/2005 |
| EP | 2105511 A1 | 9/2009 |
| EP | 2390363 A1 | 11/2011 |
| JP | 2003517274 A | 5/2003 |
| JP | 2003523365 A | 8/2003 |
| JP | 2003535024 A | 11/2003 |
| JP | 2019513373 A | 5/2019 |
| WO | WO-0066153 A1 | 11/2000 |
| WO | WO-0100225 A1 | 1/2001 |
| WO | WO-0155177 A2 | 8/2001 |
| WO | WO-2006121168 A1 | 11/2006 |
| WO | WO-2007066366 A1 | 6/2007 |
| WO | WO-2008096831 A1 | 8/2008 |
| WO | WO-2010033949 A1 | 3/2010 |
| WO | WO-2011146862 A1 | 11/2011 |
| WO | WO-2012079000 A1 | 6/2012 |
| WO | WO-2012095639 A2 | 7/2012 |
| WO | WO-2012101112 A1 | 8/2012 |
| WO | WO-2012159643 A1 | 11/2012 |
| WO | WO-2012159754 A2 | 11/2012 |
| WO | WO-2013026027 A1 | 2/2013 |
| WO | WO-2013039889 A1 | 3/2013 |
| WO | WO-2013086464 A1 | 6/2013 |
| WO | WO-2013123031 A2 | 8/2013 |
| WO | WO-2013151672 A2 | 10/2013 |
| WO | WO-2013166321 A1 | 11/2013 |
| WO | WO-2013173223 A1 | 11/2013 |
| WO | WO-2013176915 A1 | 11/2013 |
| WO | WO-2014011987 A1 | 1/2014 |
| WO | WO-2014012051 A1 | 1/2014 |
| WO | WO-2014018863 A1 | 1/2014 |
| WO | WO-2014056986 A1 | 4/2014 |
| WO | WO-2014134165 A1 | 9/2014 |
| WO | WO-2014150924 A2 | 9/2014 |
| WO | WO-2014172606 A1 | 10/2014 |
| WO | WO-2014184744 A1 | 11/2014 |
| WO | WO-2014191128 A1 | 12/2014 |
| WO | WO-2014197369 A1 | 12/2014 |
| WO | WO-2015085233 A1 | 6/2015 |
| WO | WO-2015107081 A1 | 7/2015 |
| WO | WO-2016011487 A1 | 1/2016 |
| WO | WO-2016020710 A1 | 2/2016 |
| WO | WO-2016100975 A1 | 6/2016 |
| WO | WO-2016141324 A2 | 9/2016 |
| WO | WO-2016144976 A1 | 9/2016 |
| WO | WO-2016144976 A9 | 10/2016 |
| WO | WO-2016156478 A1 | 10/2016 |
| WO | WO-2016187508 A2 | 11/2016 |
| WO | WO-2017004153 A1 | 1/2017 |
| WO | WO-2017011710 A2 | 1/2017 |
| WO | WO-2017069958 A2 | 4/2017 |
| WO | WO-2017074788 A1 | 5/2017 |
| WO | WO-2017088012 A1 | 6/2017 |
| WO | WO-2017139694 A1 | 8/2017 |
| WO | WO-2017148888 A1 | 9/2017 |
| WO | WO-2017173321 A1 | 10/2017 |
| WO | WO-2017180989 A2 | 10/2017 |
| WO | WO-2017184590 A1 | 10/2017 |
| WO | WO-2018005712 A1 * | 1/2018 | ............. A61K 35/17 |
| WO | WO-2018037416 A1 | 3/2018 |
| WO | WO-2018140391 A1 | 8/2018 |
| WO | WO-2019246286 A1 | 12/2019 |
| WO | WO-2019246315 A1 | 12/2019 |

OTHER PUBLICATIONS

Bremel et al., An integrated approach to epitope analysis I: Dimensional reduction, visualization and prediction of MHC binding using amino acid principal components and regression approaches, Immunome Res, 6:7 (2010).

Brito, Luis et al., Self-amplifying mRNA Vaccines, Adv. Genet. 2015; 89:179-233.

Brown et al., Integrative genomic analysis implicates gain of PIK3CA at 3g26 and MYC at 8q24 in chronic lymphocytic leukemia, Clin Cancer Res, 8:3791-802 (2012).

Buchschacher et al. Human immunodeficiency virus vectors for inducible expression of foreign genes. J. Virol. 66:2731-2739 (1992).

Busch et al., Degenerate binding of immunogenic peptides to HLA-DR proteins on B cell surfaces, Int. Immunol. 2:443 (1990).

Carithers, L.J.,et al. (2015). A Novel Approach to High-Quality Postmortem Tissue Procurement: The GTEx Project. Biopreservation Biobanking 13, 311-319.

Ceppellini et al., Binding of labelled influenza matrix peptide to HLA DR in living B lymphoid cells, Nature 339:392 (1989).

Cerundolo et al., The binding affinity and dissociated rates of peptides for class I major histocompatibility complex molecules, Eur. Immunol., 21:2069-75 (1991).

Chen et al., Impact of replication timing on non-CpG and CpG substitution rates in mammalian genomes, Genome Res, 20:447-457 (2010).

Christnick et al., Peptide binding to class 1MHC on living cells and quantitation of complexes required for CTL lysis, Nature 352:67 (1991).

Consolidated Table of Documents filed in Opposition to date in Response to Notices of Opposition of EP2569633 dated Jun. 28, 2017.

Corpet et al., Multiple sequence alignment with hierarichal clustering, Nucleic Acids Res., 16:10881-10890 (1988).

De et al., Aberration in DNA methylation in B-cell lymphomas has a complex origin and increases with disease severity, PLoS Genet. 9:e1003137 (2013).

Declaration by Stephen Johnston filed during the prosecution of granted U.S. Pat. No. 8,796,414 Nov. 20, 2013.

Del Guercio, M.F., et al., Binding of a peptide antigen to multiple HLA alleles allows definition of an A2-like supertype, J. Immunol. 154:685-693 (1995).

(56) References Cited

OTHER PUBLICATIONS

Dengjel et al., "Glycan side chains on naturally presented MHC class II ligands," J. Mass Spectrom, 40:100-104 (2005).
Dupont, J., et al., Artificial Antigen-Presenting Cells Transduces with Telomerase Efficiently Expand Epitope-Specific, Human Leukocyte Antigen-Restricted Cytotoxic T Cells, 2005 Cancer Res 65:5417-5427.
Eden et al., Discovering motifs in ranked lists of DNA sequences, PLoS computational biology, 3, e39 (2007).
Eden et al., GOrilla: a tool for discovery and visualization of enriched GO terms in ranked gene lists, BMCBioinformatics, 10:48 (2009).
Eggermont et al., Ulceration and stage are predictive of interferon efficacy in melanoma: results of the phase III adjuvant trials EORTC 18952 and EORTC 18991, EurJ Cancer, 48(2):218-225 (2012).
Ehrlich, DNA hypomethylation in cancer cells, Epigenomics, 1:239-259 (2009).
European Search Report dated Oct. 24, 2019, for EP Appl. No. 177768116.
Extended European Search Report dated Apr. 11, 2016, which issued during prosecution of EP Application No. 15198284.0.
Extended European Search Report received for EP patent application No. EP11781409, dated Apr. 10, 2014.
Extended Search Report in Corresponding European Application No. 11781409.5, dated Apr. 14, 2014.
Final Rejection for U.S. Appl. No. 15/187,174, Compositions and Methods of Identifying Tumor Specific Neoantigens, dated Oct. 12, 2018.
Fransen et al., Controlled local delivery of CTLA-4 blocking antibody induces CD8+ T-cell-dependent tumor eradication and decreases risk of toxic side effects, Clin Cancer Res, 19(19):5381-5389 (2013).
Gamvrellis, A. et al., Vaccines that facilitate antigen entry into dendritic cells, Immunol & Cell Biol. 2004; 82:506-516.
Greiner, Jochen, Mutated Regions of Nucleophosmin 1 Elicit Both CD4 and CD8 T-cell Responses in Patients with Acute Myeloid Leukemia, Blood, 2012 12):1281-1289. doi:10.1182/blood-2011-11-394395.
Hammer, J. et al., Precise prediction of major histocompatibility complex class II-peptide interaction based on peptide side chain scanning, J. Exp. Med. 180:2353 (1994).
Hei et al., "Potentiation of simian immunodeficiency virus (SIV)-specific CD4+ and CD8+ T cell responses by a DNA-SIV and NYVAC-SIV prime/boost regimen," The Journal of Immunology, 167(12):7180-7191 (2001).
Henikoff & Henikoff, Amino acide substitution matrices from protein blocks, Proc. Natl. Acad. Sci. USA 89:10915-10919, (1992).
Higgins et al.: CLUSTAL: a package for performing multiple sequence alignment on a microcomputer; Elsevier Science Publishers B.V. (Biomedical Division); Gene. 73 (1988) 237-244.
Higgins, et al. Fast and Sensitive Multiple Sequence Alignments on a Microcomputer. CABIOS Commun. 1989; 5(2):151-153.
Hodi et al., "Biologic Activity of Cytotoxic T Lymphocyte-Associated Antigen 4 Antibody Blockade in Previously Vaccinated Metastatic Melanoma and Ovarian Carcinoma Patients," PNAS, 100: 4712-4717 (2003).
Hodi et al., "Immunologic and Clinical Effects of Antibody Blockade of Cytotoxic T Lymphocyte-Associated Antigen 4 in Previously Vaccinated Cancer Patients," PNAS, 105: 3005-3010 (2008).
Hombrink et al., High-Throughput Identification of Potential Minor Histocompatibility Antigens by MHC Tetramer-Based Screening: Feasibility and Limitations, Plos One, 6(8):1-11 (2011).
Hu et al. The immunostimulating complex (ISCOM) is an efficient mucosal delivery system for respiratory syncytial virus (RSV) envelope antigens inducing high local and systemic antibody responses. Clin Exp Immunol 113(2):235-43 (1998).
Huang, et al. Parallelization of a Local Similarity Algorithm. CABIOS. 1992; 8(2): 155-165.
International Preliminary Report on Patentability for International Application No. PCT/US2011/036665 dated Nov. 20, 2012.
International Preliminary Report on Patentability for International Application No. PCT/US2014/033185 dated Oct. 22, 2015.
International Preliminary Report on Patentability for International Application No. PCT/US2014/067146 dated May 31, 2016.
International Preliminary Report on Patentability for International Application No. PCT/US2014/068746 dated Jun. 7, 2016.
International Preliminary Report on Patentability for International Application No. PCT/US2014/068893 dated Jun. 7, 2016.
International Preliminary Report on Patentability for International Application No. PCT/US2014/071707 dated Jun. 21, 2016.
Johann et al. GLVR1, a receptor for gibbon ape leukemia virus, is homologous to a phosphate permease of Neurospora crassa and is expressed at high levels in the brain and thymus. J Virol. 66(3):1635-1640 (1992).
Johnston, S.A., Biolistic transformation: microbes to mice, Nature, 346: 776-777 (1990).
Jones et al., Functions of DNA methylation: islands, start sites, gene bodies and beyond, Nat Rev Genet, 13:484-492 (2012).
Khilko, Sergi N. et al., Direct Detection of Major Histocompatibility Complex Class I Binding to Antigenic Peptides Using Surface Plasmon Resonance, J. Biol. Chem. 268:15425 (1993).
Kim et al., A Myc network accounts for similarities between embryonic stem and cancer cell transcription programs, Cell, 143:313-324 (2010).
Kim et al., TopHat2: accurate alignment of transcriptomes in the presence of insertions, deletions and gene fusions, Genome biology, 14:R36 (2013).
Ljunggren et al., Empty MHC class I molecules come out in the cold, Nature 346:476 (1990).
Mayr, et al. Infection rate and acute organ dysfunction risk as explanations for racial differences in severe sepsis. JAMA. Jun. 23, 2010;303(24):2495-503. doi: 10.1001/jama.2010.851.
Mosca, Paul J. et al., Dendritic cell vaccines, Frontiers in Bioscience, (2007) 12:4050-4060).
Mumtaz et al. Design of liposomes for circumventing the reticuloendothelial cells. Glycobiology 5:505-510 (1991).
Murray E. Gene Transfer and Expression Protocols (Methods in Molecular Biology), J. (ed.), vol. 7, Humana Press (1991).
Non-Final Office Action for U.S. Appl. No. 13/108,610, Compositions and Methods of Identifying Tumor Specific Neoantigens, dated Dec. 3, 2014.
Non-Final Office Action for U.S. Appl. No. 14/794,449, Compositions and Methods of Identifying Tumor Specific Neoantigens, dated Dec. 29, 2016.
Non-Final Office Action for U.S. Appl. No. 14/794,449, "Compositions and Methods of Identifying Tumor Specific Neoantigens," dated Jul. 24, 2018.
Non-Final Office Action for U.S. Appl. No. 14/877,125, Compositions and Methods for Personalized Neoplasia Vaccines, dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504, Compositions and Methods for Diagnosing, Evaluating and Treating Cancer By Means of the DNA Methyl, dated Sep. 6, 2017.
Non-Final Office Action for U.S. Appl. No. 15/102,129, Formulations for Neoplasia Vaccines, dated Dec. 17, 2018.
Non-Final Office Action for U.S. Appl. No. 15/102,129, Formulations for Neoplasia Vaccines, dated Jul. 28, 2017.
Non-Final Office Action for U.S. Appl. No. 15/102,129, Formulations for Neoplasia Vaccines, dated Mar. 7, 2018.
Non-Final Office Action for U.S. Appl. No. 15/105,961, Combination Therapy With Neoantigen Vaccine, dated Jan. 8, 2019.
Non-Final Office Action for U.S. Appl. No. 15/105,961, Combination Therapy With Neoantigen Vaccine, dated Nov. 20, 2017.
Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, Compositions and Methods of Identifying Tumor Specific Neoantigens, dated Jan. 22, 2018.

(56) References Cited

OTHER PUBLICATIONS

Non-Final Office Action for U.S. Appl. No. 15/513,127, Use of Clonal Evolution Analysis for Ibrutinib Resistance in Chronic Lymphocytic Leukemia Patients, dated Nov. 26, 2018.
Non-Final Office Action for U.S. Appl. No. 15/537,785, Methods for Profiling the T Cell Repertoire, dated Dec. 21, 2018.
Non-Final Office Action for U.S. Appl. No. 16/181,098, Compositions and Methods of Identifying Tumor Specific Neoantigens, dated Jan. 31, 2019.
Notice of Allowance for U.S. Appl. No. 13/108,610, Compositions and Methods of Identifying Tumor Specific Neoantigens, dated Jun. 11, 2015.
Notice of Allowance for U.S. Appl. No. 13/108,610, Compositions and Methods of Identifying Tumor Specific Neoantigens, dated May 12, 2015.
Notice of Allowance for U.S. Appl. No. 15/102,129, Formulations for Neoplasia Vaccines, dated Oct. 12, 2018.
Ohnishi et al., Premature Termination of Reprogramming In Vivo Leads to Cancer Development through Altered Epigenetic Regulation, Cell, 156(4):663-677 (2014).
PAIR Assignment Register extract (accessed Oct. 20, 2016).
Parker et al., The beta 2-microglobulin dissociation rate is an accurate measure of the stability of MHC Class I heterotrimers and depends on which peptide is bound, J. Immunol. 149:1896 (1992).
PCT/US2017/025462 International Search Report dated Sep. 11, 2017.
PCT/US2018/025933 International Search Report and Written Opinion dated Oct. 9, 2018.
Pearson, W.R. Using the FASTA Program to Search Protein and DNA Sequence Databases. Meth. Mol. Biol. 1994; 24:307-331.
Pieters et al., On guard: coronin proteins in innate and adaptive immunity, Nat Rev Immunol, 13:510-518 (2013).
Shipony et al., Dynamic and static maintenance of epigenetic memory in pluripotent and somatic cells, Nature, 513:115-119 (2014).
Smoley et al., "Standardization of fluorescence in situ hybridization studies on chronic lymphocytic leukemia (CLL) blood and marrow cells by the CLL Research Consortium," Cancer Genet Cytogenet, 203(2):141-148 (2010).
Spencer et al., Non-genetic origins of cell-to-cell variability in TRAIL-induced apoptosis, Nature, 459:428-432 (2009).
Spranger et al., Up-regulation of Pd—Li, IDO, and Tregs in the melanoma tumor microenvironment is driven by CD8+ T cells, Sci Trans! Med, 5(200):200ra116 (2013).
Subramanian et al., Gene set enrichment analysis: a knowledge-based approach for interpreting genome-wide expression profiles, PNAS, 102:15545-15550 (2005).
Vitiello et al. Development of a lipopeptide-based therapeutic vaccine to treat chronic HBV infection. I. Induction of a primary cytotoxic T lymphocyte response in humans. J Clin Invest 95:341-349 (1995).
De, Subhajyoti et al., Aberration in DNA Methylation in B-Cell Lymphoma Has a Complex Origin and Increases with Disease Severity, PLOS Genetics Jan. 2013, vol. 9, 1-14.
Acevedo et al., Analysis of the mechanisms mediating tumor-specific changes in gene expression in human liver tumors, Cancer Res, 68(8):2641-2651 (2008).
Acknowledgment of Receipt dated Jun. 28, 2017 for Response to Notices of Opposition of EP2569633.
Adams, Toll-like receptor agonists in cancer therapy, Immunotherapy, 1(6):949-964 (2009).
Adomas, et al. "Breast tumor specific mutation in GATA3 affects physiological mechanisms regulating transcription factor turnover," BMC Cancer 2014, 14:278.
Akiyama et al., GATA-4 and GATA-5 transcription factor genes and potential downstream antitumor target genes are epigenetically silenced in colorectal and gastric cancer, Mol Cell Biol, 23:8429-8439 (2003).

Alarcon et al., DNA vaccines: technology and application as anti-parasite and anti-microbial agents, Advances in Parasitology, 42:343-410 (1999).
Albert et al., "Direct Selection of Human Genomic Loci by Microarray Hybridization," Nat Methods, 4(11): 903-905 (2007).
Ali et al., In situ regulation of DC subsets and T cells mediates tumor regression in mice, Cancer Immunotherapy, 1(8):1-10 (2009).
Ali et al., "Infection-mimicking materials to program dendritic cells in situ," Nat Mater, 8:151-8 (2009).
Allison, "The Mode of Action of Immunological Adjuvants," Dev Biol Stand, 92: 3-11 (1998).
Almeida et al., "CTdatabase: a knowledge-base of high-throughput and curated data on cancer-testis antigens," Nucleic acids research, 37:D816-819 (2008).
Alvarez, Present and future evolution of advanced breast cancer therapy, Breast Cancer Research, 12(Suppl 2):S1 (2010).
Alyea et al., "Toxicity and Efficacy of Defined Doses of CD4+ Donor Lymphocytes for Treatment of Relapse After Allogeneic Bone Marrow Transplant," Blood, 91(10):3671-3680 (1998).
Amara et al., "Control of a mucosal challenge and prevention of AIDS by a multiprotein DNA/MVA vaccine," Science, 292(5514):69-74 (2001).
Amato et al., "Vaccination of metastatic renal cancer patients with MVA-5T4: a randomized, double-blind, placebo-controlled phase III study," Clin Can Res, 16(22):5539-47 (2010).
Amato et al., "Vaccination of renal cell cancer patients with modified vaccinia ankara delivering tumor antigen 5T4 (TroVax) administered with interleukin 2: a phase II trial," Clin Cancer Res, 14(22):7504-10 (2008).
Anders et al., HTSeq—A Python framework to work with high-throughput sequencing data, Bioinformatics, 31(2):166-169 (2015).
Andersen et al., Parallel detection of antigen-specific T cell responses by combinatorial encoding of MHC multimers, Nature protocols, 7(5):891-902 (2012).
Anderson et al., "Next Generation DNA Sequencing and the Future of Genomic Medicine," Genes, 1:38-69 (2010).
Andreatta et al., Gapped sequence alignment using artificial neural networks: application to the MHC class I system, Bioinformatics 32(4):511-517 (2016).
Annunziata et al., "Frequent Engagement of the Classical and Alternative NF-KB Pathways by Diverse Genetic Abnormalities in Multiple Myeloma," Cancer Cell, 12(2):115-130 (2007).
Antoine et al., "The complete genomic sequence of the modified vaccinia Ankara strain: comparison with other orthopoxviruses," Virology, 244(2):365-96 (1998).
Antonis et al., "Vaccination with recombinant modified vaccinia virus Ankara expressing bovine respiratory syncytial virus (bRSV) proteins protects calves against RSV challenge," Vaccine, 25(25):4818-4827 (2007).
Attia et al., "Autoimmunity Correlates With Tumor Regression in Patients With Metastatic Melanoma Treated with Anti-Cytotoxic T-Lymphocyte Antigen-4," J Clin Oncol, 23.(25): 6043-6053 (2005).
Aucouturier et al., "Adjuvants designed for veterinary and human vaccines," Vaccine, 19(17-19):2666-2672 (2001).
Austen et al., "Mutations in the ATM Gene Lead to Impaired Overall and Treatment-Free Survival that is Independent of IGVH Mutation Status in Patients with B-CLL," Blood, 106(9): 3175-3182 (2005).
Ausubel, A botanical macroscope, Proceedings of the National Academy of Sciences, 106(31):12569-12570 (2009).
Avogadri et al. "Modulation of CTLA-4 and GITR for Cancer Immunotherapy," Curr Top Microbiol Immunol, 344:211 (2011).
Azvolinsky et al., "PD-1 Inhibitor MK-3475 Again Shows Promise in Advanced Melanoma," Cancer Network, 2013. [Retrieved online] http://www.cancernetwork.com/melanoma/pd-1-inhibitor-mk-3475-again-shows-promise-advanced-melanoma.
Bachem et al., "Superior antigen cross-presentation and XCR1 expression define human CD11c+ CD141+ cells as homologues of mouse CD8+ dendritic cells," Journal of Experimental Medicine, 207(6):1273-1281 (2010).
Bachireddy et al., "Reversal of in situ T cell exhaustion during effective human anti-leukemia responses to donor lymphocyte infusion," Blood, 123(9):1412-1421 (2013).

(56) References Cited

OTHER PUBLICATIONS

Backert et al., Immunoinformatics and epitope prediction in the age of genomic medicine, Genome Medicine, 7:119 (2015).
Baden et al., "First-in-human evaluation of the safety and immunogenicity of a recombinant adenovirus serotype 26 FflV-1 Env vaccine (IPCAVD 001)," J Infect Dis, 207(2):240-247 (2012).
Balaggan et al., "Stable and efficient intraocular gene transfer using pseudotyped EIAV lentiviral vectors," J Gene Med, 8:275-285 (2005).
Balakrishnan et al, "Novel Somatic and Germline Mutations in Cancer Candidate Genes in Glioblastoma, Melanoma, and Pancreatic Carcinoma," Cancer Res, 67: 3545-3550 (2007).
Balazsi et al., Cellular decision making and biological noise: from microbes to mammals, Cell, 144(6):910-925 (2011).
Balch et al., Final version of 2009 AJCC melanoma staging and classification, Journal of clinical oncology, 27(36):6199-6206 (2009).
Barbie et al., Systematic RNA interference reveals that oncogenic KRAS-driven cancers require TBK1, Nature, 462:108-112 (2009).
Barretina et al., The Cancer Cell Line Encyclopedia enables predictive modelling of anticancer drug sensitivity, Nature, 483:603-607 (2012).
Baskar et al., "Autologous Lymphoma Vaccines Induce Human T Cell Responses Against Multiple, Unique Epitopes," J Clin Invest, 113:1498-1510 (2004).
Bassani-Sternberg et al., Mass Spectrometry of Human Leukocyte Antigen Class I Peptidomes Reveals Strong Effects of Protein Abundance and Turnover on Antigen Presentation, Mol Cell Proteomics, 14:658-673 (2015).
Baurain et al., "High Frequency of Autologous Anti-Melanoma CTL Directed Against an Antigen Generated by a Point Mutation in a New Helicase Gene," J Immunol, 164: 6057-6066 (2000).
Baylin, A decade of exploring the cancer epigenome-biological and translational implications, Nat Rev Cancer, 11:726-734 (2005).
Baylin, DNA methylation and gene silencing in cancer, Nat Clin Pract Oncol 2, Suppl 1, S4-11 (2005).
Beck et al., "Enterocolitis in Patients With Cancer After Antibody Blockade of Cytotoxicity TLymphocyte-Associated Antigen 4," J Clin Oncol, 24(15): 2283-2289 (2006).
Behrends et al., Network organization of the human autophagy system, Nature, 466(7302):68-76 (2010).
Bellucci et al., "Complete Response to Donor Lymphocyte Infusion in Multiple Myeloma is Associated with Antibody Responses to Highly Expressed Antigens," Blood, 103: 656-663 (2004).
Benson, Tandem repeats finder: a program to analyze DNA sequences, Nucleic acids research, 27(2):573-580 (1999).
Bentley et al., "Accurate Whole Human Genome Sequencing using Reversible Terminator Chemistry," Nature, 456(7218): 53-59 (2008).
Benton et al., Screening lambdagt recombinant clones by hybridization to single plaques in situ, Science, 196(4285):180-182 (1977).
Berg et al., Detection of artifacts and peptide modifications in liquid chromatography/mass spectrometry data using two-dimensional signal intensity map data visualization, Rapid Commun Mass Spectrom, 20(10):1558-1562 (2006).
Berger et al., Melanoma genome sequencing reveals frequent PREX2 mutations, Nature, 485(7399):502 (2012).
Berger et al., The genomic complexity of primary human prostate cancer, Nature, 470:214-220 (2011).
Berman et al., Regions of focal DNA hypermethylation and long-range hypomethylation in colorectal cancer coincide with nuclear lamina-associated domains, Nat Genet, 44:40-46 (2012).
Bettelli et al., "TH-17 cells in the circle of immunity and autoimmunity," Nat Immunol, 8:345-350 (2007).
Bhardwaj et al., "TLR Agonists: Are They Good Adjuvants?," Cancer J, 16:382-391 (2010).
Bindea et al., Spatiotemporal dynamics of intratumoral immune cells reveal the immune landscape in human cancer, Immunity, 39:782-795 (2013).
Bird, DNA methylation patterns and epigenetic memory, Genes Dev, 16:6-21 (2002).
Birrell et al., A genome-wide screen in *Saccharomyces cerevisiae* for genes affecting UV radiation sensitivity, Proceedings of the National Academy of Sciences 98(22):12608-12613 (2001).
Bishop et al., APOBEC-mediated editing of viral RNA, Science, 305:645 (2004).
Bisht et al., "Severe acute respiratory syndrome coronavirus spike protein expressed by attenuated vaccinia virus protectively immunizes mice," Proc Natl Acad Sci, 101:6641-46 (2004).
Blanchard et al., "Modified vaccinia virus Ankara undergoes limited replication in human cells and lacks several immunomodulatory proteins: implications for use as a human vaccine," Journal of General Virology, 79(5):1159-1167 (1998).
Bock et al., BiQ Analyzer: visualization and quality control for DNA methylation data from bisulfite sequencing, Bioinformatics, 21:4067-4068 (2005).
Boen et al., Identification of T Cell Ligands in a Library of Peptides Covalently Attached to HLA-DR4, J Immunol, 165:2040-2047 (2000).
Bogunovic et al., TLR4 engagement during TLR3-induced proinflammatory signaling in dendritic cells promotes IL-10-mediated suppression of antitumor immunity, Cancer Res, 71(16):5467-5476 (2011).
Bohm et al., DNA vector constructs that prime hepatitis B surface antigen-specific cytotoxic T lymphocyte and antibody responses in mice after intramuscular injection. Journal of immunological methods 193(1): 29-40 (1996).
Boisgerault et al., Definition of the HLA-A29 peptide ligand motif allows prediction of potential T-cell epitopes from the retinal soluble antigen, a candidate autoantigen in birdshot retinopathy, PNAS, 93:3466-3470 (1996).
Boisguerin et al., "Translation of genomis-guided RNA-based personalised cancer vaccaines: towards the bedside," British J Cancer, 111:1469-1475 (2014).
Boller et al. Characterization of the antibody response specific for the human endogenous retrovirus HTDV/HERV-K, Journal of virology, 71(6):4581-4588 (1997).
Boni et al. "Adoptive transfer of allogeneic tumor-specific T cells mediates effective regression of large tumors across major histocompatibility barriers," Blood, 112(12):4746-4754 (2008).
Boon et al., Human T Cell Responses Against Melanoma, Annu Rev Immunol, 24: 175-208 (2006).
Boon, "Toward a Genetic Analysis of Tumor Rejection Antigens," Adv Cancer Res, 58:177-210 (1992).
Boquest et al., Isolation and transcription profiling of purified uncultured human stromal stem cells: alteration of gene expression after in vitro cell culture, Molecular biology of the cell, 16(3):1131-1141 (2005).
Boscardin et al., "Antigen targeting to dendritic cells elicits long-lived T cell help for antibody responses," Journal of Experimental Medicine, 203(3):599-606 (2006).
Bourdetsky et al., The nature and extent of contributions by defective ribosome products to the HLA peptidome, PNAS, III, E1591-E1599 (2014).
Bowerman et al., "Engineering the binding properties of the T cell receptor:peptide:MHC ternary complex that governs T cell activity," Mol Immunol, 46(15):3000-3008 (2009).
Boyle et al., "Tapasin-related protein TAPBPR is an additional component of the MHC class I presentation pathway," Proceedings of the National Academy of Sciences, 110: 3465-3470 (2013).
Bozic et al., Dynamics of targeted cancer therapy, Trends Mol Med, 18:311-316 (2012).
Bozic et al., Evolutionary dynamics of cancer in response to targeted combination therapy, Elife, 2:e00747 (2013).
Brahmer et al. Safety and activity of anti-PD-L1 antibody in patients with advanced cancer. N Engl J Med 366(26):2455-2465 (2012).
Brandle et al., "A Mutated HLA-A2 Molecule Recognized by Autologous Cytotoxic T Lymphocytes on a Human Renal Cell Carcinoma," J Exp Med, 183: 2501-2508 (1996).
Brinckerhoff et al., "Melanoma Vaccines," Curr Opin Oncol, 12:163-173 (2000).
Broad Institute Article, Jan. 29, 2009, "Turning Cancer's Strength Into Weakness," (2009).

(56) References Cited

OTHER PUBLICATIONS

Brochier et al., "Large-scale eradication of rabies using recombinant vaccinia-rabies vaccine," Nature, 354:520-552 (1991).
Brown et al., "Neo-antigens predicted by tumor genome meta-analysis correlate with increased patient survival," Genome Res, 24(5):743-750 (2014).
Brunsvig et al., "Telomerase Peptide Vaccination: A Phase I/II Study in Patients with Non-Small Cell Lung Cancer," Cancer Immunol Immunother, 55(12): 1553-1564 (2006).
Buckwaiter et al., "'It is the antigen(s), stupid' and other lessons from over a decade of vaccitherapy of human cancer," Seminar in Immunology, 20(5):296-300 (2008).
Buller et al., "Decreased virulence of recombinant vaccinia virus expression vectors is associated with a thymidine kinase-negative phenotype," Nature, 317:813-815 (1985).
Buller et al., "Deletion of the vaccinia virus growth factor gene reduces virus virulence," Journal of virology, 62(3):866-874 (1988).
Burger et al., "Safety and activity of ibrutinib plus rituximab for patients with high-risk chronic lymphocytic leukaemia: a single-arm, phase 2 study," Lancet Oncology, 15(10):1090-1099 (2014).
Burger et al., B cell receptor signaling in chronic lymphocytic leukemia, Trends Immunol, 34:592-601 (2013).
Burkhardt et al., Autologous CLL cell vaccination early after transplant induces leukemia-specific T cells, The Journal of clinical investigation, 123(9):3756-3765 (2013).
Buser et al., Unique composite hematolymphoid tumor consisting of a pro-T lymphoblastic lymphoma and an indeterminate dendritic cell tumor: evidence for divergent common progenitor cell differentiation, Pathobiology, 81:199-205 (2014).
Byrd et al., Targeting BTK with ibrutinib in relapsed chronic lymphocytic leukemia, The New England journal of medicine, 369:32-42 (2013).
Bystryn et al., Double-blind trial of a polyvalent, shed-antigen, melanoma vaccine, Clin Cancer Res, 7(7):1882-1887 (2001).
Cahill et al., 450K-array analysis of chronic lymphocytic leukemia cells reveals global DNA methylation to be relatively stable over-time and similar in resting and proliferative compartments, Leukemia, 27:150-158 (2013).
Cai et al., "Peptides Derived From Mutated BCR-ABL Elicit T Cell Immunity In CML Patients," Blood, 116(21): 388-388 (2010).
Cancer Genome Atlas Network, Comprehensive molecular portraits of human breast tumours, Nature, 490:61-70 (2012).
Cancer Genome Atlas Research Network, Comprehensive genomic characterization defines human glioblastoma genes and core pathways, Nature, 455(7216):1061-1068 (2008).
Cancer Genome Atlas Research Network, "Comprehensive genomic characterization of squamous cell lung cancers," Nature, 489, 519-525 (2012).
Cancer Genome Atlas Research Network, Comprehensive molecular characterization of clear cell renal cell carcinoma, Nature, 499:43-49 (2013).
Cancer Genome Atlas Research Network, Comprehensive molecular characterization of gastric adenocarcinoma, Nature, 513:202-209 (2014).
Cancer Genome Atlas Research Network, Genomic and epigenomic landscapes of adult de novo acute myeloid leukemia, New England Journal of Medicine, 368(22):2059-2074 (2013).
Cancer Genome Atlas Research Network, Integrated genomic analyses of ovarian carcinoma, Nature, 474: 609-615 (2011).
Caron et al., Analysis of MHC immunopeptidomes using mass spectrometry, Mol Cell Proteomics (2015), doi: 10.1074/mcp.0115.052431.
Carpten et al., "A transforming mutation in the pleckstrin homology domain of AKT1 in cancer," Nature, 448(26):439-444 (2004).
Carreno et al., A dendritic cell vaccine increases the breadth and diversity of melanoma neoantigen-specific T cells, Science, 348(6239):803-808 (2015).
Carreno et al., "IL-12p70-producing patient DC vaccine elicits Tc1-polarized immunity," Journal of Clinical Investigation, 123(8):3383-94 (2013).
Carter et al., Absolute quantification of somatic DNA alterations in human cancer, Nat Biotechnol, 30:413-21 (2012).
Carter et al., Accurate estimation of homologue-specific DNA concentration-ratios in cancer samples allows long-range haplotyping, Nature Precedings, 59-87 (2011).
Carter et al., "Identification and validation of cell surface antigens for antibody targeting in oncology," Endocrine-Related Cancer, 11:659-687 (2004).
Caskey et al., "Synthetic double-stranded RNA induces innate immune responses similar to a live viral vaccine in humans," The Journal of experimental medicine, 208(12):2357-2366 (2011).
Castle et al., Exploiting the mutanome for tumor vaccination, Cancer research, 72(5):1081-1091 (2012).
CBOL Plant Working Group, A DNA barcode for land plants, PNAS, 106(31):12794-12797 (2009).
Chang et al., Immune selection of hot-spot beta 2-microglobulin gene mutations, HLA-A2 allospecificity loss, and antigen-processing machinery component down-regulation in melanoma cells derived from recurrent metastases following immunotherapy, Journal of immunology, 174:1462-1471 (2005).
Chang et al., "Peptide length-based prediction of peptide-MHC class II binding," Bioinformatics, 22(22): 2761-2767 (2006).
Chapman et al., Initial genome sequencing and analysis of multiple myeloma, Nature, 471:467-472 (2011).
Chatila, "The Regulatory T Cell Transcriptosome: E Pluribus Unum," Immunity, 27(5):693-695 (2007).
Cheever, Twelve immunotherapy drugs that could cure cancers, Immunological reviews, 222:357-368 (2008).
Chen, et al."Hotspot mutations delineating diverse mutational signatures and biological utilities across cancer types," BMC Genomics (2016)17(Suppl 2):394.
Chen et al., "Langerhans Cell Sarcoma Arising from Chronic Lymphocytic Lymphoma/Small Lymphocytic Leukemia: Lineage Analysis and BRAF V600E Mutation Study," N Am J Sci, 5:386-91 (2013).
Chen et al., Molecular mechanisms of T cell co-stimulation and co-inhibition, Nature reviews Immunology, 13:227-242 (2013).
Chen et al., "Recombinant modified vaccinia virus Ankara expressing the spike glycoprotein of severe acute respiratory syndrome coronavirus induces protective neutralizing antibodies primarily targeting the receptor binding region," Journal of virology, 79.5:2678-2688 (2005).
Chianese-Bullock et al., "Multi-peptide vaccines vialed as peptide mixtures can be stable reagents for use in peptide-based immune therapies," Vaccine, 27(11):1764-1770 (2009).
Chiari et al., "Two Antigens Recognized by Autologous Cytolytic T Lymphocytes on a Melanoma Result from a Single Point Mutation in an Essential Housekeeping Gene," Cancer Res, 59: 5785-5792 (1999).
Child et al., "Insertional inactivation of the large subunit of ribonucleotide reductase encoded by vaccinia virus is associated with reduced virulence in vivo," Virology, 174(2):625-629 (1990).
Chim et al., Epigenetic dysregulation of the Wnt signalling pathway in chronic lymphocytic leukaemia, J Clin Pathol, 61:1214-1219 (2008).
Chiron et al., Cell-cycle reprogramming for P13K inhibition overrides a relapse-specific C4815 BTK mutation revealed by longitudinal functional genomics in mantle cell lymphoma, Cancer Discov, 4:1022-35 (2014).
Chowell et al., TCR contact residue hydrophobicity is a hallmark of immunogenic CD8(+) T cell epitopes, PNAS, 112:E1754-E1762 (2015).
Christian et al., Targeting DNA double-strand breaks with TAL effector nucleases, Genetics, 186(2):757-761 (2010).
Christianson et al., Defining human ERAD networks through an integrative mapping strategy, Nat Cell Biol, 14:93-105 (2012).
Chroboczek et al., "The Sequence of the Genome of Adenovirus Type 5 and Its Comparison with the Genome of Adenovirus Type 2," Virology, 186:280-285 (1992).
Church, Genomes for all, Sci Am, 294(1):46-54 (2006).
Cibulskis et al., ContEst: estimating cross-contamination of human samples in next-generation sequencing data, Bioinformatics, 27:2601-2602 (2011).

(56) References Cited

OTHER PUBLICATIONS

Cibulskis et al. Sensitive detection of somatic point mutations in impure and heterogenous cencer samples. Nat Biotechnol 31:213-219 (2013).
Ciofani et al., "A Validated Regulatory Network for Th17 Cell Specification," Cell, 151(2):289-303 (2012).
Cleveland, Lowess: A program for smoothing scatterplots by robust locally weighted regression, The American Statistician, 35:54 (1981).
Clinical trial NCT 01970358, Patrick Ott, A Phase I Study With a Personalized NeoAntigen Cancer Vaccine in Melanoma, p. 1-6, Retrieved from https://clinicaltrials.gov/ct2/show/NCT01970358 downloaded Jun. 20, 2017.
Coffman et al., "Vaccine Adjuvants: Putting Innate Immunity to Work," Immunity 33:492-503 (2010).
Cohen, et al. "Shift in GATA3 functions, and GATA3 mutations, control progression and clinical presentation in breast cancer," Breast Cancer Research DOI 10.1186/s13058-014-0464-0.
Conlon et al., "Mouse, but not Human STING, Binds and Signals in Response to the Vascular Disrupting Agent 5,6-Dimethylxanthenone-4-Acetic Acid," Journal of Immunology, 190:5216-25 (2013).
Corbett et al., "Aerosol immunization with NYVAC and MVA vectored vaccines is safe, simple, and immunogenic," Proc Natl Acad Sci, 105(6):2046-51 (2008).
Coulie et al., A mutated intron sequence codes for an antigenic peptide recognized by cytolytic T lymphocytes on a human melanoma, Proc Natl Acad Sci USA, 92(17):7976-7980 (1995).
Cox et al., "Induction of cytotoxic T lymphocytes by recombinant canarypox (ALVAC) and attenuated vaccinia (NYVAC) viruses expressing the HIV-1 envelope glycoprotein," Virology, 195(2):845-850 (1993).
Crozat et al., "The XC chemokine receptor 1 is a conserved selective marker of mammalian cells homologous to mouse CD8a+ dendritic cells," Journal of Experimental Medicine, 207(6):1283-1292 (2010).
CT-011 and p53 Genetic Vaccine for Advance Solid Tumor, National Library of Medicine, updated:Jun. 30, 2011, XP002738554.
Daheshia et al., "Suppression of ongoing ocular inflammatory disease by topical administration of plasmid DNA encoding IL-10," The Journal of Immunology 159(4):1945-1952 (1997).
De Magalhaes et al., Next-generation sequencing in aging research: emerging applications, problems, pitfalls and possible solutions, Ageing Research Reviews, 9(3):315-323 (2010).
De Plaen et al., "Immunogenic (tum-) Variants of Mouse Tumor P815: Cloning of the Gene of Tum-Antigen P91A and Identification of the Tum-Mutation," PNAS, 85: 2274-2278 (1988).
DeLuca et al., RNA-SeQC: RNA-seq metrics for quality control and process optimization, Bioinformatics, 28:1530-2 (2012).
Depristo et al. A framework for variation discovery and genotyping using next generation DNA sequencing data. Nat Genetics 43:491-498 (2011).
Dermer et al., "Another Anniversary for the War on Cancer," Biotech, 12:320 (1994).
Di Stasi et al., "Inducible apoptosis as a safety switch for adoptive cell therapy," New England Journal of Medicine, 365(18):1673-1683 (2011).
Didierlaurent et al., "Attenuated poxviruses expressing a synthetic HIV protein stimulate HLA-A2-restricted cytotoxic T-cell responses," Vaccine, 22(25-26):3395-3403 (2004).
Ding et al., "Genome remodelling in a basal-like breast cancer metastasis and xenograft," Nature, 464:999-1005 (2010).
Ding et al., Somatic mutations affect key pathways in lung adenocarcinoma, Nature, 455:1069-1075 (2008).
Dohner et al., Genomic aberrations and survival in chronic lymphocytic leukemia, The New England journal of medicine, 343:1910-1916 (2000).
Doody et al., "PRDMI/BLIMP-1 Modulates IFN--Dependent Control of the MHC Class I Antigen-Processing and Peptide-Loading Pathway," The Journal of Immunology, 179:7614-7623 (2007).
Dossinger et al., MHC multimer-guided and cell culture-independent isolation of functional T cell receptors from single cells facilitates TCR identification for immunotherapy, PloS one, 8(4):e61384 (2013).
Dreicer et al., "MVA-MUC1-IL2 vaccine immunotherapy (TG4010) improves PSA doubling time in patients with prostate cancer with biochemical failure," Investigational new drugs, 27(4):379-386 (2009).
Dubey et al., The immunodominant antigen of an ultraviolet-induced regressor tumor is generated by a somatic point mutation in the Dead (SEQ ID No. 62) box helicase p68, The Journal of experimental medicine, 185(4):695-705 (1997).
DuPage et al., "Expression of tumour-specific antigens underlies cancer immunoediting," Nature, 482(7385):405-409 (2012).
Dupuis et al., "Dendritic Cells Internalize Vaccine Adjuvant after Intramuscular Injection," Cell Immunol, 186(1): 18-27 (1998).
Earl et al., "Immunogenicity of a highly attenuated MVA smallpox vaccine and protection against monkeypox," Nature, 428:182 (2004).
Eckhardt et al., DNA methylation profiling of human chromosomes 6, 20 and 22, Nat Genet, 38:1378-1385 (2006).
Eichmann et al., Identification and characterisation of peptide binding motifs of six autoimmune disease-associated human leukocyte antigen-class I molecules including HLA-B*39:06, Tissue Antigens 84(4):378-388 (2014).
Eldridge et al. Biodegradable microspheres as a vaccine delivery system. Mol Immunol. 28(3):287-94 (1991).
Elias et al., Target-decoy search strategy for increased confidence in large-scale protein identifications by mass spectrometry, Nat Meth, 4:207-214 (2007).
Engelhard, "Structure of peptides associated with MHC class I molecules," Curr Opin Immunol, 6(1):13-23 (1994).
Engler et al., A one pot, one step, precision cloning method with high throughput capability, PloS one 3(11):e3647 (2008).
Engler et al., Golden gate shuffling: a one-pot DNA shuffling method based on type IIs restriction enzymes, PloS one, 4(5):e5553 (2009).
Erlich et al., "Next-generation sequencing for HLA typing of class 1 loci," BMC Genomics, 12:42 (2011).
Escobar et al., Bayesian density estimation and inference using mixtures, Journal of the American Statistical Association, 90:577-588 (1995).
Esteban, "Attenuated poxvirus vectors MVA and NYVAC as promising vaccine cadidates against HIV/AIDS," Human vaccines, 5(12):867-871 (2009).
Estep et al., "Mutation Analysis of BRAF, MEK1 and MEK2 in 15 Ovarian Cancer Cell Lines: Implications for Therapy," Plos One, 12:e1279 (2007).
Eyers et al., CONSeQuence: prediction of reference peptides for absolute quantitative proteomics using consensus machine learning approaches, Mol Cell Proteomics (2011); 10(11):M110.003384. doi: 10.1074/mcp.MI 10.003384. Epub Aug. 3, 2011.
Ezzell, "Cancer 'Vaccines': An idea whose time has come?," J Nih Res, 7:46 (1995).
Fais et al., Chronic lymphocytic leukemia B cells express restricted sets of mutated and unmutated antigen receptors, The Journal of clinical investigation, 102:1515-25 (1998).
Fan et al., The multi substrate adapter Gabi regulates hepatocyte growth factor (scatter factor)-c-Met signaling for cell survival and DNA repair, Molecular and Cellular Biology, 21:4968-4984 (2001).
Fantom Consortium et al., A promoter-level mammalian expression atlas, Nature, 507:462-470 (2014).
Farsaci et al.,Consequence of dose scheduling of sunitinib on host immune response elements and vaccine combination therapy, Int J Cancer, 130:1948-1959 (2012).
Feigner et al., Lipofection: A Highly Efficient, Lipid-Mediated DNA-Transfection Procedure, PNAS, 84(21): 7413-7417 (1987).
Feng, Du et al., The Significance and Therapeutic Potential of GATA3 Expression and Mutation in Breast Cancer: A Systematic Review, Medicinal Research Reviews, vol. 35, No. 6, Nov. 1, 1015, pp. 1300-1315, XP002791786.
Ferrier-Rembert et al., Short-and long-term immunogenicity and protection induced by non-replicating smallpox vaccine candidates

(56) References Cited

OTHER PUBLICATIONS in mice and comparison with the traditional 1st generation vaccine, Vaccine, 26(14):1794-1804 (2008).
Finke et al., Sunitinib Reverses Type-1 Immune Suppression and Decreases T-Regulatory Cells in Renal Cell Carcinoma Patients, Clin Cancer Res, 14(20):6674-6682 (2008).
Fisher et al., A scalable, fully automated process for construction of sequence-ready human exome targeted capture libraries, Genome Biol, 12:R1 (2011).
Flaherty et al., From genes to drugs: targeted strategies for melanoma, Nat Rev Cancer, 12(5):349-361 (2012).
Flexner et al., "Prevention of vaccinia virus infection in imiminodeficient mice by vector-directed IL-2 expression," Nature, 330(6145):259-262 (1987).
Flynn et al., Immunization with HIV Gag targeted to dendritic cells followed by recombinant New York vaccinia virus induces robust T-cell immunity in nonhuman primates, Proc Natl Acad Sci, 108(17):7131-7136 (2011).
Forconi et al., Genome-wide DNA analysis identifies recurrent imbalances predicting outcome in chronic lymphocytic leukaemia with 17p deletion, British journal of haematology, 143:532-6 (2008).
Frederick et al., "BRAF inhibition is associated with enhanced melanoma antigen expression and a more favorable tumor microenvironment in patients with metastatic melanoma," Clin Cancer Res, 19:1225-1231 (2013).
Friedberg et al., Inhibition of Syk with fostamatinib disodium has significant clinical activity in non-Hodgkin lymphoma and chronic lymphocytic leukemia, Blood, 115:2578-2585 (2011).
Fritsch, Edward F. et al., HLA-binding properties of tumor neoepitopes in humans, Cancer Immunology Research, Jun. 2014, vol. 2, No. 6, Jun. 2014, pp. 522-529.
Fritsch et al., "Personal neoantigen cancer vaccines: The momentum builds," Oncoimmunology, 3(6):e29311 (2014).
Fritsch et al., Translational repression of MCL-1 couples stress-induced eIF2 alpha phosphorylation to mitochondria! apoptosis initiation, The Journal of biological chemistry, 282:22551-62 (2007).
Fruci et al., Altered expression of endoplasmic reticulum aminopeptidases ERAP1 and ERAP2 in transformed non-lymphoid human tissues, J Cell Physiol, 2I6(3):742-749 (2008).
Fukami, et al. GATA3 abnormalities in six patients with HDR syndrome, Endocrine Journal 2011, 58 (2), 117-121.
Furman et al., Ibrutinib resistance in chronic lymphocytic leukemia, The New England journal of medicine, 370(24):2352 (2014).
Furman et al., Idelalisib and rituximab in relapsed chronic lymphocytic leukemia, The New England journal of medicine, 370:997-1007 (2014).
Fusaro et al., Prediction of high-responding peptides for targeted protein assays by mass spectrometry, Nat Biotechnol, 27(2):190-198 (2009).
Fynan et al., "DNA vaccines: protective immunizations by parenteral, mucosal, and gene-gun inoculations," PNAS, 90 (24): 11478-82 (1993).
Gabrilovich, et al., "IL-12 and Mutant P53 Peptide-Pulsed Dendritic Cells for the Specific Immunotherapy of Cancer," J Immunother Emphasis Tumor Immunol, 19(6): 414-418 (1997).
Gallego-Gomez et al., "Differences in virus-induced cell morphology and in virus maturation between MVA and other strains (WR, Ankara, and NYCBH) of vaccinia virus in infected human cells," Journal of virology, 77(19):10606-10622 (2003).
Gallois et al., A needle in the 'cancer vaccine' haystack, Nature medicine, 16(8):854-856 (2010).
Gao et al., Integrative analysis of complex cancer genomics and clinical profiles using the cBioPortal, Science signaling, 6(269):pi1 (2013).
Garcia-Marco et al., Frequent Somatic Deletion of the 13q12.3 locus Encompassing BRCA2 in Chronic Lymphocytic Leukemia, Blood, 88: 1568-1575 (1996).
Garimella et al., Identification of novel molecular regulators of tumor necrosis factor-related apoptosis-inducing ligand (TRAIL)-induced apoptosis in breast cancer cells by RNAi screening, Breast cancer research, 16(2):R41 (2014).
Garofalo et al., miR-221&222 regulate TRAIL resistance and enhance tumorigenicity through PTEN and TIMP3 downregulation, Cancer Cell, 16(6):498-509 (2009).
Garraway et al., Lessons from the cancer genome, Cell, 153:17-37 (2013).
Gaucher et al., Yellow fever vaccine induces integrated multilineage and polyfunctional immune responses, The Journal of experimental medicine, 205(13):3119-3131 (2008).
Gazdar, Activating and resistance mutations of EGFR in non-small-cell lung cancer: role in clinical response to EGFR tyrosine kinase inhibitors, Oncogene, 28:S24-S31 (2009).
Gevaert et al., Protein identification methods in proteomics, Electrophoresis: An International Journal, 21(6):1145-1154 (2000).
Gherardi et al., Prime-boost immunization schedules based on influenza virus and vaccinia virus vectors potentiate cellular immune responses against human immunodeficiency virus Env protein systemically and in the genitorectal draining lymph nodes, Journal of virology, 77(12):7048-7057 (2003).
Ghiringhelli et al., "Metronomic cyclophosphamide regimen selectively depletes CD4+CD25+ regulatory T cells and restores T and NK effector functions in end stage cancer patients," Cancer Immunol Immunother, 56:641-648 (2007).
Giaever et al., Functional profiling of the *Saccharomyces cerevisiae* genome, Nature, 418(6896):387-391 (2002).
Giannopoulos et al., Peptide vaccination elicits leukemia-associated antigen-specific cytotoxic CD8+ T-cell responses in patients with chronic lymphocytic leukemia, Leukemia, 24(4):798-805 (2010).
Gibbs et al., Abundant quantitative trait loci exist for DNA methylation and gene expression in human brain, PLoS genetics, 6:e1000952 (2010).
Gibney et al., "Safety and efficacy of adjuvant anti-PD1 therapy (nivolumab) in combination with vaccine in resected high-risk metastatic melanoma.," J Clin Oncol, Abstract 9056 (2013).
Gilboa, "The Makings of a Tumor Rejection Antigen," Immunity, 11: 263-270 (1999).
Gluzman, Yakov, SV40-transformed simian cells support the replication of early SV40 mutants, Cell, 23:175-182 (1981).
Gnirke et al., "Solution Hybrid Selection with Ultra-Long Oligonucleotides for Massively Parallel Targeted Sequencing," Nat Biotechnol, 27(2): 182-189 (2009).
Goebel et al., "The complete DNA sequence of vaccinia virus," Virology, 179(1):247-266 (1990).
Gomez et al., "Efficient CD8+ T cell response to the HIV-env V3 loop epitope from multiple virus isolates by a DNA prime/vaccinia virus boost (rWR and rMVA strains) immunization regime and enhancement by the cytokine IFN-y," Virus research, 105:11-22 (2004).
Gomez et al., Head-to-head comparison on the immunogenicity of two HIV/AIDS vaccine candidates based on the attenuated poxvirus strains MVA and NYVAC co-expressing in a single locus the HIV-1 BX08 gp120 and HIV-111IB Gag-Pol-Nef proteins of Glade B, Vaccine, 25(15):2863-2885 (2007).
Gomez et al., MVA and NYVAC as vaccines against emergent infectious diseases and cancer, Current gene therapy, 11(:3):189-217 (2011).
Gomez et al., The poxvirus vectors MVA and NYVAC as gene delivery systems for vaccination against infectious diseases and cancer, Current gene therapy, 8(2):97-120 (2008).
Gomez et al., Virus distribution of the attenuated MVA and NYVAC poxvirus strains in mice, Journal of General Virology, 88(9):2473-2478 (2007).
Gotter et al., "Medullary Epithelial Cells of the Human Thymus Express a Highly Diverse Selection of Tissue-specific Genes Colocalized in Chromosomal Clusters," J Exp Med, 199(2): 155-166 (2004).
Goya et al., "SNVMix:predicting single nucleotide variants from next-generation sequencing of tumors," Bioinformatics, Original Paper, 26(6): 730-736 (2010).
Greco et al., Improving the safety of cell therapy with the TK-suicide gene, Front Pharmacol, 6:95 (2015).

(56) References Cited

OTHER PUBLICATIONS

Greenman et al., Patterns of somatic mutation in human cancer genomes, Nature, 446:153-158 (2007).
Gregoriadis et al., "Improving the therapeutic efficacy of peptides and proteins: A role for polysialic acids," Int J Pharmaceutics, 300(1-2):125-30 (2005).
Gros et al. PD-1 identifies the patient-specific CD8+ tumor-reactive repertoire infiltrating human tumors. The Journal of clinical investigation, 124(5):2246-2259 (2014).
Grunstein et al., Colony hybridization: a method for the isolation of cloned DNAs that contain a specific gene, PNAS, 72(10):3961-3965 (1975).
GTEx Consortium, The Genotype-Tissue Expression (GTEx) project, Nature genetics, 45:580-585 (2013).
Guasp et al., The Peptidome of Behcet's Disease-Associated HLA-B*51 :01 Includes Two Subpeptidomes Differentially Shaped by Endoplasmic Reticulum Aminopeptidase 1, Arthritis Rheumatol, 68:505-515 (2016).
Gubin et al., Checkpoint blockade cancer immunotherapy targets tumor-specific mutant antigens, Nature, 515:577-581 (2014).
Gueguen et al., An Antigen Recognized by Autologous CTLs on a Human Bladder Carcinoma, J Immunol, 160(12): 6188-6194 (1998).
Guo et al., Different length peptids bind to HLA-Aw68 similarity at their ends but bulge on in the middle, Nature, 360:364-366 (1992).
Guo et al., Droplet microfluidics for high-throughput biological assays, Lab Chip, 12:2146-55 (2012).
Guruprasad et al., Correlation between stability of a protein and its dipeptide composition: a novel approach for predicting in vivo stability of a protein from its primary sequence, Protein Eng, 4(2):155-161 (1990).
Gustin, et al. GATA3 frameshift mutation promotes tumor grouwth in human luminal breast cancer cells and induces transcriptional changes seen in primary GATA3 mutant breast cancers, Oncotarget, 2017, vol. 8, (No. 61), pp. 103415-103427.
Guthals et al., Shotgun Protein Sequencing with Meta-contig Assembly, Molecular and Cellular Proteomics, 1(10):1084-96 (2012).
Hacohen et al., "Getting Personal with Neoantigen-Based Therapeutic Cancer Vaccines," Cancer Immunol. Res, 1(1):11-15 (2013).
Hadrup et al., Parallel detection of antigen-specific T-eeil responses by multidimensional encoding of MHC multimers, Nature Methods, 6(7):520-26 (2009).
Halabi et al., "Prognostic model for predicting survival in men with hormone-refractory metastatic prostate cancer," Journal of Clinical Oncology, 21(7):1232-1237 (2003).
Hall, Advanced sequencing technologies and their wider impact in microbiology, Journal of experimental biology, 210(9):1518-1525 (2007).
Han et al., Linking T-Cell Receptor Sequence to Fucntional Phenotype at the Single-Cell Level, Nat Biotechnol, 32:684-692 (2014).
Hanahan et al., Hallmarks of cancer: the next generation, Cell, 144:646-674 (2011).
Hansen et al., Increased methylation variation in epigenetic domains across cancer types, Nat Genet, 43:768-775 (2011).
Hanzelmann et al., GSVA: gene set variation analysis for microarray and RNA-Seq data, BMC bioinformatics, 14:7 (2013).
Harndahl et al., Peptide-MHC class I stability is a better predictor than peptide affinity of CTL immunogenicity, Eur J Immunol, 42:1405-1416 (2012).
Harndahl et al., Real-time, High-Throughput Measurements of Peptide-MHC-I Dissociation Using a Scintillation Proximity Assay, J Immunol Methods, 374:5-12 (2011).
Harris et al., Comparison of sequencing-based methods to profile DNA methylation and identification of monoallelic epigenetic modifications, Nat Biotechnol, 28:1097-1105 (2010).
Harris et al., RNA editing enzyme APOBECI and some of its homologs can act as DNA mutators, Molecular cell, 1095):1247-1253 (2002).
Heemskerk et al., The cancer antigenome, EMBO Journal, 32(2):194-203 (2013).
Herbeuval et al., HAART reduces death ligand but not death receptors in lymphoid tissue of HIV-infected patients and simian immunodeficiency virus-infected macaques, AIDS, 23:35-40 (2009).
Herbst et al., "Predictive Correlates of Response to the Anti-PD-L1 Antibody MPDL3280A in Cancer Patients," Nature, 515(7528):563-567 (2014).
Herman et al., "Differences in the Recognition by CTL of Peptides Presented by the HLAB*4402 and the HLA-B*4403 Molecules Which Differ by a Single Amino Acid," Tissue Antigens, 53: 111-121 (1999).
Herman et al., ibrutinib-induced lymphocytosis in patients with chronic lymphocytic leukemia: correlative analyses from a phase II study, Leukemia, 28:2188 (2014).
Hersey et al., "Phase I/II study of treatment with dendritic cell vaccines in patient with disseminated melanoma," Cancer Immunol Immunother, 53:125-134 (2004).
HHS Public Access "Comprehensive molecular portraits of human breast tumors," Nature Oct. 4, 2012; 490(7418): 61-70. doi:10.1038/nature11412.
Hickman et al., Toward a Definition of Self: Proteomic Evaluation of the Class I Peptide Repertoire, J Immunol, 172:2944-2952 (2004).
Hill et al., Conformational and structural characteristics of peptides binding to HLA-DR molecules, J. Immunol. 147:189 (1991).
Hill et al., Exploration of requirements for peptide binding to HLA DRB10101 and DRBI*0401, J. Immunol. 152, 2890 (1994).
Hinrichs et al., Exploiting the curative potential of adoptive T-cell therapy for cancer, Immunological reviews, 257:56-71 (2014).
Hocker et al., "Ultraviolet Radiation and Melanoma: A Systematic Review and Analysis of Reported Sequence Variants," Hum Mutat, 28(6): 578-588 (2007).
Hodi et al., "Improved Survival with Ipilimumab in Patients with Metastatic Melanoma," New Engl J Med, 363:711-723 (2010).
Hombrink et al., Identification of Biological Relevant Minor Histocompatibility Antigens within the B-lymphocyte—Derived HLA-Ligandome Using a Reverse Immunology Approach, Clin Cancer Res, 21(9):2177-2186 (2015).
Honig et al., "Phase 1 clinical trial of a recombinant canarypoxvirus (ALVAC) vaccine expressing human carcinoembryonic antigen and the B7.1 co-stimulatory molecule," Cancer Immunol Immunother, 49:504-514 (2000).
Honigberg et al., The Bruton tyrosine kinase inhibitor PCI-32765 blocks B-cell activation and is efficacious in models of autoimmune disease and B-cell malignancy, PNAS, 107:13075-13080 (2010).
Hoof, et al. NetMHCpan, a method for MHC class I binding prediction beyond humans. Immunogenetics. 61.1 (2009):1-13. doi: 10.1007/s00251-008-0341-z. Epub Nov. 12, 2008.
Huang et al., "Mucosal priming with replicative Tiantan vaccinia and systemic boosting with DNA vaccine raised strong mucosal and systemic HIV-specific immune responses," Vaccine, 25(52):8874-8884 (2007).
Huang et al., "T Cells Associated With Tumor Regression Recognize Frameshifted Products of the CDKN2A Tumor Suppressor Gene Locus and a Mutated HLA Class 1 Gene Product," J Immunol, 172(10):6057-6064 (2004).
Humphries et al., "Lineage tracing reveals multipotent stem cells maintain human adenomas and the pattern of clonal expansion in tumor evolution," PNAS, 110(27):e2490-e2499 (2013).
Hunt et al., Characterization of peptides bound to the class I MHC molecule HLA-A2.1 by mass spectrometry, Science, 255:1261-1263 (1992).
Hutchings et al., "Combination of protein and viral vaccines induces potent cellular and humoral immune responses and enhanced protection from murine malaria challenge," Infect Immun, 75(12):5819-26 (2007).
Illingworth et al., Orphan CpG islands identify numerous conserved promoters in the mammalian genome, PLoS Genet, 6(9):e1001134 (2010).
Illumina, Immunotherapy, the Next Generation of Cancer Treatment, NGS-guided assessment of interactions between tumors and the immune system leads to new discoveries in immuno-oncology, (2016).

(56) References Cited

OTHER PUBLICATIONS

Inokuchi et al., DCC protein expression in hematopoietic cell populations and its relation to leukemogenesis, J Clin Invest, 97:852-857 (1996).
Ishihama et al., Exponentially Modified Protein Abundance Index (emPAI) for Estimation of Absolute Protein Amount in Proteomics by the Number of Sequenced Peptides per Protein, Mol Cell Proteomics, 4:1265-1272 (2005).
Izeradjene et al., Casein kinase II (CK2) enhances death-inducing signaling complex (DISC) activity in TRAIL-induced apoptosis in human colon carcinoma cell lines, Oncogene, 24:2050-2058 (2005).
Jaatinen et al., Global gene expression profile of human cord blood-derived CD133+ cells, Stem Cells, 24:631-641 (2006).
Jarmalavicius et al., High Immunogenicity of the Human Leukocyte Antigen Peptidomes of Melanoma Tumor Cells, J Biol Chern, 287(40):33401-33411 (2012).
Jayasinghe, et al. "Systematic Analysis of Splice-Site-creating Mutations in Cancer" Cell Reports (2018) 23, 270-281.
Jeffery et al., The Influence of HLA Class I Alleles and Heterozygosity on the Outcome of Human T Cell Lymphotropic Virus Type I Infection, J Immunol, 165:7278-7284 (2000).
Jemal et al., Cancer statistics, 2007, CA: a cancer journal for clinicians, 57:43-66 (2007).
Jennewein et al., Sumoylation of peroxisome proliferator-activated receptor gamma by apoptotic cells prevents lipopolysaccharide-induced NCoR removal from kappaB binding sites mediating transrepression of proinflammatory cytokines, Journal of immunology, 181:5646-5652 (2008).
Johnson et al., Discovery of Naturally Processed and HLA-Presented Class I Peptides from Vaccinia Virus Infection using Mass Spectrometry for Vaccine Development,Vaccine, 28(1):38-47 (2009).
Johnson et al., Single-cell perforin and granzyme expression reveals the anatomical localization of effector CD8+ T cells in influenza virus-infected mice, PNAS, 100:2657-2662 (2003).
Jones et al., InterProScan 5: genome-scale protein function classification, Bioinformatics, 30:1236-1240 (2014).
Jones et al., The epigenomics of cancer, Cell, 128:683-692 (2007).
Kalaora et al., Use of HLA peptidomics and whole exome sequencing to identify human immunogenic neo-antigens, Oncotarget, 7(5):5110-5117 (2016).
Kandoth et al., "Mutational landscape and significance across 12 major cancer types," Nature, 502:333-339 (2013).
Kannan et al., Vaccination strategies in follicular lymphoma, Current hematologic malignancy reports, 4(4):189-195 (2009).
Karnani et al., Pan-S replication patterns and chromosomal domains defined by genome-tiling arrays of ENCODE genomic areas, Genome research, 17:865-876 (2007).
Karolchik et al., The UCSC Table Browser data retrieval tool, Nucleic acids research, 32:D493-496 (2004).
Kawai et al., TLR signaling, Seminars in immunology, 19(1):24-32 (2007).
Kenter et al., Vaccination against HPV-16 oncoproteins for vulvar intraepithelial neoplasia, New England Journal of Medicine, 361(19):1838-1847 (2009).
Keskin et al., Neoantigen vaccine generates intratumoral T cell responses in phase lb glioblastoma trial, Nature, 565(7738):234-239 (2019).
Khong et al., Natural selection of tumor variants in the generation of "tumor escape" phenotypes, Nature immunology, 3:999-1005 (2002).
Kim et al., mTOR inhibitors radiosensitize PTEN-deficient non-small-cell lung cancer cells harboring an EGFR activating mutation by inducing autophagy, J Cell Biochem, 114(6):1248-1256 (2013).
Kim et al., Positional Bias of MHC Class I Restricted T-Cell Epitopes in Viral Antigens Is Likely due to a Bias in Conservation, PLoS Comput Biol, 9:e1002884 (2013).
Kimmel et al., [54] Identification and characterization of specific clones: Strategy for confirming the validity of presumptive clones, Methods in enzymology, 152:507-511 (1987).
Kirkwood et al., High- and Low-dose Interferon Alpha-2b in High-isk Melanoma: First Analysis of Intergroup Trial E1690/S9111/C9190, J Clin Oncol, 18:2444-2458 (2000).
Kirkwood et al., Interferon alfa-2b Adjuvant Therapy of High-Risk Resected Cutaneous Melanoma: The Eastern Cooperative Oncology Group Trial EST 1684, J Clin Oncol, 14:7-17 (1996).
Klebanoff et al., Therapeutic cancer vaccines:are we there yet?, Immunol Rev, 239(1):27-44 (2011).
Klein et al., Droplet Barcoding for Single-Cell Transcriptomics Applied to Embryonic Stem Cells, Cell, 161:1187-1201 (2015).
Kloor et al., Immune evasion of microsatellite unstable colorectal cancers, International journal of cancer, 127:1001-1010 (2010).
Klug et al., Characterization of MHC Ligands for Peptide Based Tumor Vaccination, Current Pharmaceutical Design, 15(28): 3221-3236 (2009).
Kobayashi, Hiroya and Cellis, Esteban, Peptide epitope identification for tumor-reactive CD4 T cells, Current Opinions in Immunology, 2008, 20:221-227.
Koch, Combining morphology and DNA barcoding resolves the taxonomy of Western Malagasy Liotrigona Moure, 1961, African Invertebrates, 51(2):413-421 (2010).
Kreso et al., Variable clonal repopulation dynamics influence chemotherapy response in colorectal cancer, Science, 339:543-548 (2013).
Kress et al., DNA barcodes: Genes, genomics, and bioinformatics, PNAS, 105(8):2761-2762 (2008).
Kress et al., Use of DNA barcodes to identify flowering plants, PNAS, 102(23):8369-8374 (2005).
Kulis et al., Epigenomic analysis detects widespread gene-body DNA hypomethylation in chronic lymphocytic leukemia, Nat Genet, 44:1236-1242 (2012).
Lahaye et al., DNA barcoding the floras of biodiversity hotspots, PNAS, 105(8):2923-2928 (2008).
Landan et al., Epigenetic polymorphism and the stochastic formation of differentially methylated regions in normal and cancerous tissues, Nat Genet, 44:1207-1214 (2012).
Landau et al., Clonal evolution in hematological malignancies and therapeutic implications, Leukemia, 28:34-43 (2014).
Landau et al., Evolution and impact of subclonal mutations in chronic lymphocytic leukemia, Cell, 152(4):714-726 (2013).
Langmead et al., Fast gapped-read alignment with Bowtie 2, Nature methods, 9:357-359 (2012).
Langmead et al., Ultrafast and memory-efficient alignment of short DNA sequences to the human genome, Genome Biology, 10:R25 (2009).
Lata et al., MHCBN 4.0: A database of MHC/TAP binding peptides and T-cell epitopes, BMC Research Notes, 2(1): 61 (2009).
Lawrence et al., Discovery and saturation analysis of cancer genes across 21 tumour types, Nature, 505:495-501 (2014).
Lawrence et al., Mutational heterogeneity in cancer and the search for new cancer-associated genes, Nature, 499:214-218 (2013).
Le et al., Evaluation of Ipilimumab in combination with allogeneic pancreatic tumor cells transfected with a GM-CSF gene in previously treated pancreatic cancer, J Immunother, 36(7):382-389 (2013).
Lee et al., Sequential amplification of cloned DNA as tandem multimers using class-IIS restriction enzymes, Genetic Analysis: Biomolecular Engineering, 13(6):139-145 (1996).
Leffers et al., "Immunization with a P53 synthetic long peptide vaccine induces P530specific immune responses in ovarian cancer patients, a phase II trial," Int J Cancer, 125(9):2104-2113 (2009).
Leffers et al., Long Oterm clinical and immunological effects of p530SLPO vaccine in patients with ovarian cancer, Int J Cancer, 130(1):105-112 (2012).
Lemay et al., Dok-3, a Novel Adapter Molecule Involved in the Negative Regulation of Immunoreceptor Signaling, Mol Cell Biol, 20:2743-2754 (2000).
Lewintre et al., Analysis of chronic lymphotic leukemia transcriptomic profile: differences between molecular subgroups, Leuk Lymphoma, 50:68-79 (2009).
Li et al., Fast and accurate short read alignment with Burrows-Wheeler Transform, Bioinformatics, 25(14):1754-1760 (2009).

(56) References Cited

OTHER PUBLICATIONS

Li et al., Inactivating mutations of the chromatin remodeling gene ARID2 in hepatocellular carcinoma, Nature Genetics, 43:828-829 (2011).
Li et al., Mapping short DNA sequencing reads and calling variants using mapping quality scores, Genome Res, 18:1851-1858 (2008).
Li et al., RSEM: accurate transcript quantification from RNA-Seq data with or without a reference genome, BMC Bioinformatics,12:323 (2011).
Li et al., The Sequence Alignment/Map format and SAMtools, Bioinformatics, 25(16):2078-2079 (2009).
Liggins et al., MORC4, a novel member of the MORC family, is highly expressed in a subset of diffuse large B-cell lymphomas, Brit J Haematol, 138:479-486 (2007).
Lim et al., Transcriptome analyses of mouse and human mammary cell subpopulations reveal multiple conserved genes and pathways, Breast Cancer Res, 12:R21 (2010).
Lin et al., Relevance of the immunoglobulin VH somatic mutation status in patients with chronic lymphocytic leukemia treated with fludarabine, cyclophosphamide, and rituximab (FCR) or related chemoimmunotherapy regimens, Blood, 113:3168-71 (2009).
Linardou et al., Assessment of somatic k-RAS mutations as a mechanism associated with resistance to EGFR-targeted agents: a systematic review and meta-analysis of studies in advanced non-small-cell lung cancer and metastatic colorectal cancer, Lancet Oncol, 9(10):962-972 (2008).
Linardou et al., Somatic EGFR mutations and efficacy of tyrosine kinase inhibitors in NSCLC, Nat Rev Clin Oncol, 6(6):352-366 (2009).
Liu et al., Systematic identification of type 1 and type II interferon-induced antiviral factors, PNAS, 109(11):4239-4244 (2012).
Livak et al. Methods for qPCR gene expression profiling applied to 1440 lymphoblastoid single cells, Methods, 59(1):71-79 (2013).
Llobet et al., CK2 controls TRAIL and Fas sensitivity by regulating FLIP levels in endometrial carcinoma cells, Oncogene, 27:2513-2524 (2008).
Lohr et al., Discovery and prioritization of somatic mutations in diffuse large B-cell lymphoma (DLBCL) by whole-exome sequencing, PNAS, 109(10):3879-3884 (2012).
Lorente et al., "Diversity of Natural Self-Derived Ligands Presented by Different HLA Class I Molecules in Transporter Antigen Processing-Deficient Cells," PLoS ONE 8:059118 (2013).
Lu et al., Mutated regions of nucleophosmin 1PPP1R3B Is Recognized by T Cells Used To Treat a Melanoma Patient Who Experienced a Durable Complete Tumor Regression, J Immunol, 190(12):6034-6042 (2013).
Lucas et al., About human tumor antigens to be used in immunotherapy, Semin Immunol, 20(5):301-307 (2008).
Luckow and Summers, Trends in the Development of Baculovirus Expression Vectors, Bio/Technology 6:47 (1988).
Lund et al., Coordination of early protective immunity to viral infection by regulatory T cells, Science, 320(5880):1220-1224 (2008).
Luo et al. Machine learning methods for Predicting hla—Peptide Binding activity, Bioinformatics and Biology Insights, 9(s3):2I-29 (2015).
Ma, Novor: Real-Time Peptide de Novo Sequencing Software, J Am Soc Mass Spectrom, 26:1885-1894 (2015).
Macosko et al., Highly Parallel Genome-wide Expression Profiling of Individual Cells Using Nanoliter Droplets, Cell, 161(5):1202-1214 (2015).
Maegawa et al., Age-related epigenetic drift in the pathogenesis of MDS and AML, Genome Res, 24:580-591 (2014).
Mair, et al. "Gain-and Loss0of-Function Mutations in the Breast Cancer Gene GATA3 Result in Differential Drug Sensitivity," PLOS Genetics.
Mandi et al., Immunotherapy with MVA-BN®-HER2 induces HER-2-specific Th1 immunity and alters the intratumoral balance of effector and regulatory T cells, Cancer Immunol Immunother. Jan. 2012; 61(1): 19-29.

Manghera et al., Endogenous retrovirus-K promoter: a landing strip for inflammatory transcription factors?, Retroviral, 10:16 (2013).
Marabelle et al., Depleting tumor-specific Tregs at a single site eradicates disseminated tumors, J Clin Invest, 1123(6):2447-2463(2013).
Marcais et al., A fast, lock-free approach for efficient parallel counting of occurrences of k-mers, Bioinformatics, 27(6):764-770 (2011).
Marshall, et al. 1999. Phase I study in cancer patients of a replication-defective avipox recombinant vaccine that expresses human carcinoembryonic antigen. J Clin Oncol 17:332-337.
Marshall, K.W. et al., "Role of the Polymorphic Residues in HLA-DR Molecules in Allele-Specific Binding of Peptide Ligands," J. Immunol. 152:4946-4956 (1994).
Matteucci, et al. Synthesis of deoxyoligonucleotides on a polymer support. J. Am. Chem. Soc. 103(11):3185-3191, 1981.
Mayer et al., A revised nomenclature for transcribed human endogenous retroviral loci, Mobile DNA, 2:7 (2011).
Mazutis et al., Single-cell analysis and sorting using droplet-based microfluidics, Nat Protoc, 8:870-891 (2013).
McCormack et al., HLA-A*3101 and Carbamazepine-Induced Hypersensitivity Reactions in Europeans, New Engl J Med, 364:1134-1143 (2011).
McDermott et al., Immune Therapy for Kidney Cancer: A Second Dawn?, Semin Oncol, 40(4):492-498 (2013).
McFadden et al., Genetic and clonal dissection of murine small cell lung carcinoma progression by genome sequencing, Cell, 156(6):1298-1311 (2014).
McKenna et al., The Genome Analysis Toolkit: a MapReduce framework for analyzing next-generation DNA sequencing data, Genome Res, 20(9):1297-1303 (2010).
McMurtrey et al., Toxoplasma gondii peptide ligands open the gate of the HLA class I binding groove, eLife 5:012556 (2016).
Medema et al., Immune Escape of Tumors in Vivo by Expression of Cellular Flice-Inhibitory Protein, J Exp Med, 190:1033-1038 (1999).
Meissner et al., Genome-scale DNA methylation maps of pluripotent and differentiated cells, Nature, 454:766-770 (2008).
Menke et al., Genetic interactions between the Wilms' tumor 1 gene and the p53 gene, Cancer Res, 62(22):6615-6620 (2002).
Mermel et al., GISTIC2.0 facilitates sensitive and confident localization of the targets of focal somatic copy-number alteration in human cancers, Genome Biol, 12:R41 (2011).
Merrifield et al. Solid Phase Peptide Synthesis I. J Am Chern Soc 85:2149-2154 (1963).
Merrifield, Solid Phase Synthesis, Science 232:341-347 (1986).
Messmer et al., In vivo measurements document the dynamic cellular kinetics of chronic lymphocytic leukemia B cells, J Clin Invest, 115(3):755-764 (2005).
Meyer, H. et al., (1991), Mapping of deletions in the genome of the highly attenuated vaccinia virus MVA and their influence on virulence, J. Gen. Virol. 72, 1031-1038.
Miller et al. Construction and properties of retrovirus packaging cells based on gibbon ape leukemia virus. J Virol. 65(5):2220-2224 (1991).
Milner et al., The Effect of Proteasome Inhibition on the Generation of the Human Leukocyte Antigen (HLA) Peptidome, Mol Cell Proteomics, 12:1853-1864 (2013).
Milner et al., The Turnover Kinetics of Major Histocompatibility Complex Peptides of Human Cancer Cells, Mol Cell Proteomics, 5:357-365 (2006).
Missale et al., HLA-A31- and HLA-Aw68-restricted cytotoxic T cell responses to a single hepatitis B virus nucleocapsid epitope during acute viral hepatitis, J Exp Med, 177(3):751-762 (1993).
Mocellin et al., Interferon Alpha Adjuvant Therapy in Patients With High-Risk Melanoma: A Systematic Review and Meta-analysis, JNCI, 102(7):493-501 (2010).
Mommen et al., "Expanding the detectable HLA peptide repertoire using electron-transfer/higher-energy collision dissociation (EThcD)," Pnas III, 4507-4512 (2014).
Mommen et al., Sampling From the Proteome to the Human Leukocyte Antigen-DR (HLA-DR) Ligandome Proceeds Via High Specificity, Mol Cell Proteomics MCP, 15:1412-1423 (2016).

(56) References Cited

OTHER PUBLICATIONS

Morgan, R. A., et al., (2006), Cancer Regression in Patients After Transfer of Genetically Engineered Lymphocytes, Science 314:126-129.
Morison et al., A census of mammalian imprinting, Trends Genet, 21(8):457-465 (2005).
Morozov et al., The Transmembrane Protein of the Human Endogenous Retrovirus—K (Herv-K) Modulates Cytokine Release and Gene Expression, PloS one 8(8):e70399 (2013).
Morton et al., Prolonged Survival of Patients Receiving Active Immunotherapy With Canvaxin Therapeutic Polyvalent Vaccine After Complete Resection of Melanoma Metastatic to Regional Lymph Nodes, Ann Surg, 236(4):438-448 (2002).
Mosmann et al., THI and TH2 Cells: Different Patterns of Lymphokine Secretion Lead to Different Functional Properties, Ann Rev Immunol, 7:145-173 (1989).
Moss, Reflections on the Early Development of Poxvirus Vectors, Vaccine. 2013; 31(39): 4220-4222.
Muntel et al., Abundance-based Classifier for the Prediction of Mass Spectrometric Peptide Detectability Upon Enrichment (PPA), Mol Cell Proteomics, 14:430-440 (2015).
Needleman et al. A general method applicable to the search for similarities in the amino acid sequence of two proteins. J. Mol. Biol. 48:443-453 (1970).
Ng et al., Dereplication and de novo sequencing of nonribosomal peptides, Nat Meth, 6:596-599 (2009).
Nielsen et al., NetMHCpan, a Method for Quantitative Predictions of Peptide Binding to Any HLA-A and -B Locus Protein of Known Sequence, PloS one, 2:e796 (2007).
Nielsen et al., NetMHCpan-3.0; improved prediction of binding to MHC class I molecules integrating information from multiple receptor and peptide length datasets, Genome Medicine, 8:33 (2016).
Nielsen et al., The role of the proteasome in generating cytotoxic T-cell epitopes: insights obtained from improved predictions of proteasomal cleavage, Immunogenetics, 57:33-41 (2005).
Non-Final Office Action dated Jun. 27, 2019 for U.S. Appl. No. 15/575,328.
Non-Final Office Action for U.S. Appl. No. 13/108,610, Compositions and Methods of Identifying Tumor Specific Neoantigens, dated Aug. 15, 2013.
Novershtern et al., Densely Interconnected Transcriptional Circuits Control Cell States in Human Hematopoiesis, Cell, 144(2):296-309 (2011).
Oh et al., Neutrophil isolation protocol, J Vis Exp (2008).
Okada et al., Induction of CD8+ T-Cell Responses Against Novel Glioma-Associated Antigen Peptides and Clinical Activity by Vaccinations With a-Type 1 Polarized Dendritic Cells and Polyinosinic-Polycytidylic Acid Stabilized by Lysine and Carboxymethylcellulose in Patients With Recurrent Malignant Glioma, J Clin Oncol, 29(3):330-336 (2011).
Oshiumi et al., Dead/H Box 3 (DDX3) helicase binds the RIG-I adaptor IPS-1 to up-regulate IFN-beta-inducing potential, Eur J Immunol, 40:940-948 (2010).
Ott et al., CTLA-4 and PD-1/PD-L1 Blockade: New Immunotherapeutic Modalities with Durable Clinical Benefit in Melanoma Patients, Clin Cancer Res, 19(19):5300-5309 (2013).
Padgett et al., Creating seamless junctions independent of restriction sites in PCR cloning, Gene, 168:31-35 (1996).
Pages, et al., Effector Memory T Cells, Early Metastasis, and Survival in Colorectal Cancer, New Engl J Med, 353:2654-2666 (2005).
Panelli, M. C., et al. (2000), A Tumor-Infiltrating from a Melanoma Metastasis with Decreased Expression of Melanoma Differentiation Antigens Recognizes MAGE-12, J Immunol 164:4382-4392.
Papanicolaou, G. A., et al., (2003), Rapid expansion of cytomegalovirus-specific cytotoxic T lymphocytes by artificial antigen-presenting cells expressing a single HLA allele, Blood 102:2498-2505).
Pearson and Lipman, Improved tools for biological sequence comparison, Proc. Nat. Acad Sci USA., 85:2444-2448, (1988).
Pei et al., Genome-wide DNA methylation analysis reveals novel epigenetic changes in chronic lymphocytic leukemia, Epigenetics, 7:567-578 (2012).
Peitras, Richard J., Biologic Basis of Sequential and Combination Therapies for Hormone-Response Breast Cancer, The Oncologist, 2006; 11:704-717.
Peng et al., DOK3 Negatively Regulates LPS Responses and Endotoxin Tolerance, PloS one 7:e39967 (2012).
Perez et al., p63 consensus DNA-binding site: identification, analysis and application into a p63MH algorithm, Oncogene, 26:7363-7370 (2007).
Pirard et al., Interferon Alpha as Adjuvant Postsurgical Treatment of Melanoma: A Meta-Analysis, Dermatology, 208(1):43-48 (2004).
Powell et al., NCoR1 Mediates Papillomavirus E8AE2C Transcriptional Repression, J Virol, 84:4451-4460 (2010).
Pujadas et al., Regulated noise in the epigenetic landscape of development and disease, Cell, 148(6):1123-1131 (2012).
Qin et al., Soft lithography for micro- and nanoscale patterning, Nat Protoc, 5:491-502 (2010).
Quesada et al., "Exome sequencing identifies recurrent mutations of the splicing factor SF3B1 gene in chronic lymphocytic leukemia," Nat Genet, 44:47-52 (2012).
Quezada et al., CTLA4 blockade and GM-CSF combination immunotherapy alters the intratumor balance of effector and regulatory T cells, J Clin Invest, 116(7):1935-1945 (2006).
Ramskold et al., Full-length mRNA-Seq from single-cell levels of RNA and individual circulating tumor cells, Nat Biotechnol, 30:777-782 (2012).
Rassenti et al., Relative value of ZAP-70, CD38, and immunoglobulin mutation status in predicting aggressive disease in chronic lymphocytic leukemia, Blood, 112:1923-1930 (2008).
Raval et al., Downregulation of Death-Associated Protein Kinase 1 (DAPK1) in Chronic Lymphocytic Leukemia, Cell, 129(5):879-890 (2007).
Ravi et al., Sensitization of Tumor Cells to Apo2 Ligand/TRAIL-induced Apoptosis by Inhibition of Casein Kinase II, Cancer Res, 62(15):4180-4185 (2002).
Reay, Phillip A. et al., (1992), pH dependence and exchange of high and low responder peptides binding to a class II MHC molecule, EMBO J. 11:2829-39.
Richter et al., Mechanistic Determinants of Biotherapeutics Absorption Following SC Administration, The AAPS Journal, 14(3):559-568 (2012).
Rini et al., Biology and Treatment of Advanced Renal Cell Carcinoma: A Global Perspective, Semin Oncol, 40(4):419-420 (2013).
Robbins et al., Mining exomic sequencing data to identify mutated antigens recognized by adoptively transferred tumor-reactive T cells, Nat Med, 19(6):747-752 (2013).
Robinson et al., A phase I-II trial of multiple-dose polyriboinosic-polyribocytidylic acid in patieonts with leukemia or solid tumors, J Natl Cancer Inst, 57(3):599-602 (1976).
Robinson et al., "DNA vaccines for viral infections: Basic studies and applications," Adv Virus Res, 55:1-74 (2000).
Robinson et al., edgeR: a Bioconductor package for differential expression analysis of digital gene expression data, Bioinformatics, 26(1):139-140 (2010).
Robinson et al., Integrative genomics viewer, Nat Biotechnol, 29:24-26 (2011).
Rolph et al., Recombinant viruses as vaccines and immunological tools. Curr Opin Immunol 9:517-524, 1997.
Rooney, M. et al., Molecular and genetic properties of tumors associated with local immune cytolytic activity. Cell. Jan. 15, 2015; 160(1-2): 48-61.doi:10.1016/j.cell.2014.12.033.
Rosenberg, Raising the Bar: The Curative Potential of Human Cancer Immunotherapy, Sci Trans! Med, 4(127):127ps128 (2012).
Rossi et al., Integrated mutational and cytogenetic analysis identifies new prognostic subgroups in chronic lymphocytic leukemia, Blood, 121:1403-1412 (2013).
Rubin et al., Mutation patterns in cancer genomes, PNAS, 106(51):21766-21770 (2009).

(56) References Cited

OTHER PUBLICATIONS

Rubio-Moscardo et al., Characterization of 8p21.3 chromosomal deletions in B-cell lymphoma: TRAIL-R1 and TRAIL-R2 as candidate dosage-dependent tumor suppressor genes, Blood, 106:3214-3222 (2005).
Rutledge et al., Tumor-Infiltrating Lymphocytes in Glioblastoma Are Associated with Specific Genomic Alterations and Related to Transcriptional Class, Clin Cancer Res, 19:4951-4960 (2013).
Sadelain et al. Targeting tumours with genetically enhanced T lymphocytes. Nat Rev Cancer 3(1):35-45 (2003).
Sahin et al., Personalized RNA mutanome vaccines mobilize poly-specific therapeutic immunity against cancer, Nature, 547(7662):222-226 (2017).
Salem et al., Defining the Antigen-Specific T-Cell Response to Vaccination and Poly(I:C)/TLR3 Signaling: Evidence of Enhanced Primary and Memory CD8 T-Cell Responses and Antitumor Immunity, J Immunother, 28(3):220-228 (2005).
Samuels et al., Oncogenic PI3K and its role in cancer, Curr Opin Oncol, 18:77-82n (2006).
Sato et al., Discovery of Novel Targets for Aberrant Methylation in Pancreatic Carcinoma Using High-Throughput Microarrays, Cancer Res, 63(13):3735-3742 (2003).
Saturno et al., Combining TRAIL with P13 Kinase or HSP90 inhibitors enhances apoptosis in colorectal cancer cells via suppression of survival signaling, Oncotarget, 4(8):1185-1198 (2013).
Saunders et al. Strelka: accurate somatic small-variant calling from sequenced tumor-normal sample pairs. Bioinformatic, 28(14):1811-1817 (2012).
Schmitt et al., Transcriptional Profiling of Human Endogenous Retrovirus Group HERV-K(HML-2) Loci in Melanoma, Genome Biol Evol, 5(2):307-328 (2013).
Schreiber et al., Cancer Immunoediting: Integrating Immunity's Roles in Cancer Suppression and Promotion, Science, 331(6024):1565-1570 (2011).
Schumacher et al., Prognostic Significance of Activated CD8+ T Cell Infiltrations within Esophageal Carcinomas, Cancer Res, 61(10):3932-3936 (2001).
Schuster et al., Vaccination With Patient-Specific Tumor-Derived Antigen in First Remission Improves Disease-Free Survival in Follicular Lymphoma, J Clin Oncol, 29(20):2787-2794 (2011).
Seberg et al., How Many Loci Does it Take to DNA Barcode a Crocus?, PLoS One 4(2):e4598 (2009).
Secchiero et al., Aberrant expression of TRAIL in B chronic lymphocytic leukemia (B-CLL) cells, J Cell Physiol, 205(2):246-252 (2005).
Sensi et al., Unique tumor antigens: evidence for immune control of genome integrity and immunogenic targets for T cell-mediated patient-specific immunotherapy, Clin Cancer, Res 12:5023-5032 (2006).
Sette, et al., (1994) Peptide binding to the most frequent HLA-A class I alleles measured by quantitative molecular bindings assays, Mol. Immunol. 31:813.
Shah et al., Multiple BCR-ABL kinase domain mutations confer polyclonal resistance to the tyrosine kinase inhibitor imatinib (STI571) in chronic phase and blast crisis chronic myeloid leukemia, Cancer Cell, 2(2):117-125 (2002).
Shalek et al., Single-cell RNA-seq reveals dynamic paracrine control of cellular variation, Nature, 510(7505):363-369 (2014).
Shannon, A Mathematical Theory of Communication, Bell System Technical Journal, 27(3):379-423 (1948).
Shao et al., Clonally related histiocytic/dendritic cell sarcoma and chronic lymphocytic leukemia/small lymphocytic lymphoma: a study of seven cases, Mod Pathol, 24:1421-1432 (2011).
Sharei, et al. A vector-free microfluidic platform for intracellular delivery. Proc Natl Acad Sci U S A. Feb. 5, 2013; 110(6): 2082-2087.
Shendure et al., Next-generation DNA sequencing, Nat Biotechnol, 26(10):1135-1145 (2008).
Sidney et al., HLA class I supertypes: a revised and updated classification, BMC Immunol, 9:1 (2008).
Sidney, John et al., Measurement of MHC/Peptide Interactions by Gel Filtration Curr Prot Immunol, 31(1):18.3.1-18.3.19 (1999).
Siegel et al., Cancer statistics, 2013, CA, 63(1):11-30 (2013).
Simmons et al., Local secretion of anti-CTLA-4 enhances the therapeutic efficacy of a cancer immunotherapy with reduced evidence of systemic autoimmunity, Cancer Immunol Immunother, 57(8):1263-1270 (2008).
Simpson et al., Cancer/testis antigens, gametogenesis and cancer, Nat Rev Cancer, 5:615-625 (2005).
Simpson et al., "Fc-dependent depletion of tumor-infiltrating regulatory T cells co-defines the efficacy of anti-CTLA-4 therapy against melanoma," J Exp Med, 210(9):1695-1710 (2013).
Slingluff et al., Randomized Multicenter Trial of the Effects of Melanoma-Associated Helper Peptides and Cyclophosphamide on the Immunogenicity of a Multipeptide Melanoma Vaccine, J Clin Oncol, 29(21):2924-2932 (2011).
Smith et al., Comparison of biosequences, Adv Appl Math, 2(4):482-489 (1981).
Soares et al., A subset of dendritic cells induces CD4+ T cells to produce IFN-gamma by an IL-12-independent but CD70-dependent mechanism in vivo, J Exp Med, 2215(11):1095-1106 (2007).
Soininen et al., Analysing diet of small herbivores: the efficiency of DNA barcoding coupled with high-throughput pyrosequencing for deciphering the composition of complex plant mixtures, Front Zool, 6:16 (2009).
Sommnerfelt et al., Receptor interference groups of 20 retroviruses plating on human cells.(1990) Virol.176:58-59.
Song et al., c-Cbl acts as a mediator of Src-induced activation of the PI3K-Akt signal transduction pathway during TRAIL treatment, Cellular Signalling, 22(3):377-385 (2010).
Song, Shengli et al., Full screening and accurate subtyping of HLA-A*02 alleles through group-specific amplification and mono-allelic sequencing, Cellular & Molecular Immunology (2013) 10, 490-496.
Sosman et al., A phase 2 trial of complete resection for stage IV melanoma: results of Southwest Oncology Group Clinical Trial S9430, Cancer, 117(20):4740-4706 (2011).
Speetjens et al., Induction of p53-Specific Immunity by a p53 Synthetic Long Peptide Vaccine in Patients Treated for Metastatic Colorectal Cancer, Clin Cancer Res, 15(3):1086-1095 (2009).
Srivastava et al., Modeling the Repertoire of True Tumor-Specific MHC I Epitopes in a Human Tumor, Plos One, 4(7):e6094 (2009).
Srivastava, Therapeutic Cancer Vaccines, Curr Opin Immunol, 18: 201-205 (2006).
Stover, C.K et al., New use of BCG for recombinant vaccines, Nature 351:456-460 (1991).
Stransky et al., The Mutational Landscape of Head and Neck Squamous Cell Carcinoma, Science, 333:1157-1160 (2011).
Stranzl et al., NetCTLpan: pan-specific MHC class I pathway epitope predictions, Immunogenetics, 62(6):357-368 (2010).
Su et al., Next-generation sequencing and its applications in molecular diagnostics Exp Rev Mol Diagn, 11(3):333-343 (2011).
Sun et al., Material bionics and Thinking Innovation, 176-177 (2012).
Suzuki et al., A Novel Glycosylphosphatidyl Inositol-Anchored Protein on Human Leukocytes: A Possible Role for Regulation of Neutrophil Adherence and Migration, J Immunol, 162(7):4277-4284 (1999).
Sykulev et al., Evidence that a Single Peptide-MHC Complex on a Target Cell Can Elicit a Cytolytic T Cell Response, Immunity, 4:565-571 (1996).
Takaku, et al. "GATA3 in Breat Cancer: tumor suppressor or oncogene?" HHS Public Access, 2015.
Takaku, et al. "GATA3 zinc finger 2 mutations reprogram the breast cancer transcriptional network," Nature Communications, (2018)9:1059.
Tam. Synthetic peptide vaccine design: synthesis and properties of a high-density multiple antigenic peptide system. PNAS USA 85(15):5409-5413 (1988).
Tang et al., NeoantigenR: An annotation based pipeline for tumor neoantigen identification from sequencing data, bioRxiv preprint first posted online Aug. 8, 2017.
Tang et al., The landscape of viral expression and host gene fusion and adaptation in human cancer, Nat Commun, 4:2513 (2013).

(56) References Cited

OTHER PUBLICATIONS

Ten Bosch et al., Keeping Up With the Next Generation: Massively Parallel Sequencing in Clinical Diagnostics, J Mol Diagn, 10(6):484-492 (2008).
Teng et al., A human TAPBP (TAPASIN)-related gene, TAPBP-R, Eur J Immunol, 32:1059-1068 (2002).
Testori et al., Phase III comparison of vitespen, an autologous tumor-derived heat shock protein gp96 peptide complex vaccine, with physician's choice of treatment for stage IV melanoma: the C-100-21 Study Group, J Clin Oncol, 26(6):955-962 (2008).
Textor et al., "Human NK cells are alerted to induction of p53 in cancer cells by upregulation of the NKG2D ligands ULBPI and ULBP2," Cancer Res, 71:5998-6009 (2011).
Timp et al., Cancer as a dysregulated epigenome allowing cellular growth advantage at the expense of the host, Nat Rev Cancer, 13:497-510 (2013).
Topalian et al., Safety, Activity, and Immune Correlates of Anti-PD-1 Antibody in Cancer, N Engl J Med, 366(26):2443-2454 (2012).
Topalian et al., Survival, Durable Tumor Remission, and Long-Term Safety in Patients With Advanced Melanoma Receiving Nivolumab, J Clin Oncol, 32(10):1020-1030 (2014).
Tough et al., Induction of bystander T cell proliferation by viruses and type I interferon in vivo, Science, 272(5270):1947-1950 (1996).
Townsend, A., et al., Assembly of MCH Class 1 molecules analyzed in vitro, Cell 62:285, Jul. 27, 1990.
Tran et al., Cancer Immunotherapy Based on Mutation-Specific CD4+ T Cells in a Patient with Epithelial Cancer, Science, 344(6184):641-645 (2014).
Trolle et al., Automated benchmarking of peptide-MHC class I binding predictions, Bioinformatics, 31(13):2174-2181 (2015).
Trumpfheller et al., ntensified and protective CD4+ T cell immunity in mice with anti-dendritic cell HIV gag fusion antibody vaccine, J Exp Med, 203(3):607-617 (2006).
Trumpfheller et al., The microbial mimic poly IC induces durable and protective CD4+ T cell immunity together with a dendritic cell targeted vaccine, PNAS, 105(7):2574-2579 (2008).
Tucker et al., Massively Parallel Sequencing:The Next Big Thing in Genetic Medicine, Am J Hum Genet, 85(2):142-154 (2009).
Turchaninova et al., Pairing of T-cell receptor chains via emulsion PCR, Eur J Immunol, 43:2507-2515 (2013).
Uderhardt et al., 12/15-lipoxygenase orchestrates the clearance of apoptotic cells and maintains immunologic tolerance, Immunity, 36(5):834-846 (2012).
Usary, et al. "Mutation of GATA3 in human breast tumors," Oncogene (2004) 23, 7669-7678.
Ushijima et al., Fidelity of the methylation pattern and its variation in the genome, Genome research, 13:868-874 (2005).
Uyttenhove et al., Evidence for a tumoral immune resistance mechanism based on tryptophan degradation by indoleamine 2,3-di oxygenase, Nature medicine, 9:1269-1274 (2003).
Vaishampayan et al., Active immunotherapy of metastatic melanoma with allogeneic melanoma lysates and interferon alpha, Clin Cancer Res, 8(12):3696-3701 (2002).
Van Buuren et al., High sensitivity of cancer exome-based CD8 T cell neo-antigen identification, OncoImmunology, 3(5):e28836 (2014).
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation, Journal of Experimental Medicine, 190(3):355-366 (1999).
Van Poelgeest et al., HPV16 synthetic long peptide (HPV16-SLP) vaccination therapy of patients with advanced or recurrent HPV16-induced gynecological carcinoma, a phase II trial, J Trans! Med, 11:88 (2013).
Van Rooij et al., Tumor exome analysis reveals neoantigen-specific T-cell reactivity in an ipilimumab-responsive melanoma, Journal of clinical oncology: official journal of the American Society of Clinical Oncology, 31:32 (2013).
Verardi et al., A vaccinia virus renaissance New vaccine and immunotherapeutic uses after smallpox eradication, Hum Vaccin Immunother. Jul. 2012;8(7):961-70.
Verhoef, et al., Des-enkephalin-Y-Error! Hyperlink reference not valid.endorphin (DEyE): Biotransformation in rat, dog, and human plasma, Eur. J. Drug Metab. Pharmacokinetics 11:291 (1986).
Vermeij et al., Potentiation of a p53-SLP vaccine by cyclophosphamide in ovarian cancer: a single-arm phase II study, Int J Cancer, 131(5):E670-680 (2012).
Vogel et al., Mass Spectrometry Reveals Changes in MHC I Antigen Presentation After Lentivector Expression of a Gene Regulation System, Molecular Therapy—Nucleic Acids, 2:e75 (2013).
Von Mehren et al., Pilot study of a dual gene recombinant avipox vaccine containing both carcinoembryonic antigen (CEA) and B7.1 transgenes in patients with recurrent CEA-expressing adenocarcinomas. Clin Cancer Res 2000;6:2219-28.
Wahl et al., [43] Molecular hybridization of immobilized nucleic acids: Theoretical concepts and practical considerations, Methods in enzymology, Academic Press, 152:399-407 (1987).
Wang et al., Functional Polymeric Material, 1-44 (2010).
Wang et al., Role of protein kinase CK2 in the regulation of tumor necrosis factor-related apoptosis inducing ligand-induced apoptosis in prostate cancer cells, Cancer research, 66:2242-2249 (2006).
Wang et al., SF3B1 and other novel cancer genes in chronic lymphocytic leukemia, N Engl J Med, 365:2497-2506 (2011).
Wang et al., Widespread plasticity in CTCF occupancy linked to DNA methylation, Genome Res, 22:1680-1688 (2012).
Weber et al., Assembly of Designer TAL Effectors by Golden Gate Cloning, PLoS ONE, 6:e19722 (2001).
Weiner et al., (1999), Genetic Vaccines, Scientific American 281 (1): 34-41.
Welters et al., Induction of tumor-specific CD4+ and CD8+ T-cell immunity in cervical cancer patients by a human papillomavirus type 16 E6 and E7 long peptides vaccine, Clinical cancer research, 14(1):178-187 (2008).
Welters et al., Success or failure of vaccination for HPV16-positive vulvar lesions correlates with kinetics and phenotype of induced T-cell responses, PNAS, 107(26):11895-11899 (2010).
Wheatley et al., Does adjuvant interferon-alpha for high-risk melanoma provide a worthwhile benefit?A meta-analysis of the randomised trials, Cancer treatment reviews, 29(4):241-252 (2003).
Widschwendter et al., Epigenetic stem cell signature in cancer, Nat Genet, 39:157-158 (2007).
Wierda et al., Multivariable model for time to first treatment in patients with chronic lymphocytic leukemia, J Clin Oncol, 29:4088-4095 (2011).
Wilson et al. Formation of infectious hybrid virions with gibbon ape leukemia virus and human T-cell leukemia virus retroviral envelope glycoproteins and the gag and pol proteins of Moloney murine leukemia virus. J Virol 63(5):2374-2378 (1989).
Winzeler et al., Functional characterization of the *S. cerevisiae* genome by gene deletion and parallel analysis, science, 285(5429):901-906 (1999).
Wolchok et al., "Nivolumab plus ipilimumab in advanced melanoma," N Engl J Med, 369(2):122-133 (2013).
Wong et al., Module map of stem cell genes guides creation of epithelial cancer stem cells, Cell Stem Cell, 2:333-344 (2008).
Woodfine et al., Quantitative analysis of DNA methylation at all human imprinted regions reveals preservation of epigenetic stability in adult somatic tissue, Epigenetics & chromatin, 4:1 (2011).
Woyach et al., Resistance mechanisms for the Bruton's tyrosine kinase inhibitor ibrutinib, The New England journal of medicine, 370:2286-94 (2014).
Wraith, The Future of Immunotherapy: A 20-Year Perspective, Front Immunol, 8:1668 (2017).
Xi et al., BSMAP: whole genome bisulfite sequence MAPping program, BMC bioinformatics, 10:232 (2009).
Xie et al., Stepwise reprogramming of B cells into macrophages, Cell, 117(5):663-676 (2004).
Xu et al., Design of 240,000 orthogonal 25mer DNA barcode probes, Proceedings of the National Academy of Sciences, pnas-0812506106 (2009).

(56) References Cited

OTHER PUBLICATIONS

Yan et al., PBAF chromatin-remodeling complex requires a novel specificity subunit, BAF200, to regulate expression of selective interferon-responsive genes, Genes & development, 19(14):1662-1667 (2005).

Yang, et al. "HDR syndrome with a novel mutation in GATA3 mimicking a congenital X-linked stapes gusher: a case report," BMC Medical Genetics (2017) 18:121.

Yang et al., Meta-analysis followed by replication identifies loci in or near CDKN1B, TET3, CD80, DRAM1, and ARID5B as associated with systemic lupus erythematosus in Asians, American journal of human genetics, 92:41-51 (2013).

Ye, et al. "Systematic Discovery of Complex Indels in Human Cancers," Nat Med. Jan. 2016; 22(1): 97-104.

Yoshihara, K. et al., Inferring tumour purity and stromal and immune cell admixture from expression data,: Nature communications 4:2612 (2013).

Yoshitake et al., Cross0 linking of GPI 080, a possible regulatory molecule of cell adhesion, induces up0 regulation of CD11b/CD18 expression on neutrophil surfaces and shedding of L0 selectin, Journal of leukocyte biology, 71(2):205-211 (2002).

Young et al., Resurrection of endogenous retroviruses in antibody-deficient mice, Nature, 491(7426):774 (2012).

Yu et al., Nucleic acid-sensing Toll-like receptors are essential for the control of endogenous retrovirus viremia and ERV-induced tumors, Immunity, 37(5):867-879 (2012).

Yuille et al., TCL1 is activated by chromosomal rearrangement or by hypomethylation, Genes, Chromosomes and Cancer, 30(4):336-341 (2001).

Zeestraten et al., "Addition of interferon-alpha to the p53-SLP(R) vaccine results in increased production of interferon-gamma in vaccinated colorectal cancer patients: a phase 1/11 clinical trial," Int J Cancer, 132(7):1581-1591 (2013).

Zhang et al., Machine learning competition in immunology-prediction of HLA class I binding peptides, J Immunol Methods 374:1-4 (2009).

Zhang et al., Oncology, 1-44 (2005).

Zhang et al., The impact of next-generation sequencing on genomics, J Genet Genomics, 38(3):95-109 (2011).

Zhou et al., A hypermorphic missense mutation in PLCG2, encoding phospholipase Cgamma2, causes a dominantly inherited autoinflammatory disease with immunodeficiency, Am J Hum Genet, 91:713-20 (2012).

Zhu et al., Toll like receptor-3 ligand poly-ICLC promotes the efficacy of peripheral vaccinations with tumor antigen-derived peptide epitopes in murine CNS tumor models, Journal of translational medicine, 5:10 (2007).

Ziller et al., Charting a dynamic DNA methylation landscape of the human genome, Nature, 500:477-481 (2013).

Zorn et al., A natural cytotoxic T cell response in a spontaneously regressing human melanoma targets a neoantigen resulting from a somatic point mutation, Eur J Immunol, 29(2):592-601 (1999).

Zwaveling et al., Established human papillomavirus type 16-expressing tumors are effectively eradicated following vaccination with long peptides, J Immunol, 169(1):350-358 (2002).

\* cited by examiner

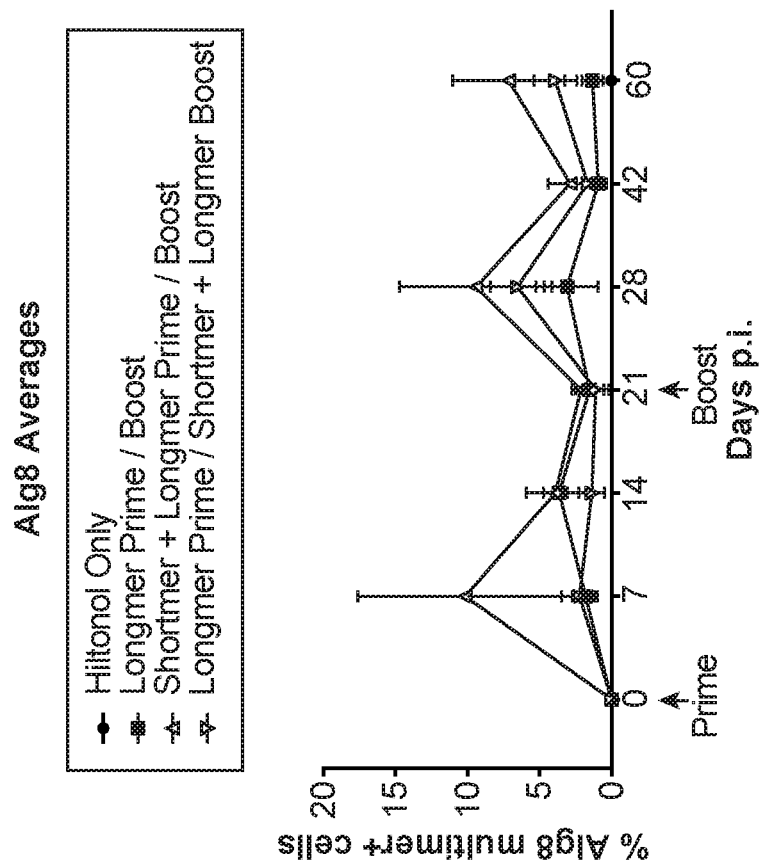
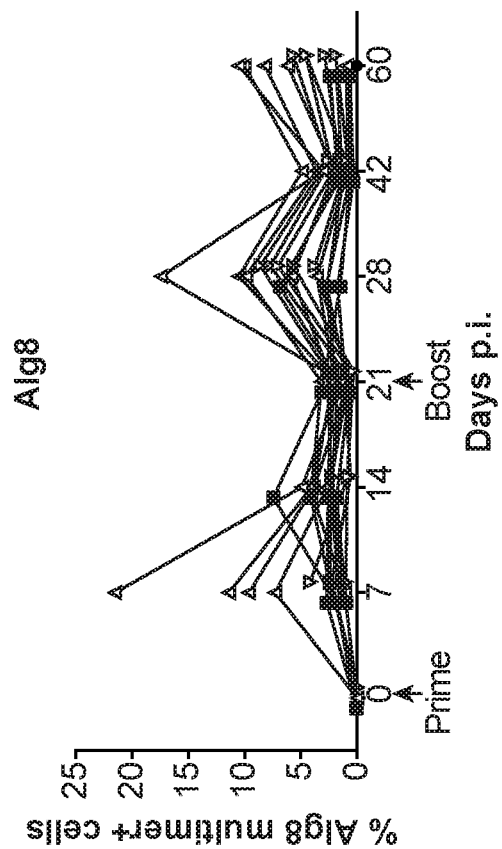
FIG. 14B
FIG. 14C

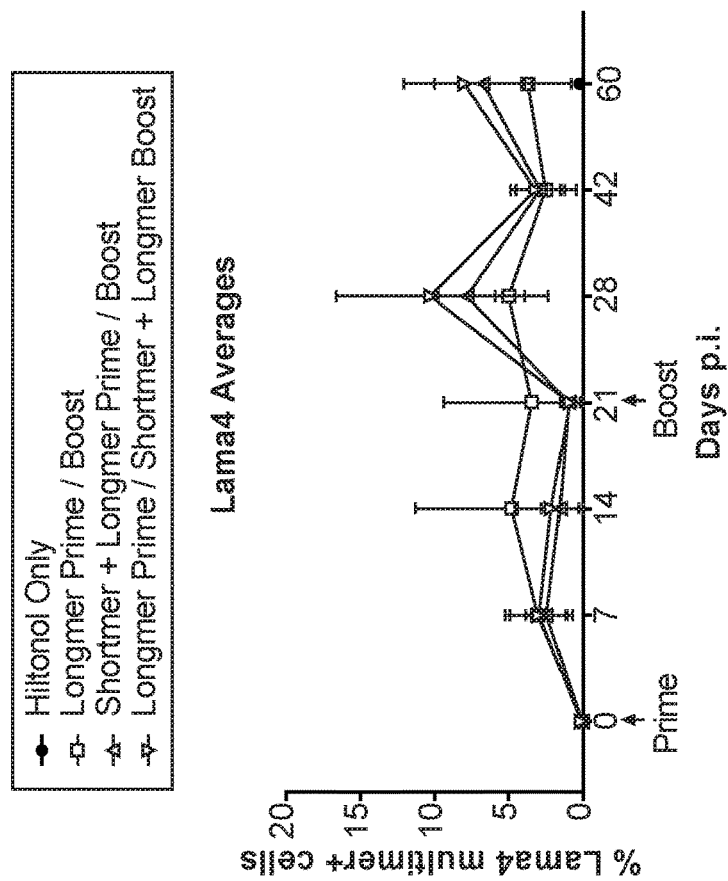
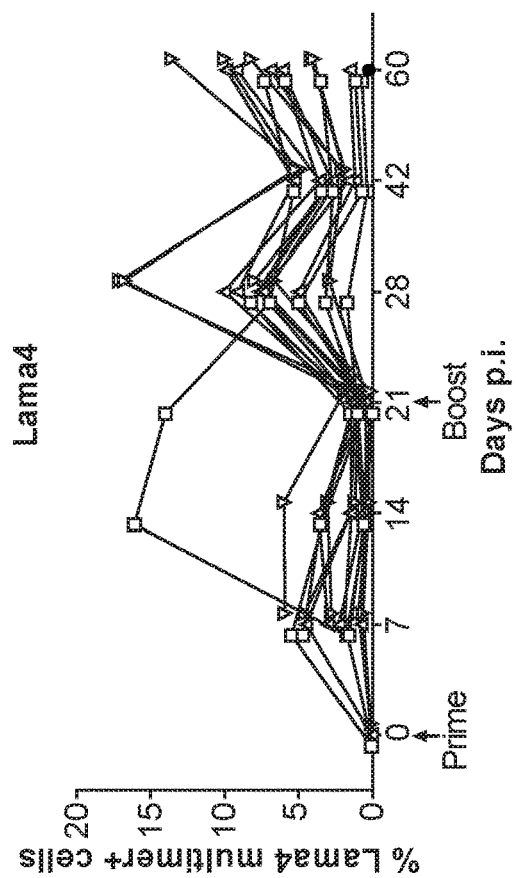
FIG. 15C
FIG. 15B

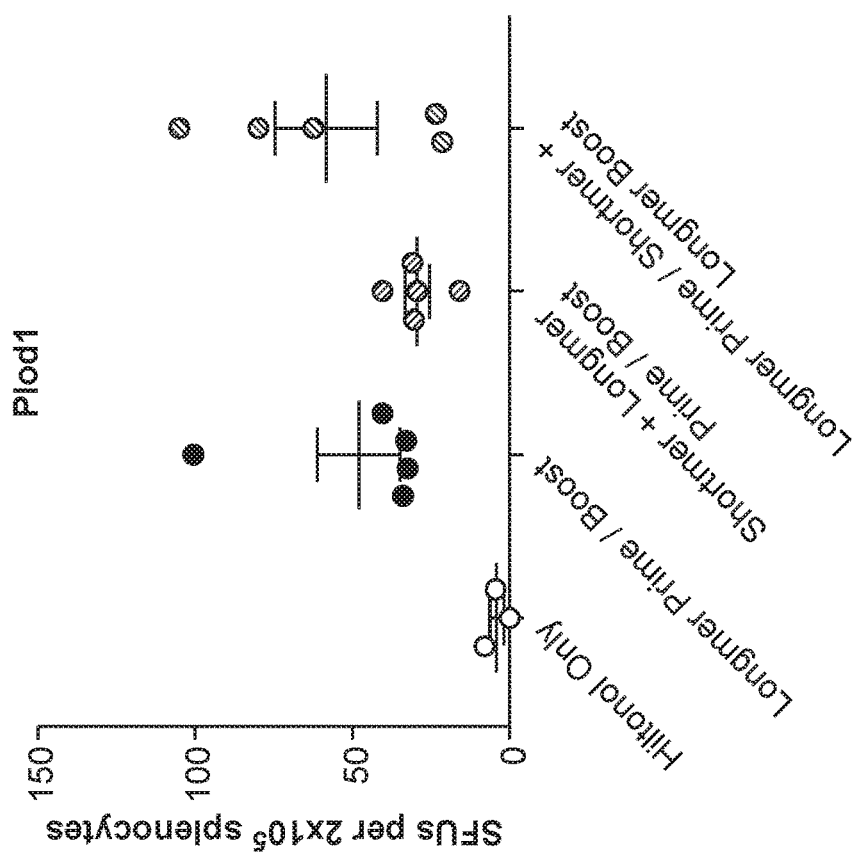
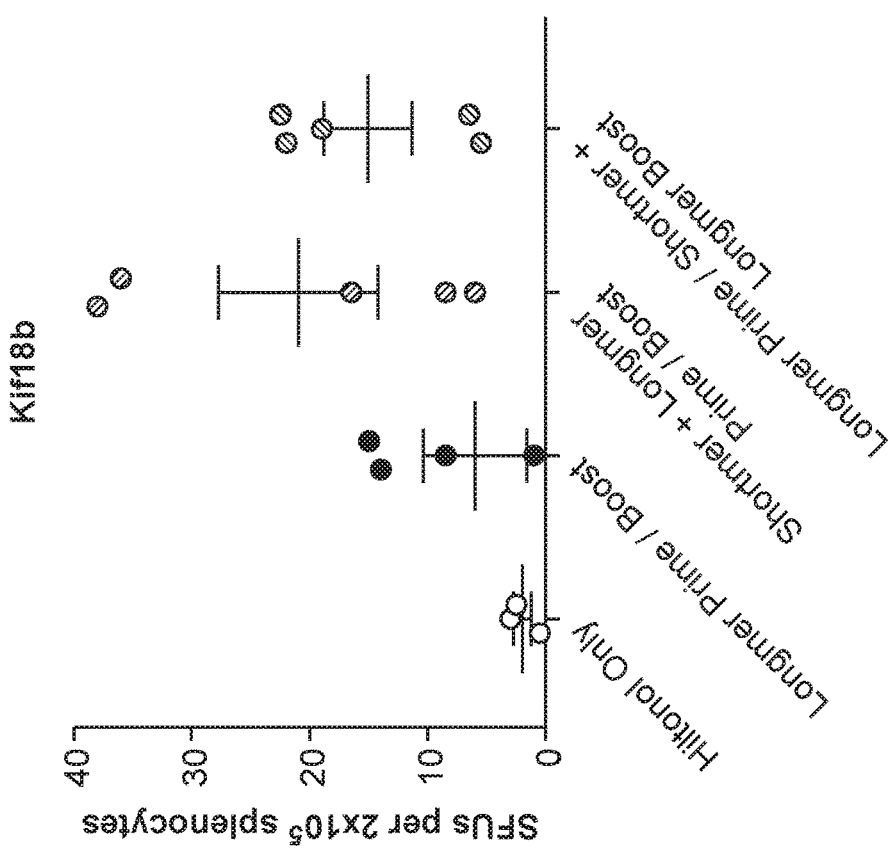
FIG. 20B
FIG. 20A

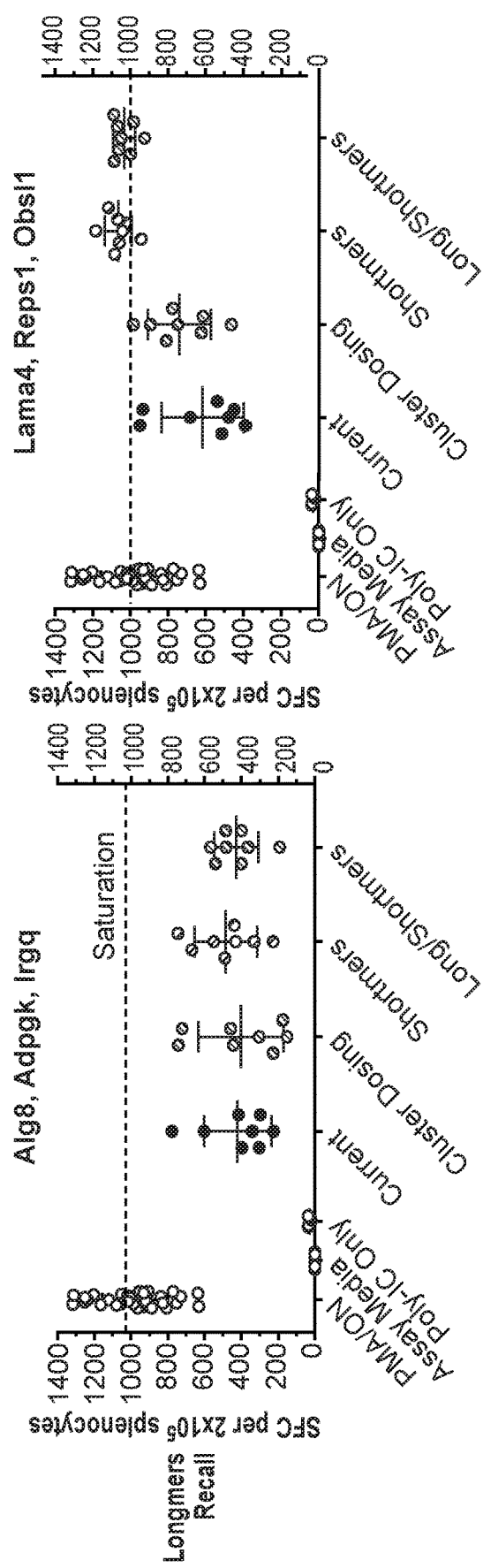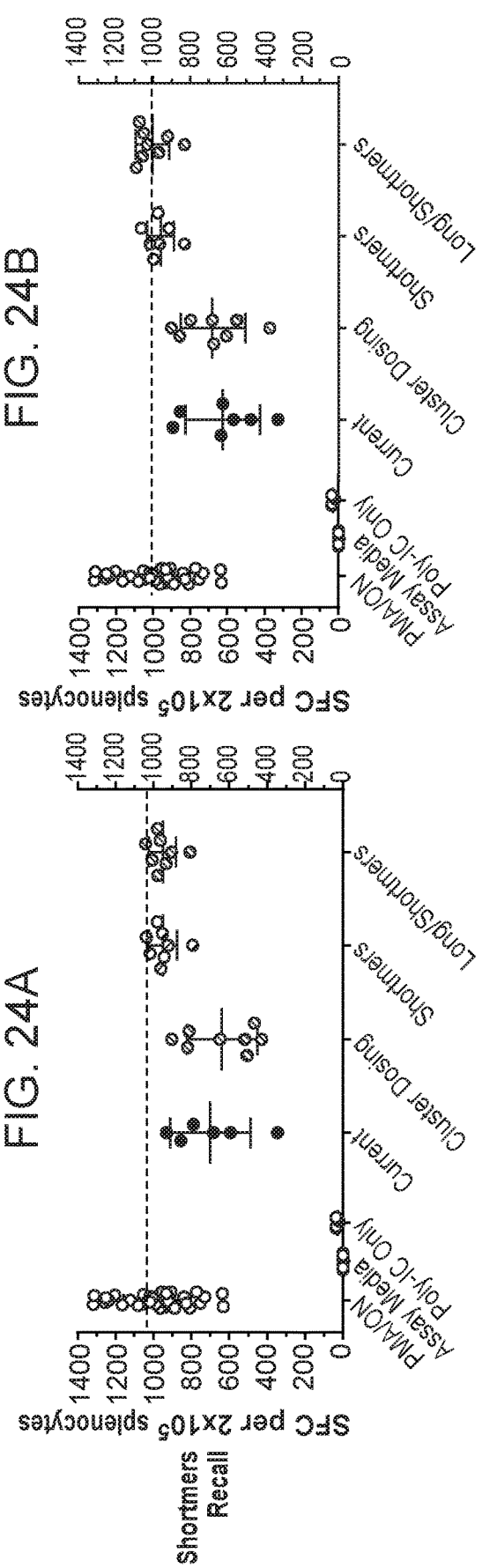
FIG. 24A
FIG. 24B
FIG. 24C
FIG. 24D

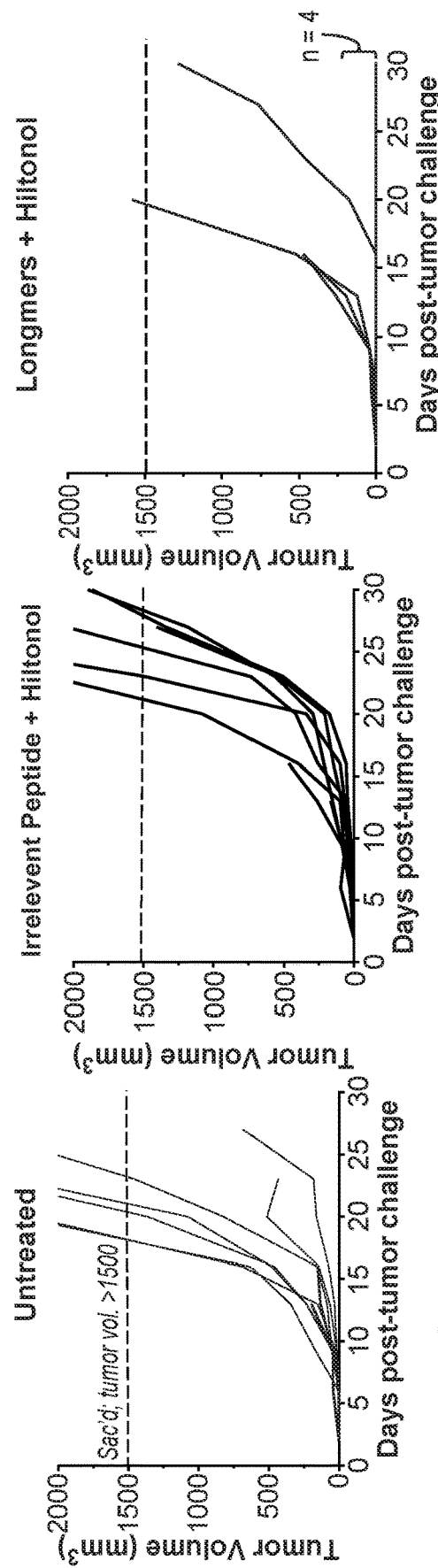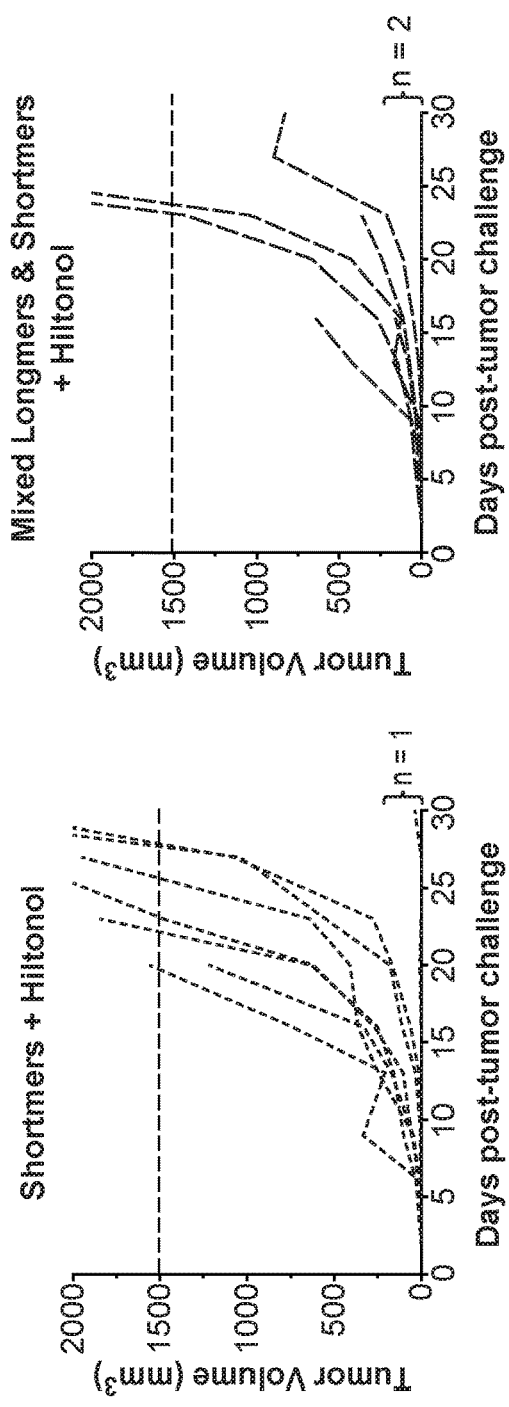
FIG. 27A
FIG. 27B
FIG. 27C
FIG. 27D
FIG. 27E

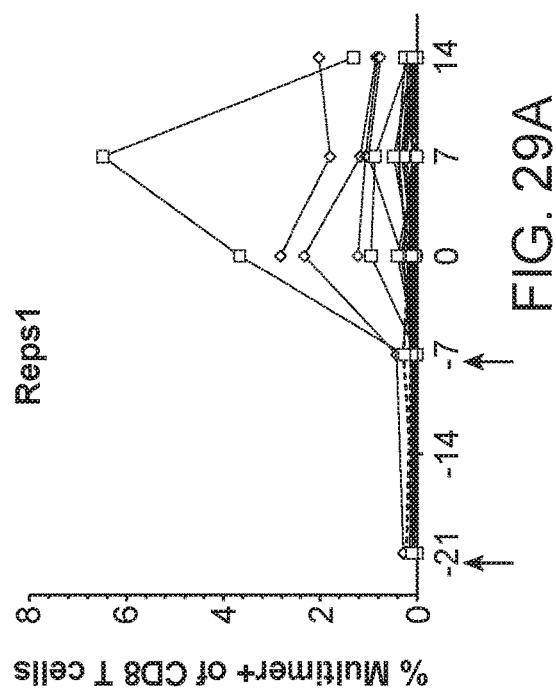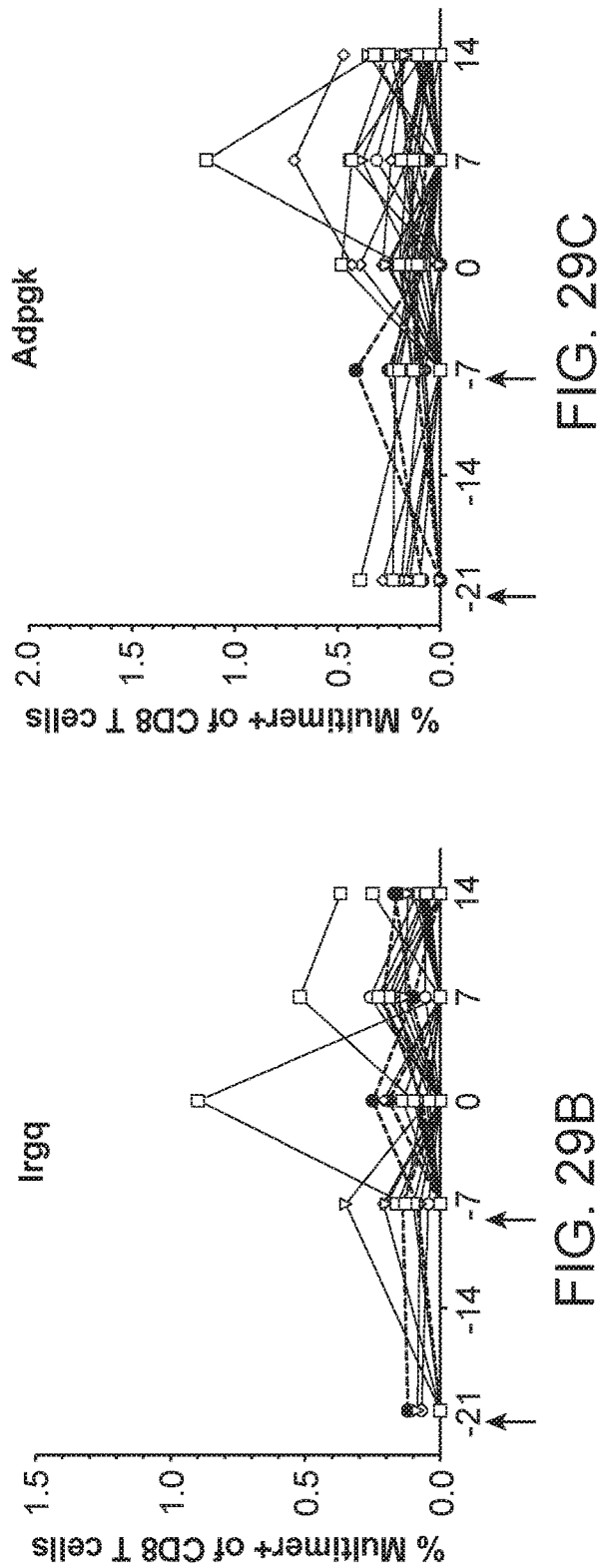
FIG. 29A
FIG. 29B
FIG. 29C

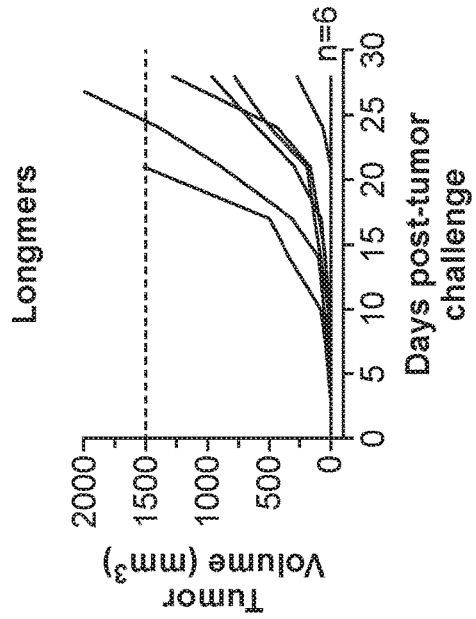
FIG. 34B
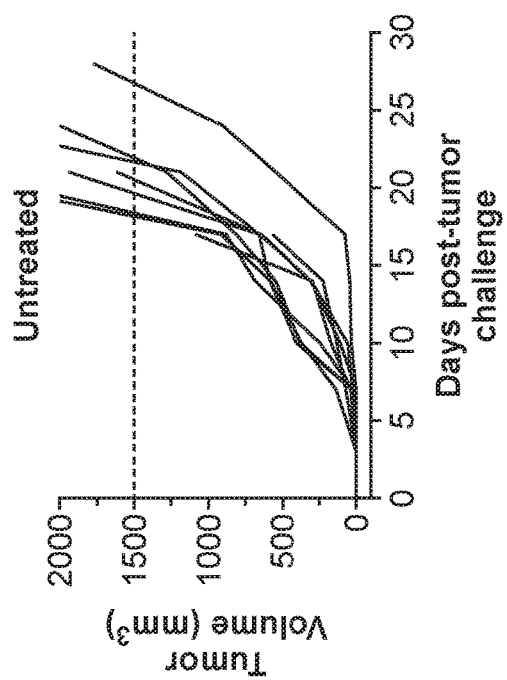
FIG. 34D
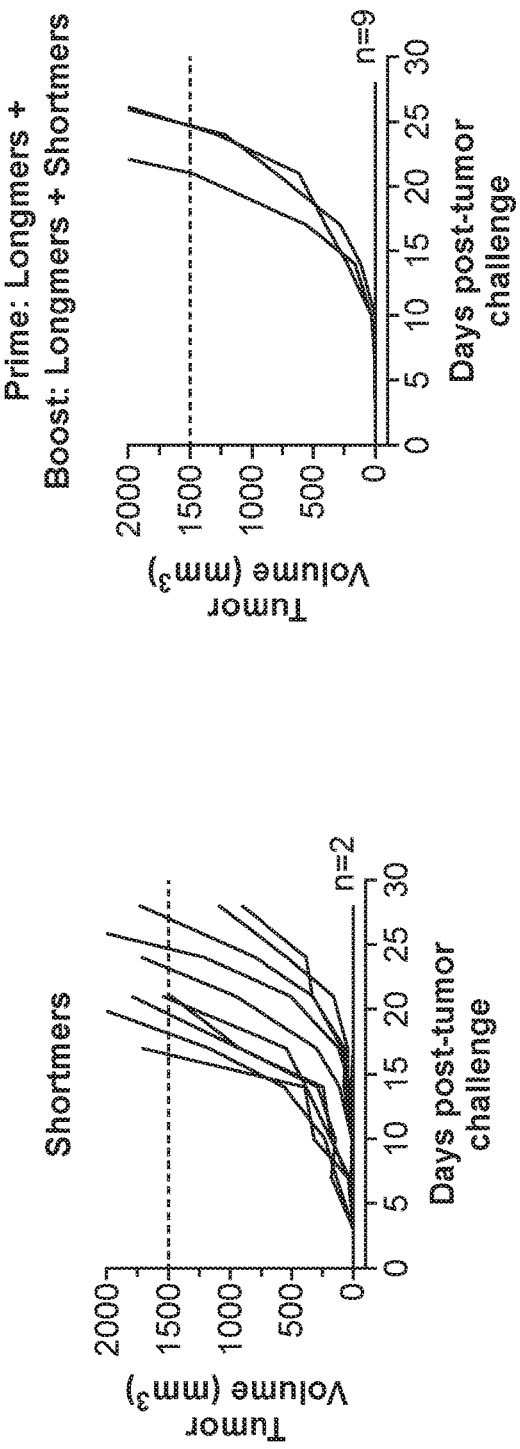
FIG. 34C
FIG. 34E

SEQUENCE LISTING

<160> NUMBER OF SEQ ID NOS: 1368

<210> SEQ ID NO 1
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Val Ala Asp Gly Leu Ile Thr Thr Leu His Tyr Pro Ala Pro Lys Arg
1               5                   10                  15

Asn Lys Pro Thr Val Tyr Gly Val Ser Pro Asn Tyr Asp Lys Trp Glu
                20                  25                  30

Met Glu Arg Thr Asp Ile Thr Met Lys His Lys Leu Gly Gly Gly Gln
            35                  40                  45

Tyr Gly Lys Val Tyr Glu Gly Val Trp Lys Lys Tyr Ser Leu Thr Val
    50                  55                  60

Ala Val Lys Thr Leu Lys Glu Asp Thr Met Glu Val Glu Glu Phe Leu
65                  70                  75                  80

Lys Glu Ala Ala Val Met Lys Glu Ile Lys His Pro Asn Leu Val Gln
                85                  90                  95

Leu Leu Gly Val Cys
            100

<210> SEQ ID NO 2
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Val Ala Asp Gly Leu Ile Thr Thr Leu His Tyr Pro Ala Pro Lys Arg
1               5                   10                  15

Asn Lys Pro Thr Val Tyr Gly Val Ser Pro Asn Tyr Asp Lys Trp Glu
                20                  25                  30

Met Glu Arg Thr Asp Ile Thr Met Lys His Lys Leu Gly Gly Gly Gln
            35                  40                  45

Tyr Gly Val Val Tyr Glu Gly Val Trp Lys Lys Tyr Ser Leu Thr Val
    50                  55                  60

Ala Val Lys Thr Leu Lys Glu Asp Thr Met Glu Val Glu Glu Phe Leu
65                  70                  75                  80

Lys Glu Ala Ala Val Met Lys Glu Ile Lys His Pro Asn Leu Val Gln
                85                  90                  95

Leu Leu Gly Val Cys
            100

<210> SEQ ID NO 3
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Leu Gly Val Cys Thr Arg Glu Pro Pro Phe Tyr Ile Ile Thr Glu
1               5                   10                  15

```
Phe Met Thr Tyr Gly Asn Leu Leu Asp Tyr Leu Arg Glu Cys Asn Arg
            20                  25                  30

Gln Glu Val Asn Ala Val Val Leu Leu Tyr Met Ala Thr Gln Ile Ser
        35                  40                  45

Ser Ala Thr Glu Tyr Leu Glu Lys Lys Asn Phe Ile His Arg Asp Leu
 50                  55                  60

Ala Ala Arg Asn Cys Leu Val Gly Glu Asn His Leu Val Lys Val Ala
65                   70                  75                  80

Asp Phe Gly Leu Ser Arg Leu Met Thr Gly Asp Thr Tyr Thr Ala His
                85                  90                  95

Ala Gly Ala Lys Phe
            100

<210> SEQ ID NO 4
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Leu Thr Val Ala Val Lys Thr Leu Lys Glu Asp Thr Met Glu Val
1               5                   10                  15

Glu Glu Phe Leu Lys Glu Ala Ala Val Met Lys Glu Ile Lys His Pro
            20                  25                  30

Asn Leu Val Gln Leu Leu Gly Val Cys Thr Arg Glu Pro Pro Phe Tyr
        35                  40                  45

Ile Ile Ile Glu Phe Met Thr Tyr Gly Asn Leu Leu Asp Tyr Leu Arg
 50                  55                  60

Glu Cys Asn Arg Gln Glu Val Asn Ala Val Val Leu Leu Tyr Met Ala
65                   70                  75                  80

Thr Gln Ile Ser Ser Ala Met Glu Tyr Leu Glu Lys Lys Asn Phe Ile
                85                  90                  95

His Arg Asp Leu Ala
            100

<210> SEQ ID NO 5
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Thr Val Ala Asp Gly Leu Ile Thr Thr Leu His Tyr Pro Ala Pro
1               5                   10                  15

Lys Arg Asn Lys Pro Thr Val Tyr Gly Val Ser Pro Asn Tyr Asp Lys
            20                  25                  30

Trp Glu Met Glu Arg Thr Asp Ile Thr Met Lys His Lys Leu Gly Gly
            35                  40                  45

Gly Gln His Gly Glu Val Tyr Glu Gly Val Trp Lys Lys Tyr Ser Leu
 50                  55                  60

Thr Val Ala Val Lys Thr Leu Lys Glu Asp Thr Met Glu Val Glu Glu
65                   70                  75                  80

Phe Leu Lys Glu Ala Ala Val Met Lys Glu Ile Lys His Pro Asn Leu
                85                  90                  95
```

Val Gln Leu Leu Gly
            100

<210> SEQ ID NO 6
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Ser Leu Ala Met Leu Asp Leu Leu His Val Ala Arg Asp Ile Ala
1               5                   10                  15

Cys Gly Cys Gln Tyr Leu Glu Glu Asn His Phe Ile His Arg Asp Ile
            20                  25                  30

Ala Ala Arg Asn Cys Leu Leu Thr Cys Pro Gly Pro Gly Arg Val Ala
        35                  40                  45

Lys Ile Ala Asp Phe Gly Met Ala Arg Asp Ile Tyr Arg Ala Ser Tyr
    50                  55                  60

Tyr Arg Lys Gly Gly Cys Ala Met Leu Pro Val Lys Trp Met Pro Pro
65                  70                  75                  80

Glu Ala Phe Met Glu Gly Ile Phe Thr Ser Lys Thr Asp Thr Trp Ser
                85                  90                  95

Phe Gly Val Leu Leu
            100

<210> SEQ ID NO 7
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Ala Val Lys Thr Leu Pro Glu Val Cys Ser Glu Gln Asp Glu
1               5                   10                  15

Leu Asp Phe Leu Met Glu Ala Leu Ile Ile Ser Lys Phe Asn His Gln
            20                  25                  30

Asn Ile Val Arg Cys Ile Gly Val Ser Leu Gln Ser Leu Pro Arg Phe
        35                  40                  45

Ile Leu Met Glu Leu Met Ala Gly Gly Asp Leu Lys Ser Phe Leu Arg
    50                  55                  60

Glu Thr Arg Pro Arg Pro Ser Gln Pro Ser Ser Leu Ala Met Leu Asp
65                  70                  75                  80

Leu Leu His Val Ala Arg Asp Ile Ala Cys Gly Cys Gln Tyr Leu Glu
                85                  90                  95

Glu Asn His Phe Ile
            100

<210> SEQ ID NO 8
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Ile Lys Leu Ile Asp Ile Ala Arg Gln Thr Ala Gln Gly Met Asp
1               5                   10                  15

Tyr Leu His Ala Lys Ser Ile Ile His Arg Asp Leu Lys Ser Asn Asn
                20                  25                  30

Ile Phe Leu His Glu Asp Leu Thr Val Lys Ile Gly Asp Phe Gly Leu
            35                  40                  45

Ala Thr Glu Lys Ser Arg Trp Ser Gly Ser His Gln Phe Glu Gln Leu
        50                  55                  60

Ser Gly Ser Ile Leu Trp Met Ala Pro Glu Val Ile Arg Met Gln Asp
65                  70                  75                  80

Lys Asn Pro Tyr Ser Phe Gln Ser Asp Val Tyr Ala Phe Gly Ile Val
                85                  90                  95

Leu Tyr Glu Leu Met
            100
```

<210> SEQ ID NO 9
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Ile Lys Glu Gly Ser Met Ser Glu Asp Glu Phe Ile Glu Glu Ala
1               5                   10                  15

Lys Val Met Met Asn Leu Ser His Glu Lys Leu Val Gln Leu Tyr Gly
                20                  25                  30

Val Cys Thr Lys Gln Arg Pro Ile Phe Ile Ile Thr Glu Tyr Met Ala
            35                  40                  45

Asn Gly Ser Leu Leu Asn Tyr Leu Arg Glu Met Arg His Arg Phe Gln
        50                  55                  60

Thr Gln Gln Leu Leu Glu Met Cys Lys Asp Val Cys Glu Ala Met Glu
65                  70                  75                  80

Tyr Leu Glu Ser Lys Gln Phe Leu His Arg Asp Leu Ala Ala Arg Asn
                85                  90                  95

Cys Leu Val Asn Asp
            100
```

<210> SEQ ID NO 10
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Gly Phe Gly Asp Leu Lys Ser Pro Ala Gly Leu Gln Val Leu Asn
1               5                   10                  15

Asp Tyr Leu Ala Asp Lys Ser Tyr Ile Glu Gly Tyr Val Pro Ser Gln
                20                  25                  30

Ala Asp Val Ala Val Phe Glu Ala Val Ser Gly Pro Pro Pro Ala Asp
            35                  40                  45

Leu Cys His Ala Leu Arg Trp Tyr Asn His Ile Lys Ser Tyr Glu Lys
        50                  55                  60

Glu Lys Ala Ser Leu Pro Gly Val Lys Lys Ala Leu Gly Lys Tyr Gly
65                  70                  75                  80
```

Pro Ala Asp Val Glu Asp Thr Thr Gly Ser Gly Ala Thr
            85                  90

<210> SEQ ID NO 11
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Leu Asn Ile Thr Ser Leu Gly Leu Arg Ser Leu Lys Glu Ile Ser
1               5                   10                  15

Asp Gly Asp Val Ile Ile Ser Gly Asn Lys Asn Leu Cys Tyr Ala Asn
            20                  25                  30

Thr Ile Asn Trp Lys Lys Leu Phe Gly Thr Ser Gly Gln Lys Thr Lys
        35                  40                  45

Ile Ile Arg Asn Arg Gly Glu Asn Ser Cys Lys Ala Thr Gly Gln Val
    50                  55                  60

Cys His Ala Leu Cys Ser Pro Glu Gly Cys Trp Gly Pro Glu Pro Arg
65                  70                  75                  80

Asp Cys Val Ser Cys Arg Asn Val Ser Arg Gly Arg Glu Cys Val Asp
                85                  90                  95

Lys Cys Asn Leu Leu
            100

<210> SEQ ID NO 12
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ile Pro Val Ala Ile Lys Glu Leu Arg Glu Ala Thr Ser Pro Lys Ala
1               5                   10                  15

Asn Lys Glu Ile Leu Asp Glu Ala Tyr Val Met Ala Ser Val Asp Asn
            20                  25                  30

Pro His Val Cys Arg Leu Leu Gly Ile Cys Leu Thr Ser Thr Val Gln
        35                  40                  45

Leu Ile Met Gln Leu Met Pro Phe Gly Cys Leu Leu Asp Tyr Val Arg
    50                  55                  60

Glu His Lys Asp Asn Ile Gly Ser Gln Tyr Leu Leu Asn Trp Cys Val
65                  70                  75                  80

Gln Ile Ala Lys Gly Met Asn Tyr Leu Glu Asp Arg Arg Leu Val His
                85                  90                  95

Arg Asp Leu Ala Ala
            100

<210> SEQ ID NO 13
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Arg Cys Glu Val Val Met Gly Asn Leu Glu Ile Val Leu Thr Gly

```
                1               5                   10                  15
            His Asn Ala Asp Leu Ser Phe Leu Gln Trp Ile Arg Glu Val Thr Gly
                            20                  25                  30
            Tyr Val Leu Val Ala Met Asn Glu Phe Ser Thr Leu Pro Leu Pro Asn
                            35                  40                  45
            Leu Arg Met Val Arg Gly Thr Gln Val Tyr Asp Gly Lys Phe Ala Ile
                            50                  55                  60
            Phe Val Met Leu Asn Tyr Asn Thr Asn Ser Ser His Ala Leu Arg Gln
            65                          70                  75                  80
            Leu Arg Leu Thr Gln Leu Thr Glu Ile Leu Ser Gly Gly Val Tyr Ile
                            85                  90                  95
            Glu Lys Asn Asp Lys
                            100

<210> SEQ ID NO 14
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

His Leu Met Ala Lys Ala Gly Leu Thr Leu Gln Gln Gln His Gln Arg
            1               5                   10                  15
            Leu Ala Gln Leu Leu Ile Leu Ser His Ile Arg His Met Ser Asn
                            20                  25                  30
            Lys Gly Met Glu His Leu Tyr Ser Met Lys Cys Lys Asn Val Val Pro
                            35                  40                  45
            Leu Tyr Gly Leu Leu Leu Glu Met Leu Asp Ala His Arg Leu His Ala
                            50                  55                  60
            Pro Thr Ser Arg Gly Gly Ala Ser Val Glu Glu Thr Asp Gln Ser His
            65                          70                  75                  80
            Leu Ala Thr Ala Gly Ser Thr Ser Ser His Ser Leu Gln Lys Tyr Tyr
                            85                  90                  95
            Ile Thr Gly Glu Ala
                            100

<210> SEQ ID NO 15
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asn Gln Gly Lys Cys Val Glu Gly Met Val Glu Ile Phe Asp Met Leu
            1               5                   10                  15
            Leu Ala Thr Ser Ser Arg Phe Arg Met Met Asn Leu Gln Gly Glu Glu
                            20                  25                  30
            Phe Val Cys Leu Lys Ser Ile Ile Leu Leu Asn Ser Gly Val Tyr Thr
                            35                  40                  45
            Phe Leu Pro Ser Thr Leu Lys Ser Leu Glu Glu Lys Asp His Ile His
                            50                  55                  60
            Arg Val Leu Asp Lys Ile Thr Asp Thr Leu Ile His Leu Met Ala Lys
            65                          70                  75                  80
            Ala Gly Leu Thr Leu Gln Gln Gln His Gln Arg Leu Ala Gln Leu Leu
```

```
                    85                  90                  95

Leu Ile Leu Ser His
            100

<210> SEQ ID NO 16
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ile His Leu Met Ala Lys Ala Gly Leu Thr Leu Gln Gln Gln His Gln
1               5                   10                  15

Arg Leu Ala Gln Leu Leu Leu Ile Leu Ser His Ile Arg His Met Ser
            20                  25                  30

Asn Lys Gly Met Glu His Leu Tyr Ser Met Lys Cys Lys Asn Val Val
        35                  40                  45

Pro Leu Cys Asp Leu Leu Leu Glu Met Leu Asp Ala His Arg Leu His
    50                  55                  60

Ala Pro Thr Ser Arg Gly Gly Ala Ser Val Glu Glu Thr Asp Gln Ser
65                  70                  75                  80

His Leu Ala Thr Ala Gly Ser Thr Ser Ser His Ser Leu Gln Lys Tyr
                85                  90                  95

Tyr Ile Thr Gly Glu
            100

<210> SEQ ID NO 17
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ile His Leu Met Ala Lys Ala Gly Leu Thr Leu Gln Gln Gln His Gln
1               5                   10                  15

Arg Leu Ala Gln Leu Leu Leu Ile Leu Ser His Ile Arg His Met Ser
            20                  25                  30

Asn Lys Gly Met Glu His Leu Tyr Ser Met Lys Cys Lys Asn Val Val
        35                  40                  45

Pro Leu Asn Asp Leu Leu Leu Glu Met Leu Asp Ala His Arg Leu His
    50                  55                  60

Ala Pro Thr Ser Arg Gly Gly Ala Ser Val Glu Glu Thr Asp Gln Ser
65                  70                  75                  80

His Leu Ala Thr Ala Gly Ser Thr Ser Ser His Ser Leu Gln Lys Tyr
                85                  90                  95

Tyr Ile Thr Gly Glu
            100

<210> SEQ ID NO 18
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

```
Ile His Leu Met Ala Lys Ala Gly Leu Thr Leu Gln Gln Gln His Gln
1               5                   10                  15

Arg Leu Ala Gln Leu Leu Leu Ile Leu Ser His Ile Arg His Met Ser
                20                  25                  30

Asn Lys Gly Met Glu His Leu Tyr Ser Met Lys Cys Lys Asn Val Val
            35                  40                  45

Pro Leu Ser Asp Leu Leu Leu Glu Met Leu Asp Ala His Arg Leu His
        50                  55                  60

Ala Pro Thr Ser Arg Gly Gly Ala Ser Val Glu Glu Thr Asp Gln Ser
65                  70                  75                  80

His Leu Ala Thr Ala Gly Ser Thr Ser Ser His Ser Leu Gln Lys Tyr
                85                  90                  95

Tyr Ile Thr Gly Glu
            100

<210> SEQ ID NO 19
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

His Arg Ile Gly Gly Ile Lys Leu Arg His Gln Gln Trp Ser Leu Val
1               5                   10                  15

Met Glu Ser Val Val Pro Ser Asp Arg Gly Asn Tyr Thr Cys Val Val
                20                  25                  30

Glu Asn Lys Phe Gly Ser Ile Arg Gln Thr Tyr Thr Leu Asp Val Leu
            35                  40                  45

Glu Arg Cys Pro His Arg Pro Ile Leu Gln Ala Gly Leu Pro Ala Asn
        50                  55                  60

Gln Thr Ala Val Leu Gly Ser Asp Val Glu Phe His Cys Lys Val Tyr
65                  70                  75                  80

Ser Asp Ala Gln Pro His Ile Gln Trp Leu Lys His Val Glu Val Asn
                85                  90                  95

Gly Ser Lys Val Gly
            100

<210> SEQ ID NO 20
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Val Lys Leu Ser Asp Ser Arg Ile Ala Leu Lys Ser Gly Tyr Gly
1               5                   10                  15

Lys Tyr Leu Gly Ile Asn Ser Asp Glu Leu Val Gly His Ser Asp Ala
                20                  25                  30

Ile Gly Pro Arg Glu Gln Trp Glu Pro Val Phe Gln Asn Gly Lys Met
            35                  40                  45

Ala Leu Ser Ala Ser Asn Ser Cys Phe Ile Arg Cys Asn Glu Ala Gly
        50                  55                  60

Asp Ile Glu Ala Lys Ser Lys Thr Ala Gly Glu Glu Met Ile Lys
65                  70                  75                  80
```

Ile Arg Ser Cys Ala Glu Lys Glu Thr Lys Lys Asp Asp Ile Pro
                85                  90                  95

Glu Glu Asp Lys Gly
            100

<210> SEQ ID NO 21
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Ser Gly Ala Phe Gly Thr Val Tyr Lys Gly Ile Trp Ile Pro Asp
1               5                   10                  15

Gly Glu Asn Val Lys Ile Pro Val Ala Ile Lys Val Leu Arg Glu Asn
                20                  25                  30

Thr Ser Pro Lys Ala Asn Lys Glu Ile Leu Asp Glu Ala Tyr Val Met
            35                  40                  45

Ala Gly Leu Gly Ser Pro Tyr Val Ser Arg Leu Leu Gly Ile Cys Leu
        50                  55                  60

Thr Ser Thr Val Gln Leu Val Thr Gln Leu Met Pro Tyr Gly Cys Leu
65                  70                  75                  80

Leu Asp His Val Arg Glu Asn Arg Gly Leu Gly Ser Gln Asp Leu
                85                  90                  95

Leu Asn Trp Cys Met
            100

<210> SEQ ID NO 22
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Arg Val Glu Glu Phe Lys Leu Lys Gln Met Trp Lys Ser Pro Asn Gly
1               5                   10                  15

Thr Ile Arg Asn Ile Leu Gly Gly Thr Val Phe Arg Glu Ala Ile Ile
                20                  25                  30

Cys Lys Asn Ile Pro Arg Leu Val Ser Gly Trp Val Lys Pro Ile Ile
            35                  40                  45

Ile Gly His His Ala Tyr Gly Asp Gln Tyr Arg Ala Thr Asp Phe Val
        50                  55                  60

Val Pro Gly Pro Gly Lys Val Glu Ile Thr Tyr Thr Pro Ser Asp Gly
65                  70                  75                  80

Thr Gln Lys Val Thr Tyr Leu Val His Asn Phe Glu Glu Gly Gly Gly
                85                  90                  95

Val Ala Met Gly Met
            100

<210> SEQ ID NO 23
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Arg Val Glu Glu Phe Lys Leu Lys Gln Met Trp Lys Ser Pro Asn Gly
1               5                   10                  15

Thr Ile Arg Asn Ile Leu Gly Gly Thr Val Phe Arg Glu Ala Ile Ile
            20                  25                  30

Cys Lys Asn Ile Pro Arg Leu Val Ser Gly Trp Val Lys Pro Ile Ile
            35                  40                  45

Ile Gly Cys His Ala Tyr Gly Asp Gln Tyr Arg Ala Thr Asp Phe Val
        50                  55                  60

Val Pro Gly Pro Gly Lys Val Glu Ile Thr Tyr Thr Pro Ser Asp Gly
65                  70                  75                  80

Thr Gln Lys Val Thr Tyr Leu Val His Asn Phe Glu Glu Gly Gly Gly
                85                  90                  95

Val Ala Met Gly Met
            100

<210> SEQ ID NO 24
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Arg Val Glu Glu Phe Lys Leu Lys Gln Met Trp Lys Ser Pro Asn Gly
1               5                   10                  15

Thr Ile Arg Asn Ile Leu Gly Gly Thr Val Phe Arg Glu Ala Ile Ile
            20                  25                  30

Cys Lys Asn Ile Pro Arg Leu Val Ser Gly Trp Val Lys Pro Ile Ile
            35                  40                  45

Ile Gly Gly His Ala Tyr Gly Asp Gln Tyr Arg Ala Thr Asp Phe Val
        50                  55                  60

Val Pro Gly Pro Gly Lys Val Glu Ile Thr Tyr Thr Pro Ser Asp Gly
65                  70                  75                  80

Thr Gln Lys Val Thr Tyr Leu Val His Asn Phe Glu Glu Gly Gly Gly
                85                  90                  95

Val Ala Met Gly Met
            100

<210> SEQ ID NO 25
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Arg Val Glu Glu Phe Lys Leu Lys Gln Met Trp Lys Ser Pro Asn Gly
1               5                   10                  15

Thr Ile Arg Asn Ile Leu Gly Gly Thr Val Phe Arg Glu Ala Ile Ile
            20                  25                  30

Cys Lys Asn Ile Pro Arg Leu Val Ser Gly Trp Val Lys Pro Ile Ile
            35                  40                  45

Ile Gly Ser His Ala Tyr Gly Asp Gln Tyr Arg Ala Thr Asp Phe Val
        50                  55                  60

```
Val Pro Gly Pro Gly Lys Val Glu Ile Thr Tyr Thr Pro Ser Asp Gly
65                  70                  75                  80

Thr Gln Lys Val Thr Tyr Leu Val His Asn Phe Glu Glu Gly Gly Gly
                85                  90                  95

Val Ala Met Gly Met
            100

<210> SEQ ID NO 26
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Val Ala Val Lys Met Leu Lys Pro Ser Ala His Leu Thr Glu Arg Glu
1               5                   10                  15

Ala Leu Met Ser Glu Leu Lys Val Leu Ser Tyr Leu Gly Asn His Met
                20                  25                  30

Asn Ile Val Asn Leu Leu Gly Ala Cys Thr Ile Gly Gly Pro Thr Leu
            35                  40                  45

Val Ile Ile Glu Tyr Cys Cys Tyr Gly Asp Leu Leu Asn Phe Leu Arg
50                  55                  60

Arg Lys Arg Asp Ser Phe Ile Cys Ser Lys Gln Glu Asp His Ala Glu
65                  70                  75                  80

Ala Ala Leu Tyr Lys Asn Leu Leu His Ser Lys Glu Ser Ser Cys Ser
                85                  90                  95

Asp Ser Thr Asn Glu
            100

<210> SEQ ID NO 27
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Glu Ala Thr Ala Tyr Gly Leu Ile Lys Ser Asp Ala Ala Met Thr
1               5                   10                  15

Val Ala Val Lys Met Leu Lys Pro Ser Ala His Leu Thr Glu Arg Glu
                20                  25                  30

Ala Leu Met Ser Glu Leu Lys Val Leu Ser Tyr Leu Gly Asn His Met
            35                  40                  45

Asn Ile Ala Asn Leu Leu Gly Ala Cys Thr Ile Gly Gly Pro Thr Leu
50                  55                  60

Val Ile Thr Glu Tyr Cys Cys Tyr Gly Asp Leu Leu Asn Phe Leu Arg
65                  70                  75                  80

Arg Lys Arg Asp Ser Phe Ile Cys Ser Lys Gln Glu Asp His Ala Glu
                85                  90                  95

Ala Ala Leu Tyr Lys
            100

<210> SEQ ID NO 28
<211> LENGTH: 101
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 28

Ile Ser Glu Leu Gly Ala Gly Asn Gly Gly Val Val Phe Lys Val Ser
1               5                   10                  15

His Lys Pro Ser Gly Leu Val Met Ala Arg Lys Leu Ile His Leu Glu
            20                  25                  30

Ile Lys Pro Ala Ile Arg Asn Gln Ile Ile Arg Glu Leu Gln Val Leu
        35                  40                  45

His Glu Ser Asn Ser Pro Tyr Ile Val Gly Phe Tyr Gly Ala Phe Tyr
    50                  55                  60

Ser Asp Gly Glu Ile Ser Ile Cys Met Glu His Met Asp Gly Gly Ser
65                  70                  75                  80

Leu Asp Gln Val Leu Lys Lys Ala Gly Arg Ile Pro Glu Gln Ile Leu
                85                  90                  95

Gly Lys Val Ser Ile
            100

<210> SEQ ID NO 29
<211> LENGTH: 101
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 29

Leu Gly Ala Gly Asn Gly Gly Val Val Phe Lys Val Ser His Lys Pro
1               5                   10                  15

Ser Gly Leu Val Met Ala Arg Lys Leu Ile His Leu Glu Ile Lys Pro
            20                  25                  30

Ala Ile Arg Asn Gln Ile Ile Arg Glu Leu Gln Val Leu His Glu Cys
        35                  40                  45

Asn Ser Leu Tyr Ile Val Gly Phe Tyr Gly Ala Phe Tyr Ser Asp Gly
    50                  55                  60

Glu Ile Ser Ile Cys Met Glu His Met Asp Gly Gly Ser Leu Asp Gln
65                  70                  75                  80

Val Leu Lys Lys Ala Gly Arg Ile Pro Glu Gln Ile Leu Gly Lys Val
                85                  90                  95

Ser Ile Ala Val Ile
            100

<210> SEQ ID NO 30
<211> LENGTH: 89
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 30

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Asn Phe Tyr
            20                  25                  30

Gln Gln Gln Gln Gln Ser Asp Leu Gln Pro Ala Pro Ser Glu Asp
        35                  40                  45

Ile Trp Lys Lys Phe Glu Leu Leu Pro Thr Pro Pro Leu Ser Pro Ser

Arg Arg Ser Gly Leu Cys Ser Pro Ser Tyr Val Ala Val Thr Pro Phe
65                  70                  75                  80

Ser Leu Arg Gly Asp Asn Asp Gly Gly
                85

<210> SEQ ID NO 31
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Phe Thr Asn Arg Asn Tyr Asp Leu Asp Tyr Asp Ser Val Gln Pro Tyr
1               5                   10                  15

Phe Tyr Cys Asp Glu Glu Glu Asn Phe Tyr Gln Gln Gln Gln Gln Ser
                20                  25                  30

Glu Leu Gln Pro Pro Ala Pro Ser Glu Asp Ile Trp Lys Lys Phe Glu
            35                  40                  45

Leu Leu Ser Thr Pro Pro Leu Ser Pro Ser Arg Arg Ser Gly Leu Cys
        50                  55                  60

Ser Pro Ser Tyr Val Ala Val Thr Pro Phe Ser Leu Arg Gly Asp Asn
65                  70                  75                  80

Asp Gly Gly Gly Gly Ser Phe Ser Thr Ala Asp Gln Leu Glu Met Val
                85                  90                  95

Thr Glu Leu Leu Gly
            100

<210> SEQ ID NO 32
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Thr Asn Arg Asn Tyr Asp Leu Asp Tyr Asp Ser Val Gln Pro Tyr Phe
1               5                   10                  15

Tyr Cys Asp Glu Glu Glu Asn Phe Tyr Gln Gln Gln Gln Gln Ser Glu
                20                  25                  30

Leu Gln Pro Pro Ala Pro Ser Glu Asp Ile Trp Lys Lys Phe Glu Leu
            35                  40                  45

Leu Pro Ile Pro Pro Leu Ser Pro Ser Arg Arg Ser Gly Leu Cys Ser
        50                  55                  60

Pro Ser Tyr Val Ala Val Thr Pro Phe Ser Leu Arg Gly Asp Asn Asp
65                  70                  75                  80

Gly Gly Gly Gly Ser Phe Ser Thr Ala Asp Gln Leu Glu Met Val Thr
                85                  90                  95

Glu Leu Leu Gly Gly
            100

<210> SEQ ID NO 33
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Val Ala Val Lys Met Leu Lys Pro Thr Ala Arg Ser Ser Glu Lys Gln
1               5                   10                  15

Ala Leu Met Ser Glu Leu Lys Ile Met Thr His Leu Gly Pro His Leu
            20                  25                  30

Asn Ile Val Asn Leu Leu Gly Ala Cys Thr Lys Ser Gly Pro Ile Tyr
        35                  40                  45

Ile Ile Ile Glu Tyr Cys Phe Tyr Gly Asp Leu Val Asn Tyr Leu His
    50                  55                  60

Lys Asn Arg Asp Ser Phe Leu Ser His His Pro Glu Lys Pro Lys Lys
65                  70                  75                  80

Glu Leu Asp Ile Phe Gly Leu Asn Pro Ala Asp Glu Ser Thr Arg Ser
                85                  90                  95

Tyr Val Ile Leu Ser
            100

<210> SEQ ID NO 34
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ile Glu Glu His Ala Asn Trp Ser Val Ser Arg Glu Ala Gly Phe Ser
1               5                   10                  15

Tyr Ser His Ala Gly Leu Ser Asn Arg Leu Ala Arg Asp Asn Glu Leu
            20                  25                  30

Arg Glu Asn Asp Lys Glu Gln Leu Lys Ala Ile Ser Thr Arg Asp Pro
        35                  40                  45

Leu Ser Lys Ile Thr Glu Gln Glu Lys Asp Phe Leu Trp Ser His Arg
    50                  55                  60

His Tyr Cys Val Thr Ile Pro Glu Ile Leu Pro Lys Leu Leu Leu Ser
65                  70                  75                  80

Val Lys Trp Asn Ser Arg Asp Glu Val Ala Gln Met Tyr Cys Leu Val
                85                  90                  95

Lys Asp Trp Pro Pro
            100

<210> SEQ ID NO 35
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

His Ala Asn Trp Ser Val Ser Arg Glu Ala Gly Phe Ser Tyr Ser His
1               5                   10                  15

Ala Gly Leu Ser Asn Arg Leu Ala Arg Asp Asn Glu Leu Arg Glu Asn
            20                  25                  30

Asp Lys Glu Gln Leu Lys Ala Ile Ser Thr Arg Asp Pro Leu Ser Glu
        35                  40                  45

Ile Thr Lys Gln Glu Lys Asp Phe Leu Trp Ser His Arg His Tyr Cys
    50                  55                  60

```
Val Thr Ile Pro Glu Ile Leu Pro Lys Leu Leu Ser Val Lys Trp
 65                  70                  75                  80

Asn Ser Arg Asp Glu Val Ala Gln Met Tyr Cys Leu Val Lys Asp Trp
                 85                  90                  95

Pro Pro Ile Lys Pro
            100

<210> SEQ ID NO 36
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Leu Phe Ile Asn Leu Phe Ser Met Met Leu Gly Ser Gly Met Pro Glu
  1               5                  10                  15

Leu Gln Ser Phe Asp Asp Ile Ala Tyr Ile Arg Lys Thr Leu Ala Leu
                 20                  25                  30

Asp Lys Thr Glu Gln Glu Ala Leu Glu Tyr Phe Met Lys Gln Met Asn
             35                  40                  45

Asp Ala Arg His Gly Gly Trp Thr Thr Lys Met Asp Trp Ile Phe His
         50                  55                  60

Thr Ile Lys Gln His Ala Leu Asn
 65                  70

<210> SEQ ID NO 37
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Arg Gly Gly Val Ile Thr Asp Glu Glu Thr Ser Lys Lys Ile
  1               5                  10                  15

Ala Asp Gln Leu Asp Asn Ile Val Asp Met Arg Glu Tyr Asp Val Pro
                 20                  25                  30

Tyr His Ile Arg Leu Ser Ile Asp Ile Glu Thr Thr Lys Leu Pro Leu
             35                  40                  45

Lys Phe Arg Asp Ala Glu Thr Asp Gln Ile Met Met Ile Ser Tyr Met
         50                  55                  60

Ile Asp Gly Gln Gly Tyr Leu Ile Thr Asn Arg Glu Ile Val Ser Glu
 65                  70                  75                  80

Asp Ile Glu Asp Phe Glu Phe Thr Pro Lys Pro Glu Tyr Glu Gly Pro
                 85                  90                  95

Phe Cys Val Phe Asn
            100

<210> SEQ ID NO 38
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38
```

```
Lys Phe Asn Cys Arg Val Ala Gln Tyr Pro Phe Glu Asp His Asn Pro
1               5                   10                  15

Pro Gln Leu Glu Leu Ile Lys Pro Phe Cys Glu Asp Leu Asp Gln Trp
            20                  25                  30

Leu Ser Glu Asp Asp Asn His Val Ala Ala Ile His Cys Lys Ala Gly
        35                  40                  45

Lys Gly Gln Thr Gly Val Met Ile Cys Ala Tyr Leu Leu His Arg Gly
    50                  55                  60

Lys Phe Leu Lys Ala Gln Glu Ala Leu Asp Phe Tyr Gly Glu Val Arg
65                  70                  75                  80

Thr Arg Asp Lys Lys Gly Val Thr Ile Pro Ser Gln Arg Arg Tyr Val
                85                  90                  95

Tyr Tyr Tyr Ser Tyr
            100
```

<210> SEQ ID NO 39
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Ser Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Val Gly Glu Thr
65                  70                  75
```

<210> SEQ ID NO 40
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ile Arg Val Glu Gly Asn Leu Arg Val Glu Tyr Leu Asp Asp Arg Asn
1               5                   10                  15

Thr Phe Arg His Ser Val Val Val Pro Tyr Glu Pro Pro Glu Val Gly
            20                  25                  30

Ser Asp Cys Thr Thr Ile His Tyr Asn Tyr Met Cys Asn Ser Ser Cys
        35                  40                  45

Met Gly Ser Met Asn Arg Arg Pro Ile Leu Thr Ile Ile Thr Leu Glu
    50                  55                  60

Asp Ser Ser Gly Asn Leu Leu Gly Arg Asn Ser Phe Glu Val Arg Val
65                  70                  75                  80

Cys Ala Cys Pro Gly Arg Asp Arg Arg Thr Glu Glu Glu Asn Leu Arg
                85                  90                  95

Lys Lys Gly Glu Pro
            100
```

<210> SEQ ID NO 41
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Thr Tyr Ser Pro Ala Leu Asn Lys Met Phe Cys Gln Leu Ala Lys Thr
1               5                   10                  15

Cys Pro Val Gln Leu Trp Val Asp Ser Thr Pro Pro Gly Thr Arg
            20                  25                  30

Val Arg Ala Met Ala Ile Tyr Lys Gln Ser Gln His Met Thr Glu Val
        35                  40                  45

Val Arg His Cys Pro His Glu Arg Cys Ser Asp Ser Asp Gly Leu
    50                  55                  60

Ala Pro Pro Gln His Leu Ile Arg Val Glu Gly Asn Leu Arg Val Glu
65                  70                  75                  80

Tyr Leu Asp Asp Arg Asn Thr Phe Arg His Ser Val Val Pro Tyr
                85                  90                  95

Glu Pro Pro Glu Val
            100
```

<210> SEQ ID NO 42
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Glu Gly Asn Leu Arg Val Glu Tyr Leu Asp Asp Arg Asn Thr Phe Arg
1               5                   10                  15

His Ser Val Val Val Pro Tyr Glu Pro Pro Glu Val Gly Ser Asp Cys
            20                  25                  30

Thr Thr Ile His Tyr Asn Tyr Met Cys Asn Ser Ser Cys Met Gly Gly
        35                  40                  45

Met Asn Gln Arg Pro Ile Leu Thr Ile Ile Thr Leu Glu Asp Ser Ser
    50                  55                  60

Gly Asn Leu Leu Gly Arg Asn Ser Phe Glu Val Arg Val Cys Ala Cys
65                  70                  75                  80

Pro Gly Arg Asp Arg Arg Thr Glu Glu Glu Asn Leu Arg Lys Lys Gly
                85                  90                  95

Glu Pro His His Glu
            100
```

<210> SEQ ID NO 43
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Glu Gly Asn Leu Arg Val Glu Tyr Leu Asp Asp Arg Asn Thr Phe Arg
1               5                   10                  15

His Ser Val Val Val Pro Tyr Glu Pro Pro Glu Val Gly Ser Asp Cys
```

```
                 20                  25                  30

Thr Thr Ile His Tyr Asn Tyr Met Cys Asn Ser Ser Cys Met Gly Gly
             35                  40                  45

Met Asn Trp Arg Pro Ile Leu Thr Ile Ile Thr Leu Glu Asp Ser Ser
         50                  55                  60

Gly Asn Leu Leu Gly Arg Asn Ser Phe Glu Val Arg Val Cys Ala Cys
 65                  70                  75                  80

Pro Gly Arg Asp Arg Arg Thr Glu Glu Glu Asn Leu Arg Lys Lys Gly
                 85                  90                  95

Glu Pro His His Glu
            100
```

<210> SEQ ID NO 44
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Pro Glu Val Gly Ser Asp Cys Thr Thr Ile His Tyr Asn Tyr Met Cys
 1               5                  10                  15

Asn Ser Ser Cys Met Gly Gly Met Asn Arg Arg Pro Ile Leu Thr Ile
             20                  25                  30

Ile Thr Leu Glu Asp Ser Ser Gly Asn Leu Leu Gly Arg Asn Ser Phe
         35                  40                  45

Glu Val Cys Val Cys Ala Cys Pro Gly Arg Asp Arg Arg Thr Glu Glu
     50                  55                  60

Glu Asn Leu Arg Lys Lys Gly Glu Pro His His Glu Leu Pro Pro Gly
 65                  70                  75                  80

Ser Thr Lys Arg Ala Leu Pro Asn Asn Thr Ser Ser Ser Pro Gln Pro
                 85                  90                  95

Lys Lys Lys Pro Leu
            100
```

<210> SEQ ID NO 45
<211> LENGTH: 53
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Gly Val Glu Pro Cys Tyr Gly Asp Lys Asp Lys Arg Arg His Cys Phe
 1               5                  10                  15

Ala Thr Trp Lys Asn Ile Ser Gly Ser Ile Glu Ile Val Lys Gln Gly
             20                  25                  30

Cys Trp Leu Asp Asp Ile Asn Cys Tyr Asp Arg Thr Asp Cys Val Glu
         35                  40                  45

Lys Lys Arg Gln Pro
     50
```

<210> SEQ ID NO 46
<211> LENGTH: 103
<212> TYPE: PRT
<213> ORGANISM: Artificial Sequence
<220> FEATURE:
<223> OTHER INFORMATION: Description of Artificial Sequence: Synthetic

```
        polypeptide

<400> SEQUENCE: 46

Gly Val Glu Pro Cys Tyr Gly Asp Lys Asp Lys Arg Arg His Cys Phe
1               5                   10                  15

Ala Thr Trp Lys Asn Ile Ser Gly Ser Ile Glu Ile Val Lys Gln Gly
            20                  25                  30

Cys Trp Leu Asp Asp Ile Asn Cys Tyr Asp Arg Thr Asp Cys Val Glu
        35                  40                  45

Lys Lys Thr Ala Leu Lys Tyr Ile Phe Val Ala Val Arg Ala Ile Cys
    50                  55                  60

Val Met Lys Ser Phe Leu Ile Phe Arg Arg Trp Lys Ser His Ser Pro
65                  70                  75                  80

Leu Gln Ile Gln Leu His Leu Ser His Pro Ile Thr Thr Ser Cys Ser
                85                  90                  95

Ile Pro Trp Cys His Leu Cys
            100

<210> SEQ ID NO 47
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Thr Ala Glu Ala Val Asn Val Ala Ile Ala Pro Pro Ser Glu Gly
1               5                   10                  15

Glu Ala Asn Ala Glu Leu Cys Arg Tyr Leu Ser Lys Val Leu Glu Leu
            20                  25                  30

Arg Lys Ser Asp Val Val Leu Asp Lys Val Gly Leu Ala Leu Phe Phe
        35                  40                  45

Phe Phe Phe Glu Thr Lys Ser Cys Ser Val Ala Gln Ala Gly Val Gln
    50                  55                  60

Trp Arg Ser Leu Gly Ser Leu Gln Pro Pro Pro Gly Phe Lys Leu
65                  70                  75                  80

Phe Ser Cys Leu Ser Phe Leu Ser Ser Trp Asp Tyr Arg Arg Met Pro
                85                  90                  95

Pro Cys Leu Ala Asn Phe Cys Ile Phe Asn Arg Asp Gly Val Ser Pro
            100                 105                 110

Cys Trp Ser Gly Trp Ser
        115

<210> SEQ ID NO 48
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Ser Val Ile Ile Phe Phe Phe Val Tyr Ile Trp His Trp Ala Leu
1               5                   10                  15

Pro Leu Ile Leu Asn Asn His His Ile Cys Leu Met Ser Ser Ile Ile
            20                  25                  30

Leu Asp Cys Asn Ser Val Arg Gln Ser Ile Met Ser Val Cys Phe Phe
        35                  40                  45
```

```
Phe Phe Ser Val Ile Phe Ser Thr Arg Cys Leu Thr Asp Ser Arg Tyr
    50                  55                  60

Pro Asn Ile Cys Trp Phe Lys
65                  70

<210> SEQ ID NO 49
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Leu Ser Val Ile Ile Phe Phe Val Tyr Ile Trp His Trp Ala Leu
1               5                   10                  15

Pro Leu Ile Leu Asn Asn His His Ile Cys Leu Met Ser Ser Ile Ile
                20                  25                  30

Leu Asp Cys Asn Ser Val Arg Gln Ser Ile Met Ser Val Cys Phe Phe
                35                  40                  45

Phe Phe Cys Tyr Ile Leu Asn Thr Met Phe Asp Arg
    50                  55                  60

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Val Leu Val Leu Ser Cys Asp Leu Ile Thr Asp Val Ala Leu His Glu
1               5                   10                  15

Val Val Asp Leu Phe Arg Ala Tyr Asp Ala Ser Leu Ala Met Leu Met
                20                  25                  30

Arg Lys Gly Gln Asp Ser Ile Glu Pro Val Pro Gly Gln Lys Gly Lys
            35                  40                  45

Lys Lys Gln Trp Ser Ser Val Thr Ser Leu Glu Trp Thr Ala Gln Glu
        50                  55                  60

Arg Gly Cys Ser Ser Trp Leu Met Lys Gln Thr Trp Met Lys Ser Trp
65                  70                  75                  80

Ser Leu Arg Asp Pro Ser Tyr Arg Ser Ile Leu Glu Tyr Val Ser Thr
                85                  90                  95

Arg Val Leu Trp Met Pro Thr Ser Thr Val
                100                 105

<210> SEQ ID NO 51
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ser Ile Gln Val Met Arg Ala Gln Met Asn Gln Ile Gln Ser Val Glu
1               5                   10                  15

Gly Gln Pro Leu Ala Arg Arg Pro Arg Ala Thr Gly Arg Thr Lys Arg
                20                  25                  30
```

```
Cys Gln Pro Arg Asp Val Thr Lys Thr Cys Asn Ser Asn Asp Gly
            35                  40                  45

Lys Lys Arg Glu Trp Glu Lys Arg Lys Gln Ile Leu Gly Gly Gly
 50                  55                  60

Lys Tyr Lys Glu Tyr Phe Leu Lys Arg Ile Leu Ile Arg Lys Ala Met
 65                  70                  75                  80

Thr Val Leu Ala Gly Asp Lys Lys Gly Leu Gly Arg Phe Met Arg Cys
                     85                  90                  95

Val Gln Ser Glu Thr Lys Ala Val Ser Leu Gln Leu Pro Leu Gly Arg
                100                 105                 110
```

<210> SEQ ID NO 52
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Leu Asp Phe Leu Gly Glu Phe Ala Thr Asp Ile Arg Thr His Gly Val
 1               5                  10                  15

His Met Val Leu Asn His Gln Gly Arg Pro Ser Gly Asp Ala Phe Ile
                20                  25                  30

Gln Met Lys Ser Ala Asp Arg Ala Phe Met Ala Ala Gln Lys Cys His
            35                  40                  45

Lys Lys Lys His Glu Gly Gln Ile Cys
 50                  55
```

<210> SEQ ID NO 53
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Leu Asp Phe Leu Gly Glu Phe Ala Thr Asp Ile Arg Thr His Gly Val
 1               5                  10                  15

His Met Val Leu Asn His Gln Gly Arg Pro Ser Gly Asp Ala Phe Ile
                20                  25                  30

Gln Met Lys Ser Ala Asp Arg Ala Phe Met Ala Ala Gln Lys Cys His
            35                  40                  45

Lys Lys Thr
 50
```

<210> SEQ ID NO 54
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gly Ala Leu Cys Lys Asp Gly Arg Phe Arg Ser Asp Ile Gly Glu Phe
 1               5                  10                  15

Glu Trp Lys Leu Lys Glu Gly His Lys Lys Ile Tyr Gly Lys Gln Ser
                20                  25                  30

Met Val Asp Glu Val Ser Gly Lys Val Leu Glu Met Asp Ile Ser Lys
```

```
                35                  40                  45
Lys Lys His Tyr Asn Arg Lys Ile Ser Ile Lys Lys Leu Asn Arg Met
    50                  55                  60
Lys Val Pro Leu Met Lys Leu Ile Thr Arg Val
65                  70                  75

<210> SEQ ID NO 55
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Arg Glu Arg Ala Gln Leu Leu Glu Gln Glu Lys Thr Leu Thr Ser
1               5                  10                  15

Lys Leu Gln Glu Gln Ala Arg Val Leu Lys Glu Arg Cys Gln Gly Glu
                20                  25                  30

Ser Thr Gln Leu Gln Asn Glu Ile Gln Lys Leu Gln Lys Thr Leu Lys
            35                  40                  45

Lys Lys Pro Arg Asp Ile Cys Arg Ile Ser
        50                  55

<210> SEQ ID NO 56
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Val Asn Thr Leu Lys Glu Gly Lys Arg Leu Pro Cys Pro Pro Asn Cys
1               5                  10                  15

Pro Asp Glu Val Tyr Gln Leu Met Arg Lys Cys Trp Glu Phe Gln Pro
                20                  25                  30

Ser Asn Arg Thr Ser Phe Gln Asn Leu Ile Glu Gly Phe Glu Ala Leu
            35                  40                  45

Leu Lys Thr Ser Asn
        50

<210> SEQ ID NO 57
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Cys Arg Pro Val Thr Pro Ser Cys Lys Glu Leu Ala Asp Leu Met Thr
1               5                  10                  15

Arg Cys Met Asn Tyr Asp Pro Asn Gln Arg Pro Phe Phe Arg Ala Ile
                20                  25                  30

Met Arg Asp Ile Asn Lys Leu Glu Glu Gln Asn Pro Asp Ile Val Ser
            35                  40                  45

Glu Lys Asn Gln Gln Leu Lys Trp Thr Pro His Ile Leu Lys Ser Ala
        50                  55                  60

Ser
65
```

<210> SEQ ID NO 58
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Asp His Asp Val Leu Ser Phe Leu Thr Phe Gln Leu Thr Glu Pro
1               5                   10                  15

Gly Lys Glu Pro Pro Thr Pro Asp Lys Glu Ile Ser Glu Lys Glu Lys
            20                  25                  30

Glu Lys Tyr Gln Glu Glu Phe Glu His Phe Gln Gln Glu Leu Asp Lys
        35                  40                  45

Lys Lys Arg Gly Ile Pro Glu Gly Pro Pro Arg Pro Pro Arg Ala Ala
    50                  55                  60

Cys Gly Gly Asn Ile
65

<210> SEQ ID NO 59
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Asp His Asp Val Leu Ser Phe Leu Thr Phe Gln Leu Thr Glu Pro
1               5                   10                  15

Gly Lys Glu Pro Pro Thr Pro Asp Lys Glu Ile Ser Glu Lys Glu Lys
            20                  25                  30

Glu Lys Tyr Gln Glu Glu Phe Glu His Phe Gln Gln Glu Leu Asp Lys
        35                  40                  45

Lys Lys Arg Asn Ser Arg Arg Ala Thr Pro Thr Ser Lys Gly Ser Leu
    50                  55                  60

Arg Arg Lys Tyr Leu Arg Val
65                  70

<210> SEQ ID NO 60
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Thr Lys Ser Thr Leu Ile Gly Glu Asp Val Asn Pro Leu Ile Lys Leu
1               5                   10                  15

Asp Asp Ala Val Asn Val Asp Glu Ile Met Thr Asp Thr Ser Thr Ser
            20                  25                  30

Tyr Leu Leu Cys Ile Ser Glu Asn Lys Glu Asn Val Arg Asp Lys Lys
        35                  40                  45

Lys Gly Gln His Phe Tyr Trp His Cys Gly Ser Ala Ala Cys His Arg
    50                  55                  60

Arg Gly Cys Val
65

<210> SEQ ID NO 61
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Leu Tyr Thr Lys Ser Thr Leu Ile Gly Glu Asp Val Asn Pro Leu Ile
1               5                   10                  15

Lys Leu Asp Asp Ala Val Asn Val Asp Glu Ile Met Thr Asp Thr Ser
                20                  25                  30

Thr Ser Tyr Leu Leu Cys Ile Ser Glu Asn Lys Glu Asn Val Arg Asp
            35                  40                  45

Lys Lys Arg Ala Thr Phe Leu Leu Ala Leu Trp Glu Cys Ser Leu Pro
50                  55                  60

Gln Ala Arg Leu Cys Leu Ile Val Ser Arg Thr Leu Leu Leu Val Gln
65                  70                  75                  80

Ser

<210> SEQ ID NO 62
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Leu Pro Pro Pro Lys Leu Thr Asp Pro Arg Leu Leu Tyr Ile Gly Phe
1               5                   10                  15

Leu Gly Tyr Cys Ser Gly Leu Ile Asp Asn Leu Ile Arg Arg Arg Pro
                20                  25                  30

Ile Ala Thr Ala Gly Leu His Arg Gln Leu Leu Tyr Ile Thr Ala Phe
            35                  40                  45

Phe Phe Cys Trp Ile Leu Ser Cys Lys Thr
    50                  55

<210> SEQ ID NO 63
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ser Leu Pro Pro Pro Lys Leu Thr Asp Pro Arg Leu Leu Tyr Ile Gly
1               5                   10                  15

Phe Leu Gly Tyr Cys Ser Gly Leu Ile Asp Asn Leu Ile Arg Arg Arg
                20                  25                  30

Pro Ile Ala Thr Ala Gly Leu His Arg Gln Leu Leu Tyr Ile Thr Ala
            35                  40                  45

Phe Phe Leu Leu Asp Ile Ile Leu
    50                  55

<210> SEQ ID NO 64
<211> LENGTH: 112
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 64

Asn Gln Ser Gly Gly Ala Gly Glu Asp Cys Gln Ile Phe Ser Thr Pro
1               5                   10                  15

Gly His Pro Lys Met Ile Tyr Ser Ser Ser Asn Leu Lys Thr Pro Ser
            20                  25                  30

Lys Leu Cys Ser Gly Ser Lys Ser His Asp Val Gln Glu Val Leu Lys
        35                  40                  45

Lys Lys Thr Gly Ser Asn Glu Val Thr Thr Arg Tyr Glu Glu Lys Lys
50                  55                  60

Thr Gly Ser Val Arg Lys Ala Asn Arg Met Pro Lys Asp Val Asn Ile
65                  70                  75                  80

Gln Val Arg Lys Lys Gln Lys His Glu Thr Arg Arg Lys Ser Lys Tyr
                85                  90                  95

Asn Glu Asp Phe Glu Arg Ala Trp Arg Glu Asp Leu Thr Ile Lys Arg
            100                 105                 110

<210> SEQ ID NO 65
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Ala Pro Val Lys Lys Leu Val Val Lys Gly Gly Lys Lys Lys Glu
1               5                   10                  15

Ala Ser Ser Glu Val His Ser
            20

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Ala Pro Val Lys Lys Leu Val Val Lys Gly Gly Lys Lys Arg Ser
1               5                   10                  15

Lys Phe

<210> SEQ ID NO 67
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Pro Ser His Gln Gly Ala Glu Gln Gln Gln Gln His His Val
1               5                   10                  15

Phe Ile Ser Gln Val Val Thr Glu Lys Glu Phe Leu Ser Arg Ser Asp
            20                  25                  30

Gln Leu Gln Gln Ala Val Gln Ser Gln Gly Phe Ile Asn Tyr Cys Gln
        35                  40                  45
```

```
Lys Lys Asn
    50

<210> SEQ ID NO 68
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Pro Ser His Gln Gly Ala Glu Gln Gln Gln Gln His His Val
1               5                   10                  15

Phe Ile Ser Gln Val Val Thr Glu Lys Glu Phe Leu Ser Arg Ser Asp
                20                  25                  30

Gln Leu Gln Gln Ala Val Gln Ser Gln Gly Phe Ile Asn Tyr Cys Gln
            35                  40                  45

Lys Lys Leu Met Leu Leu Arg Leu Asn Leu Arg Lys Met Cys Gly Pro
    50                  55                  60

Phe
65

<210> SEQ ID NO 69
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Glu Val Phe Glu Lys Glu Gln Ser Ile Cys Ala Ala Glu Glu Gln
1               5                   10                  15

Pro Ala Glu Asp Gly Gln Gly Glu Thr Asn Lys Asn Arg Thr Lys Gly
                20                  25                  30

Gly Trp Gln Gln Lys Ser Lys Gly Pro Lys Lys Thr Ala Lys Ser Lys
            35                  40                  45

Lys Lys Glu Thr Phe Lys Lys Lys Thr Tyr Thr Cys Ala Ile Thr Thr
    50                  55                  60

Val Lys Ala Thr Glu Thr Lys Ala Gly Lys Trp Ser Arg Trp Glu
65                  70                  75

<210> SEQ ID NO 70
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Ala Glu Val Phe Glu Lys Glu Gln Ser Ile Cys Ala Ala Glu Glu
1               5                   10                  15

Gln Pro Ala Glu Asp Gly Gln Gly Glu Thr Asn Lys Asn Arg Thr Lys
                20                  25                  30

Gly Gly Trp Gln Gln Lys Ser Lys Gly Pro Lys Lys Thr Ala Lys Ser
            35                  40                  45

Lys Lys Arg Asn Leu
    50
```

```
<210> SEQ ID NO 71
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71
```

Asn Ile Met Glu Ile Arg Gln Leu Pro Ser Ser His Ala Leu Glu Ala
1               5                   10                  15

Lys Leu Ser Arg Met Ser Tyr Pro Val Lys Gln Glu Ser Ile Leu
            20                  25                  30

Lys Thr Val Gly Lys Leu Thr Ala Thr Gln Val Ala Lys Ile Ser Phe
        35                  40                  45

Phe Phe Ala Leu Cys Gly Phe Trp Gln Ile Cys His Ile Lys Lys His
    50                  55                  60

Phe Gln Thr His Lys Leu Leu
65                  70

```
<210> SEQ ID NO 72
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72
```

Tyr Glu Lys Lys Lys Tyr Tyr Asp Lys Asn Ala Ile Ala Ile Thr Asn
1               5                   10                  15

Ile Ser Ser Ser Asp Ala Pro Leu Gln Pro Leu Val Ser Ser Pro Ser
            20                  25                  30

Leu Gln Ala Ala Val Asp Lys Asn Lys Leu Glu Lys Glu Lys Glu Lys
        35                  40                  45

Lys Lys Gly Arg Glu Lys Glu Arg Lys Gly Ala Arg Lys Ala Gly Lys
    50                  55                  60

Thr Thr Tyr Ser
65

```
<210> SEQ ID NO 73
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73
```

Lys Tyr Glu Lys Lys Lys Tyr Tyr Asp Lys Asn Ala Ile Ala Ile Thr
1               5                   10                  15

Asn Ile Ser Ser Ser Asp Ala Pro Leu Gln Pro Leu Val Ser Ser Pro
            20                  25                  30

Ser Leu Gln Ala Ala Val Asp Lys Asn Lys Leu Glu Lys Glu Lys Glu
        35                  40                  45

Lys Lys Arg Lys Arg Lys Arg Glu Lys Arg Ser Gln Lys Ser Arg Gln
    50                  55                  60

Asn His Leu Gln Leu Lys Ser Cys Arg Arg Lys Ile Ser Asn Trp Ser
65                  70                  75                  80

Leu Lys Lys Val Pro Ala Leu Lys Lys Leu Arg Ser Pro Leu Trp Ile 85                  90                  95

Phe

<210> SEQ ID NO 74
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ile Tyr Gln Asp Ala Tyr Arg Ala Glu Trp Gln Val Tyr Lys Glu Glu
1               5                   10                  15

Ile Ser Arg Phe Lys Glu Gln Leu Thr Pro Ser Gln Ile Met Ser Leu
            20                  25                  30

Glu Lys Glu Ile Met Asp Lys His Leu Lys Arg Lys Ala Met Thr Lys
        35                  40                  45

Lys Lys Arg Val Asn Thr Ala Trp Lys Thr Lys Thr Ser Phe Ser
    50                  55                  60

Leu
65

<210> SEQ ID NO 75
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ile Tyr Gln Asp Ala Tyr Arg Ala Glu Trp Gln Val Tyr Lys Glu Glu
1               5                   10                  15

Ile Ser Arg Phe Lys Glu Gln Leu Thr Pro Ser Gln Ile Met Ser Leu
            20                  25                  30

Glu Lys Glu Ile Met Asp Lys His Leu Lys Arg Lys Ala Met Thr Lys
        35                  40                  45

Lys Lys Ser
    50

<210> SEQ ID NO 76
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Lys Pro Gln Glu Val Cys Val Ala Val Trp Arg Lys Asn Asp Glu Asn
1               5                   10                  15

Ile Thr Leu Glu Thr Val Cys His Asp Pro Lys Leu Pro Tyr His Asp
            20                  25                  30

Phe Ile Leu Glu Asp Ala Ala Ser Pro Lys Cys Ile Met Lys Glu Lys
        35                  40                  45

Lys Lys Ala Trp
    50

<210> SEQ ID NO 77
<211> LENGTH: 84

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Lys Pro Gln Glu Val Cys Val Ala Val Trp Arg Lys Asn Asp Glu
1               5                   10                  15

Asn Ile Thr Leu Glu Thr Val Cys His Asp Pro Lys Leu Pro Tyr His
            20                  25                  30

Asp Phe Ile Leu Glu Asp Ala Ala Ser Pro Lys Cys Ile Met Lys Glu
        35                  40                  45

Lys Lys Ser Leu Val Arg Leu Ser Ser Cys Val Pro Val Ala Leu Met
50                  55                  60

Ser Ala Met Thr Thr Ser Ser Gln Lys Asn Ile Thr Pro Ala Ile
65                  70                  75                  80

Leu Thr Cys Cys

<210> SEQ ID NO 78
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Val Pro Ser Lys Tyr Gln Phe Leu Cys Ser Asp His Phe Thr Pro Asp
1               5                   10                  15

Ser Leu Asp Ile Arg Trp Gly Ile Arg Tyr Leu Lys Gln Thr Ala Val
            20                  25                  30

Pro Thr Ile Phe Ser Leu Pro Glu Asp Asn Gln Gly Lys Asp Pro Ser
        35                  40                  45

Lys Lys Asn Pro Arg Arg Lys Thr Trp Lys Met Arg Lys Lys Tyr Ala
50                  55                  60

Gln Lys Pro Ser Gln Lys Asn His Leu Tyr
65                  70

<210> SEQ ID NO 79
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gly Thr Thr Glu Glu Met Lys Tyr Val Leu Gly Gln Leu Val Gly Leu
1               5                   10                  15

Asn Ser Pro Asn Ser Ile Leu Lys Ala Ala Lys Thr Leu Tyr Glu His
            20                  25                  30

Tyr Ser Gly Gly Glu Ser His Asn Ser Ser Ser Lys Thr Phe Glu
        35                  40                  45

Lys Lys Gly Glu Lys Asn Asp Leu Gln Leu Phe Val Met Ser Asp Thr
50                  55                  60

Thr Tyr Lys Ile Tyr Trp Thr Val Ile Leu Asn Pro Cys Gly Asn
65                  70                  75                  80

Leu His Leu Lys Thr Thr Ser Leu
                85
```

```
<210> SEQ ID NO 80
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Gln Leu Ile Arg Glu Thr Leu Ile Ser Trp Leu Gln Ala Gln Met
1               5                   10                  15

Leu Asn Pro Gln Pro Glu Lys Thr Phe Ile Arg Asn Lys Ala Ala Gln
            20                  25                  30

Val Phe Ala Leu Leu Phe Val Thr Glu Tyr Leu Thr Lys Trp Pro Lys
        35                  40                  45

Phe Phe Leu Thr Phe Ser Gln
    50                  55

<210> SEQ ID NO 81
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Ala Lys Phe Gln Gln Cys His Ser Thr Leu Glu Pro Asn Pro Ala Asp
1               5                   10                  15

Cys Arg Val Leu Val Tyr Leu Gln Asn Gln Pro Gly Thr Lys Leu Leu
            20                  25                  30

Asn Phe Leu Gln Glu Arg Asn Leu Pro Pro Lys Val Val Leu Arg His
        35                  40                  45

Pro Lys Val His Leu Asn Thr Met Phe Arg Arg Pro His Ser Cys Leu
    50                  55                  60

Ala Asp Val Leu Leu Ser Val His Leu Ile Val Leu Arg Val Val Arg
65                  70                  75                  80

Leu Pro Ala Pro Phe Arg Val Asn His Ala Val Glu Trp
                85                  90

<210> SEQ ID NO 82
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Pro Val Ile Phe Gln Ile Ala Leu Asp Lys Pro Cys His Gln Ala
1               5                   10                  15

Glu Val Lys His Leu His His Leu Leu Lys Gln Leu Lys Pro Ser Glu
            20                  25                  30

Lys Tyr Leu Lys Ile Lys His Leu Leu Leu Lys Arg Glu Arg Val Asp
        35                  40                  45

Leu Ser Lys Leu Gln
    50

<210> SEQ ID NO 83
<211> LENGTH: 33
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Leu Gln Phe Arg Gly Ser Arg Phe Phe Gln Met Leu Ile Leu Tyr
1               5                   10                  15

Tyr Ile Leu Pro Arg Lys Val Leu Gln Met Asp Phe Leu Val His Pro
                20                  25                  30

Ala

<210> SEQ ID NO 84
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Leu Gly Pro His Ser Arg Ile Ser Cys Leu Pro Thr Gln Thr Arg
1               5                   10                  15

Gly Cys Ile Leu Leu Ala Ala Thr Pro Arg Ser Ser Ser Ser Ser Ser
                20                  25                  30

Ser Asn Asp Met Ile Pro Met Ala Ile Ser Ser Pro Lys Ala Pro
            35                  40                  45

Leu Leu Ala Ala Pro Ser Pro Ala Ser Arg Leu Gln Cys Ile Asn Ser
50                  55                  60

Asn Ser Arg Ile Thr Ser Gly Gln Trp Met Ala His Met Ala Leu Leu
65                  70                  75                  80

Pro Ser Gly Thr Lys Gly Arg Cys Thr Ala Cys His Thr Ala Leu Gly
                85                  90                  95

Arg Gly Ser Leu Ser Ser Ser Ser Cys Pro Gln Pro Ser Pro Ser Leu
                100                 105                 110

Pro Ala Ser Asn Lys Leu Pro Ser Leu Pro Leu Ser Lys Met Tyr Thr
                115                 120                 125

Thr Ser Met Ala Met Pro Ile Leu Pro Leu Pro Gln Leu Leu Leu Ser
130                 135                 140

Ala Asp Gln Gln Ala Ala Pro Arg Thr Asn Phe His Ser Ser Leu Ala
145                 150                 155                 160

Glu Thr Val Ser Leu His Pro Leu Ala Pro Met Pro Ser Lys Thr Cys
                165                 170                 175

His His Lys

<210> SEQ ID NO 85
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala His Gln Gly Phe Pro Ala Ala Lys Glu Ser Arg Val Ile Gln Leu
1               5                   10                  15

Ser Leu Leu Ser Leu Leu Ile Pro Pro Leu Thr Cys Leu Ala Ser Glu
                20                  25                  30
```

```
Ala Leu Pro Arg Pro Leu Leu Ala Leu Pro Pro Val Leu Leu Ser Leu
             35                  40                  45

Ala Gln Asp His Ser Arg Leu Leu Gln Cys Gln Ala Thr Arg Cys His
 50                  55                  60

Leu Gly His Pro Val Ala Ser Arg Thr Ala Ser Cys Ile Leu Pro
 65                  70                  75

<210> SEQ ID NO 86
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Pro Ile Leu Ala Ala Thr Gly Thr Ser Val Arg Thr Ala Ala Arg Thr
 1               5                  10                  15

Trp Val Pro Arg Ala Ala Ile Arg Val Pro Asp Pro Ala Ala Val Pro
             20                  25                  30

Asp Asp His Ala Gly Pro Gly Ala Glu Cys His Gly Arg Pro Leu Leu
         35                  40                  45

Tyr Thr Ala Asp Ser Ser Leu Trp Thr Thr Arg Pro Gln Arg Val Trp
 50                  55                  60

Ser Thr Gly Pro Asp Ser Ile Leu Gln Pro Ala Lys Ser Ser Pro Ser
 65                  70                  75                  80

Ala Ala Ala Ala Thr Leu Leu Pro Ala Thr Thr Val Pro Asp Pro Ser
                 85                  90                  95

Cys Pro Thr Phe Val Ser Ala Ala Thr Val Ser Thr Thr Thr Ala
             100                 105                 110

Pro Val Leu Ser Ala Ser Ile Leu Pro Ala Ala Ile Pro Ala Ser Thr
             115                 120                 125

Ser Ala Val Pro Gly Ser Ile Pro Leu Pro Ala Val Asp Asp Thr Ala
         130                 135                 140

Ala Pro Pro Glu Pro Ala Pro Leu Leu Thr Ala Thr Gly Ser Val Ser
145                 150                 155                 160

Leu Pro Ala Ala Ala Thr Ser Ala Ala Ser Thr Leu Asp Ala Leu Pro
                 165                 170                 175

Ala Gly Cys Val Ser Ser Ala Pro Val Ser Ala Val Pro Ala Asn Cys
             180                 185                 190

Leu Phe Pro Ala Ala Leu Pro Ser Thr Ala Gly Ala Ile Ser Arg Phe
         195                 200                 205

Ile Trp Val Ser Gly Ile Leu Ser Pro Leu Asn Asp Leu Gln
210                 215                 220

<210> SEQ ID NO 87
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Pro Cys Arg Ala Gly Arg Arg Val Pro Trp Ala Ala Ser Leu Ile His
 1               5                  10                  15

Ser Arg Phe Leu Leu Met Asp Asn Lys Ala Pro Ala Gly Met Val Asn
             20                  25                  30
```

```
Arg Ala Arg Leu His Ile Thr Thr Ser Lys Val Leu Thr Leu Ser Ser
            35                  40                  45

Ser Ser His Pro Thr Pro Ser Asn His Arg Pro Arg Pro Leu Met Pro
 50                  55                  60

Asn Leu Arg Ile Ser Ser Ser His Ser Leu Asn His His Ser Ser Ser
 65                  70                  75                  80

Pro Leu Ser Leu His Thr Pro Ser Ser His Pro Ser Leu His Ile Ser
                85                  90                  95

Ser Pro Arg Leu His Thr Pro Pro Ser Arg Arg His Ser Ser Ser Thr
            100                 105                 110

Pro Arg Ala Ser Pro Pro Thr His Ser His Arg Leu Ser Leu Leu Thr
            115                 120                 125

Ser Ser Ser Asn Leu Ser Ser Gln His Pro Arg Arg Ser Pro Ser Arg
130                 135                 140

Leu Arg Ile Leu Ser Pro Ser Leu Ser Ser Pro Ser Lys Leu Pro Ile
145                 150                 155                 160

Pro Ser Ser Ala Ser Leu His Arg Arg Ser Tyr Leu Lys Ile His Leu
                165                 170                 175

Gly Leu Arg His Pro Gln Pro Pro Gln
            180                 185

<210> SEQ ID NO 88
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Arg Thr Asn Pro Thr Val Arg Met Arg Pro His Cys Val Pro Phe Trp
 1               5                  10                  15

Thr Gly Arg Ile Leu Leu Pro Ser Ala Ala Ser Val Cys Pro Ile Pro
            20                  25                  30

Phe Glu Ala Cys His Leu Cys Gln Ala Met Thr Leu Arg Cys Pro Asn
        35                  40                  45

Thr Gln Gly Cys Cys Ser Ser Trp Ala Ser
     50                  55

<210> SEQ ID NO 89
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Thr Asn Gln Ala Leu Pro Lys Ile Glu Val Ile Cys Arg Gly Thr Pro
 1               5                  10                  15

Arg Cys Pro Ser Thr Val Pro Pro Ser Pro Ala Gln Pro Tyr Leu Arg
            20                  25                  30

Val Ser Leu Pro Glu Asp Arg Tyr Thr Gln Ala Trp Ala Pro Thr Ser
            35                  40                  45

Arg Thr Pro Trp Gly Ala Met Val Pro Arg Gly Val Ser Met Ala His
     50                  55                  60

Lys Val Ala Thr Pro Gly Ser Gln Thr Ile Met Pro Cys Pro Met Pro
 65                  70                  75                  80
```

```
Thr Thr Pro Val Gln Ala Trp Leu Glu Ala
                85                  90

<210> SEQ ID NO 90
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Arg Met Glu Arg Glu Leu Lys Lys Trp Ser Ile Gln Thr Cys Leu Ser
1               5                   10                  15

Ala Arg Thr Gly Leu Ser Ile Ser Cys Thr Thr Leu Asn Ser Pro Pro
            20                  25                  30

Leu Lys Lys Met Ser Met Pro Ala Val
        35                  40

<210> SEQ ID NO 91
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Leu Cys Ser Arg Tyr Ser Leu Phe Leu Ala Trp Arg Leu Ser Ser Val
1               5                   10                  15

Leu Gln Arg Phe Arg Phe Thr His Val Ile Gln Gln Arg Met Glu Ser
            20                  25                  30

Gln Ile Ser
        35

<210> SEQ ID NO 92
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Arg Ser Ala Cys Val Thr Val Lys Gly Pro Leu Ala Ser Val Gly Arg
1               5                   10                  15

His Ser Leu Ser Lys Gln Asp Cys Lys Phe Leu Pro Phe Trp Gly Phe
            20                  25                  30

Leu Glu Glu Phe Leu Leu Cys
        35

<210> SEQ ID NO 93
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ile Gln Trp Gly Thr Thr Thr Ala Pro Arg Pro Ile Arg Pro Pro Phe
1               5                   10                  15

Leu Glu Ser Lys Gln Asn Cys Ser His Phe Pro Thr Pro Leu Leu Ala
            20                  25                  30
```

```
Ser Glu Asp Arg Arg Glu Thr Gly Leu Phe Leu Pro Ser Ala Ala Gln
            35                  40                  45

Lys Met Lys Lys Ala His Phe Leu Lys Thr Trp Phe Arg Ser Asn Pro
 50                  55                  60

Thr Lys Thr Lys Lys Ala Arg Phe Ser Thr Ala Ser Leu Ala Lys Glu
 65                  70                  75                  80

Leu Thr His Pro Leu Leu Val Ser Leu Leu Lys Glu Lys Gln Asp
                85                  90                  95

Gly

<210> SEQ ID NO 94
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Pro Thr Asp Pro Phe Leu Gly Leu Arg Leu Gly Leu His Leu Gln Lys
 1               5                  10                  15

Val Phe His Gln Ser His Ala Glu Tyr Ser Gly Ala Pro Pro Pro Pro
                20                  25                  30

Pro Ala Pro Ser Gly Leu Arg Phe Trp Asn Pro Ser Arg Ile Ala His
            35                  40                  45

Ile Ser Gln Leu Leu Ser Trp Pro Gln Lys Thr Glu Glu Arg Leu Gly
 50                  55                  60

Tyr Ser Ser His Gln Leu Pro Arg Lys
 65                  70

<210> SEQ ID NO 95
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Phe Cys Cys Ser Cys Cys Phe Phe Gly Gly Glu Arg Trp Ser Lys Ser
 1               5                  10                  15

Pro Tyr Cys Pro Gln Arg Met Thr Pro Gly Thr Thr Phe Ile Thr Met
                20                  25                  30

Met Lys Lys Glu Ala Glu Lys Arg Thr Arg Thr Leu Thr
            35                  40                  45

<210> SEQ ID NO 96
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Trp Arg Arg Asn Cys Lys Ala Pro Val Ser Leu Arg Lys Ser Val Gln
 1               5                  10                  15

Thr Pro Ala Arg Ser Ser Pro Ala Arg Pro Asp Arg Thr Arg Arg Leu
                20                  25                  30

Pro Ser Leu Gly Val Pro Gly Gln Pro Trp Ala Leu Gly Ala Ala Ala
```

```
                35                  40                  45
Ser Arg Arg Cys Cys Cys Cys Arg Ser Pro Leu Gly Ser Ala Arg
 50                  55                  60

Ser Arg Ser Pro Ala Thr Leu Ala Leu Thr Pro Arg Ala Thr Arg Ser
 65                  70                  75                  80

Arg Cys Pro Gly Ala Thr Trp Arg Glu Ala Ala Ser Trp Ala Glu
                 85                  90                  95

<210> SEQ ID NO 97
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Pro Gly Arg Pro Leu Gln Thr His Val Leu Pro Glu Pro His Leu Ala
 1               5                  10                  15

Leu Gln Pro Leu Gln Pro His Ala Asp His Ala His Ala Asp Ala Pro
                20                  25                  30

Ala Ile Gln Pro Val Leu Trp Thr Thr Pro Pro Leu Gln His Gly His
                35                  40                  45

Arg His Gly Leu Glu Pro Cys Ser Met Leu Thr Gly Pro Pro Ala Arg
 50                  55                  60

Val Pro Ala Val Pro Phe Asp Leu His Phe Cys Arg Ser Ser Ile Met
 65                  70                  75                  80

Lys Pro Lys Arg Asp Gly Tyr Met Phe Leu Lys Ala Glu Ser Lys Ile
                 85                  90                  95

Met Phe Ala Thr Leu Gln Arg Ser Ser Leu Trp Cys Leu Cys Ser Asn
                100                 105                 110

His

<210> SEQ ID NO 98
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Pro Arg Pro Arg Arg Cys Thr Arg His Pro Ala Cys Pro Leu Asp His
 1               5                  10                  15

Thr Thr Pro Pro Ala Trp Ser Pro Pro Trp Val Arg Ala Leu Leu Asp
                20                  25                  30

Ala His Arg Ala Pro Ser Glu Ser Pro Cys Ser Pro Arg Leu Ala
                35                  40                  45

Phe Leu Gln Glu Gln Tyr His Glu Ala
     50                  55

<210> SEQ ID NO 99
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99
```

-continued

```
Thr Arg Arg Cys His Cys Cys Pro His Leu Arg Ser His Pro Cys Pro
  1               5                  10                  15

His His Leu Arg Asn His Pro Arg Pro His His Leu Arg His His Ala
             20                  25                  30

Cys His His His Leu Arg Asn Cys Pro His Pro His Phe Leu Arg His
         35                  40                  45

Cys Thr Cys Pro Gly Arg Trp Arg Asn Arg Pro Ser Leu Arg Arg Leu
     50                  55                  60

Arg Ser Leu Leu Cys Leu Pro His Leu Asn His His Leu Phe Leu His
 65                  70                  75                  80

Trp Arg Ser Arg Pro Cys Leu His Arg Lys Ser His Pro His Leu Leu
                 85                  90                  95

His Leu Arg Arg Leu Tyr Pro His His Leu Lys His Arg Pro Cys Pro
             100                 105                 110

His His Leu Lys Asn Leu Leu Cys Pro Arg His Leu Arg Asn Cys Pro
         115                 120                 125

Leu Pro Arg His Leu Lys His Leu Ala Cys Leu His His Leu Arg Ser
     130                 135                 140

His Pro Cys Pro Leu His Leu Lys Ser His Pro Cys Leu His His Arg
145                 150                 155                 160

Arg His Leu Val Cys Ser His His Leu Lys Ser Leu Leu Cys Pro Leu
                 165                 170                 175

His Leu Arg Ser Leu Pro Phe Pro His His Leu Arg His His Ala Cys
             180                 185                 190

Pro His His Leu Arg Thr Arg Leu Cys Pro His His Leu Lys Asn His
         195                 200                 205

Leu Cys Pro Pro His Leu Arg Tyr Arg Ala Tyr Pro Pro Cys Leu Trp
     210                 215                 220

Cys His Ala Cys Leu His Arg Leu Arg Asn Leu Pro Cys Pro His Arg
225                 230                 235                 240

Leu Arg Ser Leu Pro Arg Pro Leu His Leu Arg Leu His Ala Ser Pro
                 245                 250                 255

His His Leu Arg Thr Pro Pro His Pro His His Leu Arg Thr His Leu
             260                 265                 270

Leu Pro His His Arg Arg Thr Arg Ser Cys Pro Cys Arg Trp Arg Ser
         275                 280                 285

His Pro Cys Cys His Tyr Leu Arg Ser Arg Asn Ser Ala Pro Gly Pro
     290                 295                 300

Arg Gly Arg Thr Cys His Pro Gly Leu Arg Ser Arg Thr Cys Pro Pro
305                 310                 315                 320

Gly Leu Arg Ser His Thr Tyr Leu Arg Arg Leu Arg Ser His Thr Cys
                 325                 330                 335

Pro Pro Ser Leu Arg Ser His Ala Tyr Ala Leu Cys Leu Arg Ser His
             340                 345                 350

Thr Cys Pro Pro Arg Leu Arg Asp His Ile Cys Pro Leu Ser Leu Arg
         355                 360                 365

Asn Cys Thr Cys Pro Pro Arg Leu Arg Ser Arg Thr Cys Leu Leu Cys
     370                 375                 380

Leu Arg Ser His Ala Cys Pro Pro Asn Leu Arg Asn His Thr Cys Pro
385                 390                 395                 400

Pro Ser Leu Arg Ser His Ala Cys Pro Pro Gly Leu Arg Asn Arg Ile
                 405                 410                 415

Cys Pro Leu Ser Leu Arg Ser His Pro Cys Pro Leu Gly Leu Lys Ser
```

```
                    420                 425                 430

Pro Leu Arg Ser Gln Ala Asn Ala Leu His Leu Arg Ser Cys Pro Cys
            435                 440                 445

Ser Leu Pro Leu Gly Asn His Pro Tyr Leu Pro Cys Leu Glu Ser Gln
        450                 455                 460

Pro Cys Leu Ser Leu Gly Asn His Leu Cys Pro Leu Cys Pro Arg Ser
465                 470                 475                 480

Cys Arg Cys Pro His Leu Gly Ser His Pro Cys Arg Leu Ser
                    485                 490

<210> SEQ ID NO 100
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ser Trp Lys Gly Thr Asn Trp Cys Asn Asp Met Cys Ile Phe Ile Thr
1               5                   10                  15

Ser Gly Gln Ile Phe Lys Gly Thr Arg Gly Pro Arg Phe Leu Trp Gly
            20                  25                  30

Ser Lys Asp Gln Arg Gln Lys Gly Ser Asn Tyr Ser Gln Ser Glu Ala
        35                  40                  45

Leu Cys Val Leu Leu
    50

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Arg Thr Lys Cys Phe Thr Phe Gly
1               5

<210> SEQ ID NO 102
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Pro Ile Phe Ile Gln Thr Leu Leu Leu Trp Asp Phe Leu Gln Lys Asp
1               5                   10                  15

Leu Lys Ala Tyr Thr Gly Thr Ile Leu Met Met
            20                  25

<210> SEQ ID NO 103
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103
```

```
Gln Lys Met Ile Leu Thr Lys Gln Ile Lys Thr Lys Pro Thr Asp Thr
1               5                   10                  15

Phe Leu Gln Ile Leu Arg
            20
```

<210> SEQ ID NO 104
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gly Phe Trp Ile Gln Ser Ile Lys Thr Ile Thr Arg Tyr Thr Ile Phe
1               5                   10                  15

Val Leu Lys Asp Ile Met Thr Pro Pro Asn Leu Ile Ala Glu Leu His
            20                  25                  30

Asn Ile Leu Leu Lys Thr Ile Thr His His Ser
        35                  40
```

<210> SEQ ID NO 105
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Asn Tyr Ser Asn Val Gln Trp Arg Asn Leu Gln Ser Ser Val Cys Gly
1               5                   10                  15

Leu Pro Ala Lys Gly Glu Asp Ile Phe Leu Gln Phe Arg Thr His Thr
            20                  25                  30

Thr Gly Arg Gln Val His Val Leu
        35                  40
```

<210> SEQ ID NO 106
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Tyr Gln Ser Arg Val Leu Pro Gln Thr Glu Gln Asp Ala Lys Lys Gly
1               5                   10                  15

Gln Asn Val Ser Leu Leu Gly Lys Tyr Ile Leu His Thr Arg Thr Arg
            20                  25                  30

Gly Asn Leu Arg Lys Ser Arg Lys Trp Lys Ser Met
        35                  40
```

<210> SEQ ID NO 107
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Ser Ser Gln Asn Ala Arg Gly Cys Ser Pro Arg Gly Pro Cys Thr Ser
1               5                   10                  15
```

```
Ser Ser Tyr Thr Gly Gly Pro Cys Thr Ser Pro Leu Leu Ala Pro Val
            20                  25                  30

Ile Phe Cys Pro Phe Pro Glu Asn Leu Pro Gly Gln Leu Arg Phe Pro
            35                  40                  45

Ser Gly Leu Leu Ala Phe Trp Asp Ser Gln Val Cys Asp Leu His Val
 50                  55                  60

Leu Pro Cys Pro Gln Gln Asp Val Leu Pro Thr Gly Gln Asp Leu Pro
 65                  70                  75                  80

Cys Ala Ala Val Gly
                85

<210> SEQ ID NO 108
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gly Ala Ala Pro Thr Met Ser Ala Ala Gln Ile Ala Met Val Trp Pro
 1               5                  10                  15

Leu Leu Ser Ile Leu Ser Glu Trp Lys Glu Ile Cys Val Trp Ser Ile
            20                  25                  30

Trp Met Thr Glu Thr Leu Phe Asp Ile Val Trp Trp Cys Pro Met Ser
            35                  40                  45

Arg Leu Arg Leu Ala Leu Thr Val Pro Pro Ser Thr Thr Thr Thr Cys
 50                  55                  60

Val Thr Val Pro Ala Trp Ala Ala
 65                  70

<210> SEQ ID NO 109
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Thr Gly Gly Pro Ser Ser Pro Ser His Trp Lys Thr Pro Val Val
 1               5                  10                  15

Ile Tyr Trp Asp Gly Thr Ala Leu Arg Cys Val Phe Val Pro Val Leu
            20                  25                  30

Gly Glu Thr Gly Ala Gln Arg Lys Arg Ile Ser Ala Arg Lys Gly Ser
            35                  40                  45

Leu Thr Thr Ser Cys Pro Gln Gly Ala Leu Ser Glu His Cys Pro Thr
 50                  55                  60

Thr Pro Ala Pro Leu Pro Ser Gln Arg Arg Asn His Trp Met Glu Asn
 65                  70                  75                  80

Ile Ser Pro Phe Arg Ser Val Gly Val Ser Ala Ser Arg Cys Ser Glu
            85                  90                  95

Ser

<210> SEQ ID NO 110
<211> LENGTH: 31
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 110

Phe His Thr Pro Ala Arg His Pro Arg Pro Arg His Gly His Leu Gln
1               5                   10                  15

Ala Val Thr Ala His Asp Gly Gly Cys Glu Ala Leu Pro Pro Pro
            20                  25                  30

<210> SEQ ID NO 111
<211> LENGTH: 78
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 111

Cys Cys Pro Arg Thr Ile Leu Asn Asn Gly Ser Leu Lys Thr Gln Val
1               5                   10                  15

Gln Met Lys Leu Pro Glu Cys Gln Arg Leu Leu Pro Pro Trp Pro Leu
            20                  25                  30

His Gln Gln Leu Leu His Arg Arg Pro Leu His Gln Pro Pro Gly
        35                  40                  45

Pro Cys His Leu Leu Ser Leu Pro Arg Lys Pro Thr Arg Ala Ala Thr
    50                  55                  60

Val Ser Val Trp Ala Ser Cys Ile Leu Gly Gln Pro Ser Leu
65                  70                  75

<210> SEQ ID NO 112
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Val Arg Lys His Phe Gln Thr Tyr Gly Asn Tyr Phe Leu Lys Thr Thr
1               5                   10                  15

Phe Cys Pro Pro Cys Arg Pro Lys Gln Trp Met Ile
            20                  25

<210> SEQ ID NO 113
<211> LENGTH: 46
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 113

Leu Ala Arg Thr Pro Leu Pro Ser Thr Arg Cys Phe Ala Asn Trp Pro
1               5                   10                  15

Arg Pro Ala Leu Cys Ser Cys Gly Leu Ile Pro His Pro Arg Pro Ala
            20                  25                  30

Pro Ala Ser Ala Pro Trp Pro Ser Thr Ser Ser His Ser Thr
        35                  40                  45

<210> SEQ ID NO 114
<211> LENGTH: 81
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 114

Glu Leu Gln Glu Thr Gly His Arg Gln Val Ala Leu Arg Arg Ser Gly
1               5                   10                  15

Arg Pro Pro Lys Cys Ala Glu Arg Pro Gly Ala Ala Asp Thr Gly Ala
            20                  25                  30

His Cys Thr Ser Thr Asp Gly Arg Leu Lys Ile Ser Val Glu Thr Tyr
        35                  40                  45

Thr Val Ser Ser Gln Leu Leu Met Val Leu Met Ser Leu Asp Leu Asp
50                  55                  60

Thr Gly Leu Val Pro Ser Leu Val Ser Lys Cys Leu Ile Leu Arg Val
65                  70                  75                  80

Lys

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Lys Ser Asp Ala Ser Arg Leu Ser Gly Ala
1               5                   10

<210> SEQ ID NO 116
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Thr Ala Tyr Phe Cys Gln Tyr His Thr Ala Ser Val Tyr Ser Glu
1               5                   10                  15

Arg Ala Met Pro Pro Gly Cys Pro Glu Pro Ser Gln Ala
            20                  25

<210> SEQ ID NO 117
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Thr Arg Ala Ser Pro Pro Arg Ser Ser Ser Ala Ile Ala Val Arg Ala
1               5                   10                  15

Ser Cys Cys Pro Tyr Gly Ser Thr Thr Ala Ser Arg Ser Pro Thr
            20                  25                  30

Gln Arg Cys Arg Leu Ala Arg Ala Ala Ala Ser Thr Ala Thr Glu Val
        35                  40                  45

Thr Phe Gly Ser Ser Glu Met Gln Gly His Thr Met Gly Phe Trp Leu
50                  55                  60

Thr Lys Leu Asn Tyr Leu Cys His Leu Ser Met Leu Thr Asp Ser Leu
65                  70                  75                  80
```

```
Phe Leu Pro Ile Ser His Cys Gln Cys Ile Leu
                85                  90
```

<210> SEQ ID NO 118
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Ser Ser Leu Arg Ile Thr Gly Asp Trp Thr Ser Ser Gly Arg Ser Thr
1               5                   10                  15

Lys Ile Trp Lys Thr Thr Gln Met Cys Arg Lys Thr Trp Ser Gly
            20                  25                  30
```

<210> SEQ ID NO 119
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Arg Arg Arg Arg Gly Gly Val Gly Arg Gly Val Arg Pro Gly Arg
1               5                   10                  15

Val Arg Pro Gly Gly Thr Gly Arg Arg Gly Gly Asp Gly Gly Arg Ala
            20                  25                  30

Ala Ala Ala Arg Ala Ala Leu Gly Glu Leu Ala Arg Ala Leu Pro Gly
        35                  40                  45

His Leu Leu Gln Ser Gln Ser Ala Arg Arg Ala Ala Arg Met Ala Gln
    50                  55                  60

Leu Arg Arg Arg Ala Ala Ala Leu Pro Asn Ala Ala Trp His Gly
65                  70                  75                  80

Pro Pro His Pro Gln Leu Pro Arg Ser Pro Leu Ala Leu Gln Arg Cys
                85                  90                  95

Arg Asp Thr Arg Trp Ala Ser Gly
            100
```

<210> SEQ ID NO 120
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Ser Cys Lys Val Phe Phe Lys Arg Ala Ala Glu Gly Lys Gln Lys Tyr
1               5                   10                  15

Leu Cys Ala Ser Arg Asn Asp Cys Thr Ile Asp Lys Phe Arg Arg Lys
            20                  25                  30

Asn Cys Pro Ser Cys Arg Leu Arg Lys Cys Tyr Glu Ala Gly Met Thr
        35                  40                  45

Leu Gly Glu Lys Phe Arg Val Gly Asn Cys Lys His Leu Lys Met Thr
    50                  55                  60

Arg Pro
65
```

<210> SEQ ID NO 121
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Ala Gly Ala Pro Pro Ala Ser Leu Pro Pro Cys Ser Leu Ile
1               5                   10                  15

Ser Asp Cys Cys Ala Ser Asn Gln Arg Asp Ser Val Gly Val Gly Pro
                20                  25                  30

Ser Glu Pro Gly Asn Asn Ile Lys Ile Cys Asn Glu Ser Ala Ser Arg
            35                  40                  45

Lys

<210> SEQ ID NO 122
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

His Gly Trp Arg Pro Phe Leu Pro Val Arg Ala Arg Ser Arg Trp Asn
1               5                   10                  15

Arg Arg Leu Asp Val Thr Val Ala Asn Gly Arg Ser Trp Lys Tyr Gly
                20                  25                  30

Trp Ser Leu Leu Arg Val Pro Gln Val Asn Gly Ile Gln Val Leu Asn
            35                  40                  45

Val Ser Leu Lys Ser Ser Ser Asn Val Ile Ser Tyr Glu
        50                  55                  60

<210> SEQ ID NO 123
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Arg Leu Lys Glu Val Phe Gln Thr Lys Ile Gln Glu Phe Arg Lys Ala
1               5                   10                  15

Cys Tyr Thr Leu Thr Gly Tyr Gln Ile Asp Ile Thr Thr Glu Asn Gln
                20                  25                  30

Tyr Arg Leu Thr Ser Leu Tyr Ala Glu His Pro Gly Asp Cys Leu Ile
            35                  40                  45

Phe Lys Leu Arg Val Pro Gly Ser Ser Val Leu Val Thr Val Pro Gly
        50                  55                  60

Leu
65

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 124

Ala Glu Val Leu Lys Val Ile Arg Gln Ser Ala Gly Gln Lys Thr Thr
1               5                   10                  15

Cys Gly Gln Gly Leu Glu Gly Pro Trp Glu Arg Pro Pro Pro Leu Asp
            20                  25                  30

Glu Ser Glu Arg Asp Gly Gly Ser Glu Asp Gln Val Glu Asp Pro Ala
        35                  40                  45

Leu Ser Ala Leu Leu Arg Pro Arg Pro Pro Arg Pro Glu Val Gly
    50                  55                  60

Ala His Gln Asp Glu Gln Ala Ala Gln Gly Ala Asp Pro Arg Leu Gly
65                  70                  75                  80

Ala Gln Pro Ala Cys Arg Gly Leu Pro Gly Leu Leu Thr Val Pro Gln
                85                  90                  95

Pro Glu Pro Leu Leu Ala Pro Pro Ser Ala Ala
                100                 105

<210> SEQ ID NO 125
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Arg Ala Glu Trp Arg Glu Asn Ile Arg Glu Gln Gln Lys Lys Cys
1               5                   10                  15

Phe Arg Ser Phe Ser Leu Thr Ser Val Glu Leu Gln Met Leu Thr Asn
            20                  25                  30

Ser Cys Val Lys Leu Gln Thr Val His Ser Ile Pro Leu Thr Ile Asn
        35                  40                  45

Lys Glu Glu Ala Leu Gln Arg Pro Val Ala Ser Asp Phe Glu Pro Gln
    50                  55                  60

Gly Leu Ser Glu Ala Ala Arg Trp Asn Ser Lys Glu Asn Leu Leu Ala
65                  70                  75                  80

Gly Pro Ser Glu Asn Asp Pro Asn Leu Phe Val Ala Leu Tyr Asp Phe
                85                  90                  95

Val Ala Ser Gly
            100

<210> SEQ ID NO 126
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Leu Gln Met Leu Thr Asn Ser Cys Val Lys Leu Gln Thr Val His
1               5                   10                  15

Ser Ile Pro Leu Thr Ile Asn Lys Glu Asp Asp Glu Ser Pro Gly Leu
            20                  25                  30

Tyr Gly Phe Leu Asn Val Ile Val His Ser Ala Thr Gly Phe Lys Gln
        35                  40                  45

Ser Ser Lys Ala Leu Gln Arg Pro Val Ala Ser Asp Phe Glu Pro Gln
    50                  55                  60
```

-continued

```
Gly Leu Ser Glu Ala Ala Arg Trp Asn Ser Lys Glu Asn Leu Leu Ala
 65                  70                  75                  80

Gly Pro Ser Glu Asn Asp Pro Asn Leu Phe Val Ala Leu Tyr Asp Phe
                 85                  90                  95

Val Ala Ser Gly Asp
            100

<210> SEQ ID NO 127
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ile Ser Asn Ser Trp Asp Ala His Leu Gly Leu Gly Ala Cys Gly Glu
 1               5                  10                  15

Ala Glu Gly Leu Gly Val Gln Gly Ala Glu Glu Glu Glu Glu Glu Glu
                 20                  25                  30

Glu Glu Glu Glu Glu Glu Gly Ala Gly Val Pro Ala Cys Pro Pro Lys
             35                  40                  45

Gly Pro Glu Leu Phe Pro Leu Ile Phe Pro Ala Glu Pro Ala Gln Ala
 50                  55                  60

Ser Gly Pro Tyr Val Glu Ile Ile Glu Gln Pro Lys Gln Arg Gly Met
 65                  70                  75                  80

Arg Phe Arg Tyr Lys Cys Glu Gly Arg Ser Ala Gly Ser Ile Pro Gly
                 85                  90                  95

Glu Arg Ser Thr Asp
            100

<210> SEQ ID NO 128
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Gln Arg Leu Asp Gly Met Gly Cys Leu Glu Phe Asp Glu Glu Arg
 1               5                  10                  15

Ala Gln Gln Glu Asp Ala Leu Ala Gln Gln Ala Phe Glu Glu Ala Arg
                 20                  25                  30

Arg Arg Thr Arg Glu Phe Glu Asp Arg Asp Arg Ser His Arg Glu Glu
             35                  40                  45

Met Glu Val His Glu Leu Glu Lys Ser Lys Arg Ala Leu Glu Thr Gln
 50                  55                  60

Met Glu Glu Met Lys Thr Gln Leu Glu Leu Glu Asp Glu Leu Gln
 65                  70                  75                  80

Ala Thr Glu Asp Ala Lys Leu Arg Leu Glu Val Asn Met Gln Ala Leu
                 85                  90                  95

Lys Gly Gln Phe
            100

<210> SEQ ID NO 129
<211> LENGTH: 100
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 129

Lys Gly Ser Phe Pro Glu Asn Leu Arg His Leu Lys Asn Thr Met Glu
1               5                   10                  15

Thr Ile Asp Trp Lys Val Phe Glu Ser Trp Met His His Trp Leu Leu
            20                  25                  30

Phe Glu Met Ser Arg His Ser Leu Glu Gln Lys Pro Thr Asp Ala Pro
        35                  40                  45

Pro Lys Ala Gly Val Pro Asn Lys Pro Gly Ile Pro Lys Leu Leu Glu
    50                  55                  60

Gly Ser Lys Asn Ser Ile Gln Trp Glu Lys Ala Glu Asp Asn Gly Cys
65                  70                  75                  80

Arg Ile Thr Tyr Tyr Ile Leu Glu Ile Arg Lys Ser Thr Ser Asn Asn
                85                  90                  95

Leu Gln Asn Gln
            100

<210> SEQ ID NO 130
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

<210> SEQ ID NO 131
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Leu Pro Gln Pro Pro Ile Cys Thr Ile Asp Val Tyr Met Ile Met Val
1               5                   10                  15

Lys Cys Trp Met Ile Asp Ala Asp Ser Arg Pro Lys Phe Arg Glu Leu
            20                  25                  30

Ile Ile Glu Phe Ser Lys Met Ala Arg Asp Pro Gln Arg Tyr Leu Val
        35                  40                  45

Ile Gln Leu Gln Asp Lys Phe Glu His Leu Lys Met Ile Gln Gln Glu
    50                  55                  60

Glu Ile Arg Lys Leu Glu Glu Glu Lys Lys Gln Leu Glu Gly Glu Ile
65                  70                  75                  80

Ile Asp Phe Tyr Lys Met Lys Ala Ala Ser Glu Ala Leu Gln Thr Gln

Leu Ser Thr Asp
            100

<210> SEQ ID NO 132
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ser Trp Glu Asn Ser Asp Asp Ser Arg Asn Lys Leu Ser Lys Ile Pro
1               5                   10                  15

Ser Thr Pro Lys Leu Ile Pro Lys Val Thr Lys Thr Ala Asp Lys His
            20                  25                  30

Lys Asp Val Ile Ile Asn Gln Ala Lys Met Ser Thr Arg Glu Lys Asn
        35                  40                  45

Ser Gln Val Tyr Arg Arg Lys His Gln Glu Leu Gln Ala Met Gln Met
    50                  55                  60

Glu Leu Gln Ser Pro Glu Tyr Lys Leu Ser Lys Leu Arg Thr Ser Thr
65                  70                  75                  80

Ile Met Thr Asp Tyr Asn Pro Asn Tyr Cys Phe Ala Gly Lys Thr Ser
                85                  90                  95

Ser Ile Ser Asp Leu
            100

<210> SEQ ID NO 133
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Gly His Arg Met Asp Lys Pro Ala Asn Cys Thr His Asp Leu Tyr
1               5                   10                  15

Met Ile Met Arg Glu Cys Trp His Ala Ala Pro Ser Gln Arg Pro Thr
            20                  25                  30

Phe Lys Gln Leu Val Glu Asp Leu Asp Arg Val Leu Thr Val Thr Ser
        35                  40                  45

Thr Asp Val Lys Ala Thr Gln Glu Glu Asn Arg Glu Leu Arg Ser Arg
    50                  55                  60

Cys Glu Glu Leu His Gly Lys Asn Leu Glu Leu Gly Lys Ile Met Asp
65                  70                  75                  80

Arg Phe Glu Glu Val Val Tyr Gln Ala Met Glu Glu Val Gln Lys Gln
                85                  90                  95

Lys Glu Leu Ser
            100

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Arg Asp Asn Thr Leu Leu Arg Arg Val Glu Leu Phe Ser Leu Ser
1               5                   10                  15

Arg Gln Val Ala Arg Glu Ser Thr Tyr Leu Ser Ser Leu Lys Gly Ser
            20                  25                  30

Arg Leu His Pro Glu Glu Leu Gly Gly Pro Leu Lys Lys Leu Lys
        35                  40                  45

Gln Glu Ala Thr Ser Lys Ser Gln Ile Met Ser Leu Trp Gly Leu Val
50                  55                  60

Ser Lys Met Pro Pro Glu Lys Val Gln Arg Leu Tyr Val Asp Phe Pro
65                  70                  75                  80

Gln His Leu Arg His Leu Leu Gly Asp Trp Leu Glu Ser Gln Pro Trp
                85                  90                  95

Glu Phe Leu Val Gly Ser Asp Ala Phe Cys Cys
            100                 105

<210> SEQ ID NO 135
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Ser Arg Glu Met Gln Asp Val Asp Leu Ala Glu Val Lys Pro Leu
1               5                   10                  15

Val Glu Lys Gly Glu Thr Ile Thr Gly Leu Leu Gln Glu Phe Asp Val
            20                  25                  30

Gln Glu Ala Leu Ser Val Val Ser Glu Asp Gln Ser Leu Phe Glu Cys
        35                  40                  45

Ala Tyr Gly Thr Pro His Leu Ala Lys Thr Glu Met Thr Ala Ser Ser
    50                  55                  60

Ser Ser Asp Tyr Gly Gln Thr Ser Lys Met Ser Pro Arg Val Pro Gln
65                  70                  75                  80

Gln Asp Trp

<210> SEQ ID NO 136
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Val Leu Asp Met His Gly Phe Leu Arg Gln Ala Leu Cys Arg Leu Arg
1               5                   10                  15

Gln Glu Glu Pro Gln Ser Leu Gln Ala Ala Val Arg Thr Asp Gly Phe
            20                  25                  30

Asp Glu Phe Lys Val Arg Leu Gln Asp Leu Ser Ser Cys Ile Thr Gln
        35                  40                  45

Gly Lys Ala Ile Glu Thr Gln Ser Ser Ser Glu Glu Ile Val Pro
    50                  55                  60

Ser Pro Pro Ser Pro Pro Leu Pro Arg Ile Tyr Lys Pro Cys Phe
65                  70                  75                  80

Val Cys Gln Asp Lys Ser Ser Gly Tyr His Tyr Gly Val Ser Ala Cys
                85                  90                  95
```

Glu Gly Cys Lys Gly
            100

<210> SEQ ID NO 137
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Arg Ser Ser Pro Glu Gln Pro Arg Pro Ser Thr Ser Lys Ala Val Ser
1               5                   10                  15

Pro Pro His Leu Asp Gly Pro Pro Ser Pro Arg Ser Pro Val Ile Gly
            20                  25                  30

Ser Glu Val Phe Leu Pro Asn Ser Asn His Val Ala Ser Gly Ala Gly
        35                  40                  45

Glu Ala Ala Ile Glu Thr Gln Ser Ser Ser Glu Glu Ile Val Pro
    50                  55                  60

Ser Pro Pro Ser Pro Pro Leu Pro Arg Ile Tyr Lys Pro Cys Phe
65                  70                  75                  80

Val Cys Gln Asp Lys Ser Ser Gly Tyr His Tyr Gly Val Ser Ala Cys
                85                  90                  95

Glu Gly Cys Lys Gly
            100

<210> SEQ ID NO 138
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Val Ala Arg Phe Asn Asp Leu Arg Phe Val Gly Arg Ser Gly Arg Gly
1               5                   10                  15

Lys Ser Phe Thr Leu Thr Ile Thr Val Phe Thr Asn Pro Pro Gln Val
            20                  25                  30

Ala Thr Tyr His Arg Ala Ile Lys Ile Thr Val Asp Gly Pro Arg Glu
        35                  40                  45

Pro Arg Asn Arg Thr Glu Lys His Ser Thr Met Pro Asp Ser Pro Val
    50                  55                  60

Asp Val Lys Thr Gln Ser Arg Leu Thr Pro Thr Met Pro Pro Pro
65                  70                  75                  80

Pro Thr Thr Gln Gly Ala Pro Arg Thr Ser Ser Phe Thr Pro Thr Thr
                85                  90                  95

Leu Thr Asn Gly Thr
            100

<210> SEQ ID NO 139
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Ala Leu Asn Ser Glu Ala Leu Ser Val Val Ser Glu Asp Gln Ser

```
1               5                   10                  15
Leu Phe Glu Cys Ala Tyr Gly Thr Pro His Leu Ala Lys Thr Glu Met
                20                  25                  30

Thr Ala Ser Ser Ser Asp Tyr Gly Gln Thr Ser Lys Met Ser Pro
            35                  40                  45

Arg Val Pro Gln Gln Asp Trp
    50                  55
```

```
<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Gln Tyr Gly Lys Val Tyr Glu Gly
1               5

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Gln Tyr Gly Lys Val Tyr Glu Gly Val
1               5                   10

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Lys Leu Gly Gly Gly Gln Tyr Gly Lys
1               5

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Lys Leu Gly Gly Gly Gln Tyr Gly Lys Val
1               5                   10

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Lys Val Tyr Glu Gly Val Trp Lys Lys
```

```
<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Lys Val Tyr Glu Gly Val Trp Lys Lys Tyr
1               5                   10

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Tyr Gly Lys Val Tyr Glu Gly Val
1               5

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Tyr Gly Lys Val Tyr Glu Gly Val Trp
1               5                   10

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gln Tyr Gly Val Val Tyr Glu Gly
1               5

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gln Tyr Gly Val Val Tyr Glu Gly Val
1               5                   10

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 150

Lys Leu Gly Gly Gly Gln Tyr Gly Val
1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Lys Leu Gly Gly Gly Gln Tyr Gly Val Val
1               5                   10

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Tyr Gly Val Val Tyr Glu Gly Val
1               5

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Tyr Gly Val Val Tyr Glu Gly Val Trp
1               5                   10

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Val Val Tyr Glu Gly Val Trp Lys Lys
1               5

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Val Val Tyr Glu Gly Val Trp Lys Lys Tyr
1               5                   10

<210> SEQ ID NO 156

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Thr Gln Ile Ser Ser Ala Thr Glu Tyr
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ile Ser Ser Ala Thr Glu Tyr Leu Glu Lys
1               5                   10

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Ser Ala Thr Glu Tyr Leu Glu Lys
1               5

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Gln Ile Ser Ser Ala Thr Glu Tyr Leu
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Tyr Met Ala Thr Gln Ile Ser Ser Ala Thr
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161
```

```
Phe Tyr Ile Ile Ile Glu Phe Met Thr Tyr
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ile Ile Glu Phe Met Thr Tyr Gly Asn Leu
1               5                   10

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Ile Ile Glu Phe Met Thr Tyr Gly
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Ile Ile Glu Phe Met Thr Tyr Gly Asn
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Tyr Ile Ile Ile Glu Phe Met Thr Tyr Gly
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Gln His Gly Glu Val Tyr Glu Gly Val
1               5                   10

<210> SEQ ID NO 167
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 167

Lys Leu Gly Gly Gly Gln His Gly Glu Val
1               5                   10

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Lys Ile Ala Asp Phe Gly Met Ala Arg
1               5

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Arg Val Ala Lys Ile Ala Asp Phe Gly Met
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Phe Ile Leu Met Glu Leu Met Ala Gly Gly
1               5                   10

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ile Leu Met Glu Leu Met Ala Gly Gly
1               5

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ile Leu Met Glu Leu Met Ala Gly Gly Asp
1               5                   10
```

```
<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Met Glu Leu Met Ala Gly Gly Asp Leu
1               5                   10

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Leu Pro Arg Phe Ile Leu Met Glu Leu
1               5

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Leu Pro Arg Phe Ile Leu Met Glu Leu Met
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Leu Gln Ser Leu Pro Arg Phe Ile Leu Met
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Leu Pro Arg Phe Ile Leu Met Glu Leu
1               5                   10

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178
```

```
Leu Ala Thr Glu Lys Ser Arg Trp Ser
1               5

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Leu Ala Thr Glu Lys Ser Arg Trp Ser Gly
1               5                   10

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Glu Tyr Met Ala Asn Gly Ser Leu Leu
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Met Ala Asn Gly Ser Leu Leu Asn Tyr
1               5

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Met Ala Asn Gly Ser Leu Leu Asn Tyr Leu
1               5                   10

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Leu Leu Asn Tyr Leu Arg Glu Met
1               5

<210> SEQ ID NO 184
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 184

Tyr Met Ala Asn Gly Ser Leu Leu Asn
1               5

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Tyr Met Ala Asn Gly Ser Leu Leu Asn Tyr
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Pro Pro Pro Ala Asp Leu Cys His Ala Leu
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ile Ile Arg Asn Arg Gly Glu Asn Ser Cys Lys
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Cys Leu Thr Ser Thr Val Gln Leu Ile Met
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ile Met Gln Leu Met Pro Phe Gly Cys
1               5
```

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ile Met Gln Leu Met Pro Phe Gly Cys Leu
1               5                   10

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Leu Ile Met Gln Leu Met Pro Phe Gly
1               5

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Leu Ile Met Gln Leu Met Pro Phe Gly Cys
1               5                   10

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Leu Thr Ser Thr Val Gln Leu Ile Met
1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Met Gln Leu Met Pro Phe Gly Cys Leu
1               5

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 195

Met Gln Leu Met Pro Phe Gly Cys Leu Leu
1               5                   10

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Leu Ile Met Gln Leu Met Pro Phe
1               5

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Leu Ile Met Gln Leu Met Pro Phe Gly
1               5                   10

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Thr Val Gln Leu Ile Met Gln Leu
1               5

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Val Gln Leu Ile Met Gln Leu Met Pro Phe
1               5                   10

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Leu Leu Leu Glu Met Leu Asp Ala
1               5

<210> SEQ ID NO 201
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 201

Leu Tyr Gly Leu Leu Leu Glu Met Leu
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asn Val Val Pro Leu Tyr Gly Leu Leu
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Pro Leu Tyr Gly Leu Leu Leu Glu Met
1               5

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Pro Leu Tyr Gly Leu Leu Leu Glu Met Leu
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Val Pro Leu Tyr Gly Leu Leu Leu Glu Met
1               5                   10

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Val Val Pro Leu Tyr Gly Leu Leu Leu
1               5
```

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Phe Leu Pro Ser Thr Leu Lys Ser Leu
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Val Tyr Thr Phe Leu Pro Ser Thr
1               5

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Val Tyr Thr Phe Leu Pro Ser Thr Leu
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Phe Leu Pro Ser Thr Leu Lys Ser Leu
1               5                   10

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Tyr Thr Phe Leu Pro Ser Thr Leu
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 212

Tyr Thr Phe Leu Pro Ser Thr Leu Lys
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Asn Val Val Pro Leu Cys Asp Leu Leu
1               5

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Asn Val Val Pro Leu Cys Asp Leu Leu Leu
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Pro Leu Cys Asp Leu Leu Leu Glu Met
1               5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Pro Leu Cys Asp Leu Leu Leu Glu Met Leu
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Val Pro Leu Cys Asp Leu Leu Leu Glu Met
1               5                   10

<210> SEQ ID NO 218
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Val Val Pro Leu Cys Asp Leu Leu Leu
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Asn Val Val Pro Leu Asn Asp Leu Leu
1               5

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asn Val Val Pro Leu Asn Asp Leu Leu Leu
1               5                   10

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Pro Leu Asn Asp Leu Leu Leu Glu Met
1               5

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Pro Leu Asn Asp Leu Leu Leu Glu Met Leu
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Val Pro Leu Asn Asp Leu Leu Leu Glu Met
```

```
1               5                   10
```

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

```
Asn Val Val Pro Leu Ser Asp Leu Leu
1               5
```

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

```
Asn Val Val Pro Leu Ser Asp Leu Leu Leu
1               5                   10
```

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

```
Pro Leu Ser Asp Leu Leu Leu Glu Met
1               5
```

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

```
Pro Leu Ser Asp Leu Leu Leu Glu Met Leu
1               5                   10
```

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

```
Val Pro Leu Ser Asp Leu Leu Leu Glu Met
1               5                   10
```

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Val Val Pro Leu Ser Asp Leu Leu Leu
1               5

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Val Leu Glu Arg Cys Pro His Arg Pro Ile
1               5                   10

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Tyr Thr Leu Asp Val Leu Glu Arg Cys
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Phe Gln Asn Gly Lys Met Ala Leu Ser
1               5

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Val Met Ala Gly Leu Gly Ser Pro Tyr Val
1               5                   10

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Lys Pro Ile Ile Ile Gly His His Ala
1               5

<210> SEQ ID NO 235

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Lys Pro Ile Ile Ile Gly Cys His Ala
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Lys Pro Ile Ile Ile Gly Gly His Ala
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Lys Pro Ile Ile Ile Gly Ser His Ala
1               5

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ile Ile Glu Tyr Cys Cys Tyr Gly Asp Leu
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Thr Ile Gly Gly Pro Thr Leu Val Ile Ile
1               5                   10

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240
```

```
Val Ile Ile Glu Tyr Cys Cys Tyr Gly
1               5

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

His Met Asn Ile Ala Asn Leu Leu Gly Ala
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ile Ala Asn Leu Leu Gly Ala Cys Thr Ile
1               5                   10

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Met Asn Ile Ala Asn Leu Leu Gly Ala
1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Tyr Leu Gly Asn His Met Asn Ile Ala
1               5

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Tyr Leu Gly Asn His Met Asn Ile Ala Asn
1               5                   10

<210> SEQ ID NO 246
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 246

Val Leu His Glu Ser Asn Ser Pro Tyr
1               5

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Val Leu His Glu Ser Asn Ser Pro Tyr Ile
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Leu Gln Val Leu His Glu Cys Asn Ser Leu
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Leu Tyr Ile Val Gly Phe Tyr Gly Ala Phe
1               5                   10

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Asn Ser Leu Tyr Ile Val Gly Phe Tyr
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Val Leu His Glu Cys Asn Ser Leu
1               5
```

-continued

```
<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ser Leu Tyr Ile Val Gly Phe Tyr Gly
1               5

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Leu Tyr Ile Val Gly Phe Tyr Gly Ala
1               5                   10

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Val Leu His Glu Cys Asn Ser Leu Tyr
1               5

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Val Leu His Glu Cys Asn Ser Leu Tyr Ile
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Phe Tyr Gln Gln Gln Gln Gln Ser Asp Leu
1               5                   10

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257
```

-continued

Gln Gln Gln Ser Asp Leu Gln Pro Pro Ala
1               5                   10

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gln Gln Ser Asp Leu Gln Pro Pro Ala
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Tyr Gln Gln Gln Gln Gln Ser Asp Leu
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Phe Glu Leu Leu Ser Thr Pro Pro Leu
1               5

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Leu Leu Ser Thr Pro Pro Leu Ser Pro Ser
1               5                   10

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Phe Glu Leu Leu Pro Ile Pro Pro Leu
1               5

<210> SEQ ID NO 263
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 263

Ile Trp Lys Lys Phe Glu Leu Leu Pro Ile
1               5                   10

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Leu Leu Pro Ile Pro Pro Leu Ser Pro Ser
1               5                   10

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Leu Pro Ile Pro Pro Leu Ser Pro Ser
1               5

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ile Ile Glu Tyr Cys Phe Tyr Gly Asp Leu
1               5                   10

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ile Ile Ile Glu Tyr Cys Phe Tyr Gly
1               5

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ile Tyr Ile Ile Ile Glu Tyr Cys Phe
1               5
```

```
<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ile Tyr Ile Ile Ile Glu Tyr Cys Phe Tyr
1               5                   10

<210> SEQ ID NO 270
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Tyr Ile Ile Ile Glu Tyr Cys Phe Tyr Gly
1               5                   10

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Lys Ile Thr Glu Gln Glu Lys Asp Phe Leu
1               5                   10

<210> SEQ ID NO 272
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ser Thr Arg Asp Pro Leu Ser Glu Ile Thr Lys
1               5                   10

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Asp Pro Leu Ser Glu Ile Thr Lys
1               5

<210> SEQ ID NO 274
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 274

Leu Pro Leu Lys Phe Arg Asp Ala Glu Thr
1               5                   10

<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gln Thr Gly Val Met Ile Cys Ala Tyr Leu
1               5                   10

<210> SEQ ID NO 276
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ala Phe Ser Gly Glu Tyr Ile Pro Thr Val
1               5                   10

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ser Met Asn Arg Arg Pro Ile Leu Thr
1               5

<210> SEQ ID NO 278
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Tyr Met Cys Asn Ser Ser Cys Met Gly Ser
1               5                   10

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Met Asn Gln Arg Pro Ile Leu Thr
1               5

<210> SEQ ID NO 280
<211> LENGTH: 9
<212> TYPE: PRT

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gly Met Asn Trp Arg Pro Ile Leu Thr
1               5

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Leu Leu Gly Arg Asn Ser Phe Glu Val Cys
1               5                   10

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ala Leu Lys Tyr Ile Phe Val Ala Val
1               5

<210> SEQ ID NO 283
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ala Leu Lys Tyr Ile Phe Val Ala Val Arg
1               5                   10

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Val Arg Ala Ile Cys Val Met Lys
1               5

<210> SEQ ID NO 285
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Val Arg Ala Ile Cys Val Met Lys Ser
1               5                   10

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Cys Val Glu Lys Lys Thr Ala Leu Lys
1               5

<210> SEQ ID NO 287
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Cys Val Glu Lys Lys Thr Ala Leu Lys Tyr
1               5                   10

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Cys Val Met Lys Ser Phe Leu Ile Phe
1               5

<210> SEQ ID NO 289
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Cys Val Met Lys Ser Phe Leu Ile Phe Arg
1               5                   10

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Phe Leu Ile Phe Arg Arg Trp Lys Ser
1               5

<210> SEQ ID NO 291
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 291

Phe Arg Arg Trp Lys Ser His Ser Pro Leu
1               5                   10

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Phe Val Ala Val Arg Ala Ile Cys Val
1               5

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Phe Val Ala Val Arg Ala Ile Cys Val Met
1               5                   10

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ile Gln Leu His Leu Ser His Pro Ile
1               5

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Lys Ser Phe Leu Ile Phe Arg Arg Trp Lys
1               5                   10

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Lys Thr Ala Leu Lys Tyr Ile Phe Val
1               5

<210> SEQ ID NO 297
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Lys Tyr Ile Phe Val Ala Val Arg Ala Ile
1               5                   10

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Arg Trp Lys Ser His Ser Pro Leu Gln Ile
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Thr Ala Leu Lys Tyr Ile Phe Val Ala Val
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Val Ala Val Arg Ala Ile Cys Val Met Lys
1               5                   10

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Val Met Lys Ser Phe Leu Ile Phe Arg
1               5

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Val Met Lys Ser Phe Leu Ile Phe Arg Arg
```

```
1               5                   10
```

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

```
Tyr Ile Phe Val Ala Val Arg Ala Ile
1               5
```

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

```
Ala Leu Phe Phe Phe Phe Phe Glu Thr
1               5
```

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

```
Ala Leu Phe Phe Phe Phe Phe Glu Thr Lys
1               5                   10
```

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

```
Ala Gln Ala Gly Val Gln Trp Arg Ser Leu
1               5                   10
```

<210> SEQ ID NO 307
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

```
Cys Leu Ala Asn Phe Cys Ile Phe Asn Arg
1               5                   10
```

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Cys Leu Ser Phe Leu Ser Ser Trp Asp Tyr
1               5                   10

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Phe Phe Glu Thr Lys Ser Cys Ser Val
1               5

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Phe Phe Phe Glu Thr Lys Ser Cys Ser Val
1               5                   10

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Phe Lys Leu Phe Ser Cys Leu Ser Phe Leu
1               5                   10

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Phe Leu Ser Ser Trp Asp Tyr Arg Arg Met
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gly Phe Lys Leu Phe Ser Cys Leu Ser Phe
1               5                   10

<210> SEQ ID NO 314

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Lys Leu Phe Ser Cys Leu Ser Phe Leu
1               5

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Lys Leu Phe Ser Cys Leu Ser Phe Leu Ser
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Leu Ala Leu Phe Phe Phe Phe Phe Glu Thr
1               5                   10

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Leu Phe Phe Phe Phe Phe Glu Thr Lys
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Leu Ser Phe Leu Ser Ser Trp Asp Tyr
1               5

<210> SEQ ID NO 319
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319
```

```
Leu Ser Phe Leu Ser Ser Trp Asp Tyr Arg
1               5                   10

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Arg Met Pro Pro Cys Leu Ala Asn Phe
1               5

<210> SEQ ID NO 321
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Arg Arg Met Pro Pro Cys Leu Ala Asn Phe
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Ser Leu Gln Pro Pro Pro Pro Gly Phe Lys
1               5                   10

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Val Gln Trp Arg Ser Leu Gly Ser Leu
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Phe Phe Phe Ser Val Ile Phe Ser Thr
1               5

<210> SEQ ID NO 325
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 325

Met Ser Val Cys Phe Phe Phe Ser Val
1               5                  10

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Ser Val Cys Phe Phe Phe Phe Ser Val
1               5

<210> SEQ ID NO 327
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ser Val Cys Phe Phe Phe Phe Ser Val Ile
1               5                  10

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Phe Phe Cys Tyr Ile Leu Asn Thr Met Phe
1               5                  10

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Met Ser Val Cys Phe Phe Phe Phe Cys Tyr
1               5                  10

<210> SEQ ID NO 330
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Val Cys Phe Phe Phe Phe Cys Tyr Ile
1               5                  10

```
<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Lys Gln Trp Ser Ser Val Thr Ser Leu
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Val Leu Trp Met Pro Thr Ser Thr Val
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ile Leu Ile Arg Lys Ala Met Thr Val
1               5

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Arg Met Lys Val Pro Leu Met Lys
1               5

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Thr Leu Lys Lys Lys Pro Arg Asp Ile
1               5

<210> SEQ ID NO 336
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336
```

-continued

```
Leu Ile Glu Gly Phe Glu Ala Leu Leu Lys
1               5                   10

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Gln Gln Leu Lys Trp Thr Pro His Ile
1               5

<210> SEQ ID NO 338
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gln Leu Lys Trp Thr Pro His Ile Leu Lys
1               5                   10

<210> SEQ ID NO 339
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ile Val Ser Glu Lys Asn Gln Gln Leu Lys
1               5                   10

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gln Leu Lys Trp Thr Pro His Ile Leu Lys
1               5                   10

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gln Gln Leu Lys Trp Thr Pro His Ile
1               5

<210> SEQ ID NO 342
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 342

Asn Gln Gln Leu Lys Trp Thr Pro His Ile Leu
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Asn Gln Gln Leu Lys Trp Thr Pro His Ile
1               5                   10

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gln Leu Lys Trp Thr Pro His Ile Leu
1               5

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gly Pro Pro Arg Pro Pro Arg Ala Ala Cys
1               5                   10

<210> SEQ ID NO 346
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Pro Pro Arg Pro Pro Arg Ala Ala Cys
1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ser Leu Arg Arg Lys Tyr Leu Arg Val
1               5
```

<210> SEQ ID NO 348
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ser Ala Ala Cys His Arg Arg Gly Cys Val
1               5                   10

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ala Leu Trp Glu Cys Ser Leu Pro Gln Ala
1               5                   10

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Cys Leu Ile Val Ser Arg Thr Leu Leu
1               5

<210> SEQ ID NO 351
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Cys Leu Ile Val Ser Arg Thr Leu Leu Leu
1               5                   10

<210> SEQ ID NO 352
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Phe Leu Leu Ala Leu Trp Glu Cys Ser
1               5

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 353

Phe Leu Leu Ala Leu Trp Glu Cys Ser Leu
1               5                   10

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ile Val Ser Arg Thr Leu Leu Leu Val
1               5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Leu Ile Val Ser Arg Thr Leu Leu Leu
1               5

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Leu Ile Val Ser Arg Thr Leu Leu Leu Val
1               5                   10

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Leu Leu Ala Leu Trp Glu Cys Ser Leu
1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Leu Pro Gln Ala Arg Leu Cys Leu Ile
1               5

<210> SEQ ID NO 359
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 359

Leu Pro Gln Ala Arg Leu Cys Leu Ile Val
1               5                   10

<210> SEQ ID NO 360
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Asn Val Arg Asp Lys Lys Arg Ala Thr Phe
1               5                   10

<210> SEQ ID NO 361
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ser Leu Pro Gln Ala Arg Leu Cys Leu Ile
1               5                   10

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Phe Phe Cys Trp Ile Leu Ser Cys Lys
1               5

<210> SEQ ID NO 363
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Phe Phe Phe Cys Trp Ile Leu Ser Cys Lys
1               5                   10

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ile Thr Ala Phe Phe Phe Cys Trp Ile
1               5
```

<210> SEQ ID NO 365
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Leu Tyr Ile Thr Ala Phe Phe Phe Cys Trp
1               5                   10

<210> SEQ ID NO 366
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Tyr Ile Thr Ala Phe Phe Phe Cys Trp Ile
1               5                   10

<210> SEQ ID NO 367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ile Thr Ala Phe Phe Leu Leu Asp Ile
1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Leu Leu Tyr Ile Thr Ala Phe Phe Leu
1               5

<210> SEQ ID NO 369
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Leu Leu Tyr Ile Thr Ala Phe Phe Leu Leu
1               5                   10

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 370

Leu Tyr Ile Thr Ala Phe Phe Leu Leu
1               5

<210> SEQ ID NO 371
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Leu Tyr Ile Thr Ala Phe Phe Leu Leu Asp
1               5                   10

<210> SEQ ID NO 372
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Tyr Ile Thr Ala Phe Phe Leu Leu Asp Ile
1               5                   10

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Gly Ser Asn Glu Val Thr Thr Arg Tyr
1               5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Met Pro Lys Asp Val Asn Ile Gln Val
1               5

<210> SEQ ID NO 375
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Thr Gly Ser Asn Glu Val Thr Thr Arg Tyr
1               5                   10

<210> SEQ ID NO 376
<211> LENGTH: 10
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Lys Lys Leu Met Leu Leu Arg Leu Asn Leu
1               5                   10

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Lys Leu Met Leu Leu Arg Leu Asn Leu
1               5

<210> SEQ ID NO 378
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Lys Leu Met Leu Leu Arg Leu Asn Leu Arg
1               5                   10

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Leu Leu Arg Leu Asn Leu Arg Lys Met
1               5

<210> SEQ ID NO 380
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Leu Met Leu Leu Arg Leu Asn Leu
1               5

<210> SEQ ID NO 381
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Leu Met Leu Leu Arg Leu Asn Leu Arg Lys

```
1               5                   10

<210> SEQ ID NO 382
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Leu Asn Leu Arg Lys Met Cys Gly Pro Phe
1               5                   10

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Met Leu Leu Arg Leu Asn Leu Arg Lys
1               5

<210> SEQ ID NO 384
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Met Leu Leu Arg Leu Asn Leu Arg Lys Met
1               5                   10

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Asn Leu Arg Lys Met Cys Gly Pro Phe
1               5

<210> SEQ ID NO 386
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Asn Tyr Cys Gln Lys Lys Leu Met Leu Leu
1               5                   10

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 387

Tyr Cys Gln Lys Lys Leu Met Leu Leu
1               5

<210> SEQ ID NO 388
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Phe Lys Lys Lys Thr Tyr Thr Cys Ala Ile
1               5                   10

<210> SEQ ID NO 389
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Ile Thr Thr Val Lys Ala Thr Glu Thr Lys
1               5                   10

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Lys Ser Lys Lys Lys Glu Thr Phe Lys
1               5

<210> SEQ ID NO 391
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Lys Ser Lys Lys Lys Glu Thr Phe Lys Lys
1               5                   10

<210> SEQ ID NO 392
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Lys Thr Tyr Thr Cys Ala Ile Thr Thr Val
1               5                   10

<210> SEQ ID NO 393

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Thr Phe Lys Lys Lys Thr Tyr Thr Cys
1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Thr Tyr Thr Cys Ala Ile Thr Thr Val
1               5

<210> SEQ ID NO 395
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Thr Tyr Thr Cys Ala Ile Thr Thr Val Lys
1               5                   10

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Tyr Thr Cys Ala Ile Thr Thr Val Lys
1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Thr Ala Lys Ser Lys Lys Arg Asn Leu
1               5

<210> SEQ ID NO 398
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398
```

```
Phe Ala Leu Cys Gly Phe Trp Gln Ile
1               5
```

<210> SEQ ID NO 399
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

```
Leu Lys Lys Leu Arg Ser Pro Leu
1               5
```

<210> SEQ ID NO 400
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

```
Ser Leu Lys Lys Val Pro Ala Leu
1               5
```

<210> SEQ ID NO 401
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

```
Arg Lys Ile Ser Asn Trp Ser Leu Lys Lys
1               5                   10
```

<210> SEQ ID NO 402
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

```
Val Pro Ala Leu Lys Lys Leu Arg Ser Pro Leu
1               5                   10
```

<210> SEQ ID NO 403
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

```
Lys Arg Val Asn Thr Ala Trp Lys Thr Lys
1               5                   10
```

<210> SEQ ID NO 404
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 404

Met Thr Lys Lys Lys Arg Val Asn Thr Ala
1               5                   10

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Arg Val Asn Thr Ala Trp Lys Thr Lys
1               5

<210> SEQ ID NO 406
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Arg Val Asn Thr Ala Trp Lys Thr Lys Lys
1               5                   10

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Thr Lys Lys Lys Arg Val Asn Thr Ala
1               5

<210> SEQ ID NO 408
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Trp Lys Thr Lys Lys Thr Ser Phe Ser Leu
1               5                   10

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Ala Leu Met Ser Ala Met Thr Thr Ser
1               5

```
<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Ala Met Thr Thr Ser Ser Ser Gln Lys
1               5

<210> SEQ ID NO 411
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Ala Met Thr Thr Ser Ser Ser Gln Lys Asn
1               5                   10

<210> SEQ ID NO 412
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Cys Ile Met Lys Glu Lys Lys Ser Leu
1               5

<210> SEQ ID NO 413
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Cys Ile Met Lys Glu Lys Lys Ser Leu Val
1               5                   10

<210> SEQ ID NO 414
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Ile Met Lys Glu Lys Lys Ser Leu
1               5

<210> SEQ ID NO 415
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415
```

```
Ile Met Lys Glu Lys Lys Ser Leu Val
1               5

<210> SEQ ID NO 416
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Lys Ser Leu Val Arg Leu Ser Ser Cys Val
1               5                   10

<210> SEQ ID NO 417
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Leu Val Arg Leu Ser Ser Cys Val Pro Val
1               5                   10

<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Arg Leu Ser Ser Cys Val Pro Val Ala
1               5

<210> SEQ ID NO 419
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Arg Leu Ser Ser Cys Val Pro Val Ala Leu
1               5                   10

<210> SEQ ID NO 420
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ser Ala Met Thr Thr Ser Ser Ser Gln Lys
1               5                   10

<210> SEQ ID NO 421
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 421

Ser Leu Val Arg Leu Ser Ser Cys Val
1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Val Pro Val Ala Leu Met Ser Ala Met
1               5

<210> SEQ ID NO 423
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Val Arg Leu Ser Ser Cys Val Pro Val Ala
1               5                   10

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Lys Met Arg Lys Lys Tyr Ala Gln Lys
1               5

<210> SEQ ID NO 425
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Phe Val Met Ser Asp Thr Thr Tyr Lys
1               5

<210> SEQ ID NO 426
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Phe Val Met Ser Asp Thr Thr Tyr Lys Ile
1               5                   10
```

<210> SEQ ID NO 427
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Lys Thr Phe Glu Lys Lys Gly Glu Lys
1               5

<210> SEQ ID NO 428
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Leu Phe Val Met Ser Asp Thr Thr Tyr Lys
1               5                   10

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Met Ser Asp Thr Thr Tyr Lys Ile Tyr
1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Val Met Ser Asp Thr Thr Tyr Lys Ile
1               5

<210> SEQ ID NO 431
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Val Met Ser Asp Thr Thr Tyr Lys Ile Tyr
1               5                   10

<210> SEQ ID NO 432
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 432

Tyr Leu Thr Lys Trp Pro Lys Phe Phe Leu
1               5                   10

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Phe Leu Gln Glu Arg Asn Leu Pro Pro
1               5

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Phe Arg Arg Pro His Ser Cys Leu Ala
1               5

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Leu Ile Val Leu Arg Val Val Arg Leu
1               5

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Leu Leu Ser Val His Leu Ile Val Leu
1               5

<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Glu Val Lys His Leu His His Leu Leu
1               5

<210> SEQ ID NO 438
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 438

His Leu His His Leu Leu Lys Gln Leu Lys
1               5                   10

<210> SEQ ID NO 439
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

His Leu Leu Leu Lys Arg Glu Arg Val
1               5

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Lys Ile Lys His Leu Leu Leu Lys Arg
1               5

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Lys Pro Ser Glu Lys Tyr Leu Lys Ile
1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Lys Tyr Leu Lys Ile Lys His Leu Leu
1               5

<210> SEQ ID NO 443
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Lys Tyr Leu Lys Ile Lys His Leu Leu Leu
1               5                   10
```

<210> SEQ ID NO 444
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Leu Leu Lys Gln Leu Lys Pro Ser Glu Lys
1               5                   10

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Leu Leu Lys Arg Glu Arg Val Asp Leu
1               5

<210> SEQ ID NO 446
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Leu Leu Leu Lys Arg Glu Arg Val Asp Leu
1               5                   10

<210> SEQ ID NO 447
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Gln Leu Lys Pro Ser Glu Lys Tyr Leu Lys
1               5                   10

<210> SEQ ID NO 448
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Tyr Leu Lys Ile Lys His Leu Leu Leu
1               5

<210> SEQ ID NO 449
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Tyr Leu Lys Ile Lys His Leu Leu Leu Lys
1               5                   10

<210> SEQ ID NO 450
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Ile Leu Pro Arg Lys Val Leu Gln Met
1               5

<210> SEQ ID NO 451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Lys Val Leu Gln Met Asp Phe Leu Val
1               5

<210> SEQ ID NO 452
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Leu Pro Arg Lys Val Leu Gln Met Asp Phe
1               5                   10

<210> SEQ ID NO 453
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Leu Gln Met Asp Phe Leu Val His Pro Ala
1               5                   10

<210> SEQ ID NO 454
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Gln Met Asp Phe Leu Val His Pro Ala
1               5

<210> SEQ ID NO 455
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Tyr Ile Leu Pro Arg Lys Val Leu Gln Met
1               5                   10

<210> SEQ ID NO 456
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Ala Pro Ser Pro Ala Ser Arg Leu Gln Cys
1               5                   10

<210> SEQ ID NO 457
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

His Pro Leu Ala Pro Met Pro Ser Lys Thr
1               5                   10

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Ile Leu Pro Leu Pro Gln Leu Leu Leu
1               5

<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Leu Leu Leu Ser Ala Asp Gln Gln Ala
1               5

<210> SEQ ID NO 460
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Leu Pro Thr Gln Thr Arg Gly Cys Ile
```

```
1               5

<210> SEQ ID NO 461
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Leu Pro Thr Gln Thr Arg Gly Cys Ile Leu
1               5                   10

<210> SEQ ID NO 462
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Arg Ile Ser Cys Leu Pro Thr Gln Thr Arg
1               5                   10

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Ser Leu Ala Glu Thr Val Ser Leu His
1               5

<210> SEQ ID NO 464
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Thr Pro Arg Ser Ser Ser Ser Ser Ser
1               5

<210> SEQ ID NO 465
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Thr Pro Arg Ser Ser Ser Ser Ser Ser
1               5                   10

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 466

Ala Leu Pro Pro Val Leu Leu Ser Leu
1               5

<210> SEQ ID NO 467
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Ala Leu Pro Pro Val Leu Leu Ser Leu Ala
1               5                   10

<210> SEQ ID NO 468
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Ala Leu Pro Arg Pro Leu Leu Ala Leu
1               5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Ala Ser Arg Thr Ala Ser Cys Ile Leu
1               5

<210> SEQ ID NO 470
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Glu Ala Leu Pro Arg Pro Leu Leu Ala Leu
1               5                   10

<210> SEQ ID NO 471
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

His Leu Gly His Pro Val Ala Ser Arg
1               5

<210> SEQ ID NO 472

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

His Pro Val Ala Ser Arg Thr Ala Ser
1               5

<210> SEQ ID NO 473
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

His Pro Val Ala Ser Arg Thr Ala Ser Cys
1               5                   10

<210> SEQ ID NO 474
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Ile Ile Gln Leu Ser Leu Leu Ser Leu Leu
1               5                   10

<210> SEQ ID NO 475
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Ile Gln Leu Ser Leu Leu Ser Leu Leu
1               5

<210> SEQ ID NO 476
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Ile Gln Leu Ser Leu Leu Ser Leu Leu Ile
1               5                   10

<210> SEQ ID NO 477
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477
```

```
Leu Leu Ala Leu Pro Pro Val Leu Leu
1               5

<210> SEQ ID NO 478
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Leu Leu Ile Pro Pro Leu Thr Cys Leu
1               5

<210> SEQ ID NO 479
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Leu Leu Ile Pro Pro Leu Thr Cys Leu Ala
1               5                   10

<210> SEQ ID NO 480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Leu Leu Ser Leu Leu Ile Pro Pro Leu
1               5

<210> SEQ ID NO 481
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Leu Leu Ser Leu Leu Ile Pro Pro Leu Thr
1               5                   10

<210> SEQ ID NO 482
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Leu Pro Arg Pro Leu Leu Ala Leu Pro Pro
1               5                   10

<210> SEQ ID NO 483
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 483

Gln Leu Ser Leu Leu Ser Leu Leu Ile
1               5

<210> SEQ ID NO 484
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Arg Leu Leu Gln Cys Gln Ala Thr Arg
1               5

<210> SEQ ID NO 485
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Arg Pro Leu Leu Ala Leu Pro Pro Val
1               5

<210> SEQ ID NO 486
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Arg Pro Leu Leu Ala Leu Pro Pro Val Leu
1               5                   10

<210> SEQ ID NO 487
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Ser Leu Ala Gln Asp His Ser Arg Leu
1               5

<210> SEQ ID NO 488
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Ser Leu Ala Gln Asp His Ser Arg Leu Leu
1               5                   10
```

```
<210> SEQ ID NO 489
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Ser Leu Leu Ile Pro Pro Leu Thr Cys Leu
1               5                   10

<210> SEQ ID NO 490
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Ser Leu Leu Ser Leu Leu Ile Pro Pro
1               5

<210> SEQ ID NO 491
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Ser Leu Leu Ser Leu Leu Ile Pro Pro Leu
1               5                   10

<210> SEQ ID NO 492
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Ala Ala Ala Thr Ser Ala Ala Ser Thr Leu
1               5                   10

<210> SEQ ID NO 493
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Ala Ala Ile Pro Ala Ser Thr Ser Ala Val
1               5                   10

<210> SEQ ID NO 494
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494
```

Ala Ile Pro Ala Ser Thr Ser Ala Val
1               5

<210> SEQ ID NO 495
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Ala Leu Pro Ala Gly Cys Val Ser Ser Ala
1               5                   10

<210> SEQ ID NO 496
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Ala Pro Leu Leu Thr Ala Thr Gly Ser Val
1               5                   10

<210> SEQ ID NO 497
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Ala Pro Val Leu Ser Ala Ser Ile Leu
1               5

<210> SEQ ID NO 498
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Ala Thr Leu Leu Pro Ala Thr Thr Val
1               5

<210> SEQ ID NO 499
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Ala Thr Val Ser Thr Thr Thr Ala Pro Val
1               5                   10

<210> SEQ ID NO 500
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 500

Ala Val Pro Ala Asn Cys Leu Phe Pro Ala
1               5                   10

<210> SEQ ID NO 501
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Cys Leu Phe Pro Ala Ala Leu Pro Ser Thr
1               5                   10

<210> SEQ ID NO 502
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Cys Pro Thr Phe Val Ser Ala Ala Ala
1               5

<210> SEQ ID NO 503
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Phe Pro Ala Ala Leu Pro Ser Thr Ala
1               5

<210> SEQ ID NO 504
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Phe Pro Ala Ala Leu Pro Ser Thr Ala Gly
1               5                   10

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Gly Ala Glu Cys His Gly Arg Pro Leu
1               5
```

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Gly Ala Ile Ser Arg Phe Ile Trp Val
1               5

<210> SEQ ID NO 507
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Ile Leu Pro Ala Ala Ile Pro Ala Ser Thr
1               5                   10

<210> SEQ ID NO 508
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Ile Trp Val Ser Gly Ile Leu Ser Pro Leu
1               5                   10

<210> SEQ ID NO 509
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Leu Leu Thr Ala Thr Gly Ser Val Ser Leu
1               5                   10

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Leu Leu Tyr Thr Ala Asp Ser Ser Leu
1               5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 511

Leu Pro Ala Ala Ala Thr Ser Ala Ala
1               5

<210> SEQ ID NO 512
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Leu Pro Ala Ala Ala Thr Ser Ala Ala Ser
1               5                   10

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Leu Pro Ala Ala Ile Pro Ala Ser Thr
1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Leu Pro Ala Gly Cys Val Ser Ser Ala
1               5

<210> SEQ ID NO 515
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Leu Pro Ala Gly Cys Val Ser Ser Ala Pro
1               5                   10

<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Leu Tyr Thr Ala Asp Ser Ser Leu Trp
1               5

<210> SEQ ID NO 517
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 517

Gln Pro Ala Lys Ser Ser Pro Ser Ala
1               5

<210> SEQ ID NO 518
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Gln Pro Ala Lys Ser Ser Pro Ser Ala Ala
1               5                   10

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Arg Phe Ile Trp Val Ser Gly Ile Leu
1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Arg Pro Gln Arg Val Trp Ser Thr Gly
1               5

<210> SEQ ID NO 521
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Arg Val Trp Ser Thr Gly Pro Asp Ser Ile
1               5                   10

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Ser Ala Val Pro Gly Ser Ile Pro Leu
1               5
```

<210> SEQ ID NO 523
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Ser Ile Leu Pro Ala Ala Ile Pro Ala
1               5

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Ser Leu Pro Ala Ala Ala Thr Ser Ala
1               5

<210> SEQ ID NO 525
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Ser Leu Pro Ala Ala Ala Thr Ser Ala Ala
1               5                   10

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Ser Leu Trp Thr Thr Arg Pro Gln Arg
1               5

<210> SEQ ID NO 527
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Ser Leu Trp Thr Thr Arg Pro Gln Arg Val
1               5                   10

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Ser Pro Ser Ala Ala Ala Ala Thr Leu
1               5

<210> SEQ ID NO 529
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Ser Pro Ser Ala Ala Ala Ala Thr Leu Leu
1               5                   10

<210> SEQ ID NO 530
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Thr Leu Asp Ala Leu Pro Ala Gly Cys Val
1               5                   10

<210> SEQ ID NO 531
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Thr Val Ser Thr Thr Thr Ala Pro Val
1               5

<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Val Leu Ser Ala Ser Ile Leu Pro Ala
1               5

<210> SEQ ID NO 533
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Val Leu Ser Ala Ser Ile Leu Pro Ala Ala
1               5                   10

<210> SEQ ID NO 534
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Val Pro Ala Asn Cys Leu Phe Pro Ala
1               5

<210> SEQ ID NO 535
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Val Pro Ala Asn Cys Leu Phe Pro Ala Ala
1               5                   10

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Val Pro Asp Pro Ser Cys Pro Thr Phe
1               5

<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Val Pro Gly Ser Ile Pro Leu Pro Ala
1               5

<210> SEQ ID NO 538
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Val Pro Gly Ser Ile Pro Leu Pro Ala Val
1               5                   10

<210> SEQ ID NO 539
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Trp Val Ser Gly Ile Leu Ser Pro Leu
```

```
1               5
```

<210> SEQ ID NO 540
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

```
Tyr Thr Ala Asp Ser Ser Leu Trp Thr Thr
1               5                   10
```

<210> SEQ ID NO 541
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

```
Ala Pro Ala Gly Met Val Asn Arg Ala
1               5
```

<210> SEQ ID NO 542
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

```
Ala Ser Leu His Arg Arg Ser Tyr Leu
1               5
```

<210> SEQ ID NO 543
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

```
Ala Ser Leu His Arg Arg Ser Tyr Leu Lys
1               5                   10
```

<210> SEQ ID NO 544
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

```
Phe Leu Leu Met Asp Asn Lys Ala Pro Ala
1               5                   10
```

<210> SEQ ID NO 545
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 545

His Pro Arg Arg Ser Pro Ser Arg Leu
1               5

<210> SEQ ID NO 546
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

His Pro Ser Leu His Ile Ser Ser Pro
1               5

<210> SEQ ID NO 547
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

His Arg Arg Ser Tyr Leu Lys Ile His Leu
1               5                   10

<210> SEQ ID NO 548
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

His Ser Arg Phe Leu Leu Met Asp Asn Lys
1               5                   10

<210> SEQ ID NO 549
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Lys Leu Pro Ile Pro Ser Ser Ala Ser Leu
1               5                   10

<210> SEQ ID NO 550
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Lys Val Leu Thr Leu Ser Ser Ser Ser His
1               5                   10

<210> SEQ ID NO 551

```
<210> SEQ ID NO 551
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Leu Ile His Ser Arg Phe Leu Leu Met
1               5

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Leu Leu Met Asp Asn Lys Ala Pro Ala
1               5

<210> SEQ ID NO 553
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Leu Met Asp Asn Lys Ala Pro Ala Gly Met
1               5                   10

<210> SEQ ID NO 554
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Leu Pro Ile Pro Ser Ser Ala Ser Leu
1               5

<210> SEQ ID NO 555
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Met Pro Asn Leu Arg Ile Ser Ser Ser
1               5

<210> SEQ ID NO 556
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556
```

```
Met Pro Asn Leu Arg Ile Ser Ser Ser His
1               5                   10

<210> SEQ ID NO 557
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Asn Leu Arg Ile Ser Ser Ser His Ser Leu
1               5                   10

<210> SEQ ID NO 558
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Pro Pro Thr His Ser His Arg Leu Ser Leu
1               5                   10

<210> SEQ ID NO 559
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Arg Ala Gly Arg Arg Val Pro Trp Ala Ala
1               5                   10

<210> SEQ ID NO 560
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Arg Ala Arg Leu His Ile Thr Thr Ser Lys
1               5                   10

<210> SEQ ID NO 561
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Arg Ile Ser Ser Ser His Ser Leu Asn His
1               5                   10

<210> SEQ ID NO 562
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 562

Arg Leu His Thr Pro Pro Ser Ser Arg
1               5

<210> SEQ ID NO 563
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Arg Leu His Thr Pro Pro Ser Ser Arg Arg
1               5                   10

<210> SEQ ID NO 564
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Arg Leu Arg Ile Leu Ser Pro Ser Leu
1               5

<210> SEQ ID NO 565
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Arg Pro Leu Met Pro Asn Leu Arg Ile
1               5

<210> SEQ ID NO 566
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Arg Pro Arg Pro Leu Met Pro Asn Leu
1               5

<210> SEQ ID NO 567
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Ser Ala Ser Leu His Arg Arg Ser Tyr Leu
1               5                   10
```

```
<210> SEQ ID NO 568
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Ser Leu His Ile Ser Ser Pro Arg Leu
1               5

<210> SEQ ID NO 569
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Ser Leu His Arg Arg Ser Tyr Leu Lys
1               5

<210> SEQ ID NO 570
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Ser Leu His Arg Arg Ser Tyr Leu Lys Ile
1               5                   10

<210> SEQ ID NO 571
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Ser Leu Ile His Ser Arg Phe Leu Leu
1               5

<210> SEQ ID NO 572
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Ser Leu Ile His Ser Arg Phe Leu Leu Met
1               5                   10

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573
```

Ser Leu Leu Thr Ser Ser Ser Asn Leu
1               5

<210> SEQ ID NO 574
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Ser Leu Asn His His Ser Ser Ser Pro Leu
1               5                   10

<210> SEQ ID NO 575
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Ser Leu Ser Ser Pro Ser Lys Leu Pro Ile
1               5                   10

<210> SEQ ID NO 576
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Ser Pro Leu Ser Leu His Thr Pro Ser
1               5

<210> SEQ ID NO 577
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Ser Pro Leu Ser Leu His Thr Pro Ser Ser
1               5                   10

<210> SEQ ID NO 578
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Ser Pro Pro Thr His Ser His Arg Leu
1               5

<210> SEQ ID NO 579
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 579

Ser Pro Arg Leu His Thr Pro Pro Ser
1               5

<210> SEQ ID NO 580
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Ser Pro Arg Leu His Thr Pro Pro Ser Ser
1               5                   10

<210> SEQ ID NO 581
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Ser Pro Ser Leu Ser Ser Pro Ser Lys Leu
1               5                   10

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Ser Tyr Leu Lys Ile His Leu Gly Leu
1               5

<210> SEQ ID NO 583
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Thr Pro Ser Asn His Arg Pro Arg Pro Leu
1               5                   10

<210> SEQ ID NO 584
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Thr Pro Ser Ser His Pro Ser Leu His Ile
1               5                   10
```

<210> SEQ ID NO 585
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Cys Val Pro Phe Trp Thr Gly Arg Ile Leu
1               5                   10

<210> SEQ ID NO 586
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

His Cys Val Pro Phe Trp Thr Gly Arg Ile Leu
1               5                   10

<210> SEQ ID NO 587
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Ile Leu Leu Pro Ser Ala Ala Ser Val
1               5

<210> SEQ ID NO 588
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Ile Leu Leu Pro Ser Ala Ala Ser Val Cys
1               5                   10

<210> SEQ ID NO 589
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Leu Leu Pro Ser Ala Ala Ser Val Cys Pro Ile
1               5                   10

<210> SEQ ID NO 590
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 590

Leu Pro Ser Ala Ala Ser Val Cys Pro Ile
1               5                   10

<210> SEQ ID NO 591
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Met Arg Pro His Cys Val Pro Phe
1               5

<210> SEQ ID NO 592
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Arg Ile Leu Leu Pro Ser Ala Ala Ser Val
1               5                   10

<210> SEQ ID NO 593
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Arg Met Arg Pro His Cys Val Pro Phe
1               5

<210> SEQ ID NO 594
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Arg Met Arg Pro His Cys Val Pro Phe Trp
1               5                   10

<210> SEQ ID NO 595
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Arg Thr Asn Pro Thr Val Arg Met Arg
1               5

<210> SEQ ID NO 596
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 596

Ser Val Cys Pro Ile Pro Phe Glu Ala
1               5

<210> SEQ ID NO 597
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Thr Val Arg Met Arg Pro His Cys Val
1               5

<210> SEQ ID NO 598
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Thr Val Arg Met Arg Pro His Cys Val Pro Phe
1               5                   10

<210> SEQ ID NO 599
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Val Pro Phe Trp Thr Gly Arg Ile Leu
1               5

<210> SEQ ID NO 600
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Val Pro Phe Trp Thr Gly Arg Ile Leu Leu
1               5                   10

<210> SEQ ID NO 601
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Val Arg Met Arg Pro His Cys Val Pro Phe
1               5                   10
```

<210> SEQ ID NO 602
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Ala Met Val Pro Arg Gly Val Ser Met
1               5

<210> SEQ ID NO 603
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Ala Met Val Pro Arg Gly Val Ser Met Ala
1               5                   10

<210> SEQ ID NO 604
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Ala Trp Ala Pro Thr Ser Arg Thr Pro Trp
1               5                   10

<210> SEQ ID NO 605
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Cys Pro Met Pro Thr Thr Pro Val Gln Ala
1               5                   10

<210> SEQ ID NO 606
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Cys Pro Ser Thr Val Pro Pro Ser Pro Ala
1               5                   10

<210> SEQ ID NO 607
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 607

Gly Ala Met Val Pro Arg Gly Val Ser Met
1               5                   10

<210> SEQ ID NO 608
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Met Pro Cys Pro Met Pro Thr Thr Pro Val
1               5                   10

<210> SEQ ID NO 609
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Met Pro Thr Thr Pro Val Gln Ala Trp
1               5

<210> SEQ ID NO 610
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Met Pro Thr Thr Pro Val Gln Ala Trp Leu
1               5                   10

<210> SEQ ID NO 611
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Ser Leu Pro Glu Asp Arg Tyr Thr Gln Ala
1               5                   10

<210> SEQ ID NO 612
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Ser Pro Ala Gln Pro Tyr Leu Arg Val
1               5

<210> SEQ ID NO 613
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Ser Pro Ala Gln Pro Tyr Leu Arg Val Ser
1               5                   10

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Thr Ile Met Pro Cys Pro Met Pro Thr
1               5

<210> SEQ ID NO 615
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Thr Pro Val Gln Ala Trp Leu Glu Ala
1               5

<210> SEQ ID NO 616
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Thr Ser Arg Thr Pro Trp Gly Ala Met
1               5

<210> SEQ ID NO 617
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Val Pro Pro Ser Pro Ala Gln Pro Tyr Leu
1               5                   10

<210> SEQ ID NO 618
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Val Pro Arg Gly Val Ser Met Ala His
```

```
1               5
```

<210> SEQ ID NO 619
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

```
Cys Leu Ser Ala Arg Thr Gly Leu Ser Ile
1               5                   10
```

<210> SEQ ID NO 620
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

```
Cys Thr Thr Leu Asn Ser Pro Pro Leu Lys
1               5                   10
```

<210> SEQ ID NO 621
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

```
Gly Leu Ser Ile Ser Cys Thr Thr Leu
1               5
```

<210> SEQ ID NO 622
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

```
Ser Pro Pro Leu Lys Lys Met Ser Met
1               5
```

<210> SEQ ID NO 623
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

```
Thr Leu Asn Ser Pro Pro Leu Lys Lys
1               5
```

<210> SEQ ID NO 624
<211> LENGTH: 9
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 624

Thr Thr Leu Asn Ser Pro Pro Leu Lys
1               5

<210> SEQ ID NO 625
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Thr Thr Leu Asn Ser Pro Pro Leu Lys Lys
1               5                   10

<210> SEQ ID NO 626
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Leu Gln Arg Phe Arg Phe Thr His Val
1               5

<210> SEQ ID NO 627
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Leu Gln Arg Phe Arg Phe Thr His Val Ile
1               5                   10

<210> SEQ ID NO 628
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Arg Leu Ser Ser Val Leu Gln Arg Phe
1               5

<210> SEQ ID NO 629
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Arg Leu Ser Ser Val Leu Gln Arg Phe Arg
1               5                   10

<210> SEQ ID NO 630
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Val Leu Gln Arg Phe Arg Phe Thr His Val
1               5                   10

<210> SEQ ID NO 631
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Ala Ser Val Gly Arg His Ser Leu Ser Lys
1               5                   10

<210> SEQ ID NO 632
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Lys Phe Leu Pro Phe Trp Gly Phe Leu
1               5

<210> SEQ ID NO 633
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Leu Ala Ser Val Gly Arg His Ser Leu
1               5

<210> SEQ ID NO 634
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Leu Pro Phe Trp Gly Phe Leu Glu Glu Phe
1               5                   10

<210> SEQ ID NO 635
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635
```

```
Pro Phe Trp Gly Phe Leu Glu Glu Phe
1               5

<210> SEQ ID NO 636
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Ser Val Gly Arg His Ser Leu Ser Lys
1               5

<210> SEQ ID NO 637
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Ala Pro Arg Pro Ile Arg Pro Pro Phe
1               5

<210> SEQ ID NO 638
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Ala Pro Arg Pro Ile Arg Pro Pro Phe Leu
1               5                   10

<210> SEQ ID NO 639
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Ala Gln Lys Met Lys Lys Ala His Phe Leu
1               5                   10

<210> SEQ ID NO 640
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Phe Leu Pro Ser Ala Ala Gln Lys Met
1               5

<210> SEQ ID NO 641
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 641

Gly Leu Phe Leu Pro Ser Ala Ala Gln Lys
1               5                   10

<210> SEQ ID NO 642
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

His Pro Leu Leu Val Ser Leu Leu Leu
1               5

<210> SEQ ID NO 643
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Lys Ala His Phe Leu Lys Thr Trp Phe Arg
1               5                   10

<210> SEQ ID NO 644
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Lys Ala Arg Phe Ser Thr Ala Ser Leu
1               5

<210> SEQ ID NO 645
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Lys Met Lys Lys Ala His Phe Leu Lys
1               5

<210> SEQ ID NO 646
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Lys Thr Trp Phe Arg Ser Asn Pro Thr Lys
1               5                   10

```
<210> SEQ ID NO 647
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Leu Ala Lys Glu Leu Thr His Pro Leu
1               5

<210> SEQ ID NO 648
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Leu Ala Lys Glu Leu Thr His Pro Leu Leu
1               5                   10

<210> SEQ ID NO 649
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Asn Pro Thr Lys Thr Lys Lys Ala Arg Phe
1               5                   10

<210> SEQ ID NO 650
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Gln Lys Met Lys Lys Ala His Phe Leu
1               5

<210> SEQ ID NO 651
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Arg Phe Ser Thr Ala Ser Leu Ala Lys
1               5

<210> SEQ ID NO 652
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652
```

```
Arg Pro Ile Arg Pro Pro Phe Leu Glu Ser
1               5                   10

<210> SEQ ID NO 653
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Arg Ser Asn Pro Thr Lys Thr Lys Lys
1               5

<210> SEQ ID NO 654
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Ser Leu Ala Lys Glu Leu Thr His Pro Leu
1               5                   10

<210> SEQ ID NO 655
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Thr Lys Lys Ala Arg Phe Ser Thr Ala
1               5

<210> SEQ ID NO 656
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Gly Leu Arg Phe Trp Asn Pro Ser Arg
1               5

<210> SEQ ID NO 657
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Ile Ser Gln Leu Leu Ser Trp Pro Gln Lys
1               5                   10

<210> SEQ ID NO 658
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 658

Arg Ile Ala His Ile Ser Gln Leu Leu
1               5

<210> SEQ ID NO 659
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Arg Leu Gly Tyr Ser Ser His Gln Leu
1               5

<210> SEQ ID NO 660
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Ser Gln Leu Leu Ser Trp Pro Gln Lys
1               5

<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Ser Arg Ile Ala His Ile Ser Gln Leu
1               5

<210> SEQ ID NO 662
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Trp Pro Gln Lys Thr Glu Glu Arg Leu
1               5

<210> SEQ ID NO 663
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Tyr Ser Ser His Gln Leu Pro Arg Lys
1               5
```

```
<210> SEQ ID NO 664
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Cys Pro Gln Arg Met Thr Pro Gly Thr Thr
1               5                   10

<210> SEQ ID NO 665
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Glu Ala Glu Lys Arg Thr Arg Thr Leu
1               5

<210> SEQ ID NO 666
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Gly Thr Thr Phe Ile Thr Met Met Lys
1               5

<210> SEQ ID NO 667
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Gly Thr Thr Phe Ile Thr Met Met Lys Lys
1               5                   10

<210> SEQ ID NO 668
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Ile Thr Met Met Lys Lys Glu Ala Glu Lys
1               5                   10

<210> SEQ ID NO 669
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 669

Arg Met Thr Pro Gly Thr Thr Phe Ile
1               5

<210> SEQ ID NO 670
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Ser Pro Tyr Cys Pro Gln Arg Met Thr
1               5

<210> SEQ ID NO 671
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Thr Met Met Lys Lys Glu Ala Glu Lys
1               5

<210> SEQ ID NO 672
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Thr Pro Gly Thr Thr Phe Ile Thr Met
1               5

<210> SEQ ID NO 673
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Thr Pro Gly Thr Thr Phe Ile Thr Met Met
1               5                   10

<210> SEQ ID NO 674
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Thr Thr Phe Ile Thr Met Met Lys Lys
1               5

<210> SEQ ID NO 675
<211> LENGTH: 9
<212> TYPE: PRT
```

<210> SEQ ID NO 675
<211> LENGTH: 8 (implied)
<212> TYPE: PRT
<213> ORGANISM: Artificial Sequence
<220> FEATURE:
<223> OTHER INFORMATION: Description of Artificial Sequence: Synthetic peptide

<400> SEQUENCE: 675

Cys Pro Gly Ala Thr Trp Arg Glu Ala
1               5

<210> SEQ ID NO 676
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 676

Cys Pro Gly Ala Thr Trp Arg Glu Ala Ala
1               5                   10

<210> SEQ ID NO 677
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 677

Arg Ser Arg Cys Pro Gly Ala Thr Trp Arg
1               5                   10

<210> SEQ ID NO 678
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 678

Thr Pro Arg Ala Thr Arg Ser Arg Cys
1               5

<210> SEQ ID NO 679
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 679

His Val Leu Pro Glu Pro His Leu Ala Leu
1               5                   10

<210> SEQ ID NO 680
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 680

Arg Pro Leu Gln Thr His Val Leu Pro Glu
1               5                   10

<210> SEQ ID NO 681
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Val Leu Trp Thr Thr Pro Pro Leu Gln His
1               5                   10

<210> SEQ ID NO 682
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

Ala Pro Ser Glu Ser Pro Cys Ser Pro Phe
1               5                   10

<210> SEQ ID NO 683
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Cys Pro Leu Asp His Thr Thr Pro Pro Ala
1               5                   10

<210> SEQ ID NO 684
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

Phe Leu Gln Glu Gln Tyr His Glu Ala
1               5

<210> SEQ ID NO 685
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Arg Leu Ala Phe Leu Gln Glu Gln Tyr His
1               5                   10

<210> SEQ ID NO 686
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 686

Ser Pro Cys Ser Pro Phe Arg Leu Ala Phe
1               5                   10

<210> SEQ ID NO 687
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 687

Ser Pro Pro Trp Val Arg Ala Leu Leu
1               5

<210> SEQ ID NO 688
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 688

Tyr Pro Ala Cys Pro Leu Asp His Thr Thr
1               5                   10

<210> SEQ ID NO 689
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

Ala Leu His Leu Arg Ser Cys Pro Cys
1               5

<210> SEQ ID NO 690
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

Cys Leu His His Arg Arg His Leu Val
1               5

<210> SEQ ID NO 691
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Cys Leu His His Arg Arg His Leu Val Cys
1               5                   10

<210> SEQ ID NO 692
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 692

Cys Leu His Arg Lys Ser His Pro His Leu
1               5                   10

<210> SEQ ID NO 693
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Cys Leu Arg Ser His Ala Cys Pro Pro
1               5

<210> SEQ ID NO 694
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Cys Leu Arg Ser His Thr Cys Pro Pro
1               5

<210> SEQ ID NO 695
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695

Cys Leu Trp Cys His Ala Cys Leu His
1               5

<210> SEQ ID NO 696
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Cys Pro His His Leu Lys Asn His Leu
1               5

<210> SEQ ID NO 697
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Cys Pro His His Leu Lys Asn Leu Leu
```

<210> SEQ ID NO 698
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

Cys Pro His His Leu Arg Thr Arg Leu
1               5

<210> SEQ ID NO 699
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Cys Pro Leu His Leu Arg Ser Leu Pro Phe
1               5                   10

<210> SEQ ID NO 700
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Cys Pro Leu Pro Arg His Leu Lys His Leu
1               5                   10

<210> SEQ ID NO 701
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Cys Pro Leu Ser Leu Arg Ser His Pro Cys
1               5                   10

<210> SEQ ID NO 702
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Cys Pro Arg His Leu Arg Asn Cys Pro Leu
1               5                   10

<210> SEQ ID NO 703
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 703

Phe Pro His His Leu Arg His His Ala
1               5

<210> SEQ ID NO 704
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Phe Pro His His Leu Arg His His Ala Cys
1               5                   10

<210> SEQ ID NO 705
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Gly Leu Arg Ser Arg Thr Cys Pro Pro
1               5

<210> SEQ ID NO 706
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

His Ala Cys Leu His Arg Leu Arg Asn Leu
1               5                   10

<210> SEQ ID NO 707
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

His Leu Ala Cys Leu His His Leu Arg
1               5

<210> SEQ ID NO 708
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

His Leu Cys Pro Pro His Leu Arg Tyr
1               5

<210> SEQ ID NO 709

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 709

His Leu Cys Pro Pro His Leu Arg Tyr Arg
1               5                   10

<210> SEQ ID NO 710
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

His Leu Lys His Leu Ala Cys Leu His
1               5

<210> SEQ ID NO 711
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

His Leu Lys His Arg Pro Cys Pro His
1               5

<210> SEQ ID NO 712
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

His Leu Lys Asn His Leu Cys Pro Pro
1               5

<210> SEQ ID NO 713
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

His Leu Lys Ser His Pro Cys Leu His
1               5

<210> SEQ ID NO 714
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714
```

```
His Leu Lys Ser Leu Leu Cys Pro Leu
1               5

<210> SEQ ID NO 715
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

His Leu Leu His Leu Arg Arg Leu Tyr
1               5

<210> SEQ ID NO 716
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 716

His Leu Arg Asn Cys Pro Leu Pro Arg
1               5

<210> SEQ ID NO 717
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 717

His Leu Arg Asn Cys Pro Leu Pro Arg His
1               5                   10

<210> SEQ ID NO 718
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 718

His Leu Arg Arg Leu Tyr Pro His His Leu
1               5                   10

<210> SEQ ID NO 719
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

His Leu Arg Ser His Pro Cys Pro Leu
1               5

<210> SEQ ID NO 720
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 720

His Leu Arg Ser His Pro Cys Pro Leu His
1               5                   10

<210> SEQ ID NO 721
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 721

His Leu Arg Ser Leu Pro Phe Pro His
1               5

<210> SEQ ID NO 722
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 722

His Leu Arg Thr Arg Leu Cys Pro His
1               5

<210> SEQ ID NO 723
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

His Leu Val Cys Ser His His Leu Lys
1               5

<210> SEQ ID NO 724
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 724

His Pro Cys Leu His His Arg Arg His Leu
1               5                   10

<210> SEQ ID NO 725
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

His Pro Gly Leu Arg Ser Arg Thr Cys
1               5
```

```
<210> SEQ ID NO 726
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

His Pro His Leu Leu His Leu Arg Arg Leu
1               5                   10

<210> SEQ ID NO 727
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 727

His Arg Lys Ser His Pro His Leu Leu
1               5

<210> SEQ ID NO 728
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

His Arg Arg Thr Arg Ser Cys Pro Cys
1               5

<210> SEQ ID NO 729
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 729

Lys Ser His Pro His Leu Leu His Leu Arg
1               5                   10

<210> SEQ ID NO 730
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Lys Ser Leu Leu Cys Pro Leu His Leu Arg
1               5                   10

<210> SEQ ID NO 731
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731
```

```
Leu Leu Cys Pro Leu His Leu Arg Ser Leu
1               5                   10

<210> SEQ ID NO 732
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Leu Leu His Leu Arg Arg Leu Tyr Pro His
1               5                   10

<210> SEQ ID NO 733
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 733

Leu Pro Arg His Leu Lys His Leu Ala
1               5

<210> SEQ ID NO 734
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Leu Pro Arg His Leu Lys His Leu Ala Cys
1               5                   10

<210> SEQ ID NO 735
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Leu Arg Arg Leu Arg Ser His Thr Cys
1               5

<210> SEQ ID NO 736
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Leu Arg Arg Leu Tyr Pro His His Leu
1               5

<210> SEQ ID NO 737
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 737

Leu Val Cys Ser His His Leu Lys Ser Leu
1               5                   10

<210> SEQ ID NO 738
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Asn Leu Arg Asn His Thr Cys Pro Pro Ser
1               5                   10

<210> SEQ ID NO 739
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

Pro Leu His Leu Arg Ser Leu Pro Phe
1               5

<210> SEQ ID NO 740
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Arg Leu Cys Pro His His Leu Lys Asn His
1               5                   10

<210> SEQ ID NO 741
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Arg Leu Tyr Pro His His Leu Lys His
1               5

<210> SEQ ID NO 742
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Arg Leu Tyr Pro His His Leu Lys His Arg
1               5                   10
```

<210> SEQ ID NO 743
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Arg Pro Cys Pro His His Leu Lys Asn Leu
1               5                   10

<210> SEQ ID NO 744
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Arg Ser His Pro Cys Pro Leu His Leu Lys
1               5                   10

<210> SEQ ID NO 745
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Arg Ser Leu Pro Phe Pro His His Leu Arg
1               5                   10

<210> SEQ ID NO 746
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Arg Thr Arg Leu Cys Pro His His Leu
1               5

<210> SEQ ID NO 747
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Arg Thr Arg Leu Cys Pro His His Leu Lys
1               5                   10

<210> SEQ ID NO 748
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 748

Ser Leu Leu Cys Pro Leu His Leu Arg
1               5

<210> SEQ ID NO 749
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

Ser Leu Arg Ser His Ala Cys Pro Pro
1               5

<210> SEQ ID NO 750
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Ser Pro Leu Arg Ser Gln Ala Asn Ala
1               5

<210> SEQ ID NO 751
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Tyr Leu Arg Arg Leu Arg Ser His Thr
1               5

<210> SEQ ID NO 752
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Tyr Pro His His Leu Lys His Arg Pro Cys
1               5                   10

<210> SEQ ID NO 753
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Phe Ile Thr Ser Gly Gln Ile Phe Lys
1               5

<210> SEQ ID NO 754
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 754

Ile Phe Ile Thr Ser Gly Gln Ile Phe
1               5

<210> SEQ ID NO 755
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Ser Gln Ser Glu Ala Leu Cys Val Leu
1               5

<210> SEQ ID NO 756
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Ser Gln Ser Glu Ala Leu Cys Val Leu Leu
1               5                   10

<210> SEQ ID NO 757
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Ala Tyr Thr Gly Thr Ile Leu Met Met
1               5

<210> SEQ ID NO 758
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Asp Leu Lys Ala Tyr Thr Gly Thr Ile Leu
1               5                   10

<210> SEQ ID NO 759
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 759

Ile Leu Thr Lys Gln Ile Lys Thr Lys
1               5
```

```
<210> SEQ ID NO 760
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 760

Lys Met Ile Leu Thr Lys Gln Ile Lys
1               5

<210> SEQ ID NO 761
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 761

Lys Pro Thr Asp Thr Phe Leu Gln Ile
1               5

<210> SEQ ID NO 762
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 762

Lys Pro Thr Asp Thr Phe Leu Gln Ile Leu
1               5                   10

<210> SEQ ID NO 763
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 763

Met Ile Leu Thr Lys Gln Ile Lys Thr Lys
1               5                   10

<210> SEQ ID NO 764
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 764

Ile Thr Arg Tyr Thr Ile Phe Val Leu Lys
1               5                   10

<210> SEQ ID NO 765
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 765

Leu Ile Ala Glu Leu His Asn Ile Leu
1               5

<210> SEQ ID NO 766
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766

Leu Ile Ala Glu Leu His Asn Ile Leu Leu
1               5                   10

<210> SEQ ID NO 767
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

Met Thr Pro Pro Asn Leu Ile Ala Glu Leu
1               5                   10

<210> SEQ ID NO 768
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 768

Asn Leu Ile Ala Glu Leu His Asn Ile
1               5

<210> SEQ ID NO 769
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 769

Asn Leu Ile Ala Glu Leu His Asn Ile Leu
1               5                   10

<210> SEQ ID NO 770
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 770

Arg Tyr Thr Ile Phe Val Leu Lys Asp Ile
1               5                   10

<210> SEQ ID NO 771
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 771

Thr Ile Thr Arg Tyr Thr Ile Phe Val Leu
1               5                   10

<210> SEQ ID NO 772
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 772

Thr Pro Pro Asn Leu Ile Ala Glu Leu
1               5

<210> SEQ ID NO 773
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 773

Phe Leu Gln Phe Arg Thr His Thr Thr
1               5

<210> SEQ ID NO 774
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 774

Leu Pro Ala Lys Gly Glu Asp Ile Phe Leu
1               5                   10

<210> SEQ ID NO 775
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 775

Leu Gln Phe Arg Thr His Thr Thr Gly Arg
1               5                   10

<210> SEQ ID NO 776
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Asn Leu Gln Ser Ser Val Cys Gly Leu
```

```
1               5
```

<210> SEQ ID NO 777
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

```
Ser Ser Val Cys Gly Leu Pro Ala Lys
1               5
```

<210> SEQ ID NO 778
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

```
Val Gln Trp Arg Asn Leu Gln Ser Ser Val
1               5                   10
```

<210> SEQ ID NO 779
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 779

```
Gly Gln Asn Val Ser Leu Leu Gly Lys
1               5
```

<210> SEQ ID NO 780
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 780

```
His Thr Arg Thr Arg Gly Asn Leu Arg Lys
1               5                   10
```

<210> SEQ ID NO 781
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

```
Ile Leu His Thr Arg Thr Arg Gly Asn Leu
1               5                   10
```

<210> SEQ ID NO 782
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 782

Lys Gly Gln Asn Val Ser Leu Leu Gly Lys
1               5                   10

<210> SEQ ID NO 783
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 783

Leu Leu Gly Lys Tyr Ile Leu His Thr
1               5

<210> SEQ ID NO 784
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 784

Leu Arg Lys Ser Arg Lys Trp Lys Ser Met
1               5                   10

<210> SEQ ID NO 785
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 785

Ser Leu Leu Gly Lys Tyr Ile Leu His
1               5

<210> SEQ ID NO 786
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 786

Ser Leu Leu Gly Lys Tyr Ile Leu His Thr
1               5                   10

<210> SEQ ID NO 787
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 787

Cys Thr Ser Pro Leu Leu Ala Pro Val
1               5

<210> SEQ ID NO 788

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 788

Phe Pro Glu Asn Leu Pro Gly Gln Leu
1               5

<210> SEQ ID NO 789
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 789

Gly Leu Leu Ala Phe Trp Asp Ser Gln Val
1               5                   10

<210> SEQ ID NO 790
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 790

Ile Phe Cys Pro Phe Pro Glu Asn Leu
1               5

<210> SEQ ID NO 791
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 791

Leu Leu Ala Phe Trp Asp Ser Gln Val
1               5

<210> SEQ ID NO 792
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 792

Leu Leu Ala Pro Val Ile Phe Cys Pro
1               5

<210> SEQ ID NO 793
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 793
```

```
Leu Leu Ala Pro Val Ile Phe Cys Pro Phe
1               5                   10
```

<210> SEQ ID NO 794
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 794

```
Leu Pro Cys Pro Gln Gln Asp Val Leu
1               5
```

<210> SEQ ID NO 795
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 795

```
Arg Phe Pro Ser Gly Leu Leu Ala Phe
1               5
```

<210> SEQ ID NO 796
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

```
Arg Phe Pro Ser Gly Leu Leu Ala Phe Trp
1               5                   10
```

<210> SEQ ID NO 797
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 797

```
Ser Pro Leu Leu Ala Pro Val Ile Phe
1               5
```

<210> SEQ ID NO 798
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

```
Ser Pro Arg Gly Pro Cys Thr Ser Ser
1               5
```

<210> SEQ ID NO 799
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 799

Ser Pro Arg Gly Pro Cys Thr Ser Ser Ser
1               5                   10

<210> SEQ ID NO 800
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Ser Gln Val Cys Asp Leu His Val Leu
1               5

<210> SEQ ID NO 801
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Val Ile Phe Cys Pro Phe Pro Glu Asn Leu
1               5                   10

<210> SEQ ID NO 802
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Ala Met Val Trp Pro Leu Leu Ser Ile
1               5

<210> SEQ ID NO 803
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Ala Met Val Trp Pro Leu Leu Ser Ile Leu
1               5                   10

<210> SEQ ID NO 804
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Ala Gln Ile Ala Met Val Trp Pro Leu
1               5
```

```
<210> SEQ ID NO 805
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 805

Ala Gln Ile Ala Met Val Trp Pro Leu Leu
1               5                   10

<210> SEQ ID NO 806
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 806

Cys Pro Met Ser Arg Leu Arg Leu Ala
1               5

<210> SEQ ID NO 807
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Cys Pro Met Ser Arg Leu Arg Leu Ala Leu
1               5                   10

<210> SEQ ID NO 808
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 808

Ile Ala Met Val Trp Pro Leu Leu Ser Ile
1               5                   10

<210> SEQ ID NO 809
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 809

Ile Leu Ser Glu Trp Lys Glu Ile Cys Val
1               5                   10

<210> SEQ ID NO 810
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 810
```

```
Ile Val Trp Trp Cys Pro Met Ser Arg
1               5

<210> SEQ ID NO 811
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 811

Ile Val Trp Trp Cys Pro Met Ser Arg Leu
1               5                   10

<210> SEQ ID NO 812
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 812

Ile Trp Met Thr Glu Thr Leu Phe Asp Ile
1               5                   10

<210> SEQ ID NO 813
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 813

Leu Leu Ser Ile Leu Ser Glu Trp Lys
1               5

<210> SEQ ID NO 814
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 814

Met Ser Ala Ala Gln Ile Ala Met Val
1               5

<210> SEQ ID NO 815
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 815

Met Ser Arg Leu Arg Leu Ala Leu Thr
1               5

<210> SEQ ID NO 816
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 816

Met Ser Arg Leu Arg Leu Ala Leu Thr Val
1               5                   10

<210> SEQ ID NO 817
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 817

Met Val Trp Pro Leu Leu Ser Ile Leu
1               5

<210> SEQ ID NO 818
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 818

Arg Leu Ala Leu Thr Val Pro Pro Ser Thr
1               5                   10

<210> SEQ ID NO 819
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 819

Thr Leu Phe Asp Ile Val Trp Trp Cys
1               5

<210> SEQ ID NO 820
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 820

Thr Leu Phe Asp Ile Val Trp Trp Cys Pro
1               5                   10

<210> SEQ ID NO 821
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 821

Thr Met Ser Ala Ala Gln Ile Ala Met Val
1               5                   10
```

<210> SEQ ID NO 822
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 822

Val Trp Ser Ile Trp Met Thr Glu Thr Leu
1               5                   10

<210> SEQ ID NO 823
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 823

Trp Met Thr Glu Thr Leu Phe Asp Ile
1               5

<210> SEQ ID NO 824
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 824

Trp Met Thr Glu Thr Leu Phe Asp Ile Val
1               5                   10

<210> SEQ ID NO 825
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 825

Ala Leu Arg Cys Val Phe Val Pro Val
1               5

<210> SEQ ID NO 826
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 826

Ala Leu Arg Cys Val Phe Val Pro Val Leu
1               5                   10

<210> SEQ ID NO 827
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 827

Ala Leu Ser Glu His Cys Pro Thr Thr
1               5

<210> SEQ ID NO 828
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 828

Ala Gln Arg Lys Arg Ile Ser Ala Arg Lys
1               5                   10

<210> SEQ ID NO 829
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 829

Gly Ala Gln Arg Lys Arg Ile Ser Ala
1               5

<210> SEQ ID NO 830
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 830

His Trp Met Glu Asn Ile Ser Pro Phe
1               5

<210> SEQ ID NO 831
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 831

Leu Pro Ser Gln Arg Arg Asn His Trp
1               5

<210> SEQ ID NO 832
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 832

Leu Pro Ser Gln Arg Arg Asn His Trp Met
1               5                   10

<210> SEQ ID NO 833
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 833

Asn Ile Ser Pro Phe Arg Ser Val Gly Val
1               5                   10

<210> SEQ ID NO 834
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 834

Arg Ile Ser Ala Arg Lys Gly Ser Leu
1               5

<210> SEQ ID NO 835
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 835

Ser Pro Phe Arg Ser Val Gly Val Ser Ala
1               5                   10

<210> SEQ ID NO 836
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 836

Ser Pro Ser Ser His Trp Lys Thr Pro Val
1               5                   10

<210> SEQ ID NO 837
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 837

Thr Ala Leu Arg Cys Val Phe Val Pro Val
1               5                   10

<210> SEQ ID NO 838
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 838

Val Ile Tyr Trp Asp Gly Thr Ala Leu
1               5
```

<210> SEQ ID NO 839
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 839

Val Ile Tyr Trp Asp Gly Thr Ala Leu Arg
1               5                   10

<210> SEQ ID NO 840
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 840

Val Leu Gly Glu Thr Gly Ala Gln Arg Lys
1               5                   10

<210> SEQ ID NO 841
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 841

His Pro Arg Pro Arg His Gly His Leu
1               5

<210> SEQ ID NO 842
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 842

His Pro Arg Pro Arg His Gly His Leu Gln
1               5                   10

<210> SEQ ID NO 843
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 843

Arg Pro Arg His Gly His Leu Gln Ala
1               5

<210> SEQ ID NO 844
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 844

Arg Pro Arg His Gly His Leu Gln Ala Val
1               5                   10

<210> SEQ ID NO 845
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 845

Gly Ser Leu Lys Thr Gln Val Gln Met Lys
1               5                   10

<210> SEQ ID NO 846
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 846

Pro Pro Gly Pro Cys His Leu Leu Ser Leu
1               5                   10

<210> SEQ ID NO 847
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 847

Arg Thr Ile Leu Asn Asn Gly Ser Leu Lys
1               5                   10

<210> SEQ ID NO 848
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 848

Ser Leu Lys Thr Gln Val Gln Met Lys
1               5

<210> SEQ ID NO 849
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 849

Ser Leu Lys Thr Gln Val Gln Met Lys Leu
1               5                   10

<210> SEQ ID NO 850
<211> LENGTH: 9

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 850

Thr Ile Leu Asn Asn Gly Ser Leu Lys
1               5

<210> SEQ ID NO 851
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 851

Cys Pro Pro Cys Arg Pro Lys Gln Trp Met
1               5                   10

<210> SEQ ID NO 852
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 852

Thr Thr Phe Cys Pro Pro Cys Arg Pro Lys
1               5                   10

<210> SEQ ID NO 853
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 853

Cys Phe Ala Asn Trp Pro Arg Pro Ala Leu
1               5                   10

<210> SEQ ID NO 854
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 854

Phe Ala Asn Trp Pro Arg Pro Ala Leu
1               5

<210> SEQ ID NO 855
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 855

Gly Leu Ile Pro His Pro Arg Pro Ala

```
1               5
```

<210> SEQ ID NO 856
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 856

```
His Pro Arg Pro Ala Pro Ala Ser Ala
1               5
```

<210> SEQ ID NO 857
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857

```
His Pro Arg Pro Ala Pro Ala Ser Ala Pro
1               5                   10
```

<210> SEQ ID NO 858
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

```
Ile Pro His Pro Arg Pro Ala Pro Ala
1               5
```

<210> SEQ ID NO 859
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 859

```
Ile Pro His Pro Arg Pro Ala Pro Ala Ser
1               5                   10
```

<210> SEQ ID NO 860
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

```
Arg Pro Ala Leu Cys Ser Cys Gly Leu
1               5
```

<210> SEQ ID NO 861
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 861

Arg Pro Ala Leu Cys Ser Cys Gly Leu Ile
1               5                   10

<210> SEQ ID NO 862
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 862

Thr Pro Leu Pro Ser Thr Arg Cys Phe
1               5

<210> SEQ ID NO 863
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 863

Trp Pro Arg Pro Ala Leu Cys Ser Cys
1               5

<210> SEQ ID NO 864
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 864

Trp Pro Arg Pro Ala Leu Cys Ser Cys Gly
1               5                   10

<210> SEQ ID NO 865
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 865

Ala Leu Arg Arg Ser Gly Arg Pro Pro Lys
1               5                   10

<210> SEQ ID NO 866
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 866

Gly Leu Val Pro Ser Leu Val Ser Lys
1               5

<210> SEQ ID NO 867

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 867

Lys Ile Ser Val Glu Thr Tyr Thr Val
1               5

<210> SEQ ID NO 868
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 868

Leu Leu Met Val Leu Met Ser Leu Asp Leu
1               5                   10

<210> SEQ ID NO 869
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 869

Leu Met Ser Leu Asp Leu Asp Thr Gly Leu
1               5                   10

<210> SEQ ID NO 870
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 870

Leu Met Val Leu Met Ser Leu Asp Leu
1               5

<210> SEQ ID NO 871
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 871

Leu Val Ser Lys Cys Leu Ile Leu Arg Val
1               5                   10

<210> SEQ ID NO 872
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 872
```

Gln Leu Leu Met Val Leu Met Ser Leu
1               5

<210> SEQ ID NO 873
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 873

Arg Pro Gly Ala Ala Asp Thr Gly Ala
1               5

<210> SEQ ID NO 874
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874

Arg Pro Gly Ala Ala Asp Thr Gly Ala His
1               5                   10

<210> SEQ ID NO 875
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Ser Leu Asp Leu Asp Thr Gly Leu Val
1               5

<210> SEQ ID NO 876
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 876

Ser Leu Val Ser Lys Cys Leu Ile Leu
1               5

<210> SEQ ID NO 877
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 877

Ser Gln Leu Leu Met Val Leu Met Ser Leu
1               5                   10

<210> SEQ ID NO 878
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 878

Thr Val Ser Ser Gln Leu Leu Met Val
1               5

<210> SEQ ID NO 879
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 879

Thr Tyr Thr Val Ser Ser Gln Leu Leu
1               5

<210> SEQ ID NO 880
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 880

Thr Tyr Thr Val Ser Ser Gln Leu Leu Met
1               5                   10

<210> SEQ ID NO 881
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 881

Val Leu Met Ser Leu Asp Leu Asp Thr
1               5

<210> SEQ ID NO 882
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 882

Val Pro Ser Leu Val Ser Lys Cys Leu
1               5

<210> SEQ ID NO 883
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883

Val Ser Lys Cys Leu Ile Leu Arg Val Lys
1               5                   10

```
<210> SEQ ID NO 884
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

Tyr Thr Val Ser Ser Gln Leu Leu Met
1               5

<210> SEQ ID NO 885
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 885

Tyr Thr Val Ser Ser Gln Leu Leu Met Val
1               5                   10

<210> SEQ ID NO 886
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 886

Phe Cys Gln Tyr His Thr Ala Ser Val
1               5

<210> SEQ ID NO 887
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 887

Cys Pro Tyr Gly Ser Thr Ser Thr Ala
1               5

<210> SEQ ID NO 888
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 888

Cys Pro Tyr Gly Ser Thr Ser Thr Ala Ser
1               5                   10

<210> SEQ ID NO 889
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 889
```

```
Leu Ala Arg Ala Ala Ala Ser Thr Ala Thr
1               5                   10

<210> SEQ ID NO 890
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 890

Met Leu Thr Asp Ser Leu Phe Leu Pro
1               5

<210> SEQ ID NO 891
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 891

Pro Pro Arg Ser Ser Ser Ala Ile Ala Val
1               5                   10

<210> SEQ ID NO 892
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 892

Arg Ala Ala Ala Ser Thr Ala Thr Glu Val
1               5                   10

<210> SEQ ID NO 893
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

Ser Pro Pro Arg Ser Ser Ser Ala Ile
1               5

<210> SEQ ID NO 894
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 894

Ser Pro Pro Arg Ser Ser Ser Ala Ile Ala
1               5                   10

<210> SEQ ID NO 895
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 895

Ser Pro Thr Gln Arg Cys Arg Leu Ala
1               5

<210> SEQ ID NO 896
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 896

Thr Gln Arg Cys Arg Leu Ala Arg Ala
1               5

<210> SEQ ID NO 897
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 897

Thr Gln Arg Cys Arg Leu Ala Arg Ala Ala
1               5                   10

<210> SEQ ID NO 898
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 898

Lys Ile Trp Lys Thr Thr Gln Met Cys Arg
1               5                   10

<210> SEQ ID NO 899
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 899

Trp Thr Ser Ser Gly Arg Ser Thr Lys
1               5

<210> SEQ ID NO 900
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 900

Ala Leu Gly Glu Leu Ala Arg Ala Leu
1               5
```

<210> SEQ ID NO 901
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 901

Ala Gln Leu Arg Arg Arg Ala Ala Ala
1               5

<210> SEQ ID NO 902
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 902

Ala Gln Leu Arg Arg Arg Ala Ala Ala Leu
1               5                   10

<210> SEQ ID NO 903
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 903

Ala Arg Arg Ala Ala Arg Met Ala Gln Leu
1               5                   10

<210> SEQ ID NO 904
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 904

His Pro Gln Leu Pro Arg Ser Pro Leu
1               5

<210> SEQ ID NO 905
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 905

His Pro Gln Leu Pro Arg Ser Pro Leu Ala
1               5                   10

<210> SEQ ID NO 906
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 906

Leu Ala Arg Ala Leu Pro Gly His Leu
1               5

<210> SEQ ID NO 907
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 907

Leu Ala Arg Ala Leu Pro Gly His Leu Leu
1               5                   10

<210> SEQ ID NO 908
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 908

Met Ala Gln Leu Arg Arg Arg Ala Ala
1               5

<210> SEQ ID NO 909
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 909

Met Ala Gln Leu Arg Arg Arg Ala Ala Ala
1               5                   10

<210> SEQ ID NO 910
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 910

Gln Leu Arg Arg Arg Ala Ala Ala Leu
1               5

<210> SEQ ID NO 911
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 911

Arg Ala Ala Ala Leu Pro Asn Ala Ala Ala
1               5                   10

<210> SEQ ID NO 912
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 912

Arg Met Ala Gln Leu Arg Arg Arg Ala Ala
1               5                   10

<210> SEQ ID NO 913
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 913

Ser Gln Ser Ala Arg Arg Ala Ala Arg Met
1               5                   10

<210> SEQ ID NO 914
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 914

Gly Met Thr Leu Gly Glu Lys Phe Arg Val
1               5                   10

<210> SEQ ID NO 915
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 915

Arg Val Gly Asn Cys Lys His Leu Lys
1               5

<210> SEQ ID NO 916
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 916

Gly Pro Ser Glu Pro Gly Asn Asn Ile
1               5

<210> SEQ ID NO 917
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 917

Lys Ile Cys Asn Glu Ser Ala Ser Arg Lys
1               5                   10
```

```
<210> SEQ ID NO 918
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 918

Gly Ile Gln Val Leu Asn Val Ser Leu Lys
1               5                   10

<210> SEQ ID NO 919
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Ile Gln Val Leu Asn Val Ser Leu Lys
1               5

<210> SEQ ID NO 920
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 920

Lys Ser Ser Ser Asn Val Ile Ser Tyr
1               5

<210> SEQ ID NO 921
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 921

Lys Tyr Gly Trp Ser Leu Leu Arg Val
1               5

<210> SEQ ID NO 922
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 922

Arg Ser Trp Lys Tyr Gly Trp Ser Leu
1               5

<210> SEQ ID NO 923
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 923

Ser Leu Lys Ser Ser Ser Asn Val Ile
1               5

<210> SEQ ID NO 924
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

Ser Trp Lys Tyr Gly Trp Ser Leu Leu
1               5

<210> SEQ ID NO 925
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Thr Val Ala Asn Gly Arg Ser Trp Lys
1               5

<210> SEQ ID NO 926
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 926

Val Pro Gln Val Asn Gly Ile Gln Val
1               5

<210> SEQ ID NO 927
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 927

Val Pro Gln Val Asn Gly Ile Gln Val Leu
1               5                   10

<210> SEQ ID NO 928
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 928

Val Thr Val Ala Asn Gly Arg Ser Trp Lys
1               5                   10

<210> SEQ ID NO 929
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 929

Trp Ser Leu Leu Arg Val Pro Gln Val
1               5

<210> SEQ ID NO 930
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 930

His Pro Gly Asp Cys Leu Ile Phe Lys Leu
1               5                   10

<210> SEQ ID NO 931
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 931

Lys Leu Arg Val Pro Gly Ser Ser Val
1               5

<210> SEQ ID NO 932
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 932

Lys Leu Arg Val Pro Gly Ser Ser Val Leu
1               5                   10

<210> SEQ ID NO 933
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 933

Arg Val Pro Gly Ser Ser Val Leu Val
1               5

<210> SEQ ID NO 934
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 934

Ser Val Leu Val Thr Val Pro Gly Leu
```

```
1               5
```

<210> SEQ ID NO 935
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 935

```
Val Pro Gly Ser Ser Val Leu Val Thr Val
1               5                   10
```

<210> SEQ ID NO 936
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 936

```
Ala Leu Leu Leu Arg Pro Arg Pro Pro Arg
1               5                   10
```

<210> SEQ ID NO 937
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 937

```
Ala Leu Ser Ala Leu Leu Leu Arg Pro Arg
1               5                   10
```

<210> SEQ ID NO 938
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 938

```
Leu Thr Ile Asn Lys Glu Glu Ala Leu
1               5
```

<210> SEQ ID NO 939
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 939

```
Ile Val His Ser Ala Thr Gly Phe Lys
1               5
```

<210> SEQ ID NO 940
<211> LENGTH: 9
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 940

Ala Thr Gly Phe Lys Gln Ser Ser Lys
1               5

<210> SEQ ID NO 941
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 941

Glu Leu Phe Pro Leu Ile Phe Pro Ala
1               5

<210> SEQ ID NO 942
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 942

Lys Gly Pro Glu Leu Phe Pro Leu Ile
1               5

<210> SEQ ID NO 943
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 943

Lys Gly Pro Glu Leu Phe Pro Leu Ile Phe
1               5                   10

<210> SEQ ID NO 944
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 944

Lys Pro Thr Asp Ala Pro Pro Lys Ala Gly Val
1               5                   10

<210> SEQ ID NO 945
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 945

Ala Leu Glu Glu Lys Lys Gly Asn Tyr Val
1               5                   10

<210> SEQ ID NO 946

<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 946

Ile Gln Leu Gln Asp Lys Phe Glu His Leu
1               5                   10

<210> SEQ ID NO 947
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 947

Gln Leu Gln Asp Lys Phe Glu His Leu
1               5

<210> SEQ ID NO 948
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 948

Gln Leu Gln Asp Lys Phe Glu His Leu Lys
1               5                   10

<210> SEQ ID NO 949
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 949

Tyr Leu Val Ile Gln Leu Gln Asp Lys Phe
1               5                   10

<210> SEQ ID NO 950
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 950

Gln Val Tyr Arg Arg Lys His Gln Glu Leu
1               5                   10

<210> SEQ ID NO 951
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 951

```
Ser Thr Arg Glu Lys Asn Ser Gln Val
1               5
```

```
<210> SEQ ID NO 952
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 952

Val Tyr Arg Arg Lys His Gln Glu Leu
1               5
```

```
<210> SEQ ID NO 953
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 953

Val Leu Thr Val Thr Ser Thr Asp Val
1               5
```

```
<210> SEQ ID NO 954
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 954

Val Leu Thr Val Thr Ser Thr Asp Val Lys
1               5                   10
```

```
<210> SEQ ID NO 955
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 955

Ile Met Ser Leu Trp Gly Leu Val Ser
1               5
```

```
<210> SEQ ID NO 956
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 956

Ile Met Ser Leu Trp Gly Leu Val Ser Lys
1               5                   10
```

```
<210> SEQ ID NO 957
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 957

Lys Leu Lys Gln Glu Ala Thr Ser Lys
1               5

<210> SEQ ID NO 958
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 958

Gln Ile Met Ser Leu Trp Gly Leu Val
1               5

<210> SEQ ID NO 959
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 959

Ser Gln Ile Met Ser Leu Trp Gly Leu
1               5

<210> SEQ ID NO 960
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 960

Ser Gln Ile Met Ser Leu Trp Gly Leu Val
1               5                   10

<210> SEQ ID NO 961
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 961

Thr Ser Lys Ser Gln Ile Met Ser Leu
1               5

<210> SEQ ID NO 962
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 962

Leu Leu Gln Glu Phe Asp Val Gln Glu Ala
1               5                   10
```

```
<210> SEQ ID NO 963
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 963

Leu Gln Glu Phe Asp Val Gln Glu Ala Leu
1               5                   10

<210> SEQ ID NO 964
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 964

Gly Pro Arg Glu Pro Arg Asn Arg Thr
1               5

<210> SEQ ID NO 965
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 965

Arg Asn Arg Thr Glu Lys His Ser Thr Met
1               5                   10

<210> SEQ ID NO 966
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 966

Ala Leu Asn Ser Glu Ala Leu Ser Val
1               5

<210> SEQ ID NO 967
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 967

Ala Leu Asn Ser Glu Ala Leu Ser Val Val
1               5                   10

<210> SEQ ID NO 968
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 968
```

```
Met Ala Leu Asn Ser Glu Ala Leu Ser Val
1               5                   10

<210> SEQ ID NO 969
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 969

Met Ser Asp Val Ala Ile Val Lys Glu Gly Trp Leu His Lys Arg Gly
1               5                   10                  15

Lys Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
            35                  40                  45

Glu Ala Pro Leu Asn Asn Phe Ser Val Ala Gln Cys Gln Leu Met Lys
        50                  55                  60

Thr Glu Arg
65

<210> SEQ ID NO 970
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 970

Thr Met Leu Val Leu Glu Gly Ser Gly Asn Leu Val Leu Tyr Thr Gly
1               5                   10                  15

Val Val Arg Val Gly Lys Val Phe Ile Pro Gly Leu Pro Ala Pro Ser
                20                  25                  30

Leu Thr Met Ser Asn Thr Met Pro Arg Pro Ser Thr Pro Leu Asp Gly
            35                  40                  45

Val Ser Ala Pro Lys Pro Leu Ser Lys Leu Leu Gly Ser Leu Asp Glu
        50                  55                  60

Val Val Leu Leu Ser Pro Val Pro Glu Leu Arg Asp Ser Ser Lys Leu
65                  70                  75                  80

His Asp Ser Leu Tyr Asn Glu Asp Cys Thr Phe Gln Gln Leu Gly Thr
                85                  90                  95

Tyr Ile His Ser Ile
            100

<210> SEQ ID NO 971
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 971

His Arg Ile Gly Gly Ile Lys Leu Arg His Gln Gln Trp Ser Leu Val
1               5                   10                  15

Met Glu Ser Val Val Pro Ser Asp Arg Gly Asn Tyr Thr Cys Val Val
                20                  25                  30
```

```
Glu Asn Lys Phe Gly Ser Ile Arg Gln Thr Tyr Thr Leu Asp Val Leu
            35                  40                  45

Glu Arg Cys Pro His Arg Pro Ile Leu Gln Ala Gly Leu Pro Ala Asn
 50                  55                  60

Gln Thr Ala Val Leu Gly Ser Asp Val Glu Phe His Cys Lys Val Tyr
 65                  70                  75                  80

Ser Asp Ala Gln Pro His Ile Gln Trp Leu Lys His Val Glu Val Asn
                 85                  90                  95

Gly Ser Lys Val Gly
            100

<210> SEQ ID NO 972
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 972

Met Arg Glu Pro Ile Tyr Met His Ser Thr Met Val Phe Leu Pro Trp
 1               5                  10                  15

Glu Leu His Thr Lys Lys Gly Pro Ser Pro Glu Gln Phe Met Ala
            20                  25                  30

Val Lys Leu Ser Asp Ser Arg Thr Ala Leu Lys Ser Gly Tyr Gly Lys
            35                  40                  45

Tyr Leu Gly Ile Asn Ser Asp Glu Leu Val Gly His Ser Asp Ala Ile
 50                  55                  60

Gly Pro Arg Glu Gln Trp Glu Pro Val Phe Gln Asn Gly Lys Met Ala
 65                  70                  75                  80

Leu Leu Ala Ser Asn Ser Cys Phe Ile Arg
                 85                  90

<210> SEQ ID NO 973
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 973

Ala Val Lys Leu Ser Asp Ser Arg Ile Ala Leu Lys Ser Gly Tyr Gly
 1               5                  10                  15

Lys Tyr Leu Gly Ile Asn Ser Asp Glu Leu Val Gly His Ser Asp Ala
            20                  25                  30

Ile Gly Pro Arg Glu Gln Trp Glu Pro Val Phe Gln Asn Gly Lys Met
            35                  40                  45

Ala Leu Ser Ala Ser Asn Ser Cys Phe Ile Arg Cys Asn Glu Ala Gly
 50                  55                  60

Asp Ile Glu Ala Lys Ser Lys Thr Ala Gly Glu Glu Met Ile Lys
 65                  70                  75                  80

Ile Arg Ser Cys Ala Glu Lys Glu Thr Lys Lys Asp Asp Ile Pro
                 85                  90                  95

Glu Glu Asp Lys Gly
            100

<210> SEQ ID NO 974
<211> LENGTH: 101
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 974

Ala Met Pro Asn Gln Ala Gln Met Arg Ile Leu Lys Glu Thr Glu Leu
1               5                   10                  15

Arg Lys Val Lys Val Leu Gly Ser Gly Ala Phe Gly Thr Val Tyr Lys
            20                  25                  30

Gly Ile Trp Ile Pro Asp Gly Glu Asn Val Lys Ile Pro Val Ala Ile
        35                  40                  45

Lys Val Ser Arg Glu Asn Thr Ser Pro Lys Ala Asn Lys Glu Ile Leu
    50                  55                  60

Asp Glu Ala Tyr Val Met Ala Gly Val Gly Ser Pro Tyr Val Ser Arg
65                  70                  75                  80

Leu Leu Gly Ile Cys Leu Thr Ser Thr Val Gln Leu Val Thr Gln Leu
                85                  90                  95

Met Pro Tyr Gly Cys
            100

<210> SEQ ID NO 975
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 975

Arg Val Glu Glu Phe Lys Leu Lys Gln Met Trp Lys Ser Pro Asn Gly
1               5                   10                  15

Thr Ile Arg Asn Ile Leu Gly Gly Thr Val Phe Arg Glu Ala Ile Ile
            20                  25                  30

Cys Lys Asn Ile Pro Arg Leu Val Ser Gly Trp Val Lys Pro Ile Ile
        35                  40                  45

Ile Gly Gly His Ala Tyr Gly Asp Gln Tyr Arg Ala Thr Asp Phe Val
    50                  55                  60

Val Pro Gly Pro Gly Lys Val Glu Ile Thr Tyr Thr Pro Ser Asp Gly
65                  70                  75                  80

Thr Gln Lys Val Thr Tyr Leu Val His Asn Phe Glu Glu Gly Gly Gly
                85                  90                  95

Val Ala Met Gly Met
            100

<210> SEQ ID NO 976
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 976

Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
```

```
                35                  40                  45

Glu Thr Cys Leu Leu Asp Ile Leu Asp Thr Ala Gly Gln Glu
    50                  55                  60

<210> SEQ ID NO 977
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 977

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu
    50                  55                  60

<210> SEQ ID NO 978
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 978

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu
    50                  55                  60

<210> SEQ ID NO 979
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 979

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly His Glu Glu Tyr Ser Ala Met Arg Asp Gln Tyr Met Arg Thr
    50                  55                  60

Gly Glu Gly Phe Leu Cys Val Phe Ala Ile Asn Asn Thr Lys Ser Phe
65                  70                  75                  80

Glu Asp Ile His His Tyr Arg Glu Gln Ile Lys Arg Val Lys Asp Ser
                85                  90                  95
```

Glu Asp Val Pro Met
            100

<210> SEQ ID NO 980
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 980

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly Leu Glu Glu Tyr Ser Ala Met Arg Asp Gln Tyr Met Arg Thr
    50                  55                  60

Gly Glu Gly Phe Leu Cys Val Phe Ala Ile Asn Asn Thr Lys Ser Phe
65                  70                  75                  80

Glu Asp Ile His His Tyr Arg Glu Gln Ile Lys Arg Val Lys Asp Ser
                85                  90                  95

Glu Asp Val Pro Met
            100

<210> SEQ ID NO 981
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 981

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly Lys Glu Glu Tyr Ser Ala Met Arg Asp Gln Tyr Met Arg Thr
    50                  55                  60

Gly Glu Gly Phe Leu Cys Val Phe Ala Ile Asn Asn Ser Lys Ser Phe
65                  70                  75                  80

Ala Asp Ile Asn Leu Tyr Arg Glu Gln Ile Lys Arg Val Lys Asp Ser
                85                  90                  95

Asp Asp Val Pro Met
            100

<210> SEQ ID NO 982
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 982

```
Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
            35                  40                  45

Ala Gly Arg Glu Glu Tyr Ser Ala Met Arg Asp Gln Tyr Met Arg Thr
50                  55                  60

Gly Glu Gly Phe Leu Cys Val Phe Ala Ile Asn Asn Ser Lys Ser Phe
65                  70                  75                  80

Ala Asp Ile Asn Leu Tyr Arg Glu Gln Ile Lys Arg Val Lys Asp Ser
                85                  90                  95

Asp Asp Val Pro Met
            100
```

<210> SEQ ID NO 983
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 983

```
Ile Glu Glu His Ala Asn Trp Ser Val Ser Arg Glu Ala Gly Phe Ser
1               5                   10                  15

Tyr Ser His Ala Gly Leu Ser Asn Arg Leu Ala Arg Asp Asn Glu Leu
            20                  25                  30

Arg Glu Asn Asp Lys Glu Gln Leu Lys Ala Ile Ser Thr Arg Asp Pro
            35                  40                  45

Leu Ser Lys Ile Thr Glu Gln Glu Lys Asp Phe Leu Trp Ser His Arg
50                  55                  60

His Tyr Cys Val Thr Ile Pro Glu Ile Leu Pro Lys Leu Leu Leu Ser
65                  70                  75                  80

Val Lys Trp Asn Ser Arg Asp Glu Val Ala Gln Met Tyr Cys Leu Val
                85                  90                  95

Lys Asp Trp Pro Pro
            100
```

<210> SEQ ID NO 984
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 984

```
Lys Phe Asn Cys Arg Val Ala Gln Tyr Pro Phe Glu Asp His Asn Pro
1               5                   10                  15

Pro Gln Leu Glu Leu Ile Lys Pro Phe Cys Glu Asp Leu Asp Gln Trp
            20                  25                  30

Leu Ser Glu Asp Asn His Val Ala Ala Ile His Cys Lys Ala Gly Lys
            35                  40                  45

Lys Gly Gln Thr Gly Val Met Ile Cys Ala Tyr Leu Leu His Arg Gly
50                  55                  60

Lys Phe Leu Lys Ala Gln Glu Ala Leu Asp Phe Tyr Gly Glu Val Arg
65                  70                  75                  80
```

```
Thr Arg Asp Lys Lys Gly Val Thr Ile Pro Ser Gln Arg Arg Tyr Val
                85                  90                  95

Tyr Tyr Tyr Ser Tyr
            100

<210> SEQ ID NO 985
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 985

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Ser Gly Glu Tyr
                20                  25                  30

Ile Pro Thr Val Phe Asp Asn Tyr Ser Ala Asn Val Met Val Asp Gly
                35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Val Gly Glu Thr
65                  70                  75

<210> SEQ ID NO 986
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 986

Ala Val Cys Lys Ser Lys Lys Ser Trp Gln Ala Arg His Thr Gly Ile
1               5                   10                  15

Lys Ile Val Gln Gln Ile Ala Ile Leu Met Gly Cys Ala Ile Leu Pro
                20                  25                  30

His Leu Arg Ser Leu Val Glu Ile Ile Glu His Gly Leu Val Asp Glu
                35                  40                  45

Gln Gln Glu Val Arg Thr Ile Ser Ala Leu Ala Ile Ala Ala Leu Ala
        50                  55                  60

Glu Ala Ala Thr Pro Tyr Gly Ile Glu Ser Phe Asp Ser Val Leu Lys
65                  70                  75                  80

Pro Leu Trp Lys Gly Ile Arg Gln His Arg Gly Lys Gly Leu Ala Ala
                85                  90                  95

Phe Leu Lys Ala Ile
            100

<210> SEQ ID NO 987
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 987

Tyr Leu Ser Leu Tyr Leu Leu Leu Val Ser Cys Pro Lys Ser Glu Val
1               5                   10                  15

Arg Ala Lys Phe Lys Phe Ser Ile Leu Asn Ala Lys Gly Glu Glu Thr
```

20                  25                  30

Lys Ala Met Glu Ser Gln Arg Ala Tyr Arg Phe Val Gln Gly Lys Asp
            35                  40                  45

Trp Gly Leu Lys Lys Phe Ile Arg Arg Asp Phe Leu Leu Asp Glu Ala
 50                  55                  60

Asn Gly Leu Leu Pro Asp Asp Lys Leu Thr Leu Phe Cys Glu Val Ser
65                  70                  75                  80

Val Val Gln Asp Ser Val Asn Ile Ser Gly Gln Asn Thr Met Asn Met
                85                  90                  95

Val Lys Val Pro Glu
            100

<210> SEQ ID NO 988
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 988

Tyr Leu Ser Leu Tyr Leu Leu Val Ser Cys Pro Lys Ser Glu Val
1               5                   10                  15

Arg Ala Lys Phe Lys Phe Ser Ile Leu Asn Ala Lys Gly Glu Glu Thr
            20                  25                  30

Lys Ala Met Glu Ser Gln Arg Ala Tyr Arg Phe Val Gln Gly Lys Asp
            35                  40                  45

Trp Gly Val Lys Lys Phe Ile Arg Arg Asp Phe Leu Leu Asp Glu Ala
 50                  55                  60

Asn Gly Leu Leu Pro Asp Asp Lys Leu Thr Leu Phe Cys Glu Val Ser
65                  70                  75                  80

Val Val Gln Asp Ser Val Asn Ile Ser Gly Gln Asn Thr Met Asn Met
                85                  90                  95

Val Lys Val Pro Glu
            100

<210> SEQ ID NO 989
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 989

Ile Arg Val Glu Gly Asn Leu Arg Val Glu Tyr Leu Asp Asp Arg Asn
1               5                   10                  15

Thr Phe Arg His Ser Val Val Val Pro Tyr Glu Pro Pro Glu Val Gly
            20                  25                  30

Ser Asp Cys Thr Thr Ile His Tyr Asn Tyr Met Cys Asn Ser Ser Cys
            35                  40                  45

Met Gly Ser Met Asn Arg Arg Pro Ile Leu Thr Ile Ile Thr Leu Glu
 50                  55                  60

Asp Ser Ser Gly Asn Leu Leu Gly Arg Asn Ser Phe Glu Val Arg Val
65                  70                  75                  80

Cys Ala Cys Pro Gly Arg Asp Arg Arg Thr Glu Glu Glu Asn Leu Arg
                85                  90                  95

Lys Lys Gly Glu Pro

<210> SEQ ID NO 990
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 990

Glu Gly Asn Leu Arg Val Glu Tyr Leu Asp Asp Arg Asn Thr Phe Arg
1               5                   10                  15

His Ser Val Val Val Pro Tyr Glu Pro Pro Glu Val Gly Ser Asp Cys
                20                  25                  30

Thr Thr Ile His Tyr Asn Tyr Met Cys Asn Ser Ser Cys Met Gly Gly
            35                  40                  45

Met Asn Gln Arg Pro Ile Leu Thr Ile Ile Thr Leu Glu Asp Ser Ser
    50                  55                  60

Gly Asn Leu Leu Gly Arg Asn Ser Phe Glu Val Arg Val Cys Ala Cys
65                  70                  75                  80

Pro Gly Arg Asp Arg Arg Thr Glu Glu Glu Asn Leu Arg Lys Lys Gly
                85                  90                  95

Glu Pro His His Glu
            100

<210> SEQ ID NO 991
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 991

Glu Gly Asn Leu Arg Val Glu Tyr Leu Asp Asp Arg Asn Thr Phe Arg
1               5                   10                  15

His Ser Val Val Val Pro Tyr Glu Pro Pro Glu Val Gly Ser Asp Cys
                20                  25                  30

Thr Thr Ile His Tyr Asn Tyr Met Cys Asn Ser Ser Cys Met Gly Gly
            35                  40                  45

Met Asn Trp Arg Pro Ile Leu Thr Ile Ile Thr Leu Glu Asp Ser Ser
    50                  55                  60

Gly Asn Leu Leu Gly Arg Asn Ser Phe Glu Val Arg Val Cys Ala Cys
65                  70                  75                  80

Pro Gly Arg Asp Arg Arg Thr Glu Glu Glu Asn Leu Arg Lys Lys Gly
                85                  90                  95

Glu Pro His His Glu
            100

<210> SEQ ID NO 992
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 992

Pro Glu Val Gly Ser Asp Cys Thr Thr Ile His Tyr Asn Tyr Met Cys
1               5                   10                  15

-continued

```
Asn Ser Ser Cys Met Gly Gly Met Asn Arg Arg Pro Ile Leu Thr Ile
            20                  25                  30

Ile Thr Leu Glu Asp Ser Ser Gly Asn Leu Leu Gly Arg Asn Ser Phe
        35                  40                  45

Glu Val Cys Val Cys Ala Cys Pro Gly Arg Asp Arg Arg Thr Glu Glu
    50                  55                  60

Glu Asn Leu Arg Lys Lys Gly Glu Pro His His Glu Leu Pro Pro Gly
65                  70                  75                  80

Ser Thr Lys Arg Ala Leu Pro Asn Asn Thr Ser Ser Pro Gln Pro
                85                  90                  95

Lys Lys Lys Pro Leu
            100

<210> SEQ ID NO 993
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 993

Pro Glu Val Gly Ser Asp Cys Thr Thr Ile His Tyr Asn Tyr Met Cys
1               5                   10                  15

Asn Ser Ser Cys Met Gly Gly Met Asn Arg Arg Pro Ile Leu Thr Ile
            20                  25                  30

Ile Thr Leu Glu Asp Ser Ser Gly Asn Leu Leu Gly Arg Asn Ser Phe
        35                  40                  45

Glu Val His Val Cys Ala Cys Pro Gly Arg Asp Arg Arg Thr Glu Glu
    50                  55                  60

Glu Asn Leu Arg Lys Lys Gly Glu Pro His His Glu Leu Pro Pro Gly
65                  70                  75                  80

Ser Thr Lys Arg Ala Leu Pro Asn Asn Thr Ser Ser Pro Gln Pro
                85                  90                  95

Lys Lys Lys Pro Leu
            100

<210> SEQ ID NO 994
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 994

Thr Glu Val Val Arg Arg Cys Pro His His Glu Arg Cys Ser Asp Ser
1               5                   10                  15

Asp Gly Leu Ala Pro Pro Gln His Leu Ile Arg Val Glu Gly Asn Leu
            20                  25                  30

Arg Val Glu Tyr Leu Asp Asp Arg Asn Thr Phe Arg His Ser Val Val
        35                  40                  45

Val Pro Cys Glu Pro Pro Glu Val Gly Ser Asp Cys Thr Thr Ile His
    50                  55                  60

Tyr Asn Tyr Met Cys Asn Ser Ser Cys Met Gly Gly Met Asn Arg Arg
65                  70                  75                  80

Pro Ile Leu Thr Ile Ile Thr Leu Glu Asp Ser Ser Gly Asn Leu Leu
                85                  90                  95
```

```
Gly Arg Asn Ser Phe
            100

<210> SEQ ID NO 995
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 995

Tyr Asn Phe Asp Lys Asn Tyr Lys Asp Trp Gln Ser Ala Val Glu Cys
1               5                   10                  15

Ile Ala Val Leu Asp Val Leu Leu Cys Leu Ala Asn Tyr Ser Arg Gly
                20                  25                  30

Gly Asp Gly Pro Met Cys Arg Pro Val Ile Leu Leu Pro Glu Asp Thr
            35                  40                  45

Pro Pro Leu Leu Arg Ala
        50

<210> SEQ ID NO 996
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 996

Ala Lys Phe Gln Gln Cys His Ser Thr Leu Glu Pro Asn Pro Ala Asp
1               5                   10                  15

Cys Arg Val Leu Val Tyr Leu Gln Asn Gln Pro Gly Thr Lys Leu Leu
                20                  25                  30

Asn Phe Leu Gln Glu Arg Asn Leu Pro Pro Lys Val Val Leu Arg His
            35                  40                  45

Pro Lys Val His Leu Asn Thr Met Phe Arg Arg Pro His Ser Cys Leu
        50                  55                  60

Ala Asp Val Leu Leu Ser Val His Leu Ile Val Leu Arg Val Val Arg
65                  70                  75                  80

Leu Pro Ala Pro Phe Arg Val Asn His Ala Val Glu Trp
                85                  90

<210> SEQ ID NO 997
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 997

Ala Leu Gly Pro His Ser Arg Ile Ser Cys Leu Pro Thr Gln Thr Arg
1               5                   10                  15

Gly Cys Ile Leu Leu Ala Ala Thr Pro Arg Ser Ser Ser Ser Ser Ser
                20                  25                  30

Ser Asn Asp Met Ile Pro Met Ala Ile Ser Ser Pro Pro Lys Ala Pro
            35                  40                  45

Leu Leu Ala Ala Pro Ser Pro Ala Ser Arg Leu Gln Cys Ile Asn Ser
        50                  55                  60
```

```
Asn Ser Arg Ile Thr Ser Gly Gln Trp Met Ala His Met Ala Leu Leu
 65                  70                  75                  80

Pro Ser Gly Thr Lys Gly Arg Cys Thr Ala Cys His Thr Ala Leu Gly
                 85                  90                  95

Arg Gly Ser Leu Ser Ser Ser Cys Pro Gln Pro Ser Pro Ser Leu
            100                 105                 110

Pro Ala Ser Asn Lys Leu Pro Ser Leu Pro Leu Ser Lys Met Tyr Thr
            115                 120                 125

Thr Ser Met Ala Met Pro Ile Leu Pro Leu Pro Gln Leu Leu Leu Ser
130                 135                 140

Ala Asp Gln Gln Ala Ala Pro Arg Thr Asn Phe His Ser Ser Leu Ala
145                 150                 155                 160

Glu Thr Val Ser Leu His Pro Leu Ala Pro Met Pro Ser Lys Thr Cys
                165                 170                 175

His His Lys

<210> SEQ ID NO 998
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 998

Arg Ser Tyr Arg Arg Met Ile His Leu Trp Trp Thr Ala Gln Ile Ser
1               5                   10                  15

Leu Gly Val Cys Arg Ser Leu Thr Val Ala Cys Cys Thr Gly Gly Leu
            20                  25                  30

Val Gly Gly Thr Pro Leu Ser Ile Ser Arg Pro Thr Ser Arg Ala Arg
        35                  40                  45

Gln Ser Cys Cys Leu Pro Gly Leu Thr His Pro Ala His Gln Pro Leu
    50                  55                  60

Gly Ser Met
65

<210> SEQ ID NO 999
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 999

Gln His Ser Gly Arg Asp Val Ser Leu Arg Gly Leu Ser Cys Ala Arg
1               5                   10                  15

Ala Thr Leu Ser Phe Trp Pro Gly Gly Tyr Pro Ala Tyr Ser Lys Asp
            20                  25                  30

Ser Gly Leu Leu Thr Ser Ser Arg Glu Trp Lys Val Lys Phe Pro
        35                  40                  45

Glu Leu Leu Cys Val Trp Val Ser Ser Ile Arg His
    50                  55                  60

<210> SEQ ID NO 1000
<211> LENGTH: 48
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 1000

Ala Gln Ala Lys Ala Val Cys Ser Gln Glu Ser Arg Asp Val Leu Cys
1               5                   10                  15
Glu Leu Ser Asp His His Asn His Thr Leu Glu Glu Glu Cys Gln Trp
            20                  25                  30
Gly Pro Cys Leu Gln Cys Leu Trp Ala Leu Leu Gln Ala Ser Gln Tyr
        35                  40                  45

<210> SEQ ID NO 1001
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1001

Pro Gly Arg Pro Leu Gln Thr His Val Leu Pro Glu Pro His Leu Ala
1               5                   10                  15
Leu Gln Pro Leu Gln Pro His Ala Asp His Ala His Ala Asp Ala Pro
            20                  25                  30
Ala Ile Gln Pro Val Leu Trp Thr Thr Pro Leu Gln His Gly His
        35                  40                  45
Arg His Gly Leu Glu Pro Cys Ser Met Leu Thr Gly Pro Pro Ala Arg
    50                  55                  60
Val Pro Ala Val Pro Phe Asp Leu His Phe Cys Arg Ser Ser Ile Met
65                  70                  75                  80
Lys Pro Lys Arg Asp Gly Tyr Met Phe Leu Lys Ala Glu Ser Lys Ile
                85                  90                  95
Met Phe Ala Thr Leu Gln Arg Ser Ser Leu Trp Cys Leu Cys Ser Asn
            100                 105                 110
His

<210> SEQ ID NO 1002
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1002

Thr Arg Arg Cys His Cys Cys Pro His Leu Arg Ser His Pro Cys Pro
1               5                   10                  15
His His Leu Arg Asn His Pro Arg Pro His His Leu Arg His His Ala
            20                  25                  30
Cys His His His Leu Arg Asn Cys Pro His Pro His Phe Leu Arg His
        35                  40                  45
Cys Thr Cys Pro Gly Arg Trp Arg Asn Arg Pro Ser Leu Arg Arg Leu
    50                  55                  60
Arg Ser Leu Leu Cys Leu Pro His Leu Asn His His Leu Phe Leu His
65                  70                  75                  80
Trp Arg Ser Arg Pro Cys Leu His Arg Lys Ser His Pro His Leu Leu
                85                  90                  95
His Leu Arg Arg Leu Tyr Pro His Leu Lys His Arg Pro Cys Pro
            100                 105                 110

His His Leu Lys Asn Leu Leu Cys Pro Arg His Leu Arg Asn Cys Pro
            115                 120                 125

Leu Pro Arg His Leu Lys His Leu Ala Cys Leu His His Leu Arg Ser
130                 135                 140

His Pro Cys Pro Leu His Leu Lys Ser His Pro Cys Leu His His Arg
145                 150                 155                 160

Arg His Leu Val Cys Ser His Leu Lys Ser Leu Leu Cys Pro Leu
            165                 170                 175

His Leu Arg Ser Leu Pro Phe Pro His His Leu Arg His Ala Cys
            180                 185                 190

Pro His His Leu Arg Thr Arg Leu Cys Pro His His Leu Lys Asn His
            195                 200                 205

Leu Cys Pro Pro His Leu Arg Tyr Arg Ala Tyr Pro Pro Cys Leu Trp
210                 215                 220

Cys His Ala Cys Leu His Arg Leu Arg Asn Leu Pro Cys Pro His Arg
225                 230                 235                 240

Leu Arg Ser Leu Pro Arg Pro Leu His Leu Arg Leu His Ala Ser Pro
            245                 250                 255

His His Leu Arg Thr Pro Pro His Pro His His Leu Arg Thr His Leu
            260                 265                 270

Leu Pro His His Arg Arg Thr Arg Ser Cys Pro Cys Arg Trp Arg Ser
275                 280                 285

His Pro Cys Cys His Tyr Leu Arg Ser Arg Asn Ser Ala Pro Gly Pro
            290                 295                 300

Arg Gly Arg Thr Cys His Pro Gly Leu Arg Ser Arg Thr Cys Pro Pro
305                 310                 315                 320

Gly Leu Arg Ser His Thr Tyr Leu Arg Arg Leu Arg Ser His Thr Cys
            325                 330                 335

Pro Pro Ser Leu Arg Ser His Ala Tyr Ala Leu Cys Leu Arg Ser His
            340                 345                 350

Thr Cys Pro Pro Arg Leu Arg Asp His Ile Cys Pro Leu Ser Leu Arg
            355                 360                 365

Asn Cys Thr Cys Pro Pro Arg Leu Arg Ser Arg Thr Cys Leu Leu Cys
370                 375                 380

Leu Arg Ser His Ala Cys Pro Pro Asn Leu Arg Asn His Thr Cys Pro
385                 390                 395                 400

Pro Ser Leu Arg Ser His Ala Cys Pro Pro Gly Leu Arg Asn Arg Ile
            405                 410                 415

Cys Pro Leu Ser Leu Arg Ser His Pro Cys Pro Leu Gly Leu Lys Ser
            420                 425                 430

Pro Leu Arg Ser Gln Ala Asn Ala Leu His Leu Arg Ser Cys Pro Cys
            435                 440                 445

Ser Leu Pro Leu Gly Asn His Pro Tyr Leu Pro Cys Leu Glu Ser Gln
450                 455                 460

Pro Cys Leu Ser Leu Gly Asn His Leu Cys Pro Leu Cys Pro Arg Ser
465                 470                 475                 480

Cys Arg Cys Pro His Leu Gly Ser His Pro Cys Arg Leu Ser
            485                 490

<210> SEQ ID NO 1003
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1003

Gly Pro Arg Ser His Pro Leu Pro Arg Leu Trp His Leu Leu Leu Gln
1               5                   10                  15

Val Thr Gln Thr Ser Phe Ala Leu Ala Pro Thr Leu Thr His Met Leu
            20                  25                  30

Ser Pro His
        35

<210> SEQ ID NO 1004
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1004

Pro Leu Gly Leu Val Pro Trp Thr Arg Trp Cys Pro Gln Gly Lys Pro
1               5                   10                  15

Arg Phe Pro Ala Met Ser Thr Thr Thr Ala Thr Gly Thr Thr Thr Thr
            20                  25                  30

Lys Ser Gly Ser Ser Gly Met Ala Gly Ser Leu Ala Gln Lys Pro Glu
        35                  40                  45

Ser Pro Ser Pro Gly Leu Leu Phe Leu Gly His Ser Pro Ser Gln Ser
    50                  55                  60

His Leu Leu Leu Ile Ser Lys Ser Pro Asp Pro Thr Gln Gln Pro Leu
65                  70                  75                  80

Arg Gly Gly Ser Leu Thr His Ser Ala Pro Gly Pro Ser Leu Ser Gln
                85                  90                  95

Pro Leu Ala Gln Leu Thr Pro Pro Ala Ser Ala Pro Val Pro Ala Val
            100                 105                 110

Cys Ser Thr Cys Lys Asn Pro Ala Ser Leu Pro Asp Thr His Arg Gly
        115                 120                 125

Lys Gly Gly Val Pro Pro Ser Pro Pro Leu Ala Leu Gly Pro Arg
    130                 135                 140

Met Gln Leu Cys Thr Gln Leu Ala Arg Phe Phe Pro Ile Thr Pro Pro
145                 150                 155                 160

Val Trp His Ile Leu Gly Pro Gln Arg His Thr Pro
                165                 170

<210> SEQ ID NO 1005
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1005

Lys Tyr Glu Lys Lys Tyr Asp Lys Asn Ala Ile Ala Ile Thr
1               5                   10                  15

Asn Ile Ser Ser Ser Asp Ala Pro Leu Gln Pro Leu Val Ser Ser Pro
            20                  25                  30

Ser Leu Gln Ala Ala Val Asp Lys Asn Lys Leu Glu Lys Glu Lys Glu
        35                  40                  45

Lys Lys Arg Lys Arg Lys Arg Glu Lys Arg Ser Gln Lys Ser Arg Gln
    50                  55                  60

Asn His Leu Gln Leu Lys Ser Cys Arg Arg Lys Ile Ser Asn Trp Ser
65                  70                  75                  80

Leu Lys Lys Val Pro Ala Leu Lys Lys Leu Arg Ser Pro Leu Trp Ile
                85                  90                  95

Phe

<210> SEQ ID NO 1006
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1006

Cys Cys Pro Arg Thr Ile Leu Asn Asn Gly Ser Leu Lys Thr Gln Val
1               5                   10                  15

Gln Met Lys Leu Pro Glu Cys Gln Arg Leu Leu Pro Pro Trp Pro Leu
                20                  25                  30

His Gln Gln Leu Leu His Arg Arg Pro Leu His Gln Pro Pro Pro Gly
            35                  40                  45

Pro Cys His Leu Leu Ser Leu Pro Arg Lys Pro Thr Arg Ala Ala Thr
    50                  55                  60

Val Ser Val Trp Ala Ser Cys Ile Leu Gly Gln Pro Ser Leu
65                  70                  75

<210> SEQ ID NO 1007
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1007

Leu Ala Arg Thr Pro Leu Pro Ser Thr Arg Cys Phe Ala Asn Trp Pro
1               5                   10                  15

Arg Pro Ala Leu Cys Ser Cys Gly Leu Ile Pro His Pro Arg Pro Ala
                20                  25                  30

Pro Ala Ser Ala Pro Trp Pro Ser Thr Ser Ser His Ser Thr
            35                  40                  45

<210> SEQ ID NO 1008
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1008

Ser Gln Gly Leu Tyr Ser Ser Ser Ala Ser Ser Gly Lys Cys Leu Met
1               5                   10                  15

Glu Val Thr Val Asp Arg Asn Cys Leu Glu Val Leu Pro Thr Lys Met
                20                  25                  30

Ser Tyr Ala Ala Asn Leu Lys Asn Val Met Asn Met Gln Asn Arg Gln
            35                  40                  45

Lys Lys Lys Gly Lys Asn Ser Pro Cys Cys Gln Lys Lys Leu Arg Val
    50                  55                  60

Gln Asn Gln Gly His Leu Leu Met Ile Leu Leu His Asn 65                  70                  75

<210> SEQ ID NO 1009
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1009

Thr Arg Ala Ser Pro Arg Ser Ser Ala Ile Ala Val Arg Ala
1               5                   10                  15

Ser Cys Cys Pro Tyr Gly Ser Thr Ser Thr Ala Ser Arg Ser Pro Thr
                20                  25                  30

Gln Arg Cys Arg Leu Ala Arg Ala Ala Ala Ser Thr Ala Thr Glu Val
            35                  40                  45

Thr Phe Gly Ser Ser Glu Met Gln Gly His Thr Met Gly Phe Trp Leu
        50                  55                  60

Thr Lys Leu Asn Tyr Leu Cys His Leu Ser Met Leu Thr Asp Ser Leu
65                  70                  75                  80

Phe Leu Pro Ile Ser His Cys Gln Cys Ile Leu
                85                  90

<210> SEQ ID NO 1010
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1010

Leu Gly Ser Gly Ala Phe Gly Thr Val Tyr Lys Gly Ile Trp Ile Pro
1               5                   10                  15

Asp Gly Glu Asn Val Lys Ile Pro Val Ala Ile Lys Val Leu Arg Glu
                20                  25                  30

Asn Thr Ser Pro Lys Ala Asn Lys Glu Ile Leu Asp Glu Ala Tyr Val
            35                  40                  45

Met Ala Tyr Val Met Ala Gly Val Gly Ser Pro Tyr Val Ser Arg Leu
        50                  55                  60

Leu Gly Ile Cys Leu Thr Ser Thr Val Gln Leu Val Thr Gln Leu Met
65                  70                  75                  80

Pro Tyr Gly Cys Leu Leu Asp His Val Arg Glu Asn Arg Gly Arg Leu
                85                  90                  95

Gly Ser Gln Asp Leu Leu Asn Trp
            100

<210> SEQ ID NO 1011
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1011

Lys Tyr Ile Lys Thr Trp Arg Pro Arg Tyr
1               5                   10

<210> SEQ ID NO 1012

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1012

Trp Leu His Lys Arg Gly Lys Tyr Ile
1               5

<210> SEQ ID NO 1013
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1013

Trp Leu His Lys Arg Gly Lys Tyr Ile Lys
1               5                   10

<210> SEQ ID NO 1014
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1014

Ala Pro Lys Pro Leu Ser Lys Leu Leu
1               5

<210> SEQ ID NO 1015
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1015

Gly Val Ser Ala Pro Lys Pro Leu Ser Lys
1               5                   10

<210> SEQ ID NO 1016
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1016

Val Ser Ala Pro Lys Pro Leu Ser Lys
1               5

<210> SEQ ID NO 1017
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1017
```

```
Cys Pro His Arg Pro Ile Leu Gln Ala
1               5
```

<210> SEQ ID NO 1018
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1018

```
Lys Leu Ser Asp Ser Arg Thr Ala Leu
1               5
```

<210> SEQ ID NO 1019
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1019

```
Lys Leu Ser Asp Ser Arg Thr Ala Leu Lys
1               5                   10
```

<210> SEQ ID NO 1020
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1020

```
Leu Ser Asp Ser Arg Thr Ala Leu Lys
1               5
```

<210> SEQ ID NO 1021
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1021

```
Arg Thr Ala Leu Lys Ser Gly Tyr Gly Lys
1               5                   10
```

<210> SEQ ID NO 1022
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1022

```
Thr Ala Leu Lys Ser Gly Tyr Gly Lys
1               5
```

<210> SEQ ID NO 1023
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 1023

Ala Leu Ser Ala Ser Asn Ser Cys Phe
1               5

<210> SEQ ID NO 1024
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1024

Ala Leu Ser Ala Ser Asn Ser Cys Phe Ile
1               5                   10

<210> SEQ ID NO 1025
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1025

Phe Gln Asn Gly Lys Met Ala Leu Ser Ala
1               5                   10

<210> SEQ ID NO 1026
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1026

Lys Val Ser Arg Glu Asn Thr Ser Pro Lys
1               5                   10

<210> SEQ ID NO 1027
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1027

Lys Pro Ile Ile Ile Gly Gly His Ala Tyr
1               5                   10

<210> SEQ ID NO 1028
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1028

Lys Leu Val Val Val Gly Ala Cys Gly Val
1               5                   10
```

```
<210> SEQ ID NO 1029
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1029

Leu Val Val Val Gly Ala Cys Gly Val
1               5

<210> SEQ ID NO 1030
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1030

Val Val Gly Ala Cys Gly Val Gly Lys
1               5

<210> SEQ ID NO 1031
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1031

Val Val Val Gly Ala Cys Gly Val Gly Lys
1               5                   10

<210> SEQ ID NO 1032
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1032

Val Val Gly Ala Asp Gly Val Gly Lys
1               5

<210> SEQ ID NO 1033
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1033

Val Val Val Gly Ala Asp Gly Val Gly Lys
1               5                   10

<210> SEQ ID NO 1034
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1034
```

```
Lys Leu Val Val Gly Ala Asp Gly Val
1               5                   10

<210> SEQ ID NO 1035
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1035

Leu Val Val Val Gly Ala Asp Gly Val
1               5

<210> SEQ ID NO 1036
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1036

Lys Leu Val Val Gly Ala Val Gly Val
1               5                   10

<210> SEQ ID NO 1037
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1037

Leu Val Val Val Gly Ala Val Gly Val
1               5

<210> SEQ ID NO 1038
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1038

Val Val Gly Ala Val Gly Val Gly Lys
1               5

<210> SEQ ID NO 1039
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1039

Val Val Val Gly Ala Val Gly Val Gly Lys
1               5                   10

<210> SEQ ID NO 1040
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1040

Ile Leu Asp Thr Ala Gly His Glu Glu Tyr
1               5                   10

<210> SEQ ID NO 1041
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1041

Ile Leu Asp Thr Ala Gly Leu Glu Glu Tyr
1               5                   10

<210> SEQ ID NO 1042
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1042

Leu Leu Asp Ile Leu Asp Thr Ala Gly Leu
1               5                   10

<210> SEQ ID NO 1043
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1043

Ile Leu Asp Thr Ala Gly Lys Glu Glu Tyr
1               5                   10

<210> SEQ ID NO 1044
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1044

Ile Leu Asp Thr Ala Gly Arg Glu Glu Tyr
1               5                   10

<210> SEQ ID NO 1045
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1045

Ala Ile Ser Thr Arg Asp Pro Leu Ser Lys
1               5                   10
```

<210> SEQ ID NO 1046
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1046

Gln Thr Gly Val Met Ile Cys Ala Tyr
1               5

<210> SEQ ID NO 1047
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1047

Phe Ser Gly Glu Tyr Ile Pro Thr Val
1               5

<210> SEQ ID NO 1048
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1048

Thr Thr Asn Ala Phe Ser Gly Glu Tyr
1               5

<210> SEQ ID NO 1049
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1049

Tyr Thr Thr Asn Ala Phe Ser Gly Glu Tyr
1               5                   10

<210> SEQ ID NO 1050
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1050

Gly Leu Val Asp Glu Gln Gln Glu Val
1               5

<210> SEQ ID NO 1051
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1051

Phe Val Gln Gly Lys Asp Trp Gly Leu
1               5

<210> SEQ ID NO 1052
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1052

Phe Val Gln Gly Lys Asp Trp Gly Val
1               5

<210> SEQ ID NO 1053
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1053

Cys Met Gly Ser Met Asn Arg Arg Pro Ile
1               5                   10

<210> SEQ ID NO 1054
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1054

Gly Ser Met Asn Arg Arg Pro Ile Leu
1               5

<210> SEQ ID NO 1055
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1055

Met Gly Ser Met Asn Arg Arg Pro Ile
1               5

<210> SEQ ID NO 1056
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1056

Met Gly Ser Met Asn Arg Arg Pro Ile Leu
1               5                   10

<210> SEQ ID NO 1057
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 1057

Ser Met Asn Arg Arg Pro Ile Leu Thr Ile
1               5                   10

<210> SEQ ID NO 1058
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1058

Cys Met Gly Gly Met Asn Gln Arg Pro Ile
1               5                   10

<210> SEQ ID NO 1059
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1059

Gly Met Asn Gln Arg Pro Ile Leu Thr Ile
1               5                   10

<210> SEQ ID NO 1060
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1060

Asn Gln Arg Pro Ile Leu Thr Ile Ile
1               5

<210> SEQ ID NO 1061
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1061

Cys Met Gly Gly Met Asn Trp Arg Pro Ile
1               5                   10

<210> SEQ ID NO 1062
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1062

Gly Met Asn Trp Arg Pro Ile Leu Thr Ile
1               5                   10
```

<210> SEQ ID NO 1063
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1063

Met Asn Trp Arg Pro Ile Leu Thr Ile
1               5

<210> SEQ ID NO 1064
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1064

Met Asn Trp Arg Pro Ile Leu Thr Ile Ile
1               5                   10

<210> SEQ ID NO 1065
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1065

Asn Ser Phe Glu Val Cys Val Cys Ala
1               5

<210> SEQ ID NO 1066
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1066

Asn Ser Phe Glu Val His Val Cys Ala
1               5

<210> SEQ ID NO 1067
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1067

Val Val Pro Cys Glu Pro Pro Glu Val
1               5

<210> SEQ ID NO 1068
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1068

Val Val Val Pro Cys Glu Pro Pro Glu Val
1               5                   10

<210> SEQ ID NO 1069
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1069

Ile Leu Leu Pro Glu Asp Thr Pro Pro Leu
1               5                   10

<210> SEQ ID NO 1070
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1070

Leu Leu Pro Glu Asp Thr Pro Pro Leu
1               5

<210> SEQ ID NO 1071
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1071

Ala Pro Phe Arg Val Asn His Ala Val
1               5

<210> SEQ ID NO 1072
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1072

Cys Leu Ala Asp Val Leu Leu Ser Val
1               5

<210> SEQ ID NO 1073
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1073

Phe Leu Gln Glu Arg Asn Leu Pro Pro Lys
1               5                   10

<210> SEQ ID NO 1074
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1074

His Leu Ile Val Leu Arg Val Val Arg Leu
1               5                   10

<210> SEQ ID NO 1075
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1075

His Pro Lys Val His Leu Asn Thr Met
1               5

<210> SEQ ID NO 1076
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1076

His Pro Lys Val His Leu Asn Thr Met Phe
1               5                   10

<210> SEQ ID NO 1077
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1077

Lys Val His Leu Asn Thr Met Phe Arg
1               5

<210> SEQ ID NO 1078
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1078

Lys Val His Leu Asn Thr Met Phe Arg Arg
1               5                   10

<210> SEQ ID NO 1079
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1079

Leu Pro Ala Pro Phe Arg Val Asn His Ala
```

```
1               5                    10
```

<210> SEQ ID NO 1080
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1080

```
Met Phe Arg Arg Pro His Ser Cys Leu
1               5
```

<210> SEQ ID NO 1081
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1081

```
Met Phe Arg Arg Pro His Ser Cys Leu Ala
1               5                    10
```

<210> SEQ ID NO 1082
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1082

```
Asn Thr Met Phe Arg Arg Pro His Ser Cys
1               5                    10
```

<210> SEQ ID NO 1083
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1083

```
Arg Pro His Ser Cys Leu Ala Asp Val
1               5
```

<210> SEQ ID NO 1084
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1084

```
Arg Pro His Ser Cys Leu Ala Asp Val Leu
1               5                    10
```

<210> SEQ ID NO 1085
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1085

Arg Val Val Arg Leu Pro Ala Pro Phe Arg
1               5                   10

<210> SEQ ID NO 1086
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1086

Ser Val His Leu Ile Val Leu Arg Val
1               5

<210> SEQ ID NO 1087
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1087

Thr Met Phe Arg Arg Pro His Ser Cys
1               5

<210> SEQ ID NO 1088
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1088

Thr Met Phe Arg Arg Pro His Ser Cys Leu
1               5                   10

<210> SEQ ID NO 1089
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1089

Val Leu Leu Ser Val His Leu Ile Val
1               5

<210> SEQ ID NO 1090
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1090

Val Leu Leu Ser Val His Leu Ile Val Leu
1               5                   10

<210> SEQ ID NO 1091

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1091

Val Leu Arg Val Val Arg Leu Pro Ala
1               5

<210> SEQ ID NO 1092
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1092

Val Val Arg Leu Pro Ala Pro Phe Arg
1               5

<210> SEQ ID NO 1093
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1093

Ala Met Pro Ile Leu Pro Leu Pro Gln Leu
1               5                   10

<210> SEQ ID NO 1094
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1094

Ala Pro Leu Leu Ala Ala Pro Ser Pro Ala
1               5                   10

<210> SEQ ID NO 1095
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1095

Ala Pro Arg Thr Asn Phe His Ser Ser
1               5

<210> SEQ ID NO 1096
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1096
```

```
Ala Pro Arg Thr Asn Phe His Ser Ser Leu
1               5                   10
```

<210> SEQ ID NO 1097
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1097

```
Cys Pro Gln Pro Ser Pro Ser Leu Pro Ala
1               5                   10
```

<210> SEQ ID NO 1098
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1098

```
Gly Gln Trp Met Ala His Met Ala Leu
1               5
```

<210> SEQ ID NO 1099
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1099

```
Gly Gln Trp Met Ala His Met Ala Leu Leu
1               5                   10
```

<210> SEQ ID NO 1100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1100

```
His Met Ala Leu Leu Pro Ser Gly Thr Lys
1               5                   10
```

<210> SEQ ID NO 1101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1101

```
His Thr Ala Leu Gly Arg Gly Ser Leu
1               5
```

<210> SEQ ID NO 1102
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 1102

Ile Pro Met Ala Ile Ser Ser Pro Pro
1               5

<210> SEQ ID NO 1103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1103

Ile Pro Met Ala Ile Ser Ser Pro Pro Lys
1               5                   10

<210> SEQ ID NO 1104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1104

Lys Leu Pro Ser Leu Pro Leu Ser Lys
1               5

<210> SEQ ID NO 1105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1105

Lys Leu Pro Ser Leu Pro Leu Ser Lys Met
1               5                   10

<210> SEQ ID NO 1106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1106

Lys Met Tyr Thr Thr Ser Met Ala Met
1               5

<210> SEQ ID NO 1107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1107

Leu Leu Ala Ala Pro Ser Pro Ala Ser Arg
1               5                   10
```

```
<210> SEQ ID NO 1108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1108

Leu Leu Leu Ser Ala Asp Gln Gln Ala Ala
1               5                   10

<210> SEQ ID NO 1109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1109

Leu Leu Ser Ala Asp Gln Gln Ala Ala
1               5

<210> SEQ ID NO 1110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1110

Leu Pro Ala Ser Asn Lys Leu Pro Ser
1               5

<210> SEQ ID NO 1111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1111

Leu Pro Ala Ser Asn Lys Leu Pro Ser Leu
1               5                   10

<210> SEQ ID NO 1112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1112

Leu Pro Leu Pro Gln Leu Leu Leu Ser Ala
1               5                   10

<210> SEQ ID NO 1113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1113
```

```
Leu Pro Ser Leu Pro Leu Ser Lys Met
1               5

<210> SEQ ID NO 1114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1114

Leu Ser Lys Met Tyr Thr Thr Ser Met
1               5

<210> SEQ ID NO 1115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1115

Met Ala Leu Leu Pro Ser Gly Thr Lys
1               5

<210> SEQ ID NO 1116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1116

Met Pro Ile Leu Pro Leu Pro Gln Leu
1               5

<210> SEQ ID NO 1117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1117

Met Pro Ile Leu Pro Leu Pro Gln Leu Leu
1               5                   10

<210> SEQ ID NO 1118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1118

Met Tyr Thr Thr Ser Met Ala Met Pro Ile
1               5                   10

<210> SEQ ID NO 1119
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1119

Pro Met Ala Ile Ser Ser Pro Pro Lys
1               5

<210> SEQ ID NO 1120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1120

Gln Trp Met Ala His Met Ala Leu Leu
1               5

<210> SEQ ID NO 1121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1121

Ser Lys Met Tyr Thr Thr Ser Met Ala Met
1               5                   10

<210> SEQ ID NO 1122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1122

Ser Met Ala Met Pro Ile Leu Pro Leu
1               5

<210> SEQ ID NO 1123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1123

Ser Asn Lys Leu Pro Ser Leu Pro Leu
1               5

<210> SEQ ID NO 1124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1124

Ser Pro Ala Ser Arg Leu Gln Cys Ile
1               5
```

<210> SEQ ID NO 1125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1125

Ser Pro Pro Lys Ala Pro Leu Leu Ala Ala
1               5                   10

<210> SEQ ID NO 1126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1126

Ser Pro Ser Leu Pro Ala Ser Asn Lys Leu
1               5                   10

<210> SEQ ID NO 1127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1127

Tyr Thr Thr Ser Met Ala Met Pro Ile
1               5

<210> SEQ ID NO 1128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1128

Tyr Thr Thr Ser Met Ala Met Pro Ile Leu
1               5                   10

<210> SEQ ID NO 1129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1129

Cys Leu Pro Gly Leu Thr His Pro Ala
1               5

<210> SEQ ID NO 1130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1130

Gly Leu Thr His Pro Ala His Gln Pro Leu
1               5                   10

<210> SEQ ID NO 1131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1131

His Pro Ala His Gln Pro Leu Gly Ser Met
1               5                   10

<210> SEQ ID NO 1132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1132

Leu Thr His Pro Ala His Gln Pro Leu
1               5

<210> SEQ ID NO 1133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1133

Arg Pro Thr Ser Arg Ala Arg Gln Ser Cys
1               5                   10

<210> SEQ ID NO 1134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1134

Arg Gln Ser Cys Cys Leu Pro Gly Leu
1               5

<210> SEQ ID NO 1135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1135

Thr Ser Arg Ala Arg Gln Ser Cys Cys Leu
1               5                   10

<210> SEQ ID NO 1136
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 1136

Glu Leu Leu Cys Val Trp Val Ser Ser Ile
1               5                   10

<210> SEQ ID NO 1137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1137

Glu Trp Lys Val Lys Phe Pro Glu Leu
1               5

<210> SEQ ID NO 1138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1138

Lys Phe Pro Glu Leu Leu Cys Val Trp
1               5

<210> SEQ ID NO 1139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1139

Leu Leu Cys Val Trp Val Ser Ser Ile
1               5

<210> SEQ ID NO 1140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1140

Leu Leu Thr Ser Ser Ser Arg Glu Trp Lys
1               5                   10

<210> SEQ ID NO 1141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1141

Leu Thr Ser Ser Ser Arg Glu Trp Lys
1               5
```

<210> SEQ ID NO 1142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1142

Tyr Pro Ala Tyr Ser Lys Asp Ser Gly Leu
1               5                   10

<210> SEQ ID NO 1143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1143

Cys Leu Gln Cys Leu Trp Ala Leu Leu
1               5

<210> SEQ ID NO 1144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1144

Cys Gln Trp Gly Pro Cys Leu Gln Cys Leu
1               5                   10

<210> SEQ ID NO 1145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1145

Gln Trp Gly Pro Cys Leu Gln Cys Leu
1               5

<210> SEQ ID NO 1146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1146

Gln Trp Gly Pro Cys Leu Gln Cys Leu Trp
1               5                   10

<210> SEQ ID NO 1147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1147

Ala Ile Gln Pro Val Leu Trp Thr Thr
1               5

<210> SEQ ID NO 1148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1148

Ala Leu Gln Pro Leu Gln Pro His Ala
1               5

<210> SEQ ID NO 1149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1149

Asp Leu His Phe Cys Arg Ser Ser Ile Met
1               5                   10

<210> SEQ ID NO 1150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1150

Glu Pro His Leu Ala Leu Gln Pro Leu
1               5

<210> SEQ ID NO 1151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1151

Glu Ser Lys Ile Met Phe Ala Thr Leu
1               5

<210> SEQ ID NO 1152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1152

Phe Ala Thr Leu Gln Arg Ser Ser Leu
1               5

<210> SEQ ID NO 1153
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1153

Phe Leu Lys Ala Glu Ser Lys Ile Met
1               5

<210> SEQ ID NO 1154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1154

Phe Leu Lys Ala Glu Ser Lys Ile Met Phe
1               5                   10

<210> SEQ ID NO 1155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1155

Gly Pro Pro Ala Arg Val Pro Ala Val
1               5

<210> SEQ ID NO 1156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1156

Ile Met Lys Pro Lys Arg Asp Gly Tyr Met
1               5                   10

<210> SEQ ID NO 1157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1157

Lys Ile Met Phe Ala Thr Leu Gln Arg
1               5

<210> SEQ ID NO 1158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1158

Lys Pro Lys Arg Asp Gly Tyr Met Phe
```

<210> SEQ ID NO 1159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1159

Lys Pro Lys Arg Asp Gly Tyr Met Phe Leu
1               5                   10

<210> SEQ ID NO 1160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1160

Leu His Phe Cys Arg Ser Ser Ile Met
1               5

<210> SEQ ID NO 1161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1161

Leu Gln His Gly His Arg His Gly Leu
1               5

<210> SEQ ID NO 1162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1162

Met Phe Ala Thr Leu Gln Arg Ser Ser Leu
1               5                   10

<210> SEQ ID NO 1163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1163

Met Phe Leu Lys Ala Glu Ser Lys Ile
1               5

<210> SEQ ID NO 1164
<211> LENGTH: 9
<212> TYPE: PRT
<213> ORGANISM: Artificial Sequence
<220> FEATURE:
<223> OTHER INFORMATION: Description of Artificial Sequence: Synthetic

```
                           peptide

<400> SEQUENCE: 1164

Met Leu Thr Gly Pro Pro Ala Arg Val
1               5

<210> SEQ ID NO 1165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1165

Gln Pro Val Leu Trp Thr Thr Pro Pro Leu
1               5                   10

<210> SEQ ID NO 1166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1166

Ser Met Leu Thr Gly Pro Pro Ala Arg Val
1               5                   10

<210> SEQ ID NO 1167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1167

Thr Leu Gln Arg Ser Ser Leu Trp Cys Leu
1               5                   10

<210> SEQ ID NO 1168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1168

Val Leu Pro Glu Pro His Leu Ala Leu
1               5

<210> SEQ ID NO 1169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1169

Val Pro Ala Val Pro Phe Asp Leu His Phe
1               5                   10

<210> SEQ ID NO 1170
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1170

Tyr Met Phe Leu Lys Ala Glu Ser Lys
1               5

<210> SEQ ID NO 1171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1171

Tyr Met Phe Leu Lys Ala Glu Ser Lys Ile
1               5                   10

<210> SEQ ID NO 1172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1172

Ala Pro Gly Pro Arg Gly Arg Thr Cys
1               5

<210> SEQ ID NO 1173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1173

Cys Leu Arg Ser His Thr Cys Pro Pro Arg
1               5                   10

<210> SEQ ID NO 1174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1174

Cys Leu Trp Cys His Ala Cys Leu His Arg
1               5                   10

<210> SEQ ID NO 1175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1175
```

```
Cys Pro His Leu Gly Ser His Pro Cys
1               5

<210> SEQ ID NO 1176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1176

Cys Pro Leu Gly Leu Lys Ser Pro Leu
1               5

<210> SEQ ID NO 1177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1177

Cys Pro Arg Ser Cys Arg Cys Pro His
1               5

<210> SEQ ID NO 1178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1178

Cys Pro Arg Ser Cys Arg Cys Pro His Leu
1               5                   10

<210> SEQ ID NO 1179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1179

Cys Ser Leu Pro Leu Gly Asn His Pro Tyr
1               5                   10

<210> SEQ ID NO 1180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1180

Gly Leu Arg Asn Arg Ile Cys Pro Leu
1               5

<210> SEQ ID NO 1181
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 1181

Gly Leu Arg Ser His Thr Tyr Leu Arg
1               5

<210> SEQ ID NO 1182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1182

Gly Leu Arg Ser His Thr Tyr Leu Arg Arg
1               5                   10

<210> SEQ ID NO 1183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1183

Gly Pro Arg Gly Arg Thr Cys His Pro Gly
1               5                   10

<210> SEQ ID NO 1184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1184

His Leu Gly Ser His Pro Cys Arg Leu
1               5

<210> SEQ ID NO 1185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1185

His Leu Arg Leu His Ala Ser Pro His
1               5

<210> SEQ ID NO 1186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1186

His Leu Arg Ser Cys Pro Cys Ser Leu
1               5
```

```
<210> SEQ ID NO 1187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1187

His Leu Arg Thr His Leu Leu Pro His
1               5

<210> SEQ ID NO 1188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1188

His Leu Arg Thr His Leu Leu Pro His His
1               5                   10

<210> SEQ ID NO 1189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1189

His Leu Arg Tyr Arg Ala Tyr Pro Pro
1               5

<210> SEQ ID NO 1190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1190

His Leu Arg Tyr Arg Ala Tyr Pro Pro Cys
1               5                   10

<210> SEQ ID NO 1191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1191

His Pro His His Leu Arg Thr His Leu
1               5

<210> SEQ ID NO 1192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1192
```

His Pro His His Leu Arg Thr His Leu Leu
1               5                   10

<210> SEQ ID NO 1193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1193

His Thr Tyr Leu Arg Arg Leu Arg Ser His
1               5                   10

<210> SEQ ID NO 1194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1194

Leu Pro Cys Pro His Arg Leu Arg Ser Leu
1               5                   10

<210> SEQ ID NO 1195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1195

Leu Pro His His Arg Arg Thr Arg Ser Cys
1               5                   10

<210> SEQ ID NO 1196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1196

Leu Pro Leu Gly Asn His Pro Tyr Leu
1               5

<210> SEQ ID NO 1197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1197

Leu Pro Arg Pro Leu His Leu Arg Leu
1               5

<210> SEQ ID NO 1198
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1198

Asn Leu Arg Asn His Thr Cys Pro Pro
1               5

<210> SEQ ID NO 1199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1199

Pro Pro Arg Leu Arg Ser Arg Thr Cys Leu
1               5                   10

<210> SEQ ID NO 1200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1200

Arg Leu His Ala Ser Pro His His Leu
1               5

<210> SEQ ID NO 1201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1201

Arg Leu His Ala Ser Pro His His Leu Arg
1               5                   10

<210> SEQ ID NO 1202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1202

Arg Leu Arg Asp His Ile Cys Pro Leu
1               5

<210> SEQ ID NO 1203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1203

Arg Leu Arg Asn Leu Pro Cys Pro His
1               5
```

<210> SEQ ID NO 1204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1204

Arg Leu Arg Asn Leu Pro Cys Pro His Arg
1               5                   10

<210> SEQ ID NO 1205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1205

Arg Leu Arg Ser His Thr Cys Pro Pro
1               5

<210> SEQ ID NO 1206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1206

Arg Leu Arg Ser Leu Pro Arg Pro Leu
1               5

<210> SEQ ID NO 1207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1207

Arg Leu Arg Ser Leu Pro Arg Pro Leu His
1               5                   10

<210> SEQ ID NO 1208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1208

Arg Leu Arg Ser Arg Thr Cys Leu Leu
1               5

<210> SEQ ID NO 1209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1209

Arg Asn Arg Ile Cys Pro Leu Ser Leu
1               5

<210> SEQ ID NO 1210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1210

Arg Pro Leu His Leu Arg Leu His Ala
1               5

<210> SEQ ID NO 1211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1211

Arg Pro Leu His Leu Arg Leu His Ala Ser
1               5                   10

<210> SEQ ID NO 1212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1212

Arg Ser His Ala Cys Pro Pro Gly Leu Arg
1               5                   10

<210> SEQ ID NO 1213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1213

Arg Ser His Ala Cys Pro Pro Asn Leu Arg
1               5                   10

<210> SEQ ID NO 1214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1214

Arg Ser His Ala Tyr Ala Leu Cys Leu Arg
1               5                   10

<210> SEQ ID NO 1215
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 1215

Arg Ser His Pro Cys Cys His Tyr Leu Arg
1               5                   10

<210> SEQ ID NO 1216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1216

Arg Ser His Pro Cys Pro Leu Gly Leu Lys
1               5                   10

<210> SEQ ID NO 1217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1217

Arg Ser His Thr Cys Pro Pro Ser Leu Arg
1               5                   10

<210> SEQ ID NO 1218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1218

Arg Ser Leu Pro Arg Pro Leu His Leu Arg
1               5                   10

<210> SEQ ID NO 1219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1219

Arg Ser Arg Thr Cys Leu Leu Cys Leu
1               5

<210> SEQ ID NO 1220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1220

Arg Ser Arg Thr Cys Leu Leu Cys Leu Arg
1               5                   10
```

```
<210> SEQ ID NO 1221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1221

Arg Ser Arg Thr Cys Pro Pro Gly Leu
1               5

<210> SEQ ID NO 1222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1222

Arg Ser Arg Thr Cys Pro Pro Gly Leu Arg
1               5                   10

<210> SEQ ID NO 1223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1223

Arg Thr His Leu Leu Pro His His Arg Arg
1               5                   10

<210> SEQ ID NO 1224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1224

Arg Thr Arg Ser Cys Pro Cys Arg Trp Arg
1               5                   10

<210> SEQ ID NO 1225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1225

Arg Tyr Arg Ala Tyr Pro Pro Cys Leu
1               5

<210> SEQ ID NO 1226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1226

Arg Tyr Arg Ala Tyr Pro Pro Cys Leu Trp
1               5                   10

<210> SEQ ID NO 1227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1227

Ser Leu Gly Asn His Leu Cys Pro Leu
1               5

<210> SEQ ID NO 1228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1228

Ser Leu Pro Leu Gly Asn His Pro Tyr Leu
1               5                   10

<210> SEQ ID NO 1229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1229

Ser Leu Pro Arg Pro Leu His Leu Arg Leu
1               5                   10

<210> SEQ ID NO 1230
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1230

Ser Leu Arg Asn Cys Thr Cys Pro Pro Arg
1               5                   10

<210> SEQ ID NO 1231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1231

Ser Leu Arg Ser His Ala Tyr Ala Leu
1               5

<210> SEQ ID NO 1232
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1232

Ser Leu Arg Ser His Pro Cys Pro Leu
1               5

<210> SEQ ID NO 1233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1233

Ser Pro His His Leu Arg Thr Pro Pro
1               5

<210> SEQ ID NO 1234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1234

Ser Pro His His Leu Arg Thr Pro Pro His
1               5                   10

<210> SEQ ID NO 1235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1235

Ser Pro Leu Arg Ser Gln Ala Asn Ala Leu
1               5                   10

<210> SEQ ID NO 1236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1236

Tyr Leu Arg Arg Leu Arg Ser His Thr Cys
1               5                   10

<210> SEQ ID NO 1237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1237

Tyr Leu Arg Ser Arg Asn Ser Ala Pro
```

```
1               5
```

<210> SEQ ID NO 1238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1238

```
Tyr Leu Arg Ser Arg Asn Ser Ala Pro Gly
1               5                   10
```

<210> SEQ ID NO 1239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1239

```
Ala Leu Ala Pro Thr Leu Thr His Met
1               5
```

<210> SEQ ID NO 1240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1240

```
Ala Leu Ala Pro Thr Leu Thr His Met Leu
1               5                   10
```

<210> SEQ ID NO 1241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1241

```
Leu Leu Gln Val Thr Gln Thr Ser Phe Ala
1               5                   10
```

<210> SEQ ID NO 1242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1242

```
Leu Gln Val Thr Gln Thr Ser Phe Ala Leu
1               5                   10
```

<210> SEQ ID NO 1243
<211> LENGTH: 9
<212> TYPE: PRT
<213> ORGANISM: Artificial Sequence
<220> FEATURE:
<223> OTHER INFORMATION: Description of Artificial Sequence: Synthetic -continued

```
        peptide

<400> SEQUENCE: 1243

Arg Leu Trp His Leu Leu Leu Gln Val
1               5

<210> SEQ ID NO 1244
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 1244

Arg Leu Trp His Leu Leu Leu Gln Val Thr
1               5                   10

<210> SEQ ID NO 1245
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 1245

Cys Thr Gln Leu Ala Arg Phe Phe Pro Ile
1               5                   10

<210> SEQ ID NO 1246
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 1246

Phe Phe Pro Ile Thr Pro Pro Val Trp
1               5

<210> SEQ ID NO 1247
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 1247

Phe Pro Ile Thr Pro Pro Val Trp His Ile
1               5                   10

<210> SEQ ID NO 1248
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 1248

Gly Pro Arg Met Gln Leu Cys Thr Gln Leu
1               5                   10

<210> SEQ ID NO 1249
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1249

Ile Thr Pro Pro Val Trp His Ile Leu
1               5

<210> SEQ ID NO 1250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1250

Leu Ala Leu Gly Pro Arg Met Gln Leu
1               5

<210> SEQ ID NO 1251
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1251

Met Gln Leu Cys Thr Gln Leu Ala Arg Phe
1               5                   10

<210> SEQ ID NO 1252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1252

Arg Phe Phe Pro Ile Thr Pro Pro Val
1               5

<210> SEQ ID NO 1253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1253

Arg Phe Phe Pro Ile Thr Pro Pro Val Trp
1               5                   10

<210> SEQ ID NO 1254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1254
```

Arg Met Gln Leu Cys Thr Gln Leu Ala
1               5

<210> SEQ ID NO 1255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1255

Arg Met Gln Leu Cys Thr Gln Leu Ala Arg
1               5                   10

<210> SEQ ID NO 1256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1256

Ser Pro Pro Leu Ala Leu Gly Pro Arg Met
1               5                   10

<210> SEQ ID NO 1257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1257

Thr Gln Leu Ala Arg Phe Phe Pro Ile
1               5

<210> SEQ ID NO 1258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1258

Lys Ser Arg Gln Asn His Leu Gln Leu
1               5

<210> SEQ ID NO 1259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1259

Ala Leu Lys Lys Leu Arg Ser Pro Leu
1               5

<210> SEQ ID NO 1260
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 1260

His Leu Gln Leu Lys Ser Cys Arg Arg Lys
1               5                   10

<210> SEQ ID NO 1261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1261

Lys Ile Ser Asn Trp Ser Leu Lys Lys
1               5

<210> SEQ ID NO 1262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1262

Lys Ile Ser Asn Trp Ser Leu Lys Lys Val
1               5                   10

<210> SEQ ID NO 1263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1263

Lys Leu Arg Ser Pro Leu Trp Ile Phe
1               5

<210> SEQ ID NO 1264
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1264

Lys Ser Arg Gln Asn His Leu Gln Leu Lys
1               5                   10

<210> SEQ ID NO 1265
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1265

Asn Trp Ser Leu Lys Lys Val Pro Ala Leu
1               5                   10
```

```
<210> SEQ ID NO 1266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1266

Ser Leu Lys Lys Val Pro Ala Leu Lys
1               5

<210> SEQ ID NO 1267
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1267

Ser Leu Lys Lys Val Pro Ala Leu Lys Lys
1               5                   10

<210> SEQ ID NO 1268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1268

Ser Gln Lys Ser Arg Gln Asn His Leu
1               5

<210> SEQ ID NO 1269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1269

Trp Ser Leu Lys Lys Val Pro Ala Leu
1               5

<210> SEQ ID NO 1270
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1270

Trp Ser Leu Lys Lys Val Pro Ala Leu Lys
1               5                   10

<210> SEQ ID NO 1271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1271
```

```
Lys Leu Pro Glu Cys Gln Arg Leu Leu
1               5
```

<210> SEQ ID NO 1272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 1272

```
Lys Pro Thr Arg Ala Ala Thr Val Ser Val
1               5                   10
```

<210> SEQ ID NO 1273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 1273

```
Leu Pro Pro Trp Pro Leu His Gln Gln Leu
1               5                   10
```

<210> SEQ ID NO 1274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 1274

```
Leu Pro Arg Lys Pro Thr Arg Ala Ala
1               5
```

<210> SEQ ID NO 1275
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 1275

```
Leu Pro Arg Lys Pro Thr Arg Ala Ala Thr
1               5                   10
```

<210> SEQ ID NO 1276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 1276

```
Gln Gln Leu Leu His Arg Arg Pro Leu
1               5
```

<210> SEQ ID NO 1277
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1277

Arg Leu Leu Pro Pro Trp Pro Leu His
1               5

<210> SEQ ID NO 1278
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1278

Ala Pro Ala Ser Ala Pro Trp Pro Ser Thr
1               5                   10

<210> SEQ ID NO 1279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1279

Ala Pro Trp Pro Ser Thr Ser Ser His
1               5

<210> SEQ ID NO 1280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1280

Arg Pro Ala Pro Ala Ser Ala Pro Trp
1               5

<210> SEQ ID NO 1281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1281

Trp Pro Ser Thr Ser Ser His Ser Thr
1               5

<210> SEQ ID NO 1282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1282

Arg Val Gln Asn Gln Gly His Leu Leu
1               5
```

<210> SEQ ID NO 1283
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1283

Phe Leu Pro Ile Ser His Cys Gln Cys Ile
1               5                   10

<210> SEQ ID NO 1284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1284

Phe Trp Leu Thr Lys Leu Asn Tyr Leu
1               5

<210> SEQ ID NO 1285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1285

His Leu Ser Met Leu Thr Asp Ser Leu
1               5

<210> SEQ ID NO 1286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1286

His Thr Met Gly Phe Trp Leu Thr Lys
1               5

<210> SEQ ID NO 1287
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1287

His Thr Met Gly Phe Trp Leu Thr Lys Leu
1               5                   10

<210> SEQ ID NO 1288
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1288

Lys Leu Asn Tyr Leu Cys His Leu Ser Met
1               5                   10

<210> SEQ ID NO 1289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1289

Leu Pro Ile Ser His Cys Gln Cys Ile
1               5

<210> SEQ ID NO 1290
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1290

Leu Pro Ile Ser His Cys Gln Cys Ile Leu
1               5                   10

<210> SEQ ID NO 1291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1291

Leu Thr Asp Ser Leu Phe Leu Pro Ile
1               5

<210> SEQ ID NO 1292
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1292

Leu Thr Lys Leu Asn Tyr Leu Cys His Leu
1               5                   10

<210> SEQ ID NO 1293
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1293

Met Leu Thr Asp Ser Leu Phe Leu Pro Ile
1               5                   10

<210> SEQ ID NO 1294
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 1294

Met Gln Gly His Thr Met Gly Phe Trp Leu
1               5                   10

<210> SEQ ID NO 1295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1295

Asn Tyr Leu Cys His Leu Ser Met Leu
1               5

<210> SEQ ID NO 1296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1296

Ser Met Leu Thr Asp Ser Leu Phe Leu
1               5

<210> SEQ ID NO 1297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1297

Thr Met Gly Phe Trp Leu Thr Lys Leu
1               5

<210> SEQ ID NO 1298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1298

Tyr Leu Cys His Leu Ser Met Leu Thr
1               5

<210> SEQ ID NO 1299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1299

Ile Leu Asp Glu Ala Tyr Val Met Ala Tyr
1               5                   10
```

```
<210> SEQ ID NO 1300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1300

Val Met Ala Tyr Val Met Ala Gly Val
1               5

<210> SEQ ID NO 1301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1301

Tyr Val Met Ala Tyr Val Met Ala Gly
1               5

<210> SEQ ID NO 1302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1302

Tyr Val Met Ala Tyr Val Met Ala Gly Val
1               5                   10

<210> SEQ ID NO 1303
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1303

Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu
    50                  55                  60

<210> SEQ ID NO 1304
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1304

Lys Leu Val Val Val Gly Ala Cys Gly Val
1               5                   10
```

<210> SEQ ID NO 1305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1305

Leu Val Val Val Gly Ala Cys Gly Val
1               5

<210> SEQ ID NO 1306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1306

Val Val Gly Ala Cys Gly Val Gly Lys
1               5

<210> SEQ ID NO 1307
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1307

Val Val Val Gly Ala Cys Gly Val Gly Lys
1               5                   10

<210> SEQ ID NO 1308
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1308

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu
    50                  55                  60

<210> SEQ ID NO 1309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1309

Val Val Gly Ala Asp Gly Val Gly Lys
1               5

```
<210> SEQ ID NO 1310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1310

Val Val Val Gly Ala Asp Gly Val Gly Lys
1               5                   10

<210> SEQ ID NO 1311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1311

Lys Leu Val Val Val Gly Ala Asp Gly Val
1               5                   10

<210> SEQ ID NO 1312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1312

Leu Val Val Val Gly Ala Asp Gly Val
1               5

<210> SEQ ID NO 1313
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1313

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu
    50                  55                  60

<210> SEQ ID NO 1314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1314

Lys Leu Val Val Val Gly Ala Val Gly Val
1               5                   10
```

<210> SEQ ID NO 1315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1315

Leu Val Val Val Gly Ala Val Gly Val
1               5

<210> SEQ ID NO 1316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1316

Val Val Gly Ala Val Gly Val Gly Lys
1               5

<210> SEQ ID NO 1317
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1317

Val Val Val Gly Ala Val Gly Val Gly Lys
1               5                   10

<210> SEQ ID NO 1318
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1318

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly His Glu Glu Tyr Ser Ala Met Arg Asp Gln Tyr Met Arg Thr
    50                  55                  60

Gly Glu Gly Phe Leu Cys Val Phe Ala Ile Asn Asn Thr Lys Ser Phe
65                  70                  75                  80

Glu Asp Ile His His Tyr Arg Glu Gln Ile Lys Arg Val Lys Asp Ser
                85                  90                  95

Glu Asp Val Pro Met
            100

<210> SEQ ID NO 1319
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 1319

Ile Leu Asp Thr Ala Gly His Glu Glu Tyr
1               5                   10

<210> SEQ ID NO 1320
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1320

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly Leu Glu Glu Tyr Ser Ala Met Arg Asp Gln Tyr Met Arg Thr
    50                  55                  60

Gly Glu Gly Phe Leu Cys Val Phe Ala Ile Asn Asn Thr Lys Ser Phe
65                  70                  75                  80

Glu Asp Ile His His Tyr Arg Glu Gln Ile Lys Arg Val Lys Asp Ser
                85                  90                  95

Glu Asp Val Pro Met
            100

<210> SEQ ID NO 1321
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1321

Ile Leu Asp Thr Ala Gly Leu Glu Glu Tyr
1               5                   10

<210> SEQ ID NO 1322
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1322

Leu Leu Asp Ile Leu Asp Thr Ala Gly Leu
1               5                   10

<210> SEQ ID NO 1323
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 1323

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly Lys Glu Glu Tyr Ser Ala Met Arg Asp Gln Tyr Met Arg Thr
50                  55                  60

Gly Glu Gly Phe Leu Cys Val Phe Ala Ile Asn Asn Ser Lys Ser Phe
65                  70                  75                  80

Ala Asp Ile Asn Leu Tyr Arg Glu Gln Ile Lys Arg Val Lys Asp Ser
                85                  90                  95

Asp Asp Val Pro Met
            100

<210> SEQ ID NO 1324
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1324

Ile Leu Asp Thr Ala Gly Lys Glu Glu Tyr
1               5                   10

<210> SEQ ID NO 1325
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1325

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly Arg Glu Glu Tyr Ser Ala Met Arg Asp Gln Tyr Met Arg Thr
50                  55                  60

Gly Glu Gly Phe Leu Cys Val Phe Ala Ile Asn Asn Ser Lys Ser Phe
65                  70                  75                  80

Ala Asp Ile Asn Leu Tyr Arg Glu Gln Ile Lys Arg Val Lys Asp Ser
                85                  90                  95

Asp Asp Val Pro Met
            100

<210> SEQ ID NO 1326
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1326
```

```
Ile Leu Asp Thr Ala Gly Arg Glu Glu Tyr
1               5                  10
```

<210> SEQ ID NO 1327
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1327

```
Met Ala Leu Asn Ser Glu Ala Leu Ser Val Val Ser Glu Asp Gln Ser
1               5                   10                  15

Leu Phe Glu Cys Ala Tyr Gly Thr Pro His Leu Ala Lys Thr Glu Met
            20                  25                  30

Thr Ala Ser Ser Ser Ser Asp Tyr Gly Gln Thr Ser Lys Met Ser Pro
        35                  40                  45

Arg Val Pro Gln Gln Asp Trp Ala Leu Asn Ser Glu Ala Leu Ser Val
    50                  55                  60
```

<210> SEQ ID NO 1328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1328

```
Ala Leu Asn Ser Glu Ala Leu Ser Val Val
1               5                   10
```

<210> SEQ ID NO 1329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1329

```
Met Ala Leu Asn Ser Glu Ala Leu Ser Val
1               5                   10
```

<210> SEQ ID NO 1330
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1330

```
Met Ala Leu Asn Ser Glu Ala Leu Ser Val Val Ser Glu Asp Gln Ser
1               5                   10                  15

Leu Phe Glu Cys Ala Tyr Gly Thr Pro His Leu Ala Lys Thr Glu Met
            20                  25                  30

Thr Ala Ser Ser Ser Ser Asp Tyr Gly Gln Thr Ser Lys Met Ser Pro
        35                  40                  45

Arg Val Pro Gln Gln Asp Trp Ala Leu Asn Ser Glu Ala Leu Ser Val
    50                  55                  60
```

```
<210> SEQ ID NO 1331
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1331

Ala Leu Asn Ser Glu Ala Leu Ser Val Val
1               5                   10

<210> SEQ ID NO 1332
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1332

Met Ala Leu Asn Ser Glu Ala Leu Ser Val
1               5                   10

<210> SEQ ID NO 1333
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1333

Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu
    50                  55                  60

<210> SEQ ID NO 1334
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1334

Lys Leu Val Val Val Gly Ala Cys Gly Val
1               5                   10

<210> SEQ ID NO 1335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1335

Leu Val Val Val Gly Ala Cys Gly Val
1               5
```

```
<210> SEQ ID NO 1336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1336

Val Val Gly Ala Cys Gly Val Gly Lys
1               5

<210> SEQ ID NO 1337
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1337

Val Val Val Gly Ala Cys Gly Val Gly Lys
1               5                   10

<210> SEQ ID NO 1338
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1338

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Val Val
    50                  55                  60

Gly Ala Asp Gly Val Gly Lys
65                  70

<210> SEQ ID NO 1339
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1339

Val Val Val Gly Ala Asp Gly Val Gly Lys
1               5                   10

<210> SEQ ID NO 1340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1340

Lys Leu Val Val Val Gly Ala Asp Gly Val
```

```
<210> SEQ ID NO 1341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1341

Leu Val Val Val Gly Ala Asp Gly Val
1               5

<210> SEQ ID NO 1342
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1342

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Ile Asp Gly
        35                  40                  45

Glu Thr Cys Leu Leu Asp Ile Leu Asp Thr Ala Gly Gln Glu
    50                  55                  60

<210> SEQ ID NO 1343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1343

Lys Leu Val Val Val Gly Ala Val Gly Val
1               5                   10

<210> SEQ ID NO 1344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1344

Leu Val Val Val Gly Ala Val Gly Val
1               5

<210> SEQ ID NO 1345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1345

Val Val Gly Ala Val Gly Val Gly Lys
```

```
1               5

<210> SEQ ID NO 1346
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1346

Val Val Val Gly Ala Val Gly Val Gly Lys
1               5                   10

<210> SEQ ID NO 1347
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1347

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly His Glu Glu Tyr Ser Ala Met Arg Asp Gln Tyr Met Arg Thr
    50                  55                  60

Gly Glu Gly Phe Leu Cys Val Phe Ala Ile Asn Asn Thr Lys Ser Phe
65                  70                  75                  80

Glu Asp Ile His His Tyr Arg Glu Gln Ile Lys Arg Val Lys Asp Ser
                85                  90                  95

Glu Asp Val Pro Met
            100

<210> SEQ ID NO 1348
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1348

Ile Leu Asp Thr Ala Gly His Glu Glu Tyr
1               5                   10

<210> SEQ ID NO 1349
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1349

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30
```

-continued

Gln Val Val Ile Asp Gly Glu Thr Cys Leu Leu Asp Ile Leu Asp Thr
            35                  40                  45

Ala Gly Leu Glu Glu Tyr Ser Ala Met Arg Asp Gln Tyr Met Arg Thr
 50                      55                  60

Gly Glu Gly Phe Leu Cys Val Phe Ala Ile Asn Asn Thr Lys Ser Phe
 65                  70                  75                  80

Glu Asp Ile His His Tyr Arg Glu Gln Ile Lys Arg Val Lys Asp Ser
                85                  90                  95

Glu Asp Val Pro Met
            100

<210> SEQ ID NO 1350
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1350

Ile Leu Asp Thr Ala Gly Leu Glu Glu Tyr
1               5                   10

<210> SEQ ID NO 1351
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1351

Leu Leu Asp Ile Leu Asp Thr Ala Gly Leu
1               5                   10

<210> SEQ ID NO 1352
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1352

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
            35                  40                  45

Ala Gly Lys Glu Glu Tyr Ser Ala Met Arg Asp Gln Tyr Met Arg Thr
 50                      55                  60

Gly Glu Gly Phe Leu Cys Val Phe Ala Ile Asn Asn Ser Lys Ser Phe
 65                  70                  75                  80

Ala Asp Ile Asn Leu Tyr Arg Glu Gln Ile Lys Arg Val Lys Asp Ser
                85                  90                  95

Asp Asp Val Pro Met
            100

<210> SEQ ID NO 1353
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 1353

Ile Leu Asp Thr Ala Gly Lys Glu Glu Tyr
1               5                   10

<210> SEQ ID NO 1354
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1354

Ala Gly Gly Val Gly Lys Ser Ala Leu Thr Ile Gln Leu Ile Gln Asn
1               5                   10                  15

His Phe Val Asp Glu Tyr Asp Pro Thr Ile Glu Asp Ser Tyr Arg Lys
            20                  25                  30

Gln Val Val Ile Asp Gly Glu Thr Cys Leu Leu Asp Ile Leu Asp Thr
        35                  40                  45

Ala Gly Arg Glu Glu Tyr Ser Ala Met Arg Asp Gln Tyr Met Arg Thr
    50                  55                  60

Gly Glu Gly Phe Leu Cys Val Phe Ala Ile Asn Asn Ser Lys Ser Phe
65                  70                  75                  80

Ala Asp Ile Asn Leu Tyr Arg Glu Gln Ile Lys Arg Val Lys Asp Ser
                85                  90                  95

Asp Asp Val Pro Met
            100

<210> SEQ ID NO 1355
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1355

Ile Leu Asp Thr Ala Gly Arg Glu Glu Tyr
1               5                   10

<210> SEQ ID NO 1356
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1356

His His His His His His
1               5

<210> SEQ ID NO 1357
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1357

Ala Val Gly Ile Thr Tyr Thr Trp Thr Arg Leu Tyr Ala Ser Val Leu
1               5                   10                  15

Thr Gly Ser Leu Val Ser Lys Thr Lys Lys
            20                  25

<210> SEQ ID NO 1358
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1358

Ile Gln Lys Ile Ser Phe Phe Asp Gly Phe Glu Val Gly Phe Asn Phe
1               5                   10                  15

Arg Thr Leu Gln Pro Asn Gly Leu Leu Phe Tyr Tyr Thr
            20                  25

<210> SEQ ID NO 1359
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1359

Gly Ile Pro Val His Leu Glu Leu Ala Ser Met Thr Asn Met Glu Leu
1               5                   10                  15

Met Ser Ser Ile Val His Gln Gln Val Phe Pro Thr
            20                  25

<210> SEQ ID NO 1360
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1360

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg
            20                  25

<210> SEQ ID NO 1361
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1361

Lys Ala Arg Asp Glu Thr Ala Ala Leu Leu Asn Ser Ala Val Leu Gly
1               5                   10                  15

Ala Ala Pro Leu Phe Val Pro Pro Ala Asp
            20                  25

<210> SEQ ID NO 1362
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1362

Arg Glu Gly Val Glu Leu Cys Pro Gly Asn Lys Tyr Glu Met Arg Arg
1               5                   10                  15
His Gly Thr Thr His Ser Leu Val Ile His Asp
            20                  25

<210> SEQ ID NO 1363
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1363

Ile Thr Tyr Thr Trp Thr Arg Leu
1               5

<210> SEQ ID NO 1364
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1364

Val Gly Phe Asn Phe Arg Thr Leu
1               5

<210> SEQ ID NO 1365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1365

Ala Ser Met Thr Asn Met Glu Leu Met
1               5

<210> SEQ ID NO 1366
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1366

Ala Gln Leu Ala Asn Asp Val Val Leu
1               5

<210> SEQ ID NO 1367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
-continued

<400> SEQUENCE: 1367

Ala Ala Leu Leu Asn Ser Ala Val Leu
1               5

<210> SEQ ID NO 1368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1368

Leu Cys Pro Gly Asn Lys Tyr Glu Met
1               5
```

NEOANTIGENS AND USES THEREOF

CROSS-REFERENCE

This application claims the benefit of U.S. Provisional Application No. 62/607,148, filed Dec. 18, 2017; which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 10, 2019, is named 50401-721_601_SL.txt and is 452,220 bytes in size.

BACKGROUND

Cancer immunotherapy is the use of the immune system to treat cancer. Immunotherapies exploit the fact that cancer cells often have molecules on their surface that can be detected by the immune system, known as tumor antigens, which are often proteins or other macromolecules (e.g. carbohydrates). Active immunotherapy directs the immune system to attack tumor cells by targeting tumor antigens. Passive immunotherapies enhance existing anti-tumor responses and include the use of monoclonal antibodies, lymphocytes and cytokines. Tumor vaccines are typically composed of tumor antigens and immunostimulatory molecules (e.g., adjuvants, cytokines or TLR ligands) that work together to induce antigen-specific cytotoxic T cells (CTLs) that recognize and lyse tumor cells. One of the critical barriers to developing curative and tumor-specific immunotherapy is the identification and selection of highly specific and restricted tumor antigens to avoid autoimmunity.

Tumor neoantigens, which arise as a result of genetic change (e.g., inversions, translocations, deletions, missense mutations, splice site mutations, etc.) within malignant cells, represent the most tumor-specific class of antigens and can be patient-specific or shared. Tumor neoantigens are unique to the tumor cell as the mutation and its corresponding protein are present only in the tumor. They also avoid central tolerance and are therefore more likely to be immunogenic. Therefore, tumor neoantigens provide an excellent target for immune recognition including by both humoral and cellular immunity. However, tumor neoantigens have rarely been used in cancer vaccine or immunogenic compositions due to technical difficulties in identifying them, selecting optimized antigens, and producing neoantigens for use in a vaccine or immunogenic composition. Accordingly, there is still a need for developing additional cancer therapeutics.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

In some aspects provided herein is a composition comprising: (a) a first peptide comprising a first neoepitope of a region of a protein and a second peptide comprising a second neoepitope of the region of the same protein, (b) a polynucleotide encoding the first peptide and the second peptide, (c) one or more antigen presenting cells (APCs) comprising the first peptide and the second peptide, or (d) a first T cell receptor (TCR) specific for the first neoepitope in complex with an HLA protein and a second TCR specific for the second neoepitope in complex with an HLA protein, wherein the first peptide is different from the second peptide, and wherein the first neoepitope comprises a mutation and the second neoepitope comprises the same mutation.

In some embodiments, the first peptide is at least one amino acid in length longer than the second peptide, and the second peptide is at most 13 amino acids in length. In some embodiments, the second neoepitope is comprised within the first neoepitope. In some embodiments, the first peptide comprises a sequence of at least 9 or 10 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99 identity to a corresponding wild-type sequence. In some embodiments, the second peptide comprises a sequence of at least 8 or 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99 identity to a corresponding wild-type sequence.

In some embodiments, the first neoepitope binds to a class I HLA protein to form a class I HLA-peptide complex or the first neoepitope binds to a class II HLA protein to form a class II HLA-peptide complex. In some embodiments, the second neoepitope binds to a class II HLA protein to form a class II HLA-peptide complex or the second neoepitope binds to a class I HLA protein to form a class I HLA-peptide complex. In some embodiments, the first neoepitope is a first neoepitope peptide processed from the first peptide by an APC and the second neoepitope is a second neoepitope peptide that is not processed from the second peptide by an APC.

In some embodiments, the first neoepitope is shorter in length than the first peptide and the second neoepitope is the same length as the second peptide. In some embodiments, the second neoepitope activates CD8+ T cells. In some embodiments, the first neoepitope and the second neoepitope activates CD8+T cells. In some embodiments, the second neoepitope activates CD4+ T cells. In some embodiments, the mutation is selected from the group consisting of a point mutation, a splice-site mutation, a frameshift mutation, a read-through mutation, a gene fusion mutation, an indel and any combination thereof. In some embodiments, the first neoepitope and the second neoepitope comprises a sequence encoded by a gene of Table 1 or 2. In some embodiments, the protein is encoded by a gene of Table 1 or 2. In some embodiments, the mutation is a mutation of column 2 of Table 1 or 2. In some embodiments, the protein is a TMRS22::ERG protein, a RAS protein, a BTK protein, an EGFR protein, or a GATA3 protein.

In some aspects, provided herein is a pharmaceutical composition comprising: (a) a composition described herein; and (b) pharmaceutically acceptable excipient.

In some aspects, provided herein is a method of treating cancer, preventing resistance to a cancer therapy or inducing an immune response, the method comprising administering to a subject in need thereof the pharmaceutical composition according to aspects described above.

In some aspects, provided herein is a method of treating cancer, preventing cancer, preventing resistance to a cancer therapy or inducing an immune response, the method comprising: (a) administering to the subject at least one dose of a first immunogenic composition a first peptide comprising a first neoepitope of a region of a protein; and (b) sequentially administering to the subject at least one dose of a second immunogenic composition comprising a second peptide comprising a second neoepitope of the region of the same protein, wherein the first peptide is at least one amino acid in length longer than the second peptide, and the second peptide is at most 13 amino acids in length.

In some embodiments, the method comprises inducing an enhanced immune response than that achieved by administering one or more doses of the first immunogenic composition or one or more doses of the second immunogenic compositions alone, thereby treating the cancer, preventing the cancer or preventing resistance to cancer therapy. In some embodiments, the method comprises inducing an enhanced immune response than that achieved by administering two or more doses of the first immunogenic composition or two or more doses of the second immunogenic compositions alone, thereby treating the cancer, preventing the cancer or preventing resistance to cancer therapy. In some embodiments, the enhanced immune response comprises increase in level of CD8+ T cells.

In some embodiments, a TCR of a CD8+ T cell binds to a class I HLA-peptide complex comprising the first peptide or the second peptide. In some embodiments, a TCR of a CD8+ T cell binds to a class II HLA-peptide complex comprising the first peptide or the second peptide. In some embodiments, the enhanced immune response comprises increase in level of CD4+ T cells. In some embodiments, a TCR of a CD4+ cell binds to a class I HLA-peptide complex comprising the first peptide or the second peptide. In some embodiments, a TCR of a CD4+ T cell binds to a class II HLA-peptide complex comprising the first peptide or the second peptide.

In some embodiments, the CD8+ T cells are effector memory T cells. In some embodiments, the CD4+ T cells are effector memory T cells. In some embodiments, the enhanced immune response comprises sustaining the immune response for a longer duration than that achieved by administering one or more doses of the first immunogenic composition or one or more doses of the second immunogenic composition alone.

In some embodiments, the enhanced immune response is sustained for at least one day, 2 days, 5 days, 10 days, 20 days, 1 month, 2 months, 3 months, 6 months, or 1 year. In some embodiments, the first immunogenic composition further comprises the second peptide. In some embodiments, the second immunogenic composition further comprises the first peptide. In some embodiments, the first neoepitope and the second neoepitope comprises the same mutation. In some embodiments, the first neoepitope and the second neoepitope comprise at least one amino acid of the region that is the same.

In some embodiments, the second peptide has a length of at least 8, 9; 10; 11; or 12 amino acids. In some embodiments, the first peptide has a length of at least 9 amino acids. In some embodiments, the second peptide comprises a sequence of at least 8 or 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99 identity to a corresponding wild-type sequence.

In some embodiments, the first peptide comprises a sequence of at least 9 or 10 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99 identity to a corresponding wild-type sequence. In some embodiments, the first neoepitope is longer than the second neoepitope. In some embodiments, the second neoepitope has a length of from 8 to 13 amino acids. In some embodiments, the first neoepitope has a length of from 9 to 25 amino acids.

In some embodiments, the sequential administering of step (b) is done at least 1, 2, 3, 4, 5, 6, 7, 8, 9, 10, 14, 21, 25, 50, 100, or 200 days after step (a). In some embodiments, the method further comprises administering 1, 2, 3, 4, or 5 doses of the second immunogenic composition. In some embodiments, a dose of the second immunogenic composition is lower than a dose of the first immunogenic composition.

In some embodiments, the treatment comprises reduction of tumor growth, tumor volume, number of metastases, tumor reoccurrence, or combination thereof to a level greater than that achieved by administering one or more doses of the first immunogenic composition or one or more doses of the second immunogenic composition alone. In some embodiments, the treatment comprises enhanced survival of the subject to a level greater than that achieved by administering one or more doses of the first immunogenic composition or one or more doses of the second immunogenic composition alone.

In some aspects, provided herein is a method for inducing an enhanced immune response in a subject suffering from cancer or is at risk of cancer, the method comprising, administering to the subject at least one dose of a second immunogenic composition comprising a second peptide comprising a second neoepitope of a protein, wherein the subject has been previously administered at least one dose of a first immunogenic composition comprising a first peptide comprising a first neoepitope of the same protein, wherein the second peptide has a length of at most 13 amino acids, and wherein the first peptide is at least one amino acid in length longer than the second peptide.

BRIEF DESCRIPTION OF THE DRAWINGS

The features of the present disclosure are set forth with particularity in the appended claims. A better understanding of the features and advantages of the present will be obtained by reference to the following detailed description that sets forth illustrative embodiments, in which the principles of the disclosure are utilized, and the accompanying drawings of which:

FIG. 4A shows graph of splenocytes assayed by ELISpot assay for reactivity to pool of antigens Alg8, Adpgk, Irgq. FIG. 4B shows graph of splenocytes assayed by ELISpot assay for reactivity to pool of antigens; Lama4, Reps1, and Obsl1. The administration of the prime and boost dose was done according to regimen depicted in FIG. 3

FIG. 8A shows representative flow cytometry gating and FIG. 8B shows a graph of % of CD8 T cells.

FIG. 9A shows a graph of % of CD8 T cells that are not antigen specific. FIG. 9B shows a graph of % of CD8 T cells that are antigen specific.

FIG. 12A depicts TCR avidities observed after longmer Alg8 vaccination. FIG. 12B depicts TCR avidities observed after shortmer Alg8 vaccination.

FIGS. 14A-14C depict use of shortmers in prime and boost increases immunogenicity of Alg8.

FIGS. 15A-15C show inclusion of shortmers in day 21 boost increase % Lama4 Multimer+ cells.

FIGS. 20A-20B shows a graph of splenocytes assayed for reactivity to Kif18B (FIG. 20A) and Plod1 (FIG. 20B) using an ELISpot Assay.

FIGS. 24A-24D show a graphs of splenocytes assayed using an ELISpot Assay for reactivity to Alg8, Adpgk, Irgq longmer pool (FIG. 24A), Alg8, Adpgk, Irgq shortmer pool (FIG. 24B), Lama4, Reps1, Obsl1 longer pool (FIG. 24C), and Lama4, Reps1, Obsl1 shortmer pool (FIG. 24D).

FIGS. 27A-27E shows tumor volume measurements in untreated mice (FIG. 27A), mice treated with irrelevant peptide (FIG. 27B), prime and boost of longmers (FIG. 27C), prime and boost of shortmers (FIG. 27D), or prime and boost of longmers and shortmers (FIG. 27E). The administration of prime and boost dose are done as depicted in FIG. 25. The graph indicates administration of longmer at prime and boost increases number of tumor free mice.

FIGS. 29A-29C show immunizing with longmers at prime and boost result in increased frequencies of CD8 T cells specific for Reps1 (FIG. 29A), Irgq (FIG. 29B), and Adpgk (FIG. 29C). The administration regimen followed is depicted in FIG. 25.

FIGS. 34B-34E depicts measurements of tumor volume in untreated mice (FIG. 34B), mice administered with prime dose and boost of longmers (FIG. 34C), administered with prime dose and boost of shortmers (FIG. 34D), or administered with prime dose of longmers and boost of longmers and shortmers (FIG. 34E) according to regimen described in FIG. 34A. A prime dose is administered on day (−21) relative to implantation of tumor cells (day 0). A first boost dose is administered on day (−14) and second boost dose is administered on day (−7) relative to implantation of tumor cells on day 0. FIGS. 34B-34E indicate addition of shortmers at boost lead to higher number of tumor free subjects.

FIG. 35A depict T cell response in mice administered with a prime and boost of longmers according to regimen of FIG. 34A and corresponding changes in tumor volume. FIG. 35B depicts T cell responses in mice administered with a prime and boost of shortmers according to regimen of FIG. 34A and corresponding changes in tumor volume. FIG. 35C depicts T cell responses in mice administered with a prime dose of longmers and boost of longmers and shortmers according to regimen of FIG. 34A and corresponding changes in tumor volume.

DETAILED DESCRIPTION

Figure 1:
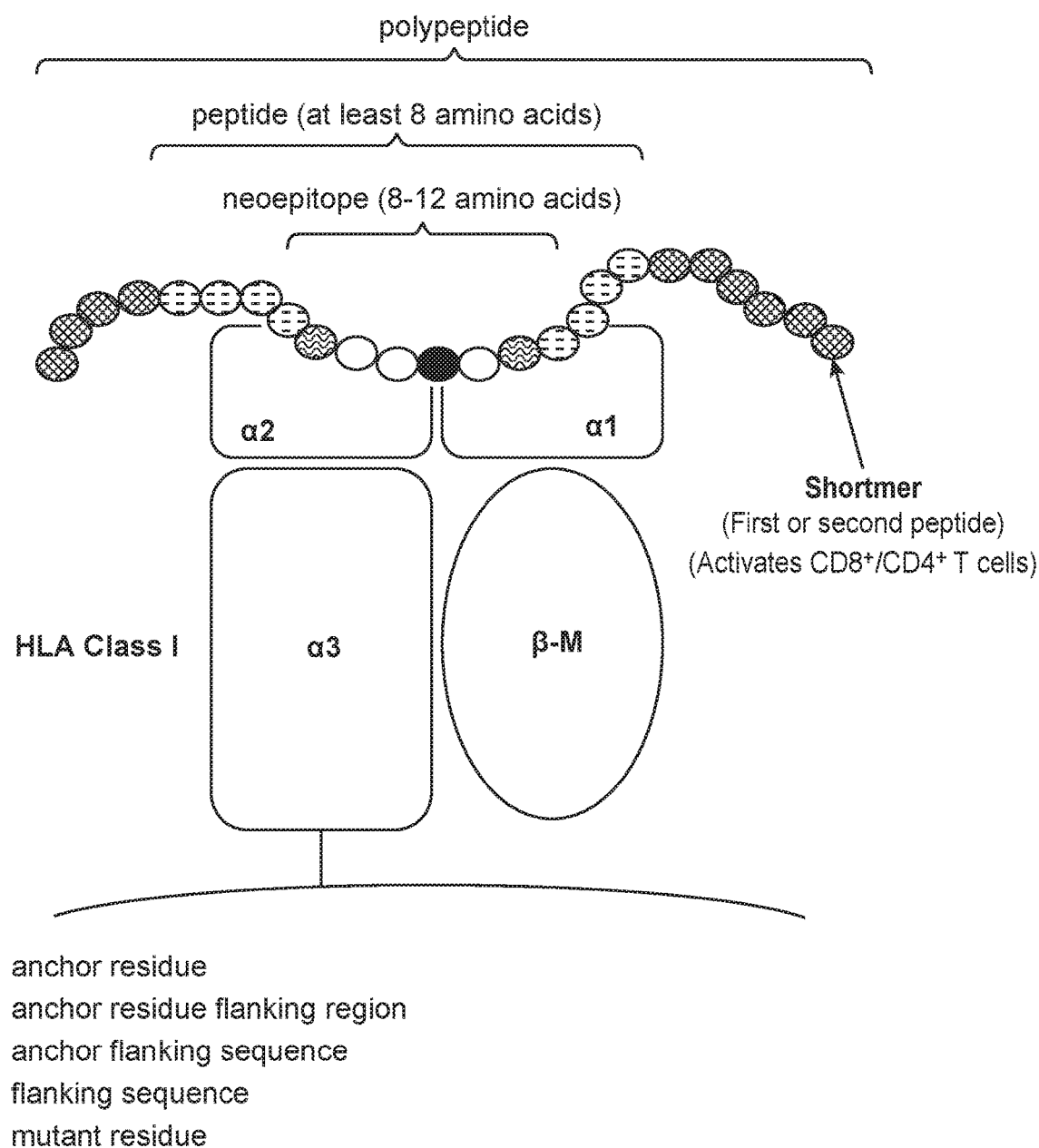
FIG. 1 illustrates a first peptide comprising a first neoepitope in HLA class I peptide binding groove. Anchor residues in the first neoepitope bind to the allele specific pockets of the HLA class I molecule.
Figure 2:
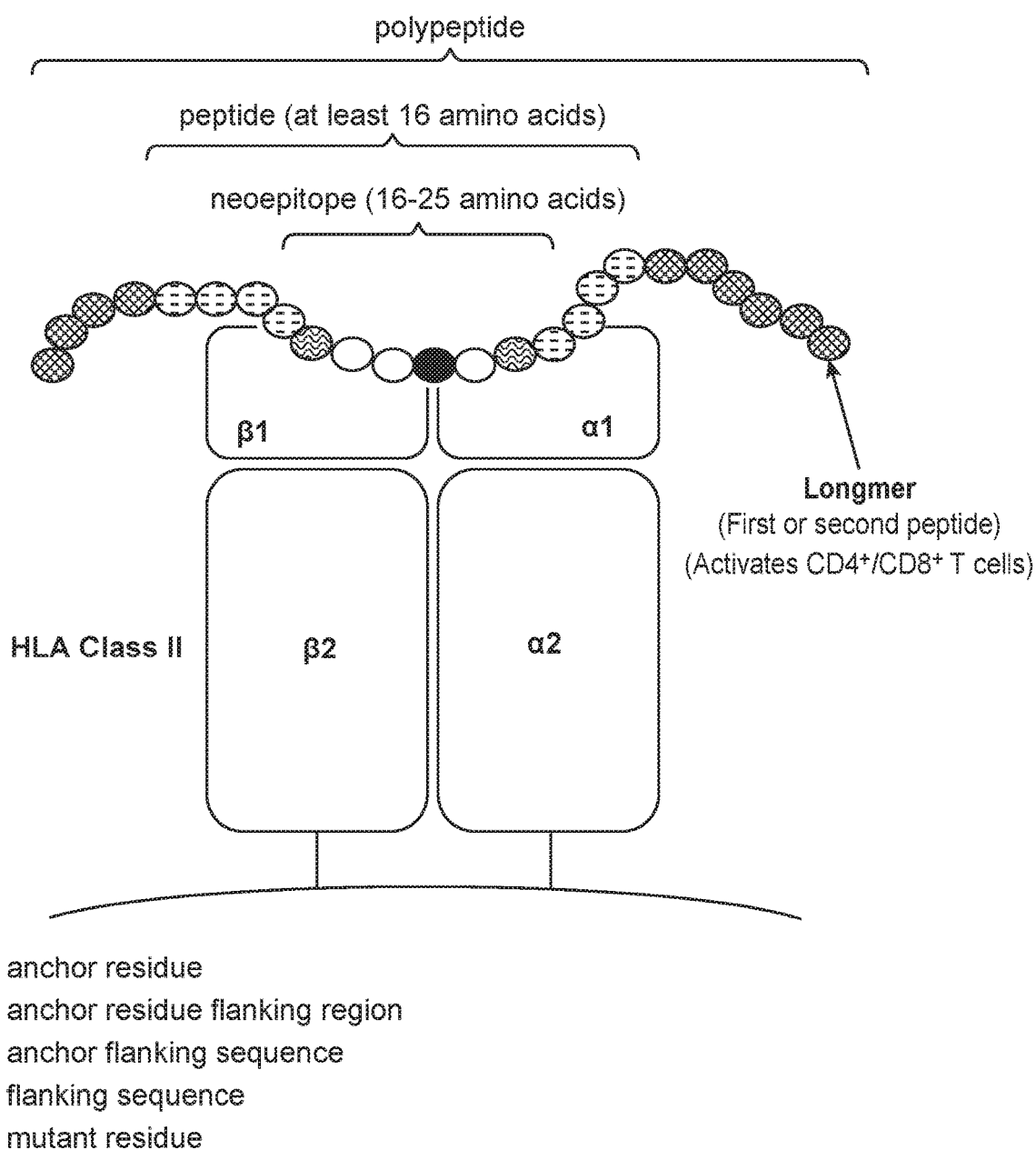
FIG. 2 illustrates a second peptide comprising a second neoepitope in HLA class II peptide binding groove. Anchor residues in the second neoepitope bind to the allele specific pockets of the HLA class II molecule.
Figure 3:
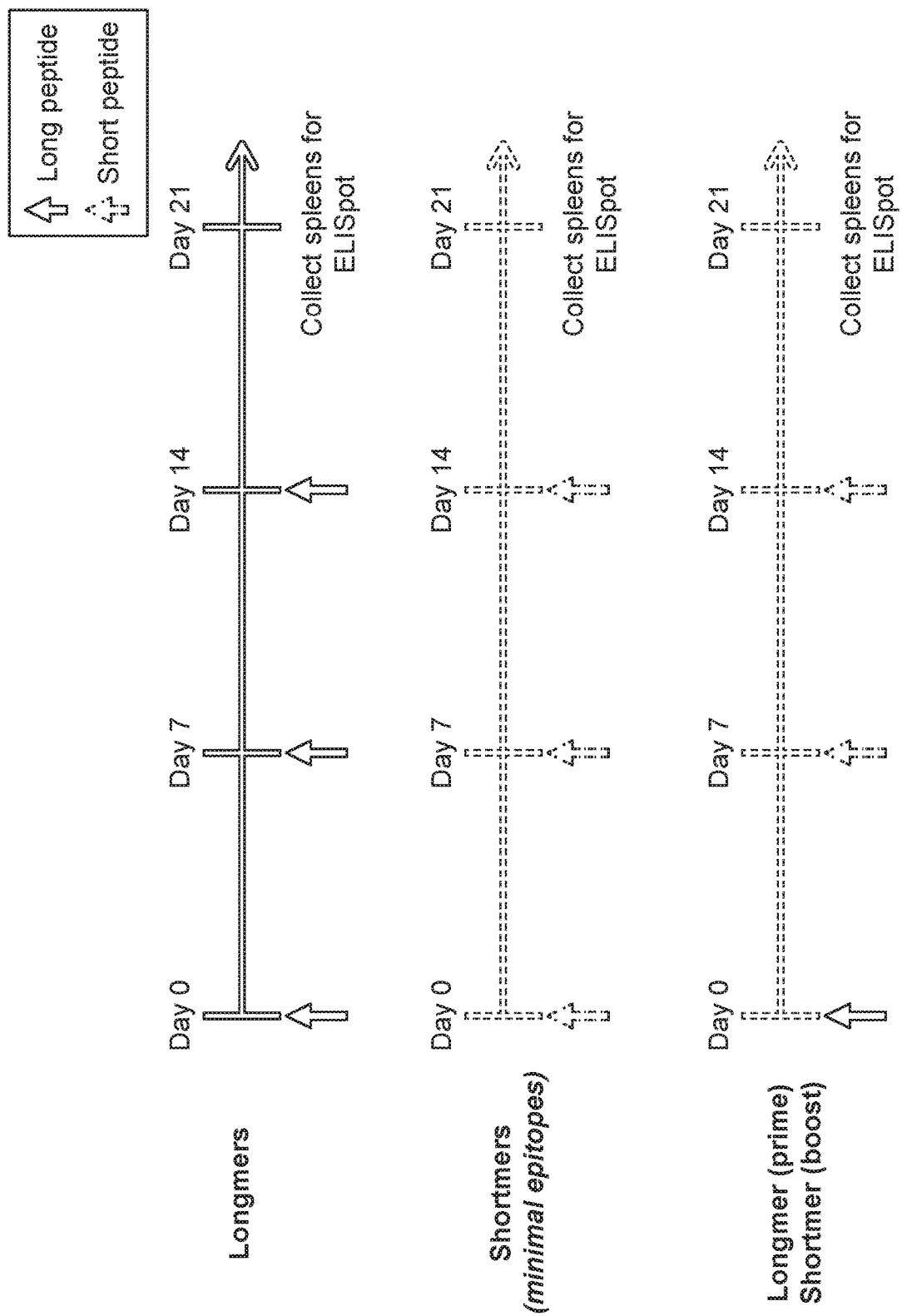
FIG. 3 illustrates exemplary administration regimen for peptides comprising neoepitopes. The top panel depicts administering a prime dose and boost of longmer. The middle panel depicts administering a prime dose and boost of shortmer. The lower panel depicts administering a prime dose of longmer and boost of shortmer. The boost dose is administered on day 7, 14, and day 21 after the prime dose.
Figure 4A:
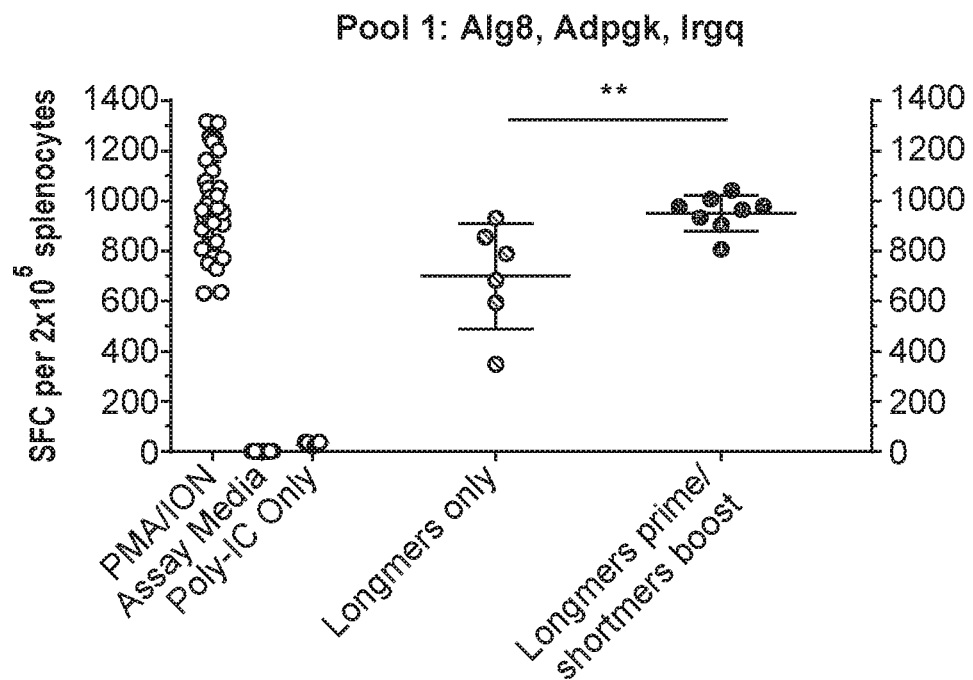
FIGS. 4A-4B show boosting with short peptides elicits higher T cell responses upon recall.
Figure 4B:
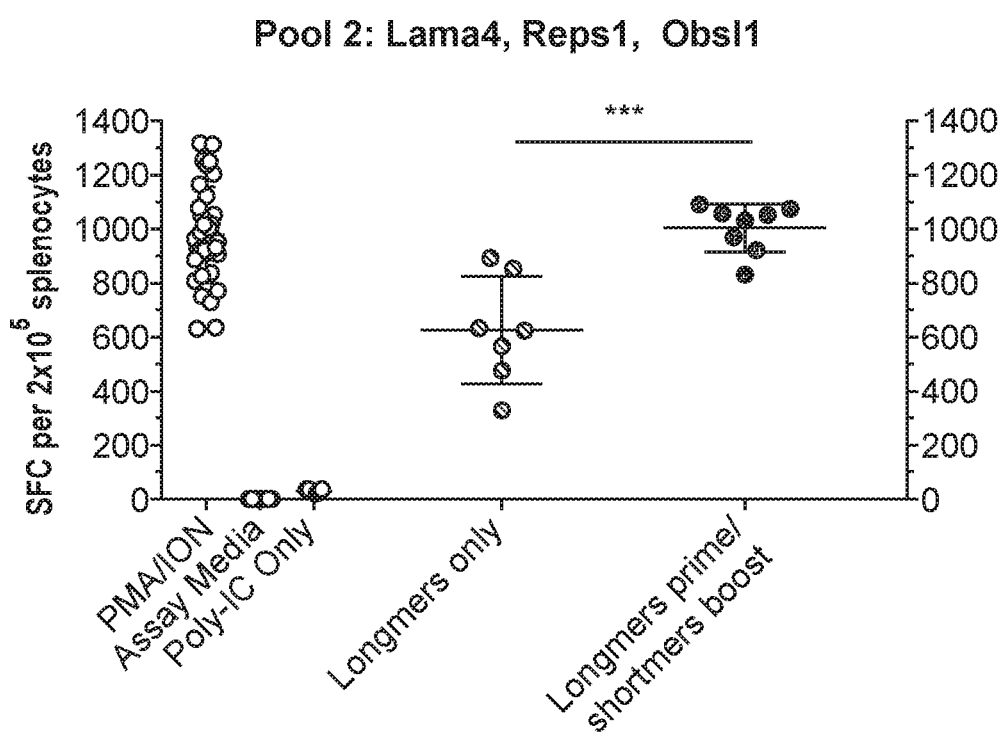
Figure 5B:
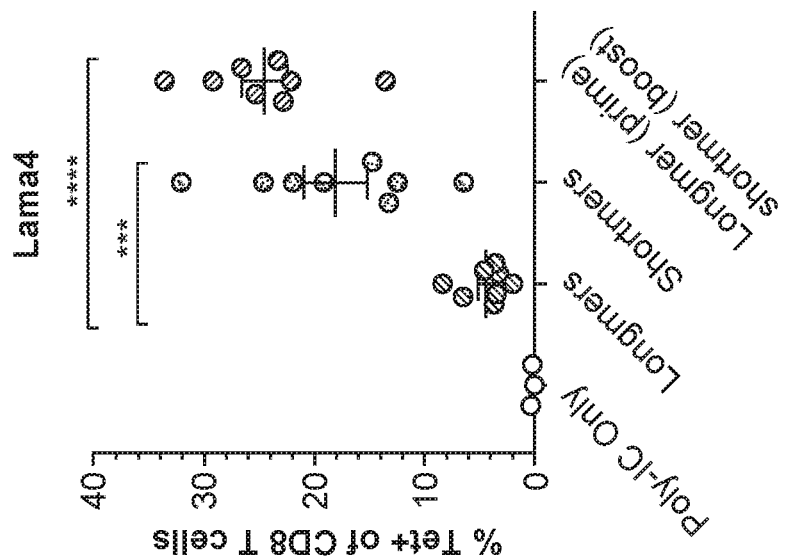
FIGS. 5A-5F show antigen specific T cell frequency after treatment according to regimen shown in FIG. 3. ** indicates p<0.0001, and * indicates p 0.0005. The plots show frequency of T cells specific for antigens; Alg8 (FIG. 5A), Lama4 (FIG. 5B), Adpgk (FIG. 5C), Reps1 (FIG. 5D), Irgq (FIG. 5E), and Obsl1 (FIG. 5F).
Figure 5A:
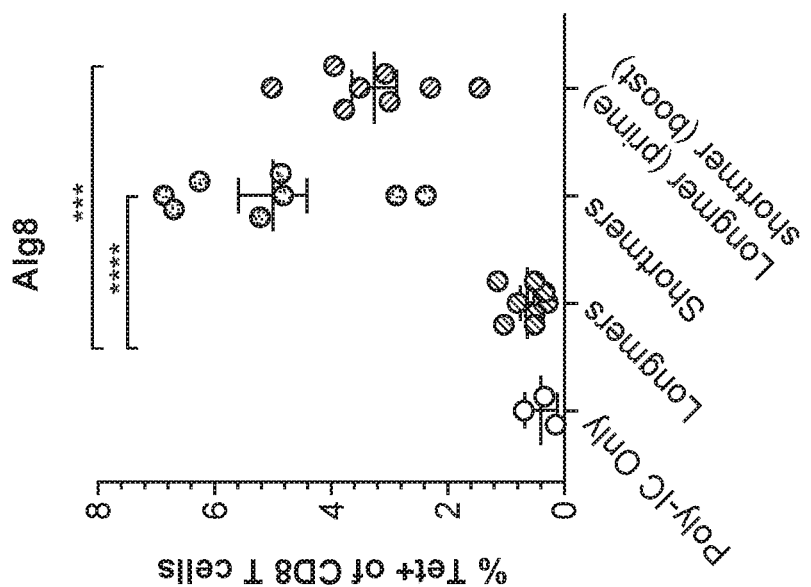
Figure 5C:
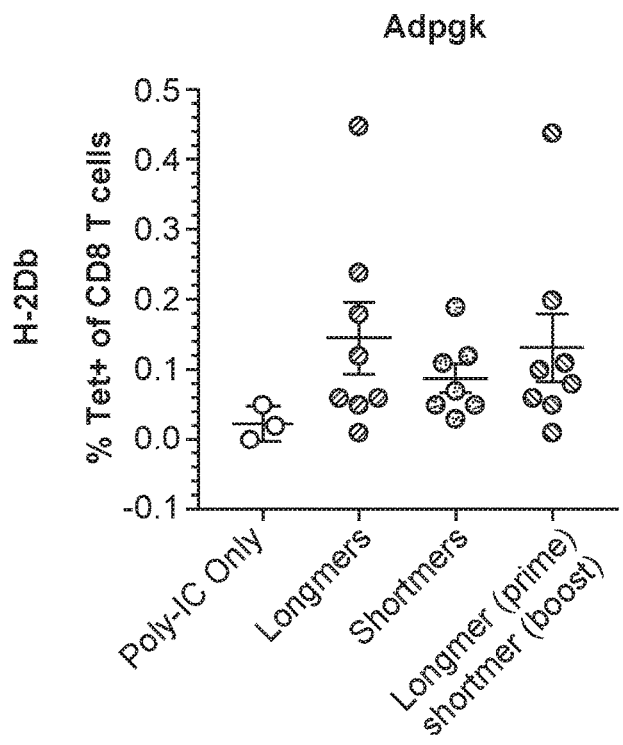
Figure 5D:
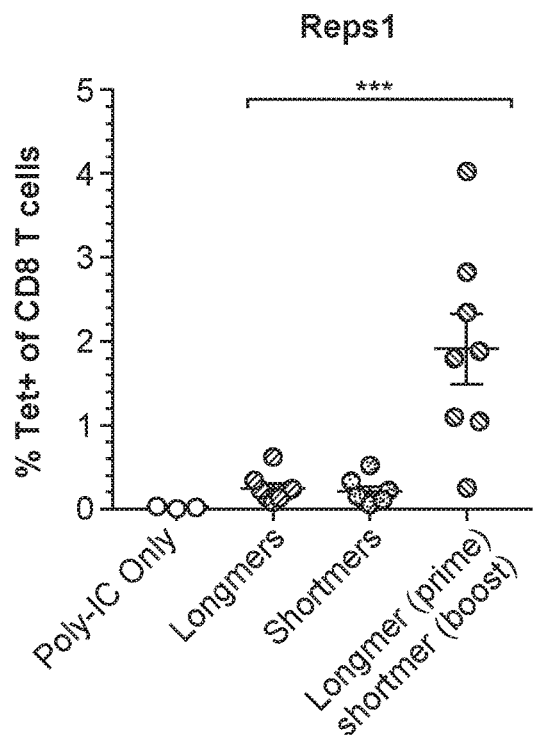
Figure 5E:
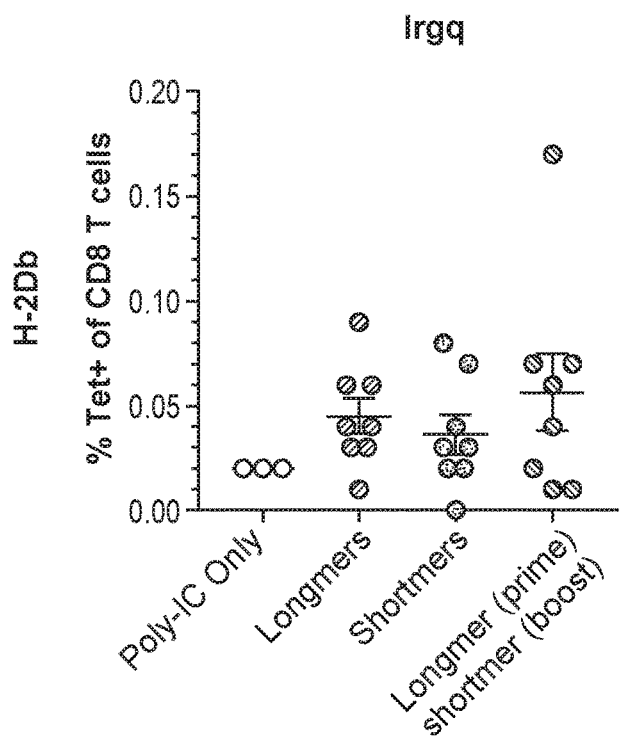
Figure 5F:
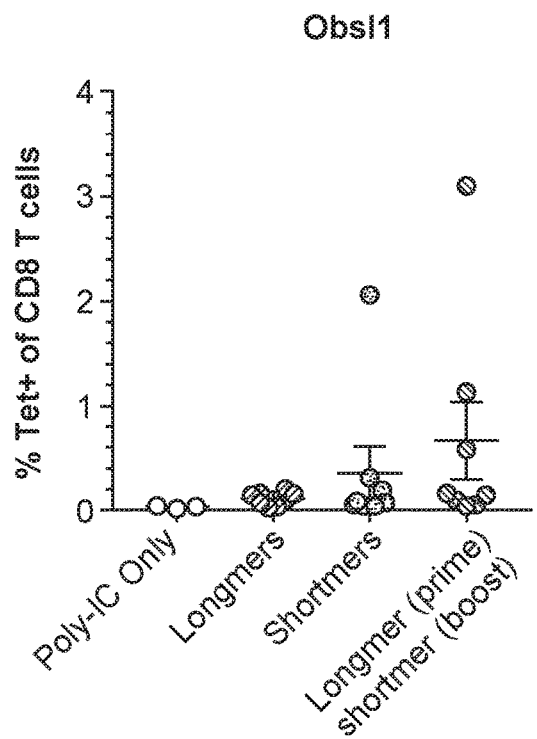
Figure 6C:
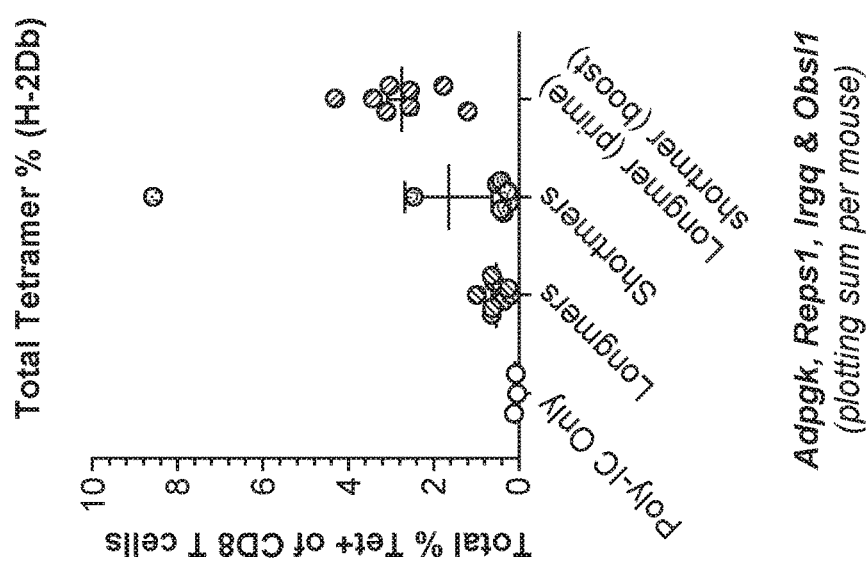
FIGS. 6A-6C depict longmer prime/shortmer boost regimen gives highest frequency of antigen-specific T cells when administered according to regimen depicted in FIG. 3. The plots show frequency of T cells to all antigens (FIG. 6A), Alg8 and Lama4 (FIG. 6B), and Adpgk, Reps1, Irgq & Obsl1 (FIG. 6C).
Figure 6B:
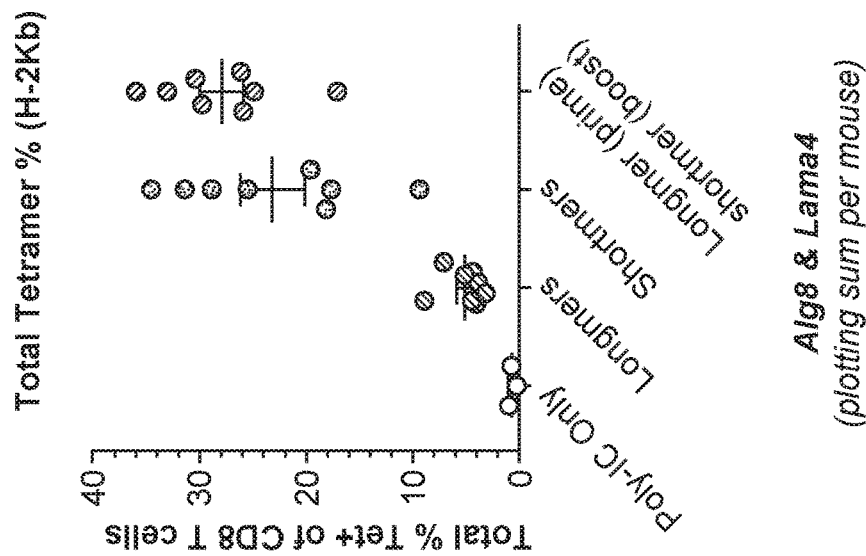
Figure 6A:
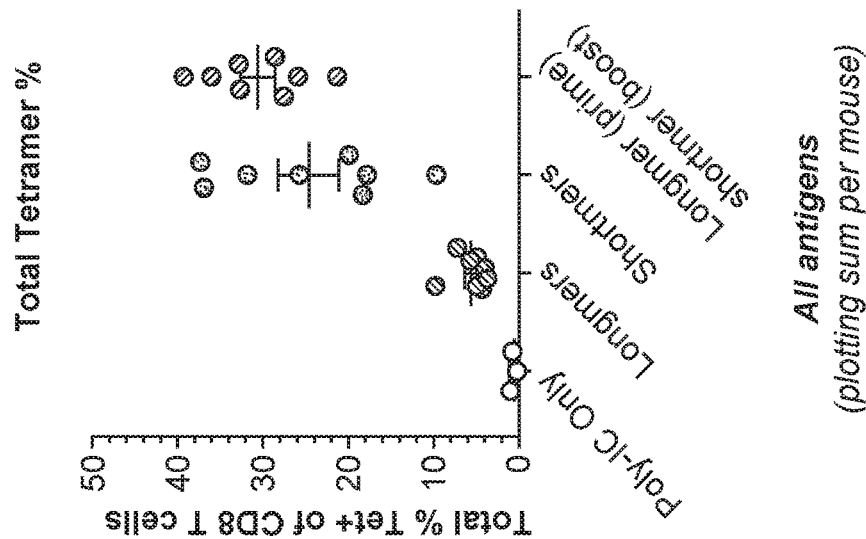
Figures 7A, 7B:
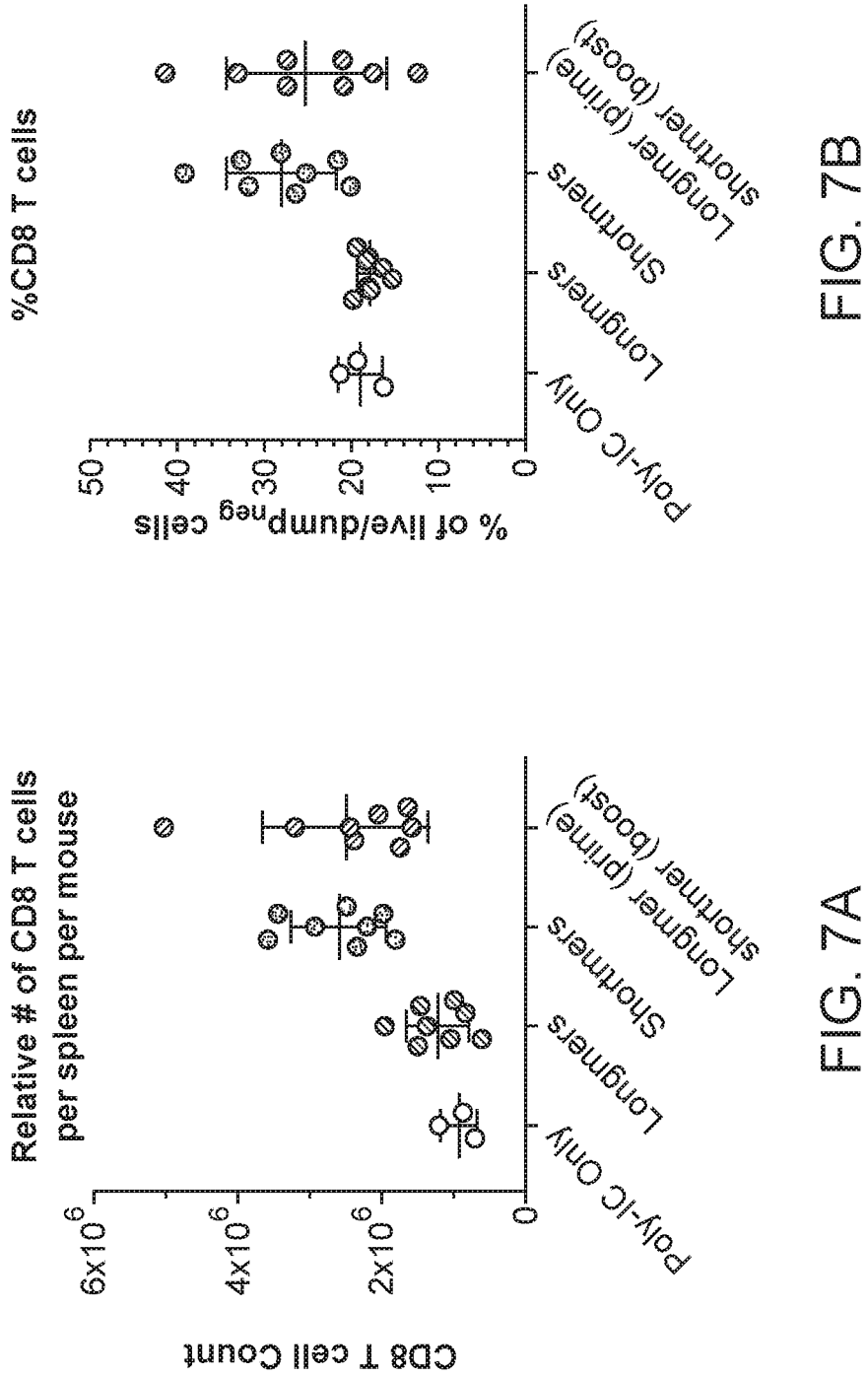
FIGS. 7A-7B show effect of immunizing with shortmer in prime or boost on numbers of CD8 (FIGS. 7A and 7B).
Figure 8A:
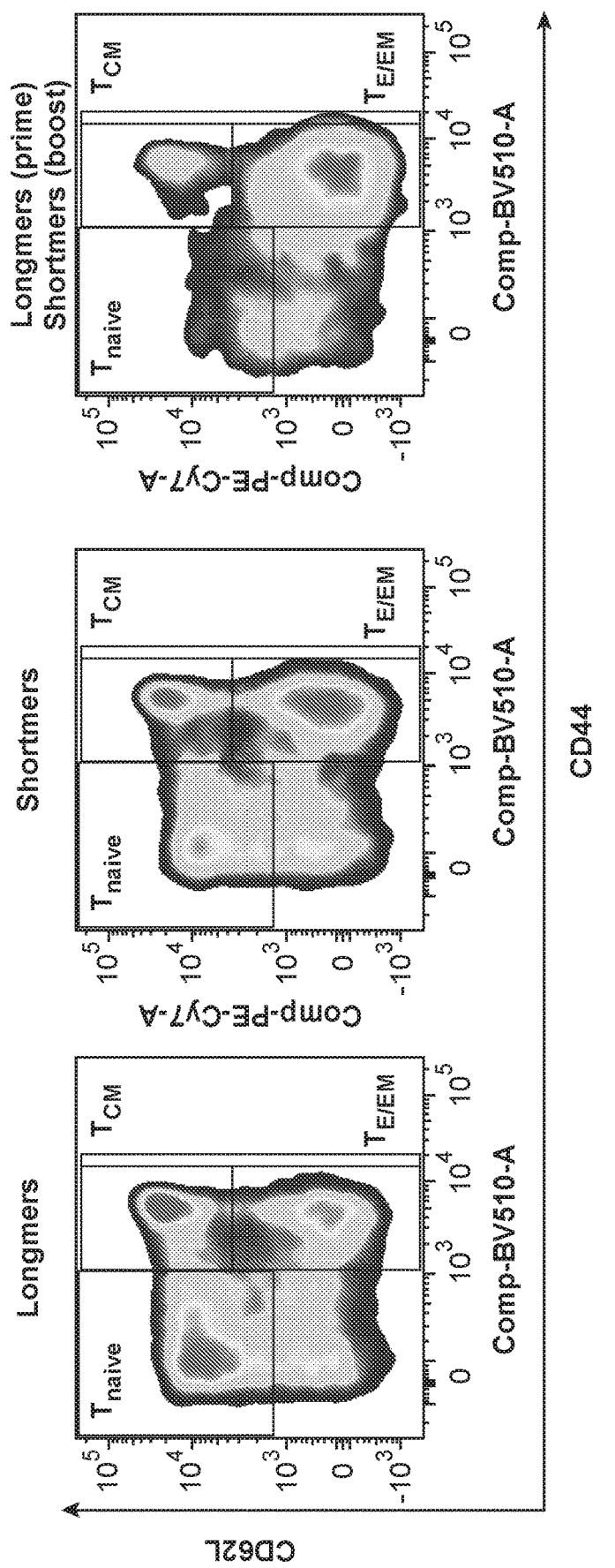
FIGS. 8A-8B show immunizing with shortmer in prime or boost increases the percentage of TE/EM cells.
Figure 8B:
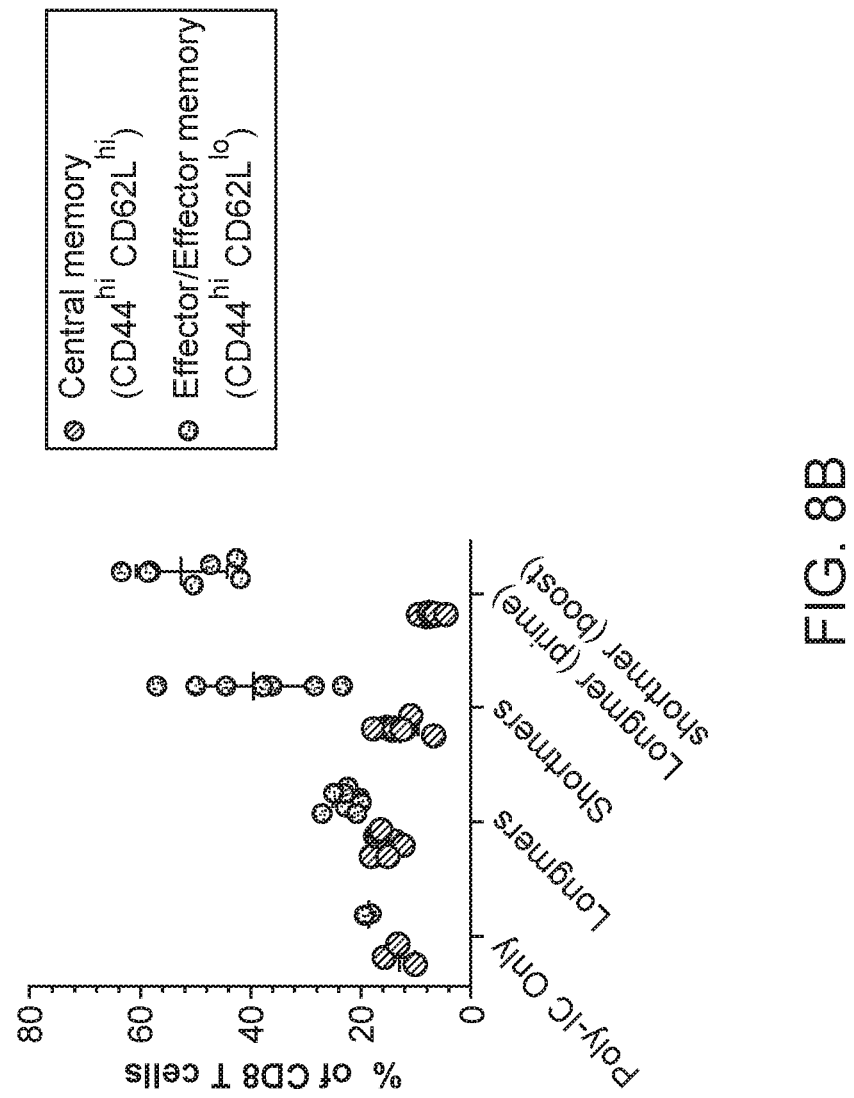
Figure 9A:
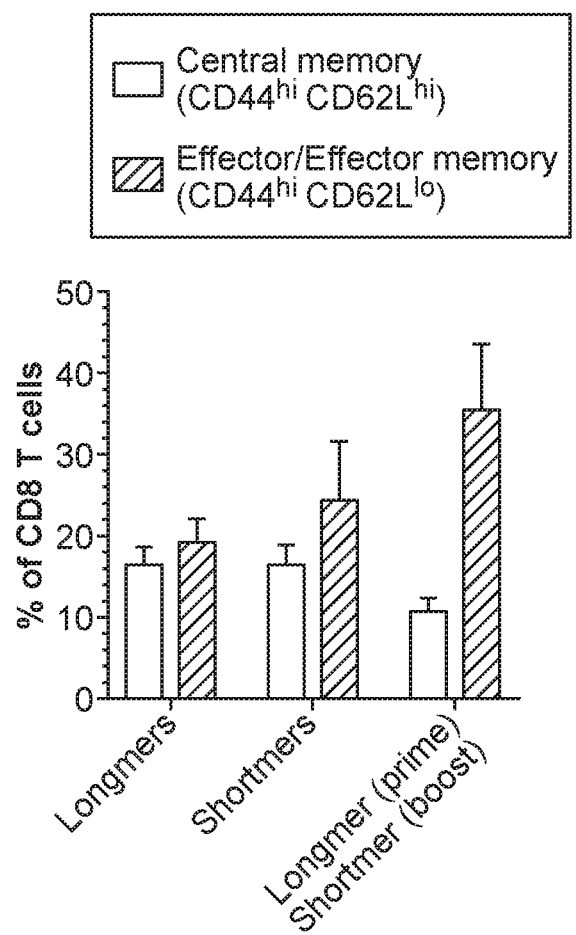
FIGS. 9A-9B shows that antigen-specific CD8 T cells are TE/EM cells.
Figure 9B:
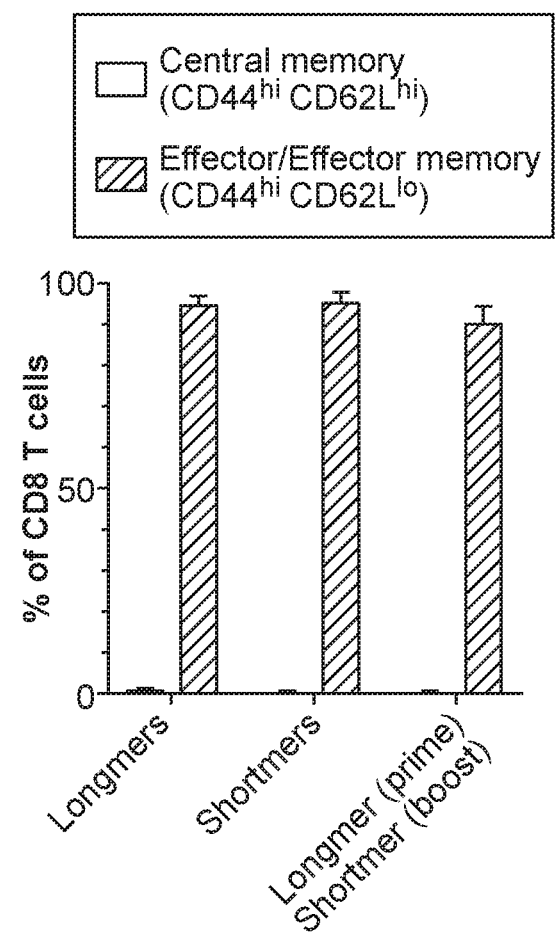
Figure 10A:
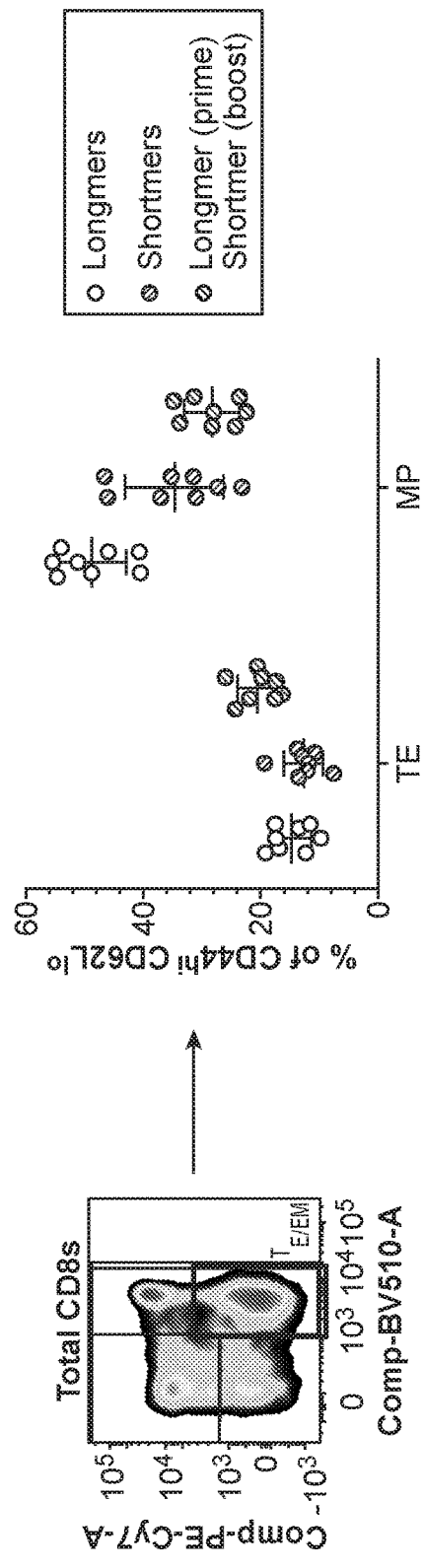
FIGS. 10A-10B show increase in terminal effector phenotype on antigen-specific T cells (FIG. 11B) relative to total T cells (FIG. 11A) by longmer-only immunization.
Figure 10B:
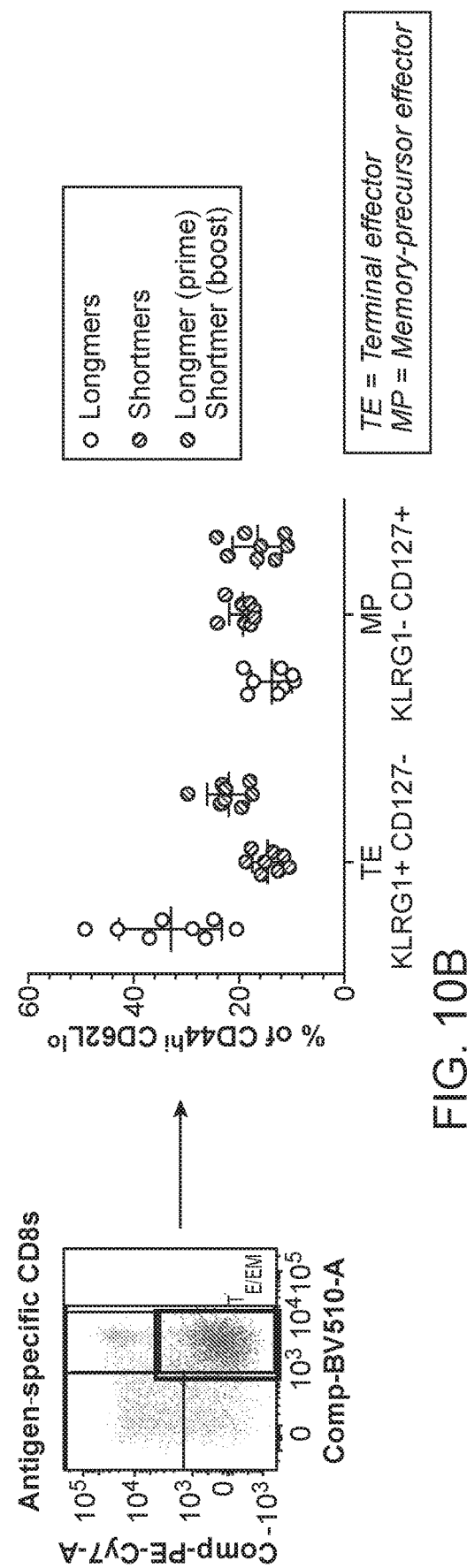
Figure 11A:
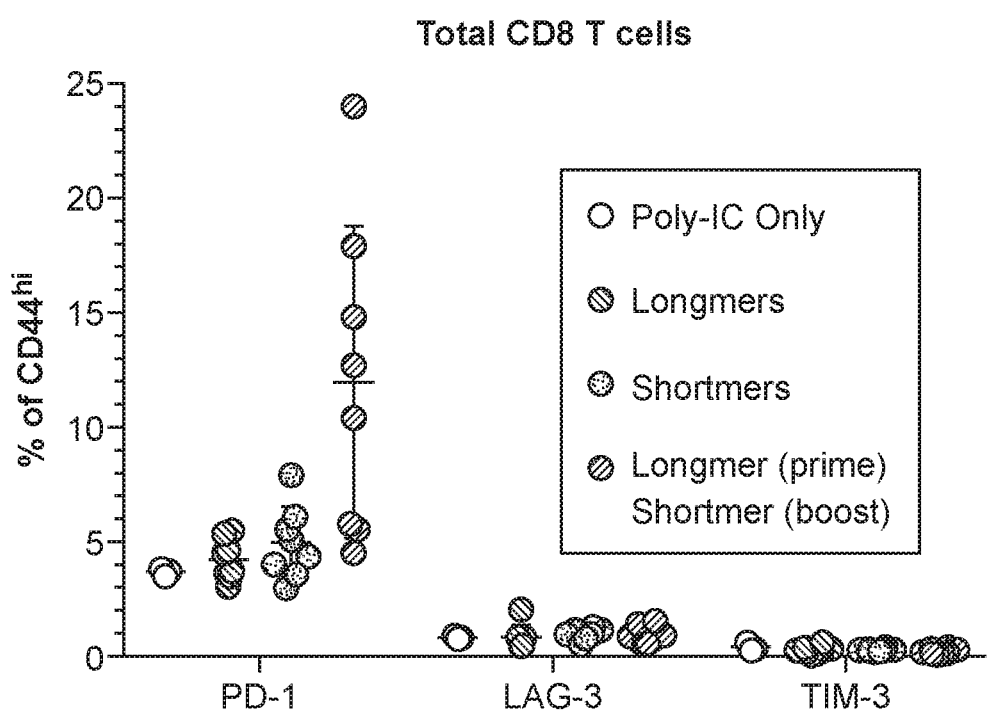
FIGS. 11A-11C show longmer prime/shortmer boost immunization shows higher percentage of PD-1+ cells, in population of total CD8 T cell (FIG. 11A), antigen-specific CD8 T cells (FIG. 11B), and non-antigen specific CD8 T cells, indicative of activation (FIG. 11C).
Figure 11B:
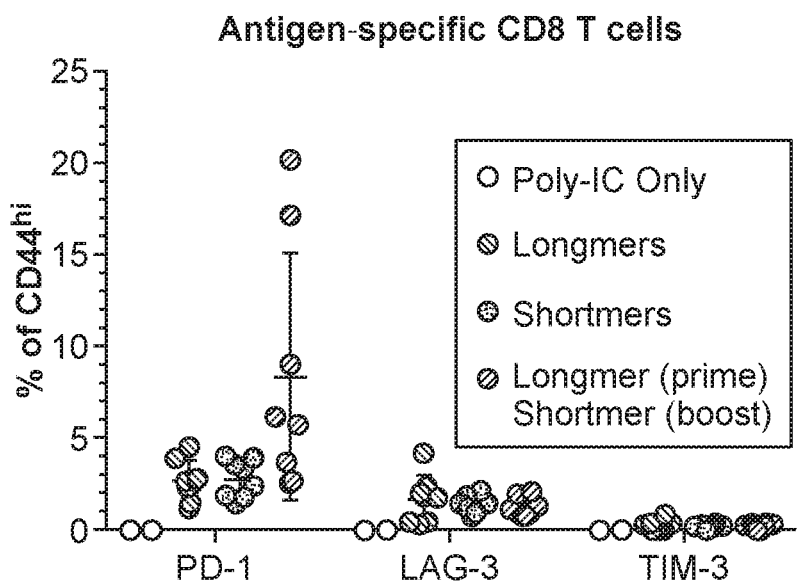
Figure 11C:
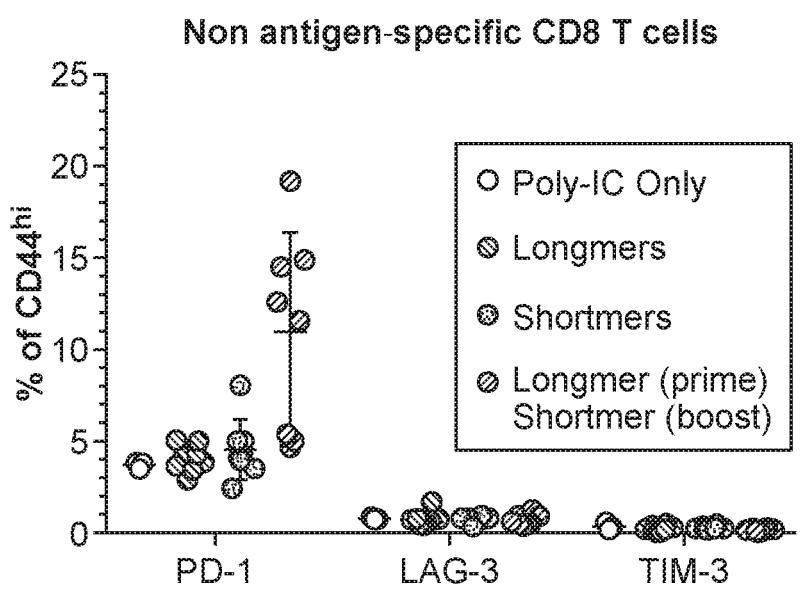
Figure 12A:
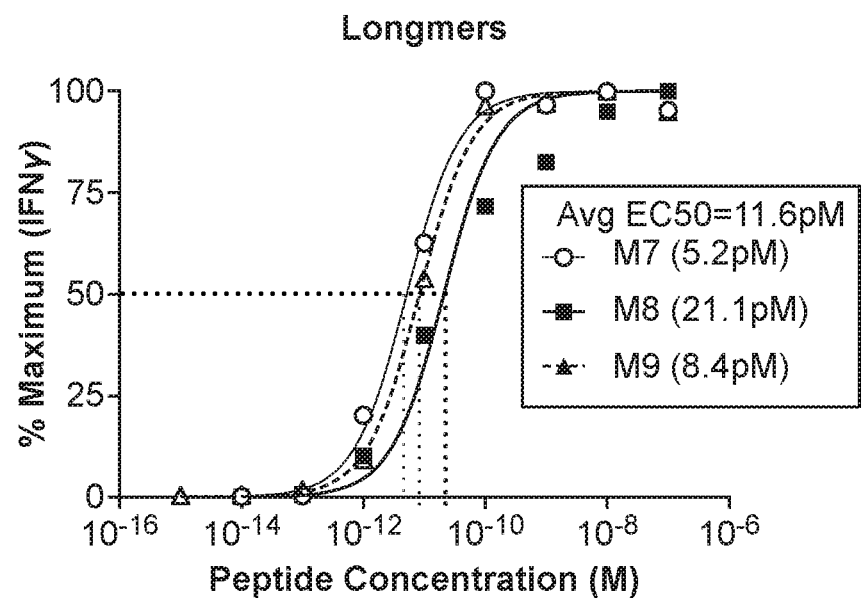
FIGS. 12A-12B illustrates TCR avidity (EC50) is similar in CD8T cells induced by shortmer and longmer vaccination.
Figure 12B:
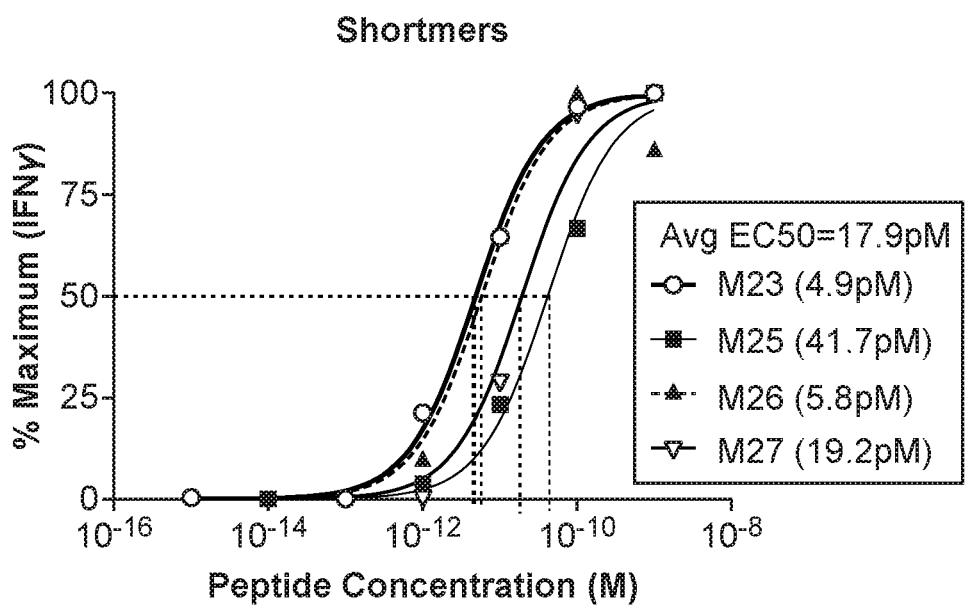

Described herein are new immunotherapeutic agents and uses thereof based on the discovery of neoantigens arising from mutational events unique to an individual's tumor. Accordingly, the present disclosure described herein provides peptides, polynucleotides encoding the peptides, and peptide binding agents that can be used, for example, to stimulate an immune response to a tumor associated antigen or neoepitope, to create an immunogenic composition or cancer vaccine for use in treating disease.

The following description and examples illustrate embodiments of the present disclosure in detail. It is to be understood that this present disclosure is not limited to the particular embodiments described herein and as such can vary. Those of skill in the art will recognize that there are numerous variations and modifications of this present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

Definitions

The terminology used herein is for the purpose of describing particular cases only and is not intended to be limiting. In this application, the use of the singular includes the plural unless specifically stated otherwise. As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

"Major Histocompatibility Complex" or "MHC" is a cluster of genes that plays a role in control of the cellular interactions responsible for physiologic immune responses. In humans, the MHC complex is also known as the human leukocyte antigen (HLA) complex. For a detailed description of the MHC and HLA complexes, see, Paul, Fundamental Immunology, 3rd Ed., Raven Press, New York (1993). "Proteins or molecules of the major histocompatibility complex (MHC)", "MHC molecules", "MHC proteins" or "HLA proteins" are to be understood as meaning proteins capable of binding peptides resulting from the proteolytic cleavage of protein antigens and representing potential lymphocyte epitopes, (e.g., T cell epitope and B cell epitope) transporting them to the cell surface and presenting them there to specific cells, in particular cytotoxic T-lymphocytes, T-helper cells, or B cells. The major histocompatibility complex in the genome comprises the genetic region whose gene products expressed on the cell surface are important for binding and presenting endogenous and/or foreign antigens and thus for regulating immunological processes. The major histocompatibility complex is classified into two gene groups coding for different proteins, namely molecules of MHC class I and molecules of MHC class II. The cellular biology and the expression patterns of the two MHC classes are adapted to these different roles.

"Human Leukocyte Antigen" or "HLA" is a human class I or class II Major Histocompatibility Complex (MHC) protein (see, e.g., Stites, et al., Immunology, 8th Ed., Lange Publishing, Los Altos, Calif. (1994).

"Polypeptide", "peptide" and their grammatical equivalents as used herein refer to a polymer of amino acid residues. A "mature protein" is a protein which is full-length and which, optionally, includes glycosylation or other modifications typical for the protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides described herein in an engineered cell can be associated with post-translational modifications of one or more amino acids of the polypeptide constructs. Non-limiting examples of post-translational modifications include phosphorylation, acylation including acetylation and formylation, glycosylation (including N-linked and O-linked), amidation, hydroxylation, alkylation including methylation and ethylation, ubiquitination, addition of pyrrolidone carboxylic acid, formation of disulfide bridges, sulfation, myristoylation, palmitoylation, isoprenylation, farnesylation, geranylation, glypiation, lipoylation and iodination.

An "immunogenic" peptide or an "immunogenic" epitope is a peptide or an epitope that comprises an allele-specific motif such that the peptide or epitope will bind an HLA molecule and induce a cell-mediated or humoral response, for example, cytotoxic T lymphocyte (CTL (e.g., CD8+)), helper T lymphocyte (Th (e.g., CD4+)) and/or B lymphocyte response. Thus, immunogenic peptides described herein are capable of binding to an appropriate HLA molecule and thereafter inducing a CTL (cytotoxic) response, or a HTL (and humoral) response, to the peptide.

"Neoantigen" means a class of tumor antigens which arise from tumor-specific changes in proteins. Neoantigens encompass, but are not limited to, tumor antigens which arise from, for example, substitution in the protein sequence, frame shift mutation, fusion polypeptide, in-frame deletion, insertion, expression of endogenous retroviral polypeptides, and tumor-specific overexpression of polypeptides.

The term "mutant peptide", "neoantigen peptide" and "neoantigenic peptide", used interchangeably with "peptide" in the present specification, refers to a series of residues, typically L-amino acids, connected one to the other, typically by peptide bonds between the α-amino and carboxyl groups of adjacent amino acids. Similarly, the term "polypeptide" is used interchangeably with "mutant polypeptide", "neoantigen polypeptide" and "neoantigenic polypeptide" in the present specification to designate a series of residues, e.g., L-amino acids, connected one to the other, typically by peptide bonds between the α-amino and carboxyl groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described. A peptide or polypeptide as used herein comprises at least one flanking sequence. The term "flanking sequence" as used herein refers to a fragment or region of the neoantigen peptide that is not a part of the neoepitope.

The term "residue" refers to an amino acid residue or amino acid mimetic residue incorporated into a peptide or protein by an amide bond or amide bond mimetic, or nucleic acid (DNA or RNA) that encodes the amino acid or amino acid mimetic.

A "neoepitope", "tumor specific neoepitope" or "tumor antigen" refers to an epitope or antigenic determinant region that is not present in a reference, such as a non-diseased cell, e.g., a non-cancerous cell or a germline cell, but is found in a diseased cell, e.g., a cancer cell. This includes situations where a corresponding epitope is found in a normal non-diseased cell or a germline cell but, due to one or more mutations in a diseased cell, e.g., a cancer cell, the sequence of the epitope is changed so as to result in the neoepitope. The term "neoepitope" as used herein refers to an antigenic determinant region within the peptide or neoantigenic peptide. A neoepitope may comprise at least one "anchor residue" and at least one "anchor residue flanking region." A neoepitope may further comprise a "separation region." The term "anchor residue" refers to an amino acid residue that binds to specific pockets on HLAs, resulting in specificity of interactions with HLAs. In some cases, an anchor residue may be at a canonical anchor position. In other cases, an anchor residue may be at a non-canonical anchor position. Neoepitopes may bind to HLA molecules through primary and secondary anchor residues protruding into the pockets in the peptide-binding grooves. In the peptide-binding grooves, specific amino acids compose pockets that accommodate the corresponding side chains of the anchor residues of the presented neoepitopes. Peptide-binding preferences exist among different alleles of both of HLA I and HLA II molecules. HLA class I molecules bind short neoepitopes, whose N- and C-terminal ends are anchored into the pockets located at the ends of the neoepitope binding groove. While the majority of the HLA class I binding neoepitopes are of about 9 amino acids, longer neoepitopes can be accommodated by the bulging of their central portion, resulting in binding neoepitopes of about 8 to 12 amino acids. Neoepitopes binding to HLA class II proteins are not constrained in size and can vary from about 16 to 25 amino acids. The neoepitope binding groove in the HLA class II molecules is open at both ends, which enables binding of peptides with relatively longer length. Though the core 9 amino acid residues long segment contributes the most to the recognition of the neoepitope, the anchor residue flanking regions are also important for the specificity of the peptide to the HLA class II allele. In some cases, the anchor residue flanking region is N-terminus residues. In another case, the anchor residue flanking region is C-terminus residues. In yet another case, the anchor residue flanking region is both N-terminus residues and C-terminus residues. In some cases, the anchor residue flanking region is flanked by at least two anchor residues. An anchor residue flanking region flanked by anchor residues is a "separation region."

A "reference" can be used to correlate and compare the results obtained in the methods of the present disclosure from a tumor specimen. Typically the "reference" may be obtained on the basis of one or more normal specimens, in particular specimens which are not affected by a cancer disease, either obtained from a patient or one or more different individuals, for example, healthy individuals, in particular individuals of the same species. A "reference" can be determined empirically by testing a sufficiently large number of normal specimens.

An "epitope" is the collective features of a molecule, such as primary, secondary and tertiary peptide structure, and charge, that together form a site recognized by, for example, an immunoglobulin, T cell receptor, HLA molecule, or chimeric antigen receptor. Alternatively, an epitope can be defined as a set of amino acid residues which is involved in recognition by a particular immunoglobulin, or in the context of T cells, those residues necessary for recognition by T cell receptor proteins, chimeric antigen receptors, and/or Major Histocompatibility Complex (MHC) receptors. A "T cell epitope" is to be understood as meaning a peptide sequence which can be bound by the MHC molecules of class I or II in the form of a peptide-presenting MHC molecule or MHC complex and then, in this form, be recognized and bound by T cells, such as T-lymphocytes or T-helper cells. Epitopes can be prepared by isolation from a natural source, or they can be synthesized according to standard protocols in the art. Synthetic epitopes can comprise artificial amino acid residues, "amino acid mimetics," such as D isomers of naturally-occurring L amino acid residues or non-naturally-occurring amino acid residues such as cyclohexylalanine Throughout this disclosure, epitopes may be referred to in some cases as peptides or peptide epitopes. It is to be appreciated that proteins or peptides that comprise an epitope or an analog described herein as well as additional amino acid(s) are still within the bounds of the present disclosure. In certain embodiments, the peptide comprises a fragment of an antigen. In certain embodiments, there is a limitation on the length of a peptide of the present disclosure. The embodiment that is length-limited occurs when the protein or peptide comprising an epitope described herein comprises a region (i.e., a contiguous series of amino acid residues) having 100% identity with a native sequence. In order to avoid the definition of epitope from reading, e.g., on whole natural molecules, there is a limitation on the length of any region that has 100% identity with a native peptide sequence. Thus, for a peptide comprising an epitope described herein and a region with 100% identity with a native peptide sequence, the region with 100% identity to a native sequence generally has a length of: less than or equal to 600 amino acid residues, less than or equal to 500 amino acid residues, less than or equal to 400 amino acid residues, less than or equal to 250 amino acid residues, less than or equal to 100 amino acid residues, less than or equal to 85 amino acid residues, less than or equal to 75 amino acid residues, less than or equal to 65 amino acid residues, and less than or equal to 50 amino acid residues. In certain embodiments, an "epitope" described herein is comprised by a peptide having a region with less than 51 amino acid residues that has 100% identity to a native peptide sequence, in any increment down to 5 amino acid residues; for example 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 amino acid residues.

The nomenclature used to describe peptides or proteins follows the conventional practice wherein the amino group is presented to the left (the amino- or N-terminus) and the carboxyl group to the right (the carboxy- or C-terminus) of each amino acid residue. When amino acid residue positions are referred to in a peptide epitope they are numbered in an amino to carboxyl direction with position one being the residue located at the amino terminal end of the epitope, or the peptide or protein of which it can be a part. In the formula representing selected specific embodiments of the present disclosure, the amino- and carboxyl-terminal groups, although not specifically shown, are in the form they would assume at physiologic pH values, unless otherwise specified. In the amino acid structure formula, each residue is generally represented by standard three letter or single letter designations. The L-form of an amino acid residue is represented by a capital single letter or a capital first letter of a three-letter symbol, and the D-form for those amino acid residues having D-forms is represented by a lower case single letter or a lower case three letter symbol. However, when three letter symbols or full names are used without capitals, they can refer to L amino acid residues. Glycine has no asymmetric carbon atom and is simply referred to as "Gly" or "G". The amino acid sequences of peptides set forth herein are generally designated using the standard single letter symbol. (A, Alanine; C, Cysteine; D, Aspartic Acid; E, Glutamic Acid; F, Phenylalanine; G, Glycine; H, Histidine; I, Isoleucine; K, Lysine; L, Leucine; M, Methionine; N, Asparagine; P, Proline; Q, Glutamine; R, Arginine; S, Serine; T, Threonine; V, Valine; W, Tryptophan; and Y, Tyrosine.)

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. In some embodiments, a mutation is a non-synonymous mutation. The term "non-synonymous mutation" refers to a mutation, for example, a nucleotide substitution, which does result in an amino acid change such as an amino acid substitution in the translation product. A "frameshift" occurs when a mutation disrupts the normal phase of a gene's codon periodicity (also known as "reading frame"), resulting in the translation of a non-native protein sequence. It is possible for different mutations in a gene to achieve the same altered reading frame.

A "conservative amino acid substitution" is one in which one amino acid residue is replaced with another amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate peptide function are well-known in the art.

As used herein, the term "affinity" refers to a measure of the strength of binding between two members of a binding pair, for example, an HLA-binding peptide and a class I or II HLA. KD is the dissociation constant and has units of molarity. The affinity constant is the inverse of the dissociation constant. An affinity constant is sometimes used as a generic term to describe this chemical entity. It is a direct measure of the energy of binding. Affinity may be determined experimentally, for example by surface plasmon resonance (SPR) using commercially available Biacore SPR units. Affinity may also be expressed as the inhibitory concentration 50 (IC50), that concentration at which 50% of the peptide is displaced. Likewise, ln(IC50) refers to the natural log of the IC50. Koff refers to the off-rate constant, for example, for dissociation of an HLA-binding peptide and a class I or II HLA. Throughout this disclosure, "binding data" results can be expressed in terms of "IC50." IC50 is the concentration of the tested peptide in a binding assay at which 50% inhibition of binding of a labeled reference peptide is observed. Given the conditions in which the assays are run (i.e., limiting HLA protein and labeled reference peptide concentrations), these values approximate KD values. Assays for determining binding are well known in the art and are described in detail, for example, in PCT publications WO 94/20127 and WO 94/03205, and other publications such Sidney et al., Current Protocols in Immunology 18.3.1 (1998); Sidney, et al., J. Immunol. 154:247 (1995); and Sette, et al., Mol. Immunol. 31:813 (1994). Alternatively, binding can be expressed relative to binding by a reference standard peptide. For example, can be based on its IC50, relative to the IC50 of a reference standard peptide. Binding can also be determined using other assay systems including those using: live cells (e.g., Ceppellini et al., Nature 339:392 (1989); Christnick et al., Nature 352:67 (1991); Busch et al., Int. Immunol. 2:443 (1990); Hill et al., J. Immunol. 147:189 (1991); del Guercio et al., J. Immunol. 154:685 (1995)), cell free systems using detergent lysates (e.g., Cerundolo et al., J. Immunol. 21:2069 (1991)), immobilized purified MHC (e.g., Hill et al., J. Immunol. 152, 2890 (1994); Marshall et al., J. Immunol. 152:4946 (1994)), ELISA systems (e.g., Reay et al., EMBO J. 11:2829 (1992)), surface plasmon resonance (e.g., Khilko et al., J. Biol. Chem. 268:15425 (1993)); high flux soluble phase assays (Hammer et al., J. Exp. Med. 180:2353 (1994)), and measurement of class I MHC stabilization or assembly (e.g., Ljunggren et al., Nature 346:476 (1990); Schumacher et al., Cell 62:563 (1990); Townsend et al., Cell 62:285 (1990); Parker et al., J. Immunol. 149:1896 (1992)). "Cross-reactive binding" indicates that a peptide is bound by more than one HLA molecule; a synonym is degenerate binding.

The term "derived" and its grammatical equivalents when used to discuss an epitope is a synonym for "prepared" and its grammatical equivalents. A derived epitope can be isolated from a natural source, or it can be synthesized according to standard protocols in the art. Synthetic epitopes can comprise artificial amino acid residues "amino acid mimetics," such as D isomers of natural occurring L amino acid residues or non-natural amino acid residues such as cyclohexylalanine A derived or prepared epitope can be an analog of a native epitope.

A "diluent" includes sterile liquids, such as water and oils, including those of petroleum, animal, vegetable or synthetic origin, such as peanut oil, soybean oil, mineral oil, sesame oil and the like. Water is also a diluent for pharmaceutical compositions. Saline solutions and aqueous dextrose and glycerol solutions can also be employed as diluents, for example, in injectable solutions.

A "native" or a "wild type" sequence refers to a sequence found in nature. Such a sequence can comprise a longer sequence in nature.

A "receptor" is to be understood as meaning a biological molecule or a molecule grouping capable of binding a ligand. A receptor may serve, to transmit information in a cell, a cell formation or an organism. The receptor comprises at least one receptor unit, for example, where each receptor unit may consist of a protein molecule. The receptor has a structure which complements that of a ligand and may complex the ligand as a binding partner. The information is transmitted in particular by conformational changes of the receptor following complexation of the ligand on the surface of a cell. In some embodiments, a receptor is to be understood as meaning in particular proteins of MHC classes I and II capable of forming a receptor/ligand complex with a ligand, in particular a peptide or peptide fragment of suitable length.

A "ligand" is to be understood as meaning a molecule which has a structure complementary to that of a receptor and is capable of forming a complex with this receptor. In some embodiments, a ligand is to be understood as meaning a peptide or peptide fragment which has a suitable length and suitable binding motifs in its amino acid sequence, so that the peptide or peptide fragment is capable of forming a complex with proteins of MHC class I or MHC class II.

In some embodiments, a "receptor/ligand complex" is also to be understood as meaning a "receptor/peptide complex" or "receptor/peptide fragment complex", including a peptide- or peptide fragment-presenting MHC molecule of class I or of class II.

The terms "peptide" " " refers to a series of amino acid residues connected one to the other, typically by peptide bonds between the α-amino and carboxyl groups of adjacent amino acid residues.

"Synthetic peptide" refers to a peptide that is obtained from a non-natural source, e.g., is man-made. Such peptides can be produced using such methods as chemical synthesis or recombinant DNA technology. "Synthetic peptides" include "fusion proteins."

The term "motif" refers to a pattern of residues in an amino acid sequence of defined length, for example, a peptide of less than about 15 amino acid residues in length, or less than about 13 amino acid residues in length, for example, from about 8 to about 13 amino acid residues (e.g., 8, 9, 10, 11, 12, or 13) for a class I HLA motif and from about 6 to about 25 amino acid residues (e.g., 6, 7, 8, 9, 10, 11, 12, 13, 14, 15, 16, 17, 18, 19, 20, 21, 22, 23, 24, or 25) for a class II HLA motif, which is recognized by a particular HLA molecule. Motifs are typically different for each HLA protein encoded by a given human HLA allele. These motifs differ in their pattern of the primary and secondary anchor residues. In some embodiments, an MHC class I motif identifies a peptide of 9, 10, or 11 amino acid residues in length.

The term "naturally occurring" and its grammatical equivalents as used herein refer to the fact that an object can be found in nature. For example, a peptide or nucleic acid that is present in an organism (including viruses) and can be isolated from a source in nature and which has not been intentionally modified by man in the laboratory is naturally occurring.

According to the present disclosure, the term "vaccine" relates to a pharmaceutical preparation (pharmaceutical composition) or product that upon administration induces an immune response, for example, a cellular or humoral immune response, which recognizes and attacks a pathogen or a diseased cell such as a cancer cell. A vaccine may be used for the prevention or treatment of a disease. The term "individualized cancer vaccine" or "personalized cancer vaccine" concerns a particular cancer patient and means that a cancer vaccine is adapted to the needs or special circumstances of an individual cancer patient.

A "protective immune response" or "therapeutic immune response" refers to a CTL and/or an HTL response to an antigen derived from an pathogenic antigen (e.g., a tumor antigen), which in some way prevents or at least partially arrests disease symptoms, side effects or progression. The immune response can also include an antibody response which has been facilitated by the stimulation of helper T cells.

"Antigen processing" or "processing" and its grammatical equivalents refers to the degradation of a polypeptide or antigen into procession products, which are fragments of said polypeptide or antigen (e.g., the degradation of a polypeptide into peptides) and the association of one or more of these fragments (e.g., via binding) with MHC molecules for presentation by cells, for example, antigen presenting cells, to specific T cells.

"Antigen presenting cells" (APC) are cells which present peptide fragments of protein antigens in association with MHC molecules on their cell surface. Some APCs may activate antigen specific T cells. Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen presenting cell. An additional co-stimulatory signal is then produced by the antigen presenting cell, leading to activation of the T cell. The expression of co-stimulatory molecules is a defining feature of professional antigen-presenting cells. The main types of professional antigen-presenting cells are dendritic cells, which have the broadest range of antigen presentation, and are probably the most important antigen presenting cells, macrophages, B-cells, and certain activated epithelial cells. Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells are conveniently categorized as "immature" and "mature" cells, which can be used as a simple way to discriminate between two well characterized phenotypes. However, this nomenclature should not be construed to exclude all possible intermediate stages of differentiation. Immature dendritic cells are characterized as antigen presenting cells with a high capacity for antigen uptake and processing, which correlates with the high expression of Fc receptor (FcR) and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1 BB).

The terms "identical" and its grammatical equivalents as used herein or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman, Adv. Appl. Math., 2:482 (1981); by the alignment algorithm of Needleman and Wunsch, J. Mol. Biol., 48:443 (1970); by the search for similarity method of Pearson and Lipman, Proc. Nat. Acad. Sci. U.S.A., 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, Gene, 73:237-244 (1988) and Higgins and Sharp, CABIOS, 5:151-153 (1989); Corpet et al., Nucleic Acids Res., 16:10881-10890 (1988); Huang et al., Computer Applications in the Biosciences, 8:155-165 (1992); and Pearson et al., Methods in Molecular Biology, 24:307-331 (1994). Alignment is also often performed by inspection and manual alignment. In one class of embodiments, the polypeptides herein have at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can have 50%, 60%, 70%, 75%, 80%, 85%, 90%, 98%, 99% or 100% sequence identity to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "substantially identical" and its grammatical equivalents as applied to nucleic acid or amino acid sequences mean that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In embodiments, the substantial identity exists over a region of the sequences that is at least about 50 residues in length, over a region of at least about 100 residues, and in embodiments, the sequences are substantially identical over at least about 150 residues. In embodiments, the sequences are substantially identical over the entire length of the coding regions.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure. In some embodiments, an "isolated polynucleotide" encompasses a PCR or quantitative PCR reaction comprising the polynucleotide amplified in the PCR or quantitative PCR reaction.

The term "isolated", "biologically pure" or their grammatical equivalents refers to material which is substantially or essentially free from components which normally accompany the material as it is found in its native state. Thus, isolated peptides described herein do not contain some or all of the materials normally associated with the peptides in their in situ environment. An "isolated" epitope refers to an epitope that does not include the whole sequence of the antigen from which the epitope was derived. Typically the "isolated" epitope does not have attached thereto additional amino acid residues that result in a sequence that has 100% identity over the entire length of a native sequence. The native sequence can be a sequence such as a tumor-associated antigen from which the epitope is derived. Thus, the term "isolated" means that the material is removed from its original environment (e.g., the natural environment if it is naturally occurring). An "isolated" nucleic acid is a nucleic acid removed from its natural environment. For example, a naturally-occurring polynucleotide or peptide present in a living animal is not isolated, but the same polynucleotide or peptide, separated from some or all of the coexisting materials in the natural system, is isolated. Such a polynucleotide could be part of a vector, and/or such a polynucleotide or peptide could be part of a composition, and still be "isolated" in that such vector or composition is not part of its natural environment. Isolated RNA molecules include in vivo or in vitro RNA transcripts of the DNA molecules described herein, and further include such molecules produced synthetically.

The term "substantially purified" and its grammatical equivalents as used herein refer to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

The term "substantially pure" as used herein refers to material which is at least 50% pure (i.e., free from contaminants), at least 90% pure, at least 95% pure, at least 98% pure, or at least 99% pure.

The terms "polynucleotide", "nucleotide", "nucleic acid", "polynucleic acid" or "oligonucleotide" and their grammatical equivalents are used interchangeably herein and refer to polymers of nucleotides of any length, and include DNA and RNA, for example, mRNA. Thus, these terms includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs. The nucleic acid sequences and vectors disclosed or contemplated herein may be introduced into a cell by, for example, transfection, transformation, or transduction. The nucleotides can be deoxyribonucleotides, ribonucleotides, modified nucleotides or bases, and/or their analogs, or any substrate that can be incorporated into a polymer by DNA or RNA polymerase. In some embodiments, the polynucleotide and nucleic acid can be in vitro transcribed mRNA. In some embodiments, the polynucleotide that is administered using the methods of the present disclosure is mRNA.

"Transfection," "transformation," or "transduction" as used herein refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)). Phage or viral vectors can be introduced into host cells, after growth of infectious particles in suitable packaging cells, many of which are commercially available.

Nucleic acids and/or nucleic acid sequences are "homologous" when they are derived, naturally or artificially, from a common ancestral nucleic acid or nucleic acid sequence. Proteins and/or protein sequences are "homologous" when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The terms "effective amount" or "therapeutically effective amount" or "therapeutic effect" refer to an amount of a therapeutic effective to "treat" a disease or disorder in a subject or mammal. The therapeutically effective amount of a drug has a therapeutic effect and as such can prevent the development of a disease or disorder; slow down the development of a disease or disorder; slow down the progression of a disease or disorder; relieve to some extent one or more of the symptoms associated with a disease or disorder; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder; and (2) prophylactic or preventative measures that prevent or slow the development of a targeted pathologic condition or disorder. Thus those in need of treatment include those already with the disorder; those prone to have the disorder; and those in whom the disorder is to be prevented.

"Pharmaceutically acceptable" refers to a generally non-toxic, inert, and/or physiologically compatible composition or component of a composition.

A "pharmaceutical excipient" or "excipient" comprises a material such as an adjuvant, a carrier, pH-adjusting and buffering agents, tonicity adjusting agents, wetting agents, preservatives, and the like. A "pharmaceutical excipient" is an excipient which is pharmaceutically acceptable.

Neoantigens and Uses Thereof

One of the critical barriers to developing curative and tumor-specific immunotherapy is the identification and selection of highly specific and restricted tumor antigens to avoid autoimmunity. Tumor neoantigens, which arise as a result of genetic change (e.g., inversions, translocations, deletions, missense mutations, splice site mutations, etc.) within malignant cells, represent the most tumor-specific class of antigens. Neoantigens have rarely been used in cancer vaccine or immunogenic compositions due to technical difficulties in identifying them, selecting optimized antigens, and producing neoantigens for use in a vaccine or immunogenic composition. These problems may be addressed by: identifying mutations in neoplasias/tumors which are present at the DNA level in tumor but not in matched germline samples from a high proportion of subjects having cancer; analyzing the identified mutations with one or more peptide-MHC binding prediction algorithms to generate a plurality of neoantigen T cell epitopes that are expressed within the neoplasia/tumor and that bind to a high proportion of patient HLA alleles; and synthesizing the plurality of neoantigenic peptides selected from the sets of all neoantigen peptides and predicted binding peptides for use in a cancer vaccine or immunogenic composition suitable for treating a high proportion of subjects having cancer.

For example, translating peptide sequencing information into a therapeutic vaccine may include prediction of mutated peptides that can bind to HLA molecules of a high proportion of individuals. Efficiently choosing which particular mutations to utilize as immunogen requires the ability to predict which mutated peptides would efficiently bind to a high proportion of patient's HLA alleles. Recently, neural network based learning approaches with validated binding and non-binding peptides have advanced the accuracy of prediction algorithms for the major HLA-A and -B alleles. However, even using advanced neural network-based algorithms to encode HLA-peptide binding rules, several factors limit the power to predict peptides presented on HLA alleles.

Another example of translating peptide sequencing information into a therapeutic vaccine may include formulating the drug as a multi-epitope vaccine of long peptides. Targeting as many mutated epitopes as practically possible takes advantage of the enormous capacity of the immune system, prevents the opportunity for immunological escape by down-modulation of an immune targeted gene product, and compensates for the known inaccuracy of epitope prediction approaches. Synthetic peptides provide a useful means to prepare multiple immunogens efficiently and to rapidly translate identification of mutant epitopes to an effective vaccine. Peptides can be readily synthesized chemically and easily purified utilizing reagents free of contaminating bacteria or animal substances. The small size allows a clear focus on the mutated region of the protein and also reduces irrelevant antigenic competition from other components (non-mutated protein or viral vector antigens).

Yet another example of translating peptide sequencing information into a therapeutic vaccine may include a combination with a strong vaccine adjuvant. Effective vaccines may require a strong adjuvant to initiate an immune response. For example, poly-ICLC, an agonist of TLR3 and the RNA helicase-domains of MDA5 and RIG3, has shown several desirable properties for a vaccine adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NYESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile.

In some aspects, provided herein is a composition comprising: a first peptide comprising a first neoepitope of a protein and a second peptide comprising a second neoepitope of the same protein, a polynucleotide encoding the first peptide and the second peptide, one or more APCs comprising the first peptide and the second peptide, or a first T cell receptor (TCR) specific for the first neoepitope in complex with an HLA protein and a second TCR specific for the second neoepitope in complex with an HLA protein; wherein the first peptide is different from the second peptide, and wherein the first neoepitope comprises a mutation and the second neoepitope comprises the same mutation.

In some aspects, provided herein is a composition comprising: a first peptide comprising a first neoepitope of a region of a protein and a second peptide comprising a second neoepitope of the region of the same protein, wherein the first neoepitope and the second neoepitope comprise at least one amino acid of the region that is the same, a polynucleotide encoding the first peptide and the second peptide, on or more APCs comprising the first peptide and the second peptide, or a first T cell receptor (TCR) specific for the first neoepitope in complex with an HLA protein and a second TCR specific for the second neoepitope in complex with an HLA protein; wherein the first peptide is different from the second peptide, and wherein the first neoepitope comprises a first mutation and the second neoepitope comprises a second mutation.

In some embodiments, the first mutation and the second mutation are the same. In some embodiments, the first peptide and the second peptide are different molecules. In some embodiments, the first neoepitope comprises a first neoepitope of a region of the same protein, wherein the second neoepitope comprises a second neoepitope of the region of the same protein. In some embodiments, the first neoepitope and the second neoepitope comprise at least one amino acid of the region that is the same. In some embodiments, the region of the protein comprises at least 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500, 600, 700, 800, 900, or 1,000 contiguous amino acids of the protein. In some embodiments, the region of the protein comprises at most 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500, 600, 700, 800, 900, or 1,000 contiguous amino acids of the protein. In some embodiments, the first neoepitope binds to a class I HLA protein to form a class I HLA-peptide complex. In some embodiments, the second neoepitope binds to a class II HLA protein to form a class II HLA-peptide complex. In some embodiments, the second neoepitope binds to a class I HLA protein to form a class I HLA-peptide complex. In some embodiments, the first neoepitope binds to a class II HLA protein to form a class II HLA-peptide complex. In some embodiments, the first neoepitope is a first neoepitope peptide processed from the first peptide and/or the second neoepitope is a second neoepitope peptide processed from the second peptide. In some embodiments, the first neoepitope is shorter in length than first peptide and/or the second neoepitope is shorter in length than second peptide. In some embodiments, the first neoepitope peptide is processed by an antigen presenting cell (APC) comprising the first peptide and/or the second neoepitope peptide is processed by an APC comprising the second peptide. In some embodiments, the first neoepitope activates CD8+ T cells. In some embodiments, the second neoepitope activates CD4+ T cells. In some embodiments, the second neoepitope activates CD8+ T cells. In some embodiments, the first neoepitope activates CD4+ T cells. In some embodiments, a TCR of a CD4+ T cell binds to a class II HLA-peptide complex comprising the first or second peptide. In some embodiments, a TCR of a CD8+ T cell binds to a class I HLA-peptide complex comprising the first or second peptide. In some embodiments, a TCR of a CD4+ T cell binds to a class I HLA-peptide complex comprising the first or second peptide. In some embodiments, a TCR of a CD8+ T cell binds to a class II HLA-peptide complex comprising the first or second peptide. In some embodiments, the one or more APCs comprise a first APC comprising the first peptide and a second APC comprising the second peptide. In some embodiments, the mutation is selected from the group consisting of a point mutation, a splice-site mutation, a frameshift mutation, a read-through mutation, a gene fusion mutation and any combination thereof. In some embodiments, the first neoepitope and the second neoepitope comprises a sequence encoded by a gene of Table 1 or 2. In some embodiments, the protein is encoded by a gene of Table 1 or 2. In some embodiments, the mutation is a mutation of column 2 of Table 1 or 2. In some embodiments, the protein is KRAS. In some embodiments, a single polypeptide comprises the first peptide and the second peptide, or a single polynucleotide encodes the first peptide and the second peptide. In some embodiments, the first peptide and the second peptide are encoded by a sequence transcribed from a same transcription start site. In some embodiments, the first peptide is encoded by a sequence transcribed from a first transcription start site and the second peptide is encoded by a sequence transcribed from a second transcription start site. In some embodiments, the single polypeptide has a length of at least 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the polypeptide comprises a first sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, sequence identity to a first corresponding wild-type sequence; and a second sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, sequence identity to a corresponding second wild-type sequence. In some embodiments, the polypeptide comprises a first sequence of at least 8 or 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, sequence identity to a corresponding first wild-type sequence; and a second sequence of at least 16 or 17 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, sequence identity to a corresponding second wild-type sequence. In some embodiments, the second peptide is longer than the first peptide. In some embodiments, the first peptide is longer than the second peptide. In some embodiments, the first peptide has a length of at least 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the second peptide has a length of at least 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the first peptide comprises a sequence of at least 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the second peptide comprises a sequence of at least 17 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the second neoepitope is longer than the first neoepitope. In some embodiments, the first neoepitope has a length of at least 8 amino acids. In some embodiments, the first neoepitope has a length of from 8 to 12 amino acids. In some embodiments, the first neoepitope comprises a sequence of at least 8 contiguous amino acids, wherein at least 2 of the 8 contiguous amino acids are different at corresponding positions of a wild-type sequence. In some embodiments, the second neoepitope has a length of at least 16 amino acids. In some embodiments, the second neoepitope has a length of from 16 to 25 amino acids. In some embodiments, the second neoepitope comprises a sequence of at least 16 contiguous amino acids, wherein at least 2 of the 16 contiguous amino acids are different at corresponding positions of a wild-type sequence.

In some embodiments, the second peptide has a length of at most 13 amino acids. In some embodiments, the second peptide has a length of at least 8; 9; 10; 11; or 12 amino acids. In some embodiments, the first peptide has a length of at least one amino acid longer than the second peptide. In some embodiments, the first peptide has a length of at least 9, 10, 11, 12, 13, 14, 15, 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the second peptide comprises a sequence of at least 8 or 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the first peptide comprises a sequence of at least 9 or 10 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the second neoepitope is longer than the first neoepitope. In some embodiments, the second neoepitope has a length of at least 8 amino acids. In some embodiments, the second neoepitope has a length of from 8 to 12 amino acids. In some embodiments, the second neoepitope comprises a sequence of at least 8 contiguous amino acids, wherein at least 2 of the 8 contiguous amino acids are different at corresponding positions of a wild-type sequence. In some embodiments, the second neoepitope is comprised within the first peptide. In some embodiments, the first neoepitope has a length of at least 9 amino acids. In some embodiments, the first neoepitope has a length of from 9 to 25 amino acids. In some embodiments, the first neoepitope comprises a sequence of at least 9 contiguous amino acids, wherein at least 2 of the 16 contiguous amino acids are different at corresponding positions of a wild-type sequence.

In some embodiments, the first peptide comprises at least one an additional mutation. In some embodiments, one or more of the at least one additional mutation is not a mutation in the first neoepitope. In some embodiments, one or more of the at least one additional mutation is a mutation in the first neoepitope. In some embodiments, the second peptide comprises at least one additional mutation. In some embodiments, one or more of the at least one additional mutation is not a mutation in the second neoepitope. In some embodiments, one or more of the at least one additional mutation is a mutation in the second neoepitope. In some embodiments, the first peptide, the second peptide or both comprise at least one flanking sequence, wherein the at least one flanking sequence is upstream or downstream of the neoepitope. In some embodiments, the at least one flanking sequence has at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a corresponding wild-type sequence. In some embodiments, the at least one flanking sequence comprises a non-wild-type sequence. In some embodiments, the at least one flanking sequence is a N-terminus flanking sequence. In some embodiments, the at least one flanking sequence is a C-terminus flanking sequence. In some embodiments, the at least one flanking sequence of the first peptide has at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the at least one flanking sequence of the second peptide. In some embodiments, the at least one flanking region of the first peptide is different from the at least one flanking region of the second peptide. In some embodiments, the at least one flanking residue comprises the mutation. In some embodiments, the first neoepitope, the second neoepitope or both comprises at least one anchor residue. In some embodiments, the at least one anchor residue of the first neoepitope is at a canonical anchor position. In some embodiments, the at least one anchor residue of the first neoepitope is at a non-canonical anchor position. In some embodiments, the at least one anchor residue of the second neoepitope is at a canonical anchor position. In some embodiments, the at least one anchor residue of the second neoepitope is at a non-canonical anchor position. In some embodiments, the at least one anchor residue of the first neoepitope is different from the at least one anchor residue of the second neoepitope. In some embodiments, the at least one anchor residue is a wild-type residue. In some embodiments, the at least one anchor residue is a substitution. In some embodiments, the first neoepitope and/or the second neoepitope binds to an HLA protein with a greater affinity than a corresponding neoepitope without the substitution. In some embodiments, the first neoepitope and/or the second neoepitope binds to an HLA protein with a greater affinity than a corresponding wild-type sequence without the substitution. In some embodiments, at least one anchor residue does not comprise the mutation. In some embodiments, the first neoepitope, the second neoepitope or both comprise at least one anchor residue flanking region. In some embodiments, the neoepitope comprises at least one anchor residue. In some embodiments, the at least one anchor residues comprises at least two anchor residues. In some embodiments, the at least two anchor residues are separated by a separation region comprising at least 1 amino acid. In some embodiments, the at least one anchor residue flanking region is not within the separation region. In some embodiments, the at least one anchor residue flanking region is upstream of a N-terminal anchor residue of the at least two anchor residues downstream of a C-terminal anchor residue of the at least two anchor residue both (a) and (b).

In some embodiments, composition comprises an adjuvant. In some embodiments, the composition comprises one or more additional peptides, wherein the one or more additional peptides comprise a third neoepitope. In some embodiments, the first and/or second neoepitope binds to an HLA protein with a greater affinity than a corresponding wild-type sequence. In some embodiments, the first and/or second neoepitope binds to an HLA protein with a KD or an IC50 less than 1000 nM, 900 nM, 800 nM, 700 nM, 600 nM, 500 nM, 250 nM, 150 nM, 100 nM, 50 nM, 25 nM or 10 nM. In some embodiments, the first and/or second neoepitope binds to an HLA class I protein with a KD or an IC50 less than 1000 nM, 900 nM, 800 nM, 700 nM, 600 nM, 500 nM, 250 nM, 150 nM, 100 nM, 50 nM, 25 nM or 10 nM. In some embodiments, the first and/or second neoepitope binds to an HLA class II protein with a KD or an IC50 less than 1000 nM, 900 nM, 800 nM, 700 nM, 600 nM, 500 nM, 250 nM, 150 nM, 100 nM, 50 nM, 25 nM or 10 nM. In some embodiments, the first and/or second neoepitope binds to a protein encoded by an HLA allele expressed by a subject. In some embodiments, the mutation is not present in non-cancer cells of a subject. In some embodiments, the first and/or second neoepitope is encoded by a gene or an expressed gene of a subject's cancer cells. In some embodiments, the composition comprises a first T cell comprising the first TCR. In some embodiments, the composition comprises a second T cell comprising the second TCR. In some embodiments, the first TCR comprises a non-native intracellular domain and/or the second TCR comprises a non-native intracellular domain. In some embodiments, the first TCR is a soluble TCR and/or the second TCR is a soluble TCR. In some embodiments, the first and/or second T cell is a cytotoxic T cell. In some embodiments, the first and/or second T cell is a gamma delta T cell. In some embodiments, the first and/or second T cell is a helper T cell. In some embodiments, the first T cell is a T cell stimulated, expanded or induced with the first neoepitope and/or the second T cell is a T cell stimulated, expanded or induced with the second neoepitope. In some embodiments, the first and/or second T cell is an autologous T cell. In some embodiments, the first and/or second T cell is an allogenic T cell. In some embodiments, the first and/or second T cell is an engineered T cell. In some embodiments, the first and/or second T cell is a T cell of a cell line. In some embodiments, the first and/or second TCR binds to an HLA-peptide complex with a KD or an IC50 of less than 1000 nM, 900 nM, 800 nM, 700 nM, 600 nM, 500 nM, 250 nM, 150 nM, 100 nM, 50 nM, 25 nM or 10 nM. In some aspects, provided herein is a vector comprising a polynucleotide encoding a first and a second peptide described herein. In some embodiments, the polynucleotide is operably linked to a promoter. In some embodiments, the vector is a self-amplifying RNA replicon, plasmid, phage, transposon, cosmid, virus, or virion. In some embodiments, the vector is a viral vector. In some embodiments, the vector is derived from a retrovirus, lentivirus, adenovirus, adeno-associated virus, herpes virus, pox virus, alpha virus, vaccina virus, hepatitis B virus, human papillomavirus or a pseudotype thereof. In some embodiments, the vector is a non-viral vector. In some embodiments, the non-viral vector is a nanoparticle, a cationic lipid, a cationic polymer, a metallic nanopolymer, a nanorod, a liposome, a micelle, a microbubble, a cell-penetrating peptide, or a liposphere.

In some aspects, provided herein is a pharmaceutical composition comprising: a composition described herein, or a vector described herein; and a pharmaceutically acceptable excipient.

In some embodiments, the plurality of cells is autologous cells. In some embodiments, the plurality of APC cells is autologous cells. In some embodiments, the plurality of T cells is autologous cells. In some embodiments, the pharmaceutical composition further comprises an immunomodulatory agent or an adjuvant. In some embodiments, the immunomodulatory agent is a cytokine. In some embodiments, the adjuvant is Hiltonol.

In some aspects, provided herein is a method of treating cancer, the method comprising administering to a subject in need thereof a pharmaceutical composition described herein.

In some aspects, provided herein is a method of preventing resistance to a cancer therapy, the method comprising administering to a subject in need thereof a pharmaceutical composition described herein.

In some aspects, provided herein is a method of inducing an immune response, the method comprising administering to a subject in need thereof a pharmaceutical composition described herein.

In some embodiments, the immune response is a humoral response. In some embodiments, the first peptide and the second peptide are administered simultaneously, separately or sequentially. In some embodiments, the first peptide is sequentially administered after the second peptide. In some embodiments, the second peptide is sequentially administered after the first peptide. In some embodiments, the first peptide is sequentially administered after a time period sufficient for the second peptide to activate the T cells. In some embodiments, the second peptide is sequentially administered after a time period sufficient for the first peptide to activate the T cells. In some embodiments, the first peptide is sequentially administered after the second peptide to restimulate the T cells. In some embodiments, the second peptide is sequentially administered after the first peptide to restimulate the T cells. In some embodiments, the first peptide is administered to stimulate the T cells and the second peptide is administered after the first peptide to restimulate the T cells. In some embodiments, the second peptide is administered to stimulate the T cells and the first peptide is administered after the second peptide to restimulate the T cells. In some embodiments, the subject has cancer, wherein the cancer is selected from the group consisting of melanoma, ovarian cancer, lung cancer, prostate cancer, breast cancer, colorectal cancer, endometrial cancer, and chronic lymphocytic leukemia (CLL). In some embodiments, the subject has a breast cancer that is resistant to anti-estrogen therapy. In some embodiments, the breast cancer expresses an estrogen receptor with a mutation. In some embodiments, the subject has a CLL that is resistant to ibrutinib therapy. In some embodiments, the CLL expresses a Bruton tyrosine kinase with a mutation, such as a C481S mutation. In some embodiments, the subject has a lung cancer that is resistant to a tyrosine kinase inhibitor. In some embodiments, the lung cancer expresses an epidermal growth factor receptor (EGFR) with a mutation, such as a T790M, L792F, or C797S mutation. In some embodiments, the plurality of APC cells comprising the first peptide and the plurality of APC cells comprising the second peptide are administered simultaneously, separately or sequentially. In some embodiments, the plurality of T cells comprising the first TCR and the plurality of T cells comprising the second TCR are administered simultaneously, separately or sequentially. In some embodiments, the method further comprises administering at least one additional therapeutic agent or modality. In some embodiments, the at least one additional therapeutic agent or modality is surgery, a checkpoint inhibitor, an antibody or fragment thereof, a chemotherapeutic agent, radiation, a vaccine, a small molecule, a T cell, a vector, and APC, a polynucleotide, an oncolytic virus or any combination thereof. In some embodiments, the at least one additional therapeutic agent is an anti-PD-1 agent and anti-PD-L1 agent, an anti-CTLA-4 agent, or an anti-CD40 agent. In some embodiments, the additional therapeutic agent is administered before, simultaneously, or after administering a pharmaceutical composition according described herein.

Peptides

In aspects, the present disclosure provides isolated peptides that comprise a tumor specific mutation from Table 1 or 2. These peptides and polypeptides are referred to herein as "neoantigenic peptides" or "neoantigenic polypeptides". The term "peptide" is used interchangeably with "mutant peptide", "neoantigen peptide" and "neoantigenic peptide" in the present specification to designate a series of residues, typically L-amino acids, connected one to the other, typically by peptide bonds between the α-amino and carboxyl groups of adjacent amino acids. Similarly, the term "polypeptide" is used interchangeably with "mutant polypeptide", "neoantigen polypeptide" and "neoantigenic polypeptide" in the present specification to designate a series of residues, e.g., L-amino acids, connected one to the other, typically by peptide bonds between the α-amino and carboxyl groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

TABLE 1

| Gene | Exemplary Protein Change | Mutation Sequence Context | Peptides (HLA allele example(s)) | Exemplary Diseases |
|------|--------------------------|---------------------------|----------------------------------|---------------------|
| TABLE 1A | | POINT MUTATION [1] | | |
| ABL1 | E255K | VADGLITTLHYPAPK RNKPTVYGVSPNYD KWEMERTDITMKHK LGGGQYGKVYEGV WKKYSLTVAVKTLK EDTMEVEEFLKEAAV MKEIKHPNLVQLLGV C (SEQ ID NO: 1) | GQYGKVYEG (A02.01) (SEQ ID NO: 140) GQYGKVYEGV (A02.01) (SEQ ID NO: 141) KLGGGQYGK (A03.01) (SEQ ID NO: 142) KLGGGQYGKV (A02.01) (SEQ ID NO: 143) KVYEGVWKK (A02.01, A03.01) (SEQ ID NO: 144) KVYEGVWKKY (A03.01) (SEQ ID NO: 145) QYGKVYEGV (A24.02) (SEQ ID NO: 146) QYGKVYEGVW (A24.02) (SEQ ID NO: 147) | Chronic myeloid leukemia (CML), Acute lymphocytic leukemia (ALL), Gastrointestinal stromal tumors (GIST) |
| ABL1 | E255V | VADGLITTLHYPAPK RNKPTVYGVSPNYD KWEMERTDITMKHK LGGGQYGVVYEGV WKKYSLTVAVKTLK EDTMEVEEFLKEAAV | GQYGVVYEG (A02.01) (SEQ ID NO: 148) GQYGVVYEGV (A02.01) (SEQ ID NO: 149) KLGGGQYGV (A02.01) (SEQ ID NO: 150) | Chronic myeloid leukemia (CML), Acute lymphocytic leukemia (ALL), Gastrointestinal stromal tumors (GIST) |

TABLE 1-continued

| Gene | Exemplary Protein Change | Mutation Sequence Context | Peptides (HLA allele example(s)) | Exemplary Diseases |
|---|---|---|---|---|
| | | MKEIKHPNLVQLLGV C (SEQ ID NO: 2) | KLGGGQYGVV (A02.01) (SEQ ID NO: 151) QYGVVYEGV (A24.02) (SEQ ID NO: 152) QYGVVYEGVW (A24.02) (SEQ ID NO: 153) VVYEGVWKK (A02.01, A03.01) (SEQ ID NO: 154) VVYEGVWKKY (A03.01) (SEQ ID NO: 155) | |
| ABL1 | M351T | LLGVCTREPPFYIITEF MTYGNLLDYLRECN RQEVNAVVLLYMAT QISSATEYLEKKNFIH RDLAARNCLVGENH LVKVADFGLSRLMT GDTYTAHAGAKF (SEQ ID NO: 3) | ATQISSATEY (A01.01) (SEQ ID NO: 156) ISSATEYLEK (A03.01) (SEQ ID NO: 157) SSATEYLEK (A03.01) (SEQ ID NO: 158) TQISSATEYL (A02.01) (SEQ ID NO: 159) YMATQISSAT (A02.01) (SEQ ID NO: 160) | Chronic myeloid leukemia (CML), Acute lymphocytic leukemia (ALL), Gastrointestinal stromal tumors (GIST) |
| ABL1 | T315I | SLTVAVKTLKEDTME VEEFLKEAAVMKEIK HPNLVQLLGVCTREP PFYIIIEFMTYGNLLD YLRECNRQEVNAVV LLYMATQISSAMEYL EKKNFIHRDLA (SEQ ID NO: 4) | FYIIIEFMTY (A24.02) (SEQ ID NO: 161) IIEFMTYGNL (A02.01) (SEQ ID NO: 162) IIIEFMTYG (A02.01) (SEQ ID NO: 163) IIIEFMTYGN (A02.01) (SEQ ID NO: 164) YIIIEFMTYG (A02.01) (SEQ ID NO: 165) | Chronic myeloid leukemia (CML), Acute lymphocytic leukemia (ALL), Gastrointestinal stromal tumors (GIST) |
| ABL1 | Y253H | STVADGLITTLHYPA PKRNKPTVYGVSPNY DKWEMERTDITMKH KLGGGQHGEVYEGV WKKYSLTVAVKTLK EDTMEVEEFLKEAAV MKEIKHPNLVQLLG (SEQ ID NO: 5) | GQHGEVYEGV (A02.01) (SEQ ID NO: 166) KLGGGQHGEV (A02.01) (SEQ ID NO: 167) | Chronic myeloid leukemia (CML), Acute lymphocytic leukemia (ALL), Gastrointestinal stromal tumors (GIST) |
| ALK | G1269A | SSLAMLDLLHVARDI ACGCQYLEENHFIHR DIAARNCLLTCPGPG RVAKIADFGMARDIY RASYYRKGGCAMLP VKWMPPEAFMEGIFT SKTDTWSFGVLL (SEQ ID NO: 6) | KIADFGMAR (A03.01) (SEQ ID NO: 168) RVAKIADFGM (A02.01, B07.02) (SEQ ID NO: 169) | NSCLC |
| ALK | L1196M | QVAVKTLPEVCSEQD ELDFLMEALIISKFNH QNIVRCIGVSLQSLPR FILMELMAGGDLKSF LRETRPRPSQPSSLA MLDLLHVARDIACG CQYLEENHFI (SEQ ID NO: 7) | FILMELMAGG (A02.01) (SEQ ID NO: 170) ILMELMAGG (A02.01) (SEQ ID NO: 171) ILMELMAGGD (A02.01) (SEQ ID NO: 172) LMELMAGGDL (A02.01) (SEQ ID NO: 173) LPRFILMEL (B07.02, B08.01) (SEQ ID NO: 174) LPRFILMELM (B07.02) (SEQ ID NO: 175) LQSLPRFILM (A02.01, B08.01) (SEQ ID NO: 176) SLPRFILMEL (A02.01, A24.02, B07.02, B08.01) (SEQ ID NO: 177) | NSCLC |

TABLE 1-continued

| Gene | Exemplary Protein Change | Mutation Sequence Context | Peptides (HLA allele example(s)) | Exemplary Diseases |
|---|---|---|---|---|
| BRAF | V600E | MIKLIDIARQTAQGM DYLHAKSIIHRDLKS NNIFLHEDLTVKIGDF GLATEKSRWSGSHQF EQLSGSILWMAPEVI RMQDKNPYSFQSDV YAFGIVLYELM (SEQ ID NO: 8) | LATEKSRWS (A02.01, B08.01) (SEQ ID NO: 178) LATEKSRWSG (A02.01, B08.01) (SEQ ID NO: 179) | CRC, GBM, KIRP, LUAD, SKCM, THCA |
| BTK | C481S | MIKEGSMSEDEFIEEA KVMMNLSHEKLVQL YGVCTKQRPIFIITEY MANGSLLNYLREMR HRFQTQQLLEMCKD VCEAMEYLESKQFLH RDLAARNCLVND (SEQ ID NO: 9) | EYMANGSLL (A24.02) (SEQ ID NO: 180) MANGSLLNY (A01.01, A03.01, A11.01) (SEQ ID NO: 181) MANGSLLNYL (A02.01, B07.02, B08.01) (SEQ ID NO: 182) SLLNYLREM (A02.01, B07.02, B08.01) (SEQ ID NO: 183) YMANGSLLN (A02.01) (SEQ ID NO: 184) YMANGSLLNY (A01.01, A03.01, A11.01) (SEQ ID NO: 185) | CLL |
| EEF1B2 | S43G | MGFGDLKSPAGLQV LNDYLADKSYIEGYV PSQADVAVFEAVSGP PPADLCHALRWYNHI KSYEKEKASLPGVKK ALGKYGPADVEDTT GSGAT (SEQ ID NO: 10) | GPPPADLCHAL (B07.02) (SEQ ID NO: 186) | BLCA, KIRP, PRAD, SKCM |
| EGFR | S492R | SLNITSLGLRSLKEIS DGDVIISGNKNLCYA NTINWKKLFGTSGQK TKIIRNRGENSCKAT GQVCHALCSPEGCW GPEPRDCVSCRNVSR GRECVDKCNLL (SEQ ID NO: 11) | IIRNRGENSCK (A03.01) (SEQ ID NO: 187) | CRC |
| EGFR | T790M | IPVAIKELREATSPKA NKEILDEAYVMASV DNPHVCRLLGICLTS TVQLIMQLMPFGCLL DYVREHKDNIGSQYL LNWCVQIAKGMNYL EDRRLVHRDLAA (SEQ ID NO: 12) | CLTSTVQLIM (A01.01, A02.01) (SEQ ID NO: 188) IMQLMPFGC (A02.01) (SEQ ID NO: 189) IMQLMPFGCL (A02.01, A24.02, B08.01) (SEQ ID NO: 190) LIMQLMPFG (A02.01) (SEQ ID NO: 191) LIMQLMPFGC (A02.01) (SEQ ID NO: 192) LTSTVQLIM (A01.01) (SEQ ID NO: 193) MQLMPFGCL (A02.01, B07.02, B08.01) (SEQ ID NO: 194) MQLMPFGCLL (A02.01, A24.02, B08.01) (SEQ ID NO: 195) QLIMQLMPF (A02.01, A24.02, B08.01) (SEQ ID NO: 196) QLIMQLMPFG (A02.01) (SEQ ID NO: 197) STVQLIMQL (A02.01) (SEQ ID NO: 198) VQLIMQLMPF (A02.01, A24.02, B08.01) (SEQ ID NO: 199) | NSCLC, PRAD |

TABLE 1-continued

| Gene | Exemplary Protein Change | Mutation Sequence Context | Peptides (HLA allele example(s)) | Exemplary Diseases |
|---|---|---|---|---|
| ERBB3 | V104M | ERCEVVMGNLEIVLT GHNADLSFLQWIREV TGYVLVAMNEFSTLP LPNLRMVRGTQVYD GKFAIFVMLNYNTNS SHALRQLRLTQLTEIL SGGVYIEKNDK (SEQ ID NO: 13) | | CRC, Stomach Cancer |
| ESR1 | D538G | HLMAKAGLTLQQQH QRLAQLLLILSHIRH MSNKGMEHLYSMKC KNVVPLYGLLLEML DAHRLHAPTSRGGAS VEETDQSHLATAGST SSHSLQKYYITGEA (SEQ ID NO: 14) | GLLLEMLDA (A02.01) (SEQ ID NO: 200) LYGLLLEML (A24.02) (SEQ ID NO: 201) NVVPLYGLL (A02.01) (SEQ ID NO: 202) PLYGLLLEM (A02.01) (SEQ ID NO: 203) PLYGLLLEML (A02.01, A24.02) (SEQ ID NO: 204) VPLYGLLLEM (B07.02) (SEQ ID NO: 205) VVPLYGLLL (A02.01, A24.02) (SEQ ID NO: 206) | Breast Cancer |
| ESR1 | S463P | NQGKCVEGMVEIFD MLLATSSRFRMMNL QGEEFVCLKSIILLNS GVYTFLPSTLKSLEE KDHIHRVLDKITDTLI HLMAKAGLTLQQQH QRLAQLLLILSH (SEQ ID NO: 15) | FLPSTLKSL (A02.01, A24.02, B08.01) (SEQ ID NO: 207) GVYTFLPST (A02.01) (SEQ ID NO: 208) GVYTFLPSTL (A02.01, A24.02) (SEQ ID NO: 209) TFLPSTLKSL (A24.02) (SEQ ID NO: 210) VYTFLPSTL (A24.02) (SEQ ID NO: 211) YTFLPSTLK (A03.01) (SEQ ID NO: 212) | Breast Cancer |
| ESR1 | Y537C | IHLMAKAGLTLQQQ HQRLAQLLLILSHIRH MSNKGMEHLYSMKC KNVVPLCDLLLEML DAHRLHAPTSRGGAS VEETDQSHLATAGST SSHSLQKYYITGE (SEQ ID NO: 16) | NVVPLCDLL (A02.01) (SEQ ID NO: 213) NVVPLCDLLL (A02.01) (SEQ ID NO: 214) PLCDLLLEM (A02.01) (SEQ ID NO: 215) PLCDLLLEML (A02.01) (SEQ ID NO: 216) VPLCDLLLEM (B07.02) (SEQ ID NO: 217) VVPLCDLLL (A02.01, A24.02) (SEQ ID NO: 218) | Breast Cancer |
| ESR1 | Y537N | IHLMAKAGLTLQQQ HQRLAQLLLILSHIRH MSNKGMEHLYSMKC KNVVPLNDLLLEML DAHRLHAPTSRGGAS VEETDQSHLATAGST SSHSLQKYYITGE (SEQ ID NO: 17) | NVVPLNDLL (A02.01) (SEQ ID NO: 219) NVVPLNDLLL (A02.01) (SEQ ID NO: 220) PLNDLLLEM (A02.01) (SEQ ID NO: 221) PLNDLLLEML (A02.01) (SEQ ID NO: 222) VPLNDLLLEM (B07.02) (SEQ ID NO: 223) | Breast Cancer |
| ESR1 | Y537S | IHLMAKAGLTLQQQ HQRLAQLLLILSHIRH MSNKGMEHLYSMKC KNVVPLSDLLLEMLD AHRLHAPTSRGGASV EETDQSHLATAGSTS SHSLQKYYITGE (SEQ ID NO: 18) | NVVPLSDLL (A02.01) (SEQ ID NO: 224) NVVPLSDLLL (A02.01) (SEQ ID NO: 225) PLSDLLLEM (A02.01) (SEQ ID NO: 226) PLSDLLLEML (A02.01) (SEQ ID NO: 227) VPLSDLLLEM (B07.02) (SEQ ID NO: 228) | Breast Cancer |

TABLE 1-continued

| Gene | Exemplary Protein Change | Mutation Sequence Context | Peptides (HLA allele example(s)) | Exemplary Diseases |
|---|---|---|---|---|
| | | | VVPLSDLLL (A02.01, A24.02) (SEQ ID NO: 229) | |
| FGFR3 | S249C | HRIGGIKLRHQQWSL VMESVVPSDRGNYT CVVENKFGSIRQTYT LDVLERCPHRPILQA GLPANQTAVLGSDVE FHCKVYSDAQPHIQ WLKHVEVNGSKVG (SEQ ID NO: 19) | VLERCPHRPI (A02.01, B08.01) (SEQ ID NO: 230) YTLDVLERC (A02.01) (SEQ ID NO: 231) | BLCA, HNSC, KIRP, LUSC |
| FRG1B | L52S | AVKLSDSRIALKSGY GKYLGINSDELVGHS DAIGPREQWEPVFQN GKMALSASNSCFIRC NEAGDIEAKSKTAGE EEMIKIRSCAEKETK KKDDIPEEDKG (SEQ ID NO: 20) | FQNGKMALS (A02.01) (SEQ ID NO: 232) | GBM, KIRP, PRAD, SKCM |
| HER2 | V777L (Resistance) | GSGAFGTVYKGIWIP DGENVKIPVAIKVLR ENTSPKANKEILDEA YVMAGLGSPYVSRL LGICLTSTVQLVTQL MPYGCLLDHVRENR GRLGSQDLLNWCM (SEQ ID NO: 21) | VMAGLGSPYV (A02.01, A03.01) (SEQ ID NO: 233) | BRCA |
| IDH1 | R132H | RVEEFKLKQMWKSP NGTIRNILGGTVFREA IICKNIPRLVSGWVKP IIIGHHAYGDQYRAT DFVVPGPGKVEITYT PSDGTQKVTYLVHNF EEGGGVAMGM (SEQ ID NO: 22) | KPIIIGHHA (B07.02) (SEQ ID NO: 234) | BLCA, GBM, PRAD |
| IDH1 | R132C | RVEEFKLKQMWKSP NGTIRNILGGTVFREA IICKNIPRLVSGWVKP IIIGCHAYGDQYRAT DFVVPGPGKVEITYT PSDGTQKVTYLVHNF EEGGGVAMGM (SEQ ID NO: 23) | KPIIIGCHA (B07.02) (SEQ ID NO: 235) | BLCA, GBM, PRAD |
| IDH1 | R132G | RVEEFKLKQMWKSP NGTIRNILGGTVFREA IICKNIPRLVSGWVKP IIIGGHAYGDQYRAT DFVVPGPGKVEITYT PSDGTQKVTYLVHNF EEGGGVAMGM (SEQ ID NO: 24) | KPIIIGGHA (B07.02) (SEQ ID NO: 236) | BLCA, BRCA, CRC, GBM, HNSC, LUAD, PAAD, PRAD, UCEC |
| IDH1 | R132S | RVEEFKLKQMWKSP NGTIRNILGGTVFREA IICKNIPRLVSGWVKP IIIGSHAYGDQYRATD FVVPGPGKVEITYTPS DGTQKVTYLVHNFE EGGGVAMGM (SEQ ID NO: 25) | KPIIIGSHA (B07.02) (SEQ ID NO: 237) | BLCA, BRCA, GBM, HNSC, LIHC, LUAD, LUSC, PAAD, SKCM, UCEC |
| KIT | T670I | VAVKMLKPSAHLTE REALMSELKVLSYLG NHMNIVNLLGACTIG GPTLVIIEYCCYGDLL NFLRRKRDSFICSKQE DHAEAALYKNLLHS KESSCSDSTNE (SEQ ID NO: 26) | IIEYCCYGDL (A02.01) (SEQ ID NO: 238) TIGGPTLVII (A02.01) (SEQ ID NO: 239) VIIEYCCYG (A02.01) (SEQ ID NO: 240) | Gastrointestinal stromal tumors (GIST) |

TABLE 1-continued

| Gene | Exemplary Protein Change | Mutation Sequence Context | Peptides (HLA allele example(s)) | Exemplary Diseases |
|---|---|---|---|---|
| KIT | V654A | VEATAYGLIKSDAA MTVAVKMLKPSAHL TEREALMSELKVLSY LGNHMNIANLLGAC TIGGPTLVITEYCCYG DLLNFLRRKRDSFICS KQEDHAEAALYK (SEQ ID NO: 27) | HMNIANLLGA (A02.01) (SEQ ID NO: 241) IANLLGACTI (A02.01) (SEQ ID NO: 242) MNIANLLGA (A02.01) (SEQ ID NO: 243) YLGNHMNIA (A02.01, B08.01) (SEQ ID NO: 244) YLGNHMNIAN (A02.01) (SEQ ID NO: 245) | Gastrointestinal stromal tumors (GIST) |
| MEK | C121S | ISELGAGNGGVVFKV SHKPSGLVMARKLIH LEIKPAIRNQIIRELQV LHESNSPYIVGFYGA FYSDGEISICMEHMD GGSLDQVLKKAGRIP EQILGKVSI (SEQ ID NO: 28) | VLHESNSPY (A03.01) (SEQ ID NO: 246) VLHESNSPYI (A02.01) (SEQ ID NO: 247) | Melanoma |
| MEK | P124L | LGAGNGGVVFKVSH KPSGLVMARKLIHLE IKPAIRNQHIRELQVL HECNSLYIVGFYGAF YSDGEISICMEHMDG GSLDQVLKKAGRIPE QILGKVSIAVI (SEQ ID NO: 29) | LQVLHECNSL (A02.01, B08.01) (SEQ ID NO: 248) LYIVGFYGAF (A24.02) (SEQ ID NO: 249) NSLYIVGFY (A01.01) (SEQ ID NO: 250) QVLHECNSL (A02.01, B08.01) (SEQ ID NO: 251) SLYIVGFYG (A02.01) (SEQ ID NO: 252) SLYIVGFYGA (A02.01) (SEQ ID NO: 253) VLHECNSLY (A03.01) (SEQ ID NO: 254) VLHECNSLYI (A02.01, A03.01) (SEQ ID NO: 255) | Melanoma |
| MYC | E39D | MPLNVSFTNRNYDL DYDSVQPYFYCDEEE NFYQQQQQSDLQPPA PSEDIWKKFELLPTPP LSPSRRSGLCSPSYVA VTPFSLRGDNDGG (SEQ ID NO: 30) | FYQQQQQSDL (A24.02) (SEQ ID NO: 256) QQQSDLQPPA (A02.01) (SEQ ID NO: 257) QQSDLQPPA (A02.01) (SEQ ID NO: 258) YQQQQQSDL (A02.01, B08.01) (SEQ ID NO: 259) | Lymphoid Cancer; Burkitt Lymphoma |
| MYC | P57S | FTNRNYDLDYDSVQP YFYCDEEENFYQQQ QQSELQPPAPSEDIW KKFELLSTPPLSPSRR SGLCSPSYVAVTPFSL RGDNDGGGSFSTA DQLEMVTELLG (SEQ ID NO: 31) | FELLSTPPL (A02.01, B08.01) (SEQ ID NO: 260) LLSTPPLSPS (A02.01) (SEQ ID NO: 261) | Lymphoid Cancer |
| MYC | T58I | TNRNYDLDYDSVQP YFYCDEEENFYQQQ QQSELQPPAPSEDIW KKFELLPIPPLSPSRRS GLCSPSYVAVTPFSL RGDNDGGGSFSTA DQLEMVTELLGG (SEQ ID NO: 32) | FELLPIPPL (A02.01) (SEQ ID NO: 262) IWKKFELLPI (A24.02) (SEQ ID NO: 263) LLPIPPLSPS (A02.01, B07.02) (SEQ ID NO: 264) LPIPPLSPS (B07.02) (SEQ ID NO: 265) | Neuroblastoma |
| PDGFRa | T674I | VAVKMLKPTARSSE KQALMSELKIMTHLG PHLNIVNLLGACTKS GPIYIIIEYCFYGDLV NYLHKNRDSFLSHHP EKPKKELDIFGLNPA | IIEYCFYGDL (A02.01) (SEQ ID NO: 266) IIIEYCFYG (A02.01) (SEQ ID NO: 267) IYIIIEYCF (A24.02) (SEQ ID NO: 268) | Chronic Eosinophilic Leukemia |

TABLE 1-continued

| Gene | Exemplary Protein Change | Mutation Sequence Context | Peptides (HLA allele example(s)) | Exemplary Diseases |
|---|---|---|---|---|
| | | DESTRSYVILS (SEQ ID NO: 33) | IYIIIEYCFY (A24.02) (SEQ ID NO: 269) YIIIEYCFYG (A02.01) (SEQ ID NO: 270) | |
| PIK3CA | E542K | IEEHANWSVSREAGF SYSHAGLSNRLARDN ELRENDKEQLKAIST RDPLSKITEQEKDFL WSHRHYCVTIPEILPK LLLSVKWNSRDEVA QMYCLVKDWPP (SEQ ID NO: 34) | KITEQEKDFL (A02.01) (SEQ ID NO: 271) | BLCA, BRCA, CESC, CRC, GBM, HNSC, KIRC, KIRP, LIHC, LUAD, LUSC, PRAD, UCEC |
| PIK3CA | E545K | HANWSVSREAGFSYS HAGLSNRLARDNELR ENDKEQLKAISTRDP LSEITKQEKDFLWSH RHYCVTIPEILPKLLL SVKWNSRDEVAQMY CLVKDWPPIKP (SEQ ID NO: 35) | STRDPLSEITK (A03.01) (SEQ ID NO: 272) DPLSEITK (A03.01) (SEQ ID NO: 273) | BLCA, BRCA, CESC, CRC, GBM, HNSC, KIRC, KIRP, LIHC, LUAD, LUSC, PRAD, SKCM, UCEC |
| PIK3CA | H1047R | LFINLFSMMLGSGMP ELQSFDDIAYIRKTLA LDKTEQEALEYFMK QMNDARHGGWTTK MDWIFHTIKQHALN (SEQ ID NO: 36) | | BRCA, CESC, CRC, GBM, HNSC, LIHC, LUAD, LUSC, PRAD, UCEC |
| POLE | P286R | QRGGVITDEEETSKKI ADQLDNIVDMREYD VPYHIRLSIDIETTKLP LKFRDAETDQIMMIS YMIDGQGYLITNREI VSEDIEDFEFTPKPEY EGPFCVFN (SEQ ID NO: 37) | LPLKFRDAET (B07.02) (SEQ ID NO: 274) | Colorectal adenocarcinoma; Uterine/Endometrium Adenocarcinoma; Colorectal adenocarcinoma, MSI+; Uterine/Endometrium Adenocarcinoma, MSI+; Endometrioid carcinoma; Endometrium Serous carcinoma; Endometrium Carcinosarcoma-malignant mesodermal mixed tumor; Glioma; Astrocytoma; GBM |
| PTEN | R130Q | KFNCRVAQYPFEDH NPPQLELIKPFCEDLD QWLSEDDNHVAAIH CKAGKGQTGVMICA YLLHRGKFLKAQEAL DFYGEVRTRDKKGV TIPSQRRYVYYYSY (SEQ ID NO: 38) | QTGVMICAYL (A02.01) (SEQ ID NO: 275) | BRCA, CESC, CRC, GBM, KIRC, LUSC, UCEC |
| RAC1 | P29S | MQAIKCVVVGDGAV GKTCLLISYTTNAFSG EYIPTVFDNYSANVM VDGKPVNLGLWDTA GQEDYDRLRPLSYPQ TVGET (SEQ ID NO: 39) | AFSGEYIPTV (A02.01, A24.02) (SEQ ID NO: 276) | Melanoma |
| TP53 | G245S | IRVEGNLRVEYLDDR NTFRHSVVVPYEPPE VGSDCTTIHYNYMC NSSCMGSMNRRPILTI ITLEDSSGNLLGRNSF EVRVCACPGRDRRTE EENLRKKGEP (SEQ ID NO: 40) | SMNRRPILT (A02.01, B08.01) (SEQ ID NO: 277) YMCNSSCMGS (A02.01) (SEQ ID NO: 278) | BLCA, BRCA, CRC, GBM, HNSC, LUSC, PAAD, PRAD |

TABLE 1-continued

| Gene | Exemplary Protein Change | Mutation Sequence Context | Peptides (HLA allele example(s)) | Exemplary Diseases |
|---|---|---|---|---|
| TP53 | R175H | TYSPALNKMFCQLA KTCPVQLWVDSTPPP GTRVRAMAIYKQSQ HMTEVVRHCPHHER CSDSDGLAPPQHLIR VEGNLRVEYLDDRN TFRHSVVVPYEPPEV (SEQ ID NO: 41) | | BLCA, BRCA, CRC, GBM, HNSC, LUAD, PAAD, PRAD, UCEC |
| TP53 | R248Q | EGNLRVEYLDDRNTF RHSVVVPYEPPEVGS DCTTIHYNYMCNSSC MGGMNQRPILTIITLE DSSGNLLGRNSFEVR VCACPGRDRRTEEEN LRKKGEPHHE (SEQ ID NO: 42) | GMNQRPILT (A02.01) (SEQ ID NO: 279) | BLCA, BRCA, CRC, GBM, HNSC, KIRC, LIHC, LUSC, PAAD, PRAD, UCEC |
| TP53 | R248W | EGNLRVEYLDDRNTF RHSVVVPYEPPEVGS DCTTIHYNYMCNSSC MGGMNWRPILTIITL EDSSGNLLGRNSFEV RVCACPGRDRRTEEE NLRKKGEPHHE (SEQ ID NO: 43) | GMNWRPILT (A02.01) (SEQ ID NO: 280) | BLCA, BRCA, CRC, GBM, HNSC, LIHC, LUSC, PAAD, SKCM, UCEC |
| TP53 | R273C | PEVGSDCTTIHYNYM CNSSCMGGMNRRPIL TIITLEDSSGNLLGRN SFEVCVCACPGRDRR TEEENLRKKGEPHHE LPPGSTKRALPNNTSS SPQPKKKPL (SEQ ID NO: 44) | LLGRNSFEVC (A02.01) (SEQ ID NO: 281) | BLCA, BRCA, CRC, GBM, HNSC, LUSC, PAAD, UCEC |
| TABLE 1B | | MSI-ASSOCIATED FRAMESHIFTS [1] | | |
| ACVR2 | D96fs; +1 | GVEPCYGDKDKRRH CFATWKNISGSIEIVK QGCWLDDINCYDRT DCVEKKRQP* (SEQ ID NO: 45) | | MSI+ CRC, MSI+ Uterine/Endometrium Cancer, MSI+ Stomach Cancer, Lynch syndrome |
| ACVR2A | D96fs; -1 | GVEPCYGDKDKRRH CFATWKNISGSIEIVK QGCWLDDINCYDRT DCVEKKTALKYIFVA VRAICVMKSFLIFRR WKSHSPLQIQLHLSH PITTSCSIPWCHLC* (SEQ ID NO: 46) | ALKYIFVAV (A02.01, B08.01) (SEQ ID NO: 282) ALKYIFVAVR (A03.01) (SEQ ID NO: 283) AVRAICVMK (A03.01) (SEQ ID NO: 284) AVRAICVMKS (A03.01) (SEQ ID NO: 285) CVEKKTALK (A03.01) (SEQ ID NO: 286) CVEKKTALKY (A01.01) (SEQ ID NO: 287) CVMKSFLIF (A24.02, B08.01) (SEQ ID NO: 288) CVMKSFLIFR (A03.01) (SEQ ID NO: 289) FLIFRRWKS (A02.01, B08.01) (SEQ ID NO: 290) FRRWKSHSPL (B08.01) (SEQ ID NO: 291) FVAVRAICV (A02.01, B08.01) (SEQ ID NO: 292) FVAVRAICVM (B08.01) (SEQ ID NO: 293) IQLHLSHPI (A02.01) (SEQ ID NO: 294) | MSI+ CRC, MSI+ Uterine/Endometrium Cancer, MSI+ Stomach Cancer, Lynch syndrome |

TABLE 1-continued

| Gene | Exemplary Protein Change | Mutation Sequence Context | Peptides (HLA allele example(s)) | Exemplary Diseases |
|---|---|---|---|---|
| | | | KSFLIFRRWK (A03.01) (SEQ ID NO: 295) KTALKYIFV (A02.01) (SEQ ID NO: 296) KYIFVAVRAI (A24.02) (SEQ ID NO: 297) RWKSHSPLQI (A24.02) (SEQ ID NO: 298) TALKYIFVAV (A02.01, B08.01) (SEQ ID NO: 299) VAVRAICVMK (A03.01) (SEQ ID NO: 300) VMKSFLIFR (A03.01) (SEQ ID NO: 301) VMKSFLIFRR (A03.01) (SEQ ID NO: 302) YIFVAVRAI (A02.01) (SEQ ID NO: 303) | |
| C15ORF40 | L132fs; +1 | TAEAVNVAIAAPPSE GEANAELCRYLSKVL ELRKSDVVLDKVGL ALFFFFFETKSCSVAQ AGVQWRSLGSLQPPP PGFKLFSCLSFLSSWD YRRMPPCLANFCIFN RDGVSPCWSGWS* (SEQ ID NO: 47) | ALFFFFFET (A02.01) (SEQ ID NO: 304) ALFFFFFETK (A03.01) (SEQ ID NO: 305) AQAGVQWRSL (A02.01) (SEQ ID NO: 306) CLANFCIFNR (A03.01) (SEQ ID NO: 307) CLSFLSSWDY (A01.01, A03.01) (SEQ ID NO: 308) FFETKSCSV (B08.01) (SEQ ID NO: 309) FFFETKSCSV (A02.01) (SEQ ID NO: 310) FKLFSCLSFL (A02.01) (SEQ ID NO: 311) FLSSWDYRRM (A02.01) (SEQ ID NO: 312) GFKLFSCLSF (A24.02) (SEQ ID NO: 313) KLFSCLSFL (A02.01, A03.01) (SEQ ID NO: 314) KLFSCLSFLS (A02.01, A03.01) (SEQ ID NO: 315) LALFFFFFET (A02.01) (SEQ ID NO: 316) LFFFFFETK (A03.01) (SEQ ID NO: 317) LSFLSSWDY (A01.01) (SEQ ID NO: 318) LSFLSSWDYR (A03.01) (SEQ ID NO: 319) RMPPCLANF (A24.02) (SEQ ID NO: 320) RRMPPCLANF (A24.02) (SEQ ID NO: 321) SLQPPPPGFK (A03.01) (SEQ ID NO: 322) VQWRSLGSL (A02.01) (SEQ ID NO: 323) | MSI+ CRC, MSI+ Uterine/Endometrium Cancer, MSI+ Stomach Cancer, Lynch syndrome |
| CNOT1 | L1544fs; +1 | LSVIIFFFFVYIWHWAL PLILNNHHICLMSSIIL DCNSVRQSIMSVCFF FFSVIFSTRCLTDSRY PNICWFK* (SEQ ID NO: 48) | FFFSVIFST (A02.01) (SEQ ID NO: 324) MSVCFFFFSV (A02.01) (SEQ ID NO: 325) SVCFFFFSV (A02.01, B08.01) (SEQ ID NO: 326) SVCFFFFSVI (A02.01) (SEQ ID NO: 327) | MSI+ CRC, MSI+ Uterine/Endometrium Cancer, MSI+ Stomach Cancer, Lynch syndrome |

TABLE 1-continued

| Gene | Exemplary Protein Change | Mutation Sequence Context | Peptides (HLA allele example(s)) | Exemplary Diseases |
|---|---|---|---|---|
| CNOT1 | L1544fs; -1 | LSVIIFFFVYIWHWAL PLILNNHHICLMSSIIL DCNSVRQSIMSVCFF FFCYILNTMFDR* (SEQ ID NO: 49) | FFCYILNTMF (A24.02) (SEQ ID NO: 328) MSVCFFFFCY (A01.01) (SEQ ID NO: 329) SVCFFFFCYI (A02.01) (SEQ ID NO: 330) | MSI+ CRC, MSI+ Uterine/Endometrium Cancer, MSI+ Stomach Cancer, Lynch syndrome |
| EIF2B3 | A151fs; -1 | VLVLSCDLITDVALH EVVDLFRAYDASLA MLMRKGQDSIEPVPG QKGKKKQWSSVTSL EWTAQERGCSSWLM KQTWMKSWSLRDPS YRSILEYVSTRVLWM PTSTV* (SEQ ID NO: 50) | KQWSSVTSL (A02.01) (SEQ ID NO: 331) VLWMPTSTV (A02.01) (SEQ ID NO: 332) | MSI+ CRC, MSI+ Uterine/Endometrium Cancer, MSI+ Stomach Cancer, Lynch syndrome |
| EPHB2 | K1020fs; -1 | SIQVMRAQMNQIQSV EGQPLARRPRATGRT KRCQPRDVTKKTCNS NDGKKREWEKRKQI LGGGGKYKEYFLKRI LIRKAMTVLAGDKK GLGRFMRCVQSETK AVSLQLPLGR* (SEQ ID NO: 51) | ILIRKAMTV (A02.01) (SEQ ID NO: 333) | MSI+ CRC, MSI+ Uterine/Endometrium Cancer, MSI+ Stomach Cancer, Lynch syndrome |
| ESRP1 | N512fs; +1 | LDFLGEFATDIRTHG VHMVLNHQGRPSGD AFIQMKSADRAFMA AQKCHKKKHEGQIC* (SEQ ID NO: 52) | | MSI+ CRC, MSI+ Uterine/Endometrium Cancer, MSI+ Stomach Cancer, Lynch syndrome |
| ESRP1 | N512fs; -1 | LDFLGEFATDIRTHG VHMVLNHQGRPSGD AFIQMKSADRAFMA AQKCHKKT* (SEQ ID NO: 53) | | MSI+ CRC, MSI+ Uterine/Endometrium Cancer, MSI+ Stomach Cancer, Lynch syndrome |
| FAM111B | A273fs; -1 | GALCKDGRFRSDIGE FEWKLKEGHKKIYG KQSMVDEVSGKVLE MDISKKKHYNRKISI KKLNRMKVPLMKLI TRV* (SEQ ID NO: 54) | RMKVPLMK (A03.01) (SEQ ID NO: 334) | MSI+ CRC, MSI+ Uterine/Endometrium Cancer, MSI+ Stomach Cancer, Lynch syndrome |
| GBP3 | T585fs; -1 | RERAQLLEEQEKTLT SKLQEQARVLKERCQ GESTQLQNEIQKLQK TLKKKPRDICRIS* (SEQ ID NO: 55) | TLKKKPRDI (B08.01) (SEQ ID NO: 335) | MSI+ CRC, MSI+ Uterine/Endometrium Cancer, MSI+ Stomach Cancer, Lynch syndrome |
| JAK1 | P861fs; +1 | VNTLKEGKRLPCPPN CPDEVYQLMRKCWE FQPSNRTSFQNLIEGF EALLKTSN* (SEQ ID NO: 56) | LIEGFEALLK (A03.01) (SEQ ID NO: 336) | MSI+ CRC, MSI+ Uterine/Endometrium Cancer, MSI+ Stomach Cancer, Lynch syndrome |
| JAK1 | K860fs; -1 | CRPVTPSCKELADLM TRCMNYDPNQRPFFR AIMRDINKLEEQNPDI VSEKNQQLKWTPHIL KSAS* (SEQ ID NO: 57) | QQLKWTPHI (A02.01) (SEQ ID NO: 337) QLKWTPHILK (A03.01) (SEQ ID NO: 338) IVSEKNQQLK (A03.01) (SEQ ID NO: 339) QLKWTPHILK (A03.01) (SEQ ID NO: 340) QQLKWTPHI (A24.02) (SEQ ID NO: 341) NQQLKWTPHIL (B08.01) (SEQ ID NO: 342) NQQLKWTPHI (B08.01) (SEQ ID NO: 343) QLKWTPHIL (B08.01) (SEQ ID NO: 344) | MSI+ CRC, MSI+ Uterine/Endometrium Cancer, MSI+ Stomach Cancer, Lynch syndrome |

TABLE 1-continued

| Gene | Exemplary Protein Change | Mutation Sequence Context | Peptides (HLA allele example(s)) | Exemplary Diseases |
|---|---|---|---|---|
| LMAN1 | E305fs; +1 | DDHDVLSFLTFQLTE PGKEPPTPDKEISEKE KEKYQEEFEHFQQEL DKKKRGIPEGPPRPPR AACGGNI* (SEQ ID NO: 58) | GPPRPPRAAC (B07.02) (SEQ ID NO: 345) PPRPPRAAC (B07.02) (SEQ ID NO: 346) | MSI+ CRC, MSI+ Uterine/Endometrium Cancer, MSI+ Stomach Cancer, Lynch syndrome |
| LMAN1 | E305fs; -1 | DDHDVLSFLTFQLTE PGKEPPTPDKEISEKE KEKYQEEFEHFQQEL DKKKRNSRRATPTSK GSLRRKYLRV* (SEQ ID NO: 59) | SLRRKYLRV (B08.01) (SEQ ID NO: 347) | MSI+ CRC, MSI+ Uterine/Endometrium Cancer, MSI+ Stomach Cancer, Lynch syndrome |
| MSH3 | N385fs; +1 | TKSTLIGEDVNPLIKL DDAVNVDEIMTDTST SYLLCISENKENVRD KKKGQHFYWHCGSA ACHRRGCV* (SEQ ID NO: 60) | SAACHRRGCV (B08.01) (SEQ ID NO: 348) | MSI+ CRC, MSI+ Uterine/Endometrium Cancer, MSI+ Stomach Cancer, Lynch syndrome |
| MSH3 | K383fs; -1 | LYTKSTLIGEDVNPLI KLDDAVNVDEIMTD TSTSYLLCISENKENV RDKKRATFLLALWE CSLPQARLCLIVSRTL LLVQS* (SEQ ID NO: 61) | ALWECSLPQA (A02.01) (SEQ ID NO: 349) CLIVSRTLL (B08.01) (SEQ ID NO: 350) CLIVSRTLLL (A02.01, B08.01) (SEQ ID NO: 351) FLLALWECS (A02.01) (SEQ ID NO: 352) FLLALWECSL (A02.01, B08.01) (SEQ ID NO: 353) IVSRTLLLV (A02.01) (SEQ ID NO: 354) LIVSRTLLL (A02.01, B08.01) (SEQ ID NO: 355) LIVSRTLLLV (A02.01) (SEQ ID NO: 356) LLALWECSL (A02.01, B08.01) (SEQ ID NO: 357) LPQARLCLI (B08.01, B07.02) (SEQ ID NO: 358) LPQARLCLIV (B08.01) (SEQ ID NO: 359) NVRDKKRATF (B08.01) (SEQ ID NO: 360) SLPQARLCLI (A02.01, B08.01) (SEQ ID NO: 361) | MSI+CRC, MSI+ Uterine/Endometrium Cancer, MSI+ Stomach Cancer, Lynch syndrome |
| NDUFC2 | A70fs; +1 | LPPPKLTDPRLLYIGF LGYCSGLIDNLIRRRP IATAGLHRQLLYITAF FFCWILSCKT* (SEQ ID NO: 62) | FFCWILSCK (A03.01) (SEQ ID NO: 362) FFFCWILSCK (A03.01) (SEQ ID NO: 363) ITAFFFCWI (A02.01) (SEQ ID NO: 364) LYITAFFFCW (A24.02) (SEQ ID NO: 365) YITAFFFCWI (A02.01) (SEQ ID NO: 366) | MSI+ CRC, MSI+ Uterine/Endometrium Cancer, MSI+ Stomach Cancer, Lynch syndrome |
| NDUFC2 | F69fs; -1 | SLPPPKLTDPRLLYIG FLGYCSGLIDNLIRRR PIATAGLHRQLLYITA FFLLDIIL* (SEQ ID NO: 63) | ITAFFLLDI (A02.01) (SEQ ID NO: 367) LLYITAFFL (A02.01, B08.01) (SEQ ID NO: 368) LLYITAFFLL (A02.01, A24.02) (SEQ ID NO: 369) LYITAFFLL (A24.02) (SEQ ID NO: 370) | MSI+ CRC, MSI+ Uterine/Endometrium Cancer, MSI+ Stomach Cancer, Lynch syndrome |

TABLE 1-continued

| Gene | Exemplary Protein Change | Mutation Sequence Context | Peptides (HLA allele example(s)) | Exemplary Diseases |
|---|---|---|---|---|
| | | | LYITAFFLLD (A24.02) (SEQ ID NO: 371) YITAFFLLDI (A02.01) (SEQ ID NO: 372) | |
| RBM27 | Q817; +1 | NQSGGAGEDCQIFST PGHPKMIYSSSNLKT PSKLCSGSKSHDVQE VLKKKTGSNEVTTRY EEKKTGSVRKANRM PKDVNIQVRKKQKH ETRRKSKYNEDFERA WREDLTIKR* (SEQ ID NO: 64) | GSNEVTTRY (A01.01) (SEQ ID NO: 373) MPKDVNIQV (B07.02) (SEQ ID NO: 374) TGSNEVTTRY (A01.01) (SEQ ID NO: 375) | MSI+ CRC, MSI+ Uterine/Endometrium Cancer, MSI+ Stomach Cancer, Lynch syndrome |
| RPL22 | K16fs; +1 | MAPVKKLVVKGGKK KEASSEVHS* (SEQ ID NO: 65) | | MSI+ CRC, MSI+ Uterine/Endometrium Cancer, MSI+ Stomach Cancer, Lynch syndrome |
| RPL22 | K15fs; -1 | MAPVKKLVVKGGKK RSKF* (SEQ ID NO: 66) | | MSI+ CRC, MSI+ Uterine/Endometrium Cancer, MSI+ Stomach Cancer, Lynch syndrome |
| SEC31A | I462fs; +1 | MPSHQGAEQQQQQH HVFISQVVTEKEFLSR SDQLQQAVQSQGFIN YCQKKN* (SEQ ID NO: 67) | | MSI+ CRC, MSI+ Uterine/Endometrium Cancer, MSI+ Stomach Cancer, Lynch syndrome |
| SEC31A | I462fs; -1 | MPSHQGAEQQQQQH HVFISQVVTEKEFLSR SDQLQQAVQSQGFIN YCQKKLMLLRLNLR KMCGPF* (SEQ ID NO: 68) | KKLMLLRLNL (A02.01) (SEQ ID NO: 376) KLMLLRLNL (A02.01, A03.01, B07.02, B08.01) (SEQ ID NO: 377) KLMLLRLNLR (A03.01) (SEQ ID NO: 378) LLRLNLRKM (B08.01) (SEQ ID NO: 379) LMLLRLNL (B08.01) (SEQ ID NO: 380) LMLLRLNLRK (A03.01) (SEQ ID NO: 381) LNLRKMCGPF (B08.01) (SEQ ID NO: 382) MLLRLNLRK (A03.01) (SEQ ID NO: 383) MLLRLNLRKM (A02.01, A03.01, B08.01) (SEQ ID NO: 384) NLRKMCGPF (B08.01) (SEQ ID NO: 385) NYCQKKLMLL (A24.02) (SEQ ID NO: 386) YCQKKLMLL (B08.01) (SEQ ID NO: 387) | MSI+ CRC, MSI+ Uterine/Endometrium Cancer, MSI+ Stomach Cancer, Lynch syndrome |
| SEC63 | K530fs; +1 | AEVFEKEQSICAAEE QPAEDGQGETNKNR TKGGWQQKSKGPKK TAKSKKKETFKKKTY TCAITTVKATETKAG KWSRWE* (SEQ ID NO: 69) | FKKKTYTCAI (B08.01) (SEQ ID NO: 388) ITTVKATETK (A03.01) (SEQ ID NO: 389) KSKKKETFK (A03.01) (SEQ ID NO: 390) KSKKKETFKK (A03.01) (SEQ ID NO: 391) KTYTCAITTV (A02.01, A24.02) (SEQ ID NO: 392) TFKKKTYTC (B08.01) (SEQ ID NO: 393) TYTCAITTV (A24.02) (SEQ ID NO: 394) TYTCAITTVK (A03.01) (SEQ ID NO: 395) | MSI+ CRC, MSI+ Uterine/Endometrium Cancer, MSI+ Stomach Cancer, Lynch syndrome |

TABLE 1-continued

| Gene | Exemplary Protein Change | Mutation Sequence Context | Peptides (HLA allele example(s)) | Exemplary Diseases |
|---|---|---|---|---|
| | | | YTCAITTVK (A03.01) (SEQ ID NO: 396) | |
| SEC63 | K529fs; -1 | MAEVFEKEQSICAAE EQPAEDGQGETNKN RTKGGWQQKSKGPK KTAKSKKRNL* (SEQ ID NO: 70) | TAKSKKRNL (B08.01) (SEQ ID NO: 397) | MSI+ CRC, MSI+ Uterine/Endometrium Cancer, MSI+ Stomach Cancer, Lynch syndrome |
| SLC35F5 | C248fs; -1 | NIMEIRQLPSSHALEA KLSRMSYPVKEQESI LKTVGKLTATQVAKI SFFFALCGFWQICHIK KHFQTHKLL* (SEQ ID NO: 71) | FALCGFWQI (A02.01) (SEQ ID NO: 398) | MSI+ CRC, MSI+ Uterine/Endometrium Cancer, MSI+ Stomach Cancer, Lynch syndrome |
| SMAP1 | K172fs; +1 | YEKKKYYDKNAIAIT NISSSDAPLQPLVSSP SLQAAVDKNKLEKE KEKKKGREKERKGA RKAGKTTYS* (SEQ ID NO: 72) | | MSI+ CRC, MSI+ Uterine/Endometrium Cancer, MSI+ Stomach Cancer, Lynch syndrome |
| SMAP1 | K171fs; -1 | KYEKKKYYDKNAIAI TNISSSDAPLQPLVSS PSLQAAVDKNKLEKE KEKKRKRKREKRSQ KSRQNHLQLKSCRRK ISNWSLKKVPALKKL RSPLWIF* (SEQ ID NO: 73) | LKKLRSPL (B08.01) (SEQ ID NO: 399) SLKKVPAL (B08.01) (SEQ ID NO: 400) RKISNWSLKK (A03.01) (SEQ ID NO: 401) VPALKKLRSPL (B07.02) (SEQ ID NO: 402) | MSI+ CRC, MSI+ Uterine/Endometrium Cancer, MSI+ Stomach Cancer, Lynch syndrome |
| TFAM | E148fs; +1 | IYQDAYRAEWQVYK EEISRFKEQLTPSQIM SLEKEIMDKHLKRKA MTKKKRVNTAWKT KKTSFSL* (SEQ ID NO: 74) | KRVNTAWKTK (A03.01) (SEQ ID NO: 403) MTKKKRVNTA (B08.01) (SEQ ID NO: 404) RVNTAWKTK (A03.01) (SEQ ID NO: 405) RVNTAWKTKK (A03.01) (SEQ ID NO: 406) TKKKRVNTA (B08.01) (SEQ ID NO: 407) WKTKKTSFSL (B08.01) (SEQ ID NO: 408) | MSI+ CRC, MSI+ Uterine/Endometrium Cancer, MSI+ Stomach Cancer, Lynch syndrome |
| TFAM | E148fs; -1 | IYQDAYRAEWQVYK EEISRFKEQLTPSQIM SLEKEIMDKHLKRKA MTKKKS* (SEQ ID NO: 75) | | MSI+ CRC, MSI+ Uterine/Endometrium Cancer, MSI+ Stomach Cancer, Lynch syndrome |
| TGFBR2 | P129fs; +1 | KPQEVCVAVWRKND ENITLETVCHDPKLP YHDFILEDAASPKCI MKEKKKAW* (SEQ ID NO: 76) | | MSI+ CRC, MSI+ Uterine/Endometrium Cancer, MSI+ Stomach Cancer, Lynch syndrome |
| TGFBR2 | K128fs; -1 | EKPQEVCVAVWRKN DENITLETVCHDPKL PYHDFILEDAASPKCI MKEKKSLVRLSSCVP VALMSAMTTSSSQK NITPAILTCC* (SEQ ID NO: 77) | ALMSAMTTS (A02.01) (SEQ ID NO: 409) AMTTSSSQK (A03.01, A11.01) (SEQ ID NO: 410) AMTTSSSQKN (A03.01) (SEQ ID NO: 411) CIMKEKKSL (B08.01) (SEQ ID NO: 412) CIMKEKKSLV (B08.01) (SEQ ID NO: 413) IMKEKKSL (B08.01) (SEQ ID NO: 414) IMKEKKSLV (B08.01) (SEQ ID NO: 415) KSLVRLSSCV (A02.01) (SEQ ID NO: 416) LVRLSSCVPV (A02.01) (SEQ ID NO: 417) | MSI+ CRC, MSI+ Uterine/Endometrium Cancer, MSI+ Stomach Cancer, Lynch syndrome |

TABLE 1-continued

| Gene | Exemplary Protein Change | Mutation Sequence Context | Peptides (HLA allele example(s)) | Exemplary Diseases |
|---|---|---|---|---|
| | | | RLSSCVPVA (A02.01, A03.01) (SEQ ID NO: 418) RLSSCVPVAL (A02.01) (SEQ ID NO: 419) SAMTTSSSQK (A03.01, A11.01) (SEQ ID NO: 420) SLVRLSSCV (A02.01) (SEQ ID NO: 421) VPVALMSAM (B07.02) (SEQ ID NO: 422) VRLSSCVPVA (A02.01) (SEQ ID NO: 423) | |
| THAP5 | K99fs; -1 | VPSKYQFLCSDHFTP DSLDIRWGIRYLKQT AVPTIFSLPEDNQGK DPSKKNPRRKTWKM RKKYAQKPSQKNHL Y* (SEQ ID NO: 78) | KMRKKYAQK (A03.01) (SEQ ID NO: 424) | MSI+ CRC, MSI+ Uterine/Endometrium Cancer, MSI+ Stomach Cancer, Lynch syndrome |
| TTK | R854fs; -1 | GTTEEMKYVLGQLV GLNSPNSILKAAKTL YEHYSGGESHNSSSS KTFEKKGEKNDLQLF VMSDTTYKIYWTVIL LNPCGNLHLKTTSL* (SEQ ID NO: 79) | FVMSDTTYK (A03.01) (SEQ ID NO: 425) FVMSDTTYKI (A02.01) (SEQ ID NO: 426) KTFEKKGEK (A03.01) (SEQ ID NO: 427) LFVMSDTTYK (A03.01) (SEQ ID NO: 428) MSDTTYKIY (A01.01) (SEQ ID NO: 429) VMSDTTYKI (A02.01) (SEQ ID NO: 430) VMSDTTYKIY (A01.01) (SEQ ID NO: 431) | MSI+ CRC, MSI+ Uterine/Endometrium Cancer, MSI+ Stomach Cancer, Lynch syndrome |
| XPOT | F126fs; -1 | QQLIRETLISWLQAQ MLNPQPEKTFIRNKA AQVFALLFVTEYLTK WPKFFLTFSQ* (SEQ ID NO: 80) | YLTKWPKFFL (A02.01) (SEQ ID NO: 432) | MSI+ CRC, MSI+ Uterine/Endometrium Cancer, MSI+ Stomach Cancer, Lynch syndrome |
| TABLE 1C | | FRAMESHIFT [1] | | |
| APC | V1352fs F1354fs Q1378fs S1398fs | AKFQQCHSTLEPNPA DCRVLVYLQNQPGT KLLNFLQERNLPPKV VLRHPKVHLNTMFR RPHSCLADVLLSVHL IVLRVVRLPAPFRVN HAVEW* (SEQ ID NO: 81) | FLQERNLPP (A02.01) (SEQ ID NO: 433) FRRPHSCLA (B08.01) (SEQ ID NO: 434) LIVLRVVRL (B08.01) (SEQ ID NO: 435) LLSVHLIVL (A02.01, B08.01) (SEQ ID NO: 436) | CRC, LUAD, UCEC, STAD |
| APC | S1421fs R1435fs T1438fs P1442fs P1443fs V1452fs P1453fs K1462fs E1464fs | APVIFQIALDKPCHQ AEVKHLHHLLKQLK PSEKYLKIKHLLLKR ERVDLSKLQ* (SEQ ID NO: 82) | EVKHLHHLL (B08.01) (SEQ ID NO: 437) HLHHLLKQLK (A03.01) (SEQ ID NO: 438) HLLLKRERV (B08.01) (SEQ ID NO: 439) KIKHLLLKR (A03.01) (SEQ ID NO: 440) KPSEKYLKI (B07.02) (SEQ ID NO: 441) KYLKIKHLL (A24.02) (SEQ ID NO: 442) KYLKIKHLLL (A24.02) (SEQ ID NO: 443) LLKQLKPSEK (A03.01) (SEQ ID NO: 444) LLKRERVDL (B08.01) (SEQ ID NO: 445) | CRC, LUAD, UCEC, STAD |

TABLE 1-continued

| Gene | Exemplary Protein Change | Mutation Sequence Context | Peptides (HLA allele example(s)) | Exemplary Diseases |
|---|---|---|---|---|
| | | | LLLKRERVDL (B08.01) (SEQ ID NO: 446) QLKPSEKYLK (A03.01) (SEQ ID NO: 447) YLKIKHLLL (A02.01, B08.01) (SEQ ID NO: 448) YLKIKHLLLK (A03.01) (SEQ ID NO: 449) | |
| APC | T1487fs H1490fs L1488fs | MLQFRGSRFFQMLIL YYILPRKVLQMDFLV HPA* (SEQ ID NO: 83) | ILPRKVLQM (B08.01) (SEQ ID NO: 450) KVLQMDFLV (A02.01, A24.02) (SEQ ID NO: 451) LPRKVLQMDF (B07.02, B08.01) (SEQ ID NO: 452) LQMDFLVHPA (A02.01) (SEQ ID NO: 453) QMDFLVHPA (A02.01) (SEQ ID NO: 454) YILPRKVLQM (A02.01, B08.01) (SEQ ID NO: 455) | CRC, LUAD, UCEC, STAD |
| ARID1A | Q1306fs S1316fs Y1324fs T1348fs G1351fs G1378fs P1467fs | ALGPHSRISCLPTQTR GCILLAATPRSSSSSS SNDMIPMAISSPPKAP LLAAPSPASRLQCINS NSRITSGQWMAHMA LLPSGTKGRCTACHT ALGRGSLSSSSCPQPS PSLPASNKLPSLPLSK MYTTSMAMPILPLPQ LLLSADQQAAPRTNF HSSLAETVSLHPLAP MPSKTCHHK* (SEQ ID NO: 84) | APSPASRLQC (B07.02) (SEQ ID NO: 456) HPLAPMPSKT (B07.02) (SEQ ID NO: 457) ILPLPQLLL (A02.01) (SEQ ID NO: 458) LLLSADQQA (A02.01) (SEQ ID NO: 459) LPTQTRGCI (B07.02) (SEQ ID NO: 460) LPTQTRGCIL (B07.02) (SEQ ID NO: 461) RISCLPTQTR (A03.01) (SEQ ID NO: 462) SLAETVSLH (A03.01) (SEQ ID NO: 463) TPRSSSSSS (B07.02) (SEQ ID NO: 464) TPRSSSSSSS (B07.02) (SEQ ID NO: 465) | STAD, UCEC, BLCA, BRCA, LUSC, CESC, KIRC, UCS |
| ARID1A | S674fs P725fs R727fs I736fs | AHQGFPAAKESRVIQ LSLLSLLIPPLTCLASE ALPRPLLALPPVLLSL AQDHSRLLQCQATR CHLGHPVASRTASCI LP* (SEQ ID NO: 85) | ALPPVLLSL (A02.01) (SEQ ID NO: 466) ALPPVLLSLA (A02.01) (SEQ ID NO: 467) ALPRPLLAL (A02.01) (SEQ ID NO: 468) ASRTASCIL (B07.02) (SEQ ID NO: 469) EALPRPLLAL (B08.01) (SEQ ID NO: 470) HLGHPVASR (A03.01) (SEQ ID NO: 471) HPVASRTAS (B07.02) (SEQ ID NO: 472) HPVASRTASC (B07.02) (SEQ ID NO: 473) IIQLSLLSLL (A02.01) (SEQ ID NO: 474) IQLSLLSLL (A02.01) (SEQ ID NO: 475) IQLSLLSLLI (A02.01, A24.02) (SEQ ID NO: 476) LLALPPVLL (A02.01) (SEQ ID NO: 477) LLIPPLTCL (A02.01) (SEQ ID NO: 478) LLIPPLTCLA (A02.01) (SEQ ID NO: 479) | STAD, UCEC, BLCA, BRCA, LUSC, CESC, KIRC, UCS |

TABLE 1-continued

| Gene | Exemplary Protein Change | Mutation Sequence Context | Peptides (HLA allele example(s)) | Exemplary Diseases |
|---|---|---|---|---|
| | | | LLSLLIPPL (A02.01) (SEQ ID NO: 480) | |
| | | | LLSLLIPPLT (A02.01) (SEQ ID NO: 481) | |
| | | | LPRPLLALPP (B07.02) (SEQ ID NO: 482) | |
| | | | QLSLLSLLI (A02.01) (SEQ ID NO: 483) | |
| | | | RLLQCQATR (A03.01) (SEQ ID NO: 484) | |
| | | | RPLLALPPV (B07.02) (SEQ ID NO: 485) | |
| | | | RPLLALPPVL (B07.02) (SEQ ID NO: 486) | |
| | | | SLAQDHSRL (A02.01) (SEQ ID NO: 487) | |
| | | | SLAQDHSRLL (A02.01) (SEQ ID NO: 488) | |
| | | | SLLIPPLTCL (A02.01) (SEQ ID NO: 489) | |
| | | | SLLSLLIPP (A02.01) (SEQ ID NO: 490) | |
| | | | SLLSLLIPPL (A02.01, B08.01) (SEQ ID NO: 491) | |
| ARID1A | G414fs Q473fs H477fs S499fs P504fs Q548fs P549fs | PILAATGTSVRTAAR TWVPRAAIRVPDPAA VPDDHAGPGAECHG RPLLYTADSSLWTTR PQRVWSTGPDSILQP AKSSPSAAAATLLPA TTVPDPSCPTFVSAA ATVSTTTAPVLSASIL PAAIPASTSAVPGSIP LPAVDDTAAPPEPAP LLTATGSVSLPAAAT SAASTLDALPAGCVS SAPVSAVPANCLFPA ALPSTAGAISRFIWVS GILSPLNDLQ* (SEQ ID NO: 86) | AAATSAASTL (B07.02) (SEQ ID NO: 492) AAIPASTSAV (B07.02) (SEQ ID NO: 493) AIPASTSAV (A02.01) (SEQ ID NO: 494) ALPAGCVSSA (A02.01) (SEQ ID NO: 495) APLLTATGSV (B07.02) (SEQ ID NO: 496) APVLSASIL (B07.02) (SEQ ID NO: 497) ATLLPATTV (A02.01) (SEQ ID NO: 498) ATVSTTTAPV (A02.01) (SEQ ID NO: 499) AVPANCLFPA (A02.01) (SEQ ID NO: 500) CLFPAALPST (A02.01) (SEQ ID NO: 501) CPTFVSAAA (B07.02) (SEQ ID NO: 502) FPAALPSTA (B07.02) (SEQ ID NO: 503) FPAALPSTAG (B07.02) (SEQ ID NO: 504) GAECHGRPL (B07.02) (SEQ ID NO: 505) GAISRFIWV (A02.01) (SEQ ID NO: 506) ILPAAIPAST (A02.01) (SEQ ID NO: 507) IWVSGILSPL (A24.02) (SEQ ID NO: 508) LLTATGSVSL (A02.01) (SEQ ID NO: 509) LLYTADSSL (A02.01) (SEQ ID NO: 510) LPAAATSAA (B07.02) (SEQ ID NO: 511) LPAAATSAAS (B07.02) (SEQ ID NO: 512) LPAAIPAST (B07.02) (SEQ ID NO: 513) LPAGCVSSA (B07.02) (SEQ ID NO: 514) LPAGCVSSAP (B07.02) (SEQ ID NO: 515) LYTADSSLW (A24.02) (SEQ ID NO: 516) | STAD, UCEC, BLCA, BRCA, LUSC, CESC, KIRC, UCS |

TABLE 1-continued

| Gene | Exemplary Protein Change | Mutation Sequence Context | Peptides (HLA allele example(s)) | Exemplary Diseases |
|---|---|---|---|---|
| | | | QPAKSSPSA (B07.02) (SEQ ID NO: 517) | |
| | | | QPAKSSPSAA (B07.02) (SEQ ID NO: 518) | |
| | | | RFIWVSGIL (A24.02) (SEQ ID NO: 519) | |
| | | | RPQRVWSTG (B07.02) (SEQ ID NO: 520) | |
| | | | RVWSTGPDSI (A02.01) (SEQ ID NO: 521) | |
| | | | SAVPGSIPL (B07.02) (SEQ ID NO: 522) | |
| | | | SILPAAIPA (A02.01) (SEQ ID NO: 523) | |
| | | | SLPAAATSA (A02.01) (SEQ ID NO: 524) | |
| | | | SLPAAATSAA (A02.01) (SEQ ID NO: 525) | |
| | | | SLWTTRPQR (A03.01) (SEQ ID NO: 526) | |
| | | | SLWTTRPQRV (A02.01) (SEQ ID NO: 527) | |
| | | | SPSAAAATL (B07.02) (SEQ ID NO: 528) | |
| | | | SPSAAAATLL (B07.02) (SEQ ID NO: 529) | |
| | | | TLDALPAGCV (A02.01) (SEQ ID NO: 530) | |
| | | | TVSTTTAPV (A02.01) (SEQ ID NO: 531) | |
| | | | VLSASILPA (A02.01) (SEQ ID NO: 532) | |
| | | | VLSASILPAA (A02.01) (SEQ ID NO: 533) | |
| | | | VPANCLFPA (B07.02) (SEQ ID NO: 534) | |
| | | | VPANCLFPAA (B07.02) (SEQ ID NO: 535) | |
| | | | VPDPSCPTF (B07.02) (SEQ ID NO: 536) | |
| | | | VPGSIPLPA (B07.02) (SEQ ID NO: 537) | |
| | | | VPGSIPLPAV (B07.02) (SEQ ID NO: 538) | |
| | | | WVSGILSPL (A02.01) (SEQ ID NO: 539) | |
| | | | YTADSSLWTT (A02.01) (SEQ ID NO: 540) | |
| ARID1A | T433fs A441fs Y447fs P483fs P484fs P504fs S519fs H544fs P549fs P554fs Q563fs | PCRAGRRVPWAASLI HSRFLLMDNKAPAG MVNRARLHITTSKVL TLSSSSHPTPSNHRPR PLMPNLRISSSHSLNH HSSSPLSLHTPSSHPS LHISSPRLHTPPSSRR HSSTPRASPPTHSHRL SLLTSSSNLSSQHPRR SPSRLRILSPSLSSPSK LPIPSSASLHRRSYLKI HLGLRHPQPPQ* (SEQ ID NO: 87) | APAGMVNRA (B07.02) (SEQ ID NO: 541) ASLHRRSYL (B08.01) (SEQ ID NO: 542) ASLHRRSYLK (A03.01) (SEQ ID NO: 543) FLLMDNKAPA (A02.01) (SEQ ID NO: 544) HPRRSPSRL (B07.02, B08.01) (SEQ ID NO: 545) HPSLHISSP (B07.02) (SEQ ID NO: 546) HRRSYLKIHL (B08.01) (SEQ ID NO: 547) HSRFLLMDNK (A03.01) (SEQ ID NO: 548) KLPIPSSASL (A02.01) (SEQ ID NO: 549) KVLTLSSSSH (A03.01) (SEQ ID NO: 550) LIHSRFLLM (B08.01) (SEQ ID NO: 551) LLMDNKAPA (A02.01) (SEQ ID NO: 552) LMDNKAPAGM (A02.01) (SEQ ID NO: 553) | STAD, UCEC, BLCA, BRCA, LUSC, CESC, KIRC, UCS |

TABLE 1-continued

| Gene | Exemplary Protein Change | Mutation Sequence Context | Peptides (HLA allele example(s)) | Exemplary Diseases |
|---|---|---|---|---|
| | | | LPIPSSASL (B07.02) (SEQ ID NO: 554) | |
| | | | MPNLRISSS (B07.02, B08.01) (SEQ ID NO: 555) | |
| | | | MPNLRISSSH (B07.02) (SEQ ID NO: 556) | |
| | | | NLRISSSHSL (B07.02, B08.01) (SEQ ID NO: 557) | |
| | | | PPTHSHRLSL (B07.02) (SEQ ID NO: 558) | |
| | | | RAGRRVPWAA (B08.01) (SEQ ID NO: 559) | |
| | | | RARLHITTSK (A03.01) (SEQ ID NO: 560) | |
| | | | RISSSHSLNH (A03.01) (SEQ ID NO: 561) | |
| | | | RLHTPPSSR (A03.01) (SEQ ID NO: 562) | |
| | | | RLHTPPSSRR (A03.01) (SEQ ID NO: 563) | |
| | | | RLRILSPSL (A02.01, B07.02, B08.01) (SEQ ID NO: 564) | |
| | | | RPLMPNLRI (B07.02) (SEQ ID NO: 565) | |
| | | | RPRPLMPNL (B07.02) (SEQ ID NO: 566) | |
| | | | SASLHRRSYL (B07.02, B08.01) (SEQ ID NO: 567) | |
| | | | SLHISSPRL (A02.01) (SEQ ID NO: 568) | |
| | | | SLHRRSYLK (A03.01) (SEQ ID NO: 569) | |
| | | | SLHRRSYLKI (B08.01) (SEQ ID NO: 570) | |
| | | | SLIHSRFLL (A02.01) (SEQ ID NO: 571) | |
| | | | SLIHSRFLLM (A02.01, B08.01) (SEQ ID NO: 572) | |
| | | | SLLTSSSNL (A02.01) (SEQ ID NO: 573) | |
| | | | SLNHHSSSPL (A02.01, B07.02, B08.01) (SEQ ID NO: 574) | |
| | | | SLSSPSKLPI (A02.01) (SEQ ID NO: 575) | |
| | | | SPLSLHTPS (B07.02) (SEQ ID NO: 576) | |
| | | | SPLSLHTPSS (B07.02) (SEQ ID NO: 577) | |
| | | | SPPTHSHRL (B07.02) (SEQ ID NO: 578) | |
| | | | SPRLHTPPS (B07.02) (SEQ ID NO: 579) | |
| | | | SPRLHTPPSS (B07.02) (SEQ ID NO: 580) | |
| | | | SPSLSSPSKL (B07.02) (SEQ ID NO: 581) | |
| | | | SYLKIHLGL (A24.02) (SEQ ID NO: 582) | |
| | | | TPSNHRPRPL (B07.02, B08.01) (SEQ ID NO: 583) | |
| | | | TPSSHPSLHI (B07.02) (SEQ ID NO: 584) | |
| ARID1A | A2137fs P2139fs L1970fs V1994fs | RTNPTVRMRPHCVPF WTGRILLPSAASVCPI PFEACHLCQAMTLRC PNTQGCCSSWAS* (SEQ ID NO: 88) | CVPFWTGRIL (B07.02) (SEQ ID NO: 585) HCVPFWTGRIL (B07.02) (SEQ ID NO: 586) ILLPSAASV (A02.01) (SEQ ID NO: 587) | STAD, UCEC, BLCA, BRCA, LUSC, CESC, KIRC, UCS |

TABLE 1-continued

| Gene | Exemplary Protein Change | Mutation Sequence Context | Peptides (HLA allele example(s)) | Exemplary Diseases |
|---|---|---|---|---|
| | | | ILLPSAASVC (A02.01) (SEQ ID NO: 588) LLPSAASVCPI (A02.01) (SEQ ID NO: 589) LPSAASVCPI (B07.02) (SEQ ID NO: 590) MRPHCVPF (B08.01) (SEQ ID NO: 591) RILLPSAASV (A02.01) (SEQ ID NO: 592) RMRPHCVPF (A24.02, B07.02, B08.01) (SEQ ID NO: 593) RMRPHCVPFW (A24.02) (SEQ ID NO: 594) RTNPTVRMR (A03.01) (SEQ ID NO: 595) SVCPIPFEA (A02.01) (SEQ ID NO: 596) TVRMRPHCV (B08.01) (SEQ ID NO: 597) TVRMRPHCVPF (B08.01) (SEQ ID NO: 598) VPFWTGRIL (B07.02) (SEQ ID NO: 599) VPFWTGRILL (B07.02) (SEQ ID NO: 600) VRMRPHCVPF (B08.01) (SEQ ID NO: 601) | |
| ARID1A | N756fs S764fs T783fs Q799fs A817fs | TNQALPKIEVICRGTP RCPSTVPPSPAQPYLR VSLPEDRYTQAWAPT SRTPWGAMVPRGVS MAHKVATPGSQTIMP CPMPTTPVQAWLEA* (SEQ ID NO: 89) | AMVPRGVSM (B07.02, B08.01) (SEQ ID NO: 602) AMVPRGVSMA (A02.01) (SEQ ID NO: 603) AWAPTSRTPW (A24.02) (SEQ ID NO: 604) CPMPTTPVQA (B07.02) (SEQ ID NO: 605) CPSTVPPSPA (B07.02) (SEQ ID NO: 606) GAMVPRGVSM (B07.02, B08.01) (SEQ ID NO: 607) MPCPMPTTPV (B07.02) (SEQ ID NO: 608) MPTTPVQAW (B07.02) (SEQ ID NO: 609) MPTTPVQAWL (B07.02) (SEQ ID NO: 610) SLPEDRYTQA (A02.01) (SEQ ID NO: 611) SPAQPYLRV (B07.02) (SEQ ID NO: 612) SPAQPYLRVS (B07.02) (SEQ ID NO: 613) TIMPCPMPT (A02.01) (SEQ ID NO: 614) TPVQAWLEA (B07.02) (SEQ ID NO: 615) TSRTPWGAM (B07.02) (SEQ ID NO: 616) VPPSPAQPYL (B07.02) (SEQ ID NO: 617) VPRGVSMAH (B07.02) (SEQ ID NO: 618) | STAD, UCEC, BLCA, BRCA, LUSC, CESC, KIRC, UCS |
| β2M | N62fs E67fs L74fs F82fs T91fs E94fs | RMERELKKWSIQTCL SARTGLSISCTTLNSP PLKKMSMPAV* (SEQ ID NO: 90) | CLSARTGLSI (B08.01) (SEQ ID NO: 619) CTTLNSPPLK (A03.01) (SEQ ID NO: 620) GLSISCTTL (A02.01) (SEQ ID NO: 621) SPPLKKMSM (B07.02, B08.01) (SEQ ID NO: 622) | CRC, STAD, SKCM, HNSC |

TABLE 1-continued

| Gene | Exemplary Protein Change | Mutation Sequence Context | Peptides (HLA allele example(s)) | Exemplary Diseases |
|---|---|---|---|---|
| | | | TLNSPPLKK (A03.01) (SEQ ID NO: 623) TTLNSPPLK (A03.01) (SEQ ID NO: 624) TTLNSPPLKK (A03.01) (SEQ ID NO: 625) | |
| β2M | L13fs S14fs | LCSRYSLFLAWRLSS VLQRFRFTHVIQQRM ESQIS* (SEQ ID NO: 91) | LQRFRFTHV (B08.01) (SEQ ID NO: 626) LQRFRFTHVI (B08.01) (SEQ ID NO: 627) RLSSVLQRF (A24.02) (SEQ ID NO: 628) RLSSVLQRFR (A03.01) (SEQ ID NO: 629) VLQRFRFTHV (A02.01, B08.01) (SEQ ID NO: 630) | CRC, STAD, SKCM, HNSC |
| CDH1 | A691fs P708fs L711fs | RSACVTVKGPLASVG RHSLSKQDCKFLPFW GFLEEFLLC* (SEQ ID NO: 92) | ASVGRHSLSK (A03.01) (SEQ ID NO: 631) KFLPFWGFL (A24.02) (SEQ ID NO: 632) LASVGRHSL (B07.02) (SEQ ID NO: 633) LPFWGFLEEF (B07.02) (SEQ ID NO: 634) PFWGFLEEF (A24.02) (SEQ ID NO: 635) SVGRHSLSK (A03.01) (SEQ ID NO: 636) | ILC LumA Breast Cancer |
| CDH1 | H121fs P126fs H128fs N144fs V157fs P159fs N166fs N181fs F189fs P201fs F205fs | IQWGTTTAPRPIRPPF LESKQNCSHFPTPLL ASEDRRETGLFLPSA AQKMKKAHFLKTWF RSNPTKTKKARFSTA SLAKELTHPLLVSLLL KEKQDG* (SEQ ID NO: 93) | APRPIRPPF (B07.02) (SEQ ID NO: 637) APRPIRPPFL (B07.02) (SEQ ID NO: 638) AQKMKKAHFL (B08.01) (SEQ ID NO: 639) FLPSAAQKM (A02.01) (SEQ ID NO: 640) GLFLPSAAQK (A03.01) (SEQ ID NO: 641) HPLLVSLLL (B07.02) (SEQ ID NO: 642) KAHFLKTWFR (A03.01) (SEQ ID NO: 643) KARFSTASL (B07.02) (SEQ ID NO: 644) KMKKAHFLK (A03.01) (SEQ ID NO: 645) KTWFRSNPTK (A03.01) (SEQ ID NO: 646) LAKELTHPL (B07.02, B08.01) (SEQ ID NO: 647) LAKELTHPLL (B08.01) (SEQ ID NO: 648) NPTKTKKARF (B07.02) (SEQ ID NO: 649) QKMKKAHFL (B08.01) (SEQ ID NO: 650) RFSTASLAK (A03.01) (SEQ ID NO: 651) RPIRPPFLES (B07.02) (SEQ ID NO: 652) RSNPTKTKK (A03.01) (SEQ ID NO: 653) SLAKELTHPL (A02.01, B08.01) (SEQ ID NO: 654) TKKARFSTA (B08.01) (SEQ ID NO: 655) | ILC LumA Breast Cancer |

TABLE 1-continued

| Gene | Exemplary Protein Change | Mutation Sequence Context | Peptides (HLA allele example(s)) | Exemplary Diseases |
|---|---|---|---|---|
| CDH1 | V114fs<br>P127fs<br>V132fs<br>P160fs | PTDPFLGLRLGLHLQ<br>KVFHQSHAEYSGAPP<br>PPPAPSGLRFWNPSRI<br>AHISQLLSWPQKTEE<br>RLGYSSHQLPRK*<br>(SEQ ID NO: 94) | GLRFWNPSR (A03.01)<br>(SEQ ID NO: 656)<br>ISQLLSWPQK (A03.01)<br>(SEQ ID NO: 657)<br>RIAHISQLL (A02.01)<br>(SEQ ID NO: 658)<br>RLGYSSHQL (A02.01)<br>(SEQ ID NO: 659)<br>SQLLSWPQK (A03.01)<br>(SEQ ID NO: 660)<br>SRIAHISQL (B08.01)<br>(SEQ ID NO: 661)<br>WPQKTEERL (B07.02)<br>(SEQ ID NO: 662)<br>YSSHQLPRK (A03.01)<br>(SEQ ID NO: 663) | ILC LumA Breast Cancer |
| CDH1 | L731fs<br>R749fs<br>E757fs<br>G759fs | FCCSCCFFGGERWSK<br>SPYCPQRMTPGTTFIT<br>MMKKEAEKRTRTLT*<br>(SEQ ID NO: 95) | CPQRMTPGTT (B07.02)<br>(SEQ ID NO: 664)<br>EAEKRTRTL (B08.01)<br>(SEQ ID NO: 665)<br>GTTFITMMK (A03.01)<br>(SEQ ID NO: 666)<br>GTTFITMMKK (A03.01)<br>(SEQ ID NO: 667)<br>ITMMKKEAEK (A03.01)<br>(SEQ ID NO: 668)<br>RMTPGTTFI (A02.01)<br>(SEQ ID NO: 669)<br>SPYCPQRMT (B07.02)<br>(SEQ ID NO: 670)<br>TMMKKEAEK (A03.01)<br>(SEQ ID NO: 671)<br>TPGTTFITM (B07.02)<br>(SEQ ID NO: 672)<br>TPGTTFITMM (B07.02)<br>(SEQ ID NO: 673)<br>TTFITMMKK (A03.01)<br>(SEQ ID NO: 674) | ILC LumA Breast Cancer |
| CDH1 | S19fs<br>E24fs<br>S36fs | WRRNCKAPVSLRKS<br>VQTPARSSPARPDRT<br>RRLPSLGVPGQPWAL<br>GAAASRRCCCCCRSP<br>LGSARSRSPATLALTP<br>RATRSRCPGATWRE<br>AASWAE*<br>(SEQ ID NO: 96) | CPGATWREA (B07.02)<br>(SEQ ID NO: 675)<br>CPGATWREAA (B07.02)<br>(SEQ ID NO: 676)<br>RSRCPGATWR (A03.01)<br>(SEQ ID NO: 677)<br>TPRATRSRC (B07.02)<br>(SEQ ID NO: 678) | ILC LumA Breast Cancer |
| GATA3 | P394fs<br>P387fs<br>S398fs<br>H400fs<br>M401fs<br>S408fs<br>P409fs<br>S408fs<br>P409fs<br>T419fs<br>H424fs<br>P425fs<br>S427fs<br>F431fs<br>S430fs<br>H434fs<br>H435fs<br>S438fs<br>M443fs<br>G444fs<br>*445fs | PGRPLQTHVLPEPHL<br>ALQPLQPHADHAHA<br>DAPAIQPVLWTTPPL<br>QHGHRHGLEPCSML<br>TGPPARVPAVPFDLH<br>FCRSSIMKPKRDGYM<br>FLKAESKIMFATLQR<br>SSLWCLCSNH*<br>(SEQ ID NO: 97) | HVLPEPHLAL (B07.02)<br>(SEQ ID NO: 679)<br>RPLQTHVLPE (B07.02)<br>(SEQ ID NO: 680)<br>VLWTTPPLQH (A03.01)<br>(SEQ ID NO: 681) | Breast Cancer |

TABLE 1-continued

| Gene | Exemplary Protein Change | Mutation Sequence Context | Peptides (HLA allele example(s)) | Exemplary Diseases |
|---|---|---|---|---|
| GATA3 | P426fs<br>H434fs<br>P433fs<br>T441fs | PRPRRCTRHPACPLD<br>HTTPPAWSPPWVRAL<br>LDAHRAPSESPCSPFR<br>LAFLQEQYHEA*<br>(SEQ ID NO: 98) | APSESPCSPF (B07.02)<br>(SEQ ID NO: 682)<br>CPLDHTTPPA (B07.02)<br>(SEQ ID NO: 683)<br>FLQEQYHEA (A02.01, B08.01)<br>(SEQ ID NO: 684)<br>RLAFLQEQYH (A03.01)<br>(SEQ ID NO: 685)<br>SPCSPFRLAF (B07.02)<br>(SEQ ID NO: 686)<br>SPPWVRALL (B07.02)<br>(SEQ ID NO: 687)<br>YPACPLDHTT (B07.02)<br>(SEQ ID NO: 688) | Breast Cancer |
| MLL2 | P519fs<br>E524fs<br>P647fs<br>S654fs<br>L656fs<br>R755fs<br>L761fs<br>Q773fs | TRRCHCCPHLRSHPC<br>PHHLRNHPRPHHLRH<br>HACHHHLRNCPHPHF<br>LRHCTCPGRWRNRPS<br>LRRLRSLLCLPHLNH<br>HLFLHWRSRPCLHRK<br>SHPHLLHLRRLYPHH<br>LKHRPCPHHLKNLLC<br>PRHLRNCPLPRHLKH<br>LACLHHLRSHPCPLH<br>LKSHPCLHHRRHLVC<br>SHHLKSLLCPHLRS<br>LPFPHHLRHHACPHH<br>LRTRLCPHHLKNHLC<br>PPHLRYAYPPCLWC<br>HACLHRLRNLPCPHR<br>LRSLPRPLHLRLHASP<br>HHLRTPPHPHHLRTH<br>LLPHHRRTRSCPCRW<br>RSHPCCHYLRSRNSA<br>PGPRGRTCHPGLRSR<br>TCPPGLRSHTYLRRL<br>RSHTCPPSLRSHAYA<br>LCLRSHTCPPRLRDHI<br>CPLSLRNCTCPPRLRS<br>RTCLLCLRSHACPPN<br>LRNHTCPPSLRSHAC<br>PPGLRNRICPLSLRSH<br>PCPLGLKSPLRSQAN<br>ALHLRSCPCSLPLGN<br>HPYLPCLESQPCLSLG<br>NHLCPLCPRSCRCPH<br>LGSHPCRLS*<br>(SEQ ID NO: 99) | ALHLRSCPC (B08.01)<br>(SEQ ID NO: 689)<br>CLHHRRHLV (B08.01)<br>(SEQ ID NO: 690)<br>CLHHRRHLVC (B08.01)<br>(SEQ ID NO: 691)<br>CLHRKSHPHL (B08.01)<br>(SEQ ID NO: 692)<br>CLRSHACPP (B08.01)<br>(SEQ ID NO: 693)<br>CLRSHTCPP (B08.01)<br>(SEQ ID NO: 694)<br>CLWCHACLH (A03.01)<br>(SEQ ID NO: 695)<br>CPHHLKNHL (B07.02)<br>(SEQ ID NO: 696)<br>CPHHLKNLL (B07.02)<br>(SEQ ID NO: 697)<br>CPHHLRTRL (B07.02, B08.01)<br>(SEQ ID NO: 698)<br>CPLHLRSLPF (B07.02, B08.01)<br>(SEQ ID NO: 699)<br>CPLPRHLKHL (B07.02, B08.01)<br>(SEQ ID NO: 700)<br>CPLSLRSHPC (B07.02)<br>(SEQ ID NO: 701)<br>CPRHLRNCPL (B07.02, B08.01)<br>(SEQ ID NO: 702)<br>FPHHLRHHA (B07.02, B08.01)<br>(SEQ ID NO: 703)<br>FPHHLRHHAC (B07.02, B08.01)<br>(SEQ ID NO: 704)<br>GLRSRTCPP (B08.01)<br>(SEQ ID NO: 705)<br>HACLHRLRNL (B08.01)<br>(SEQ ID NO: 706)<br>HLACLHHLR (A03.01)<br>(SEQ ID NO: 707)<br>HLCPPHLRY (A03.01)<br>(SEQ ID NO: 708)<br>HLCPPHLRYR (A03.01)<br>(SEQ ID NO: 709)<br>HLKHLACLH (A03.01)<br>(SEQ ID NO: 710)<br>HLKHRPCPH (B08.01)<br>(SEQ ID NO: 711)<br>HLKNHLCPP (B08.01)<br>(SEQ ID NO: 712)<br>HLKSHPCLH (A03.01)<br>(SEQ ID NO: 713)<br>HLKSLLCPL (A02.01, B08.01)<br>(SEQ ID NO: 714) | STAD, BLCA, CRC, HNSC, BRCA |

TABLE 1-continued

| Gene | Exemplary Protein Change | Mutation Sequence Context | Peptides (HLA allele example(s)) | Exemplary Diseases |
|---|---|---|---|---|
| | | | HLLHLRRLY (A03.01) (SEQ ID NO: 715) | |
| | | | HLRNCPLPR (A03.01) (SEQ ID NO: 716) | |
| | | | HLRNCPLPRH (A03.01) (SEQ ID NO: 717) | |
| | | | HLRRLYPHHL (B08.01) (SEQ ID NO: 718) | |
| | | | HLRSHPCPL (B07.02, B08.01) (SEQ ID NO: 719) | |
| | | | HLRSHPCPLH (A03.01) (SEQ ID NO: 720) | |
| | | | HLRSLPFPH (A03.01) (SEQ ID NO: 721) | |
| | | | HLRTRLCPH (A03.01, B08.01) (SEQ ID NO: 722) | |
| | | | HLVCSHHLK (A03.01) (SEQ ID NO: 723) | |
| | | | HPCLHHRRHL (B07.02, B08.01) (SEQ ID NO: 724) | |
| | | | HPGLRSRTC (B07.02) (SEQ ID NO: 725) | |
| | | | HPHLLHLRRL (B07.02, B08.01) (SEQ ID NO: 726) | |
| | | | HRKSHPHLL (B08.01) (SEQ ID NO: 727) | |
| | | | HRRTRSCPC (B08.01) (SEQ ID NO: 728) | |
| | | | KSHPHLLHLR (A03.01) (SEQ ID NO: 729) | |
| | | | KSLLCPLHLR (A03.01) (SEQ ID NO: 730) | |
| | | | LLCPLHLRSL (A02.01, B08.01) (SEQ ID NO: 731) | |
| | | | LLHLRRLYPH (B08.01) (SEQ ID NO: 732) | |
| | | | LPRHLKHLA (B07.02) (SEQ ID NO: 733) | |
| | | | LPRHLKHLAC (B07.02, B08.01) (SEQ ID NO: 734) | |
| | | | LRRLRSHTC (B08.01) (SEQ ID NO: 735) | |
| | | | LRRLYPHHL (B08.01) (SEQ ID NO: 736) | |
| | | | LVCSHHLKSL (B08.01) (SEQ ID NO: 737) | |
| | | | NLRNHTCPPS (B08.01) (SEQ ID NO: 738) | |
| | | | PLHLRSLPF (B08.01) (SEQ ID NO: 739) | |
| | | | RLCPHHLKNH (A03.01) (SEQ ID NO: 740) | |
| | | | RLYPHHLKH (A03.01) (SEQ ID NO: 741) | |
| | | | RLYPHHLKHR (A03.01) (SEQ ID NO: 742) | |
| | | | RPCPHHLKNL (B07.02) (SEQ ID NO: 743) | |
| | | | RSHPCPLHLK (A03.01) (SEQ ID NO: 744) | |
| | | | RSLPFPHHLR (A03.01) (SEQ ID NO: 745) | |
| | | | RTRLCPHHL (B07.02) (SEQ ID NO: 746) | |
| | | | RTRLCPHHLK (A03.01) (SEQ ID NO: 747) | |
| | | | SLLCPLHLR (A03.01) (SEQ ID NO: 748) | |
| | | | SLRSHACPP (B08.01) (SEQ ID NO: 749) | |

TABLE 1-continued

| Gene | Exemplary Protein Change | Mutation Sequence Context | Peptides (HLA allele example(s)) | Exemplary Diseases |
|---|---|---|---|---|
| | | | SPLRSQANA (B07.02) (SEQ ID NO: 750) YLRRLRSHT (B08.01) (SEQ ID NO: 751) YPHHLKHRPC (B07.02, B08.01) (SEQ ID NO: 752) | |
| PTEN | I122fs I135fs A148fs L152fs D162fs I168fs | SWKGTNWCNDMCIF ITSGQIFKGTRGPRFL WGSKDQRQKGSNYS QSEALCVLL* (SEQ ID NO: 100) | FITSGQIFK (A03.01) (SEQ ID NO: 753) IFITSGQIF (A24.02) (SEQ ID NO: 754) SQSEALCVL (A02.01) (SEQ ID NO: 755) SQSEALCVLL (A02.01) (SEQ ID NO: 756) | UCEC, PRAD, SKCM, STAD, BRCA, LUSC, KIRC, LIHC, KIRP, GBM |
| PTEN | L265fs K266fs | KRTKCFTFG* (SEQ ID NO: 101) | | UCEC, PRAD, SKCM, STAD, BRCA, LUSC, KIRC, LIHC, KIRP, GBM |
| PTEN | A39fs E40fs V45fs R47fs N48fs | PIFIQTLLLWDFLQKD LKAYTGTILMM* (SEQ ID NO: 102) | AYTGTILMM (A24.02) (SEQ ID NO: 757) DLKAYTGTIL (B08.01) (SEQ ID NO: 758) | UCEC, PRAD, SKCM, STAD, BRCA, LUSC, KIRC, LIHC, KIRP, GBM |
| PTEN | T319fs T321fs K327fs A328fs A333fs | QKMILTKQIKTKPTD TFLQILR* (SEQ ID NO: 103) | ILTKQIKTK (A03.01) (SEQ ID NO: 759) KMILTKQIK (A03.01) (SEQ ID NO: 760) KPTDTFLQI (B07.02) (SEQ ID NO: 761) KPTDTFLQIL (B07.02) (SEQ ID NO: 762) MILTKQIKTK (A03.01) (SEQ ID NO: 763) | UCEC, PRAD, SKCM, STAD, BRCA, LUSC, KIRC, LIHC, KIRP, GBM |
| PTEN | N63fs E73fs A86fs N94fs | GFWIQSIKTITRYTIFV LKDIMTPPNLIAELHN ILLKTITHHS* (SEQ ID NO: 104) | ITRYTIFVLK (A03.01) (SEQ ID NO: 764) LIAELHNIL (A02.01) (SEQ ID NO: 765) LIAELHNILL (A02.01) (SEQ ID NO: 766) MTPPNLIAEL (A02.01) (SEQ ID NO: 767) NLIAELHNI (A02.01) (SEQ ID NO: 768) NLIAELHNIL (A02.01) (SEQ ID NO: 769) RYTIFVLKDI (A24.02) (SEQ ID NO: 770) TITRYTIFVL (A02.01) (SEQ ID NO: 771) TPPNLIAEL (B07.02) (SEQ ID NO: 772) | UCEC, PRAD, SKCM, STAD, BRCA, LUSC, KIRC, LIHC, KIRP, GBM |
| PTEN | T202fs G209fs C211fs I224fs G230fs P231fs R233fs D236fs | NYSNVQWRNLQSSV CGLPAKGEDIFLQFR THTTGRQVHVL* (SEQ ID NO: 105) | FLQFRTHTT (A02.01, B08.01) (SEQ ID NO: 773) LPAKGEDIFL (B07.02) (SEQ ID NO: 774) LQFRTHTTGR (A03.01) (SEQ ID NO: 775) NLQSSVCGL (A02.01) (SEQ ID NO: 776) SSVCGLPAK (A03.01) (SEQ ID NO: 777) VQWRNLQSSV (A02.01) (SEQ ID NO: 778) | UCEC, PRAD, SKCM, STAD, BRCA, LUSC, KIRC, LIHC, KIRP, GBM |
| PTEN | G251fs E256fs K260fs Q261fs | YQSRVLPQTEQDAK KGQNVSLLGKYILHT RTRGNLRKSRKWKS M* | GQNVSLLGK (A03.01) (SEQ ID NO: 779) HTRTRGNLRK (A03.01) (SEQ ID NO: 780) | UCEC, PRAD, SKCM, STAD, BRCA, LUSC, KIRC, LIHC, KIRP, GBM |

TABLE 1-continued

| Gene | Exemplary Protein Change | Mutation Sequence Context | Peptides (HLA allele example(s)) | Exemplary Diseases |
| --- | --- | --- | --- | --- |
| | L265fs<br>M270fs<br>H272fs<br>T286fs<br>E288fs | (SEQ ID NO: 106) | ILHTRTRGNL (B08.01)<br>(SEQ ID NO: 781)<br>KGQNVSLLGK (A03.01)<br>(SEQ ID NO: 782)<br>LLGKYILHT (A02.01)<br>(SEQ ID NO: 783)<br>LRKSRKWKSM (B08.01)<br>(SEQ ID NO: 784)<br>SLLGKYILH (A03.01)<br>(SEQ ID NO: 785)<br>SLLGKYILHT (A02.01)<br>(SEQ ID NO: 786) | |
| TP53 | A70fs<br>P72fs<br>A76fs<br>A79fs<br>P89fs<br>W91fs<br>S96fs<br>V97fs<br>V97fs<br>G108fs<br>G117fs<br>S121fs<br>V122fs<br>C124fs<br>K139fs<br>V143fs | SSQNARGCSPRGPCT<br>SSSYTGGPCTSPLLAP<br>VIFCPFPENLPGQLRF<br>PSGLLAFWDSQVCDL<br>HVLPCPQQDVLPTGQ<br>DLPCAAVG*<br>(SEQ ID NO: 107) | CTSPLLAPV (A02.01)<br>(SEQ ID NO: 787)<br>FPENLPGQL (B07.02)<br>(SEQ ID NO: 788)<br>GLLAFWDSQV (A02.01)<br>(SEQ ID NO: 789)<br>IFCPFPENL (A24.02)<br>(SEQ ID NO: 790)<br>LLAFWDSQV (A02.01)<br>(SEQ ID NO: 791)<br>LLAPVIFCP (A02.01)<br>(SEQ ID NO: 792)<br>LLAPVIFCPF (A02.01, A24.02)<br>(SEQ ID NO: 793)<br>LPCPQQDVL (B07.02)<br>(SEQ ID NO: 794)<br>RFPSGLLAF (A24.02)<br>(SEQ ID NO: 795)<br>RFPSGLLAFW (A24.02)<br>(SEQ ID NO: 796)<br>SPLLAPVIF (B07.02)<br>(SEQ ID NO: 797)<br>SPRGPCTSS (B07.02)<br>(SEQ ID NO: 798)<br>SPRGPCTSSS (B07.02)<br>(SEQ ID NO: 799)<br>SQVCDLHVL (A02.01)<br>(SEQ ID NO: 800)<br>VIFCPFPENL (A02.01)<br>(SEQ ID NO: 801) | BRCA, CRC, LUAD, PRAD, HNSC, LUSC, PAAD, STAD, BLCA, OV, LIHC, SKCM, UCEC, LAML, UCS, KICH, GBM, ACC |
| TP53 | V173fs<br>H178fs<br>D186fs<br>H193fs<br>L194fs<br>E198fs<br>V203fs<br>E204fs<br>L206fs<br>D207fs<br>N210fs<br>T211fs<br>F212fs<br>V225fs<br>S241fs | GAAPTMSAAQIAMV<br>WPLLSILSEWKEICV<br>WSIWMTETLFDIVW<br>WCPMSRLRLALTVPP<br>STTTTCVTVPAWAA*<br>(SEQ ID NO: 108) | AMVWPLLSI (A02.01)<br>(SEQ ID NO: 802)<br>AMVWPLLSIL (A02.01)<br>(SEQ ID NO: 803)<br>AQIAMVWPL (A02.01, A24.02)<br>(SEQ ID NO: 804)<br>AQIAMVWPLL (A02.01)<br>(SEQ ID NO: 805)<br>CPMSRLRLA (B07.02, B08.01)<br>(SEQ ID NO: 806)<br>CPMSRLRLAL (B07.02, B08.01)<br>(SEQ ID NO: 807)<br>IAMVWPLLSI (A02.01, A24.02, B08.01)<br>(SEQ ID NO: 808)<br>ILSEWKEICV (A02.01)<br>(SEQ ID NO: 809)<br>IVWWCPMSR (A03.01)<br>(SEQ ID NO: 810)<br>IVWWCPMSRL (A02.01)<br>(SEQ ID NO: 811)<br>IWMTETLFDI (A24.02)<br>(SEQ ID NO: 812)<br>LLSILSEWK (A03.01)<br>(SEQ ID NO: 813)<br>MSAAQIAMV (A02.01)<br>(SEQ ID NO: 814)<br>MSRLRLALT (B08.01)<br>(SEQ ID NO: 815) | BRCA, CRC, LUAD, PRAD, HNSC, LUSC, PAAD, STAD, BLCA, OV, LIHC, SKCM, UCEC, LAML, UCS, KICH, GBM, ACC |

TABLE 1-continued

| Gene | Exemplary Protein Change | Mutation Sequence Context | Peptides (HLA allele example(s)) | Exemplary Diseases |
|---|---|---|---|---|
| | | | MSRLRLALTV (B08.01) (SEQ ID NO: 816) MVWPLLSIL (A02.01) (SEQ ID NO: 817) RLALTVPPST (A02.01) (SEQ ID NO: 818) TLFDIVWWC (A02.01) (SEQ ID NO: 819) TLFDIVWWCP (A02.01) (SEQ ID NO: 820) TMSAAQIAMV (A02.01) (SEQ ID NO: 821) VWSIWMTETL (A24.02) (SEQ ID NO: 822) WMTETLFDI (A02.01, A24.02) (SEQ ID NO: 823) WMTETLFDIV (A01.01, A02.01) (SEQ ID NO: 824) | |
| TP53 | R248fs P250fs S260fs N263fs G266fs N268fs V272fs V274fs P278fs D281fs R282fs T284fs E285fs L289fs K292fs P301fs S303fs T312fs S314fs K319fs K320fs P322fs Y327fs F328fs L330fs R333fs R335fs R337fs E339fs | TGGPSSPSSHWKTPV VIYWDGTALRCVFVP VLGETGAQRKRISAR KGSLTTSCPQGALSE HCPTTPAPLPSQRRN HWMENISPFRSVGVS ASRCSES* (SEQ ID NO: 109) | ALRCVFVPV (A02.01, B08.01) (SEQ ID NO: 825) ALRCVFVPVL (A02.01, B08.01) (SEQ ID NO: 826) ALSEHCPTT (A02.01) (SEQ ID NO: 827) AQRKRISARK (A03.01) (SEQ ID NO: 828) GAQRKRISA (B08.01) (SEQ ID NO: 829) HWMENISPF (A24.02) (SEQ ID NO: 830) LPSQRRNHW (B07.02) (SEQ ID NO: 831) LPSQRRNHWM (B07.02, B08.01) (SEQ ID NO: 832) NISPFRSVGV (A02.01) (SEQ ID NO: 833) RISARKGSL (B07.02, B08.01) (SEQ ID NO: 834) SPFRSVGVSA (B07.02) (SEQ ID NO: 835) SPSSHWKTPV (B07.02, B08.01) (SEQ ID NO: 836) TALRCVFVPV (A02.01) (SEQ ID NO: 837) VIYWDGTAL (A02.01) (SEQ ID NO: 838) VIYWDGTALR (A03.01) (SEQ ID NO: 839) VLGETGAQRK (A03.01) (SEQ ID NO: 840) | BRCA, CRC, LUAD, PRAD, HNSC, LUSC, PAAD, STAD, BLCA, OV, LIHC, SKCM, UCEC, LAML, UCS, KICH, GBM, ACC |
| TP53 | S149fs P151fs P152fs V157fs Q165fs S166fs H168fs V173fs | FHTPARHPRPRHGHL QAVTAHDGGCEALP PP* (SEQ ID NO: 110) | HPRPRHGHL (B07.02, B08.01) (SEQ ID NO: 841) HPRPRHGHLQ (B07.02) (SEQ ID NO: 842) RPRHGHLQA (B07.02) (SEQ ID NO: 843) RPRHGHLQAV (B07.02, B08.01) (SEQ ID NO: 844) | BRCA, CRC, LUAD, PRAD, HNSC, LUSC, PAAD, STAD, BLCA, OV, LIHC, SKCM, UCEC, LAML, UCS, KICH, GBM, ACC |
| TP53 | P47fs D48fs D49fs Q52fs | CCPRTILNNGSLKTQ VQMKLPECQRLLPP WPLHQQLLHRRPLH QPPPGPCHLLSLPRKP | GSLKTQVQMK (A03.01) (SEQ ID NO: 845) PPGPCHLLSL (B07.02) (SEQ ID NO: 846) | BRCA, CRC, LUAD, PRAD, HNSC, LUSC, PAAD, STAD, BLCA, OV, LIHC, SKCM, |

TABLE 1-continued

| Gene | Exemplary Protein Change | Mutation Sequence Context | Peptides (HLA allele example(s)) | Exemplary Diseases |
|------|---------------------------|---------------------------|----------------------------------|---------------------|
| | F54fs E56fs P58fs P60fs E62fs M66fs P72fs V73fs P75fs A78fs P82fs P85fs S96fs P98fs T102fs Y103fs G108fs F109fs R110fs G117fs | TRAATVSVWASCILG QPSL* (SEQ ID NO: 111) | RTILNNGSLK (A03.01) (SEQ ID NO: 847) SLKTQVQMK (A03.01) (SEQ ID NO: 848) SLKTQVQMKL (B08.01) (SEQ ID NO: 849) TILNNGSLK (A03.01) (SEQ ID NO: 850) | UCEC, LAML, UCS, KICH, GBM, ACC |
| TP53 | L26fs P27fs P34fs P36fs A39fs Q38fs | VRKHFQTYGNYFLK TTFCPPCRPKQWMI* (SEQ ID NO: 112) | CPPCRPKQWM (B07.02) (SEQ ID NO: 851) TTFCPPCRPK (A03.01) (SEQ ID NO: 852) | BRCA, CRC, LUAD, PRAD, HNSC, LUSC, PAAD, STAD, BLCA, OV, LIHC, SKCM, UCEC, LAML, UCS, KICH, GBM, ACC |
| TP53 | C124fs L130fs N131fs C135fs K139fs A138fs T140fs V143fs Q144fs V147fs T150fs P151fs P152fs G154fs R156fs R158fs A161fs | LARTPLPSTRCFANW PRPALCSCGLIPHPRP APASAPWPSTSSHST* (SEQ ID NO: 113) | CFANWPRPAL (A24.02) (SEQ ID NO: 853) FANWPRPAL (B07.02, B08.01) (SEQ ID NO: 854) GLIPHPRPA (A02.01) (SEQ ID NO: 855) HPRPAPASA (B07.02, B08.01) (SEQ ID NO: 856) HPRPAPASAP (B07.02) (SEQ ID NO: 857) IPHPRPAPA (B07.02, B08.01) (SEQ ID NO: 858) IPHPRPAPAS (B07.02) (SEQ ID NO: 859) RPALCSCGL (B07.02) (SEQ ID NO: 860) RPALCSCGLI (B07.02) (SEQ ID NO: 861) TPLPSTRCF (B07.02) (SEQ ID NO: 862) WPRPALCSC (B07.02) (SEQ ID NO: 863) WPRPALCSCG (B07.02) (SEQ ID NO: 864) | BRCA, CRC, LUAD, PRAD, HNSC, LUSC, PAAD, STAD, BLCA, OV, LIHC, SKCM, UCEC, LAML, UCS, KICH, GBM, ACC |
| VHL | L178fs D179fs L184fs T202fs R205fs D213fs G212fs | ELQETGHRQVALRRS GRPPKCAERPGAADT GAHCTSTDGRLKISV ETYTVSSQLLMVLMS LDLDTGLVPSLVSKC LILRVK* (SEQ ID NO: 114) | ALRRSGRPPK (A03.01) (SEQ ID NO: 865) GLVPSLVSK (A03.01) (SEQ ID NO: 866) KISVETYTV (A02.01) (SEQ ID NO: 867) LLMVLMSLDL (A02.01, B08.01) (SEQ ID NO: 868) LMSLDLDTGL (A02.01) (SEQ ID NO: 869) LMVLMSLDL (A02.01) (SEQ ID NO: 870) LVSKCLILRV (A02.01) (SEQ ID NO: 871) QLLMVLMSL (A02.01, B08.01) (SEQ ID NO: 872) | KIRC, KIRP |

TABLE 1-continued

| Gene | Exemplary Protein Change | Mutation Sequence Context | Peptides (HLA allele example(s)) | Exemplary Diseases |
|---|---|---|---|---|
| | | | RPGAADTGA (B07.02) (SEQ ID NO: 873) | |
| | | | RPGAADTGAH (B07.02) (SEQ ID NO: 874) | |
| | | | SLDLDTGLV (A02.01) (SEQ ID NO: 875) | |
| | | | SLVSKCLIL (A02.01, B08.01) (SEQ ID NO: 876) | |
| | | | SQLLMVLMSL (A02.01) (SEQ ID NO: 877) | |
| | | | TVSSQLLMV (A02.01) (SEQ ID NO: 878) | |
| | | | TYTVSSQLL (A24.02) (SEQ ID NO: 879) | |
| | | | TYTVSSQLLM (A24.02) (SEQ ID NO: 880) | |
| | | | VLMSLDLDT (A02.01) (SEQ ID NO: 881) | |
| | | | VPSLVSKCL (B07.02) (SEQ ID NO: 882) | |
| | | | VSKCLILRVK (A03.01) (SEQ ID NO: 883) | |
| | | | YTVSSQLLM (A01.01) (SEQ ID NO: 884) | |
| | | | YTVSSQLLMV (A02.01) (SEQ ID NO: 885) | |
| VHL | L158fs K159fs R161fs Q164fs | KSDASRLSGA* (SEQ ID NO: 115) | | KIRC, KIRP |
| VHL | P146fs I147fs F148fs L158fs | RTAYFCQYHTASVYS ERAMPPGCPEPSQA* (SEQ ID NO: 116) | FCQYHTASV (B08.01) (SEQ ID NO: 886) | KIRC, KIRP |
| VHL | S68fs S72fs I75fs S80fs P86fs P97fs I109fs H115fs L116fs G123fs T124fs N131fs L135fs V137fs G144fs D143fs I147fs | TRASPPRSSSAIAVRA SCCPYGSTSTASRSPT QRCRLARAAASTATE VTFGSSEMQGHTMG FWLTKLNYLCHLSM LTDSLFLPISHCQCIL* (SEQ ID NO: 117) | CPYGSTSTA (B07.02) (SEQ ID NO: 887) CPYGSTSTAS (B07.02) (SEQ ID NO: 888) LARAAASTAT (B07.02) (SEQ ID NO: 889) MLTDSLFLP (A02.01) (SEQ ID NO: 890) PPRSSSAIAV (B07.02) (SEQ ID NO: 891) RAAASTATEV (B07.02) (SEQ ID NO: 892) SPPRSSSAI (B07.02) (SEQ ID NO: 893) SPPRSSSAIA (B07.02) (SEQ ID NO: 894) SPTQRCRLA (B07.02) (SEQ ID NO: 895) TQRCRLARA (B08.01) (SEQ ID NO: 896) TQRCRLARAA (B08.01) (SEQ ID NO: 897) | KIRC, KIRP |
| VHL | K171fs P172fs N174fs L178fs D179fs L188fs | SSLRITGDWTSSGRST KIWKTTQMCRKTWS G* (SEQ ID NO: 118) | KIWKTTQMCR (A03.01) (SEQ ID NO: 898) WTSSGRSTK (A03.01) (SEQ ID NO: 899) | KIRC, KIRP |
| VHL | V62fs V66fs Q73fs V84fs F91fs T100fs | RRRRGGVGRRGVRP GRVRPGGTGRRGGD GGRAAAARAALGEL ARALPGHLLQSQSAR RAARMAQLRRRAAA LPNAAAWHGPPHPQ | ALGELARAL (A02.01) (SEQ ID NO: 900) AQLRRRAAA (B08.01) (SEQ ID NO: 901) AQLRRRAAAL (B08.01) (SEQ ID NO: 902) | KIRC, KIRP |

TABLE 1-continued

| Gene | Exemplary Protein Change | Mutation Sequence Context | Peptides (HLA allele example(s)) | Exemplary Diseases |
|---|---|---|---|---|
| | P103fs S111fs L116fs H115fs D126fs | LPRSPLALQRCRDTR WASG* (SEQ ID NO: 119) | ARRAARMAQL (B08.01) (SEQ ID NO: 903) HPQLPRSPL (B07.02, B08.01) (SEQ ID NO: 904) HPQLPRSPLA (B07.02) (SEQ ID NO: 905) LARALPGHL (B07.02) (SEQ ID NO: 906) LARALPGHLL (B07.02) (SEQ ID NO: 907) MAQLRRRAA (B07.02, B08.01) (SEQ ID NO: 908) MAQLRRRAAA (B07.02, B08.01) (SEQ ID NO: 909) QLRRRAAAL (B07.02, B08.01) (SEQ ID NO: 910) RAAALPNAAA (B07.02) (SEQ ID NO: 911) RMAQLRRRAA (B07.02, B08.01) (SEQ ID NO: 912) SQSARRAARM (B08.01) (SEQ ID NO: 913) | |
| TABLE 1D | | CRYPTIC EXON [1] | | |
| AR-v7 | cryptic final exon | SCKVFFKRAAEGKQ KYLCASRNDCTIDKF RRKNCPSCRLRKCYE AGMTLGEKFRVGNC KHLKMTRP* (SEQ ID NO: 120) | GMTLGEKFRV (A02:01) (SEQ ID NO: 914) RVGNCKHLK (A03.01) (SEQ ID NO: 915) | Prostate Cancer, Castration-resistant Prostate Cancer |
| TABLE 1E | | OUT OF FRAME FUSIONS [1,3] | | |
| AC0119 97.1:LRRC69 | AC011997.1: LRRC69 *out-of-frame | MAGAPPPASLPPCSLI SDCCASNQRDSVGV GPSEP:G:NNIKICNES ASRK* (SEQ ID NO: 121) | GPSEPGNNI (B07.02) (SEQ ID NO: 916) KICNESASRK (A03.01) (SEQ ID NO: 917) | LUSC, Breast Cancer, Head and Neck Cancer, LUAD |
| EEF1DP3 | EEF1DP3:FRY *out-of-frame | HGWRPFLPVRARSR WNRRLDVTVANGR: S:WKYGWSLLRVPQV NGIQVLNVSLKSSSN VISYE* (SEQ ID NO: 122) | GIQVLNVSLK (A03.01) (SEQ ID NO: 918) IQVLNVSLK (A03.01) (SEQ ID NO: 919) KSSSNVISY (A01.01, A03.01) (SEQ ID NO: 920) KYGWSLLRV (A24.02) (SEQ ID NO: 921) RSWKYGWSL (A02.01) (SEQ ID NO: 922) SLKSSSNVI (B08.01) (SEQ ID NO: 923) SWKYGWSLL (A24.02) (SEQ ID NO: 924) TVANGRSWK (A03.01) (SEQ ID NO: 925) VPQVNGIQV (B07.02) (SEQ ID NO: 926) VPQVNGIQVL (B07.02) (SEQ ID NO: 927) VTVANGRSWK (A03.01) (SEQ ID NO: 928) WSLLRVPQV (B08.01) (SEQ ID NO: 929) | Breast Cancer |
| MAD1L1:MAFK | MAD1L1:MAFK | RLKEVFQTKIQEFRK ACYTLTGYQIDITTEN QYRLTSLYAEHPGDC LIFK::LRVPGSSVLV | HPGDCLIFKL (B07.02) (SEQ ID NO: 930) KLRVPGSSV (B07.02) (SEQ ID NO: 931) | CLL |

TABLE 1-continued

| Gene | Exemplary Protein Change | Mutation Sequence Context | Peptides (HLA allele example(s)) | Exemplary Diseases |
|---|---|---|---|---|
| | | TVPGL* (SEQ ID NO: 123) | KLRVPGSSVL (B07.02) (SEQ ID NO: 932) RVPGSSVLV (A02.01) (SEQ ID NO: 933) SVLVTVPGL (A02.01) (SEQ ID NO: 934) VPGSSVLVTV (B07.02) (SEQ ID NO: 935) | |
| PPP1R1B:STARD3 | PPP1R1B:STARD3 | AEVLKVIRQSAGQKT TCGQGLEGPWERPPP LDESERDGGSEDQVE DPALS:A:LLLRPRPP RPEVGAHQDEQAA QGADPRLGAQPACR GLPGLLTVPQPEPL LAPPSAA* (SEQ ID NO: 124) | ALLLRPRPPR (A03.01) (SEQ ID NO: 936) ALSALLLRPR (A03.01) (SEQ ID NO: 937) | Breast Cancer |
| Table 1F | | IN FRAME DELETIONS and FUSIONS [1,2] | | |
| BCR:ABL | BCR:ABL | ERAEWRENIREQQKK CFRSFSLTSVELQML TNSCVKLQTVHSIPLT INKE::EALQRPVASD FEPQGLSEAARWNS KENLLAGPSENDPN LFVALYDFVASG (SEQ ID NO: 125) | LTINKEEAL (A02.01, B08.01) (SEQ ID NO: 938) | CML, AML |
| BCR:ABL | BCR:ABL | ELQMLTNSCVKLQT VHSIPLTINKEDDESP GLYGFLNVIVHSATG FKQSS:K:ALQRPVAS DFEPQGLSEAARWN SKENLLAGPSENDP NLFVALYDFVASGD (SEQ ID NO: 126) | IVHSATGFK (A03.01) (SEQ ID NO: 939) ATGFKQSSK (A03.01) (SEQ ID NO: 940) | CML, AML |
| C11orf95:RELA | C11orf95:RELA | ISNSWDAHLGLGACG EAEGLGVQGAEEEEE EEEEEEEEGAGVPAC PPKGP:E:LFPLIFPAE PAQASGPYVEIIEQP KQRGMRFRYKCEG RSAGSIPGERSTD (SEQ ID NO: 127) | ELFPLIFPA (A02.01, B08.01) (SEQ ID NO: 941) KGPELFPLI (A02.01, A24.02) (SEQ ID NO: 942) KGPELFPLIF (A24.02) (SEQ ID NO: 943) | Supretentorial ependyomas |
| CBFB:MYH11 | (variant "type a") | LQRLDGMGCLEFDEE RAQQEDALAQQAFE EARRRTREFEDRDRS HREEME::VHELEKS KRALETQMEEMKT QLEELEDELQATED AKLRLEVNMQALK GQF (SEQ ID NO: 128) | | AML |
| CD74:ROS1 | (exon6:exon32) | KGSFPENLRHLKNTM ETIDWKVFESWMHH WLLFEMSRHSLEQKP TDAPPK::AGVPNKP GIPKLLEGSKNSIQ WEKAEDNGCRITYY ILEIRKSTSNNLQNQ (SEQ ID NO: 129) | KPTDAPPKAGV (B07.02) (SEQ ID NO: 944) | NSCLC, Crizotinib resistance |
| EGFR | EGFRvIII (internal deletion) | MRPSGTAGAALLALL AALCPASRALEEKK: G:NYVVTDHGSCVRA CGADSYEMEEDGVR | ALEEKKGNYV (A02.01) (SEQ ID NO: 945) | GBM |

TABLE 1-continued

| Gene | Exemplary Protein Change | Mutation Sequence Context | Peptides (HLA allele example(s)) | Exemplary Diseases |
|---|---|---|---|---|
| | | KCKKCEGPCRKVCN GIGIGEFKD (SEQ ID NO: 130) | | |
| EGFR:SEPT14 | EGFR:SEPT14 | LPQPPICTIDVYMIMV KCWMIDADSRPKFRE LIIEFSKMARDPQRYL VIQ::LQDKFEHLKM IQQEEIRKLEEEKK QLEGEIIDFYKMKA ASEALQTQLSTD (SEQ ID NO: 131) | IQLQDKFEHL (A02.01, B08.01) (SEQ ID NO: 946) QLQDKFEHL (A02.01, B08.01) (SEQ ID NO: 947) QLQDKFEHLK (A03.01) (SEQ ID NO: 948) YLVIQLQDKF (A02.01, A24.02) (SEQ ID NO: 949) | GBM, Glioma, Head and Neck Cancer |
| EML4:ALK | EML4:ALK | SWENSDDSRNKLSKI PSTPKLIPKVTKTADK HKDVIINQAKMSTRE KNSQ:V:YRRKHQEL QAMQMELQSPEYK LSKLRTSTIMTDYNP NYCFAGKTSSISDL (SEQ ID NO: 132) | QVYRRKHQEL (B08.01) (SEQ ID NO: 950) STREKNSQV (B08.01) (SEQ ID NO: 951) VYRRKHQEL (A24.02, B08.01) (SEQ ID NO: 952) | NSCLC |
| FGFR3:TACC3 | FGFR3:TACC3 | EGHRMDKPANCTHD LYMIMRECWHAAPS QRPTFKQLVEDLDRV LTVTSTD::VKATQEE NRELRSRCEELHGK NLELGKIMDRFEEV VYQAMEEVQKQKE LS (SEQ ID NO: 133) | VLTVTSTDV (A02.01) (SEQ ID NO: 953) VLTVTSTDVK (A03.01) (SEQ ID NO: 954) | Bladder Cancer, LUSC |
| NAB:STAT6 | NAB:STAT6 "" | RDNTLLLRRVELFSL SRQVARESTYLSSLK GSRLHPEELGGPPLK KLKQE::ATSKSQIMS LWGLVSKMPPEKV QRLYVDFPQHLRHL LGDWLESQPWEFL VGSDAFCC (SEQ ID NO: 134) | IMSLWGLVS (A02.01) (SEQ ID NO: 955) IMSLWGLVSK (A03.01) (SEQ ID NO: 956) KLKQEATSK (A03.01) (SEQ ID NO: 957) QIMSLWGLV (A02.01) (SEQ ID NO: 958) SQIMSLWGL (A02.01, A24.02, B08.01) (SEQ ID NO: 959) SQIMSLWGLV (A02.01) (SEQ ID NO: 960) TSKSQIMSL (B08.01) (SEQ ID NO: 961) | Solitary fibrous tumors |
| NDRG1:ERG | NDRG1:ERG | MSREMQDVDLAEVK PLVEKGETITGLLQEF DVQ::EALSVVSEDQS LFECAYGTPHLAKT EMTASSSSDYGQTS KMSPRVPQQDW (SEQ ID NO: 135) | LLQEFDVQEA (A02.01) (SEQ ID NO: 962) LQEFDVQEAL (A02.01) (SEQ ID NO: 963) | Prostate Cancer |
| PML:RARA | PML:RARA (exon3:exon3 | VLDMHGFLRQALCR LRQEEPQSLQAAVRT DGFDEFKVRLQDLSS CITQGK:A:IETQSSSS EEIVPSPPSPPPLPRI YKPCFVCQDKSSGY HYGVSACEGCKG (SEQ ID NO: 136) | | Acute promyelocytic leukemia |
| PML:RARA | PML:RARA (exon6:exon3) | RSSPEQPRPSTSKAVS PPHLDGPPSPRSPVIG SEVFLPNSNHVASGA GEA:A:IETQSSSSEEI VPSPPSPPPLPRIYKP CFVCQDKSSGYHYG VSACEGCKG (SEQ ID NO: 137) | | Acute promyelocytic leukemia |

TABLE 1-continued

| Gene | Exemplary Protein Change | Mutation Sequence Context | Peptides (HLA allele example(s)) | Exemplary Diseases |
|---|---|---|---|---|
| RUNX1 | RUNX1(ex5)-RUNX1T1(ex2) | VARFNDLRFVGRSGR GKSFTLTITVFTNPPQ VATYHRAIKITVDGP REPR:N:RTEKHSTM PDSPVDVKTQSRLT PPTMPPPPTTQGAP RTSSFTPTTLTNGT (SEQ ID NO: 138) | GPREPRNRT (B07.02) (SEQ ID NO: 964) RNRTEKHSTM (B08.01) (SEQ ID NO: 965) | AML |
| TMPRSS2:ERG | TMPRSS2:ERG | MALNS::EALSVVSED QSLFECAYGTPHLAK TEMTASSSSDYGQTS KMSPRVPQQDW (SEQ ID NO: 139) | ALNSEALSV (A02.01) (SEQ ID NO: 966) ALNSEALSVV (A02.01) (SEQ ID NO: 967) MALNSEALSV (A02.01, B08.01) (SEQ ID NO: 968) | Prostate Cancer |

[1] Underlined AAs represent non-native AAs
[2] Bolded AAs represent native AAs of the amino acid sequence encoded by the second of the two fused genes
[3] Bolded and underlined AAs represent non-native AAs of the amino acid sequence encoded by the second of the two fused genes due to a frameshift.

TABLE 2

| Gene | Exemplary Protein Change | Mutation Sequence Context | Peptides (HLA allele example(s)) | Exemplary Diseases |
|---|---|---|---|---|
| Table 2A | | POINT MUTATIONS [1] | | |
| AKT1 | E17K | MSDVAIVKEGWLHK RGKYIKTWRPRYFLL KNDGTFIGYKERPQD VDQREAPLNNFSVA QCQLMKTER (SEQ ID NO: 969) | KYIKTWRPRY (A24.02) (SEQ ID NO: 1011) WLHKRGKYI (A02.01, B07.02, B08.01) (SEQ ID NO: 1012) WLHKRGKYIK (A03.01) (SEQ ID NO: 1013) | BRCA, CESC, HNSC, LUSC, PRAD, SKCM, THCA |
| ANAPC1 | T537A | TMLVLEGSGNLVLY TGWRVGKVFIPGLP APSLTMSNTMPRPST PLDGVSAPKPLSKLL GSLDEVVLLSPVPEL RDSSKLHDSLYNEDC TFQQLGTYIHSI (SEQ ID NO: 970) | APKPLSKLL (B07.02) (SEQ ID NO: 1014) GVSAPKPLSK (A03.01) (SEQ ID NO: 1015) VSAPKPLSK (A03.01) (SEQ ID NO: 1016) | GBM, LUSC, PAAD, PRAD, SKCM |
| FGFR3 | S249C | HRIGGIKLRHQQWSL VMESVVPSDRGNYT CVVENKFGSIRQTYT LDVLERCPHRPILQA GLPANQTAVLGSDV EFHCKVYSDAQPHIQ WLKHVEVNGSKVG (SEQ ID NO: 971) | CPHRPILQA (B07.02) (SEQ ID NO: 1017) | BLCA, HNSC, KIRP, LUSC |
| FRG1B | I10T | MREPIYMHSTMVFLP WELHTKKGPSPPEQF MAVKLSDSRTALKS GYGKYLGINSDELVG HSDAIGPREQWEPVF QNGKMALLASNSCFI R (SEQ ID NO: 972) | KLSDSRTAL (A02.01, B07.02, B08.01) (SEQ ID NO: 1018) KLSDSRTALK (A03.01) (SEQ ID NO: 1019) LSDSRTALK (A01.01, A03.01) (SEQ ID NO: 1020) RTALKSGYGK (A03.01) (SEQ ID NO: 1021) TALKSGYGK (A03.01) (SEQ ID NO: 1022) | KIRP, PRAD, SKCM |
| FRG1B | L52S | AVKLSDSRIALKSGY GKYLGINSDELVGHS DAIGPREQWEPVFQN GKMALSASNSCFIRC NEAGDIEAKSKTAGE EEMIKIRSCAEKETK KKDDIPEEDKG (SEQ ID NO: 973) | ALSASNSCF (A02.01, A24.02, B07.02) (SEQ ID NO: 1023) ALSASNSCFI (A02.01) (SEQ ID NO: 1024) FQNGKMALSA (A02.01, B08.01) (SEQ ID NO: 1025) | GBM, KIRP, PRAD, SKCM |

TABLE 2-continued

| Gene | Exemplary Protein Change | Mutation Sequence Context | Peptides (HLA allele example(s)) | Exemplary Diseases |
|---|---|---|---|---|
| HER2 | L755S (Resistance) | AMPNQAQMRILKET ELRKVKVLGSGAFG TVYKGIWIPDGENVK IPVAIKVSRENTSPKA NKEILDEAYVMAGV GSPYVSRLLGICLTST VQLVTQLMPYGC (SEQ ID NO: 974) | KVSRENTSPK (A03.01) (SEQ ID NO: 1026) | BRCA |
| IDH1 | R132G | RVEEFKLKQMWKSP NGTIRNILGGTVFRE AIICKNIPRLVSGWV KPIIGGHAYGDQYR ATDFVVPGPGKVEIT YTPSDGTQKVTYLV HNFEEGGGVAMGM (SEQ ID NO: 975) | KPII1GGHAY (B07.02) (SEQ ID NO: 1027) | BLCA, BRCA, CRC, GBM, HNSC, LUAD, PAAD, PRAD, UCEC |
| KRAS | G12C | MTEYKLVVVGACGV GKSALTIQLIQNHFV DEYDPTIEDSYRKQV VIDGETCLLDILDTA GQE (SEQ ID NO: 976) | KLVVVGACGV (A02.01) (SEQ ID NO: 1028) LVVVGACGV (A02.01) (SEQ ID NO: 1029) VVGACGVGK (A03.01, A11.01) (SEQ ID NO: 1030) VVVGACGVGK (A03.01) (SEQ ID NO: 1031) | BRCA, CESC, CRC, HNSC, LUAD, PAAD, UCEC |
| KRAS | G12D | MTEYKLVVVGADGV GKSALTIQLIQNHFV DEYDPTIEDSYRKQV VIDGETCLLDILDTA GQE (SEQ ID NO: 977) | VVGADGVGK (A11.01) (SEQ ID NO: 1032) VVVGADGVGK (A11.01) (SEQ ID NO: 1033) KLVVVGADGV (A02.01) (SEQ ID NO: 1034) LVVVGADGV (A02.01) (SEQ ID NO: 1035) | BLCA, BRCA, CESC, CRC, GBM, HNSC, KIRP, LIHC, LUAD, PAAD, SKCM, UCEC |
| KRAS | G12V | MTEYKLVVVGAVGV GKSALTIQLIQNHFV DEYDPTIEDSYRKQV VIDGETCLLDILDTA GQE (SEQ ID NO: 978) | KLVVVGAVGV (A02.01) (SEQ ID NO: 1036) LVVVGAVGV (A02.01) (SEQ ID NO: 1037) VVGAVGVGK (A03.01, A11.01) (SEQ ID NO: 1038) VVVGAVGVGK (A03.01, A11.01) (SEQ ID NO: 1039) | BRCA, CESC, CRC, LUAD, PAAD, THCA, UCEC |
| KRAS | Q61H | AGGVGKSALTIQLIQ NHFVDEYDPTIEDSY RKQVVIDGETCLLDI LDTAGHEEYSAMRD QYMRTGEGFLCVFAI NNTKSFEDIHHYREQ IKRVKDSEDVPM (SEQ ID NO: 979) | ILDTAGHEEY (A01.01) (SEQ ID NO: 1040) | CRC, LUSC, PAAD, SKCM, UCEC |
| KRAS | Q61L | AGGVGKSALTIQLIQ NHFVDEYDPTIEDSY RKQVVIDGETCLLDI LDTAGLEEYSAMRD QYMRTGEGFLCVFAI NNTKSFEDIHHYREQ IKRVKDSEDVPM (SEQ ID NO: 980) | ILDTAGLEEY (A01.01) (SEQ ID NO: 1041) LLDILDTAGL (A02.01) (SEQ ID NO: 1042) | CRC, GBM, HNSC, LUAD, SKCM, UCEC |
| NRAS | Q61K | AGGVGKSALTIQLIQ NHFVDEYDPTIEDSY RKQVVIDGETCLLDI LDTAGKEEYSAMRD QYMRTGEGFLCVFAI NNSKSFADINLYREQ IKRVKDSDDVPM (SEQ ID NO: 981) | ILDTAGKEEY (A01.01) (SEQ ID NO: 1043) | BLCA, CRC, LIHC, LUAD, LUSC, SKCM, THCA, UCEC |
| NRAS | Q61R | AGGVGKSALTIQLIQ NHFVDEYDPTIEDSY RKQVVIDGETCLLDI LDTAGREEYSAMRD QYMRTGEGFLCVFAI NNSKSFADINLYREQ IKRVKDSDDVPM (SEQ ID NO: 982) | ILDTAGREEY (A01.01) (SEQ ID NO: 1044) | BLCA, CRC, LUSC, PAAD, PRAD, SKCM, THCA, UCEC |

TABLE 2-continued

| Gene | Exemplary Protein Change | Mutation Sequence Context | Peptides (HLA allele example(s)) | Exemplary Diseases |
|---|---|---|---|---|
| PIK3CA | E542K | IEEHANWSVSREAGF SYSHAGLSNRLARD NELRENDKEQLKAIS TRDPLSKITEQEKDFL WSHRHYCVTIPEILP KLLLSVKWNSRDEV AQMYCLVKDWPP (SEQ ID NO: 983) | AISTRDPLSK (A03.01) (SEQ ID NO: 1045) | BLCA, BRCA, CESC, CRC, GBM, HNSC, KIRC, KIRP, LIHC, LUAD, LUSC, PRAD, UCEC |
| PTEN | R130Q | KFNCRVAQYPFEDH NPPQLEL1KPFCEDLD QWLSEDDNHVAAIH CKAGKGQTGVMICA YLLHRGKFLKAQEA LDFYGEVRTRDKKG VTIPSQRRYVYYYSY (SEQ ID NO: 984) | QTGVMICAY (A01.01) (SEQ ID NO: 1046) | BRCA, CESC, CRC, GBM, KIRC, LUSC, UCEC |
| RAC1 | P29S | MQAIKCVVVGDGAV GKTCLLISYTTNAFS GEY1PTVFDNYSANV MVDGKPVNLGLWD TAGQEDYDRLRPLSY PQTVGET (SEQ ID NO: 985) | FSGEYIPTV (A02.01) (SEQ ID NO: 1047) TTNAFSGEY (A01.01) (SEQ ID NO: 1048) YTTNAFSGEY (A01.01) (SEQ ID NO: 1049) | Melanoma |
| SF3B1 | K700E | AVCKSKKSWQARHT GIKIVQQIAILMGCAI LPHLRSLVEIIEHGLV DEQQEVRTISALAIA ALAEAATPYGIESFD SVLKPLWKGIRQHR GKGLAAFLKAI (SEQ ID NO: 986) | GLVDEQQEV (A02.01) (SEQ ID NO: 1050) | AML associated With MDS; Chronic lymphocytic leukemia- small lymphocytic lymphoma; Mvelodysplastic syndrome; AML; Luminal NS carcinoma of breast; Chronic myeloid leukemia; Ductal carcinoma of pancreas; Chronic myelomonocytic leukemia; Chronic lymphocytic leukemia- small lymphocytic lymphoma; Myelofibrosis; Mvelodysplastic syndrome; PRAD; Essential thrombocythaemia; Medullomyoblastoma |
| SPOP | F133L | YLSLYLLLVSCPKSE VRAKFKFSILNAKGE ETKAMESQRAYRFV QGKDWGLKKFIRRD FLLDEANGLLPDDKL TLFCEVSVVQDSVN1 SGQNTMNMVKVPE (SEQ ID NO: 987) | FVQGKDWGL (A02.01, B08.01) (SEQ ID NO: 1051) | PRAD |
| SPOP | F133V | YLSLYLLLVSCPKSE VRAKFKFSILNAKGE ETKAMESQRAYRFV QGKDWGVKKFIRRD | FVQGKDWGV (A02.01) (SEQ ID NO: 1052) | PRAD |

TABLE 2-continued

| Gene | Exemplary Protein Change | Mutation Sequence Context | Peptides (HLA allele example(s)) | Exemplary Diseases |
|---|---|---|---|---|
| | | FLLDEANGLLPDDKL TLFCEVSVVQDSVNI SGQNTMNMVKVPE (SEQ ID NO: 988) | | |
| TP53 | G245S | IRVEGNLRVEYLDDR NTFRHSVVVPYEPPE VGSDCTTIHYNYMC NSSCMGSMNRRPILT IITLEDSSGNLLGRNS FEVRVCACPGRDRRT EEENLRKKGEP (SEQ ID NO: 989) | CMGSMNRRPI (A02.01, B08.01) (SEQ ID NO: 1053) GSMNRRPIL (B08.01) (SEQ ID NO: 1054) MGSMNRRPI (B08.01) (SEQ ID NO: 1055) MGSMNRRPIL (B08.01) (SEQ ID NO: 1056) SMNRRPILTI (A02.01, A24.02, B08.01) (SEQ ID NO: 1057) | BLCA, BRCA, CRC, GBM, HNSC, LUSC, PAAD, PRAD |
| TP53 | R248Q | EGNLRVEYLDDRNT FRHSVVVPYEPPEVG SDCTTIHYNYMCNSS CMGGMNQRPILTIIT LEDSSGNLLGRNSFE VRVCACPGRDRRTE EENLRKKGEPHHE (SEQ ID NO: 990) | CMGGMNQRPI (A02.01, B08.01) (SEQ ID NO: 1058) GMNQRPILTI (A02.01, B08.01) (SEQ ID NO: 1059) NQRPILTII (A02.01, B08.01) (SEQ ID NO: 1060) | BLCA, BRCA, CRC, GBM, HNSC, KIRC, LIHC, LUSC, PAAD, PRAD, UCEC |
| TP53 | R248W | EGNLRVEYLDDRNT FRHSVVVPYEPPEVG SDCTTIHYNYMCNSS CMGGMNWRPILTIIT LEDSSGNLLGRNSFE VRVCACPGRDRRTE EENLRKKGEPHHE (SEQ ID NO: 991) | CMGGMNWRPI (A02.01, A24.02, B08.01) (SEQ ID NO: 1061) GMNWRPILTI (A02.01, B08.01) (SEQ ID NO: 1062) MNWRPILTI (A02.01, A24.02, B08.01) (SEQ ID NO: 1063) MNWRPILTII (A02.01, A24.02) (SEQ ID NO: 1064) | BLCA, BRCA, CRC, GBM, HNSC, LIHC, LUSC, PAAD, SKCM, UCEC |
| TP53 | R273C | PEVGSDCTTIHYNYM CNSSCMGGMNRRPIL TIITLEDSSGNLLGRN SFEVCVCACPGRDRR TEEENLRKKGEPHHE LPPGSTKRALPNNTS SSPQPKKKPL (SEQ ID NO: 992) | NSFEVCVCA (A02.01) (SEQ ID NO: 1065) | BLCA, BRCA, CRC, GBM, HNSC, LUSC, PAAD, UCEC |
| TP53 | R273H | PEVGSDCTTIHYNYM CNSSCMGGMNRRPIL TIITLEDSSGNLLGRN SFEVHVCACPGRDRR TEEENLRKKGEPHHE LPPGSTKRALPNNTS SSPQPKKKPL (SEQ ID NO: 993) | NSFEVHVCA (A02.01) (SEQ ID NO: 1066) | BRCA, CRC, GBM, HNSC, LIHC, LUSC, PAAD, UCEC |
| TP53 | Y220C | TEVVRRCPHHERCSD SDGLAPPQHLIRVEG NLRVEYLDDRNTFR HSVVVPCEPPEVGSD CTTIHYNYMCNSSC MGGMNRRPILTIITLE DSSGNLLGRNSF (SEQ ID NO: 994) | VVPCEPPEV (A02.01) (SEQ ID NO: 1067) VVPCEPPEV (A02.01) (SEQ ID NO: 1068) | BLCA, BRCA, GBM, HNSC, LIHC, LUAD, LUSC, PAAD, SKCM, UCEC |
| Table 2B | | MSI-ASSOCIATED FRAMESHIFTS [1] | | |
| MSH6 | F1088fs; +1 | YNFDKNYKDWQSA VECIAVLDVLLCLAN YSRGGDGPMCRPVIL LPEDTPPLLRA (SEQ ID NO: 995) | ILLPEDTPPL (A02.01) (SEQ ID NO: 1069) LLPEDTPPL (A02.01) (SEQ ID NO: 1070) | MSI+ CRC, MSI Uterine/ Endometrium Cancer, MSI+ Stomach Cancer, Lynch syndrome |

TABLE 2-continued

| Gene | Exemplary Protein Change | Mutation Sequence Context | Peptides (HLA allele example(s)) | Exemplary Diseases |
|---|---|---|---|---|
| Table 2C | | FRAMESHIFT [1] | | |
| APC | F1354fs | AKFQQCHSTLEPNPA DCRVLVYLQNQPGT KLLNFLQERNLPPKV VLRHPKVHLNTMFR RPHSCLADVLLSVHL IVLRVVRLPAPFRVN HAVEW* (SEQ ID NO: 996) | APFRVNHAV (B07.02) (SEQ ID NO: 1071)<br>CLADVLLSV (A02.01) (SEQ ID NO: 1072)<br>FLQERNLPPK (A03.01) (SEQ ID NO: 1073)<br>HLIVLRVVRL (A02.01, B08.01) (SEQ ID NO: 1074)<br>HPKVHLNTM (B07.02, B08.01) (SEQ ID NO: 1075)<br>HPKVHLNTMF (B07.02, B08.01) (SEQ ID NO: 1076)<br>KVHLNTMFR (A03.01) (SEQ ID NO: 1077)<br>KVHLNTMFRR (A03.01) (SEQ ID NO: 1078)<br>LPAPFRVNHA (B07.02) (SEQ ID NO: 1079)<br>MFRRPHSCL (B07.02, B08.01) (SEQ ID NO: 1080)<br>MFRRPHSCLA (B08.01) (SEQ ID NO: 1081)<br>NTMFRRPHSC (B08.01) (SEQ ID NO: 1082)<br>RPHSCLADV (B07.02) (SEQ ID NO: 1083)<br>RPHSCLADVL (B07.02) (SEQ ID NO: 1084)<br>RVVRLPAPFR (A03.01) (SEQ ID NO: 1085)<br>SVHLIVLRV (A02.01) (SEQ ID NO: 1086)<br>TMFRRPHSC (B08.01) (SEQ ID NO: 1087)<br>TMFRRPHSCL (A02.01, B08.01) (SEQ ID NO: 1088)<br>VLLSVHLIV (A02.01) (SEQ ID NO: 1089)<br>VLLSVHLIVL (A02.01) (SEQ ID NO: 1090)<br>VLRVVRLPA (B08.01) (SEQ ID NO: 1091)<br>VVRLPAPFR (A03.01) (SEQ ID NO: 1092) | CRC, LUAD, UCEC, STAD |
| ARID1A | Y1324fs | ALGPHSRISCLPTQTR GCILLAATPRSSSSSS SNDMIPMAISSPPKAP LLAAPSPASRLQCINS NSRITSGQWMAHMA LLPSGTKGRCTACHT ALGRGSLSSSSCPQPS PSLPASNKLPSLPLSK MYTTSMAMPILPLPQ LLLSADQQAAPRTNF HSSLAETVSLHPLAP MPSKTCHHK* (SEQ ID NO: 997) | AMPILPLPQL (A02.01) (SEQ ID NO: 1093)<br>APLLAAPSPA (B07.02) (SEQ ID NO: 1094)<br>APRTNFHSS (B07.02) (SEQ ID NO: 1095)<br>APRTNFHSSL (B07.02, B08.01) (SEQ ID NO: 1096)<br>CPQPSPSLPA (B07.02) (SEQ ID NO: 1097)<br>GQWMAHMAL (A02.01) (SEQ ID NO: 1098)<br>GQWMAHMALL (A02.01) (SEQ ID NO: 1099)<br>HMALLPSGTK (A03.01) (SEQ ID NO: 1100)<br>HTALGRGSL (B07.02) (SEQ ID NO: 1101)<br>IPM AISSPP (B07.02) (SEQ ID NO: 1102)<br>IPMAISSPPK (B07.02) (SEQ ID NO: 1103)<br>KLPSLPLSK (A03.01) (SEQ ID NO: 1104)<br>KLPSLPLSKM (A02.01) (SEQ ID NO: 1105)<br>KMYTTSMAM (A02.01, A03.01) (SEQ ID NO: 1106)<br>LLAAPSPASR (A03.01) (SEQ ID NO: 1107)<br>LLLSADQQAA (A02.01) (SEQ ID NO: 1108)<br>LLSADQQAA (A02.01) (SEQ ID NO: 1109)<br>LPASNKLPS (B07.02) (SEQ ID NO: 1110)<br>LPASNKLPSL (B07.02, B08.01) (SEQ ID NO: 1111)<br>LPLPQLLLSA (B07.02) (SEQ ID NO: 1112)<br>LPSLPLSKM (B07.02) (SEQ ID NO: 1113)<br>LSKMYTTSM (B08.01) (SEQ ID NO: 1114)<br>MALLPSGTK (A03.01) (SEQ ID NO: 1115)<br>MPILPLPQL (B07.02) (SEQ ID NO: 1116)<br>MPILPLPQLL (B07.02) (SEQ ID NO: 1117)<br>MYTTSMAMPI (A24.02) (SEQ ID NO: 1118)<br>PMAISSPPK (A03.01) (SEQ ID NO: 1119)<br>QWMAHMALL (A24.02) (SEQ ID NO: 1120)<br>SKMYTTSMAM (B07.02) (SEQ ID NO: 1121)<br>SMAMPILPL (A02.01, B07.02, B08.01) (SEQ ID NO: 1122)<br>SNKLPSLPL (B08.01) (SEQ ID NO: 1123)<br>SPASRLQCI (B07.02, B08.01) (SEQ ID NO: 1124)<br>SPPKAPLLAA (B07.02) (SEQ ID NO: 1125)<br>SPSLPASNKL (B07.02) (SEQ ID NO: 1126)<br>YTTSMAMP1 (A02.01) (SEQ ID NO: 1127)<br>YTTSMAMPTL (A02.01) (SEQ ID NO: 1128) | STAD, UCEC, BLCA, BRCA, LUSC, CESC, KIRC, UCS |

TABLE 2-continued

| Gene | Exemplary Protein Change | Mutation Sequence Context | Peptides (HLA allele example(s)) | Exemplary Diseases |
|---|---|---|---|---|
| ARID1A | G1848fs | RSYRRMIHLWWTAQ ISLGVCRSLTVACCT GGLVGGTPLSISRPTS RARQSCCLPGLTHPA HQPLGSM* (SEQ ID NO: 998) | CLPGLTHPA (A02.01) (SEQ ID NO: 1129) GLTHPAHQPL (A02.01) (SEQ ID NO: 1130) HPAHQPLGSM (B07.02) (SEQ ID NO: 1131) LTHPAHQPL (B07.02) (SEQ ID NO: 1132) RPTSRARQSC (B07.02) (SEQ ID NO: 1133) RQSCCLPGL (A02.01) (SEQ ID NO: 1134) TSRARQSCCL (B08.01) (SEQ ID NO: 1135) | STAD, UCEC, BLCA, BRCA, LUSC, CESC, KIRC, UCS |
| β2M | L13fs | QHSGRDVSLRGLSCA RATLSFWPGGYPAYS KDSGLLTSSSREWKV KFPELLCVWVSSIRH* (SEQ ID NO: 999) | ELLCVWVSSI (A02.01) (SEQ ID NO: 1136) EWKVKFPEL (B08.01) (SEQ ID NO: 1137) KFPELLCVW (A24.02) (SEQ ID NO: 1138) LLCVWVSSI (A02.01) (SEQ ID NO: 1139) LLTSSSREWK (A03.01) (SEQ ID NO: 1140) LTSSSREWK (A03.01) (SEQ ID NO: 1141) YPAYSKDSGL (B07.02) (SEQ ID NO: 1142) | CRC, STAD, SKCM, HNSC |
| GATA3 | L328fs N334fs | AQAKAVCSQESRDV LCELSDHHNHTLEEE CQWGPCLQCLWALL QASQY* (SEQ ID NO: 1000) | CLQCLWALL (A02.01) (SEQ ID NO: 1143) CQWGPCLQCL (A02.01) (SEQ ID NO: 1144) QWGPCLQCL (A24.02) (SEQ ID NO: 1145) QWGPCLQCLW (A24.02) (SEQ ID NO: 1146) | Breast Cancer |
| GATA3 | H400fs S408fs S408fs S430fs H434fs H435fs | PGRPLQTHVLPEPHL ALQPLQPHADHAHA DAPAIQPVLWTTPPL QHGHRHGLEPCSML TGPPARVPAVPFDLH FCRSSIMKPKRDGYM FLKAESKIMFATLQR SSLWCLCSNH* (SEQ ID NO: 1001) | AIQPVLWTT (A02.01) (SEQ ID NO: 1147) ALQPLQPHA (A02.01) (SEQ ID NO: 1148) DLHFCRSSIM (B08.01) (SEQ ID NO: 1149) EPHLALQPL (B07.02, B08.01) (SEQ ID NO: 1150) ESKIMFATL (B08.01) (SEQ ID NO: 1151) FATLQRSSL (B07.02, B08.01) (SEQ ID NO: 1152) FLKAESKIM (B08.01) (SEQ ID NO: 1153) FLKAESKIMF (B08.01) (SEQ ID NO: 1154) GPPARVPAV (B07.02) (SEQ ID NO: 1155) IMKPKRDGYM (B08.01) (SEQ ID NO: 1156) KIMFATLQR (A03.01) (SEQ ID NO: 1157) KPKRDGYMF (B07.02) (SEQ ID NO: 1158) KPKRDGYMFL (B07.02) (SEQ ID NO: 1159) LHFCRSSIM (B08.01) (SEQ ID NO: 1160) LQHGFIRHGL (B08.01) (SEQ ID NO: 1161) MFATLQRSSL (B07.02, B08.01) (SEQ ID NO: 1162) MFLKAESKI (A24.02) (SEQ ID NO: 1163) MLTGPPARV (A02.01) (SEQ ID NO: 1164) QPVLWTTPPL (B07.02) (SEQ ID NO: 1165) SMLTGPPARV (A02.01) (SEQ ID NO: 1166) TLQRSSLWCL (A02.01) (SEQ ID NO: 1167) VLPEPHLAL (A02.01) (SEQ ID NO: 1168) VPAVPFDLHF (B07.02) (SEQ ID NO: 1169) YMFLKAESK (A03.01) (SEQ ID NO: 1170) YMFLKAESKI (A02.01, A03.01, A24.02, B08.01) (SEQ ID NO: 1171) | Breast Cancer |
| MLL2 | P647fs L656fs | TRRCHCCPHLRSHPC PHHLRNHPRPHHLRH HACHHHLRNCPHPH FLRHCTCPGRWRNR PSLRRLRSLLCLPHL NHHLFLHWRSRPCL HRKSHPHLLHLRRLY PHHLKHRPCPHHLK NLLCPRHLRNCPLPR HLKHLACLHHLRSHP CPLHLKSHPCLHHRR HLVCSHHLKSLLCPL HLRSLPFPHHLRHHA CPHHLRTRLCPHHLK NHLCPPHLRYRAYPP CLWCHACLHRLRNL PCPHRLRSLPRPLHL RLHASPHHLRTPPHP HHLRTHLLPHHRRTR SCPCRWRSHPCCHYL RSRNSAPGPRGRTCH PGLRSRTCPPGLRSH | APGPRGRTC (B07.02) (SEQ ID NO: 1172) CLRSHTCPPR (A03.01) (SEQ ID NO: 1173) CLWCHACLHR (A03.01) (SEQ ID NO: 1174) CPHLGSHPC (B07.02) (SEQ ID NO: 1175) CPLGLKSPL (B07.02) (SEQ ID NO: 1176) CPRSCRCPH (B07.02) (SEQ ID NO: 1177) CPRSCRCPHL (B07.02, B08.01) (SEQ ID NO: 1178) CSLPLGNHPY (A01.01) (SEQ ID NO: 1179) GLRNRICPL (A02.01, B07.02, B08.01) (SEQ ID NO: 1180) GLRSHTYLR (A03.01) (SEQ ID NO: 1181) GLRSHTYLRR (A03.01) (SEQ ID NO: 1182) GPRGRTCHPG (B07.02) (SEQ ID NO: 1183) HLGSHPCRL (B08.01) (SEQ ID NO: 1184) HLRLHASPH (A03.01) (SEQ ID NO: 1185) HLRSCPCSL (B07.02, B08.01) (SEQ ID NO: 1186) HLRTHLLPH (A03.01) (SEQ ID NO: 1187) HLRTHLLPHH (A03.01) (SEQ ID NO: 1188) HLRYRAYPP (B08.01) (SEQ ID NO: 1189) HLRYRAYPPC (B08.01) (SEQ ID NO: 1190) | STAD, BLCA, CRC, HNSC, BRCA |

TABLE 2-continued

| Gene | Exemplary Protein Change | Mutation Sequence Context | Peptides (HLA allele example(s)) | Exemplary Diseases |
|---|---|---|---|---|
| | | TYLRRLRSHTCPPSL RSHAYALCLRSHTCP PRLRDHICPLSLRNCT CPPRLRSRTCLLCLRS HACPPNLRNHTCPPS LRSHACPPGLRNRIC PLSLRSHPCPLGLKSP LRSQANALHLRSCPC SLPLGNHPYLPCLES QPCLSLGNHLCPLCP RSCRCPHLGSHPCRL S* (SEQ ID NO: 1002) | HPHHLRTHL (B07.02) (SEQ ID NO: 1191) HPHHLRTHLL (B07.02, B08.01) (SEQ ID NO: 1192) HTYLRRLRSH (A03.01) (SEQ ID NO: 1193) LPCPHRLRSL (B07.02, B08.01) (SEQ ID NO: 1194) LPHHRRTRSC (B07.02, B08.01) (SEQ ID NO: 1195) LPLGNHPYL (B07.02) (SEQ ID NO: 1196) LPRPLHLRL (B07.02, B08.01) (SEQ ID NO: 1197) NLRNHTCPP (B08.01) (SEQ ID NO: 1198) PPRLRSRTCL (B07.02, B08.01) (SEQ ID NO: 1199) RLHASPHHL (A02.01) (SEQ ID NO: 1200) RLHASPHHLR (A03.01) (SEQ ID NO: 1201) RLRDHICPL (A02.01, B07.02, B08.01) (SEQ ID NO: 1202) RLRNLPCPH (A03.01) (SEQ ID NO: 1203) RLRNLPCPHR (A03.01) (SEQ ID NO: 1204) RLRSHTCPP (B08.01) (SEQ ID NO: 1205) RLRSLPRPL (B07.02, B08.01) (SEQ ID NO: 1206) RLRSLPRPLH (A03.01) (SEQ ID NO: 1207) RLRSRTCLL (B07.02, B08.01) (SEQ ID NO: 1208) RNRICPLSL (B07.02, B08.01) (SEQ ID NO: 1209) RPLHRLHA (B07.02) (SEQ ID NO: 1210) RPLHRLHAS (B07.02) (SEQ ID NO: 1211) RSHACPPGLR (A03.01) (SEQ ID NO: 1212) RSHACPPNLR (A03.01) (SEQ ID NO: 1213) RSHAYALCLR (A03.01) (SEQ ID NO: 1214) RSHPCCHYLR (A03.01) (SEQ ID NO: 1215) RSHPCPLGLK (A03.01) (SEQ ID NO: 1216) RSHTCPPSLR (A03.01) (SEQ ID NO: 1217) RSLPRPLHLR (A03.01) (SEQ ID NO: 1218) RSRTCLLCL (B07.02) (SEQ ID NO: 1219) RSRTCLLCLR (A03.01) (SEQ ID NO: 1220) RSRTCPPGL (B07.02) (SEQ ID NO: 1221) RSRTCPPGLR (A03.01) (SEQ ID NO: 1222) RTHLLPHHRR (A03.01) (SEQ ID NO: 1223) RTRSCPCRWR (A03.01) (SEQ ID NO: 1224) RYRAYPPCL (A24.02) (SEQ ID NO: 1225) RYRAYPPCLW (A24.02) (SEQ ID NO: 1226) SLGNHLCPL (A02.01, B07.02, B08.01) (SEQ ID NO: 1227) SLPLGNHPYL (A02.01) (SEQ ID NO: 1228) SLPRPLHLRL (A02.01) (SEQ ID NO: 1229) SLRNCTCPPR (A03.01) (SEQ ID NO: 1230) SLRSHAYAL (A02.01, B07.02, B08.01) (SEQ ID NO: 1231) SLRSHPCPL (A02.01, B07.02, B08.01) (SEQ ID NO: 1232) SPHHLRTPP (B07.02) (SEQ ID NO: 1233) SPHHLRTPPH (B07.02) (SEQ ID NO: 1234) SPLRSQANAL (B07.02) (SEQ ID NO: 1235) YLRRLRSHTC (B08.01) (SEQ ID NO: 1236) YLRSRNSAP (B08.01) (SEQ ID NO: 1237) YLRSRNSAPG (B08.01) (SEQ ID NO: 1238) | |
| MLL2 | P2354fs | GPRSHPLPRLWHLLL QVTQTSFALAPTLTH MLSPH* (SEQ ID NO: 1003) | ALAPTLTHM (A02.01) (SEQ ID NO: 1239) ALAPTLTHML (A02.01) (SEQ ID NO: 1240) LLQVTQTSFA (A02.01) (SEQ ID NO: 1241) LQVTQTSFAL (A02.01) (SEQ ID NO: 1242) RLWHLLLQV (A02.01) (SEQ ID NO: 1243) RLWHLLLQVT (A02.01) (SEQ ID NO: 1244) | STAD, BLCA, CRC, HNSC, BRCA |
| RNF43 | G659fs | PLGLVPWTRWCPQG KPRFPAMSTTTATGT TTTKSGSSGMAGSLA QKPESPSPGLLFLGHS PSQSHLLLISKSPDPT QQPLRGGSLTHSAPG PSLSQPLAQLTPPASA PVPAVCSTCKNPASL | CTQLARFFPI (A24.02) (SEQ ID NO: 1245) FFPITPPVW (A24.02) (SEQ ID NO: 1246) FPITPPVWHI (B07.02) (SEQ ID NO: 1247) GPRMQLCTQL (B07.02, B08.01) (SEQ ID NO: 1248) ITPPVWHIL (A24.02) (SEQ ID NO: 1249) LALGPRMQL (B07.02) (SEQ ID NO: 1250) MQLCTQLARF (A24.02) (SEQ ID NO: 1251) | STAD |

TABLE 2-continued

| Gene | Exemplary Protein Change | Mutation Sequence Context | Peptides (HLA allele example(s)) | Exemplary Diseases |
|------|--------------------------|---------------------------|----------------------------------|---------------------|
| | | PDTHRGKGGGVPPSP PLALGPRMQLCTQL ARFFPITPPVWHILGP QRHTP* (SEQ ID NO: 1004) | RFFPITPPV (A02.01, A24.02) (SEQ ID NO: 1252) RFFPITPPVW (A24.02) (SEQ ID NO: 1253) RMQLCTQLA (A02.01) (SEQ ID NO: 1254) RMQLCTQLAR (A03.01) (SEQ ID NO: 1255) SPPLALGPRM (B07.02) (SEQ ID NO: 1256) TQLARFFPI (A02.01, A24.02, B08.01) (SEQ ID NO: 1257) | |
| SMAP1 | E169fs | KYEKKKYYDKNAIAI TNISSSDAPLQPLVSS PSLQAAVDKNKLEK EKEKKRKRKREKRS QKSRQNHLQLKSCR RKISNWSLKKVPALK KLRSPLWIF (SEQ ID NO: 1005) | KSRQNHLQL (B07.02) (SEQ ID NO: 1258) ALKKLRSPL (B08.01, B07.02) (SEQ ID NO: 1259) HLQLKSCRRK (A03.01) (SEQ ID NO: 1260) KISNWSLKK (A03.01, A11.01) (SEQ ID NO: 1261) KISNWSLKKV (A03.01) (SEQ ID NO: 1262) KLRSPLWIF (A24.02) (SEQ ID NO: 1263) KSRQNHLQLK (A03.01) (SEQ ID NO: 1264) NWSLKKVPAL (B08.01) (SEQ ID NO: 1265) SLKKVPALK (A03.01, A11.01) (SEQ ID NO: 1266) SLKKVPALKK (A03.01) (SEQ ID NO: 1267) SQKSRQNHL (B08.01) (SEQ ID NO: 1268) WSLKKVPAL (B08.01) (SEQ ID NO: 1269) WSLKKVPALK (A03.01) (SEQ ID NO: 1270) | MSI+ CRC, MSI Uterine/ Endometrium Cancer, MSI+ Stomach Cancer |
| TP53 | P58fs P72fs G108fs R110fs | CCPRTILNNGSLKTQ VQMKLPECQRLLPP WPLHQQLLHRRPLH QPPPGPCHLLSLPRKP TRAATVSVWASCILG QPSL* (SEQ ID NO: 1006) | KLPECQRLL (A02.01) (SEQ ID NO: 1271) KPTRAATVSV (B07.02) (SEQ ID NO: 1272) LPPWPLHQQL (B07.02) (SEQ ID NO: 1273) LPRKPTRAA (B07.02, B08.01) (SEQ ID NO: 1274) LPRKPTRAAT (B07.02) (SEQ ID NO: 1275) QQLLHRRPL (B08.01) (SEQ ID NO: 1276) RLLPPWPLH (A03.01) (SEQ ID NO: 1277) | BRCA, CRC, LUAD, PRAD, HNSC, LUSC, PAAD, STAD, BLCA, OV, LIHC, SKCM, UCEC, LAML, UCS, KICH, GBM, ACC |
| TP53 | P152fs | LARTPLPSTRCFANW PRPALCSCGLIPHPRP APASAPWPSTSSHST* (SEQ ID NO: 1007) | APASAPWPST (B07.02) (SEQ ID NO: 1278) APWPSTSSH (B07.02) (SEQ ID NO: 1279) RPAPASAPW (B07.02) (SEQ ID NO: 1280) WPSTSSHST (B07.02) (SEQ ID NO: 1281) | BRCA, CRC, LUAD, PRAD, HNSC, LUSC, PAAD, STAD, BLCA, OV, LIHC, SKCM, UCEC, LAML, UCS, KICH, GBM, ACC |
| UBR5 | K2120fs | SQGLYSSSASSGKCL MEVTVDRNCLEVLP TKMSYAANLKNVM NMQNRQKKKGKNSP CCQKKLRVQNQGHL LMILLHN* (SEQ ID NO: 1008) | RVQNQGHLL (B07.02) (SEQ ID NO: 1282) | |
| VHL | L116fs G123fs | TRASPPPRSSSAIAVRA SCCPYGSTSTASRSPT QRCRLARAAASTAT EVTFGSSEMQGHTM GFWLTKLNYLCHLS MLTDSLFLPISHCQCI LI (SEQ ID NO: 1009) | FLPISHCQCI (A02.01) (SEQ ID NO: 1283) FWLTKLNYL (A24.02, B08.01) (SEQ ID NO: 1284) HLSMLTDSL (A02.01) (SEQ ID NO: 1285) HTMGFWLTK (A03.01) (SEQ ID NO: 1286) HTMGFWLTKL (A02.01) (SEQ ID NO: 1287) KLNYLCHLSM (A02.01) (SEQ ID NO: 1288) LPISHCQCI (B07.02, B08.01) (SEQ ID NO: 1289) LPISHCQCIL (B07.02, B08.01) (SEQ ID NO: 1290) LTDSLFLPI (A01.01, A02.01) (SEQ ID NO: 1291) LTKLNYLCHL (B08.01) (SEQ ID NO: 1292) MLTDSLFLPI (A01.01, A02.01. B08.01) (SEQ ID NO: 1293) MQGHTMGFWL (A02.01) (SEQ ID NO: 1294) NYLCHLSML (A24.02) (SEQ ID NO: 1295) SMLTDSLFL (A02.01) (SEQ ID NO: 1296) TMGFWLTKL (A02.01) (SEQ ID NO: 1297) YLCHLSMLT (A02.01) (SEQ ID NO: 1298) | KIRC, KIRP |

TABLE 2-continued

| Gene | Exemplary Protein Change | Mutation Sequence Context | Peptides (HLA allele example(s)) | Exemplary Diseases |
|---|---|---|---|---|
| TABLE 2D | | INSERT [1] | | |
| HER2 | G776ins YVMA | LGSGAFGTVYKGIWI PDGENVKIPVAIKVL RENTSPKANKEILDE AYVMAYVMAGVGS PYVSRLLGICLTSTV QLVTQLMPYGCLLD HVRENRGRLGSQDL LNW (SEQ ID NO: 1010) | ILDEAYVMAY (A01.01) (SEQ ID NO: 1299) VMAYVMAGV (A02.01) (SEQ ID NO: 1300) YVMAYVMAG (A02.01, B07.02, B08.01) (SEQ ID NO: 1301) YVMAYVMAGV (A02.01, B07.02, B08.01) (SEQ ID NO: 1302) | Lung Cancer |

[1] Underlined AAs represent non-native AAs
[2] Bolded AAs represent native AAs of the amino acid sequence encoded by the second of the two fused genes
[3] Bolded and underlined AAs represent non-native AAs of the amino acid sequence encoded by the second of the two fused genes due to a frameshift.

In the Tables above, for one or more of the exemplary fusions, a sequence that comes before the first ":" belongs to an exon sequence of a polypeptide encoded by a first gene, a sequence that comes after the second ":" belongs to an exon sequence of a polypeptide encoded by a second gene, and an amino acid that appears between ":" symbols is encoded by a codon that is split between the exon sequence of a polypeptide encoded by a first gene and the exon sequence of a polypeptide encoded by a second gene.

However, in some embodiments, for example, NAB: STAT6, the NAB exon is linked to the 5' UTR of STAT6 and the first amino acid that appears after the junction is the normal start codon of STAT6 (there is no frame present at this site (as it is not normally translated).

AR-V7 in the tables above can also be considered, in some embodiments, a splice variant of the AR gene that encodes a protein that lacks the ligand binding domain found in full length AR.

In some embodiments, sequencing methods are used to identify tumor specific mutations. Any suitable sequencing method can be used according to the present disclosure, for example, Next Generation Sequencing (NGS) technologies. Third Generation Sequencing methods might substitute for the NGS technology in the future to speed up the sequencing step of the method. For clarification purposes: the terms "Next Generation Sequencing" or "NGS" in the context of the present disclosure mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, for example, within 1-7 days or within less than 24 hours and allow, in principle, single cell sequencing approaches. Multiple NGS platforms which are commercially available or which are mentioned in the literature can be used in the context of the present disclosure e.g. those described in detail in WO 2012/159643.

In certain embodiments, the peptide described herein can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120, about 150, about 200, about 300, about 350, about 400, about 450, about 500, about 600, about 700, about 800, about 900, about 1,000, about 1,500, about 2,000, about 2,500, about 3,000, about 4,000, about 5,000, about 7,500, about 10,000 amino acids or greater amino acid residues, and any range derivable therein. In specific embodiments, a neoantigenic peptide molecule is equal to or less than 100 amino acids.

In some embodiments, the peptides can be from about 8 and about 50 amino acid residues in length, or from about 8 and about 30, from about 8 and about 20, from about 8 and about 18, from about 8 and about 15, or from about 8 and about 12 amino acid residues in length. In some embodiments, the peptides can be from about 8 and about 500 amino acid residues in length, or from about 8 and about 450, from about 8 and about 400, from about 8 and about 350, from about 8 and about 300, from about 8 and about 250, from about 8 and about 200, from about 8 and about 150, from about 8 and about 100, from about 8 and about 50, or from about 8 and about 30 amino acid residues in length.

In some embodiments, the peptides can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acid residues in length. In some embodiments, the peptides can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500, or more amino acid residues in length. In some embodiments, the peptides can be at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or less amino acid residues in length. In some embodiments, the peptides can be at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500, or less amino acid residues in length.

In some embodiments, the peptides has a total length of at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 150, at least 200, at least 250, at least 300, at least 350, at least 400, at least 450, or at least 500 amino acids.

In some embodiments, the peptides has a total length of at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29, at most 30, at most 40, at most 50, at most 60, at most 70, at most 80, at most 90, at most 100, at most 150, at most 200, at most 250, at most 300, at most 350, at most 400, at most 450, or at most 500 amino acids.

A longer peptide can be designed in several ways. In some embodiments, when HLA-binding peptides are predicted or known, a longer peptide comprises (1) individual binding peptides with extensions of 2-5 amino acids toward the N- and C-terminus of each corresponding gene product; or (2) a concatenation of some or all of the binding peptides with extended sequences for each. In other embodiments, when sequencing reveals a long (>10 residues) neoepitope sequence present in the tumor (e.g., due to a frameshift, read-through or intron inclusion that leads to a novel peptide sequence), a longer peptide could consist of the entire stretch of novel tumor-specific amino acids as either a single longer peptide or several overlapping longer peptides. In some embodiments, use of a longer peptide is presumed to allow for endogenous processing by patient cells and can lead to more effective antigen presentation and induction of T cell responses. In some embodiments, two or more peptides can be used, where the peptides overlap and are tiled over the long neoantigenic peptide.

In some embodiments, the peptides can have a pI value of from about 0.5 to about 12, from about 2 to about 10, or from about 4 to about 8. In some embodiments, the peptides can have a pI value of at least 4.5, 5, 5.5, 6, 6.5, 7, 7.5, or more. In some embodiments, the peptides can have a pI value of at most 4.5, 5, 5.5, 6, 6.5, 7, 7.5, or less.

In some embodiments, the peptide described herein can be in solution, lyophilized, or can be in crystal form. In some embodiments, the peptide described herein can be prepared synthetically, by recombinant DNA technology or chemical synthesis, or can be isolated from natural sources such as native tumors or pathogenic organisms. Neoepitopes can be synthesized individually or joined directly or indirectly in the peptide. Although the peptide described herein can be substantially free of other naturally occurring host cell proteins and fragments thereof, in some embodiments, the peptide can be synthetically conjugated to be joined to native fragments or particles.

In some embodiments, the peptide described herein can be prepared in a wide variety of ways. In some embodiments, the peptides can be synthesized in solution or on a solid support according to conventional techniques. Various automatic synthesizers are commercially available and can be used according to known protocols. See, for example, Stewart & Young, Solid Phase Peptide Synthesis, 2d. Ed., Pierce Chemical Co., 1984. Further, individual peptides can be joined using chemical ligation to produce larger peptides that are still within the bounds of the present disclosure.

Alternatively, recombinant DNA technology can be employed wherein a nucleotide sequence which encodes the peptide inserted into an expression vector, transformed or transfected into an appropriate host cell and cultivated under conditions suitable for expression. These procedures are generally known in the art, as described generally in Sambrook et al., Molecular Cloning, A Laboratory Manual, Cold Spring Harbor Press, Cold Spring Harbor, N.Y. (1989). Thus, recombinant peptides, which comprise one or more neoantigenic peptides described herein, can be used to present the appropriate T cell epitope.

In some embodiments, the peptide is encoded by a gene with a point mutation resulting in an amino acid substitution of the native peptide. In some embodiments, the peptide is encoded by a gene with a point mutation resulting in frame shift mutation. A frameshift occurs when a mutation disrupts the normal phase of a gene's codon periodicity (also known as "reading frame"), resulting in the translation of a non-native protein sequence. It is possible for different mutations in a gene to achieve the same altered reading frame. In some embodiments, the peptide is encoded by a gene with a mutation resulting in fusion polypeptide, in-frame deletion, insertion, expression of endogenous retroviral polypeptides, and tumor-specific overexpression of polypeptides. In some embodiments, the peptide is encoded by a fusion of a first gene with a second gene. In some embodiments, the peptide is encoded by an in-frame fusion of a first gene with a second gene. In some embodiments, the peptide is encoded by a fusion of a first gene with an exon of a splice variant of the first gene. In some embodiments, the peptide is encoded by a fusion of a first gene with a cryptic exon of the first gene. In some embodiments, the peptide is encoded by a fusion of a first gene with a second gene, wherein the peptide comprises an amino acid sequence encoded by an out of frame sequence resulting from the fusion.

In some aspects, the present disclosure provides a composition comprising at least two or more than two peptides. In some embodiments, the composition described herein contains at least two distinct peptides. In some embodiments, the composition described herein contains a first peptide comprising a first neoepitope and a second peptide comprising a second neoepitope. In some embodiments, the first and second peptides are derived from the same protein. The at least two distinct peptides may vary by length, amino acid sequence or both. The peptides can be derived from any protein known to or have been found to contain a tumor specific mutation. In some embodiments, the composition described herein comprises a first peptide comprising a first neoepitope of a protein and a second peptide comprising a second neoepitope of the same protein, wherein the first peptide is different from the second peptide, and wherein the first neoepitope comprises a mutation and the second neoepitope comprises the same mutation. In some embodiments, the composition described herein comprises a first peptide comprising a first neoepitope of a first region of a protein and a second peptide comprising a second neoepitope of a second region of the same protein, wherein the first region comprises at least one amino acid of the second region, wherein the first peptide is different from the second peptide and wherein the first neoepitope comprises a first mutation and the second neoepitope comprises a second mutation. In some embodiments, the first mutation and the second mutation are the same. In some embodiments, the mutation is selected from the group consisting of a point mutation, a splice-site mutation, a frameshift mutation, a read-through mutation, a gene fusion mutation and any combination thereof.

In some embodiments, the peptide can be derived from a protein with a substitution mutation, e.g., the KRAS G12C, G12D, G12V, Q61H or Q61L mutation, or the NRAS Q61K or Q61R mutation. The substitution may be positioned anywhere along the length of the peptide. For example, it can be located in the N terminal third of the peptide, the central third of the peptide or the C terminal third of the peptide. In another embodiment, the substituted residue is located 2-5 residues away from the N terminal end or 2-5 residues away from the C terminal end. The peptides can similarly derived from tumor specific insertion mutations where the peptide comprises one or more, or all of the inserted residues.

In some embodiments, the first peptide comprises at least one an additional mutation. In some embodiments, one or more of the at least one additional mutation is not a mutation in the first neoepitope. In some embodiments, one or more of the at least one additional mutation is a mutation in the first neoepitope. In some embodiments, the second peptide comprises at least one additional mutation. In some embodiments, one or more of the at least one additional mutation is not a mutation in the second neoepitope. In some embodiments, one or more of the at least one additional mutation is a mutation in the second neoepitope.

In some aspects, the present disclosure provides a composition comprising a single polypeptide comprises the first peptide and the second peptide, or a single polynucleotide encodes the first peptide and the second peptide. In some embodiments, the composition provided herein comprises one or more additional peptides, wherein the one or more additional peptides comprise a third neoepitope. In some embodiments, the first peptide and the second peptide are encoded by a sequence transcribed from the same transcription start site. In some embodiments, the first peptide is encoded by a sequence transcribed from a first transcription start site and the second peptide is encoded by a sequence transcribed from a second transcription start site. In some embodiments, wherein the polypeptide has a length of at least 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the polypeptide comprises a first sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a corresponding wild-type sequence; and a second sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a corresponding wild-type sequence. In some embodiments, the polypeptide comprises a first sequence of at least 8 or 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a corresponding wild-type sequence; and a second sequence of at least 16 or 17 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a corresponding wild-type sequence.

In some embodiments, the second peptide is longer than the first peptide. In some embodiments, the first peptide is longer than the second peptide. In some embodiments, the first peptide has a length of at least 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the second peptide has a length of at least 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the first peptide comprises a sequence of at least 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the second peptide comprises a sequence of at least 17 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a corresponding wild-type sequence.

In some embodiments, the second peptide has a length of at most 13 amino acids. In some embodiments, the second peptide has a length of at least 8; 9; 10; 11; or 12 amino acids. In some embodiments, the first peptide has a length of at least one amino acid longer than the second peptide. In some embodiments, the first peptide has a length of at least 9, 10, 11, 12, 13, 14, 15, 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the second peptide comprises a sequence of at least 8 or 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the first peptide comprises a sequence of at least 9 or 10 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the second neoepitope is longer than the first neoepitope. In some embodiments, the second neoepitope has a length of at least 8 amino acids. In some embodiments, the second neoepitope has a length of from 8 to 12 amino acids. In some embodiments, the second neoepitope comprises a sequence of at least 8 contiguous amino acids, wherein at least 2 of the 8 contiguous amino acids are different at corresponding positions of a wild-type sequence. In some embodiments, the second neoepitope is comprised within the first peptide. In some embodiments, the first neoepitope has a length of at least 9 amino acids. In some embodiments, the first neoepitope has a length of from 9 to 25 amino acids. In some embodiments, the first neoepitope comprises a sequence of at least 9 contiguous amino acids, wherein at least 2 of the 16 contiguous amino acids are different at corresponding positions of a wild-type sequence.

In some embodiments, the first peptide, the second peptide or both comprise at least one flanking sequence, wherein the at least one flanking sequence is upstream or downstream of the neoepitope. In some embodiments, the at least one flanking sequence has at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild-type sequence. In some embodiments, the at least one flanking sequence comprises a non-wild-type sequence. In some embodiments, the at least one flanking sequence is a N-terminus flanking sequence. In some embodiments, the at least one flanking sequence is a C-terminus flanking sequence. In some embodiments, the at least one flanking sequence of the first peptide has at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the at least one flanking sequence of the second peptide. In some embodiments, the at least one flanking region of the first peptide is different from the at least one flanking region of the second peptide. In some embodiments, the at least one flanking residue comprises the mutation.

In some embodiments, a peptide comprises a neoepitope sequence comprising at least one mutant amino acid. In some embodiments, a peptide comprises a neoepitope sequence comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more mutant amino acids. In some embodiments, a peptide comprises a neoepitope sequence derived from a protein comprising at least one mutant amino acid and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids. In some embodiments, a peptide comprises a neoepitope sequence derived from a protein comprising at least one mutant amino acid and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids upstream of the least one mutant amino acid. In some embodiments, a peptide comprises a neoepitope sequence derived from a protein comprising at least one mutant amino acid and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids downstream of the least one mutant amino acid. In some embodiments, a peptide comprises a neoepitope sequence derived from a protein comprising at least one mutant amino acid; at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids upstream of the least one mutant amino acid; and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids downstream of the least one mutant amino acid.

In some embodiments, a peptide comprises a neoantigenic peptide sequence depicted in Tables 1 or 2. In some embodiments, a peptide comprises a neoepitope sequence depicted in Tables 1 or 2. In some embodiments, a peptide comprises a neoepitope sequence comprising at least one mutant amino acid (underlined amino acid) as depicted in Tables 1 or 2. In some embodiments, a peptide comprises a neoepitope sequence comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more mutant amino acids (underlined amino acids) as depicted in Tables 1 or 2. In some embodiments, a peptide comprises a neoepitope sequence comprising at least one mutant amino acid (underlined amino acid) and at least one bolded amino acid as depicted in Tables 1 or 2. In some embodiments, a peptide comprises a neoepitope sequence derived from a protein comprising at least one mutant amino acid (underlined amino acid) and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids as depicted in Tables 1 or 2. In some embodiments, a peptide comprises a neoepitope sequence derived from a protein comprising at least one mutant amino acid (underlined amino acid) and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids upstream of the least one mutant amino acid as depicted in Tables 1 or 2. In some embodiments, a peptide comprises a neoepitope sequence derived from a protein comprising at least one mutant amino acid (underlined amino acid) and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids downstream of the least one mutant amino acid as depicted in Tables 1 or 2. In some embodiments, a peptide comprises a neoepitope sequence derived from a protein comprising at least one mutant amino acid (underlined amino acid), at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids upstream of the least one mutant amino acid, and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-mutant amino acids downstream of the least one mutant amino acid as depicted in Tables 1 or 2.

In some embodiments, a peptide comprises a neoepitope sequence derived from a protein comprising at least one mutant amino acid and a sequence upstream of the least one mutant amino acid with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence. In some embodiments, a peptide comprises a neoepitope sequence derived from a protein comprising at least one mutant amino acid and a sequence downstream of the least one mutant amino acid with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence. In some embodiments, a peptide comprises a neoepitope sequence derived from a protein comprising at least one mutant amino acid, a sequence upstream of the least one mutant amino acid with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence, and a sequence downstream of the least one mutant amino acid with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence.

In some embodiments, a peptide comprises a neoepitope sequence derived from a protein comprising at least one mutant amino acid and a sequence upstream of the least one mutant amino acid comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence. In some embodiments, a peptide comprises a neoepitope sequence derived from a protein comprising at least one mutant amino acid and a sequence downstream of the least one mutant amino acid comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence. In some embodiments, a peptide comprises a neoepitope sequence derived from a protein comprising at least one mutant amino acid, a sequence upstream of the least one mutant amino acid comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence, and a sequence downstream of the least one mutant amino acid comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence.

In some embodiments, a peptide comprises a neoepitope sequence derived from a protein comprising at least one mutant amino acid (underlined amino acid) as depicted in Tables 1 or 2 and a sequence upstream of the least one mutant amino acid with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence. In some embodiments, a peptide comprises a neoepitope sequence derived from a protein comprising at least one mutant amino acid (underlined amino acid) as depicted in Tables 1 or 2 and a sequence downstream of the least one mutant amino acid with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence. In some embodiments, a peptide comprises a neoepitope sequence derived from a protein comprising at least one mutant amino acid (underlined amino acid) as depicted in Tables 1 or 2, a sequence upstream of the least one mutant amino acid with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence, and a sequence downstream of the least one mutant amino acid with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence.

In some embodiments, a peptide comprises a neoepitope sequence derived from a protein comprising at least one mutant amino acid (underlined amino acid) as depicted in Tables 1 or 2 and a sequence upstream of the least one mutant amino acid comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence. In some embodiments, a peptide comprises a neoepitope sequence derived from a protein comprising at least one mutant amino acid (underlined amino acid) as depicted in Tables 1 or 2 and a sequence downstream of the least one mutant amino acid comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence. In some embodiments, a peptide comprises a neoepitope sequence derived from a protein comprising at least one mutant amino acid (underlined amino acid) as depicted in Tables 1 or 2, a sequence upstream of the least one mutant amino acid comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence, and a sequence downstream of the least one mutant amino acid comprising at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a corresponding wild type sequence.

In some embodiments, a peptide comprising a KRAS G12C mutation comprises a sequence of MTEYKLVVVGACGVGKSALTIQLIQNHFVDEYDP-TIEDSYRKQVVIDGETC LLDILDTAGQE (SEQ ID NO: 1303). In some embodiments, a peptide comprising a KRAS G12 C mutation comprises a neoepitope sequence of KLVVVGACGV (SEQ ID NO: 1304). In some embodiments, a peptide comprising a KRAS G12 C mutation comprises a neoepitope sequence of LVVVGACGV (SEQ ID NO: 1305). In some embodiments, a peptide comprising a KRAS G12 C mutation comprises a neoepitope sequence of VVVGACGVK (SEQ ID NO: 1306). In some embodiments, a peptide comprising a KRAS G12 C mutation comprises a neoepitope sequence of VVVGACGVGK (SEQ ID NO: 1307).

In some embodiments, a peptide comprising a KRAS G12D mutation comprises a sequence of MTEYKLVVVGADGVGKSALTIQLIQNHFVDEYDP-TIEDSYRKQVVIDGETCLLDILDTAGQE (SEQ ID NO: 1308). In some embodiments, a peptide comprising a KRAS G12D mutation comprises a neoepitope sequence of VVGADGVGK (SEQ ID NO: 1309). In some embodiments, a peptide comprising a KRAS G12D mutation comprises a neoepitope sequence of VVVGADGVGK (SEQ ID NO: 1310). In some embodiments, a peptide comprising a KRAS G12D mutation comprises a neoepitope sequence of KLVVVGADGV (SEQ ID NO: 1311). In some embodiments, a peptide comprising a KRAS G12D mutation comprises a neoepitope sequence of LVVVGADGV (SEQ ID NO: 1312).

In some embodiments, a peptide comprising a KRAS G12V mutation comprises a sequence of MTEYKLVVVGAVGVGKSALTIQLIQNHFVDEYDP-TIEDSYRKQVVIDGETCLLDILDTAGQE (SEQ ID NO: 1313). In some embodiments, a peptide comprising a KRAS G12V mutation comprises a neoepitope sequence of KLVVVGAVGV (SEQ ID NO: 1314). In some embodiments, a peptide comprising a KRAS G12V mutation comprises a neoepitope sequence of LVVVGAVGV (SEQ ID NO: 1315). In some embodiments, a peptide comprising a KRAS G12V mutation comprises a neoepitope sequence of VVGAVGVGK (SEQ ID NO: 1316). In some embodiments, a peptide comprising a KRAS G12V mutation comprises a neoepitope sequence of VVVGAVGVGK (SEQ ID NO: 1317).

In some embodiments, a peptide comprising a KRAS Q61H mutation comprises a sequence of AGGVGKSAL-TIQLIQNHFVDEYDPTIEDSYRKQVVIDGETCLLDI-LDTAGHEEYSAMRDQYMRTGEG FLCVFAINNTKSFEDIHHYREQIKRVKDSEDVPM (SEQ ID NO: 1318). In some embodiments, a peptide comprising a KRAS Q61H mutation comprises a neoepitope sequence of ILDTAGHEEY (SEQ ID NO: 1319).

In some embodiments, a peptide comprising a KRAS Q61L mutation comprises a sequence of AGGVGKSAL-TIQLIQNHFVDEYDPTIEDSYRKQVVIDGETCLLDI-LDTAGLEEYSAMRDQYMRTGEG FLCVFAINNTKSFEDIHHYREQIKRVKDSEDVPM (SEQ ID NO: 1320). In some embodiments, a peptide comprising a KRAS Q61L mutation comprises a neoepitope sequence of ILDTAGLEEY (SEQ ID NO: 1321). In some embodiments, a peptide comprising a KRAS Q61L mutation comprises a neoepitope sequence of LLDILDTAGL (SEQ ID NO: 1322).

In some embodiments, a peptide comprising a NRAS Q61K mutation comprises a sequence of AGGVGKSAL-TIQLIQNHFVDEYDPTIEDSYRKQVVIDGETCLLDI-LDTAGKEEYSAMRDQYMRTGEG FLCVFAINNSKS-FADINLYREQIKRVKDSDDVPM (SEQ ID NO: 1323). In some embodiments, a peptide comprising a NRAS Q61K mutation comprises a neoepitope sequence of ILDTAG-KEEY (SEQ ID NO: 1324).

In some embodiments, a peptide comprising a NRAS Q61R mutation comprises a sequence of AGGVGKSAL-TIQLIQNHFVDEYDPTIEDSYRKQVVIDGETCLLDI-LDTAGREEYSAMRDQYMRTGEG FLCVFAINNSKS-FADINLYREQIKRVKDSDDVPM (SEQ ID NO: 1325). In some embodiments, a peptide comprising a NRAS Q61R mutation comprises a neoepitope sequence of ILD-TAGREEY (SEQ ID NO: 1326).

In some embodiments, a peptide comprising a mutation of a TMPRSS2:ERG fusion comprises a neoepitope sequence of MALNS::EALSVVSEDQSLFECAYGTPHLAKTEM-TASSSSDYGQTSKMSPRVPQQDWALNSEALSV (SEQ ID NO: 1327). In some embodiments, a peptide comprising a mutation of a TMPRSS2:ERG fusion comprises a neoepitope sequence of ALNSEALSVV (SEQ ID NO: 1328). In some embodiments, a peptide comprising a mutation of a TMPRSS2:ERG fusion comprises a neoepitope sequence of MALNSEALSV (SEQ ID NO: 1329).

Peptide Modification

In some embodiments, the present disclosure includes modified peptides. A modification can include a covalent chemical modification that does not alter the primary amino acid sequence of the antigenic peptide itself. Modifications can produce peptides with desired properties, for example, prolonging the in vivo half-life, increasing the stability, reducing the clearance, altering the immunogenicity or allergenicity, enabling the raising of particular antibodies, cellular targeting, antigen uptake, antigen processing, HLA affinity, HLA stability or antigen presentation. In some embodiments, a peptide may comprise one or more sequences that enhance processing and presentation of epitopes by APCs, for example, for generation of an immune response.

In some embodiments, the peptide may be modified to provide desired attributes. For instance, the ability of the peptides to induce CTL activity can be enhanced by linkage to a sequence which contains at least one epitope that is capable of inducing a T helper cell response. In some embodiments, immunogenic peptides/T helper conjugates are linked by a spacer molecule. In some embodiments, a spacer comprises relatively small, neutral molecules, such as amino acids or amino acid mimetics, which are substantially uncharged under physiological conditions. Spacers can be selected from, e.g., Ala, Gly, or other neutral spacers of nonpolar amino acids or neutral polar amino acids. It will be understood that the optionally present spacer need not be comprised of the same residues and thus may be a hetero- or homo-oligomer. The neoantigenic peptide may be linked to the T helper peptide either directly or via a spacer either at the amino or carboxy terminus of the peptide. The amino terminus of either the neoantigenic peptide or the T helper peptide may be acylated. Examples of T helper peptides include tetanus toxoid residues 830-843, influenza residues 307-319, and malaria circumsporozoite residues 382-398 and residues 378-389.

The peptide sequences of the present disclosure may optionally be altered through changes at the DNA level, particularly by mutating the DNA encoding the peptide at preselected bases such that codons are generated that will translate into the desired amino acids.

In some embodiments, the peptide described herein can contain substitutions to modify a physical property (e.g., stability or solubility) of the resulting peptide. For example, the peptides can be modified by the substitution of a cysteine (C) with α-amino butyric acid ("B"). Due to its chemical nature, cysteine has the propensity to form disulfide bridges and sufficiently alter the peptide structurally so as to reduce binding capacity. Substituting α-amino butyric acid for C not only alleviates this problem, but actually improves binding and cross-binding capability in certain instances. Substitution of cysteine with α-amino butyric acid can occur at any residue of a neoantigenic peptide, e.g., at either anchor or non-anchor positions of an epitope or analog within a peptide, or at other positions of a peptide.

The peptide may also be modified by extending or decreasing the compound's amino acid sequence, e.g., by the addition or deletion of amino acids. The peptides or analogs can also be modified by altering the order or composition of certain residues. It will be appreciated by the skilled artisan that certain amino acid residues essential for biological activity, e.g., those at critical contact sites or conserved residues, may generally not be altered without an adverse effect on biological activity. The non-critical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

In some embodiments, the peptide may be modified using a series of peptides with single amino acid substitutions to determine the effect of electrostatic charge, hydrophobicity, etc. on HLA binding. For instance, a series of positively charged (e.g., Lys or Arg) or negatively charged (e.g., Glu) amino acid substitutions may be made along the length of the peptide revealing different patterns of sensitivity towards various HLA molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an HLA molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding. Amino acid substitutions are typically of single residues. Substitutions, deletions, insertions or any combination thereof may be combined to arrive at a final peptide.

In some embodiments, the peptide described herein can comprise amino acid mimetics or unnatural amino acid residues, e.g. D- or L-naphylalanine; D- or L-phenylglycine; D- or L-2-thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoro-methyl)-phenylalanine; D-ρ-fluorophenylalanine; D- or L-ρ-biphenyl-phenylalanine; D- or L-ρ-methoxybiphenylphenylalanine; D- or L-2-indole(allyl)alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a non-acidic amino acid residues. Aromatic rings of a non-natural amino acid include, e.g., thiazolyl, thiophenyl, pyrazolyl, benzimidazolyl, naphthyl, furanyl, pyrrolyl, and pyridyl aromatic rings. Modified peptides that have various amino acid mimetics or unnatural amino acid residues may have increased stability in vivo. Such peptides may also have improved shelf-life or manufacturing properties.

In some embodiments, a peptide described herein can be modified by terminal-NH2 acylation, e.g., by alkanoyl (C1-C20) or thioglycolyl acetylation, terminal-carboxyl amidation, e.g., ammonia, methylamine, etc. In some embodiments these modifications can provide sites for linking to a support or other molecule. In some embodiments, the peptide described herein can contain modifications such as but not limited to glycosylation, side chain oxidation, biotinylation, phosphorylation, addition of a surface active material, e.g. a lipid, or can be chemically modified, e.g., acetylation, etc. Moreover, bonds in the peptide can be other than peptide bonds, e.g., covalent bonds, ester or ether bonds, disulfide bonds, hydrogen bonds, ionic bonds, etc.

In some embodiments, a peptide described herein can comprise carriers such as those well known in the art, e.g., thyroglobulin, albumins such as human serum albumin, tetanus toxoid, polyamino acid residues such as poly L-lysine and poly L-glutamic acid, influenza virus proteins, hepatitis B virus core protein, and the like.

The peptides can be further modified to contain additional chemical moieties not normally part of a protein. Those derivatized moieties can improve the solubility, the biological half-life, absorption of the protein, or binding affinity. The moieties can also reduce or eliminate any desirable side effects of the peptides and the like. An overview for those moieties can be found in Remington's Pharmaceutical Sciences, 20th ed., Mack Publishing Co., Easton, Pa. (2000). For example, neoantigenic peptides having the desired activity may be modified as necessary to provide certain desired attributes, e.g. improved pharmacological characteristics, while increasing or at least retaining substantially all of the biological activity of the unmodified peptide to bind the desired HLA molecule and activate the appropriate T cell. For instance, the peptide may be subject to various changes, such as substitutions, either conservative or non-conservative, where such changes might provide for certain advantages in their use, such as improved HLA binding. Such conservative substitutions may encompass replacing an amino acid residue with another amino acid residue that is biologically and/or chemically similar, e.g., one hydrophobic residue for another, or one polar residue for another. The effect of single amino acid substitutions may also be probed using D-amino acids. Such modifications may be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

In some embodiments, the peptide described herein may be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells.

Changes to the peptide that may include, but are not limited to, conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids.

Glycosylation can affect the physical properties of proteins and can also be important in protein stability, secretion, and subcellular localization. Proper glycosylation can be important for biological activity. In fact, some genes from eukaryotic organisms, when expressed in bacteria (e.g., *E. coli*) which lack cellular processes for glycosylating proteins, yield proteins that are recovered with little or no activity by virtue of their lack of glycosylation. Addition of glycosylation sites can be accomplished by altering the amino acid sequence. The alteration to the peptide or protein may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. Embodiments of the present disclosure comprise the generation and use of N-glycosylation variants. Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Additional suitable components and molecules for conjugation include, for example, molecules for targeting to the lymphatic system, thyroglobulin; albumins such as human serum albumin (HAS); tetanus toxoid; Diphtheria toxoid; polyamino acids such as poly(D-lysine:D-glutamic acid); VP6 polypeptides of rotaviruses; influenza virus hemagglutinin, influenza virus nucleoprotein; Keyhole Limpet Hemocyanin (KLH); and hepatitis B virus core protein and surface antigen; or any combination of the foregoing.

Another type of modification is to conjugate (e.g., link) one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule. In some embodiments, fusion of albumin to the peptide or protein of the present disclosure can, for example, be achieved by genetic manipulation, such that the DNA coding for HSA, or a fragment thereof, is joined to the DNA coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Furthermore, albumin itself may be modified to extend its circulating half-life. Fusion of the modified albumin to one or more polypeptides can be attained by the genetic manipulation techniques described above or by chemical conjugation; the resulting fusion molecule has a half-life that exceeds that of fusions with non-modified albumin (see, e.g., WO2011/051489). Several albumin-binding strategies have been developed as alternatives for direct fusion, including albumin binding through a conjugated fatty acid chain (acylation). Because serum albumin is a transport protein for fatty acids, these natural ligands with albumin-binding activity have been used for half-life extension of small protein therapeutics.

Additional candidate components and molecules for conjugation include those suitable for isolation or purification. Non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes. Purification methods such as cation exchange chromatography may be used to separate conjugates by charge difference, which effectively separates conjugates into their various molecular weights. The content of the fractions obtained by cation exchange chromatography may be identified by molecular weight using conventional methods, for example, mass spectroscopy, SDS-PAGE, or other known methods for separating molecular entities by molecular weight.

In some embodiments, the amino- or carboxyl-terminus of the peptide or protein sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamics properties of the biopharmaceutical as compared to traditional Fc-fusion conjugates.

The present disclosure contemplates the use of other modifications, currently known or developed in the future, of the peptides to improve one or more properties. One such method for prolonging the circulation half-life, increasing the stability, reducing the clearance, or altering the immunogenicity or allergenicity of the peptide of the present disclosure involves modification of the peptide sequences by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

Peptide stability can be assayed in a number of ways. For instance, peptidases and various biological media, such as human plasma and serum, have been used to test stability. See, e.g., Verhoef, et al., Eur. J. Drug Metab. Pharmacokinetics 11:291 (1986). Half-life of the peptides described herein is conveniently determined using a 25% human serum (v/v) assay. The protocol is as follows: pooled human serum (Type AB, non-heat inactivated) is dilapidated by centrifugation before use. The serum is then diluted to 25% with RPMI-1640 or another suitable tissue culture medium. At predetermined time intervals, a small amount of reaction solution is removed and added to either 6% aqueous trichloroacetic acid (TCA) or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

Issues associated with short plasma half-life or susceptibility to protease degradation may be overcome by various modifications, including conjugating or linking the peptide or protein sequence to any of a variety of non-proteinaceous polymers, e.g., polyethylene glycol (PEG), polypropylene glycol, or polyoxyalkylenes (see, for example, typically via a linking moiety covalently bound to both the protein and the nonproteinaceous polymer, e.g., a PEG). Such PEG conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide or protein sequence are generally soluble in water at room temperature, and have the general formula R—(O—CH2-CH2)n-O—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. The present disclosure also contemplates compositions of conjugates wherein the PEGs have different n values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. For example, cation exchange chromatography may be used to separate conjugates, and a fraction is then identified which contains the conjugate having, for example, the desired number of PEGs attached, purified free from unmodified protein sequences and from conjugates having other numbers of PEGs attached.

PEG may be bound to the peptide or protein of the present disclosure via a terminal reactive group (a "spacer"). The spacer is, for example, a terminal reactive group which mediates a bond between the free amino or carboxyl groups of one or more of the polypeptide sequences and PEG. The PEG having the spacer which may be bound to the free amino group includes N-hydroxysuccinylimide PEG which may be prepared by activating succinic acid ester of PEG with N-hydroxysuccinylimide. Another activated PEG which may be bound to a free amino group is 2,4-bis(O-methoxypolyethyleneglycol)-6-chloro-s-triazine which may be prepared by reacting PEG monomethyl ether with cyanuric chloride. The activated PEG which is bound to the free carboxyl group includes polyoxyethylenediamine.

Conjugation of one or more of the peptide or protein sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to peptide/protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH>7), and longer reaction time tend to increase the number of PEGs attached. Various means known in the art may be used to terminate the reaction. In some embodiments the reaction is terminated by acidifying the reaction mixture and freezing at, e.g., −20° C.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Neoepitopes

A neoepitope comprises a neoantigenic determinant part of a neoantigenic peptide or neoantigenic polypeptide that is recognized by immune system. A neoepitope refers to an epitope that is not present in a reference, such as a non-diseased cell, e.g., a non-cancerous cell or a germline cell, but is found in a diseased cell, e.g., a cancer cell. This includes situations where a corresponding epitope is found in a normal non-diseased cell or a germline cell but, due to one or more mutations in a diseased cell, e.g., a cancer cell, the sequence of the epitope is changed so as to result in the neoepitope. The term "neoepitope" is used interchangeably with "tumor specific neoepitope" in the present specification to designate a series of residues, typically L-amino acids, connected one to the other, typically by peptide bonds between the α-amino and carboxyl groups of adjacent amino acids. The neoepitope can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described. The present disclosure provides isolated neoepitopes that comprise a tumor specific mutation from Table 1 or 2.

In some embodiments, neoepitopes described herein for HLA Class I are 13 residues or less in length and usually consist of between about 8 and about 12 residues, particularly 9 or 10 residues. In some embodiments, neoepitopes described herein for HLA Class II are 25 residues or less in length and usually consist of between about 16 and about 25 residues.

In some embodiments, the composition described herein comprises a first peptide comprising a first neoepitope of a protein and a second peptide comprising a second neoepitope of the same protein, wherein the first peptide is different from the second peptide, and wherein the first neoepitope comprises a mutation and the second neoepitope comprises the same mutation. In some embodiments, the composition described herein comprises a first peptide comprising a first neoepitope of a first region of a protein and a second peptide comprising a second neoepitope of a second region of the same protein, wherein the first region comprises at least one amino acid of the second region, wherein the first peptide is different from the second peptide and wherein the first neoepitope comprises a first mutation and the second neoepitope comprises a second mutation. In some embodiments, the first mutation and the second mutation are the same. In some embodiments, the mutation is selected from the group consisting of a point mutation, a splice-site mutation, a frameshift mutation, a read-through mutation, a gene fusion mutation and any combination thereof.

In some embodiments, the first neoepitope binds to a class I HLA protein to form a class I HLA-peptide complex. In some embodiments, the second neoepitope binds to a class II HLA a protein to form a class II HLA-peptide complex. In some embodiments, the second neoepitope binds to a class I HLA protein to form a class I HLA-peptide complex. In some embodiments, the first neoepitope binds to a class II HLA protein to form a class II HLA-peptide complex. In some embodiments, the first neoepitope activates CD8+ T cells. In some embodiments, the first neoepitope activates CD4+ T cells. In some embodiments, the second neoepitope activates CD4+ T cells. In some embodiments, the second neoepitope activates CD8+ T cells. In some embodiments, a TCR of a CD4+ T cell binds to a class II HLA-peptide complex. In some embodiments, a TCR of a CD8+ T cell binds to a class II HLA-peptide complex. In some embodiments, a TCR of a CD8+ T cell binds to a class I HLA-peptide complex. In some embodiments, a TCR of a CD4+ T cell binds to a class I HLA-peptide complex.

In some embodiments, the second neoepitope is longer than the first neoepitope. In some embodiments, the first neoepitope has a length of at least 8 amino acids. In some embodiments, the first neoepitope has a length of from 8 to 12 amino acids. In some embodiments, the first neoepitope comprises a sequence of at least 8 contiguous amino acids, wherein at least 1 of the 8 contiguous amino acids are different at corresponding positions of a wild-type sequence. In some embodiments, the first neoepitope comprises a sequence of at least 8 contiguous amino acids, wherein at least 2 of the 8 contiguous amino acids are different at corresponding positions of a wild-type sequence. In some embodiments, the second neoepitope has a length of at least 16 amino acids. In some embodiments, the second neoepitope has a length of from 16 to 25 amino acids. In some embodiments, the second neoepitope comprises a sequence of at least 16 contiguous amino acids, wherein at least 1 of the 16 contiguous amino acids are different at corresponding positions of a wild-type sequence. In some embodiments, the second neoepitope comprises a sequence of at least 16 contiguous amino acids, wherein at least 2 of the 16 contiguous amino acids are different at corresponding positions of a wild-type sequence.

In some embodiments, the second peptide has a length of at most 13 amino acids. In some embodiments, the second peptide has a length of at least 8; 9; 10; 11; or 12 amino acids. In some embodiments, the first peptide has a length of at least one amino acid longer than the second peptide. In some embodiments, the first peptide has a length of at least 9, 10, 11, 12, 13, 14, 15, 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 amino acids. In some embodiments, the second peptide comprises a sequence of at least 8 or 9 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the first peptide comprises a sequence of at least 9 or 10 contiguous amino acids with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a corresponding wild-type sequence. In some embodiments, the second neoepitope is longer than the first neoepitope. In some embodiments, the second neoepitope has a length of at least 8 amino acids. In some embodiments, the second neoepitope has a length of from 8 to 12 amino acids. In some embodiments, the second neoepitope comprises a sequence of at least 8 contiguous amino acids, wherein at least 2 of the 8 contiguous amino acids are different at corresponding positions of a wild-type sequence. In some embodiments, the second neoepitope is comprised within the first peptide. In some embodiments, the first neoepitope has a length of at least 9 amino acids. In some embodiments, the first neoepitope has a length of from 9 to 25 amino acids. In some embodiments, the first neoepitope comprises a sequence of at least 9 contiguous amino acids, wherein at least 2 of the 16 contiguous amino acids are different at corresponding positions of a wild-type sequence. In some embodiments, the neoepitope comprises at least one anchor residue. In some embodiments, the first neoepitope, the second neoepitope or both comprises at least one anchor residue. In one embodiment, the at least one anchor residue of the first neoepitope is at a canonical anchor position or a non-canonical anchor position. In another embodiment, the at least one anchor residue of the second neoepitope is at a canonical anchor position or a non-canonical anchor position. In yet another embodiment, the at least one anchor residue of the first neoepitope is different from the at least one anchor residue of the second neoepitope.

In some embodiments, the at least one anchor residue is a wild-type residue. In some embodiments, the at least one anchor residue is a substitution. In some embodiments, at least one anchor residue does not comprise the mutation.

In some embodiments, the second neoepitope or both comprise at least one anchor residue flanking region. In some embodiments, the neoepitope comprises at least one anchor residue. In some embodiments, the at least one anchor residues comprises at least two anchor residues. In some embodiments, the at least two anchor residues are separated by a separation region comprising at least 1 amino acid. In some embodiments, the at least one anchor residue flanking region is not within the separation region. In some embodiments, the at least one anchor residue flanking region is (a) upstream of a N-terminal anchor residue of the at least two anchor residues; (b) downstream of a C-terminal anchor residue of the at least two anchor residues; or both (a) and (b).

In some embodiments, the neoepitopes bind an HLA protein (e.g., HLA class I or HLA class II). In some embodiments, the neoepitopes bind an HLA protein with greater affinity than the corresponding wild-type peptide. In some embodiments, the neoepitope has an IC50 of less than 5,000 nM, less than 1,000 nM, less than 500 nM, less than 100 nM, less than 50 nM, or less.

In some embodiments, the neoepitope can have an HLA binding affinity of between about 1 pM and about 1 mM, about 100 pM and about 500 µM, about 500 pM and about 10 µM, about 1 nM and about 1 µM, or about 10 nM and about 1 µM. In some embodiments, the neoepitope can have an HLA binding affinity of at least 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 700, 800, 900, or 1,000 nM, or more. In some embodiments, the neoepitope can have an HLA binding affinity of at most 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 700, 800, 900, or 1,000 nM.

In some embodiments, the first and/or second neoepitope binds to an HLA protein with a greater affinity than a corresponding wild-type neoepitope. In some embodiments, the first and/or second neoepitope binds to an HLA protein with a KD or an IC50 less than 1,000 nM, 900 nM, 800 nM, 700 nM, 600 nM, 500 nM, 250 nM, 150 nM, 100 nM, 50 nM, 25 nM or 10 nM. In some embodiments, the first and/or second neoepitope binds to an HLA class I protein with a KD or an IC50 less than 1,000 nM, 900 nM, 800 nM, 700 nM, 600 nM, 500 nM, 250 nM, 150 nM, 100 nM, 50 nM, 25 nM or 10 nM. In some embodiments, the first and/or second neoepitope binds to an HLA class II protein with a KD or an IC50 less than 2,000 nM, 1,500 nM, 1,000 nM, 900 nM, 800 nM, 700 nM, 600 nM, 500 nM, 250 nM, 150 nM, 100 nM, 50 nM, 25 nM or 10 nM.

In an aspect, the first and/or second neoepitope binds to a protein encoded by an HLA allele expressed by a subject. In another aspect, the mutation is not present in non-cancer cells of a subject. In yet another aspect, the first and/or second neoepitope is encoded by a gene or an expressed gene of a subject's cancer cells.

In some embodiments, the first neoepitope comprises a mutation as depicted in column 2 of Table 1 or 2. In some embodiments, the second neoepitope comprises a mutation as depicted in column 2 of Table 1 or 2. In some embodiments, the first neoepitope and the second neoepitope is derived from a TMPRSS2:ERG fusion protein. In some embodiments, the first neoepitope and the second neoepitope is derived from a TMPRSS2:ERG fusion protein comprising a sequence of S::E from the sequence MALNS::EALSVVSEDQSLFECAYGTPHLAKTEMTASSSSDYGQTSKMSPRVPQQDWALNSEALSV (SEQ ID NO: 1330). For example, the first neoepitope and the second neoepitope can comprise a sequence ALNSEALSVV (SEQ ID NO: 1331). For example, the first neoepitope and the second neoepitope can comprise a sequence MALNSEALSV (SEQ ID NO: 1332).

In some embodiments, the first neoepitope and the second neoepitope is derived from a KRAS protein. In some embodiments, the first neoepitope and the second neoepitope is derived from a NRAS protein. In some embodiments, the first neoepitope and the second neoepitope is derived from a KRAS protein comprising a mutation of G12C, G12D, G12V, Q61H or Q61L substitution. In some embodiments, the first neoepitope and the second neoepitope is derived from a NRAS protein comprising a mutation of Q61K or Q61R substitution. In some embodiments, the neoepitope comprises a substitution mutation, e.g., the KRAS G12C, G12D, G12V, Q61H or Q61L mutation, or the NRAS Q61K or Q61R mutation. In some embodiments, the first neoepitope and the second neoepitope is derived from a KRAS or NRAS protein sequence of MTEYKLVVVGACGVGKSALTIQLIQNHFVDEYDPTIEDSYRKQVVIDGETCLLDILDTAGQE (SEQ ID NO: 1333). For example, the first neoepitope and the second neoepitope can comprise a sequence KLVVVGACGV (SEQ ID NO: 1334). For example, the first neoepitope and the second neoepitope can comprise a sequence LVVVGACGV (SEQ ID NO: 1335). For example, the first neoepitope and the second neoepitope can comprise a sequence VVGACGVGK (SEQ ID NO: 1336). For example, the first neoepitope and the second neoepitope can comprise a sequence VVVGACGVGK (SEQ ID NO: 1337). In some embodiments, the first neoepitope and the second neoepitope is derived from a KRAS or NRAS protein sequence of MTEYKLVVVGADGVGKSALTIQLIQNHFVDEYDPTIEDSYRKQVVIDGETCLLDILDTAGQE VVGAD GVGK (SEQ ID NO: 1338). For example, the first neoepitope and the second neoepitope can comprise a sequence VVVGADGVGK (SEQ ID NO: 1339). For example, the first neoepitope and the second neoepitope can comprise a sequence KLVVVGADGV (SEQ ID NO: 1340). For example, the first neoepitope and the second neoepitope can comprise a sequence LVVVGADGV (SEQ ID NO: 1341).

In some embodiments, the first neoepitope and the second neoepitope is derived from a KRAS or NRAS protein sequence of MTEYKLVVVGAVGVGKSALTIQLIQNHFVDEYDPTIEDSYRKQVVIDGETCLLDILDTAGQE (SEQ ID NO: 1342). For example, the first neoepitope and the second neoepitope can comprise a sequence KLVVVGAVGV (SEQ ID NO: 1343). For example, the first neoepitope and the second neoepitope can comprise a sequence LVVVGAVGV (SEQ ID NO: 1344). For example, the first neoepitope and the second neoepitope can comprise a sequence VVGAVGVGK (SEQ ID NO: 1345). For example, the first neoepitope and the second neoepitope can comprise a sequence VVVGAVGVGK (SEQ ID NO: 1346).

In some embodiments, the first neoepitope and the second neoepitope is derived from a KRAS or NRAS protein sequence of AGGVGKSALTIQLIQNHFVDEYDPTIEDSYRKQVVIDGETCLLDILDTAGHEEYSAMRDQY MRTGEG FLCVFAINNTKSFEDIHHYREQIKRVKDSEDVPM (SEQ ID NO: 1347). For example, the first neoepitope and the second neoepitope can comprise a sequence ILDTAGHEEY (SEQ ID NO: 1348).

In some embodiments, the first neoepitope and the second neoepitope is derived from a KRAS or NRAS protein sequence of AGGVGKSALTIQLIQNHFVDEYDPTIEDSYRKQVVIDGETCLLDILDTAGLEEYSAMRDQYMRTGEG FLCVFAINNTKSFEDIHHYREQIKRVKDSEDVPM (SEQ ID NO: 1349). For example, the first neoepitope and the second neoepitope can comprise a sequence ILDTAGLEEY (SEQ ID NO: 1350). For example, the first neoepitope and the second neoepitope can comprise a sequence LLDILDTAGL (SEQ ID NO: 1351).

In some embodiments, the first neoepitope and the second neoepitope is derived from a KRAS or NRAS protein sequence of AGGVGKSALTIQLIQNHFVDEYDPTIEDSYRKQVVIDGETCLLDILDTAGKEEYSAMRDQYM RTGEG FLCVFAINNSKSFADINLYREQIKRVKDSDDVPM (SEQ ID NO: 1352). For example, the first neoepitope and the second neoepitope can comprise a sequence ILDTAGKEEY (SEQ ID NO: 1353).

In some embodiments, the first neoepitope and the second neoepitope is derived from a KRAS or NRAS protein sequence of AGGVGKSALTIQLIQNHFVDEYDPTIEDSYRKQVVIDGETCLLDILDTAGREEYSAMRDQY MRTGEG FLCVFAINNSKSFADINLYREQIKRVKDSDDVPM (SEQ ID NO: 1354). For example, the first neoepitope and the second neoepitope can comprise a sequence ILDTAGREEY (SEQ ID NO: 1355).

The substitution may be positioned anywhere along the length of the neoepitope. For example, it can be located in the N terminal third of the peptide, the central third of the peptide or the C terminal third of the peptide. In another embodiment, the substituted residue is located 2-5 residues away from the N terminal end or 2-5 residues away from the C terminal end. The peptides can be similarly derived from tumor specific insertion mutations where the peptide comprises one or more, or all of the inserted residues.

In some embodiments, the peptide as described herein can be readily synthesized chemically utilizing reagents that are free of contaminating bacterial or animal substances (Merrifield RB: Solid phase peptide synthesis. I. The synthesis of a tetrapeptide. J. Am. Chem. Soc. 85:2149-54, 1963). In some embodiments, peptides are prepared by (1) parallel solid-phase synthesis on multi-channel instruments using uniform synthesis and cleavage conditions; (2) purification over a RP-HPLC column with column stripping; and re-washing, but not replacement, between peptides; followed by (3) analysis with a limited set of the most informative assays. The Good Manufacturing Practices (GMP) footprint can be defined around the set of peptides for an individual patient, thus requiring suite changeover procedures only between syntheses of peptides for different patients.

Polynucleotides

Alternatively, a nucleic acid (e.g., a polynucleotide) encoding the peptide of the present disclosure may be used to produce the neoantigenic peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. In some embodiments in vitro translation is used to produce the peptide.

Provided herein are neoantigenic polynucleotides encoding each of the neoantigenic peptides described in the present disclosure. The term "polynucleotide", "nucleotides" or "nucleic acid" is used interchangeably with "mutant polynucleotide", "mutant nucleotide", "mutant nucleic acid", "neoantigenic polynucleotide", "neoantigenic nucleotide" or "neoantigenic mutant nucleic acid" in the present disclosure. Various nucleic acid sequences can encode the same peptide due to the redundancy of the genetic code. Each of these nucleic acids falls within the scope of the present disclosure. Nucleic acids encoding peptides can be DNA or RNA, for example, mRNA, or a combination of DNA and RNA. In some embodiments, a nucleic acid encoding a peptide is a self-amplifying mRNA (Brito et al., Adv. Genet. 2015; 89:179-233). Any suitable polynucleotide that encodes a peptide described herein falls within the scope of the present disclosure.

The term "RNA" includes and in some embodiments relates to "mRNA." The term "mRNA" means "messenger-RNA" and relates to a "transcript" which is generated by using a DNA template and encodes a peptide or polypeptide. Typically, an mRNA comprises a 5'-UTR, a protein coding region, and a 3'-UTR. mRNA only possesses limited half-life in cells and in vitro. In some embodiments, the mRNA is self-amplifying mRNA. In the context of the present disclosure, mRNA may be generated by in vitro transcription from a DNA template. The in vitro transcription methodology is known to the skilled person. For example, there is a variety of in vitro transcription kits commercially available.

The stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448, incorporated herein by reference. In order to increase expression of the RNA used according to the present disclosure, it may be modified within the coding region, i.e., the sequence encoding the expressed peptide or protein, without altering the sequence of the expressed peptide or protein, so as to increase the GC-content to increase mRNA stability and to perform a codon optimization and, thus, enhance translation in cells.

The term "modification" in the context of the RNA used in the present disclosure includes any modification of an RNA which is not naturally present in said RNA. In some embodiments, the RNA does not have uncapped 5'-triphosphates. Removal of such uncapped 5'-triphosphates can be achieved by treating RNA with a phosphatase. In other embodiments, the RNA may have modified ribonucleotides in order to increase its stability and/or decrease cytotoxicity. In some embodiments, 5-methylcytidine can be substituted partially or completely in the RNA, for example, for cytidine. Alternatively, pseudouridine is substituted partially or completely, for example, for uridine.

In some embodiments, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In some embodiments, this guanosine is methylated at the 7-position. The term "conventional 5'-cap" refers to a naturally occurring RNA 5'-cap, to the 7-methylguanosine cap (m G). In the context of the present disclosure, the term "5'-cap" includes a 5'-cap analog that resembles the RNA cap structure and is modified to possess the ability to stabilize RNA and/or enhance translation of RNA if attached thereto, in vivo and/or in a cell.

In certain embodiments, an mRNA encoding a neoantigenic peptide of the present disclosure is administered to a subject in need thereof. In some embodiments, the present disclosure provides RNA, oligoribonucleotide, and polyribonucleotide molecules comprising a modified nucleoside, gene therapy vectors comprising same, gene therapy methods and gene transcription silencing methods comprising same. In some embodiments, the mRNA to be administered comprises at least one modified nucleoside.

The polynucleotides encoding peptides described herein can be synthesized by chemical techniques, for example, the phosphotriester method of Matteucci, et al., J. Am. Chem. Soc. 103:3185 (1981). Polynucleotides encoding peptides comprising or consisting of an analog can be made simply by substituting the appropriate and desired nucleic acid base(s) for those that encode the native epitope.

Polynucleotides described herein can comprise one or more synthetic or naturally-occurring introns in the transcribed region. The inclusion of mRNA stabilization sequences and sequences for replication in mammalian cells can also be considered for increasing polynucleotide expression. In addition, a polynucleotide described herein can comprise immunostimulatory sequences (ISSs or CpGs). These sequences can be included in the vector, outside the polynucleotide coding sequence to enhance immunogenicity.

In some embodiments, the polynucleotides may comprise the coding sequence for the peptide or protein fused in the same reading frame to a polynucleotide which aids, for example, in expression and/or secretion of the peptide or protein from a host cell (e.g., a leader sequence which functions as a secretory sequence for controlling transport of a polypeptide from the cell). The polypeptide having a leader sequence is a pre-protein and can have the leader sequence cleaved by the host cell to form the mature form of the polypeptide.

In some embodiments, the polynucleotides can comprise the coding sequence for the peptide or protein fused in the same reading frame to a marker sequence that allows, for example, for purification of the encoded peptide, which may then be incorporated into a personalized disease vaccine or immunogenic composition. For example, the marker sequence can be a hexa-histidine tag (SEQ ID NO: 1356) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In some embodiments, the polynucleotides may comprise the coding sequence for one or more the presently described peptides or proteins fused in the same reading frame to create a single concatamerized neoantigenic peptide construct capable of producing multiple neoantigenic peptides.

In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585. In another embodiment, a DNA sequence encoding the peptide or protein of interest would be constructed by chemical synthesis using an oligonucleotide synthesizer. Such oligonucleotides can be designed based on the amino acid sequence of the desired peptide and selecting those codons that are favored in the host cell in which the recombinant polypeptide of interest is produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly Once assembled (e.g., by synthesis, site-directed mutagenesis, or another method), the polynucleotide sequences encoding a particular isolated polypeptide of interest is inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Thus, the present disclosure is also directed to vectors, and expression vectors useful for the production and administration of the neoantigenic peptides and neoepitopes described herein, and to host cells comprising such vectors. Vectors In some embodiments, an expression vector capable of expressing the peptide or protein as described herein can also be prepared. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

A large number of vectors and host systems suitable for producing and administering a neoantigenic peptide described herein are known to those of skill in the art, and are commercially available. The following vectors are provided by way of example Bacterial: pQE70, pQE60, pQE-9 (Qiagen), pBS, pD10, phagescript, psiX174, pBluescript SK, pbsks, pNH8A, pNH16a, pNH18A, pNH46A (Stratagene); ptrc99a, pKK223-3, pKK233-3, pDR540, pRIT5 (Pharmacia); pCR (Invitrogen). Eukaryotic: pWLNEO, pSV2CAT, pOG44, pXT1, pSG (Stratagene) pSVK3, pBPV, pMSG, pSVL (Pharmacia); p75.6 (Valentis); pCEP (Invitrogen); pCEI (Epimmune). However, any other plasmid or vector can be used as long as it is replicable and viable in the host.

For expression of the neoantigenic peptides described herein, the coding sequence will be provided operably linked start and stop codons, promoter and terminator regions, and in some embodiments, and a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts.

Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. Such promoters can also be derived from viral sources, such as, e.g., human cytomegalovirus (CMV-IE promoter) or herpes simplex virus type-1 (HSV TK promoter). Nucleic acid sequences derived from the SV40 splice, and polyadenylation sites can be used to provide the required nontranscribed genetic elements.

Recombinant expression vectors may be used to amplify and express DNA encoding the peptide or protein as described herein. Recombinant expression vectors are replicable DNA constructs which have synthetic or cDNA-derived DNA fragments encoding a peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail herein. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell.

Alternatively, where recombinant protein is expressed without a leader or transport sequence, it can include an N-terminal methionine residue. This residue can optionally be subsequently cleaved from the expressed recombinant protein to provide a final product.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), acid phosphatase, or heat shock proteins, among others. The heterologous structural sequence is assembled in appropriate phase with translation initiation and termination sequences, and in some embodiments, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Polynucleotides encoding neoantigenic peptides described herein can also comprise a ubiquitination signal sequence, and/or a targeting sequence such as an endoplasmic reticulum (ER) signal sequence to facilitate movement of the resulting peptide into the endoplasmic reticulum.

In some embodiments, the neoantigenic peptide described herein can also be administered and/or expressed by viral or bacterial vectors. Examples of expression vectors include attenuated viral hosts, such as vaccinia or fowlpox. As an example of this approach, vaccinia virus is used as a vector to express nucleotide sequences that encode the neoantigenic peptides described herein. Vaccinia vectors and methods useful in immunization protocols are described in, e.g., U.S. Pat. No. 4,722,848. Another vector is BCG (Bacille Calmette Guerin). BCG vectors are described by Stover et al., Nature 351:456-460 (1991).

A wide variety of other vectors useful for therapeutic administration or immunization of the neoantigenic polypeptides described herein, e.g. adeno and adeno-associated virus vectors, retroviral vectors, Salmonella typhimurium vectors, detoxified anthrax toxin vectors, Sendai virus vectors, poxvirus vectors, canarypox vectors, and fowlpox vectors, and the like, will be apparent to those skilled in the art from the description herein. In some embodiments, the vector is Modified Vaccinia Ankara (VA) (e.g. Bavarian Noridic (MVA-BN)).

Among vectors that may be used in the practice of the present disclosure, integration in the host genome of a cell is possible with retrovirus gene transfer methods, often resulting in long term expression of the inserted transgene. In some embodiments, the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors may be used in the practice of the present disclosure). Moreover, lentiviral vectors are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that may be used in the practice of the present disclosure include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700).

Also useful in the practice of the present disclosure is a minimal non-primate lentiviral vector, such as a lentiviral vector based on the equine infectious anemia virus (EIAV). The vectors may have cytomegalovirus (CMV) promoter driving expression of the target gene. Accordingly, the present disclosure contemplates amongst vector(s) useful in the practice of the present disclosure: viral vectors, including retroviral vectors and lentiviral vectors.

Also useful in the practice of the present disclosure is an adenovirus vector. One advantage is the ability of recombinant adenoviruses to efficiently transfer and express recombinant genes in a variety of mammalian cells and tissues in vitro and in vivo, resulting in the high expression of the transferred nucleic acids. Further, the ability to productively infect quiescent cells, expands the utility of recombinant adenoviral vectors. In addition, high expression levels ensure that the products of the nucleic acids will be expressed to sufficient levels to generate an immune response (see e.g., U.S. Pat. No. 7,029,848, hereby incorporated by reference).

As to adenovirus vectors useful in the practice of the present disclosure, mention is made of U.S. Pat. No. 6,955,808. The adenovirus vector used can be selected from the group consisting of the Ad5, Ad35, Ad11, C6, and C7 vectors. The sequence of the Adenovirus 5 ("Ad5") genome has been published. (Chroboczek, J., Bieber, F., and Jacrot, B. (1992) The Sequence of the Genome of Adenovirus Type 5 and Its Comparison with the Genome of Adenovirus Type 2, Virology 186, 280-285; the contents if which is hereby incorporated by reference). Ad35 vectors are described in U.S. Pat. Nos. 6,974,695, 6,913,922, and 6,869,794. Ad11 vectors are described in U.S. Pat. No. 6,913,922. C6 adenovirus vectors are described in U.S. Pat. Nos. 6,780,407; 6,537,594; 6,309,647; 6,265,189; 6,156,567; 6,090,393; 5,942,235 and 5,833,975. C7 vectors are described in U.S. Pat. No. 6,277,558. Adenovirus vectors that are E1-defective or deleted, E3-defective or deleted, and/or E4-defective or deleted may also be used. Certain adenoviruses having mutations in the E1 region have improved safety margin because E1-defective adenovirus mutants are replication-defective in non-permissive cells, or, at the very least, are highly attenuated. Adenoviruses having mutations in the E3 region may have enhanced the immunogenicity by disrupting the mechanism whereby adenovirus down-regulates MHC class I molecules. Adenoviruses having E4 mutations may have reduced immunogenicity of the adenovirus vector because of suppression of late gene expression. Such vectors may be particularly useful when repeated re-vaccination utilizing the same vector is desired. Adenovirus vectors that are deleted or mutated in E1, E3, E4; E1 and E3; and E1 and E4 can be used in accordance with the present disclosure.

Furthermore, "gutless" adenovirus vectors, in which all viral genes are deleted, can also be used in accordance with the present disclosure. Such vectors require a helper virus for their replication and require a special human 293 cell line expressing both E1a and Cre, a condition that does not exist in natural environment. Such "gutless" vectors are non-immunogenic and thus the vectors may be inoculated multiple times for re-vaccination. The "gutless" adenovirus vectors can be used for insertion of heterologous inserts/genes such as the transgenes of the present disclosure, and can even be used for co-delivery of a large number of heterologous inserts/genes.

In some embodiments, the delivery is via an adenovirus, which may be at a single booster dose. In some embodiments, the adenovirus is delivered via multiple doses. In terms of in vivo delivery, AAV is advantageous over other viral vectors due to low toxicity and low probability of causing insertional mutagenesis because it doesn't integrate into the host genome. AAV has a packaging limit of 4.5 or 4.75 Kb. Constructs larger than 4.5 or 4.75 Kb result in significantly reduced virus production. There are many promoters that can be used to drive nucleic acid molecule expression. AAV ITR can serve as a promoter and is advantageous for eliminating the need for an additional promoter element.

For ubiquitous expression, the following promoters can be used: CMV, CAG, CBh, PGK, SV40, Ferritin heavy or light chains, etc. For brain expression, the following promoters can be used: Synapsin I for all neurons, CaMK II alpha for excitatory neurons, GAD67 or GAD65 or VGAT for GABAergic neurons, etc. Promoters used to drive RNA synthesis can include: Pol III promoters such as U6 or H1. The use of a Pol II promoter and intronic cassettes can be used to express guide RNA (gRNA). With regard to AAV vectors useful in the practice of the present disclosure, mention is made of U.S. Pat. Nos. 5,658,785, 7,115,391, 7,172,893, 6,953,690, 6,936,466, 6,924,128, 6,893,865, 6,793,926, 6,537,540, 6,475,769 and 6,258,595, and documents cited therein. As to AAV, the AAV can be AAV1, AAV2, AAV5 or any combination thereof. One can select the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. In some embodiments the delivery is via an AAV. The dosage may be adjusted to balance the therapeutic benefit against any side effects.

In some embodiments, a Poxvirus is used in the presently described composition. These include orthopoxvirus, avipox, vaccinia, MVA, NYVAC, canarypox, ALVAC, fowlpox, TROVAC, etc. (see e.g., Verardi et al., Hum. Vaccin. Immunother. 2012 July; 8(7):961-70; and Moss, Vaccine. 2013; 31(39): 4220-4222). Poxvirus expression vectors were described in 1982 and quickly became widely used for vaccine development as well as research in numerous fields. Advantages of the vectors include simple construction, ability to accommodate large amounts of foreign DNA and high expression levels. Information concerning poxviruses that may be used in the practice of the present disclosure, such as Chordopoxvirinae subfamily poxviruses (poxviruses of vertebrates), for instance, orthopoxviruses and avipoxviruses, e.g., vaccinia virus (e.g., Wyeth Strain, WR Strain (e.g., ATCC® VR-1354), Copenhagen Strain, NYVAC, NYVAC.1, NYVAC.2, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia, synthetic or non-naturally occurring recombinants thereof, uses thereof, and methods for making and using such recombinants may be found in scientific and patent literature.

In some embodiments, the vaccinia virus is used in the disease vaccine or immunogenic composition to express a antigen. (Rolph et al., Recombinant viruses as vaccines and immunological tools. Curr. Opin. Immunol. 9:517-524, 1997). The recombinant vaccinia virus is able to replicate within the cytoplasm of the infected host cell and the polypeptide of interest can therefore induce an immune response. Moreover, Poxviruses have been widely used as vaccine or immunogenic composition vectors because of their ability to target encoded antigens for processing by the major histocompatibility complex class I pathway by directly infecting immune cells, in particular antigen-presenting cells, but also due to their ability to self-adjuvant.

In some embodiments, ALVAC is used as a vector in a disease vaccine or immunogenic composition. ALVAC is a canarypox virus that can be modified to express foreign transgenes and has been used as a method for vaccination against both prokaryotic and eukaryotic antigens (Honig H, Lee D S, Conkright W, et al. Phase I clinical trial of a recombinant canarypoxvirus (ALVAC) vaccine expressing human carcinoembryonic antigen and the B7.1 co-stimulatory molecule. Cancer Immunol. Immunother. 2000; 49:504-14; von Mehren M, Arlen P, Tsang K Y, et al. Pilot study of a dual gene recombinant avipox vaccine containing both carcinoembryonic antigen (CEA) and B7.1 transgenes in patients with recurrent CEA-expressing adenocarcinomas. Clin. Cancer. Res. 2000; 6:2219-28; Musey L, Ding Y, Elizaga M, et al. HIV-1 vaccination administered intramuscularly can induce both systemic and mucosal T cell immunity in HIV-1-uninfected individuals. J. Immunol. 2003; 171:1094-101; Paoletti E. Applications of pox virus vectors to vaccination: an update. Proc. Natl. Acad. Sci. USA 1996; 93:11349-53; U.S. Pat. No. 7,255,862). In a phase I clinical trial, an ALVAC virus expressing the tumor antigen CEA showed an excellent safety profile and resulted in increased CEA-specific T cell responses in selected patients; objective clinical responses, however, were not observed (Marshall J L, Hawkins M J, Tsang K Y, et al. Phase I study in cancer patients of a replication-defective avipox recombinant vaccine that expresses human carcinoembryonic antigen. J. Clin. Oncol. 1999; 17:332-7).

In some embodiments, a Modified Vaccinia Ankara (MVA) virus may be used as a viral vector for an antigen vaccine or immunogenic composition. MVA is a member of the Orthopoxvirus family and has been generated by about 570 serial passages on chicken embryo fibroblasts of the Ankara strain of Vaccinia virus (CVA) (see, e.g., Mayr, A., et al., Infection 3, 6-14, 1975). As a consequence of these passages, the resulting MVA virus contains 31 kilobases less genomic information compared to CVA, and is highly host cell restricted (Meyer, H. et al., J. Gen. Virol. 72, 1031-1038, 1991). MVA is characterized by its extreme attenuation, namely, by a diminished virulence or infectious ability, but still holds an excellent immunogenicity. When tested in a variety of animal models, MVA was proven to be avirulent, even in immuno-suppressed individuals. Moreover, MVA-BN®-HER2 is a candidate immunotherapy designed for the treatment of HER-2-positive breast cancer and is currently in clinical trials. (Mandl et al., Cancer Immunol. Immunother. January 2012; 61(1): 19-29). Methods to make and use recombinant MVA has been described (e.g., see U.S. Pat. Nos. 8,309,098 and 5,185,146 hereby incorporated in its entirety).

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), 293, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

Host cells are genetically engineered (transduced or transformed or transfected) with the vectors which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan.

As representative examples of appropriate hosts, there can be mentioned: bacterial cells, such as *E. coli, Bacillus subtilis, Salmonella typhimurium* and various species within the genera *Pseudomonas, Streptomyces*, and *Staphylococcus*; fungal cells, such as yeast; insect cells such as *Drosophila* and Sf9; animal cells such as COS-7 lines of monkey kidney fibroblasts, described by Gluzman, Cell 23:175 (1981), and other cell lines capable of expressing a compatible vector, for example, the C127, 3T3, CHO, HeLa and BHK cell lines or Bowes melanoma; plant cells, etc. The selection of an appropriate host is deemed to be within the scope of those skilled in the art from the teachings herein.

Yeast, insect or mammalian cell hosts can also be used, employing suitable vectors and control sequences. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines.

Polynucleotides described herein can be administered and expressed in human cells (e.g., immune cells, including dendritic cells). A human codon usage table can be used to guide the codon choice for each amino acid. Such polynucleotides comprise spacer amino acid residues between epitopes and/or analogs, such as those described above, or can comprise naturally-occurring flanking sequences adjacent to the epitopes and/or analogs (and/or CTL (e.g., CD8+), Th (e.g., CD4+), and B cell epitopes).

Standard regulatory sequences well known to those of skill in the art can be included in the vector to ensure expression in the human target cells. Several vector elements are desirable: a promoter with a downstream cloning site for polynucleotide, e.g., minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences. In some embodiments, the promoter is the CMV-IE promoter.

Useful expression vectors for eukaryotic hosts, especially mammals or humans include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR1, pBR322, pMB9 and their derivatives, wider host range plasmids, such as M13 and filamentous single-stranded DNA phages.

Vectors may be introduced into animal tissues by a number of different methods. The two most popular approaches are injection of DNA in saline, using a standard hypodermic needle, and gene gun delivery. A schematic outline of the construction of a DNA vaccine plasmid and its subsequent delivery by these two methods into a host is illustrated at Scientific American (Weiner et al., (1999) Scientific American 281 (1): 34-41). Injection in saline is normally conducted intramuscularly (IM) in skeletal muscle, or intradermally (ID), with DNA being delivered to the extracellular spaces. This can be assisted by electroporation by temporarily damaging muscle fibers with myotoxins such as bupivacaine; or by using hypertonic solutions of saline or sucrose (Alarcon et al., (1999). Adv. Parasitol. Advances in Parasitology 42: 343-410). Immune responses to this method of delivery can be affected by many factors, including needle type, needle alignment, speed of injection, volume of injection, muscle type, and age, sex and physiological condition of the animal being injected (Alarcon et al., (1999). Adv. Parasitol. Advances in Parasitology 42: 343-410).

Gene gun delivery, the other commonly used method of delivery, ballistically accelerates plasmid DNA (pDNA) that has been adsorbed onto gold or tungsten microparticles into the target cells, using compressed helium as an accelerant (Alarcon et al., (1999). Adv. Parasitol. Advances in Parasitology 42: 343-410; Lewis et al., (1999). Advances in Virus Research (Academic Press) 54: 129-88).

Alternative delivery methods may include aerosol instillation of naked DNA on mucosal surfaces, such as the nasal and lung mucosa, (Lewis et al., (1999). Advances in Virus Research (Academic Press) 54: 129-88) and topical administration of pDNA to the eye and vaginal mucosa (Lewis et al., (1999) Advances in Virus Research (Academic Press) 54: 129-88). Mucosal surface delivery has also been achieved using cationic liposome-DNA preparations, biodegradable microspheres, attenuated *Shigella* or *Listeria* vectors for oral administration to the intestinal mucosa, and recombinant adenovirus vectors. DNA or RNA may also be delivered to cells following mild mechanical disruption of the cell membrane, temporarily permeabilizing the cells. Such a mild mechanical disruption of the membrane can be accomplished by gently forcing cells through a small aperture (Sharei et al., Ex Vivo Cytosolic Delivery of Functional Macromolecules to Immune Cells, PLOS ONE (2015)).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5: 505-10 (1991)). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol.

In some embodiments, a vector comprises a polynucleotide encoding a first peptide comprising a first neoepitope and a second peptide comprising a second neoepitope. In some embodiments, the first and second peptides are derived from the same protein. The at least two distinct peptides may vary by length, amino acid sequence or both. The peptides are derived from any protein known to or have been found to contain a tumor specific mutation. In some embodiments, a vector comprises a first peptide comprising a first neoepitope of a protein and a second peptide comprising a second neoepitope of the same protein, wherein the first peptide is different from the second peptide, and wherein the first neoepitope comprises a mutation and the second neoepitope comprises the same mutation. In some embodiments, a vector comprises a first peptide comprising a first neoepitope of a first region of a protein and a second peptide comprising a second neoepitope of a second region of the same protein, wherein the first region comprises at least one amino acid of the second region, wherein the first peptide is different from the second peptide and wherein the first neoepitope comprises a first mutation and the second neoepitope comprises a second mutation. In some embodiments, the first mutation and the second mutation are the same. In some embodiments, the mutation is selected from the group consisting of a point mutation, a splice-site mutation, a frameshift mutation, a read-through mutation, a gene fusion mutation and any combination thereof.

In some embodiments, a vector comprises a polynucleotide operably linked to a promoter. In some embodiments, the vector is a self-amplifying RNA replicon, plasmid, phage, transposon, cosmid, virus, or virion. In some embodiments, the vector is derived from a retrovirus, lentivirus, adenovirus, adeno-associated virus, herpes virus, pox virus, alpha virus, vaccinia virus, hepatitis B virus, human papillomavirus or a pseudotype thereof. In some embodiments, the vector is a non-viral vector. In some embodiments, the non-viral vector is a nanoparticle, a cationic lipid, a cationic polymer, a metallic nanopolymer, a nanorod, a liposome, a micelle, a microbubble, a cell-penetrating peptide, or a liposphere.

T Cell Receptors

In one aspect, the present disclosure provides cells expressing a neoantigen-recognizing receptor that activates an immunoresponsive cell (e.g., T cell receptor (TCR) or chimeric antigen receptor (CAR)), and methods of using such cells for the treatment of a disease that requires an enhanced immune response. Such cells include genetically modified immunoresponsive cells (e.g., T cells, Natural Killer (NK) cells, cytotoxic T lymphocytes (CTL (e.g., CD8+)) cells, helper T lymphocyte (Th (e.g., CD4+)) cells) expressing an antigen-recognizing receptor (e.g., TCR or CAR) that binds one of the neoantigenic peptides described herein, and methods of use therefore for the treatment of neoplasia and other pathologies where an increase in an antigen-specific immune response is desired. T cell activation is mediated by a TCR or a CAR targeted to an antigen.

The present disclosure provides cells expressing a combination of an antigen-recognizing receptor that activates an immunoresponsive cell (e.g., TCR, CAR) and a chimeric co-stimulating receptor (CCR), and methods of using such cells for the treatment of a disease that requires an enhanced immune response. In some embodiments, tumor antigen-specific T cells, NK cells, CTL cells or other immunoresponsive cells are used as shuttles for the selective enrichment of one or more co-stimulatory ligands for the treatment or prevention of neoplasia. Such cells are administered to a human subject in need thereof for the treatment or prevention of a particular cancer.

In some embodiments, the tumor antigen-specific human lymphocytes that can be used in the methods of the present disclosure include, without limitation, peripheral donor lymphocytes genetically modified to express chimeric antigen receptors (CARs) (Sadelain, M., et al. 2003 Nat Rev Cancer 3:35-45), peripheral donor lymphocytes genetically modified to express a full-length tumor antigen-recognizing T cell receptor complex comprising the a and p heterodimer (Morgan, R. A., et al. 2006 Science 314:126-129), lymphocyte cultures derived from tumor infiltrating lymphocytes (TILs) in tumor biopsies (Panelli, M. C., et al. 2000 J Immunol 164:495-504; Panelli, M. C., et al. 2000 J Immunol 164: 4382-4392), and selectively in vitro-expanded antigen-specific peripheral blood leukocytes employing artificial antigen-presenting cells (AAPCs) or pulsed dendritic cells (Dupont, J., et al. 2005 Cancer Res 65:5417-5427; Papanicolaou, G. A., et al. 2003 Blood 102:2498-2505). The T cells may be autologous, allogeneic, or derived in vitro from engineered progenitor or stem cells.

In some embodiments, the immunotherapeutic is an engineered receptor. In some embodiments, the engineered receptor is a chimeric antigen receptor (CAR), a T cell receptor (TCR), or a B-cell receptor (BCR), an adoptive T cell therapy (ACT), or a derivative thereof. In other aspects, the engineered receptor is a chimeric antigen receptor (CAR). In some aspects, the CAR is a first generation CAR. In other aspects, the CAR is a second generation CAR. In still other aspects, the CAR is a third generation CAR. In some aspects, the CAR comprises an extracellular portion, a transmembrane portion, and an intracellular portion. In some aspects, the intracellular portion comprises at least one T cell co-stimulatory domain. In some aspects, the T cell co-stimulatory domain is selected from the group consisting of CD27, CD28, TNFRS9 (4-1BB), TNFRSF4 (OX40), TNFRSF8 (CD30), CD40LG (CD40L), ICOS, ITGB2 (LFA-1), CD2, CD7, KLRC2 (NKG2C), TNFRS18 (GITR), TNFRSF14 (HVEM), or any combination thereof.

In some aspects, the engineered receptor binds a target. In some aspects, the binding is specific to a peptide specific to one or more subjects suffering from a disease or condition.

In some aspects, the immunotherapeutic is a cell as described in detail herein. In some aspects, the immunotherapeutic is a cell comprising a receptor that specifically binds a peptide or neoepitope described herein. In some aspects, the immunotherapeutic is a cell used in combination with the peptides/nucleic acids of the present disclosure. In some embodiments, the cell is a patient cell. In some embodiments, the cell is a T cell. In some embodiments, the cell is tumor infiltrating lymphocyte.

In some aspects, a subject with a condition or disease is treated based on a T cell receptor repertoire of the subject. In some embodiments, a peptide or neoepitope is selected based on a T cell receptor repertoire of the subject. In some embodiments, a subject is treated with T cells expressing TCRs specific to a peptide or neoepitope as described herein. In some embodiments, a subject is treated with a peptide or neoepitope specific to TCRs, e.g., subject specific TCRs. In some embodiments, a subject is treated with a peptide or neoepitope specific to T cells expressing TCRs, e.g., subject specific TCRs. In some embodiments, a subject is treated with a peptide or neoepitope specific to subject specific TCRs.

In some embodiments, the composition as described herein is selected based on TCRs identified in one or more subjects. In some embodiments, identification of a T cell repertoire and testing in functional assays is used to determine the composition to be administered to one or more subjects with a condition or disease. In some embodiments, the composition is an antigen vaccine comprising one or more peptides or proteins as described herein. In some embodiments, the vaccine comprises subject specific neoantigenic peptides. In some embodiments, the peptides to be included in the vaccine are selected based on a quantification of subject specific TCRs that bind to the neoepitopes. In some embodiments, the peptides are selected based on a binding affinity of the peptide to a TCR. In some embodiments, the selecting is based on a combination of both the quantity and the binding affinity. For example, a TCR that binds strongly to a neoepitope in a functional assay, but that is not highly represented in a TCR repertoire may be a good candidate for an antigen vaccine because T cells expressing the TCR would be advantageously amplified.

In some embodiments, the peptide or protein is selected for administering to one or more subjects based on binding to TCRs. In some embodiments, T cells, such as T cells from a subject with a disease or condition, can be expanded. Expanded T cells that express TCRs specific to a neoantigenic peptide or neoepitope can be administered back to a subject. In some embodiments, suitable cells, e.g., PBMCs, are transduced or transfected with polynucleotides for expression of TCRs specific to a neoantigenic peptide or neoepitope and administered to a subject. T cells expressing TCRs specific to a neoantigenic peptide or neoepitope can be expanded and administered back to a subject. In some embodiments, T cells that express TCRs specific to a neoantigenic peptide or neoepitope that result in cytolytic activity when incubated with autologous diseased tissue can be expanded and administered to a subject. In some embodiments, T cells used in functional assays result in binding to a neoantigenic peptide or neoepitope can be expanded and administered to a subject. In some embodiments, TCRs that have been determined to bind to subject specific neoantigenic peptides or neoepitopes can be expressed in T cells and administered to a subject.

In an embodiment, the present disclosure provides a composition comprising a first peptide comprising a first neoepitope and a second peptide comprising a second neoepitope, wherein the first peptide is different from the second peptide, and wherein the first neoepitope comprises a mutation and the second neoepitope comprises the same mutation. In some embodiments, the composition as provided herein comprises a first T cell comprising a first T cell receptor (TCR) specific for the first neoepitope and a second T cell comprising a second TCR specific for the second neoepitope. In some embodiments, the first and second peptides are derived from the same protein.

In another embodiment, the present disclosure provides a composition comprising a first peptide comprising a first neoepitope of a first region of a protein and a second peptide comprising a second neoepitope of a second region of the same protein, wherein the first region comprises at least one amino acid of the second region, wherein the first peptide is different from the second peptide and wherein the first neoepitope comprises a first mutation and the second neoepitope comprises a second mutation. In some embodiments, the composition as provided herein comprises a first T cell comprising a first T cell receptor (TCR) specific for the first neoepitope and a second T cell comprising a second TCR specific for the second neoepitope. In some embodiments, the first mutation and the second mutation are the same.

In some embodiments, the first neoepitope binds to a class I HLA protein to form a class I HLA-peptide complex. In some embodiments, the first neoepitope binds to a class II HLA protein to form a class II HLA-peptide complex. In some embodiments, the second neoepitope binds to a class II HLA a protein to form a class II HLA-peptide complex. In some embodiments, the second neoepitope binds to a class I HLA protein to form a class I HLA-peptide complex. In some embodiments, the first neoepitope activates CD8+ T cells. In some embodiments, the first neoepitope activates CD4+ T cells. In some embodiments, the second neoepitope activates CD4+ T cells. In some embodiments, the second neoepitope activates CD8+ T cells. In some embodiments, a TCR of a CD4+ T cell binds to a class II HLA-peptide complex. In some embodiments, a TCR of a CD8+ T cell binds to a class II HLA-peptide complex. In some embodiments, a TCR of a CD8+ T cell binds to a class I HLA-peptide complex. In some embodiments, a TCR of a CD4+ T cell binds to a class I HLA-peptide complex.

In some embodiments, the first TCR is a first chimeric antigen receptor specific for the first neoepitope and the second TCR is a second chimeric antigen receptor specific for the second neoepitope. In some embodiments, the first T cell is a cytotoxic T cell. In some embodiments, the first T cell is a gamma delta T cell. In some embodiments, the second T cell is a helper T cell. In some embodiments, the first and/or second TCR binds to an HLA-peptide complex with a KD or an IC50 of less than 1,000 nM, 900 nM, 800 nM, 700 nM, 600 nM, 500 nM, 250 nM, 150 nM, 100 nM, 50 nM, 25 nM or 10 nM. In some embodiments, the first and/or second TCR binds to an HLA class I-peptide complex with a KD or an IC50 of less than 1,000 nM, 900 nM, 800 nM, 700 nM, 600 nM, 500 nM, 250 nM, 150 nM, 100 nM, 50 nM, 25 nM or 10 nM. In some embodiments, the first and/or second TCR binds to an HLA class II-peptide complex with a KD or an IC50 of less than 2,000, 1,500, 1,000 nM, 900 nM, 800 nM, 700 nM, 600 nM, 500 nM, 250 nM, 150 nM, 100 nM, 50 nM, 25 nM or 10 nM.

Antigen Presenting Cells

The neoantigenic peptide or protein can be provided as antigen presenting cells (e.g., dendritic cells) containing such peptides, proteins or polynucleotides as described herein. In other embodiments, such antigen presenting cells are used to stimulate T cells for use in patients. Thus, one embodiment of the present disclosure is a composition containing at least one antigen presenting cell (e.g., a dendritic cell) that is pulsed or loaded with one or more neoantigenic peptides or polynucleotides described herein. In some embodiments, such APCs are autologous (e.g., autologous dendritic cells). Alternatively, peripheral blood mononuclear cells (PBMCs) isolated from a patient can be loaded with neoantigenic peptides or polynucleotides ex vivo. In related embodiments, such APCs or PBMCs are injected back into the patient. In some embodiments, the antigen presenting cells are dendritic cells. In related embodiments, the dendritic cells are autologous dendritic cells that are pulsed with the neoantigenic peptide or nucleic acid. The neoantigenic peptide can be any suitable peptide that gives rise to an appropriate T cell response. T cell therapy using autologous dendritic cells pulsed with peptides from a tumor associated antigen is disclosed in Murphy et al. (1996) The Prostate 29, 371-380 and Tjua et al. (1997) The Prostate 32, 272-278. In some embodiments, the T cell is a CTL (e.g., CD8+). In some embodiments, the T cell is a helper T lymphocyte (Th (e.g., CD4+)).

In some embodiments, the present disclosure provides a composition comprising a cell-based immunogenic pharmaceutical composition that can also be administered to a subject. For example, an antigen presenting cell (APC) based immunogenic pharmaceutical composition can be formulated using any of the well-known techniques, carriers, and excipients as suitable and as understood in the art. APCs include monocytes, monocyte-derived cells, macrophages, and dendritic cells. Sometimes, an APC based immunogenic pharmaceutical composition can be a dendritic cell-based immunogenic pharmaceutical composition.

A dendritic cell-based immunogenic pharmaceutical composition can be prepared by any methods well known in the art. In some cases, dendritic cell-based immunogenic pharmaceutical compositions can be prepared through an ex vivo or in vivo method. The ex vivo method can comprise the use of autologous DCs pulsed ex vivo with the polypeptides described herein, to activate or load the DCs prior to administration into the patient. The in vivo method can comprise targeting specific DC receptors using antibodies coupled with the polypeptides described herein. The DC-based immunogenic pharmaceutical composition can further comprise DC activators such as TLR3, TLR-7-8, and CD40 agonists. The DC-based immunogenic pharmaceutical composition can further comprise adjuvants, and a pharmaceutically acceptable carrier.

Antigen presenting cells (APCs) can be prepared from a variety of sources, including human and non-human primates, other mammals, and vertebrates. In certain embodiments, APCs can be prepared from blood of a human or non-human vertebrate. APCs can also be isolated from an enriched population of leukocytes. Populations of leukocytes can be prepared by methods known to those skilled in the art. Such methods typically include collecting heparinized blood, apheresis or leukopheresis, preparation of buffy coats, rosetting, centrifugation, density gradient centrifugation (e.g., using Ficoll, colloidal silica particles, and sucrose), differential lysis non-leukocyte cells, and filtration. A leukocyte population can also be prepared by collecting blood from a subject, defibrillating to remove the platelets and lysing the red blood cells. The leukocyte population can optionally be enriched for monocytic dendritic cell precursors.

Blood cell populations can be obtained from a variety of subjects, according to the desired use of the enriched population of leukocytes. The subject can be a healthy subject. Alternatively, blood cells can be obtained from a subject in need of immunostimulation, such as, for example, a cancer patient or other patient for which immunostimulation will be beneficial. Likewise, blood cells can be obtained from a subject in need of immune suppression, such as, for example, a patient having an autoimmune disorder (e.g., rheumatoid arthritis, diabetes, lupus, multiple sclerosis, and the like). A population of leukocytes also can be obtained from an HLA-matched healthy individual.

When blood is used as a source of APC, blood leukocytes may be obtained using conventional methods that maintain their viability. According to one aspect of the present disclosure, blood can be diluted into medium that may or may not contain heparin or other suitable anticoagulant. The volume of blood to medium can be about 1 to 1. Cells can be concentrated by centrifugation of the blood in medium at about 1,000 rpm (150 g) at 4° C. Platelets and red blood cells can be depleted by resuspending the cells in any number of solutions known in the art that will lyse erythrocytes, for example ammonium chloride. For example, the mixture may be medium and ammonium chloride at about 1:1 by volume. Cells may be concentrated by centrifugation and washed in the desired solution until a population of leukocytes, substantially free of platelets and red blood cells, is obtained. Any isotonic solution commonly used in tissue culture may be used as the medium for separating blood leukocytes from platelets and red blood cells. Examples of such isotonic solutions can be phosphate buffered saline, Hanks balanced salt solution, and complete growth media. APCs and/or APC precursor cells may also purified by elutriation.

In one embodiment, the APCs can be non-nominal APCs under inflammatory or otherwise activated conditions. For example, non-nominal APCs can include epithelial cells stimulated with interferon-gamma, T cells, B cells, and/or monocytes activated by factors or conditions that induce APC activity. Such non-nominal APCs can be prepared according to methods known in the art.

The APCs can be cultured, expanded, differentiated and/or, matured, as desired, according to the according to the type of APC. The APCs can be cultured in any suitable culture vessel, such as, for example, culture plates, flasks, culture bags, and bioreactors.

In certain embodiments, APCs can be cultured in suitable culture or growth medium to maintain and/or expand the number of APCs in the preparation. The culture media can be selected according to the type of APC isolated. For example, mature APCs, such as mature dendritic cells, can be cultured in growth media suitable for their maintenance and expansion. The culture medium can be supplemented with amino acids, vitamins, antibiotics, divalent cations, and the like. In addition, cytokines, growth factors and/or hormones, can be included in the growth media. For example, for the maintenance and/or expansion of mature dendritic cells, cytokines, such as granulocyte/macrophage colony stimulating factor (GM-CSF) and/or interleukin 4 (IL-4), can be added. In other embodiments, immature APCs can be cultured and/or expanded. Immature dendritic cells can they retain the ability to uptake target mRNA and process new antigen. In some embodiments, immature dendritic cells can be cultured in media suitable for their maintenance and culture. The culture medium can be supplemented with amino acids, vitamins, antibiotics, divalent cations, and the like. In addition, cytokines, growth factors and/or hormones, can be included in the growth media.

Other immature APCs can similarly be cultured or expanded. Preparations of immature APCs can be matured to form mature APCs. Maturation of APCs can occur during or following exposure to the neoantigenic peptides. In certain embodiments, preparations of immature dendritic cells can be matured. Suitable maturation factors include, for example, cytokines TNF-α, bacterial products (e.g., BCG), and the like. In another aspect, isolated APC precursors can be used to prepare preparations of immature APCs. APC precursors can be cultured, differentiated, and/or matured. In certain embodiments, monocytic dendritic cell precursors can be cultured in the presence of suitable culture media supplemented with amino acids, vitamins, cytokines, and/or divalent cations, to promote differentiation of the monocytic dendritic cell precursors to immature dendritic cells. In some embodiments, the APC precursors are isolated from PBMCs. The PBMCs can be obtained from a donor, for example, a human donor, and can be used freshly or frozen for future usage. In some embodiments, the APC is prepared from one or more APC preparations. In some embodiments, the APC comprises an APC loaded with the first and second neoantigenic peptides comprising the first and second neoepitopes or polynucleotides encoding the first and second neoantigenic peptides comprising the first and second neoepitopes. In some embodiments, the APC is an autologous APC, an allogenic APC, or an artificial APC.

In an embodiment, the present disclosure provides a composition comprising an APC comprising a first peptide comprising a first neoepitope and a second peptide comprising a second neoepitope, wherein the first peptide is different from the second peptide, and wherein the first neoepitope comprises a mutation and the second neoepitope comprises the same mutation. In some embodiments, the first and second peptides are derived from the same protein. In another embodiment, the present disclosure provides a composition comprising an APC comprising a first peptide comprising a first neoepitope of a first region of a protein and a second peptide comprising a second neoepitope of a second region of the same protein, wherein the first region comprises at least one amino acid of the second region, wherein the first peptide is different from the second peptide and wherein the first neoepitope comprises a first mutation and the second neoepitope comprises a second mutation. In some embodiments, the first mutation and the second mutation are the same.

Adjuvants

An adjuvant can be used to enhance the immune response (humoral and/or cellular) elicited in a patient receiving a composition as provided herein. Sometimes, adjuvants can elicit a Th1-type response. Other times, adjuvants can elicit a Th2-type response. A Th1-type response can be characterized by the production of cytokines such as IFN-γ as opposed to a Th2-type response which can be characterized by the production of cytokines such as IL-4, IL-5 and IL-10.

In some aspects, lipid-based adjuvants, such as MPLA and MDP, can be used with the immunogenic pharmaceutical compositions disclosed herein. Monophosphoryl lipid A (MPLA), for example, is an adjuvant that causes increased presentation of liposomal antigen to specific T Lymphocytes. In addition, a muramyl dipeptide (MDP) can also be used as a suitable adjuvant in conjunction with the immunogenic pharmaceutical formulations described herein.

Suitable adjuvants are known in the art (see, WO 2015/095811) and include, but are not limited to, poly(I:C), poly-ICLC, Hiltonol, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel®. vector system, PLG microparticles, resiquimod, SRL172, virosomes and other virus-like particles, YF-17D, VEGF trap, R848, beta-glucan, Pam3Cys, Pam3CSK4, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants also include incomplete Freund's or GM-CSF. Several immunological adjuvants (e.g., MF59) specific for dendritic cells and their preparation have been described previously (Dupuis M, et al., Cell Immunol. 1998; 186(1):18-27; Allison A C; Dev. Biol. Stand. 1998; 92:3-11) (Mosca et al. Frontiers in Bioscience, 2007; 12:4050-4060) (Gamvrellis et al. Immunol & Cell Biol. 2004; 82: 506-516). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, PGE1, PGE2, IL-1, IL-1b, IL-4, IL-6 and CD40L) (U.S. Pat. No. 5,849,589 incorporated herein by reference in its entirety) and acting as immunoadjuvants (e.g., IL-12) (Gabrilovich D I, et al., J. Immunother. Emphasis Tumor Immunol. 1996 (6):414-418).

Adjuvant can also comprise stimulatory molecules such as cytokines. Non-limiting examples of cytokines include:

CCL20, α-interferon (IFN-α), β-interferon (IFN-β), γ-interferon, platelet derived growth factor (PDGF), TNFα, TNFβ (lymphotoxin alpha (LTα)), GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IκB, Inactive NIK, SAP K, SAP-I, JNK, interferon response genes, NFκB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, and TAP2.

Additional adjuvants include: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IκB, Inactive NIK, SAP K, SAP-1, JNK, interferon response genes, NFκB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

In some aspects, an adjuvant can be a modulator of a toll like receptor. Examples of modulators of toll-like receptors include TLR-9 agonists and are not limited to small molecule modulators of toll-like receptors such as Imiquimod. Other examples of adjuvants that are used in combination with an immunogenic pharmaceutical composition described herein can include and are not limited to saponin, CpG ODN and the like. Sometimes, an adjuvant is selected from bacteria toxoids, polyoxypropylene-polyoxyethylene block polymers, aluminum salts, liposomes, CpG polymers, oil-in-water emulsions, or a combination thereof. Sometimes, an adjuvant is an oil-in-water emulsion. The oil-in-water emulsion can include at least one oil and at least one surfactant, with the oil(s) and surfactant(s) being biodegradable (metabolisable) and biocompatible. The oil droplets in the emulsion can be less than 5 μm in diameter, and can even have a sub-micron diameter, with these small sizes being achieved with a microfluidiser to provide stable emulsions. Droplets with a size less than 220 nm can be subjected to filter sterilization.

Methods of Treatment and Pharmaceutical Compositions

The neoantigen therapeutics (e.g., peptides, polynucleotides, TCR, CAR, cells containing TCR or CAR, APC or dendritic cell containing polypeptide, dendritic cell containing polynucleotide, antibody, etc.) described herein are useful in a variety of applications including, but not limited to, therapeutic treatment methods, such as the treatment of cancer. In some embodiments, the therapeutic treatment methods comprise immunotherapy. In certain embodiments, a neoantigenic peptide is useful for activating, promoting, increasing, and/or enhancing an immune response, redirecting an existing immune response to a new target, increasing the immunogenicity of a tumor, inhibiting tumor growth, reducing tumor volume, increasing tumor cell apoptosis, and/or reducing the tumorigenicity of a tumor. The methods of use can be in vitro, ex vivo, or in vivo methods.

In some aspects, the present disclosure provides methods for activating an immune response in a subject using a neoantigenic peptide or protein described herein. In some embodiments, the present disclosure provides methods for promoting an immune response in a subject using a neoantigenic peptide described herein. In some embodiments, the present disclosure provides methods for increasing an immune response in a subject using a neoantigenic peptide described herein. In some embodiments, the present disclosure provides methods for enhancing an immune response using a neoantigenic peptide. In some embodiments, the activating, promoting, increasing, and/or enhancing of an immune response comprises increasing cell-mediated immunity. In some embodiments, the activating, promoting, increasing, and/or enhancing of an immune response comprises increasing T cell activity or humoral immunity. In some embodiments, the activating, promoting, increasing, and/or enhancing of an immune response comprises increasing CTL or Th activity. In some embodiments, the activating, promoting, increasing, and/or enhancing of an immune response comprises increasing NK cell activity. In some embodiments, the activating, promoting, increasing, and/or enhancing of an immune response comprises increasing T cell activity and increasing NK cell activity. In some embodiments, the activating, promoting, increasing, and/or enhancing of an immune response comprises increasing CTL activity and increasing NK cell activity. In some embodiments, the activating, promoting, increasing, and/or enhancing of an immune response comprises inhibiting or decreasing the suppressive activity of T regulatory (Treg) cells. In some embodiments, the immune response is a result of antigenic stimulation. In some embodiments, the antigenic stimulation is a tumor cell. In some embodiments, the antigenic stimulation is cancer.

In some embodiments, the present disclosure provides methods of activating, promoting, increasing, and/or enhancing of an immune response using a neoantigenic peptide described herein. In some embodiments, a method comprises administering to a subject in need thereof a therapeutically effective amount of a neoantigenic peptide that delivers a neoantigenic peptide or polynucleotide to an antigen presenting cell (e.g., tumor cell). In some embodiments, a method comprises administering to a subject in need thereof a therapeutically effective amount of a neoantigenic peptide internalized by the antigen presenting cell (e.g., tumor cell). In some embodiments, a method comprises administering to a subject in need thereof a therapeutically effective amount of a neoantigenic peptide that is internalized by an antigen presenting cell (e.g., tumor cell), and the neoantigenic peptide is processed by the cell. In some embodiments, a method comprises administering to a subject in need thereof a therapeutically effective amount of a neoantigenic polypeptide that is internalized by an antigen presenting cell (e.g., tumor cell) and a neoepitope is presented on the surface of the antigen presenting cell. In some embodiments, a method comprises administering to a subject in need thereof a therapeutically effective amount of a neoantigenic polypeptide that is internalized by the antigen presenting cell (e.g., tumor cell), is processed by the cell, and an antigenic peptide is presented on the surface of the antigen presenting cell.

In some embodiments, a method comprises administering to a subject in need thereof a therapeutically effective amount of a neoantigenic peptide or polynucleotide described herein that delivers an exogenous polypeptide comprising at least one neoantigenic peptide to an antigen presenting cell (e.g., tumor cell), wherein at least one neoepitope derived from the neoantigenic peptide is presented on the surface of the antigen presenting cell. In some embodiments, the antigenic peptide is presented on the surface of the antigen presenting cell in complex with a MHC class I molecule. In some embodiments, the neoepitope is presented on the surface of the antigen presenting cell in complex with a MHC class II molecule.

In some embodiments, a method comprises contacting a tumor cell with a neoantigenic polypeptide or polynucleotide described herein that delivers an exogenous polypeptide comprising at least one neoantigenic peptide to the antigen presenting cell, wherein at least one neoepitope derived from the at least one neoantigenic peptide is presented on the surface of the antigen presenting cell (e.g., tumor cell). In some embodiments, the neoepitope is presented on the surface of the antigen presenting cell (e.g., tumor cell) in complex with a MHC class I molecule. In some embodiments, the neoepitope is presented on the surface of the antigen presenting cell (e.g., tumor cell) in complex with a MHC class II molecule.

In some embodiments, a method comprises administering to a subject in need thereof a therapeutically effective amount of a neoantigenic polypeptide or polynucleotide described herein that delivers an exogenous polypeptide comprising at least one antigenic peptide to a tumor cell, wherein the neoepitope is presented on the surface of the tumor cell, and an immune response against the tumor cell is induced. In some embodiments, the immune response against the tumor cell is increased. In some embodiments, the neoantigenic polypeptide or polynucleotide delivers an exogenous polypeptide comprising at least one neoantigenic peptide to a tumor cell, wherein the neoepitope is presented on the surface of the tumor cell, and tumor growth is inhibited.

In some embodiments, a method comprises administering to a subject in need thereof a therapeutically effective amount of a neoantigenic polypeptide or polynucleotide described herein that delivers an exogenous polypeptide comprising at least one neoantigenic peptide to a tumor cell, wherein the neoepitope derived from the at least one neoantigenic peptide is presented on the surface of the tumor cell, and T cell killing directed against the tumor cell is induced. In some embodiments, T cell killing directed against the tumor cell is enhanced. In some embodiments, T cell killing directed against the tumor cell is increased.

In some embodiments, a method of increasing an immune response in a subject comprises administering to the subject a therapeutically effective amount of a neoantigenic therapeutic described herein, wherein the agent is an antibody that specifically binds the neoantigen described herein. In some embodiments, a method of increasing an immune response in a subject comprises administering to the subject a therapeutically effective amount of the antibody.

The present disclosure provides methods of redirecting an existing immune response to a tumor. In some embodiments, a method of redirecting an existing immune response to a tumor comprises administering to a subject a therapeutically effective amount of a neoantigen therapeutic described herein. In some embodiments, the existing immune response is against a virus. In some embodiments, the virus is selected from the group consisting of: measles virus, varicella-zoster virus (VZV; chickenpox virus), influenza virus, mumps virus, poliovirus, rubella virus, rotavirus, hepatitis A virus (HAV), hepatitis B virus (HBV), Epstein Barr virus (EBV), and cytomegalovirus (CMV). In some embodiments, the virus is varicella-zoster virus. In some embodiments, the virus is cytomegalovirus. In some embodiments, the virus is measles virus. In some embodiments, the existing immune response has been acquired after a natural viral infection. In some embodiments, the existing immune response has been acquired after vaccination against a virus. In some embodiments, the existing immune response is a cell-mediated response. In some embodiments, the existing immune response comprises cytotoxic T cells (CTLs) or Th cells.

In some embodiments, a method of redirecting an existing immune response to a tumor in a subject comprises administering a fusion protein comprising (i) an antibody that specifically binds a neoantigen and (ii) at least one neoantigenic peptide described herein, wherein (a) the fusion protein is internalized by a tumor cell after binding to the tumor-associated antigen or the neoepitope; (b) the neoantigenic peptide is processed and presented on the surface of the tumor cell associated with a MHC class I molecule; and (c) the neoantigenic peptide/MHC Class I complex is recognized by cytotoxic T cells. In some embodiments, the cytotoxic T cells are memory T cells. In some embodiments, the memory T cells are the result of a vaccination with the neoantigenic peptide.

The present disclosure provides methods of increasing the immunogenicity of a tumor. In some embodiments, a method of increasing the immunogenicity of a tumor comprises contacting a tumor or tumor cells with an effective amount of a neoantigen therapeutic described herein. In some embodiments, a method of increasing the immunogenicity of a tumor comprises administering to a subject a therapeutically effective amount of a neoantigen therapeutic described herein.

The present disclosure also provides methods for inhibiting growth of a tumor using a neoantigen therapeutic described herein. In certain embodiments, a method of inhibiting growth of a tumor comprises contacting a cell mixture with a neoantigen therapeutic in vitro. For example, an immortalized cell line or a cancer cell line mixed with immune cells (e.g., T cells) is cultured in medium to which a neoantigenic peptide is added. In some embodiments, tumor cells are isolated from a patient sample, for example, a tissue biopsy, pleural effusion, or blood sample, mixed with immune cells (e.g., T cells), and cultured in medium to which a neoantigen therapeutic is added. In some embodiments, a neoantigen therapeutic increases, promotes, and/or enhances the activity of the immune cells. In some embodiments, a neoantigen therapeutic inhibits tumor cell growth. In some embodiments, a neoantigen therapeutic activates killing of the tumor cells.

In certain embodiments, the subject is a human. In certain embodiments, the subject has a tumor or the subject had a tumor which was at least partially removed.

In some embodiments, a method of inhibiting growth of a tumor comprises redirecting an existing immune response to a new target, comprising administering to a subject a therapeutically effective amount of a neoantigen therapeutic, wherein the existing immune response is against an antigenic peptide delivered to the tumor cell by the neoantigenic peptide.

In certain embodiments, the tumor comprises cancer stem cells. In certain embodiments, the frequency of cancer stem cells in the tumor is reduced by administration of the neoantigen therapeutic. In some embodiments, a method of reducing the frequency of cancer stem cells in a tumor in a subject, comprising administering to the subject a therapeutically effective amount of a neoantigen therapeutic is provided.

In addition, in some aspects the present disclosure provides a method of reducing the tumorigenicity of a tumor in a subject, comprising administering to the subject a therapeutically effective amount of a neoantigen therapeutic described herein. In certain embodiments, the tumor comprises cancer stem cells. In some embodiments, the tumorigenicity of a tumor is reduced by reducing the frequency of cancer stem cells in the tumor. In some embodiments, the methods comprise using the neoantigen therapeutic described herein. In certain embodiments, the frequency of cancer stem cells in the tumor is reduced by administration of a neoantigen therapeutic described herein.

In some embodiments, the tumor is a solid tumor. In certain embodiments, the tumor is a tumor selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, and head and neck tumor. In certain embodiments, the tumor is a colorectal tumor. In certain embodiments, the tumor is an ovarian tumor. In some embodiments, the tumor is a breast tumor. In some embodiments, the tumor is a lung tumor. In certain embodiments, the tumor is a pancreatic tumor. In certain embodiments, the tumor is a melanoma tumor. In some embodiments, the tumor is a solid tumor.

The present disclosure further provides methods for treating cancer in a subject comprising administering to the subject a therapeutically effective amount of a neoantigen therapeutic described herein.

In some embodiments, a method of treating cancer comprises redirecting an existing immune response to a new target, the method comprising administering to a subject a therapeutically effective amount of neoantigen therapeutic, wherein the existing immune response is against an antigenic peptide delivered to the cancer cell by the neoantigenic peptide.

The present disclosure provides for methods of treating cancer comprising administering to a subject a therapeutically effective amount of a neoantigen therapeutic described herein (e.g., a subject in need of treatment). In certain embodiments, the subject is a human. In certain embodiments, the subject has a cancerous tumor. In certain embodiments, the subject has had a tumor at least partially removed.

Subjects can be, for example, mammal, humans, pregnant women, elderly adults, adults, adolescents, pre-adolescents, children, toddlers, infants, newborn, or neonates. A subject can be a patient. In some cases, a subject can be a human. In some cases, a subject can be a child (i.e. a young human being below the age of puberty). In some cases, a subject can be an infant. In some cases, the subject can be a formula-fed infant. In some cases, a subject can be an individual enrolled in a clinical study. In some cases, a subject can be a laboratory animal, for example, a mammal, or a rodent. In some cases, the subject can be a mouse. In some cases, the subject can be an obese or overweight subject.

In some embodiments, the subject has previously been treated with one or more different cancer treatment modalities. In some embodiments, the subject has previously been treated with one or more of radiotherapy, chemotherapy, or immunotherapy. In some embodiments, the subject has been treated with one, two, three, four, or five lines of prior therapy. In some embodiments, the prior therapy is a cytotoxic therapy.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, neuroendocrine cancer, bladder cancer, glioblastoma, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer. In certain embodiments, the cancer is melanoma. In some embodiments, the cancer is a solid cancer. In some embodiments, the cancer comprises a solid tumor.

In some embodiments, the cancer is a hematologic cancer. In some embodiment, the cancer is selected from the group consisting of: acute myelogenous leukemia (AML), Hodgkin lymphoma, multiple myeloma, T cell acute lymphoblastic leukemia (T-ALL), chronic lymphocytic leukemia (CLL), hairy cell leukemia, chronic myelogenous leukemia (CML), non-Hodgkin lymphoma, diffuse large B-cell lymphoma (DLBCL), mantle cell lymphoma (MCL), and cutaneous T cell lymphoma (CTCL).

In some embodiments, the neoantigen therapeutic is administered as a combination therapy. Combination therapy with two or more therapeutic agents uses agents that work by different mechanisms of action, although this is not required. Combination therapy using agents with different mechanisms of action can result in additive or synergetic effects. Combination therapy can allow for a lower dose of each agent than is used in monotherapy, thereby reducing toxic side effects and/or increasing the therapeutic index of the agent(s). Combination therapy can decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some instances, an immunogenic pharmaceutical composition can be administered with an additional agent. The choice of the additional agent can depend, at least in part, on the condition being treated. The additional agent can include, for example, a checkpoint inhibitor agent such as an anti-PD1, anti-CTLA4, anti-PD-L1, anti CD40, or anti-TIM3 agent (e.g., an anti-PD1, anti-CTLA4, anti-PD-L1, anti CD40, or anti-TIM3 antibody); or any agents having a therapeutic effect for a pathogen infection (e.g. viral infection), including, e.g., drugs used to treat inflammatory conditions such as an NSAID, e.g., ibuprofen, naproxen, acetaminophen, ketoprofen, or aspirin. For example, the checkpoint inhibitor can be a PD-1/PD-L1 antagonist selected from the group consisting of: nivolumab (ONO-4538/BMS-936558, MDX1 106, OPDIVO), pembrolizumab (MK-3475, KEYTRUDA), pidilizumab (CT-011), and MPDL328OA (ROCHE). As another example, formulations can additionally contain one or more supplements, such as vitamin C, E or other antioxidants.

The methods of the disclosure can be used to treat any type of cancer known in the art. Non-limiting examples of cancers to be treated by the methods of the present disclosure can include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

Additionally, the disease or condition provided herein includes refractory or recurrent malignancies whose growth may be inhibited using the methods of treatment of the present disclosure. In some embodiments, a cancer to be treated by the methods of treatment of the present disclosure is selected from the group consisting of carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, and combinations thereof. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma. In some embodiments, a cancer to be treated by the methods of the present disclosure is breast cancer. In some embodiments, a cancer to be treated by the methods of treatment of the present disclosure is triple negative breast cancer (TNBC). In some embodiments, a cancer to be treated by the methods of treatment of the present disclosure is ovarian cancer. In some embodiments, a cancer to be treated by the methods of treatment of the present disclosure is colorectal cancer.

In some embodiments, a patient or population of patients to be treated with a pharmaceutical composition of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a patient or population of patients to be treated with a pharmaceutical composition of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM"). In some embodiments, a patient or population of patients to be treated having the cancer selected from the group consisting of ovarian cancer, lung cancer and melanoma.

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polyploid), ulcerating, superficial spreading, diffusely spreading, malignant lymphoma, liposarcoma, fibrosarcoma, and carcinosarcoma; colon cancers; colorectal cancer, KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the present disclosure is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In some embodiments, the combination of an agent described herein and at least one additional therapeutic agent results in additive or synergistic results. In some embodiments, the combination therapy results in an increase in the therapeutic index of the agent. In some embodiments, the combination therapy results in an increase in the therapeutic index of the additional therapeutic agent(s). In some embodiments, the combination therapy results in a decrease in the toxicity and/or side effects of the agent. In some embodiments, the combination therapy results in a decrease in the toxicity and/or side effects of the additional therapeutic agent(s).

In certain embodiments, in addition to administering a neoantigen therapeutic described herein, the method or treatment further comprises administering at least one additional therapeutic agent. An additional therapeutic agent can be administered prior to, concurrently with, and/or subsequently to, administration of the agent. In some embodiments, the at least one additional therapeutic agent comprises 1, 2, 3, or more additional therapeutic agents.

Therapeutic agents that can be administered in combination with the neoantigen therapeutic described herein include chemotherapeutic agents. Thus, in some embodiments, the method or treatment involves the administration of an agent described herein in combination with a chemotherapeutic agent or in combination with a cocktail of chemotherapeutic agents. Treatment with an agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4th Edition, 2008, M. C. Perry, Editor, Lippincott, Williams & Wilkins, Philadelphia, PA.

Useful classes of chemotherapeutic agents include, for example, anti-tubulin agents, auristatins, DNA minor groove binders, DNA replication inhibitors, alkylating agents (e.g., platinum complexes such as cisplatin, mono(platinum), bis (platinum) and tri-nuclear platinum complexes and carboplatin), anthracyclines, antibiotics, anti-folates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, *vinca* alkaloids, or the like. In certain embodiments, the second therapeutic agent is an alkylating agent, an antimetabolite, an antimitotic, a topoisomerase inhibitor, or an angiogenesis inhibitor.

Chemotherapeutic agents useful in the present disclosure include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vinde sine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6 mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a *vinca* alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, the additional therapeutic agent is paclitaxel. In some embodiments, the additional therapeutic agent is albumin-bound paclitaxel.

In some embodiments, an additional therapeutic agent comprises an agent such as a small molecule. For example, treatment can involve the combined administration of an agent of the present disclosure with a small molecule that acts as an inhibitor against tumor-associated antigens including, but not limited to, EGFR, HER2 (ErbB2), and/or VEGF. In some embodiments, an agent of the present disclosure is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor. In another embodiment, the additional therapeutic agent is chemotherapy or other inhibitors that reduce the number of Treg cells. In certain embodiments, the therapeutic agent is cyclophosphamide or an anti-CTLA4 antibody. In another embodiment, the additional therapeutic reduces the presence of myeloid-derived suppressor cells. In a further embodiment, the additional therapeutic is carbotaxol. In another embodiment, the additional therapeutic agent shifts cells to a T helper 1 response. In a further embodiment, the additional therapeutic agent is ibrutinib.

In some embodiments, an additional therapeutic agent comprises a biological molecule, such as an antibody. For example, treatment can involve the combined administration of an agent of the present disclosure with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

The agents and compositions provided herein may be used alone or in combination with conventional therapeutic regimens such as surgery, irradiation, chemotherapy and/or bone marrow transplantation (autologous, syngeneic, allogeneic or unrelated). A set of tumor antigens can be useful, e.g., in a large fraction of cancer patients.

In some embodiments, at least one or more chemotherapeutic agents may be administered in addition to the composition comprising an immunogenic vaccine. In some embodiments, the one or more chemotherapeutic agents may belong to different classes of chemotherapeutic agents.

Examples of chemotherapy agents include, but are not limited to, alkylating agents such as nitrogen mustards (e.g. mechlorethamine (nitrogen mustard), chlorambucil, cyclophosphamide (Cytoxan®), ifosfamide, and melphalan); nitrosoureas (e.g. N-Nitroso-N-methylurea, streptozocin, carmustine (BCNU), lomustine, and semustine); alkyl sulfonates (e.g. busulfan); tetrazines (e.g. dacarbazine (DTIC), mitozolomide and temozolomide (Temodar®)); aziridines (e.g. thiotepa, mytomycin and diaziquone); and platinum drugs (e.g. cisplatin, carboplatin, and oxaliplatin); non-classical alkylating agents such as procarbazine and altretamine (hexamethylmelamine); anti-metabolite agents such as 5-fluorouracil (5-FU), 6-mercaptopurine (6-MP), capecitabine (Xeloda®), cladribine, clofarabine, cytarabine (Ara-C®), decitabine, floxuridine, fludarabine, nelarabine, gemcitabine (Gemzar®), hydroxyurea, methotrexate, pemetrexed (Alimta®), pentostatin, thioguanine, Vidaza; antimicrotubule agents such as vinca alkaloids (e.g. vincristine, vinblastine, vinorelbine, vindesine and vinflunine); taxanes (e.g. paclitaxel (Taxol®), docetaxel (Taxotere®)); podophyllotoxin (e.g. etoposide and teniposide); epothilones (e.g. ixabepilone (Ixempra®)); estramustine (Emcyt®); anti-tumor antibiotics such as anthracyclines (e.g. daunorubicin, doxorubicin (Adriamycin®, epirubicin, idarubicin); actinomycin-D; and bleomycin; topoisomerase I inhibitors such as topotecan and irinotecan (CPT-11); topoisomerase II inhibitors such as etoposide (VP-16), teniposide, mitoxantrone, novobiocin, merbarone and aclarubicin; corticosteroids such as prednisone, methylprednisolone (Solumedrol®), and dexamethasone (Decadron®); L-asparaginase; bortezomib (Velcade®); immunotherapeutic agents such as rituximab (Rituxan®), alemtuzumab (Campath®), thalidomide, lenalidomide (Revlimid®), BCG, interleukin-2, interferon-alfa and cancer vaccines such as Provenge®; hormone therapeutic agents such as fulvestrant (Faslodex®), tamoxifen, toremifene (Fareston®), anastrozole (Arimidex®), exemestan (Aromasin®), letrozole (Femara®), megestrol acetate (Megace®), estrogens, bicalutamide (Casodex®), flutamide (Eulexin®), nilutamide (Nilandron®), leuprolide (Lupron®) and goserelin (Zoladex®); differentiating agents such as retinoids, tretinoin (ATRA or Atralin®), bexarotene (Targretin®) and arsenic trioxide (Arsenox®); and targeted therapeutic agents such as imatinib (Gleevec®), gefitinib (Iressa®) and sunitinib (Sutent®). In some embodiments, the chemotherapy is a cocktail therapy. Examples of a cocktail therapy includes, but is not limited to, CHOP/R-CHOP (rituxan, cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), FOLFOX (fluorouracil (5-FU), leucovorin, oxaliplatin), ICE (ifosfamide, carboplatin, etoposide), DHAP (high-dose cytarabine [ara-C], dexamethasone, cisplatin), ESHAP (etoposide, methylprednisolone, cytarabine [ara-C], cisplatin) and CMF (cyclophosphamide, methotrexate, fluorouracil).

In certain embodiments, an additional therapeutic agent comprises a second immunotherapeutic agent. In some embodiments, the additional immunotherapeutic agent includes, but is not limited to, a colony stimulating factor, an interleukin, an antibody that blocks immunosuppressive functions (e.g., an anti-CTLA-4 antibody, anti-CD28 antibody, anti-CD3 antibody, anti-PD-1 antibody, anti-PD-L1 antibody, anti-TIGIT antibody), an antibody that enhances immune cell functions (e.g., an anti-GITR antibody, an anti-OX-40 antibody, an anti-CD40 antibody, or an anti-4-1BB antibody), a toll-like receptor (e.g., TLR4, TLR7, TLR9), a soluble ligand (e.g., GITRL, GITRL-Fc, OX-40L, OX-40L-Fc, CD40L, CD40L-Fc, 4-1BB ligand, or 4-1BB ligand-Fc), or a member of the B7 family (e.g., CD80, CD86). In some embodiments, the additional immunotherapeutic agent targets CTLA-4, CD28, CD3, PD-1, PD-L1, TIGIT, GITR, OX-40, CD-40, or 4-1BB.

In some embodiments, the additional therapeutic agent is an immune checkpoint inhibitor. In some embodiments, the immune checkpoint inhibitor is an anti-PD-1 antibody, an anti-PD-L1 antibody, an anti-CTLA-4 antibody, an anti-CD28 antibody, an anti-TIGIT antibody, an anti-LAG3 antibody, an anti-TIM3 antibody, an anti-GITR antibody, an anti-4-1BB antibody, or an anti-OX-40 antibody. In some embodiments, the additional therapeutic agent is an anti-TIGIT antibody. In some embodiments, the additional therapeutic agent is an anti-PD-1 antibody selected from the group consisting of: nivolumab (OPDIVO), pembrolizumab (KEYTRUDA), pidilzumab, MEDI0680, REGN2810, BGB-A317, and PDR001. In some embodiments, the additional therapeutic agent is an anti-PD-L1 antibody selected from the group consisting of: BMS935559 (MDX-1105), atexolizumab (MPDL3280A), durvalumab (MEDI4736), and avelumab (MSB0010718C). In some embodiments, the additional therapeutic agent is an anti-CTLA-4 antibody selected from the group consisting of: ipilimumab (YERVOY) and tremelimumab. In some embodiments, the additional therapeutic agent is an anti-LAG-3 antibody selected from the group consisting of: BMS-986016 and LAG525. In some embodiments, the additional therapeutic agent is an anti-OX-40 antibody selected from the group consisting of: MEDI6469, MEDI0562, and MOXR0916. In some embodiments, the additional therapeutic agent is an anti-4-1BB antibody selected from the group consisting of: PF-05082566.

In some embodiments, the neoantigen therapeutic can be administered in combination with a biologic molecule selected from the group consisting of: adrenomedullin (AM), angiopoietin (Ang), BMPs, BDNF, EGF, erythropoietin (EPO), FGF, GDNF, granulocyte colony stimulating factor (G-CSF), granulocyte-macrophage colony stimulating factor (GM-CSF), macrophage colony stimulating factor (M-CSF), stem cell factor (SCF), GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, gamma-IFN, IL-1, IL-2, IL-3, IL-4, IL-5, IL-6, IL-7, IL-12, IL-15, and IL-18.

In some embodiments, treatment with a neoantigen therapeutic described herein can be accompanied by surgical removal of tumors, removal of cancer cells, or any other surgical therapy deemed necessary by a treating physician.

In certain embodiments, treatment involves the administration of a neoantigen therapeutic described herein in combination with radiation therapy. Treatment with an agent can occur prior to, concurrently with, or subsequent to administration of radiation therapy. Dosing schedules for such radiation therapy can be determined by the skilled medical practitioner.

Combined administration can include co-administration, either in a single pharmaceutical formulation or using separate formulations, or consecutive administration in either order but generally within a time period such that all active agents can exert their biological activities simultaneously.

It will be appreciated that the combination of a neoantigen therapeutic described herein and at least one additional therapeutic agent can be administered in any order or concurrently. In some embodiments, the agent will be administered to patients that have previously undergone treatment with a second therapeutic agent. In certain other embodiments, the neoantigen therapeutic and a second therapeutic agent will be administered substantially simultaneously or concurrently. For example, a subject can be given an agent while undergoing a course of treatment with a second therapeutic agent (e.g., chemotherapy). In certain embodiments, a neoantigen therapeutic will be administered within 1 year of the treatment with a second therapeutic agent. It will further be appreciated that the two (or more) agents or treatments can be administered to the subject within a matter of hours or minutes (i.e., substantially simultaneously).

For the treatment of a disease, the appropriate dosage of a neoantigen therapeutic described herein depends on the type of disease to be treated, the severity and course of the disease, the responsiveness of the disease, whether the agent is administered for therapeutic or preventative purposes, previous therapy, the patient's clinical history, and so on, all at the discretion of the treating physician. The neoantigen therapeutic can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual agent. The administering physician can determine optimum dosages, dosing methodologies, and repetition rates.

In some embodiments, a neoantigen therapeutic can be administered at an initial higher "loading" dose, followed by one or more lower doses. In some embodiments, the frequency of administration can also change. In some embodiments, a dosing regimen can comprise administering an initial dose, followed by additional doses (or "maintenance" doses) once a week, once every two weeks, once every three weeks, or once every month. For example, a dosing regimen can comprise administering an initial loading dose, followed by a weekly maintenance dose of, for example, one-half of the initial dose. Or a dosing regimen can comprise administering an initial loading dose, followed by maintenance doses of, for example one-half of the initial dose every other week. Or a dosing regimen can comprise administering three initial doses for 3 weeks, followed by maintenance doses of, for example, the same amount every other week.

As is known to those of skill in the art, administration of any therapeutic agent can lead to side effects and/or toxicities. In some cases, the side effects and/or toxicities are so severe as to preclude administration of the particular agent at a therapeutically effective dose. In some cases, therapy must be discontinued, and other agents can be tried. However, many agents in the same therapeutic class display similar side effects and/or toxicities, meaning that the patient either has to stop therapy, or if possible, suffer from the unpleasant side effects associated with the therapeutic agent.

In some embodiments, the dosing schedule can be limited to a specific number of administrations or "cycles". In some embodiments, the agent is administered for 3, 4, 5, 6, 7, 8, or more cycles. For example, the agent is administered every 2 weeks for 6 cycles, the agent is administered every 3 weeks for 6 cycles, the agent is administered every 2 weeks for 4 cycles, the agent is administered every 3 weeks for 4 cycles, etc. Dosing schedules can be decided upon and subsequently modified by those skilled in the art.

The present disclosure provides methods of administering to a subject a neoantigen therapeutic described herein comprising using an intermittent dosing strategy for administering one or more agents, which can reduce side effects and/or toxicities associated with administration of an agent, chemotherapeutic agent, etc. In some embodiments, a method for treating cancer in a human subject comprises administering to the subject a therapeutically effective dose of a neoantigen therapeutic in combination with a therapeutically effective dose of a chemotherapeutic agent, wherein one or both of the agents are administered according to an intermittent dosing strategy. In some embodiments, a method for treating cancer in a human subject comprises administering to the subject a therapeutically effective dose of a neoantigen therapeutic in combination with a therapeutically effective dose of a second immunotherapeutic agent, wherein one or both of the agents are administered according to an intermittent dosing strategy. In some embodiments, the intermittent dosing strategy comprises administering an initial dose of a neoantigen therapeutic to the subject, and administering subsequent doses of the agent about once every 2 weeks. In some embodiments, the intermittent dosing strategy comprises administering an initial dose of a neoantigen therapeutic to the subject, and administering subsequent doses of the agent about once every 3 weeks. In some embodiments, the intermittent dosing strategy comprises administering an initial dose of a neoantigen therapeutic to the subject, and administering subsequent doses of the agent about once every 4 weeks. In some embodiments, the agent is administered using an intermittent dosing strategy and the additional therapeutic agent is administered weekly.

The present disclosure provides compositions comprising the neoantigen therapeutic described herein. The present disclosure also provides pharmaceutical compositions comprising a neoantigen therapeutic described herein and a pharmaceutically acceptable vehicle. In some embodiments, the pharmaceutical compositions find use in immunotherapy. In some embodiments, the compositions find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient).

Formulations are prepared for storage and use by combining a neoantigen therapeutic of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition. Exemplary formulations are listed in WO 2015/095811.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 22st Edition, 2012, Pharmaceutical Press, London.). In some embodiments, the vehicle is 5% dextrose in water.

The pharmaceutical compositions described herein can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intra-arterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories.

The neoantigenic peptides described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 22st Edition, 2012, Pharmaceutical Press, London.

In certain embodiments, pharmaceutical formulations include a neoantigen therapeutic described herein complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising the neoantigenic peptides described herein can be produced. Suitable examples of sustained-release preparations include semi-permeable matrices of solid hydrophobic polymers containing an agent, where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The present disclosure provides methods of treatment comprising an immunogenic vaccine. Methods of treatment for a disease (such as cancer or a viral infection) are provided. A method can comprise administering to a subject an effective amount of a composition comprising an immunogenic antigen. In some embodiments, the antigen comprises a viral antigen. In some embodiments, the antigen comprises a tumor antigen.

Non-limiting examples of vaccines that can be prepared include a peptide-based vaccine, a nucleic acid-based vaccine, an antibody based vaccine, a T cell based vaccine, and an antigen-presenting cell based vaccine.

Vaccine compositions can be formulated using one or more physiologically acceptable carriers including excipients and auxiliaries which facilitate processing of the active agents into preparations which can be used pharmaceutically. Proper formulation can be dependent upon the route of administration chosen. Any of the well-known techniques, carriers, and excipients can be used as suitable and as understood in the art.

In some cases, the vaccine composition is formulated as a peptide-based vaccine, a nucleic acid-based vaccine, an antibody based vaccine, or a cell based vaccine. For example, a vaccine composition can include naked cDNA in cationic lipid formulations; lipopeptides (e.g., Vitiello, A. et al., J. Clin. Invest. 95:341, 1995), naked cDNA or peptides, encapsulated e.g., in poly(DL-lactide-co-glycolide) ("PLG") microspheres (see, e.g., Eldridge, et al., Molec. Immunol. 28:287-294, 1991: Alonso et al, Vaccine 12:299-306, 1994; Jones et al, Vaccine 13:675-681, 1995); peptide composition contained in immune stimulating complexes (ISCOMS) (e.g., Takahashi et al, Nature 344:873-875, 1990; Hu et al, Clin. Exp. Immunol. 113:235-243, 1998); or multiple antigen peptide systems (MAPs) (see e.g., Tam, J. P., Proc. Natl Acad. Sci. U.S.A. 85:5409-5413, 1988; Tarn, J. P., J. Immunol. Methods 196:17-32, 1996). Sometimes, a vaccine is formulated as a peptide-based vaccine, or nucleic acid based vaccine in which the nucleic acid encodes the polypeptides. Sometimes, a vaccine is formulated as an antibody based vaccine. Sometimes, a vaccine is formulated as a cell based vaccine.

The amino acid sequence of an identified disease-specific immunogenic neoantigen peptide can be used develop a pharmaceutically acceptable composition. The source of antigen can be, but is not limited to, natural or synthetic proteins, including glycoproteins, peptides, and superantigens; antibody/antigen complexes; lipoproteins; RNA or a translation product thereof; and DNA or a polypeptide encoded by the DNA. The source of antigen may also comprise non-transformed, transformed, transfected, or transduced cells or cell lines. Cells may be transformed, transfected, or transduced using any of a variety of expression or retroviral vectors known to those of ordinary skill in the art that may be employed to express recombinant antigens. Expression may also be achieved in any appropriate host cell that has been transformed, transfected, or transduced with an expression or retroviral vector containing a DNA molecule encoding recombinant antigen(s). Any number of transfection, transformation, and transduction protocols known to those in the art may be used. Recombinant vaccinia vectors and cells infected with the vaccinia vector, may be used as a source of antigen.

A composition can comprise a synthetic disease-specific immunogenic neoantigen peptide. A composition can comprise two or more disease-specific immunogenic neoantigen peptides. A composition may comprise a precursor to a disease-specific immunogenic peptide (such as a protein, peptide, DNA and RNA). A precursor to a disease-specific immunogenic peptide can generate or be generated to the identified disease-specific immunogenic neoantigen peptide. In some embodiments, a therapeutic composition comprises a precursor of an immunogenic peptide. The precursor to a disease-specific immunogenic peptide can be a pro-drug. In some embodiments, the composition comprising a disease-specific immunogenic neoantigen peptide may further comprise an adjuvant. For example, the neoantigen peptide can be utilized as a vaccine. In some embodiments, an immunogenic vaccine may comprise a pharmaceutically acceptable immunogenic neoantigen peptide. In some embodiments, an immunogenic vaccine may comprise a pharmaceutically acceptable precursor to an immunogenic neoantigen peptide (such as a protein, peptide, DNA and RNA). In some embodiments, a method of treatment comprises administering to a subject an effective amount of an antibody specifically recognizing an immunogenic neoantigen peptide. In some embodiments, a method of treatment comprises administering to a subject an effective amount of a soluble TCR or TCR analog specifically recognizing an immunogenic neoantigen peptide.

The methods described herein are particularly useful in the personalized medicine context, where immunogenic neoantigen peptides are used to develop therapeutics (such as vaccines or therapeutic antibodies) for the same individual. Thus, a method of treating a disease in a subject can comprise identifying an immunogenic neoantigen peptide in a subject according to the methods described herein; and synthesizing the peptide (or a precursor thereof); and administering the peptide or an antibody specifically recognizing the peptide to the subject. In some embodiments, an expression pattern of an immunogenic neoantigen can serve as the essential basis for the generation of patient specific vaccines. In some embodiments, an expression pattern of an immunogenic neoantigen can serve as the essential basis for the generation of a vaccine for a group of patients with a particular disease. Thus, particular diseases, e.g., particular types of tumors, can be selectively treated in a patient group.

In some embodiments, the peptides described herein are structurally normal antigens that can be recognized by autologous anti-disease T cells in a large patient group. In some embodiments, an antigen-expression pattern of a group of diseased subjects whose disease expresses structurally normal neoantigens is determined.

In some embodiments, the peptides described herein comprises a first peptide comprising a first neoepitope of a protein and a second peptide comprising a second neoepitope of the same protein, wherein the first peptide is different from the second peptide, and wherein the first neoepitope comprises a mutation and the second neoepitope comprises the same mutation. In some embodiments, the peptides described herein comprises a first peptide comprising a first neoepitope of a first region of a protein and a second peptide comprising a second neoepitope of a second region of the same protein, wherein the first region comprises at least one amino acid of the second region, wherein the first peptide is different from the second peptide and wherein the first neoepitope comprises a first mutation and the second neoepitope comprises a second mutation. In some embodiments, the first mutation and the second mutation are the same. In some embodiments, the mutation is selected from the group consisting of a point mutation, a splice-site mutation, a frameshift mutation, a read-through mutation, a gene fusion mutation and any combination thereof.

There are a variety of ways in which to produce immunogenic neoantigens. Proteins or peptides may be made by any technique known to those of skill in the art, including the expression of proteins, polypeptides or peptides through standard molecular biological techniques, the isolation of proteins or peptides from natural sources, in vitro translation, or the chemical synthesis of proteins or peptides. In general, such disease specific neoantigens may be produced either in vitro or in vivo. Immunogenic neoantigens may be produced in vitro as peptides or polypeptides, which may then be formulated into a personalized vaccine or immunogenic composition and administered to a subject. In vitro production of immunogenic neoantigens can comprise peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, immunogenic neoantigens can be produced in vivo by introducing molecules (e.g., DNA, RNA, and viral expression systems) that encode an immunogenic neoantigen into a subject, whereupon the encoded immunogenic neoantigens are expressed. In some embodiments, a polynucleotide encoding an immunogenic neoantigen peptide can be used to produce the neoantigen peptide in vitro.

In some embodiments, a polynucleotide comprises a sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a polynucleotide encoding an immunogenic neoantigen.

The polynucleotide may be, e.g., DNA, cDNA, PNA, CNA, RNA, single- and/or double-stranded, native or stabilized forms of polynucleotides, or combinations thereof. A nucleic acid encoding an immunogenic neoantigen peptide may or may not contain introns so long as it codes for the peptide. In some embodiments in vitro translation is used to produce the peptide.

Expression vectors comprising sequences encoding the neoantigen, as well as host cells containing the expression vectors, are also contemplated. Expression vectors suitable for use in the present disclosure can comprise at least one expression control element operationally linked to the nucleic acid sequence. The expression control elements are inserted in the vector to control and regulate the expression of the nucleic acid sequence. Examples of expression control elements are well known in the art and include, for example, the lac system, operator and promoter regions of phage lambda, yeast promoters and promoters derived from polyoma, adenovirus, retrovirus or SV40. Additional operational elements include, but are not limited to, leader sequences, termination codons, polyadenylation signals and any other sequences necessary or preferred for the appropriate transcription and subsequent translation of the nucleic acid sequence in the host system. It will be understood by one skilled in the art the correct combination of expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers.

The neoantigen peptides may be provided in the form of RNA or cDNA molecules encoding the desired neoantigen peptides. One or more neoantigen peptides of the present disclosure may be encoded by a single expression vector. Generally, the DNA is inserted into an expression vector, such as a plasmid, in proper orientation and correct reading frame for expression, if necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques. Useful expression vectors for eukaryotic hosts, especially mammals or humans include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

In embodiments, a DNA sequence encoding a polypeptide of interest can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest is produced. Standard methods can be applied to synthesize an isolated polynucleotide sequence encoding an isolated polypeptide of interest.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems can also be employed. Appropriate cloning and expression vectors for use with bacterial, fungal, yeast, and mammalian cellular hosts are well known in the art. Various mammalian or insect cell culture systems can be employed to express recombinant protein. Exemplary mammalian host cell lines include, but are not limited to COS-7, L cells, C127, 3T3, Chinese hamster ovary (CHO), 293, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine (SEQ ID NO: 1356), maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

A vaccine can comprise an entity that binds a polypeptide sequence described herein. The entity can be an antibody. Antibody-based vaccine can be formulated using any of the well-known techniques, carriers, and excipients as suitable and as understood in the art. In some embodiments, the peptides described herein can be used for making neoantigen specific therapeutics such as antibody therapeutics. For example, neoantigens can be used to raise and/or identify antibodies specifically recognizing the neoantigens. These antibodies can be used as therapeutics. The antibody can be a natural antibody, a chimeric antibody, a humanized antibody, or can be an antibody fragment. The antibody may recognize one or more of the polypeptides described herein. In some embodiments, the antibody can recognize a polypeptide that has a sequence with at most 40%, 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a polypeptide described herein. In some embodiments, the antibody can recognize a polypeptide that has a sequence with at least 40%, 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a polypeptide described herein. In some embodiments, the antibody can recognize a polypeptide sequence that is at least 30%, 40%, 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of a length of a polypeptide described herein. In some embodiments, the antibody can recognize a polypeptide sequence that is at most 30%, 40%, 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of a length of a polypeptide described herein.

The present disclosure also contemplates the use of nucleic acid molecules as vehicles for delivering neoantigen peptides/polypeptides to the subject in need thereof, in vivo, in the form of, e.g., DNA/RNA vaccines.

In some embodiments, the vaccine is a nucleic acid vaccine. In some embodiments, neoantigens can be administered to a subject by use of a plasmid. Plasmids may be introduced into animal tissues by a number of different methods, e.g., injection or aerosol instillation of naked DNA on mucosal surfaces, such as the nasal and lung mucosa. In some embodiments, physical delivery, such as with a "gene-gun" may be used. The exact choice of expression vectors can depend upon the peptide/polypeptides to be expressed, and is well within the skill of the ordinary artisan.

In some embodiments, the nucleic acid encodes an immunogenic peptide or peptide precursor. In some embodiments, the nucleic acid vaccine comprises sequences flanking the sequence coding the immunogenic peptide or peptide precursor. In some embodiments, the nucleic acid vaccine comprises more than one immunogenic epitope. In some embodiments, the nucleic acid vaccine is a DNA-based vaccine. In some embodiments, the nucleic acid vaccine is a RNA-based vaccine. In some embodiments, the RNA-based vaccine comprises mRNA. In some embodiments, the RNA-based vaccine comprises naked mRNA. In some embodiments, the RNA-based vaccine comprises modified mRNA (e.g., mRNA protected from degradation using protamine. mRNA containing modified 5' CAP structure or mRNA containing modified nucleotides). In some embodiments, the RNA-based vaccine comprises single-stranded mRNA.

The polynucleotide may be substantially pure, or contained in a suitable vector or delivery system. Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers (e.g., cationic liposomes).

One or more neoantigen peptides can be encoded and expressed in vivo using a viral based system. Viral vectors may be used as recombinant vectors in the present disclosure, wherein a portion of the viral genome is deleted to introduce new genes without destroying infectivity of the virus. The viral vector of the present disclosure is a non-pathogenic virus. In some embodiments the viral vector has a tropism for a specific cell type in the mammal. In another embodiment, the viral vector of the present disclosure is able to infect professional antigen presenting cells such as dendritic cells and macrophages. In yet another embodiment of the present disclosure, the viral vector is able to infect any cell in the mammal. The viral vector may also infect tumor cells. Viral vectors used in the present disclosure include but is not limited to Poxvirus such as vaccinia virus, avipox virus, fowlpox virus and a highly attenuated vaccinia virus (Ankara or MVA), retrovirus, adenovirus, baculovirus and the like.

A vaccine can be delivered via a variety of routes. Delivery routes can include oral (including buccal and sub-lingual), rectal, nasal, topical, transdermal patch, pulmonary, vaginal, suppository, or parenteral (including intramuscular, intra-arterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999). The vaccine described herein can be administered to muscle, or can be administered via intradermal or subcutaneous injections, or transdermally, such as by iontophoresis. Epidermal administration of the vaccine can be employed.

In some instances, the vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can include material for a single immunization, or may include material for multiple immunizations (i.e. a 'multidose' kit). The inclusion of a preservative is preferred in multidose arrangements. As an alternative (or in addition) to including a preservative in multidose compositions, the compositions can be contained in a container having an aseptic adaptor for removal of material.

The vaccine can be administered in a dosage volume of about 0.5 mL, although a half dose (i.e. about 0.25 mL) can be administered to children. Sometimes the vaccine can be administered in a higher dose e.g. about 1 ml.

The vaccine can be administered as a 1, 2, 3, 4, 5, 6, 7, 8, 9, 10, or more dose-course regimen. Sometimes, the vaccine is administered as a 1, 2, 3, or 4 dose-course regimen. Sometimes the vaccine is administered as a 1 dose-course regimen. Sometimes the vaccine is administered as a 2 dose-course regimen.

The administration of the first dose and second dose can be separated by about 0 day, 1 day, 2 days, 5 days, 7 days, 14 days, 21 days, 30 days, 2 months, 4 months, 6 months, 9 months, 1 year, 1.5 years, 2 years, 3 years, 4 years, or more.

The vaccine described herein can be administered every 1, 2, 3, 4, 5, 6, 7, 8, 9, 10, or more years. Sometimes, the vaccine described herein is administered every 2, 3, 4, 5, 6, 7, or more years. Sometimes, the vaccine described herein is administered every 4, 5, 6, 7, or more years. Sometimes, the vaccine described herein is administered once.

The dosage examples are not limiting and are only used to exemplify particular dosing regiments for administering a vaccine described herein. The effective amount for use in humans can be determined from animal models. For example, a dose for humans can be formulated to achieve circulating, liver, topical and/or gastrointestinal concentrations that have been found to be effective in animals. Based on animal data, and other types of similar data, those skilled in the art can determine the effective amounts of a vaccine composition appropriate for humans.

The effective amount when referring to an agent or combination of agents will generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

In some aspects, the vaccine and kit described herein can be stored at between 2° C. and 8° C. In some instances, the vaccine is not stored frozen. In some instances, the vaccine is stored in temperatures of such as at −20° C. or −80° C. In some instances, the vaccine is stored away from sunlight.

In some aspects provided herein is a method for treatment or prevention of cancer in a subject, the method comprising, (a) administering to the subject at least one dose of a first immunogenic composition and (b) sequentially administering to the subject at least one dose of a second immunogenic. In some embodiments the first immunogenic composition comprises a first peptide comprising a first neoepitope of a protein, and optionally a second peptide comprising a second neoepitope of the same protein, and the second immunogenic composition comprises the second peptide, and optionally the first peptide.

The term "immunogenic composition" refers to any pharmaceutical composition disclosed herein comprising neoantigenic determinant (e.g., a neoepitope) of a neoantigenic protein, which can be used to elicit an immune response in a mammal. The immune response can include a T cell response, a B cell response, or both a T cell and B cell response. The composition can serve to sensitize the mammal by the presentation of neoepitope in association with MHC molecules at the cell surface. In addition, neoantigen-specific T-lymphocytes or antibodies can be generated to allow for the future protection of an immunized host. The term "immune response" is meant to refer to any response to a neoantigen or neoantigenic determinant (e.g., neoepitope) by the immune system of a vertebrate subject, including humoral immune responses (e.g. production of antigen-specific antibodies) and cell-mediated immune responses (e.g. lymphocyte proliferation and/or activation).

In some embodiments, the first immunogenic composition is a prime dose or priming dose and the second immunogenic composition is a boost dose. A "prime dose" is the first dose of a neoantigenic determinant part (e.g., a neoepitope) of a neoantigenic peptide administered to the subject. Administering a prime dose can induce a higher level of an immune response to the neoantigenic peptide upon subsequent administration with the same or a second neoepitope of the same neoantigenic peptide, than the immune response obtained by administration of the prime dose alone. A "boost dose" is a second or third, etc., dose of a neoantigenic determinant part (e.g., a neoepitope) of a neoantigenic peptide administered to a subject that has already been exposed to a neoantigenic determinant part (e.g., a neoepitope) of the same neoantigenic peptide. In some embodiments, the second immunogenic composition boosts or enhances an immune response induced by administering the first immunogenic composition.

In some embodiments, the method comprises administering at least one dose of the first immunogenic composition. In some embodiments the first immunogenic composition is administered prior to administration of the second immunogenic composition. In some embodiments, a dose of the first immunogenic composition is administered at least or about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 70 days, 80 days, 90 days, or 100 days prior to administering the second immunogenic composition.

In some embodiments, the method comprises administering multiple doses of the first immunogenic composition prior to the second immunogenic composition. In some embodiments, the method comprises administering 1, 2, 3, 4, 5 or more doses of the first immunogenic composition prior to the administration of the second immunogenic composition. The multiple doses can be referred to as comprising an initial dose or first dose and one or more subsequent doses. The subsequent dose of the first immunogenic composition when administered occurs after the first dose of the immunogenic composition. Subsequent dose(s) of the first immunogenic composition can be administered in any interval of time following a preceding dose (e.g., a first dose) of the first immunogenic composition. For example, the subsequent dose of the first immunogenic composition can be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 90 days, or 100 days after the preceding dose of the first immunogenic composition.

In some embodiments, the method comprises administering at least one dose of the second immunogenic composition sequentially after the first immunogenic composition. In some embodiments, a dose of a second immunogenic composition is administered at least or about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 70 days, 80 days, 90 days, or 100 days after administering a first immunogenic composition.

In some embodiments, the method comprises administering multiple doses of the second immunogenic composition after to the first immunogenic composition. In some embodiments, the method comprises administering 1, 2, 3, 4, 5 or more doses of the second immunogenic composition after the administration of the first immunogenic composition. The multiple doses can be referred to as comprising an initial dose or first dose of the second immunogenic composition and one or more subsequent doses. The first or initial dose of the second immunogenic composition is administered after administering the first immunogenic composition. The subsequent dose of the second immunogenic composition when administered occurs after the first dose of the second immunogenic composition. Subsequent dose(s) of the second immunogenic composition can be administered in any interval of time following a preceding dose (e.g., a first dose) of the second immunogenic composition. For example, the subsequent dose of the second immunogenic composition can be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 90 days, 100 days, 120 days, 150 days, or 180 days after the preceding dose of the second immunogenic composition.

In some embodiments, the method comprises at least two doses of the second immunogenic composition after the first immunogenic composition (e.g., a first dose of the second immunogenic composition administered after the first immunogenic composition and a subsequent dose of the second immunogenic composition administered after the preceding first dose of the second immunogenic composition). In some embodiments, the methods herein comprise at least three doses of the second immunogenic composition after the first immunogenic composition (e.g., a first dose of the second immunogenic composition administered after the first immunogenic composition and two subsequent doses of the second immunogenic composition administered after the preceding first dose of the second immunogenic composition). In some embodiments, the methods herein comprise at least four doses of the second immunogenic composition after the first immunogenic composition (e.g., a first dose of the second immunogenic composition administered after the first immunogenic composition and three subsequent dose of the second immunogenic composition administered after the preceding first dose of the second immunogenic composition). In some embodiments, the methods herein comprise at least five doses of the second immunogenic composition after the first immunogenic composition (e.g., a first dose of the second immunogenic composition administered after the first immunogenic composition and four subsequent doses of the second immunogenic composition administered after the preceding first dose of the second immunogenic composition). The methods herein are not limiting as it relates to the number of doses for the first immunogenic composition and that of the second immunogenic composition that can be administered to the subject. One of skill in the art can easily determine the number of doses required to have a beneficial effect in the subject, for example, induction of enhanced immune response, reduction in tumor growth, reduction in tumor volume, reduction in metastasis, reduction in tumor reoccurrence and the like.

The subsequent doses can be separated by about 0 day, 1 day, 2 days, 5 days, 7 days, 14 days, 21 days, 30 days, 2 months, 4 months, 6 months, 9 months, 1 year, 1.5 years, 2 years, 3 years, 4 years, or more. A dose of the second immunogenic composition can be administered every 1 month, 6 months, 1 year, 2 years, 3 years, 4 years, 5 years, 6 years, 7 years, 8 years, 9 years, 10 years, or more.

In some embodiments, the dose of the second immunogenic composition is lower than that of the first immunogenic composition. For example, the dose of the second immunogenic composition can be lower by about: 1%, 2%, 3%, 4%, 5%, 7.5%, 10%, 15%, 20%, 25%, 30%, 40%, 50%, 60%, 75% or more than the first immunogenic composition. In some embodiments, the dose of the first immunogenic composition is lower than that of the second immunogenic composition. For example, the dose of the first immunogenic composition can be lower by about: 1%, 2%, 3%, 4%, 5%, 7.5%, 10%, 15%, 20%, 25%, 30%, 40%, 50%, 60%, 75% or more than the first immunogenic composition. In some embodiments, the dose of the second immunogenic composition and the first immunogenic composition can be the same. In some embodiments, the subsequent dose can be lower than the preceding dose, for example by about: 1%, 2%, 3%, 4%, 5%, 7.5%, 10%, 15%, 20%, 25%, 30%, 40%, 50%, 60%, 75% or more.

The dosage examples are not limiting and are only used to exemplify particular dosing regiments for administering a vaccine described herein. The effective amount for use in humans can be determined from animal models. For example, a dose for humans can be formulated to achieve circulating, liver, topical and/or gastrointestinal concentrations that have been found to be effective in animals. Based on animal data, and other types of similar data, those skilled in the art can determine the effective amounts of a vaccine composition appropriate for humans.

In some embodiments, the first immunogenic composition is a prime dose or priming dose and the second immunogenic composition is a boost dose. A "prime dose" is the first dose of a neoantigenic determinant part (e.g., a neoepitope) of a neoantigenic peptide administered to the subject. A "boost dose" is a second or third, etc., dose of a neoantigenic determinant part (e.g., a neoepitope) of a neoantigenic peptide administered to a subject that has already been exposed to a neoantigenic determinant part (e.g., a neoepitope) of the same neoantigenic peptide. In some embodiments, administering the second immunogenic composition sequentially after the first immunogenic composition can, for example, induce an enhanced immune response than that induced by administration of the first immunogenic composition or second immunogenic composition alone.

The enhanced immune response comprises, for example, an increase in level of neoantigen specific immune cells (e.g., T lymphocytes, B-lymphocytes). A change in the level of an immune cell can comprise, for example, an increase in the number of immune cells or an increase in number of activated immune cells. As used herein, the terms level, number, count and concentration can be used interchangeably. The enhanced immune response can comprise, activating a T cell (e.g., from a naive T cell or a quiescent T cell). The change in level can be, for example, increase in the number of T cells, increase in the number of activated T cells, increase in the level of activity (e.g., level of effector function), rate of proliferation, or similar parameter of T cells involved in a specific response.

In some embodiments the enhanced immune response comprises increase in level of CD8+ T cells. In some embodiments, a TCR of a CD8+ T cell binds to a class I HLA-peptide complex comprising the first or second peptide disclosed herein. In some embodiments, a TCR of a CD8+ T cell binds to a class II HLA-peptide complex comprising the first or a second peptide disclosed herein. In some embodiments, the CD8+ T cell has an effector function of cytotoxicity. In some embodiments, the CD8+ T cell has an effector function of IFNγ secretion.

In some embodiments, the methods disclosed herein can increase the level of CD8+ T cells to more than about 10%, 20%, 30%, 40%, 50%, 60% of the total immune cell population. In some embodiments, the methods disclosed comprising administering a second immunogenic composition to a subject who has been administered a first immunogenic composition increases the level of CD8+ T cells relative to a level obtained by administering a first immunogenic composition or second immunogenic composition alone. In some embodiments, the methods herein increases the level of CD8+ T cells by at least 5%, at least 10%, at least 20%, at least 30%, at least 40%, at least 50%, at least 60%, at least 70%, at least 80%, at least 90%, or at least 95% than that obtained by administering a first immunogenic composition or a second immunogenic composition alone. In another embodiment, the methods disclosed herein increases the level of CD8+ Tcells by a factor of at least 10, at least 100, at least 1,000, at least 10,000. In some embodiments, the level of CD8+ T cells is increased so that CD8+ T cells comprise at least about 20%>, about 25%, about 30%>, about 35%, or about 40%> of the total immune cell population. An increase in the level of CD8+ T cells specific for the neoantigenic peptide as disclosed herein is indicative of inducing enhanced immune response, and of treatment of cancer.

In some embodiments the enhanced immune response comprises increase in level of CD4+ T cells. In some embodiments, a TCR of a CD4+ T cell binds to a class I HLA-peptide complex comprising the first or second peptide disclosed herein. In some embodiments, a TCR of a CD4+ T cell binds to a class II HLA-peptide complex comprising the first or a second peptide disclosed herein. In some embodiments, the CD4+ T cell has an effector function of activation of macrophages and/or activation of B cells.

In some embodiments, the methods disclosed herein can increase the level of CD4+ T cells to more than about 10%, 20%, 30%, 40%, 50%, 60% of the total immune cell population. In some embodiments, the methods disclosed comprising administering a second immunogenic composition to a subject who has been administered a first immunogenic composition increases the level of CD4+ T cells relative to the level obtained by administering a first immunogenic composition or second immunogenic composition alone. In some embodiments, the methods herein increases the level of CD4+ T cells by at least 5%, at least 10%, at least 20%, at least 30%, at least 40%, at least 50%, at least 60%, at least 70%, at least 80%, at least 90%, or at least 95% than that obtained by administering a first immunogenic composition or a second immunogenic composition alone. In another embodiment, the methods disclosed herein increases the level of CD4+ T cells by a factor of at least 10, at least 100, at least 1,000, at least 10,000. In some embodiments, the level of CD4+ T cells is increased so that CD4+ T cells comprise at least about 20%>, about 25%, about 30%>, about 35%, or about 40%> of the total immune cell population. An increase in the level of CD4+ T cells specific for the neoantigenic peptide as disclosed herein is indicative of inducing enhanced immune response, or treatment of cancer.

In some embodiments, the enhanced immune response comprises increases in level of effector T cells. The term "effector T cells", as used herein, refers to T cells that can specifically bind to a class I HLA-peptide complex comprising the first or second peptide disclosed herein or a class II HLA peptide complex comprising the first or second peptide disclosed herein and mediate an immune response (effector function) without the need for further differentiation. Effector T cells are generally capable of exiting the lymphatic system and entering the immunological periphery. Phenotypically they are generally CD62L-CD44hi CD107α+IGN-γ+LTβ+TNF-α+ and actively cycling. The term, "effector function" as used herein relates to acquisition of cytolytic activity and/or cytokine secretion by a T cell upon activation. Examples of effector T cells include CTLs, THI cells, and TH2 cell. In contrast to effector T cells, naive T cells have not encountered their specific antigen:MHC complex, nor responded it to it by proliferation and differentiation into an effector T cell. Effector T cells can be resting (in the Go phase of the cell cycle) or activated (proliferating). In some embodiments, the effector T cells are CD8+ T cells, In some embodiments, the effector T cells are CD4+ T cells.

In some embodiments, the CD8+ T cells and CD4+ T cells are effector memory T cells. By "effector memory T cell" herein is meant T cells that express CD44+CD62Llo CD127hi KLRG1hi, are differentiated because they have been exposed to an immunizing neoantigen and capable of responding to recall antigens, and shows efficient effector function (e.g., production of effector cytokines, cytotoxicity). The effector memory T cell can comprise increased CD95/FAS expression, and increased susceptibility to apoptosis, high levels of CD11a/CD18, and heterogenous expression of the L-selectin, a4β7 integrin, and CD27 (Picker and Siegelman, (1999) "Lymphoid Tissues and Organs" in W. E. Paul, ed., Fundamental Immunology, 4 th ed., chapter 14, pp 479-531). In some embodiments the methods disclosed herein increase the level of effector memory T cells. In some embodiments, the methods disclosed herein can increase the level of effector memory T cells to more than about 10%, 20%, 30%, 40%, 50%, 60% of the total immune cell population. In some embodiments, the methods disclosed comprising administering a second immunogenic composition to a subject who has been administered a first immunogenic composition increases the level of effector memory T cells relative to a level obtained by administering a first immunogenic composition or second immunogenic composition alone. In some embodiments, the methods herein increases the level of effector memory T cells by at least 5%, at least 10%, at least 20%, at least 30%, at least 40%, at least 50%, at least 60%, at least 70%, at least 80%, at least 90%, or at least 95% than that obtained by administering a first immunogenic composition or a second immunogenic composition alone. In another embodiment, the methods disclosed herein increases the level of effector memory T cells by a factor of at least 10, at least 100, at least 1,000, at least 10,000. In some embodiments, the level of effector memory T cells is increased so that effector memory T cells comprise at least about 20%>, about 25%, about 30%>, about 35%, or about 40%> of the total immune cell population. An increase in the level of effector memory T cells specific for the neoantigenic peptide as disclosed herein is indicative of inducing enhanced immune response, or treatment of cancer.

In some embodiments, the CD8+ T cells and CD4+ T cells are terminal effector T cells. In some embodiments, By "terminal effector T cell" herein is meant T cells that express CD44+CD62L-/loCD127-KLRG1hi surface markers. In some embodiments the methods disclosed herein increase the level of effector memory T cells. In some embodiments, the methods disclosed herein can increase the level of terminal effector T cells to more than about 10%, 20%, 30%, 40%, 50%, 60% of the total immune cell population. In some embodiments, the methods disclosed comprising administering a second immunogenic composition to a subject who has been administered a first immunogenic composition increases the level of terminal effector T cells relative to a level obtained by administering a first immunogenic composition or second immunogenic composition alone. In some embodiments, the methods herein increases the level of terminal effector T cells by at least 5%, at least 10%, at least 20%, at least 30%, at least 40%, at least 50%, at least 60%, at least 70%, at least 80%, at least 90%, or at least 95% than that obtained by administering a first immunogenic composition or a second immunogenic composition alone. In another embodiment, the methods disclosed herein increases the level of terminal effector T cells by a factor of at least 10, at least 100, at least 1,000, at least 10,000. In some embodiments, the level of terminal effector T cells is increased so that terminal effector T cells comprise at least about 20%>, about 25%, about 30%>, about 35%, or about 40%> of the total immune cell population. An increase in the level of terminal effector T cells specific for the neoantigenic peptide as disclosed herein is indicative of inducing enhanced immune response, or treatment of cancer.

In some embodiments, the CD8+ T cell and CD4+ T cell can be memory precursor. By "memory precursor" herein is meant T cells that express CD44+CD62L-/lo CD127-/+ KLRG1lo/int surface markers. In some embodiments the methods disclosed herein increase the level of memory precursors. In some embodiments, the methods disclosed herein can increase the level of memory precursor to more than about 10%, 20%, 30%, 40%, 50%, 60% of the total immune cell population. In some embodiments, the methods disclosed comprising administering a second immunogenic composition to a subject who has been administered a first immunogenic composition increases the level of memory precursors relative to a level obtained by administering a first immunogenic composition or second immunogenic composition alone. In some embodiments, the methods herein increases the level of memory precursor by at least 5%, at least 10%, at least 20%, at least 30%, at least 40%, at least 50%, at least 60%, at least 70%, at least 80%, at least 90%, or at least 95% than that obtained by administering a first immunogenic composition or a second immunogenic composition alone. In another embodiment, the methods disclosed herein increases the level of memory precursor by a factor of at least 10, at least 100, at least 1,000, at least 10,000. In some embodiments, the level of memory precursor is increased so that memory precursor comprise at least about 20%>, about 25%, about 30%>, about 35%, or about 40%> of the total immune cell population. An increase in the level of memory precursor specific for the neoantigenic peptide as disclosed herein is indicative of inducing enhanced immune response, or treatment of cancer.

In some embodiments, the CD8+ T cell and CD4+ T cell can be central memory T cell. By "central memory T cell" herein is meant T cells that express CD44+ CD62Lhi CD127hi KLRG1lo surface markers. In some embodiments the methods disclosed herein increase the level of central memory T cells. In some embodiments, the methods disclosed herein can increase the level of central memory T cell to more than about 10%, 20%, 30%, 40%, 50%, 60% of the total immune cell population. In some embodiments, the methods disclosed comprising administering a second immunogenic composition to a subject who has been administered a first immunogenic composition increases the level of central memory T cells relative to a level obtained by administering a first immunogenic composition or second immunogenic composition alone. In some embodiments, the methods herein increases the level of central memory T cells by at least 5%, at least 10%, at least 20%, at least 30%, at least 40%, at least 50%, at least 60%, at least 70%, at least 80%, at least 90%, or at least 95% than that obtained by administering a first immunogenic composition or a second immunogenic composition alone. In another embodiment, the methods disclosed herein increases the level of central memory T cells by a factor of at least 10, at least 100, at least 1,000, at least 10,000. In some embodiments, the level of central memory T cells is increased so that central memory T cells comprise at least about 20%>, about 25%, about 30%>, about 35%, or about 40%> of the total immune cell population. An increase in the level of central memory T cells specific for the neoantigenic peptide as disclosed herein is indicative of inducing enhanced immune response, or treatment of cancer.

It will be appreciated by those skilled in the art that both a cell culture system and the immune system of a subject comprise basal levels of immune cells and effector molecules (e.g. cytokines). The phrases basal level and normal level can be used interchangeably. As used herein, the basal level of a type of immune cell, or an effector molecule, refers to the average number of that cell type, or effector molecule, present in a population of individuals under a certain reference state (e.g., in an healthy individual, in an untreated individual, in an individual treated with a first immunogenic composition or a second immunogenic composition alone, or in an individual treated with conventional cancer therapy such as chemotherapy) or the basal level of a type of immune cell, or an effector molecule, refers to the average level of that cell type, or effector molecule, present in a population of cells that is not-activated. Those skilled in the art are capable of determining a level of a particular immune cell in a population of such cells, or a in a biological sample. As used herein, the term "biological sample" has its general meaning in the art and refers to any sample which may be obtained from a subject (e.g., a recipient of a transplant) for the purpose of in vitro evaluation. A preferred biological sample is a blood sample (e.g. whole blood sample, serum sample, or plasma sample).

Methods to measure immune cells are well known in the art including methods based on identifying expression of specific surface marker proteins e.g., by flow cytometry. These methods of identification and isolation include FACS, column chromatography, panning with magnetic beads, western blots, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), Immunoelectrophoresis, radioimmunoassays (RIAs), enzyme-linked immunosorbent assays (ELISAs), immuno fluorescent assays, and the like. For a review of immunological and immunoassay procedures in general, see Stites and Terr (eds.) 1991 Basic and Clinical Immunology (7th ed.) and Paul supra. For a discussion of how to make antibodies to selected antigens see Harlow and Lane (1989) supra.

Cell isolation or immunoassays for detection of cells during cell purification can be performed in any of several configurations, e.g., those reviewed in Maggio (ed.) (1980) Enzyme Immunoassay CRC Press, Boca Raton, Fla.; Tijan (1985) "Practice and Theory of Enzyme Immunoassays," Laboratory Techniques in Biochemistry and Molecular Biology, Elsevier Science Publishers B.V., Amsterdam; Harlow and Lane, supra; Chan (ed.) (1987) Immunoassay: A Practical Guide Academic Press, Orlando, Fla.; Price and Newman (eds.) (1991) Principles and Practice of Immunoassays Stockton Press, NY; and Ngo (ed.) (1988) Non-isotopic Immunoassays Plenum Press, NY. Cells can be isolated and characterized by flow cytometry methods such a FACS analysis. A wide variety of flow-cytometry methods are known. For a general overview of fluorescence activated flow cytometry see, for example, Abbas et al. (1991) Cellular and Molecular immunology W. B. Saunders Company, particularly chapter 3, and Kuby (1992) Immunology W. H. Freeman and Company, particularly chapter 6. FACS machines are available, e.g., from Becton Dickinson.

Labeling agents which can be used to label cell antigen include, but are not limited to monoclonal antibodies, polyclonal antibodies, proteins, or other polymers such as affinity matrices, carbohydrates or lipids. Detection proceeds by any known method, such as immunoblotting, western blot analysis, tracking of radioactive or bioluminescent markers, capillary electrophoresis, or other methods which track a molecule based upon size, charge or affinity.

The level of immune response or level of effector cells can also be determined by measuring effector T cell response. Effector T cell response can be detected by at least one indicator for example, a cytokine assay, an ELISPOT assay, a cytotoxicity assay, a tetramer assay, a DTH-response, a clinical response, tumor shrinkage, tumor clearance, inhibition of tumor progression, amelioration of a disease symptom, and the like. The methods can further include obtaining, detecting or assaying for an effector T cell response to a neoantigen. The effector function of T cells can be determined by the effector molecules that they release in response to specific binding of their TCR with HLA-neoantigenic peptide complex comprising the first or second peptide disclosed herein on the target cell. Cytotoxic effector molecules stored in lytic granules that can be released by cytotoxic CD8+ T cells include perform, granzymes, granulysin and Fas ligand. Perform forms transmembrane pores in the target cell. Granzymes are serine proteases which can trigger apoptosis. Granulysin induces apoptosis in the target cells. Fas ligand can also induce apoptosis in target cells. Other effector molecules that can be released by cytotoxic T cells include IFN-γ, TNF-β and TNF-α. IFN-γ inhibits viral replication and activates macrophages. TNF-β and TNF-α can participate in macrophage activation and in killing some target cells.

Macrophage activating effector molecules that can be secreted by CD4+ THI cells include IFN-γ, TNF-α, GM-CSF, CD40 ligand (CD 154) and Fas ligand. A subset of CD4+ TH1 cells can also assist in B-cell activation IFN-γ and CD40 ligand activate macrophages to destroy engulfed bacteria. Other effector molecules that can be released by THI cells include IL-3, TNF-β (which inhibits B-cells), IL-2, CXCL2 and GROβ. Fas ligand and TNF-β can kill cell chronically infected with intracellular bacteria. IL-2 induces T cell proliferation. IL-3 and GM-CSF induces macrophage differentiation. CCL2 induces chemotaxis of macrophages.

B-cell activating effector molecules that can be secreted by CD4+ TH2 cells include IL-4, IL-5, IL-9, IL-13 IL-15 and CD40 ligand. Other effector molecules that can be released by TH2 cells include IL-3, GM-CSF, IL-IO (which inhibits macrophage activation), TGF-β, IL-2, CCL1 1 (eotaxin) and CCL 17 (TARC). Activated TH2 cells (and some TH1 cells) stimulate B cells to proliferate and differentiate when they recognize a specific antigen:MHC class II complex displayed by a B cell.

In some embodiments, the enhanced immune response comprises a sustained immune response. As used herein, the term "sustained immune response" refers to maintaining in a subject an increase from the basal levels of immune cells (e.g., CD8+ T cells, CD4+ T cells, effector T cells, effector memory T cells) and effector molecules such as IFN-γ. In some embodiments, the methods comprising administering a second immunogenic composition to a subject who has been administered a first immunogenic composition as disclosed herein increases the time period for which an immune response is sustained in a subject to a level greater than that achieved by administering a first immunogenic composition or a second immunogenic composition alone. In some embodiments, the enhanced immune response is sustained for at least about one day, 2 days, 5 days, 10 days, 20 days, 1 month, 2, months, 3 months, 6 months, 1 year, 2 years, 5 years, or 10 years. The immune response can be cellular, T- and/or B-lymphocytes and/or humoral, as measured by in vitro assays such as T cell proliferation assays, cytotoxic assays, ELISA, RIA, gels, FACS analysis, Western Blot and the like. In some embodiments, the time for which the enhanced immune response is sustained is increased by at least 5%, at least 10%, at least 20%, at least 30%, at least 40%, at least 50%, at least 60%, at least 70%, at least 80%, at least 90%, or at least 95% than that obtained by administering a first immunogenic composition or a second immunogenic composition alone. In another embodiment, the methods disclosed herein increases the time for which the enhanced immune response is sustained by a factor of at least 2, 4, 6, 8, 10, 50, 60, 100, or 1,000 relative to that achieved by administration of a first immunogenic composition and a second immunogenic composition alone.

In some embodiments, the methods disclosed herein comprising administering at least one dose of a first immunogenic composition and at least one dose of a second immunogenic composition, can induce an increased anti-tumor effect than that induced by administering the first immunogenic composition or second immunogenic composition alone. The term "anti-tumor effect" as used herein, refers to a beneficial biological effect, which can be manifested by any one or more of: a decrease or stabilization of tumor volume, a decrease or stabilization of the number of tumor cells, a decrease or stabilization of the rate of tumor growth, a decrease or stabilization of the number of metastases, protection from tumor recurrence, an increase in life expectancy or survival of the subject with the tumor, an increase in life expectancy or survival without disease progression of the subject with the tumor or amelioration of various physiological symptoms associated with the cancerous condition. An "anti-tumor effect" can also be manifested by the ability of the methods and compositions disclosed herein to prevent the occurrence of tumor in the first place or the recurrence of the tumor. Given its properties, the methods disclosed herein can be used in the treatment of acute cancer, of dormant, controlled or stabilized cancer, as well as in cancer prophylaxis. In some embodiments, the enhanced immune response induced by administering a second immunogenic composition to a subject who has been previously administered a first immunogenic composition disclosed herein can reduce the tumor growth, tumor volume, number of metastases, tumor reoccurrence or a combination thereof to a level greater than that achieved by administering the first immunogenic composition or the second immunogenic composition alone.

In some embodiments, treating cancer results in a reduction tumor size. A reduction in tumor size may also be referred to as "tumor regression". Preferably, after treatment using the methods disclosed herein, tumor growth is reduced by 5%, 10%, 20%, 30%, 40%, 50%, 75% or greater relative to number prior to treatment. In some embodiments, the reduction in tumor growth is greater compared to that achieved by treatment with a first immunogenic composition or a second immunogenic composition alone. The level of reduction of tumor growth is 5%, 10%, 20%, 30%, 40%, 50%, 75%, 85%, 90%, 95%, or 99% greater compared to level with treatment with the first immunogenic composition or second immunogenic composition alone. Size of a tumor may be measured by any reproducible means of measurement. In some embodiments, size of a tumor may be measured as a diameter of the tumor.

In some embodiments, treating cancer results in a reduction in tumor volume. Preferably, after treatment with the methods disclosed herein, tumor volume is reduced by 5%, 10%, 20%, 30%, 40%, 50%, 75% or greater relative to number prior to treatment. In some embodiments, the reduction in tumor volume is greater compared to that achieved by treatment with a first immunogenic composition or a second immunogenic composition alone. The level of reduction of tumor volume is 5%, 10%, 20%, 30%, 40%, 50%, 75%, 85%, 90%, 95%, or 99% greater compared to level with treatment with the first immunogenic composition or second immunogenic composition alone. Tumor volume may be measured by any reproducible means of measurement.

In some embodiments, treating cancer results in a decrease in number of tumors. Preferably, after treatment, tumor number is reduced by 5%, 10%, 20%, 30%, 40%, 50%, 75% or greater relative to number prior to treatment. In some embodiments, the decrease in number of tumors is greater compared to that achieved by treatment with a first immunogenic composition or a second immunogenic composition alone. The level of reduction in number of tumors is 5%, 10%, 20%, 30%, 40%, 50%, 75%, 85%, 90%, 95%, or 99% greater compared to level with treatment with the first immunogenic composition or second immunogenic composition alone. Number of tumors may be measured by any reproducible means of measurement. In some embodiments, number of tumors may be measured by counting tumors visible to the naked eye or at a specified magnification. In some embodiments, the specified magnification is 2×, 3×, 4×, 5×, 10×, or 50×.

In some embodiments, treating cancer results in a decrease in number of metastatic lesions in other tissues or organs distant from the primary tumor site. Preferably, after treatment, the number of metastatic lesions is reduced by 5%, 10%, 20%, 30%, 40%, 50%, 75% or greater relative to number prior to treatment. In some embodiments, the decrease in number of metastatic lesions is greater compared to that achieved by treatment with a first immunogenic composition or a second immunogenic composition alone. The level of reduction in metastases is 5%, 10%, 20%, 30%, 40%, 50%, 75%, 85%, 90%, 95%, or 99% greater compared to level with treatment with the first immunogenic composition or second immunogenic composition alone. The number of metastatic lesions may be measured by any reproducible means of measurement. In some embodiments, the number of metastatic lesions may be measured by counting metastatic lesions visible to the naked eye or at a specified magnification. In some embodiments, the specified magnification is 2×, 3×, 4×, 5×, 10×, or 50×.

In some embodiments, treating cancer results in a decrease in tumor growth rate. Preferably, after treatment, tumor growth rate is reduced by 5%, 10%, 20%, 30%, 40%, 50%, 75% or greater relative to number prior to treatment. In some embodiments, the reduction in tumor growth is greater compared to that achieved by treatment with a first immunogenic composition or a second immunogenic composition alone. The level of reduction of tumor growth is 5%, 10%, 20%, 30%, 40%, 50%, 75%, 85%, 90%, 95%, or 99% greater compared to level with treatment with the first immunogenic composition or second immunogenic composition alone. Tumor growth rate may be measured by any reproducible means of measurement. In some embodiments, tumor growth rate is measured according to a change in tumor diameter per unit time.

In some embodiments, treating cancer results in a decrease in tumor regrowth or tumor reoccurrence. Preferably, after treatment, tumor regrowth is less than 5%, 10%, 20%, 30%, 40%, 50%, 75% or greater relative to number prior to treatment. In some embodiments, the reduction in tumor regrowth is greater compared to that achieved by treatment with a first immunogenic composition or a second immunogenic composition alone. The level of reduction of tumor regrowth is 5%, 10%, 20%, 30%, 40%, 50%, 75%, 85%, 90%, 95%, or 99% greater compared to level with treatment with the first immunogenic composition or second immunogenic composition alone. Tumor regrowth may be measured by any reproducible means of measurement. In some embodiments, tumor regrowth is measured, for example, by measuring an increase in the diameter of a tumor after a prior tumor shrinkage that followed treatment.

In some embodiments, a decrease in tumor regrowth is indicated by failure of tumors to reoccur after treatment has stopped.

In some embodiments, the methods comprising administering at least one dose of a first immunogenic composition and at least one dose of a second immunogenic composition enhances survival of the subject to a level greater than that achieved by administering the first immunogenic composition or second immunogenic composition alone. In some embodiments, the enhanced immune response induced by administering a second immunogenic composition to a subject who has been previously administered a first immunogenic composition can enhance survival of the subject to a level greater than that achieved by administering the first or second immunogenic composition alone. The term "enhanced survival", as used herein, refers to a prolonged length of time during which the subject or patient is alive following treatment with the methods and compositions disclosed herein. Enhanced survival denotes the increased probability of staying free of disease progression for an individual suffering from cancer after a particular treatment. It is also used to describe the elevated percentage of individuals in a group whose disease is likely to remain stable (not showing signs of progression) after a specified duration of time, compared to a control group. It is also used to describe the elevated percentage of individuals in a group whose disease is likely to be cured (not showing signs of disease) after a specified duration of time, compared to a control group. This parameter may be measured by any one of the customary clinical endpoints denoted as "progression-free survival", "overall survival" and "disease free survival" used as an indication of the efficacy of a particular treatment.

In some embodiments, the survival is for a period of at least one month, at least two months, at least three months, at least four months, at least five months, at least six months, at least seven months, at least eight months, at least nine months, at least ten months, at least eleven months, at least twelve months, at least thirteen months, at least fourteen months, at least fifteen months, at least sixteen months, at least seventeen months, at least eighteen months, at least nineteen months, at least twenty months, at least twenty-one months, at least twenty-two months, at least twenty-three months, or at least twenty-four months. In some embodiments, the survival is for a period of at least 1 year, at least 2 years, at least 3 years, at least 4 years, at least 5 years, at least 6 years, at least 7 years, at least 8 years, at least 9 years, or at least 10 years. In some embodiments, the enhanced survival is achieved in the absence of a booster dose or booster regimen. In some cases, the enhanced survival is achieved with an administration of a booster dose or booster regimen (e.g., administration of a second immunogenic composition after a prime dose of a first immunogenic composition) in one or multiple doses. In some cases, one or more booster doses (e.g., dose of a second immunogenic composition) are administered on the day of, or at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 65 days, 70 days, 75 days, 80 days, 85 days, 90 days, 95 days, 100 days, 105 days, 110 days, 115 days, 120 days, 125 days, 130 days, 135 days, 140 days, 145 days, 150 days, 155 days, 160 days, 165 days, 170 days 175 days, 180 days, 185 days, 190 days, 195 days, 200 days, 205 days, 210 days, 215 days, 220 days, 230 days or 240 days after the prime dose (e.g., dose of a first immunogenic composition).

Kits

The neoantigen therapeutic described herein can be provided in kit form together with instructions for administration. Typically the kit would include the desired neoantigen therapeutic in a container, in unit dosage form and instructions for administration. Additional therapeutics, for example, cytokines, lymphokines, checkpoint inhibitors, antibodies, can also be included in the kit. Other kit components that can also be desirable include, for example, a sterile syringe, booster dosages, and other desired excipients.

Kits and articles of manufacture are also provided herein for use with one or more methods described herein. The kits can contain one or more neoantigenic polypeptides comprising one or more neoepitopes. The kits can also contain nucleic acids that encode one or more of the peptides or proteins described herein, antibodies that recognize one or more of the peptides described herein, or APC-based cells activated with one or more of the peptides described herein. The kits can further contain adjuvants, reagents, and buffers necessary for the makeup and delivery of the vaccines.

The kits can also include a carrier, package, or container that is compartmentalized to receive one or more containers such as vials, tubes, and the like, each of the container(s) comprising one of the separate elements, such as the peptides and adjuvants, to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment. A kit typically includes labels listing contents and/or instructions for use, and package inserts with instructions for use. A set of instructions will also typically be included.

The present disclosure will be described in greater detail by way of specific examples. The following examples are offered for illustrative purposes, and are not intended to limit the present disclosure in any manner Those of skill in the art will readily recognize a variety of non-critical parameters that can be changed or modified to yield alternative embodiments according to the present disclosure. All patents, patent applications, and printed publications listed herein are incorporated herein by reference in their entirety.

EXAMPLES

These examples are provided for illustrative purposes only and not to limit the scope of the claims provided herein.

Example 1—Induction of CD4$^+$ and CD8$^+$ T Cell Responses

In vitro T cell inductions are used to expand neo-antigen specific T cells. Mature professional APCs are prepared for these assays in the following way. Monocytes are enriched from healthy human donor PBMCs using a bead-based kit (Miltenyi). Enriched cells are plated in GM-CSF and IL-4 to induce immature DCs. After 5 days, immature DCs are incubated at 37° C. with pools of peptides for 1 hour before addition of a cytokine maturation cocktail (GM-CSF, IL-1β, IL-4, IL-6, TNFα, PGE1β). The pools of peptides can include multiple mutations, with both shortmers and longmers to expand CD8$^+$ and CD4$^+$ T cells, respectively. Cells are incubated at 37° C. to mature DCs.

After maturation of DCs, PBMCs (either bulk or enriched for T cells) are added to mature dendritic cells with proliferation cytokines. Cultures are monitored for peptide-specific T cells using a combination of functional assays and/or tetramer staining. Parallel immunogenicity assays with the modified and parent peptides allowed for comparisons of the relative efficiency with which the peptides expanded peptide-specific T cells.

Example 2—Tetramer Staining Assay

MHC tetramers are purchased or manufactured on-site, and are used to measure peptide-specific T cell expansion in the immunogenicity assays. For the assessment, tetramer is added to $1 \times 10^5$ cells in PBS containing 1% FCS and 0.1% sodium azide (FACS buffer) according to manufacturer's instructions. Cells are incubated in the dark for 20 minutes at room temperature. Antibodies specific for T cell markers, such as CD8, are then added to a final concentration suggested by the manufacturer, and the cells are incubated in the dark at 4° C. for 20 minutes. Cells are washed with cold FACS buffer and resuspended in buffer containing 1% formaldehyde. Cells are acquired on a FACS Calibur (Becton Dickinson) instrument, and are analyzed by use of Cellquest software (Becton Dickinson). For analysis of tetramer positive cells, the lymphocyte gate is taken from the forward and side-scatter plots. Data are reported as the percentage of cells that were CD8$^+$/tetramer$^+$.

Example 3—Intracellular Cytokine Staining Assay

In the absence of well-established tetramer staining to identify antigen-specific T cell populations, antigen-specificity can be estimated using assessment of cytokine production using well-established flow cytometry assays. Briefly, T cells are stimulated with the peptide of interest and compared to a control. After stimulation, production of cytokines by CD4$^+$ T cells (e.g., IFNγ and TNFα) are assessed by intracellular staining. These cytokines, especially IFNγ, used to identify stimulated cells.

Example 4—Analysis of Antigen-Specific T Cells

ELISPOT Analysis

Peptide-specific T cells are functionally enumerated using the ELISPOT assay (BD Biosciences), which measures the release of IFNγ from T cells on a single cell basis. Cells incubated with antigen overnight (16-18 hours) at 37° C. The next day, the cell suspension was discarded, and wells were washed once with PBS, and twice with deionized water. For all wash steps in the remainder of the assay, wells were allowed to soak for 3 minutes at each wash step. Wells were then washed three times with wash buffer (PBS+0.05% Tween-20), and detection antibody (1:250) was added to all wells. Plates were incubated for two hours at room temperature. The detection antibody solution was discarded, and wells were washed three times with wash buffer. Avidin-HRP (1:250) was added to all wells, and plates were incubated for one hour at room temperature. Conjugate solution was discarded, and wells washed three times with wash buffer, then once with PBS. Substrate (3-amino-9-ethyl-carbazole, 0.1 M Acetate buffer, H2O2) was added to all wells, and spot development monitored (approximately 10 minutes). Substrate reaction was stopped by washing wells with water, and plates were allowed to air-dry overnight. The plates were analyzed on an ELISPOT reader (Cellular Technology Ltd.) with accompanying software. Spots corresponding to the number of IFNγ-producing T cells are reported as the absolute number of spots per number of T cells plated.

Flow Cytometry Analysis

MHC tetramers were purchased or manufactured on-site, and were used to measure peptide-specific T cell expansion in the immunogenicity assays. For the assessment, tetramer was added to $1 \times 10^5$ cells in PBS containing 1% FCS and 0.1% sodium azide (FACS buffer) according to manufacturer's instructions. Cells were incubated in the dark for 20 minutes at room temperature. Cell surface antibodies were then added to a final concentration suggested by the manufacturer, and the cells were incubated in the dark at 4° C. for 20 minutes. CD8 T cells were identified by presence of markers such as CD3 and CD8 and absence of markers such as CD4, CD11b, CD11c and CD19. The phenotype of cells was assessed using markers such as CD44, CD62L, KLRG1, CD127, PD-1, LAG-3 and TIM-3. Cells were washed with cold FACS buffer and resuspended in buffer containing 1% formaldehyde. Cells were acquired on a FACS Calibur (Becton Dickinson) instrument, and were analyzed by use of Cellquest software (Becton Dickinson). For analysis of tetramer positive cells, the lymphocyte gate was taken from the forward and side-scatter plots.

Example 5—CD107 Staining Assay

CD107a and b were expressed on the cell surface of CD8$^+$ T cells following activation with cognate peptide. The lytic granules of T cells have a lipid bilayer that contains lysosomal-associated membrane glycoproteins ("LAMPs"), which include the molecules CD107a and b. When cytotoxic T cells are activated through the T cell receptor, the membranes of these lytic granules mobilize and fuse with the plasma membrane of the T cell. The granule contents are released, and this leads to the death of the target cell. As the granule membrane fuses with the plasma membrane, C107a and b are exposed on the cell surface, and therefore are markers of degranulation. Because degranulation as measured by CD107a and b staining is reported on a single cell basis, the assay is used to functionally enumerate peptide-specific T cells. To perform the assay, peptide was added to HLA-A0201-transfected cells C1R to a final concentration of 20 μM, the cells were incubated for 1 hour at 37° C., and washed three times. $1 \times 10^5$ of the peptide-pulsed C1R cells were aliquoted into tubes, and antibodies specific for CD107a and b were added to a final concentration suggested by the manufacturer (Becton Dickinson). Antibodies were added prior to the addition of T cells in order to "capture" the CD107 molecules as they transiently appear on the surface during the course of the assay. $1 \times 10^5$ T cells from the immunogenicity culture were added next, and the samples were incubated for 4 hours at 37° C. The T cells were further stained for additional cell surface molecules such as CD8 and acquired on a FACS Calibur instrument (Becton Dickinson). Data was analyzed using the accompanying Cellquest software, and results were reported as the percentage of CD8$^+$/CD107a and b$^+$ cells.

Example 6—Cytotoxicity Assays

Cytotoxic activity was measured using a chromium release assay. Target T2 cells are labeled for 1 hour at 37° C. with Na$^{51}$Cr and washed $5 \times 10^3$ target T2 cells were then added to varying numbers of T cells from the immunogenicity culture. Chromium release was measured in supernatant harvested after 4 hours of incubation at 37° C. The percentage of specific lysis was calculated as:

Experimental release-spontaneous release/Total release-spontaneous release×100

Example 7—Enhanced CD8$^+$ T Cell Responses In Vivo Using Longmers and Shortmers Sequentially Vaccination with longmer peptides can induce both CD4$^+$ and CD8$^+$ T cell responses, depending on the processing and presentation of the peptides. Vaccination with minimal shortmer epitopes focuses on generating CD8$^+$ T cell responses, but does not require peptide processing before antigen presentation. As such, any cell can present the epitope readily, not just professional antigen-presenting cells (APCs). This may lead to tolerance of T cells that come in contact with healthy cells presenting antigens as part of peripheral tolerance. To circumvent this, initial immunization with longmers allows priming of CD8$^+$ T cells only by APCs that can process and present the peptides. Subsequent immunizations boosts the initial CD8$^+$ T cell responses (FIG. 3-12B).

In Vivo Immunogenicity Assays

Nineteen 8-12 week old female C57BL/6 mice (Taconic Biosciences) were randomly and prospectively assigned to treatment groups on arrival Animals were acclimated for three (3) days prior to study commencement. Animals were maintained on LabDiet™ 5053 sterile rodent chow and sterile water provided ad libitum. Animals in Group 1 served as vaccination adjuvant-only controls and were administered polyinosinic:polycytidylic acid (polyI:C) alone at 100 μg in a volume of 0.1 mL administered via subcutaneous injection (s.c.) on day 0, 7, and 14. Animals in Group 2 were administered 50 μg each of six longmer peptides (described below) along with polyI:C at 100 μg s.c. in a volume of 0.1 mL on day 0, 7 and 14 Animals in Group 3 were administered 50 μg each of six longmer peptides (described below) along with polyI:C at 100 μg s.c. in a volume of 0.1 mL on day 0 and molar-matched equivalents of corresponding shortmer peptides (described below) along with polyI:C at 100 μg s.c. in a volume of 0.1 mL on day 7 and 14. Animals were weighed and monitored for general health daily. Animals were euthanized by CO2 overdose at study completion Day 21, if an animal lost >30% of its body weight compared to weight at Day 0; or if an animal was found moribund. At sacrifice, spleens were harvested and processed into single-cell suspensions using standard protocols. Briefly, spleens were mechanical degraded through a 70 μM filter, pelleted, and lysed with ACK lysis buffer (Sigma) before resuspension in cell culture media.

Peptides

Six previously identified murine neoantigens were used based on their demonstrated ability to induce CD8$^+$ T cell responses. For each neoantigen, shortmers (8-11 amino acids) corresponding to the minimal epitope have been defined. Longmers corresponding to 20-27 amino acids surrounding the mutation were used.

TABLE 7 below shows the six peptide pairs (shortmer and longmers).

| Antigen | Sequence | Allele | Model |
|---|---|---|---|
| Alg8 | AVGITYTWTRLYA SVLTGSLVSKTKK (SEQ ID NO: 1357) | H-2Kb | T3 |
| Lama4 | IQKISFFDGFEVG FNFRTLQPNGLLF YYT (SEQ ID NO: 1358) | H-2Kb | T3 |
| Adpgk | GIPVHLELASMTN MELMSSIVHQQVF PT (SEQ ID NO: 1359) | H-2Db | MC38 |
| Reps1 | GRVLELFRAAQLA NDVVLQIMELCGA TR (SEQ ID NO: 1360) | H-2Db | MC38 |
| Irgq | KARDETAALLNSA VLGAAPLFVPPAD (SEQ ID NO: 1361) | H-2Db | MC38 |
| Obsl1 | REGVELCPGNKYE MRRHGTTHSLVIH D (SEQ ID NO: 1362) | H-2Db | B16F10 |
| Alg8-shortmer | ITYTWTRL (SEQ ID NO: 1363) | H-2Kb | T3 |
| Lama4-shortmer | VGFNFRTL (SEQ ID NO: 1364) | H-2Kb | T3 |
| Adpgk-shortmer | ASMTNMELM (SEQ ID NO: 1365) | H-2Db | MC38 |
| Resp1-shortmer | AQLANDVVL (SEQ ID NO: 1366) | H-2Db | MC38 |
| Irgq-shortmer | AALLNSAVL (SEQ ID NO: 1367) | H-2Db | MC38 |
| Obsl1-shortmer | LCPGNKYEM (SEQ ID NO: 1368) | H-2Db | B16F10 |

Example 8—Induction of Long-Term Antigen-Specific T-Cell Responses

A fundamental goal of many cancer vaccines is to elicit both short-term and long-term immunity. Short peptide vaccination may elicit ineffective long-term immunity because of suboptimal priming. To circumvent this, long peptides are using during the priming phase and short peptides are included at the boost phase to increase the T cell responses. Durability of responses can be determined by assessing T cell populations at least 60 days after initial vaccination (FIG. 13-22).

Eighteen 8-12 week old female C57BL/6 mice (Taconic Biosciences) were randomly and prospectively assigned to treatment groups on arrival Animals were acclimated for three (3) days prior to study commencement. Animals were maintained on LabDiet™ 5053 sterile rodent chow and sterile water provided ad libitum. Animals in Group 1 served as vaccination adjuvant-only controls and were administered polyinosinic:polycytidylic acid (polyI:C) alone at 100 µg in a volume of 0.1 mL administered via subcutaneous injection (s.c.) on day 0 and 21. Animals in Group 2 were administered 50 µg each of six longmer peptides (described below) along with polyI:C at 100 µg s.c. in a volume of 0.1 mL on day 0 and 21. Animals in Group 3 were administered 50 µg each of six longmer peptides and molar-matched equivalents of corresponding shortmer peptides along with polyI:C at 100 µg s.c. in a volume of 0.1 mL on day 0 and 21 Animals in Group 4 were administered 50 µg each of six longmer peptides along with polyI:C at 100 µg s.c. in a volume of 0.1 mL on day 0 and 50 µg each of six longmer peptides and molar-matched equivalents of corresponding shortmer peptides along with polyI:C at 100 µg s.c. in a volume of 0.1 mL on day 0. Animals were bled via retroorbital vein periodically throughout the study. Animals were weighed and monitored for general health daily Animals were euthanized by CO2 overdose at study completion Day 60, if an animal lost >30% of its body weight compared to weight at Day 0; or if an animal was found moribund. At sacrifice, spleens were harvested and processed into single-cell suspensions using standard protocols. Briefly, spleens were mechanical degraded through a 70 µM filter, pelleted, and lysed with ACK lysis buffer (Sigma) before resuspension in cell culture media.

TABLE 3 lists an exemplary method for immunization with peptides comprising neoepitopes (shortmers or longmers) for induction of antigen-specific T cell responses.

| Group | # mice | Adjuvant | Antigens (left side) | Antigens (right side) | Dose Schedule (days) | Bleeding | Immunization | End of study |
|---|---|---|---|---|---|---|---|---|
| 1 | 3 | (50 µg) Hiltonol (25 µg each side) | — | — | 0.21 | — | single | Day 60 |
| 2 | 5 | 50 µg Hiltonol (25 µg each side) | 10 µg each SLP Alg8 Reps1 Plod1 | 10 µg each SLP Lama4 Irgq Kif18b | 0.21 | 0, 7, 21, 28, 42 and 60 | single | Day 60 |
| 3 | 5 | 50 µg Hiltonol (25 µg each side) | (10 µg shortmers + 10 µg longmers) | (10 µg shortmers + 10 µg longmers) | 0.21 | 0, 7, 14, 21, 28, 42 and 60 | single | Day 60 |

TABLE 3-continued lists an exemplary method for immunization with peptides comprising neoepitopes (shortmers or longmers) for induction of antigen-specific T cell responses.

| Group | # mice | Adjuvant | Antigens (left side) | Antigens (right side) | Dose Schedule (days) | Bleeding | Immunization | End of study |
|---|---|---|---|---|---|---|---|---|
| 4 | 5 | 50 μg Hiltonol (25 μg each side) | Alg8 Reps1 Plod1 10 μg each (Prime - longmers) (Boost - longmers + shortmers) Alg8 Reps1 Plod1 | Lama4 Irgq Kif18b 10 μg each (Prime-longmers) (Boost - longmers + shortmers) Lama4 Irgq Kif18b | 0.21 | 0, 7, 14, 21, 28, 42 and 60 | single | Day 60 |

Figure 13:
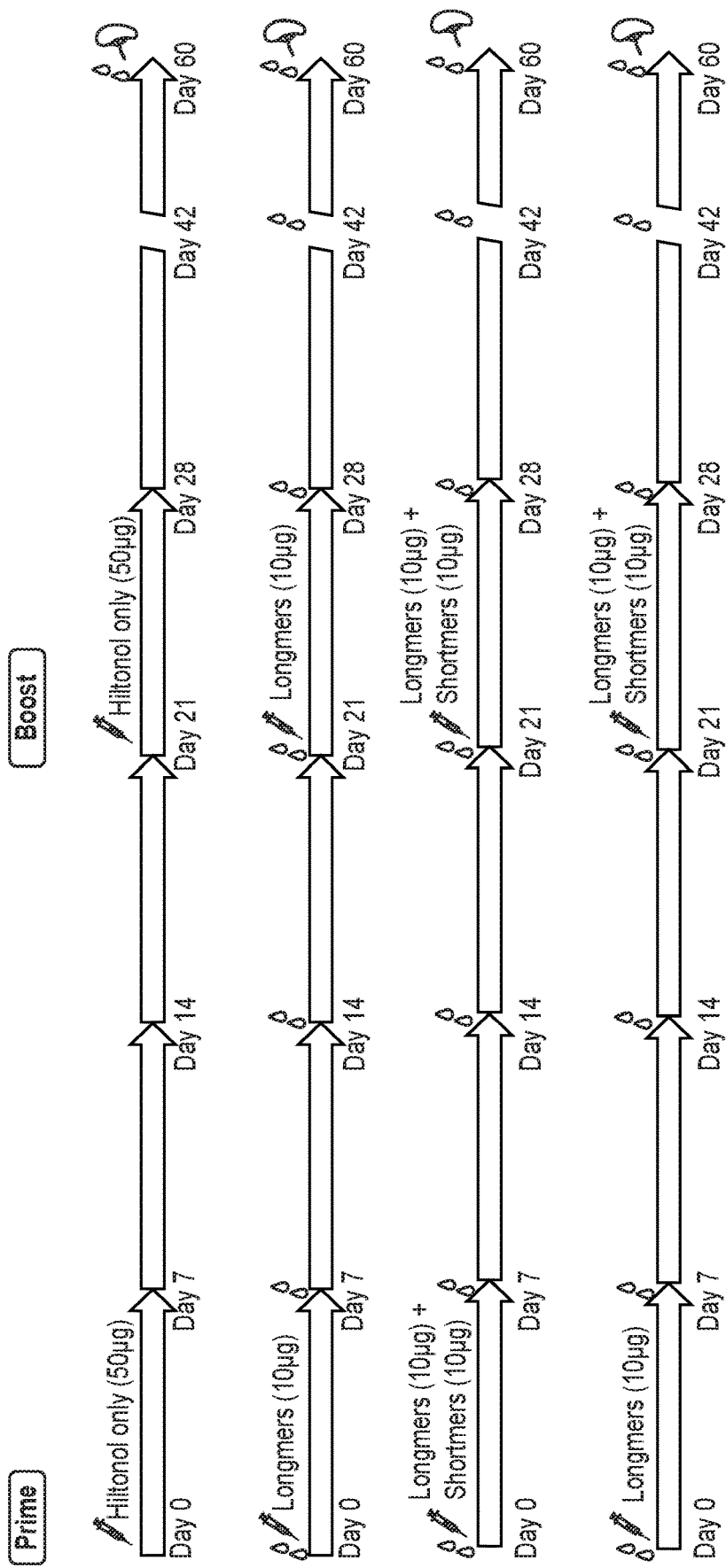
FIG. 13 illustrates an exemplary administration regimen for peptides comprising neoepitopes. A single boost dose is administered 21 days after the administration of a prime dose. Adjuvant hiltonol only is administered as prime dose and boost for control conditions (first panel). The administration regimen can comprise a prime and boost of longmers only (second panel), prime and boost of pooled mixture of longmers and shortmers (third panel), or prime dose of longmers and boost of longmers and shortmers (fourth panel).
Figure 14A:
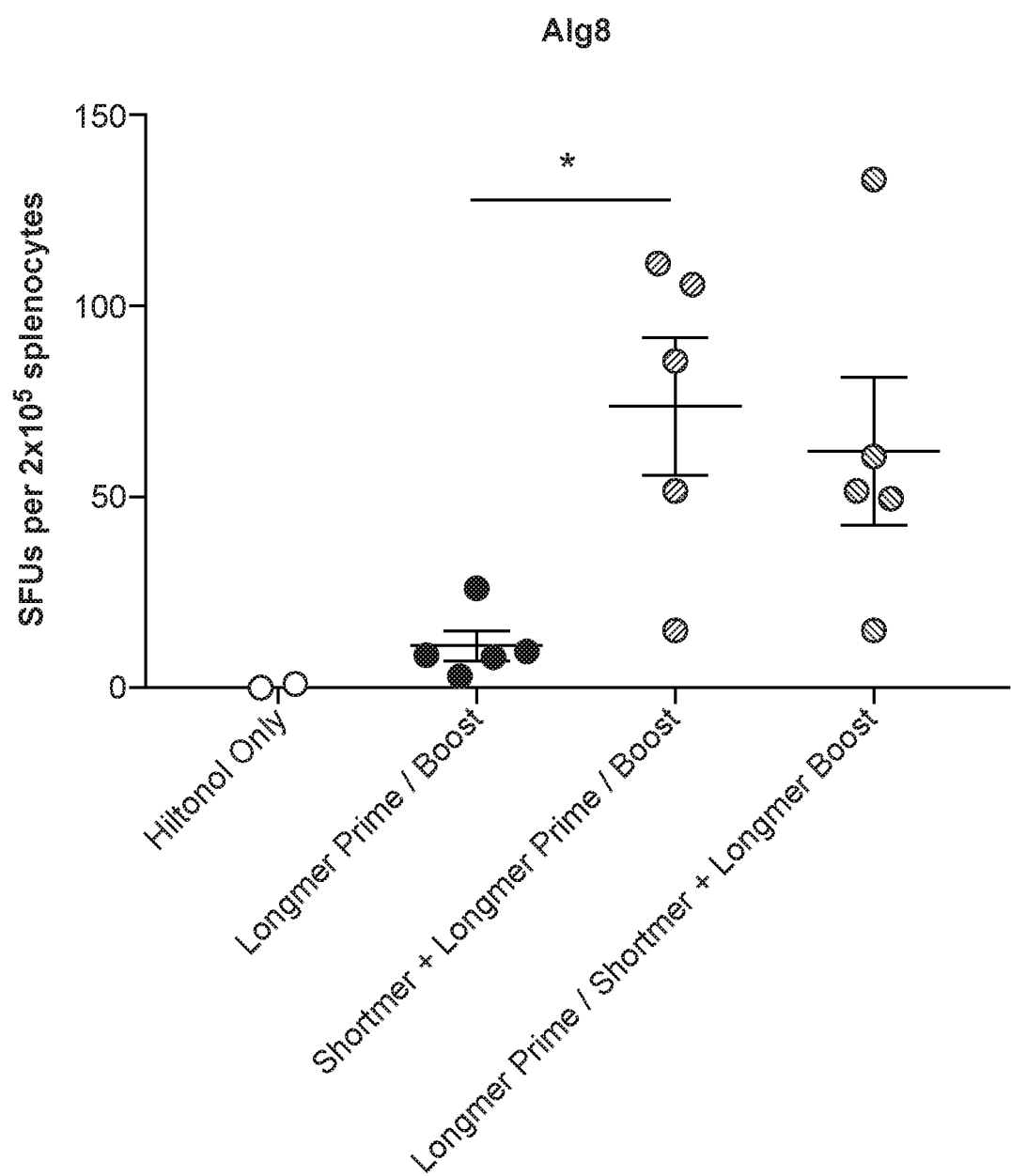
Figure 15A:
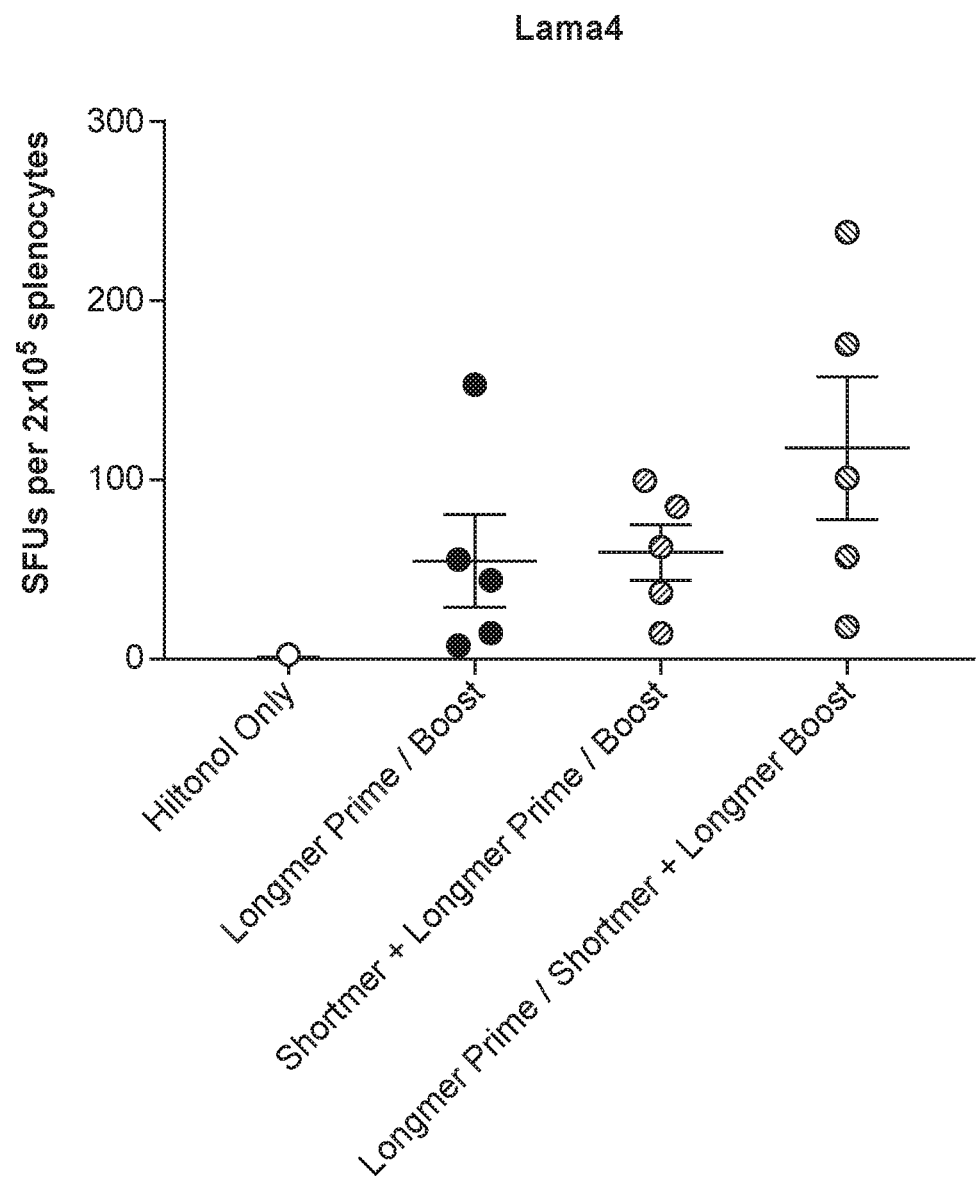
Figure 16A:
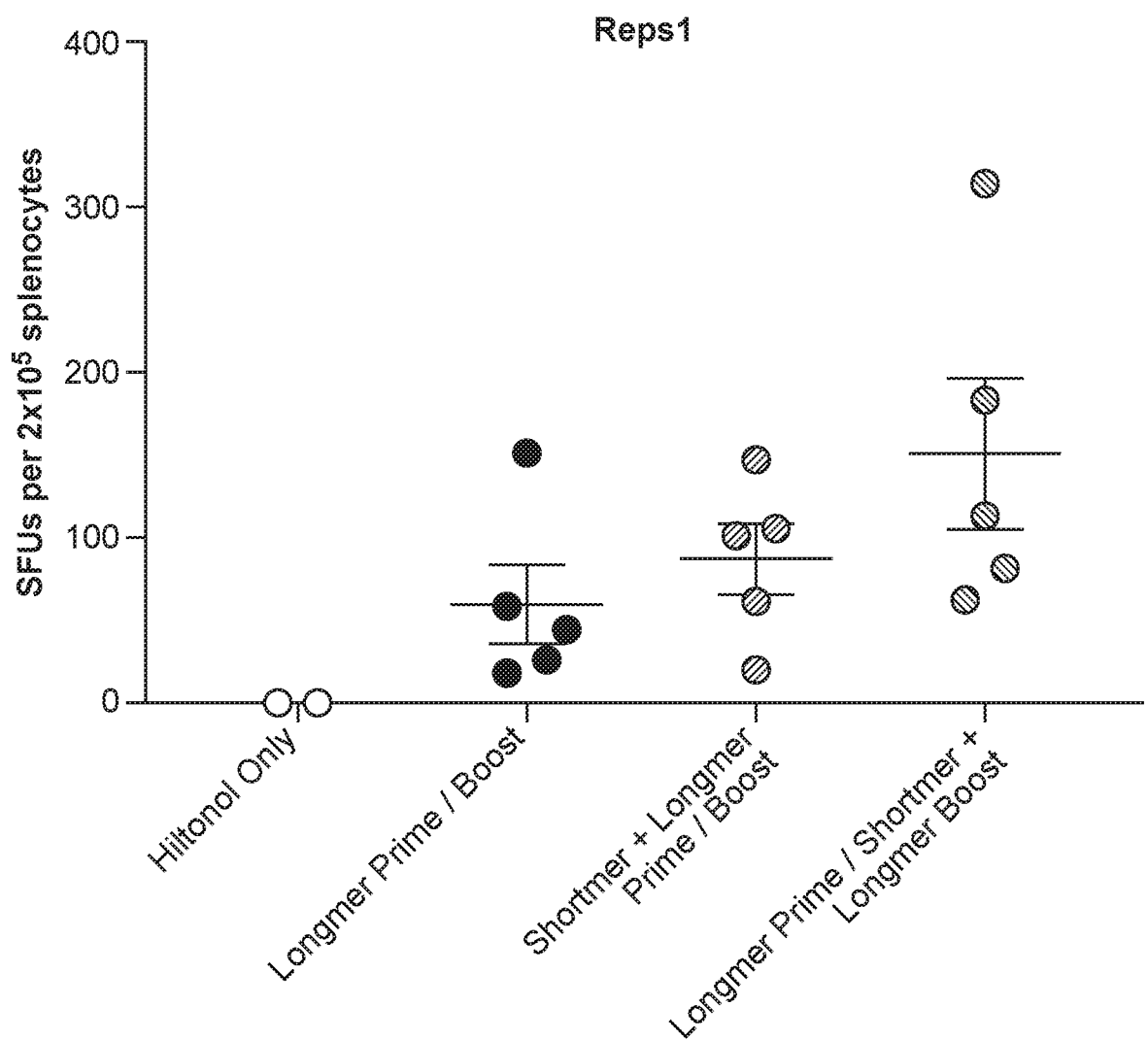
FIGS. 16A-16C show use of shortmers in boost increases immunogenicity of Reps1.
Figures 16B, 16C:
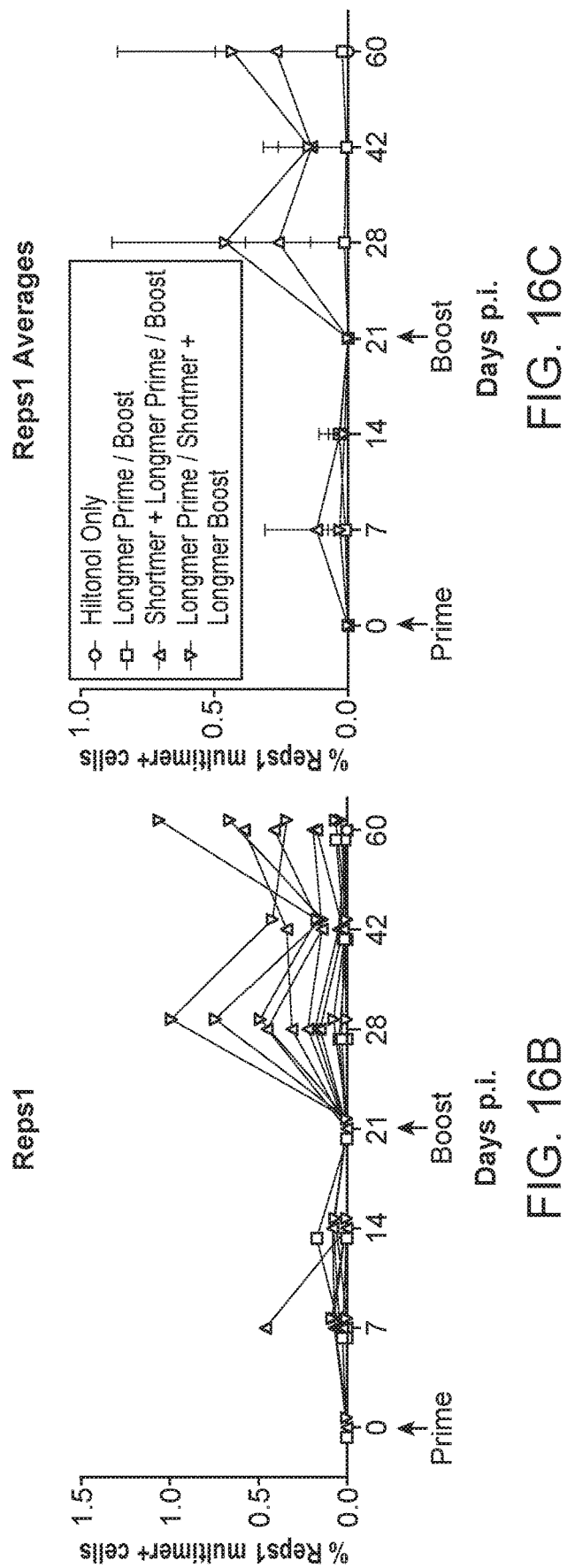
Figure 17A:
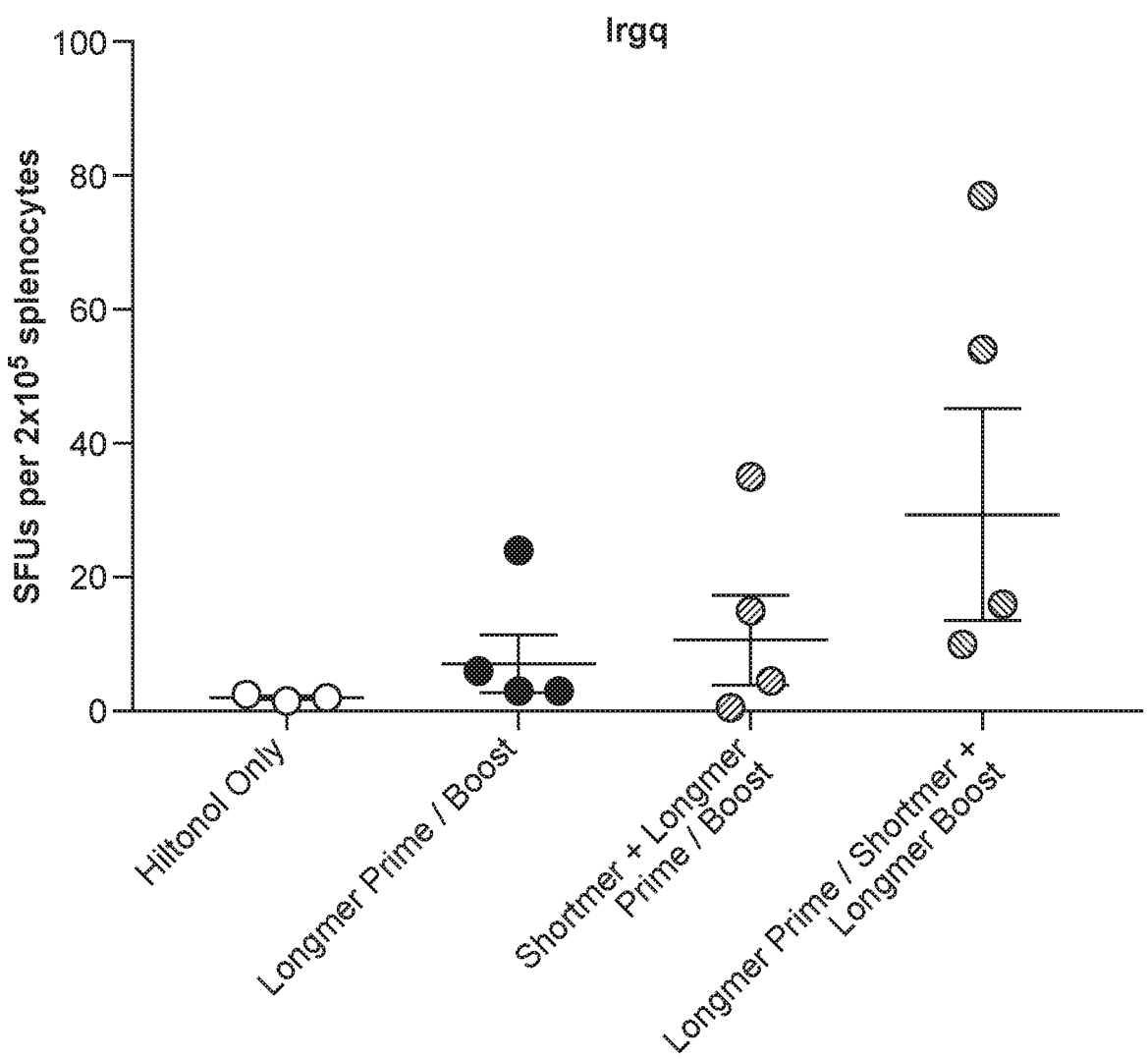
FIGS. 17A-17C show effect of use of shortmers in prime and boost on immunogenicity of Irgq. The graph shows increase in immunogenicity upon use of shortmers.
Figures 17B, 17C:
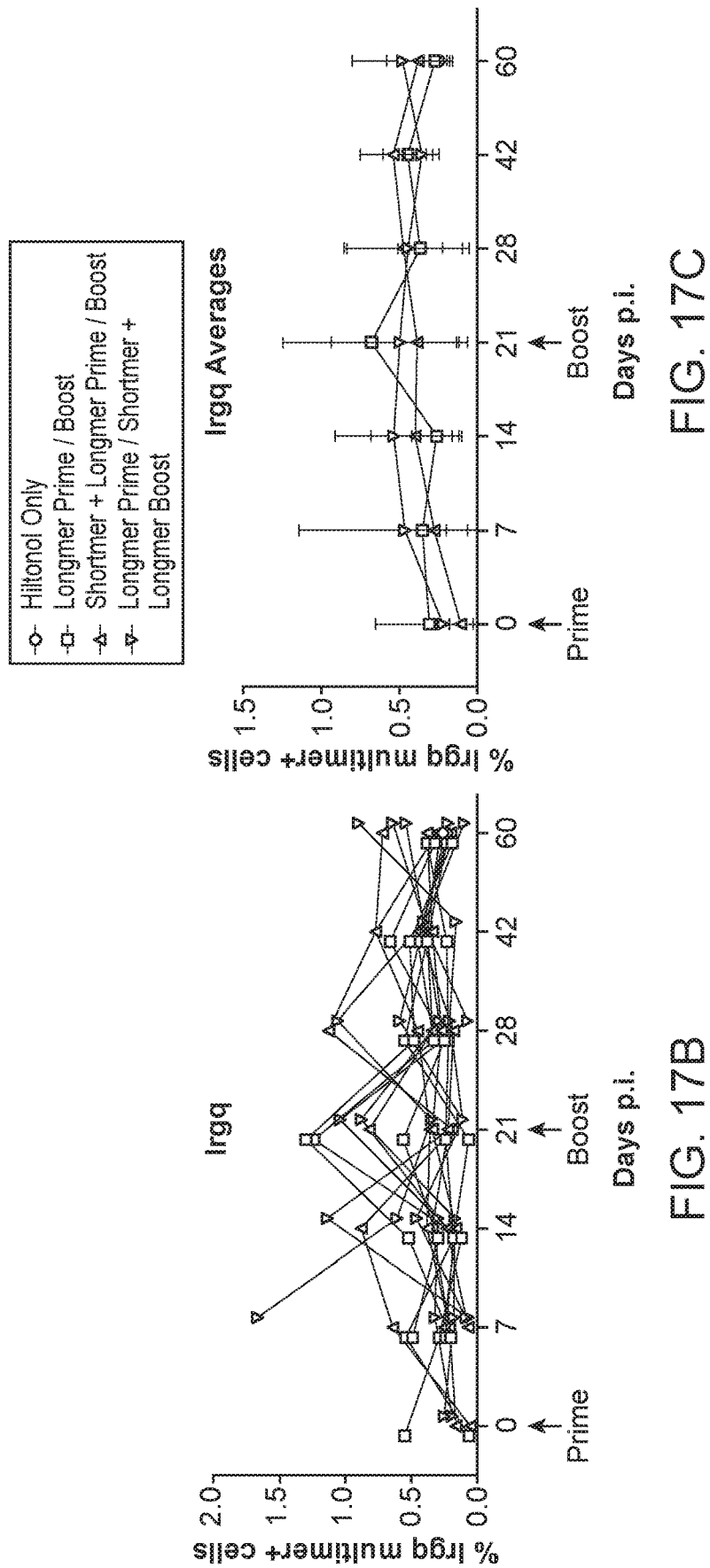
Figure 18:
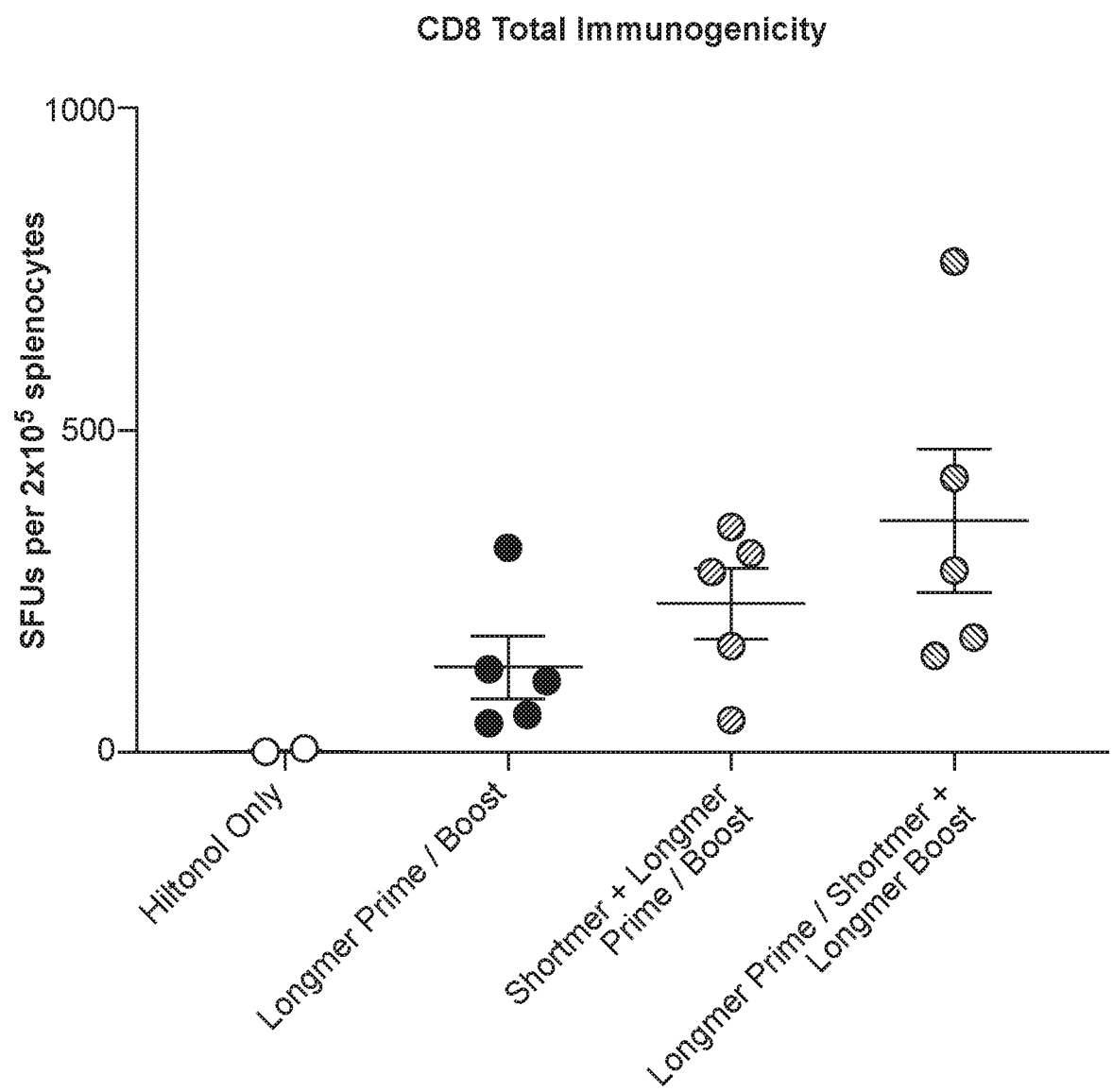
FIG. 18 shows a graph of splenocytes assayed for reactivity to specific antigens using an ELISpot Assay.
Figure 19:
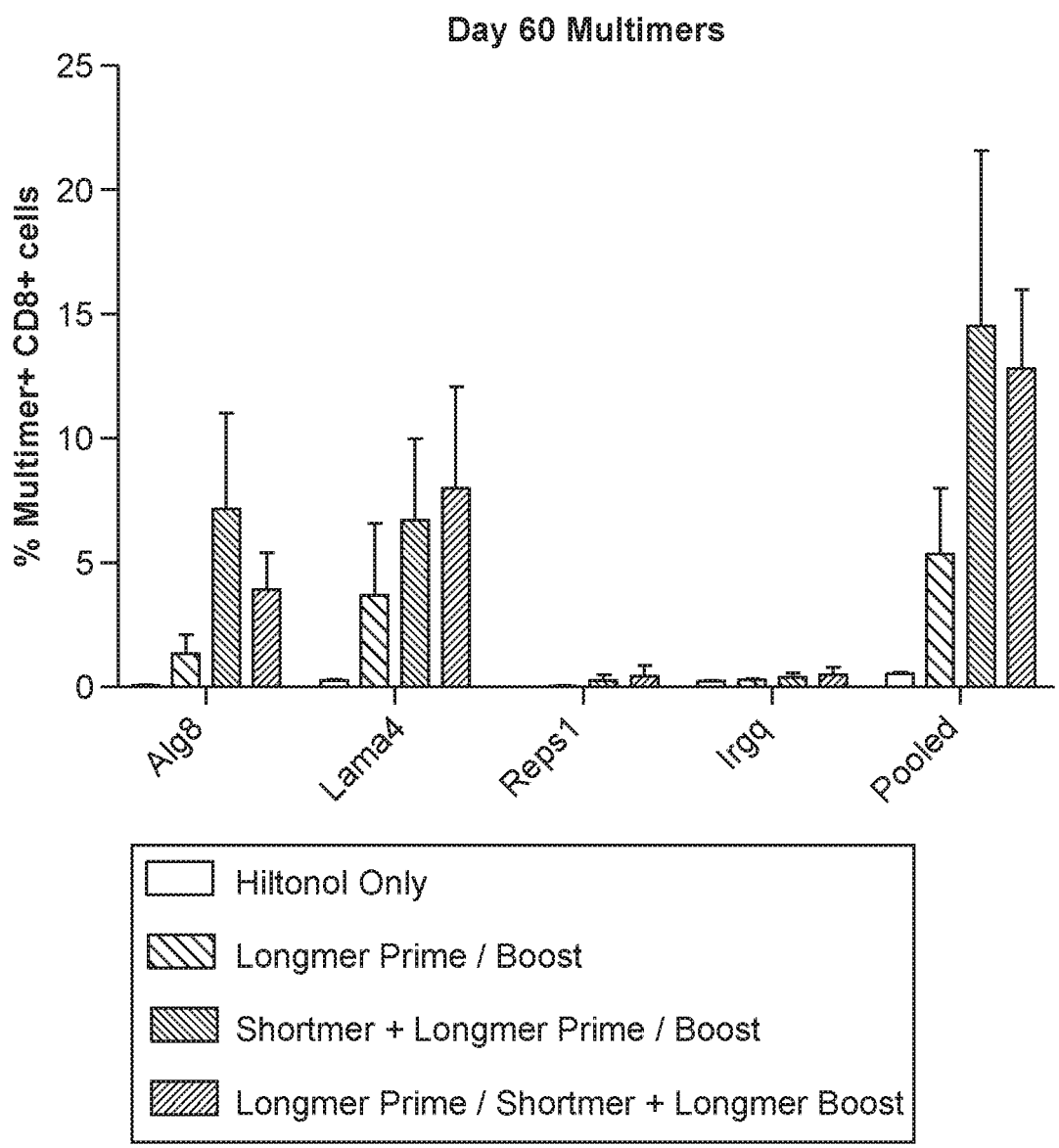
FIG. 19 shows % multimer+ T cells on day 60 after administration of a prime dose. Use of shortmers increases % multimer+ T cells on day 60.
Figure 21:
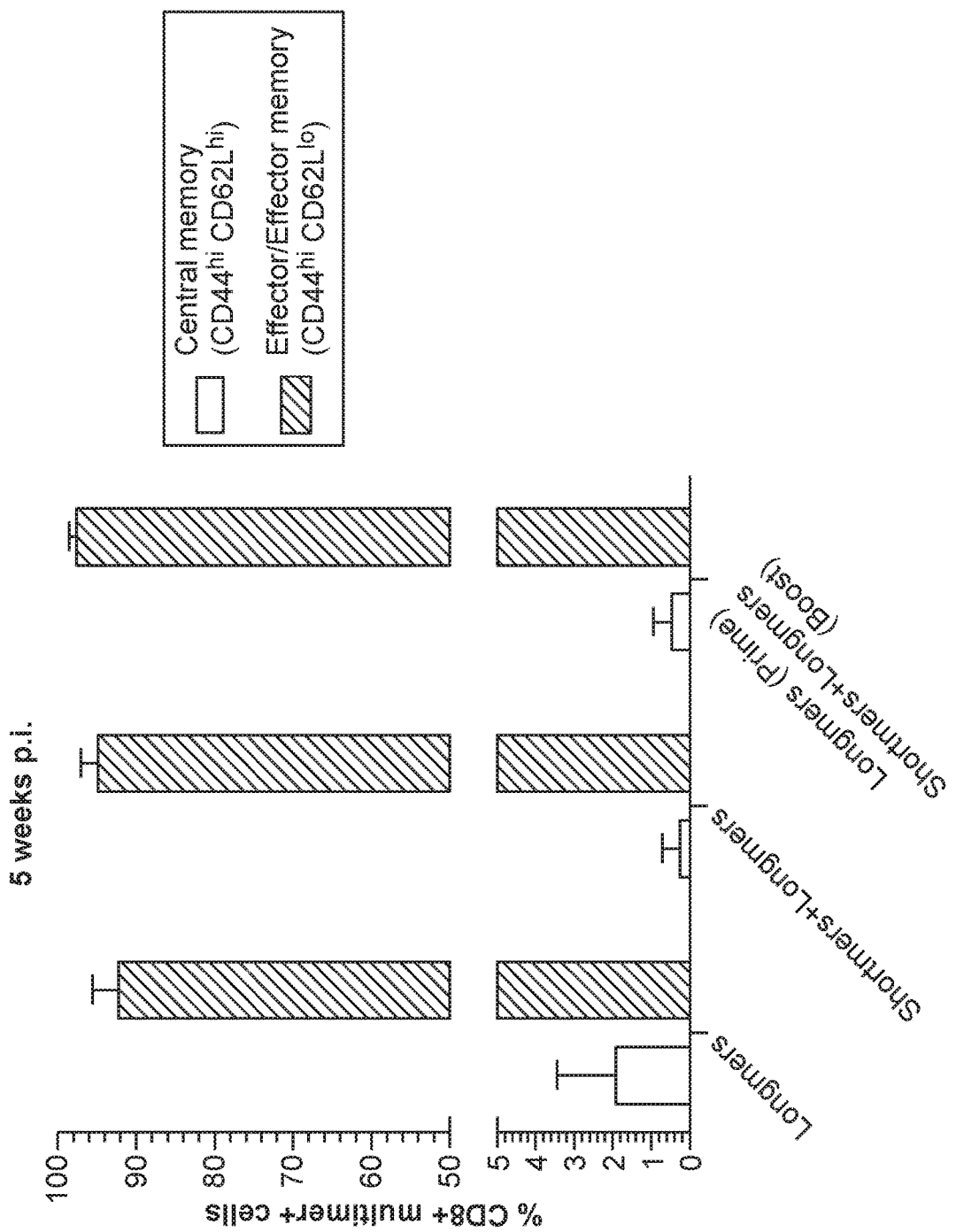
FIG. 21 show proportions of effector memory and central memory T cells 5 weeks after immunization according to the administration regimen depicted in FIG. 13.
Figure 22:
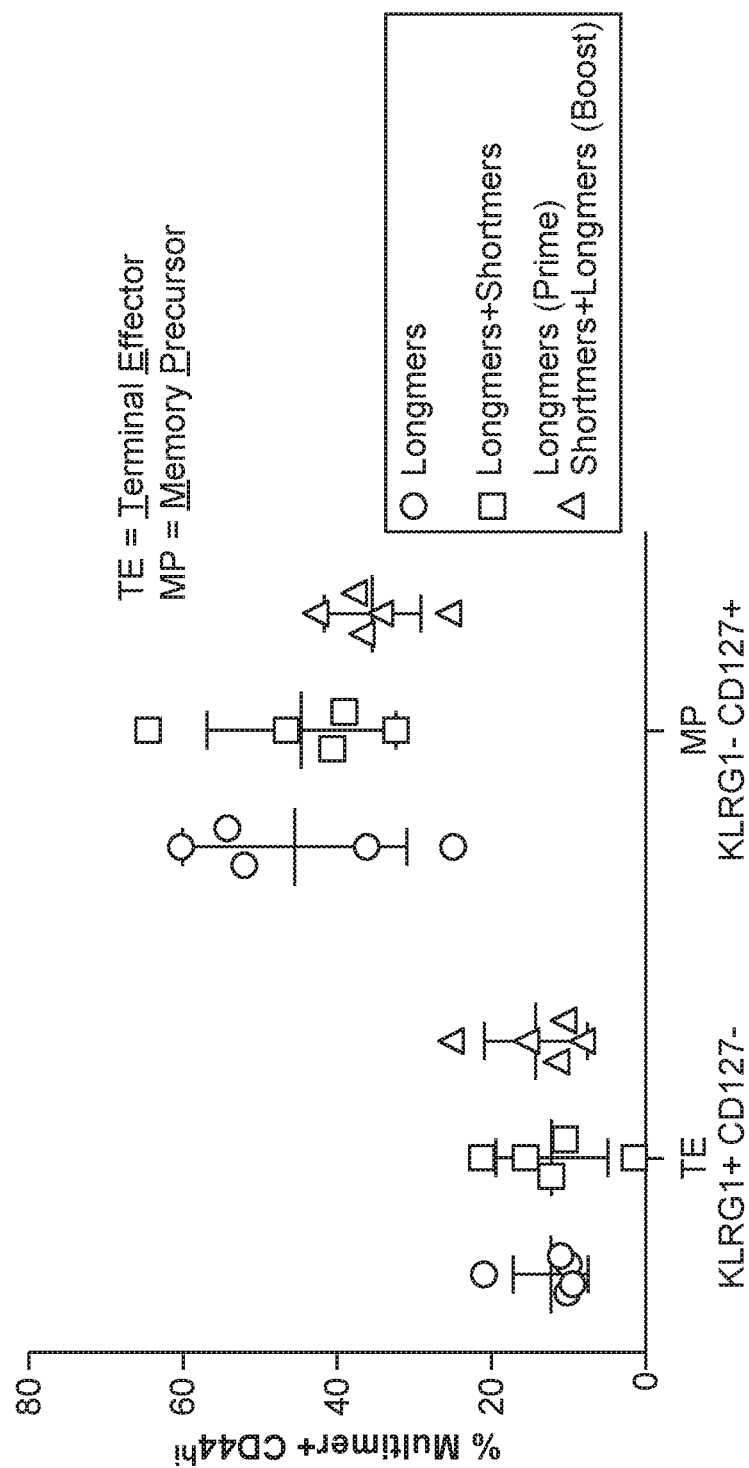
FIG. 22 show frequency of terminal effector cells and memory precursor at 5 weeks after immunization with prime and boost of longmers, prime and boost of shortmers and longmers, or a prime dose of longmers and boost of shortmers and longmers according to the administration regimen depicted in FIG. 13.
Figure 23:
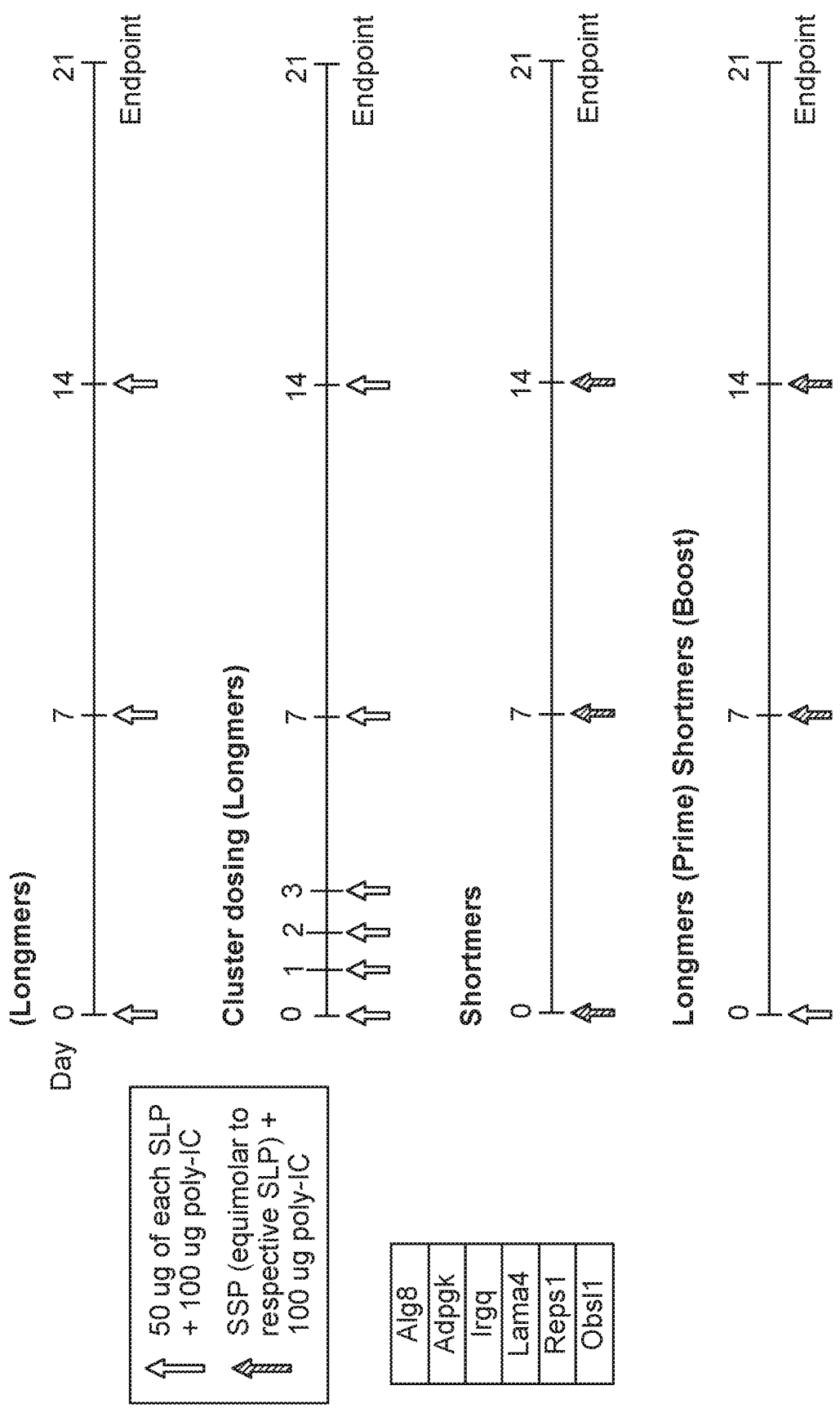
FIG. 23 illustrates an exemplary therapeutic administration regimen for peptides comprising neoepitopes. The administration regimen can comprise a prime dose and boost of longmers (first panel), a prime dose comprising cluster dosing with longmers and boost of longmers (second panel), a prime dose and boost of shortmers (third panel), a prime dose of longmers and boost of shortmers (fourth panel). A first boost is administered 7 days after the first prime dose (day 0). A second boost is administered 14 days after the first prime dose (day 0). Cluster dosing (second panel) can comprise multiple consecutive prime doses on day 1, day 2, and day 3 relative to first prime dose on day 0. The illustrated regimen is followed for FIGS. 24A-24D described below.

The administration regimen of Table 3 for the prime dose and boost are further described in FIG. 13. FIGS. 14A-22 described herein show induction of long-term antigen-specific T cell responses. The results also show inclusion of shortmers at prime and/or boost increases % Multimer+ cells as compared to use of longmers alone. Boosting at Day 21 increases % Multimer+ cells beyond the level observed after prime for most epitopes.

Example 9—Assess Memory Phenotype of Antigen-Specific CD8 T Cells

Splenocytes were obtained from mice immunized with peptides comprising neoepitopes (shortmers or longmers) on day 0 and day 21 according to method of Table 3. The splenocytes were obtained one week or 5 weeks post-immunization for analysis of memory populations.
Flow Cytometry Analysis MHC tetramers were purchased or manufactured on-site, and were used to measure peptide-specific T cell expansion in the immunogenicity assays. For the assessment, tetramer was added to $1\times10^5$ cells in PBS containing 1% FCS and 0.1% sodium azide (FACS buffer) according to manufacturer's instructions. Cells were incubated in the dark for 20 minutes at room temperature. Cell surface antibodies were then added to a final concentration suggested by the manufacturer, and the cells were incubated in the dark at 4° C. for 20 minutes. CD8 T cells were identified by presence of markers such as CD3 and CD8 and absence of markers such as CD4, CD11b, CD11c and CD19. The phenotype of cells was assessed using markers such as CD44, CD62L, KLRG1, CD127, PD-1, LAG-3 and TIM-3. Cells were washed with cold FACS buffer and resuspended in buffer containing 1% formaldehyde. Cells were acquired on a FACS Calibur (Becton Dickinson) instrument, and were analyzed by use of Cellquest software (Becton Dickinson). For analysis of tetramer positive cells, the lymphocyte gate was taken from the forward and side-scatter plots. CD8 T cell populations can be defined by surface markers, such as central memory ($CD44^{hi}CD62L^{hi}$), effector/effector memory ($CD44^{hi}CD62L^{lo}$), terminal effector ($CD44^{hi}KLRG1+CD127-$) or memory precursor ($CD44^{hi}KLRG1-CD127+$).

Example 10—Methods for Prevention of Tumor Growth by Inducing Anti-Tumor Immunity To assay the functionality of antigen-specific T cells induced by vaccination, a prophylactic tumor model can be utilized. In brief, mice were vaccinated in different experimental groups and then challenged with tumor cells on the same day. The ability to slow or prevent the outgrowth of tumor was used as a measure of the functionality of the T cells elicited by vaccination (FIGS. 25-33E).

Fifty-one 8-12 week old female C57BL/6 mice (Taconic Biosciences) were randomly and prospectively assigned to treatment groups on arrival Animals were acclimated for three (3) days prior to study commencement. Animals were maintained on LabDiet™ 5053 sterile rodent chow and sterile water provided ad libitum. Animals in Group 1 served as untreated controls Animals in Group 2 were administered 50 μg each of irrelevant peptides (i.e., peptides for mutations not present in subsequent tumor challenge) along with polyI:C at 100 μg s.c. in a volume of 0.1 mL on day −21 and −7 Animals in Group 3 were administered 50 μg each of three relevant longmer peptides (Reps1, Adpgk, Irgq) along with polyI:C at 100 μg s.c. in a volume of 0.1 mL on day −21 and −7 Animals in Group 4 were administered molar-matched shortmer peptides (Reps1, Adpgk, Irgq) along with polyI:C at 100 μg s.c. in a volume of 0.1 mL on day −21 and −7 Animals in Group 5 were administered 50 μg each of three longmer peptides (Reps1, Adpgk, Irgq) and molar-matched shortmer peptides (Reps 1, Adpgk, Irgq) along with polyI:C at 100 μg s.c. in a volume of 0.1 mL on day −21 and −7. On day 0, mice were implanted with $2\times10^5$ MC38 tumor cells subcutaneously. Animals were bled via retroorbital vein periodically throughout the study. Animals were weighed and monitored for general health daily. Animals were euthanized by CO2 overdose if tumors reached 2000 $mm^3$, if tumors ulcerated, if an animal lost >30% of its body weight compared to weight at Day 0; or if an animal was found moribund. At sacrifice, spleens were harvested and processed into single-cell suspensions using standard protocols. Briefly, spleens were mechanical degraded through a 70 μM filter, pelleted, and lysed with ACK lysis buffer (Sigma) before resuspension in cell culture media.

TABLE 4 lists an exemplary method for administration of peptides comprising neoepitopes (longmers or shortmers) for inducing anti-tumor immunity.

| Group | # of Mice | Treatment | Antigens | Dose (s.c left tail base) | Tumor (s.c right flank) | Schedule |
|---|---|---|---|---|---|---|
| 1 | 9 | Untreated | N/A | N/A | MC38, $2 \times 10^5$ | Day - 21, Day - 7 (immunization) Day 0 (tumor implantation) Day 30 (End of study) Blood, spleens collected |
| 2 | 8 | Irrelevant peptide + adjuvant | Obsl1 (B16) + Hiltonol | 10 ug/peptide 50 ug Hiltonol | | |
| 3 | 8 | Longmers + adjuvant | Adpgk, Reps1, Irgq + Hiltonol | 10 ug/peptide 50 ug Hiltonol | | |
| 4 | 8 | Shortmers + adjuvant | Adpgk, Reps1, Irgq + Hiltonol | 10 ug/peptide 50 ug Hiltonol | | |
| 5 | 8 | Mixed longmers & shortmers + adjuvant | Adpgk, Reps1, Irgq + Hiltonol | 10 ug/peptide 50 ug Hiltonol | | |

Figure 25:
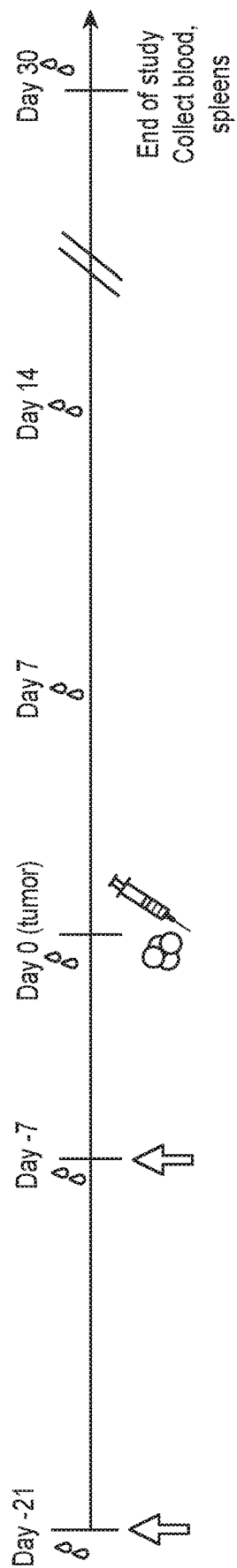
FIG. 25. Illustrates exemplary administration regimen for peptides comprising neoepitopes for prevention of tumor growth and survival. The administration regimen can comprise a prime dose 21 days before challenge with tumor cells (day 0) and a boost dose 7 before challenge with tumor cells on day 0. The illustrated administration regimen is followed for FIGS. 26A-33E described below.
Figures 26A, 26B:
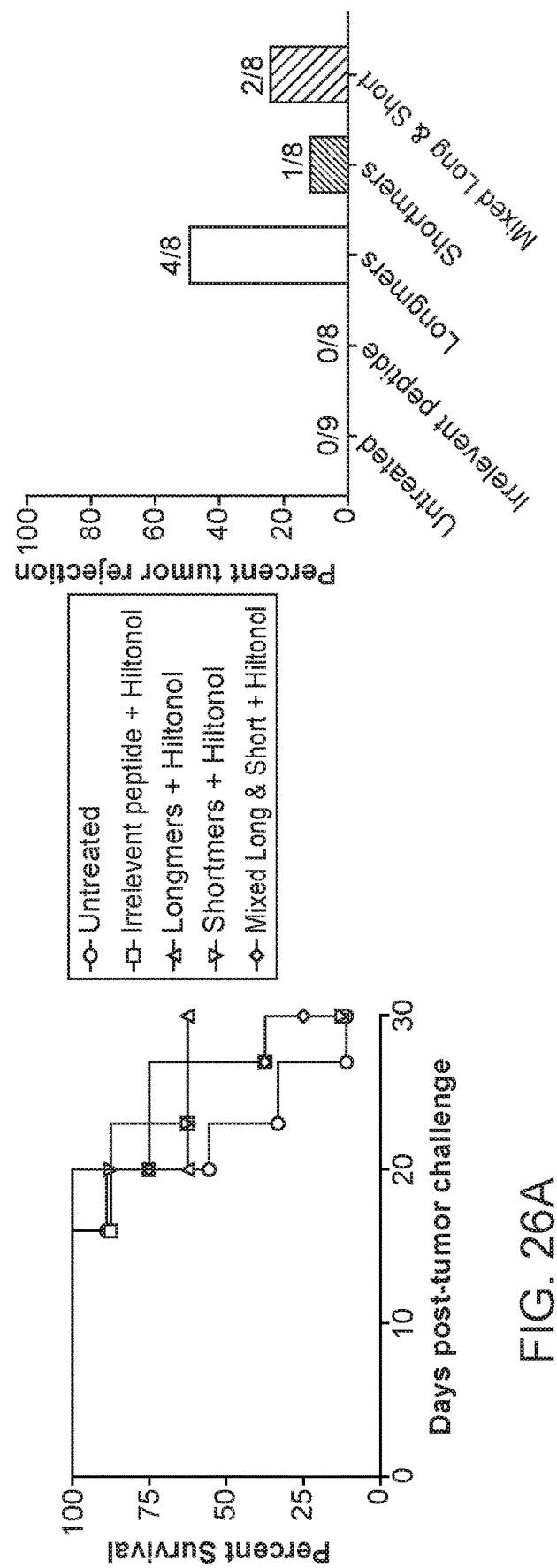
FIG. 26A illustrates percent survival at 10, 20, and 30 days post challenge with tumor cells after prophylactic administration regimen depicted in FIG. 25. The graph indicates administration of longmer at prime and boost increases survival.
FIG. 26B is a graph of number of mice showing tumor rejection after treatment with a prime and boost dose of longmers, prime and boost dose of shortmers, or prime and boost dose of longmers and shortmers according to the regimen depicted in FIG. 25. The graph indicates administration of longmer at prime and boost increases tumor rejection.
Figures 28A, 28B:
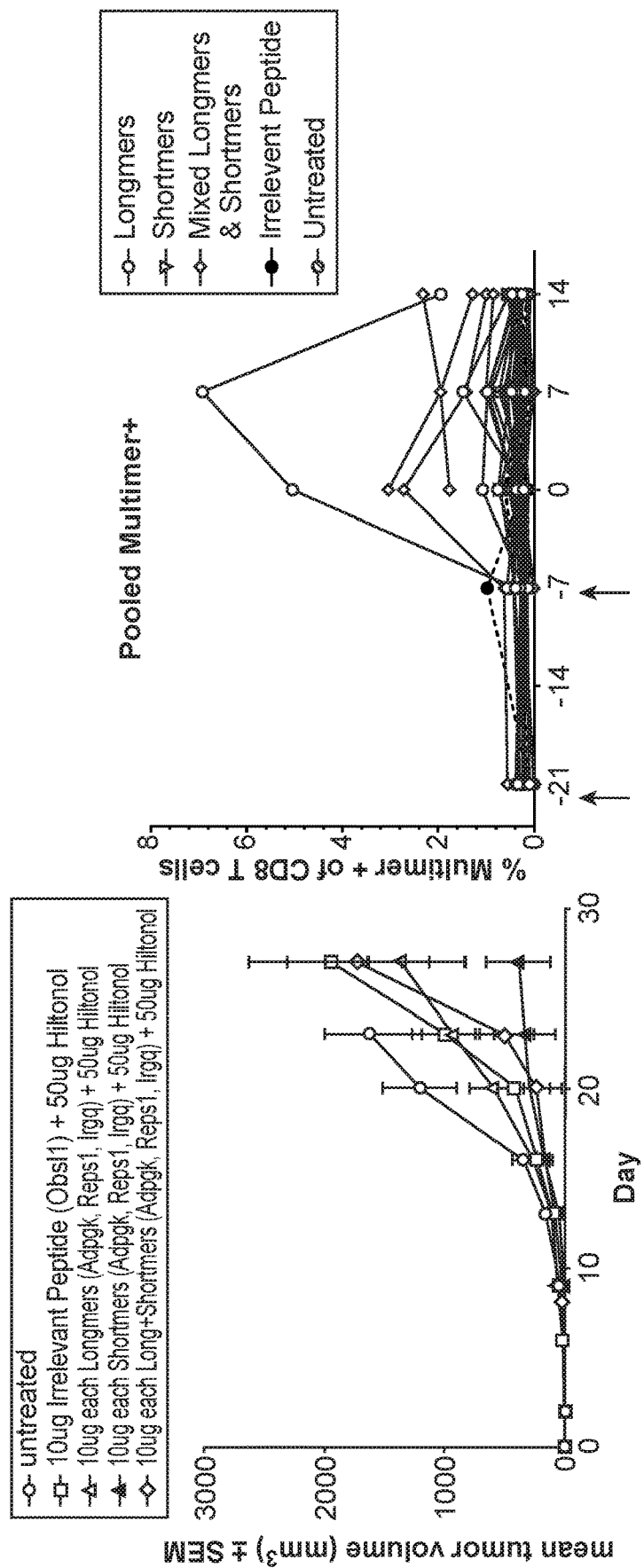
FIG. 28A shows average measurements of tumor volume.
FIG. 28B shows T cell responses are higher in mice treated with longmers at prime and boost.
Figure 30A:
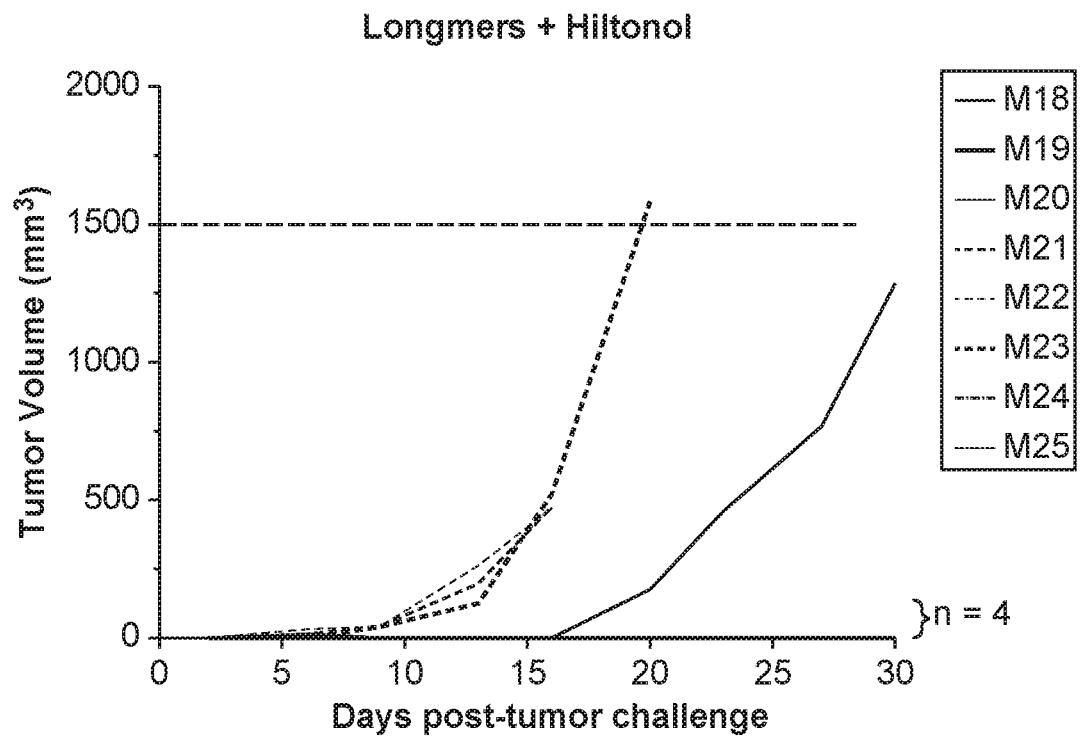
FIG. 30A shows measurements of tumor volume in mice prophylactically treated with longmers at prime and boost according to the regimen in FIG. 25.
Figure 30B:
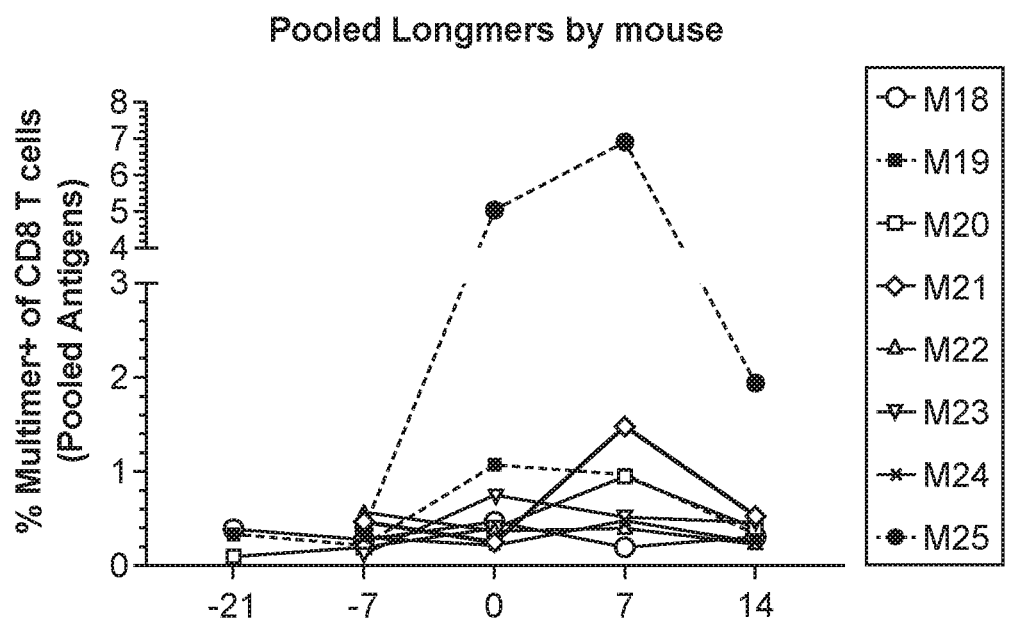
FIG. 30B shows T cell responses in mice prophylactically treated with longmers at prime and boost according to the regimen in FIG. 25.
Figure 31A:
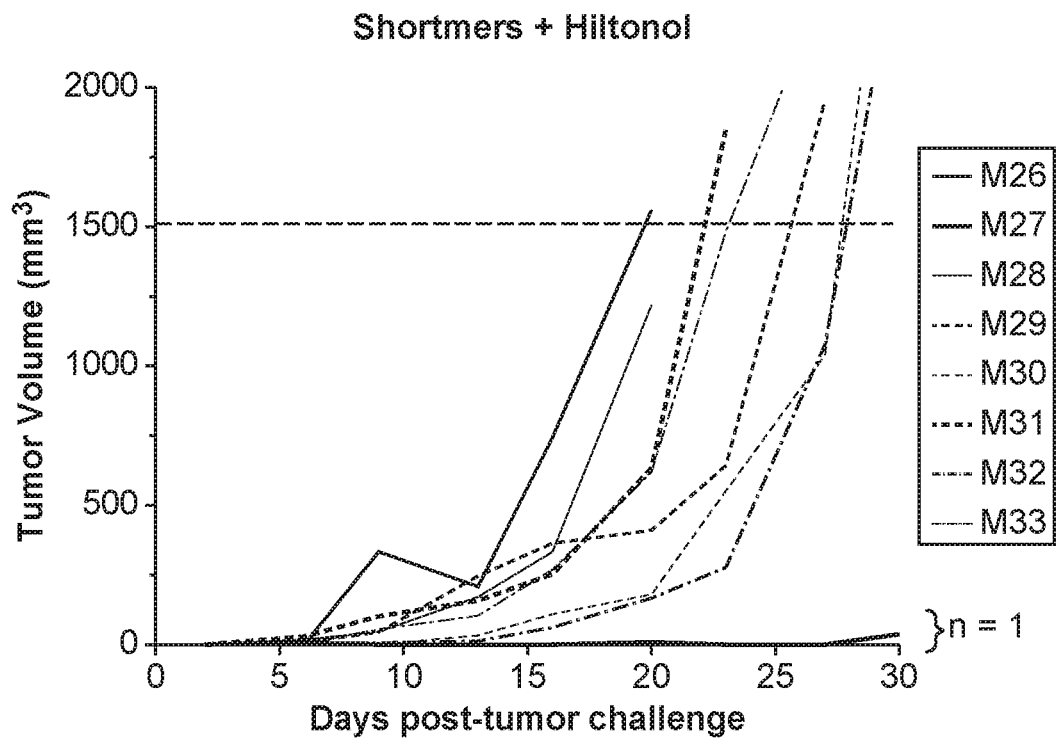
FIG. 31A shows measurements of tumor volume in mice prophylactically treated with shortmers at prime and boost according to the regimen in FIG. 25.
Figure 31B:
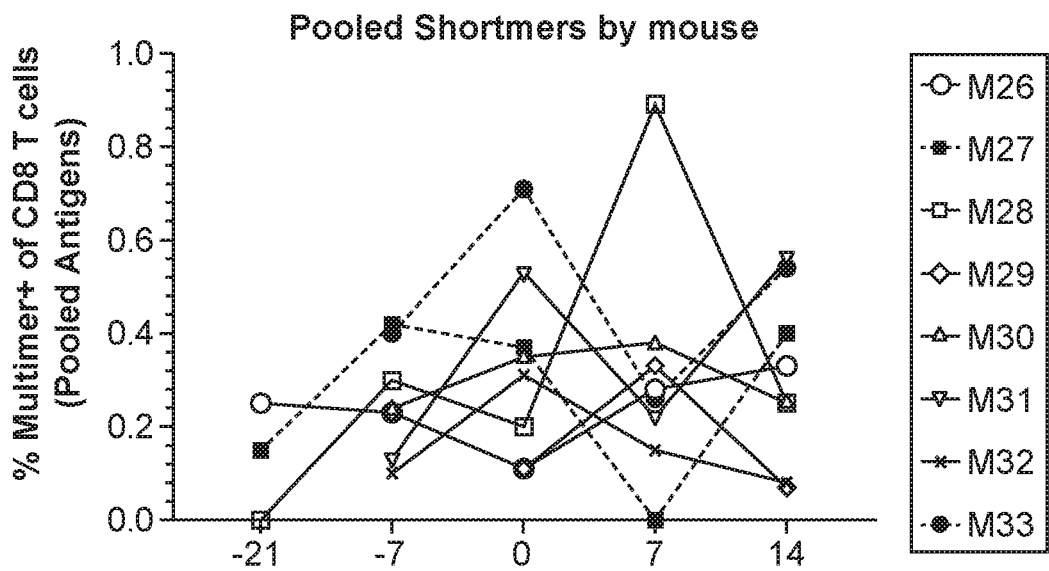
FIG. 31B shows T cell responses in mice prophylactically treated with shortmersat prime and boost according to the regimen in FIG. 25.
Figure 32A:
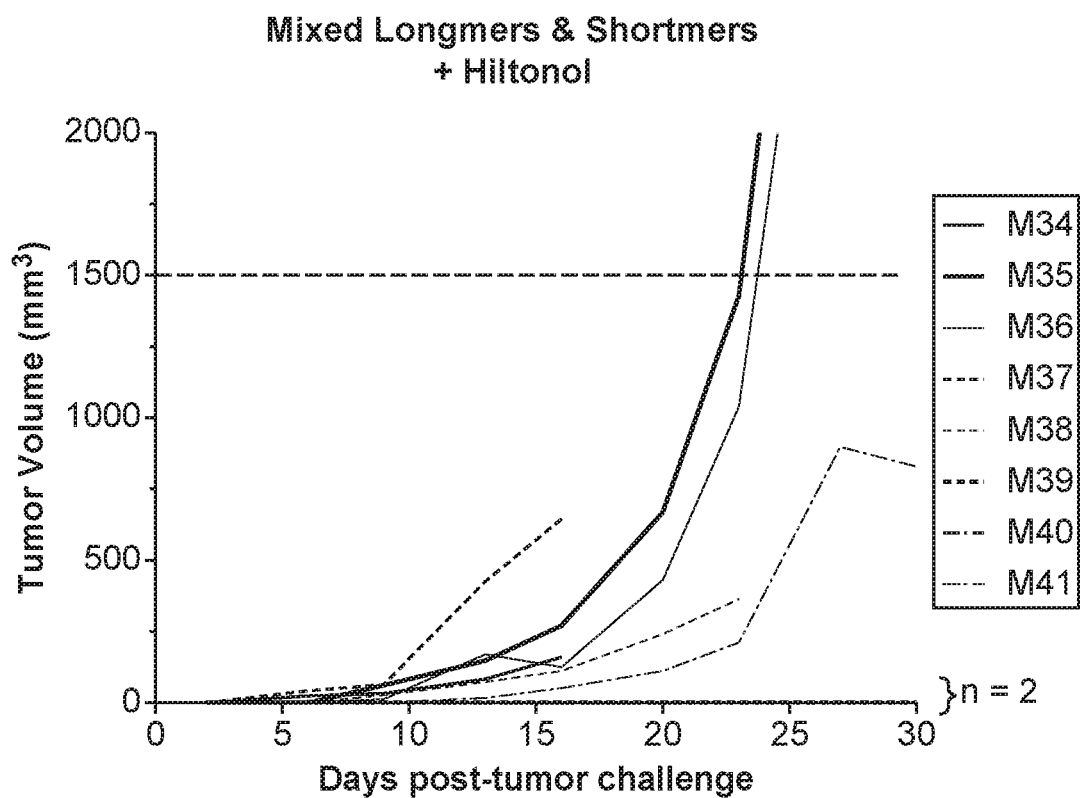
FIG. 32A shows measurements of tumor volume in mice prophylactically treated with pooled mixture of longmers and shortmers at prime and boost according to the regimen in FIG. 25.
Figure 32B:
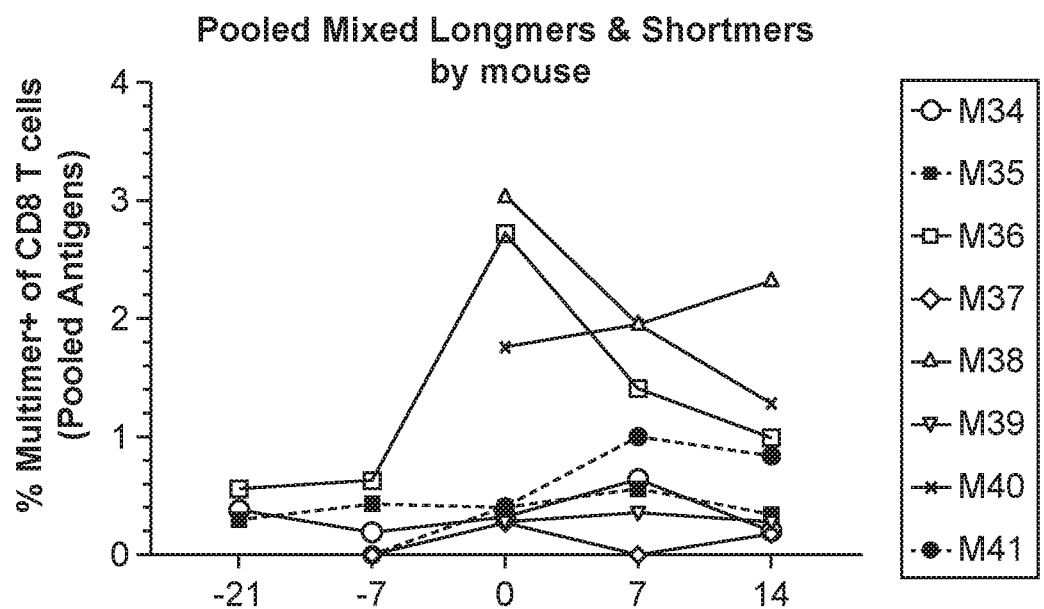
FIG. 32B shows T cell responses in mice prophylactically treated with pooled mixture of longmers and shortmers at prime and boost according to the regimen in FIG. 25.
Figure 33A:
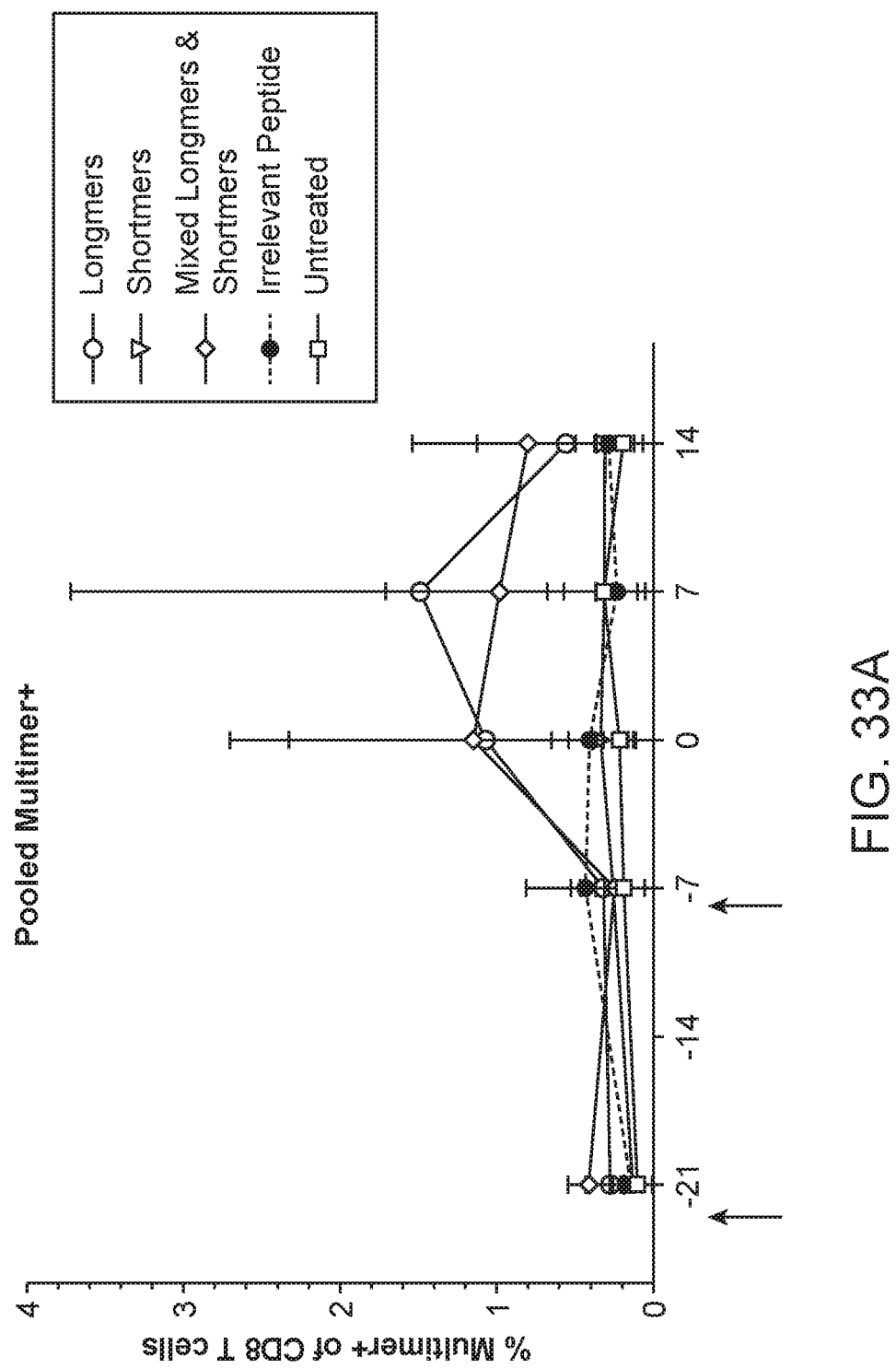
FIG. 33A-33E shows frequency of T cell responses specific for percent pooled multimer+ cells (FIG. 33A), response specific to Reps1 (FIG. 33B), Adpgk (FIG. 33C), Irgq (FIG. 33D), and tumor irrelevant antigen Obsl1 (FIG. 33E) in mice treated according to regimen in FIG. 25.
Figure 33B:
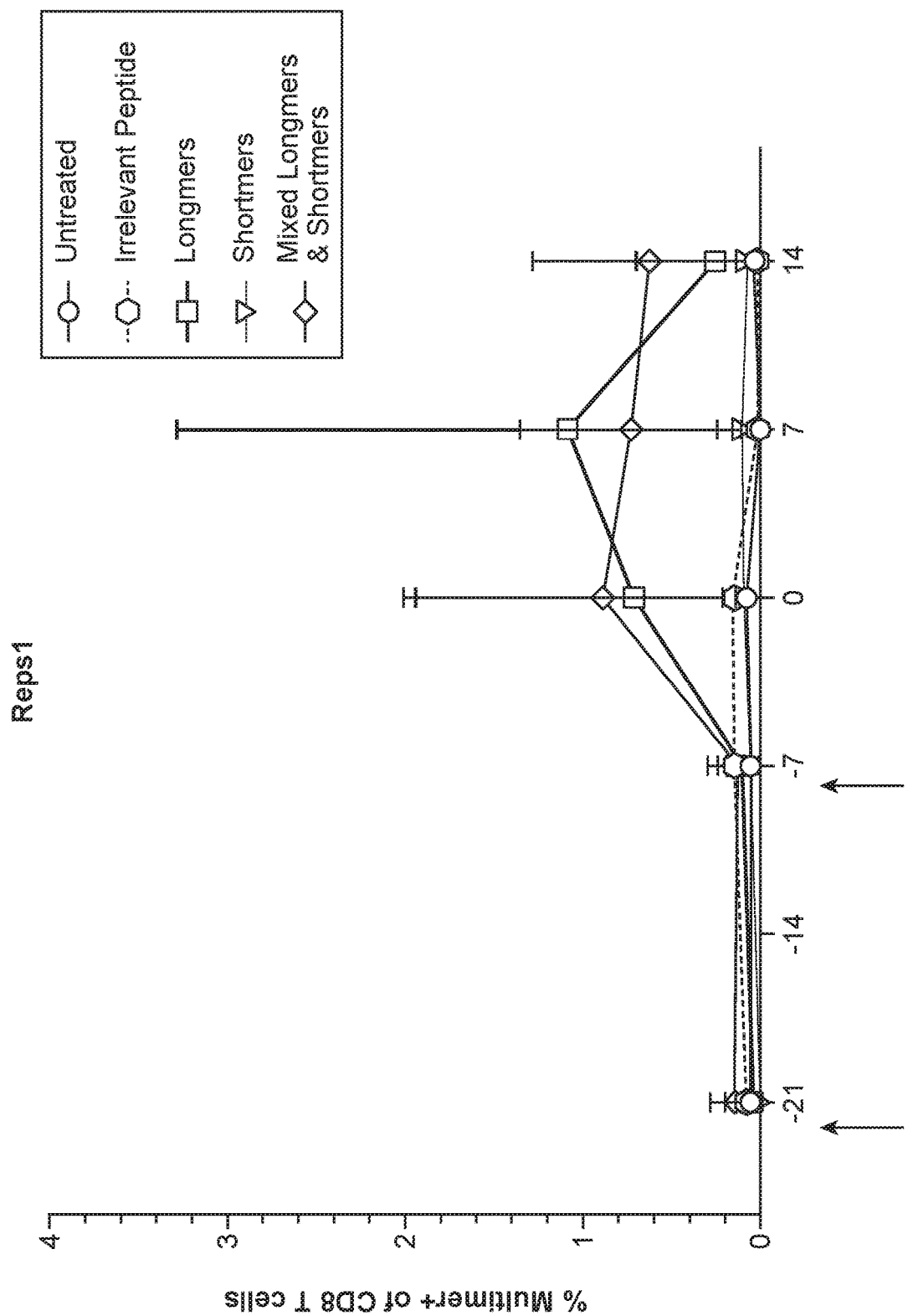
Figure 33C:
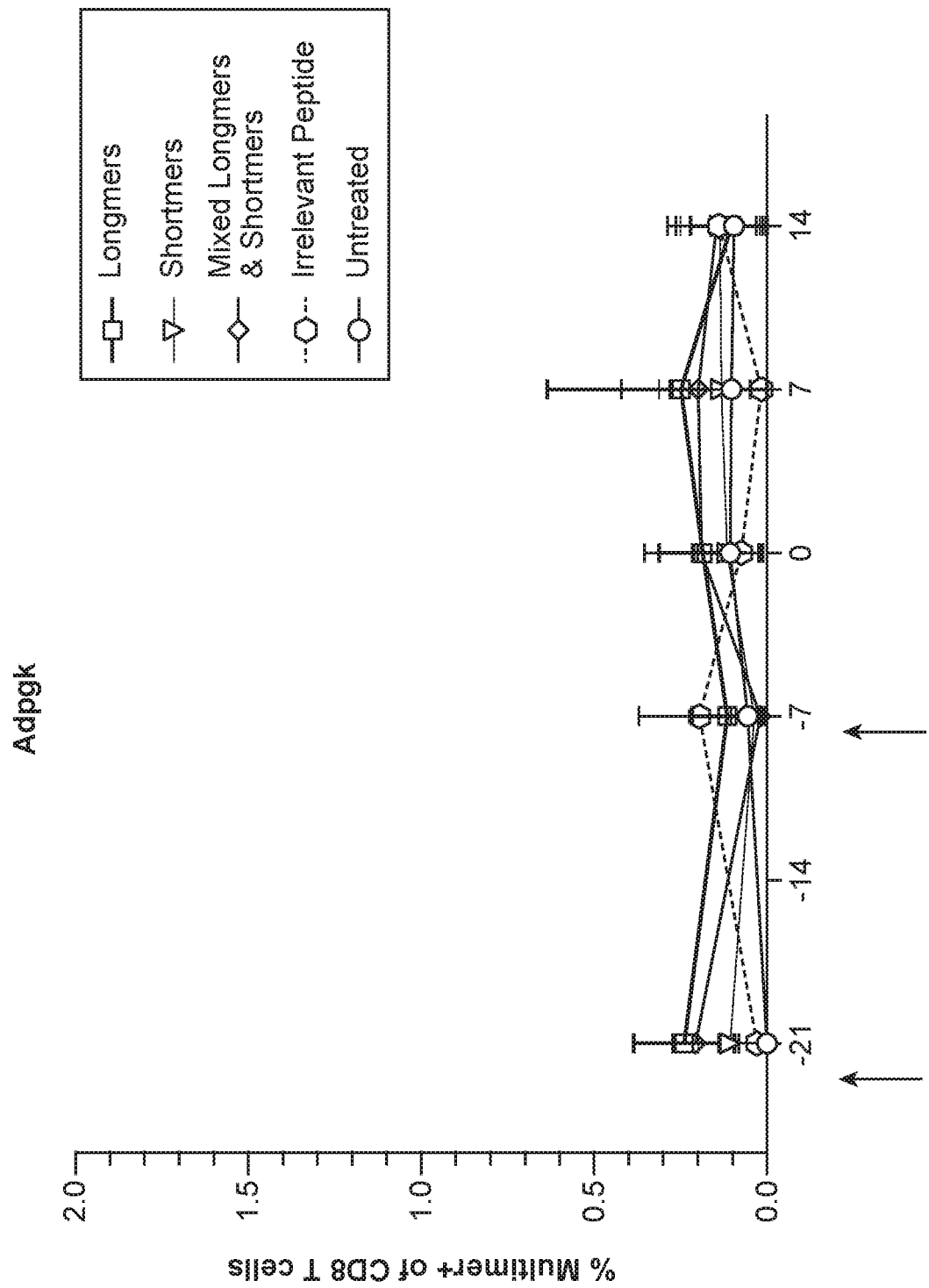
Figure 33D:
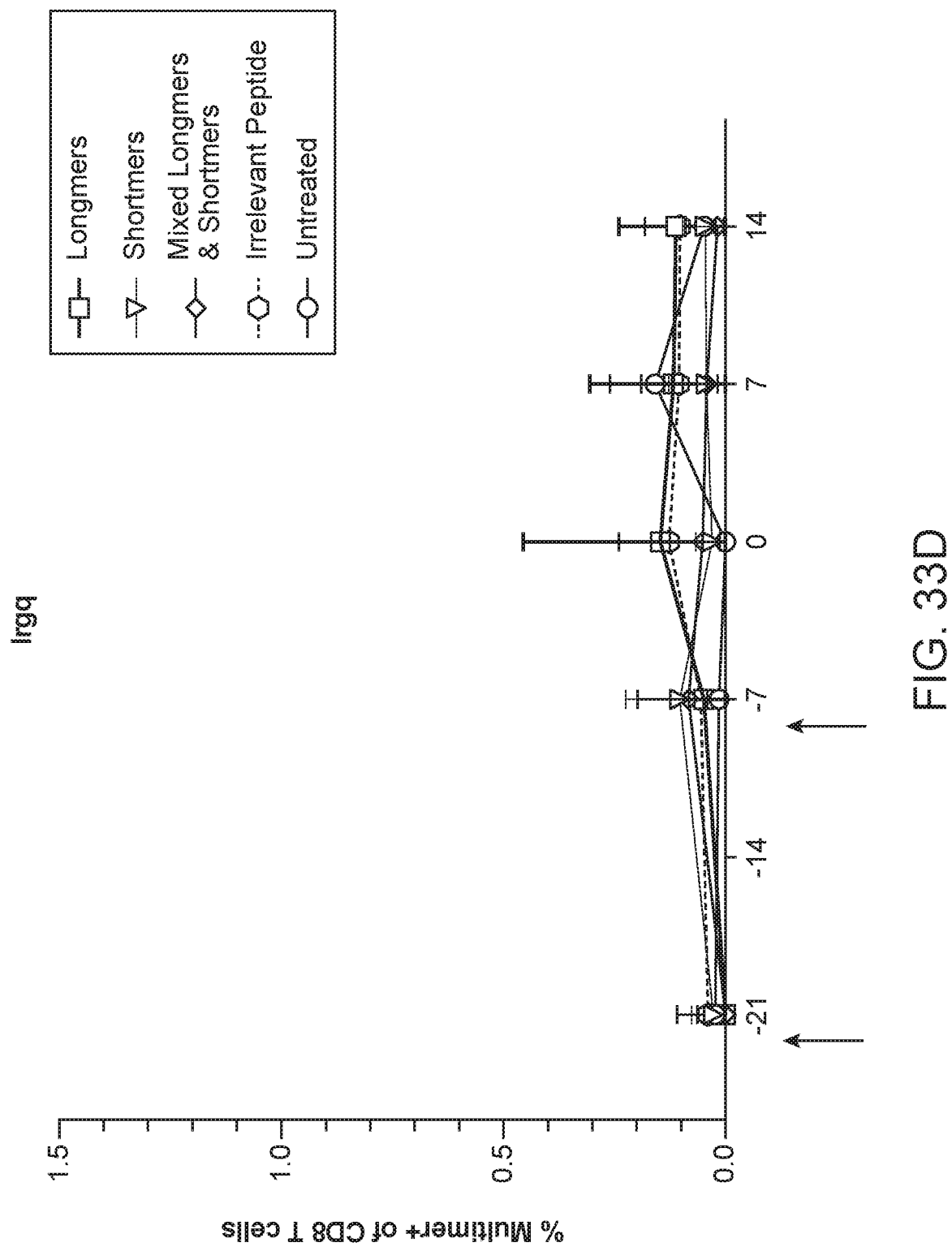
Figure 33E:
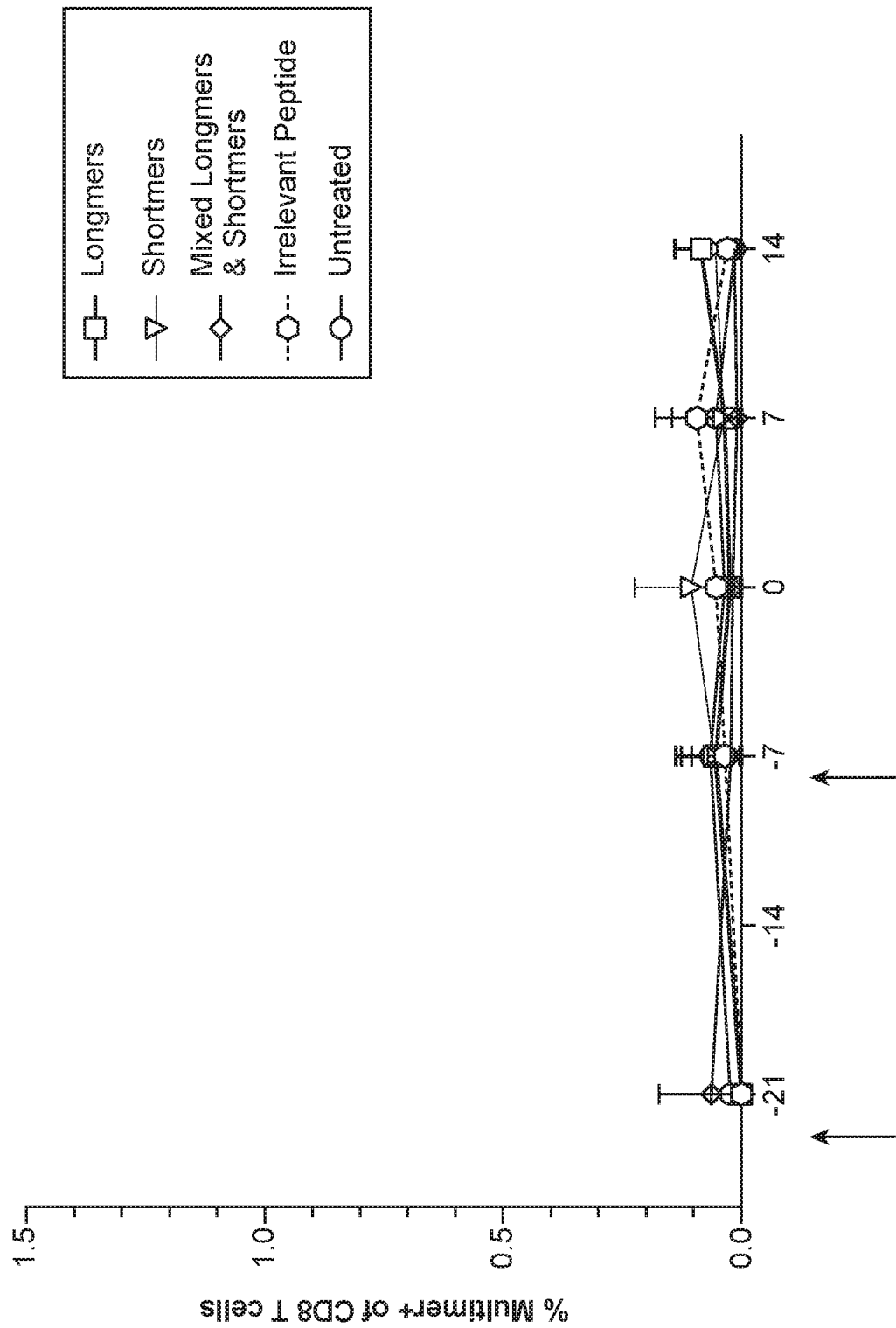

The administration regimen of Table 4 for the prime dose and boost are further described in FIG. 25. Following methods illustrated in Table 4, FIGS. 26A-33E show prime and boost immunization with longmers provided increased anti-tumor immunity compared to prime and boost immunization with shortmers or prime and boost immunization with a mixture of shortmers and longmers when administered according methods in Table 4.

Example 11—Methods for Immunization

TABLE 5 lists an exemplary method for immunization with peptides comprising neoepitopes (shortmers or longmers) for induction of antigen-specific T cell responses.

| # of Animals | Treatment (formulated in D5W) | Left Injection | Right Injection | Peptide Dose Concentration | Dose Schedule | Injection Routes | Endpoint Collections |
|---|---|---|---|---|---|---|---|
| 3 | Poly-IC Only | 50 ug poly-IC | 50 ug poly-IC | — | D0, 7, 14 | s.c. bilateral injections to each tail base | Spleens |
| 8 | Longmers | Alg8, Lama4, | 50 ug/injection. | D0, 7, 14 | | | |
| 8 | Longmers with cluster dosing | Adpgk, Irgq + 50 ug | Reps1, Obsl1 + 50 ug | 50 ug/injection | D0, 1, 2, 3, 7, 14 | | |
| 8 | Shortmers | poly-IC | poly-IC | Matched molarity/injection | D0, 7, 14 | | |
| 8 | Longmers (D0) and Shortmers (D7, 14) | | | 50 ug/injection, (D0) Matched molarity/injection. (D7, 14) | D0, 7, 14 | | |

TABLE 6 lists longmer and shortmer neoantigens used in the study

| | | Molecular weight (g/mol) | Molarity per injection (uM) | Mass per injection (ug) |
|---|---|---|---|---|
| Longmer | Alg8 | 2272 | 220.1 | 50 |
| | Adpgk | 3110.7 | 160.74 | 50 |
| | Irgq | 2608 | 191.7 | 50 |
| | Lama4 | 3463 | 144.4 | 50 |
| | Reps1 | 3087 | 162 | 50 |
| | Obsl1 | 3135 | 159.5 | 50 |
| Shortmer | Alg8 | 1053 | 220.1 | 23.2 |
| | Adpgk | 1027 | 160.74 | 16.5 |
| | Irgq | 871 | 191.7 | 16.7 |
| | Lama4 | 953 | 144.4 | 13.8 |
| | Reps1 | 942 | 162 | 15.3 |
| | Obsl1 | 1054 | 159.5 | 16.8 |

In Vivo Immunogenicity Assay

Figure 34A:
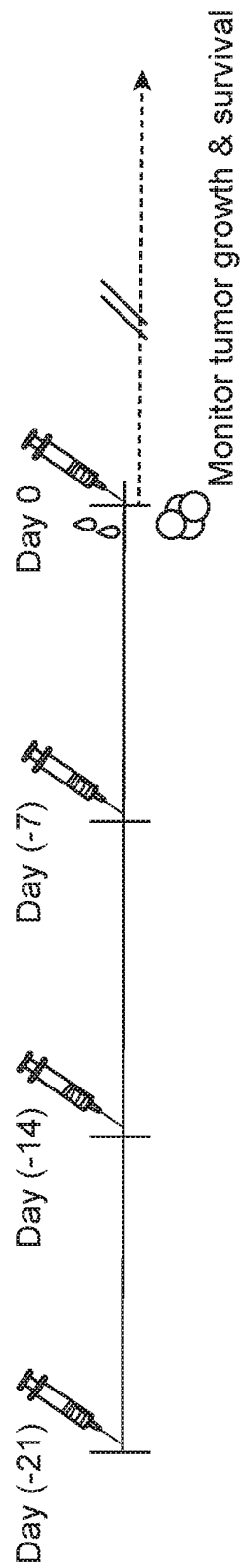
FIG. 34A illustrates exemplary administration regimen for peptides comprising neoepitopes for prevention of tumor growth and survival. The administration regimen can comprise (A) prime dose and boost of longmer, (B) prime dose and boost of shortmers or (C) prime dose of longmers and boost of longmers and shortmers. A first boost is administered 7 days post immunization with the prime dose. A second boost is administered 7 days post first boost. The illustrated regimen is followed for FIGS. 34B-36 described below.
Figure 35A:
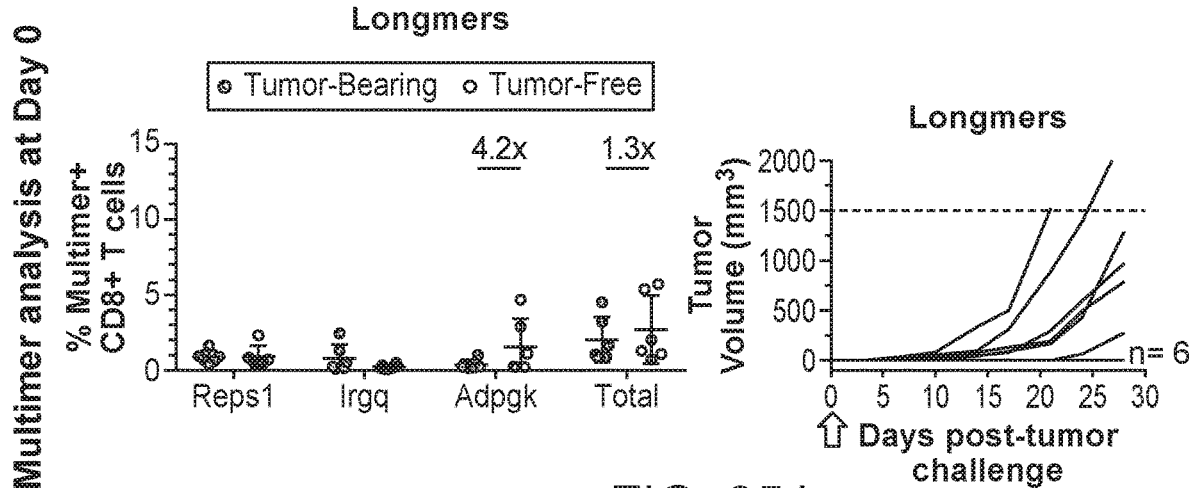
FIGS. 35A-35C illustrate increased T cell responses in tumor free mice upon addition of shortmers at boost.
Figure 35B:
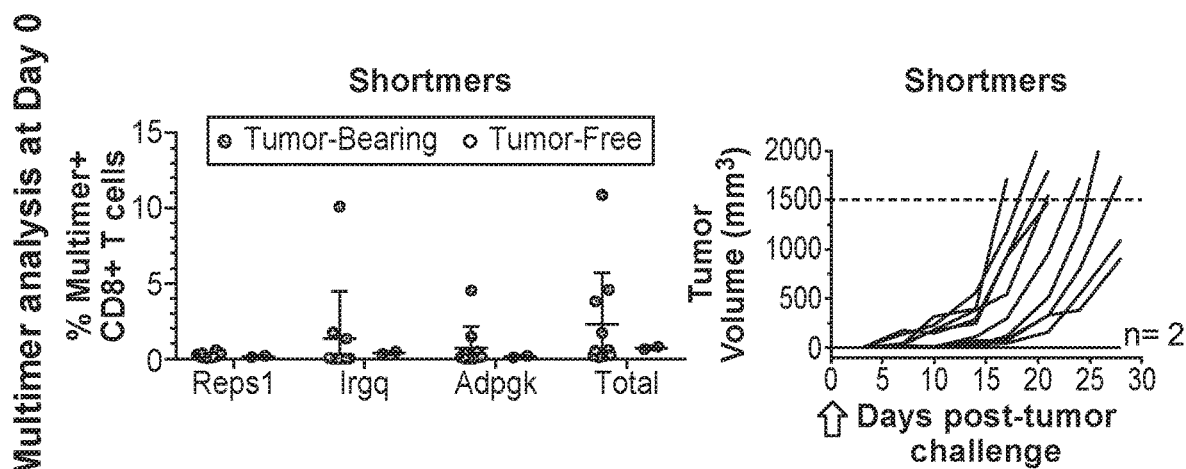
Figure 35C:
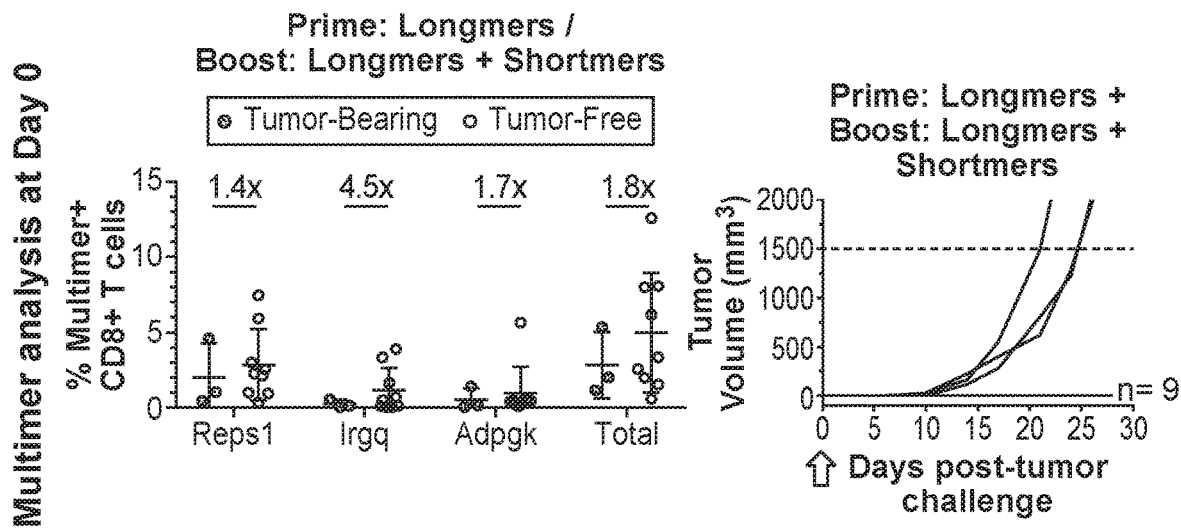
Figure 36:
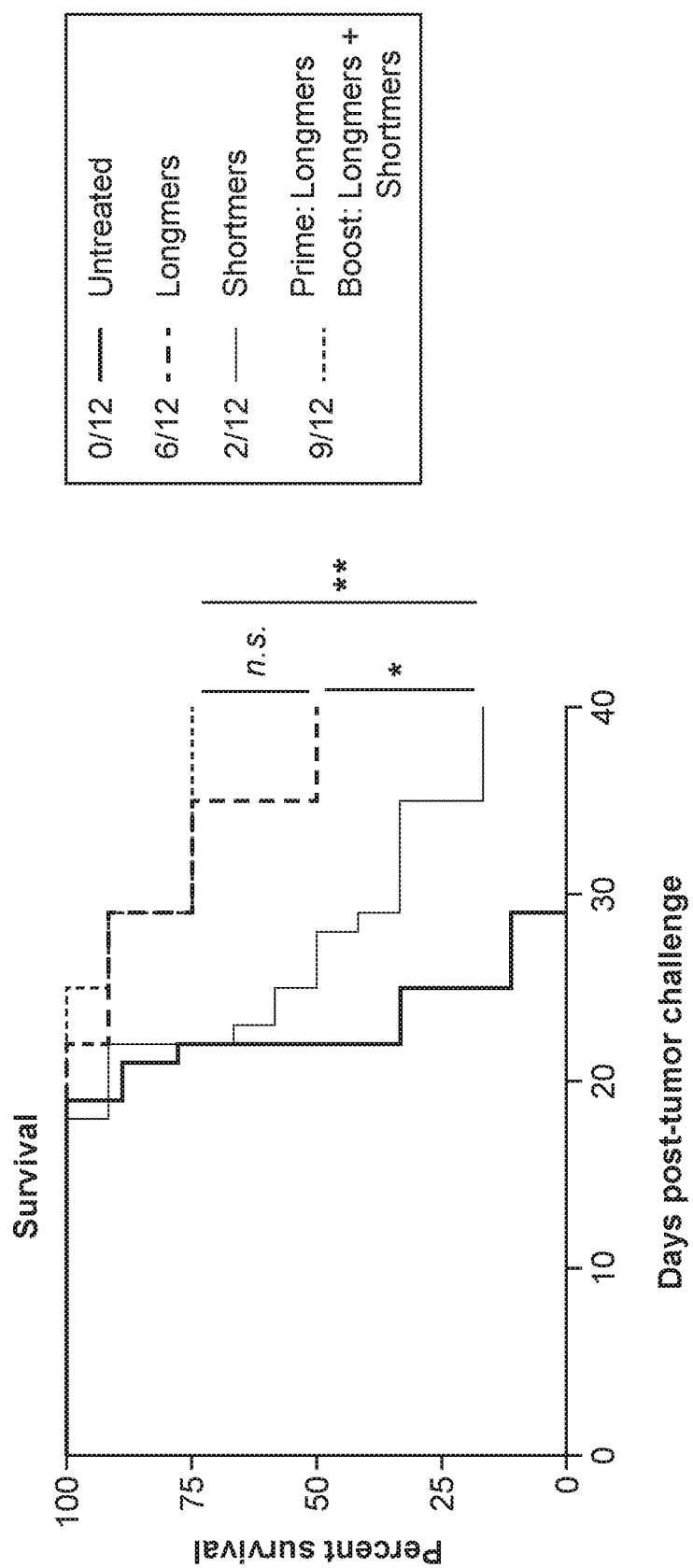
FIG. 36 illustrates effect of addition of shortmers at boost on survival of tumor bearing mice.
Figure 37:
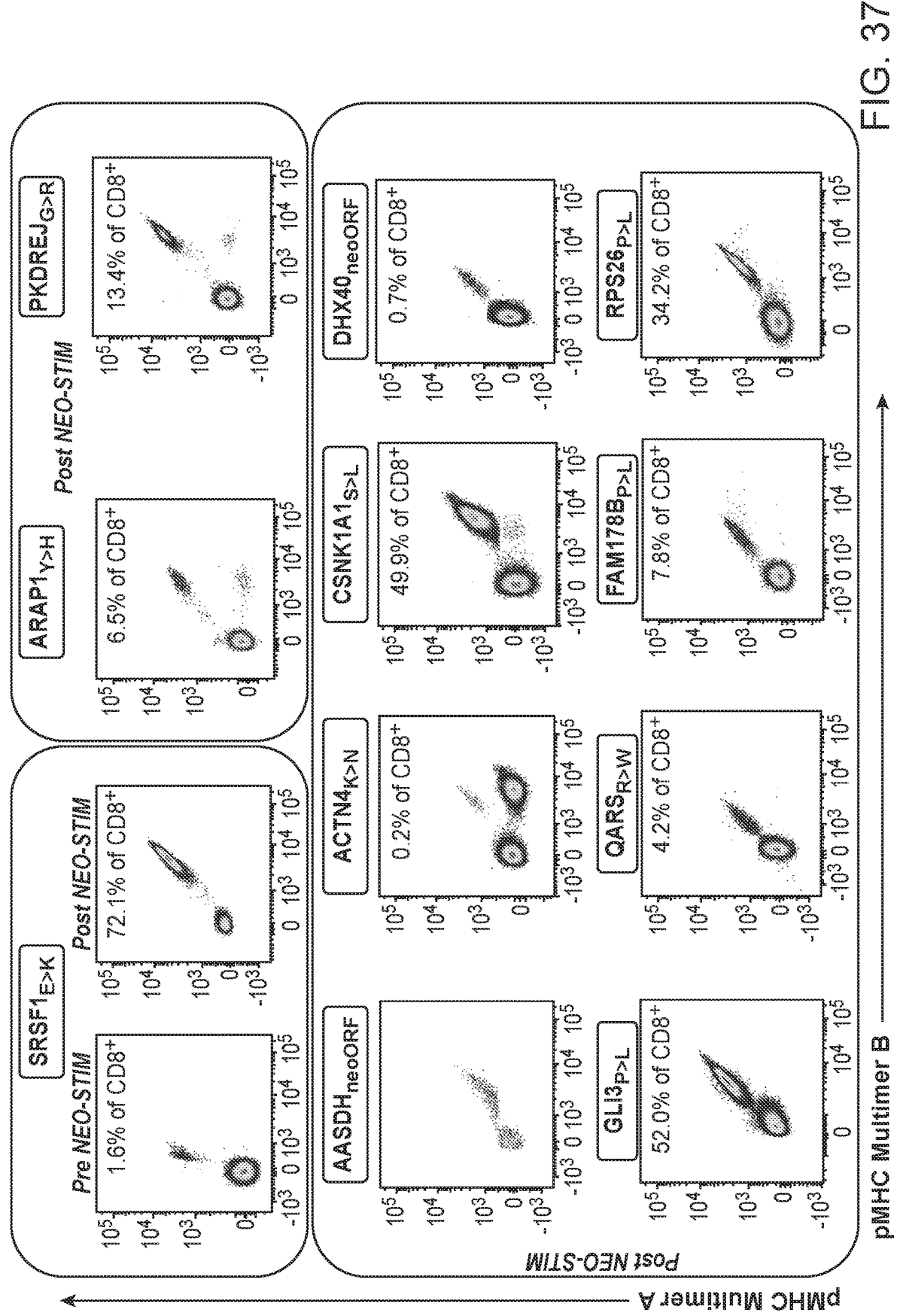
FIG. 37 demonstrates induction of antigen specific CD8+ T cell responses cells by shortmers.
Figure 38:
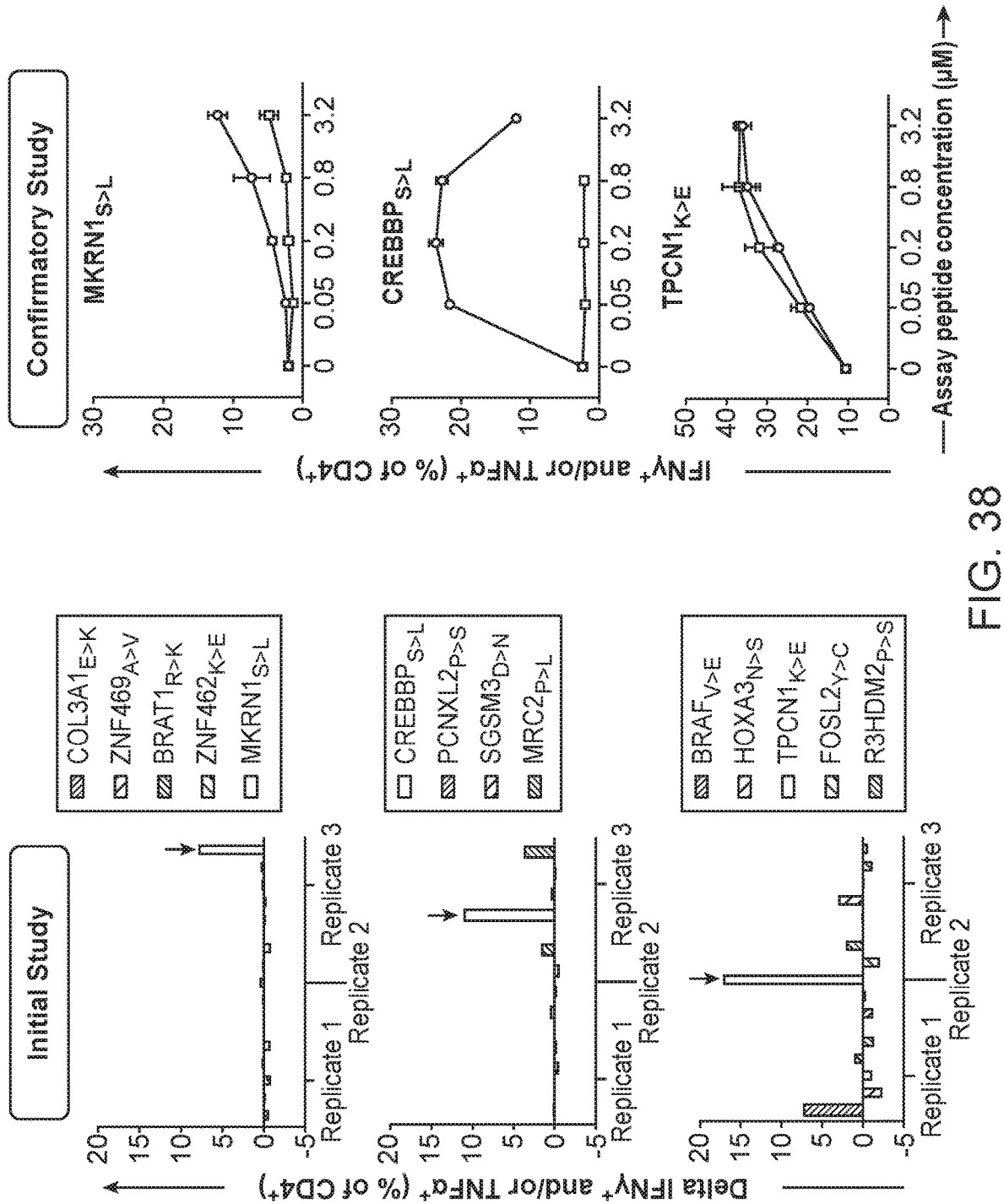
FIG. 38 demonstrates induction of antigen specific CD4+ T cell responses by longmers.

The administration regimen of Table 5 for the prime dose and boost are further described in FIG. 34A.

ELISPOT Analysis

ELISPOT analysis was conducted to measure ex vivo T cell responses to neoantigen as described above. Approximately $2 \times 10^5$ splenocytes in 100 μL was added to the wells along with 10 μM per peptide in the following antigen pools;

Longmer Stimulation Pool 1=Alg8, Adpgk, Irgq

Longmer Stimulation Pool 2=Lama4, Reps1, Obsl1

Shortmer Stimulation Pool 3=Alg8, Adpgk, Irgq

Shortmer Stimulation Pool 4=Lama4, Reps1, Obsl1, or PMA/ionomycin positive control antigen, or vehicle.

What is claimed is:

1. A method of treating cancer in a subject in need thereof, the method comprising:
   (a) administering to the subject a first pharmaceutical composition comprising autologous T cells, wherein the autologous T cells comprise:
      (i) a first plurality of autologous T cells stimulated with a first population of antigen presenting cells (APCs) having a first peptide comprising a first neoepitope of a region of a protein, wherein APCs of the first population of APCs present the first neoepitope as a complex with a class II HLA protein encoded by a class II HLA allele of the subject; and
   (b) subsequent to (a), administering to the subject a second pharmaceutical composition comprising autologous T cells, wherein the autologous T cells comprise both (i) and
      (ii) a second plurality of autologous T cells stimulated with a second population of APCs having a second peptide comprising a second neoepitope of the region of the same protein, wherein APCs of the second population of APCs present the second neoepitope as a complex with a class I HLA protein encoded by a class I HLA allele of the subject;
   wherein:
      (A) the first neoepitope and the second neoepitope comprise the same mutation,
      (B) the first peptide is different from the second peptide and the first peptide is at least one amino acid longer in length than the second peptide, and
      (C) the first neoepitope is longer than the second neoepitope, wherein the second neoepitope has a length of from 8 to 13 amino acids and the first neoepitope has a length of from 9 to 25 amino acids.

2. The method of claim 1, wherein the protein is a RAS protein and the mutation is a point mutation.

3. The method of claim 1, wherein the administering the second pharmaceutical composition of (b) is at least 3 days after administering the first pharmaceutical composition of (a).

4. The method of claim 1, wherein the second plurality of autologous T cells comprises CD8+ T cells comprising a TCR that binds to a complex comprising the second neoepitope and the class I HLA protein encoded by a class I HLA allele of the subject; and wherein the first plurality of autologous T cells comprises CD4+ T cells comprising a TCR that binds to a complex comprising the first neoepitope and the class II HLA protein encoded by a class II HLA allele of the subject.

5. The method of claim 1, wherein the first neoepitope is processed from the first peptide by the first population of APCs.

6. The method of claim 5, wherein the second neoepitope is not processed from the second peptide by the second population of APCs.

7. The method of claim 1, wherein the second neoepitope is comprised within the first neoepitope.

8. The method of claim 1, wherein the first neoepitope is shorter in length than the first peptide.

9. The method of claim 1, wherein the second neoepitope is the same length as the second peptide.

10. The method of claim 4, wherein the CD8+ T cells or the CD4+ T cells are effector memory T cells.

11. The method of claim 10, wherein the first and second populations of APCs are autologous APC populations.

12. The method of claim 1, wherein the first peptide comprises at least two first peptides and the second peptide comprises at least two second peptides; and wherein the at least two first peptides are from two distinct genes, and the at least two second peptides are from the same two distinct genes as the first two peptides respectively.

13. The method of claim 1, wherein administering the second pharmaceutical composition is at least 1 day after the first pharmaceutical composition is administered.

14. The method of claim 1, wherein the method further comprises preparing the first and second pluralities of autologous T cells by stimulating autologous T cells ex vivo with the first and the second population of APCs.

15. The method of claim 1, wherein an amount of the second plurality of autologous T cells in (ii) is lower than an amount of the first plurality of autologous T cells in (i).

16. The method of claim 1, wherein tumor growth is inhibited to a level greater than that achieved by administering one or more doses of the first plurality of autologous T cells alone or one or more doses of the second plurality of autologous T cells alone.

17. The method of claim 1, wherein the method comprises enhanced survival of the subject to a level greater than that achieved by administering the first plurality of autologous T cells alone or the second plurality of autologous T cells alone.

* * * * *